US012442042B2

(12) United States Patent
Tan et al.

(10) Patent No.: US 12,442,042 B2
(45) Date of Patent: Oct. 14, 2025

(54) EPIGENOMIC PROFILING REVEALS THE SOMATIC PROMOTER LANDSCAPE OF PRIMARY GASTRIC ADENOCARCINOMA

(71) Applicant: AGENCY FOR SCIENCE, TECHNOLOGY AND RESEARCH, Singapore (SG)

(72) Inventors: Patrick Tan, Singapore (SG); Aditi Qamra, Singapore (SG); Manjie Xing, Singapore (SG); Wen Fong Ooi, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 429 days.

(21) Appl. No.: 15/999,597

(22) PCT Filed: Feb. 16, 2017

(86) PCT No.: PCT/SG2017/050072

§ 371 (c)(1),
(2) Date: Aug. 16, 2018

(87) PCT Pub. No.: WO2017/142484

PCT Pub. Date: Aug. 24, 2017

(65) Prior Publication Data

US 2021/0301348 A1 Sep. 30, 2021

(30) Foreign Application Priority Data

Feb. 16, 2016 (SG) ........................... 10201601142V

(51) Int. Cl.
*C12Q 1/68* (2018.01)
*C12P 19/34* (2006.01)
*C12Q 1/6886* (2018.01)

(52) U.S. Cl.
CPC ...... *C12Q 1/6886* (2013.01); *C12Q 2600/118* (2013.01); *C12Q 2600/154* (2013.01)

(58) Field of Classification Search
CPC ............ C12Q 1/6886; C12Q 2600/118; C12Q 2600/154; C12Q 2600/158
See application file for complete search history.

(56) References Cited

U.S. PATENT DOCUMENTS

2012/0028817 A1 2/2012 Kelly et al.
2013/0164279 A1 6/2013 Goel et al.

FOREIGN PATENT DOCUMENTS

JP 2009-524810 A 7/2009
JP 7336193 B2 8/2023
WO 2011/137302 A1 11/2011
WO WO 2015102536 A1 7/2015
WO 2015196064 A1 12/2015

OTHER PUBLICATIONS

Moons et al Prognosis and prognostic research: what, why, and how? (2009) BMJ 338;b375. (Year: 2009).*
Li et al Association between H3K4 methylation and cancer prognosis: a meta-analysis (2018) Thoracic Cancer 9:794-799 (Year: 2018).*
Bianchi et al Not all cancers are created equal: Tissue specificity in cancer genes and pathways (2020) Current Opinion in Cell Biology 63: 135-143 (Year: 2020).*
Meghana M. Kulkarni "Digital Multiplexed Gene Expression Analysis Using the NanoString nCounter System" Unit 25B.10 in Current Protocols in Molecular Biology, Supplement 94, Apr. 2011. (Year: 2011).*
Ramana V. Davuluri, et al., "The functional consequences of alternative promoter use in mammalian genomes" Trends in Genetics vol. 24 No. 4, Mar. 2008 (Year: 2008).*
Hiromu Suzuki, et al. "Genome-wide Profiling of Chromatin Signatures Reveals Epigenetic Regulation of MicroRNA Genes in Colorectal Cancer" Cancer Res; 71(17) Sep. 1, 2011 (Year: 2011).*
Batool Akhtar-Zaidi, et al. "Epigenomic Enhancer Profiling Defines a Signature of Colon Cancer" Science, vol. 336, May 11, 2012 (Year: 2012).*
Nikolay S.Outchkourov, et al., "Balancing of Histone H3K4 Methylation States by the Kdm5c/SMCX Histone Demethylase Modulates Promoter and Enhancer Function" Cell Reports, vol. 3, Issue 4, Apr. 25, 2013, pp. 1071-1079 (Year: 2013).*
Leighton J Core, et al. "Analysis of nascent RNA identifies a unified architecture of initiation regions at mammalian promoters and enhancers" Nature Genetics vol. 46, pp. 1311-1320 (2014) (Year: 2014).*
Vivian G. Cheung, et al. "Natural variation in human gene expression assessed in lymphoblastoid cells" Nature Genetics, vol. 33, (Mar. 2003). (Year: 2003).*
Aleksandra Pekowska, et al. "H3K4 tri-methylation provides an epigenetic signature of active enhancers" The EMBO Journal (2011) 30, 4198-4210. (Year: 2011).*
Brian Magnuson, et al. "Identifying transcription start sites and active enhancer elements using BruUV-seq", Sci Rep. Dec. 11, 2015; 5:17978. (Year: 2015).*
(Continued)

*Primary Examiner* — Stephen T Kapushoc
(74) *Attorney, Agent, or Firm* — WOMBLE BOND DICKINSON (US) LLP

(57) ABSTRACT

The present invention relates to a method for determining the presence or absence of at least one promoter in a cancerous biological sample relative to a non-cancerous biological sample. The present invention also relates to a method for determining the prognosis of cancer in a subject, a method for modulating the activity of at least one cancer-associated promoter in a cell, a method for modulating the immune response of a subject to cancer, a method for determining the presence of at least one cancer-associated promoter in a cancerous biological sample relative to a non-cancerous biological sample and a biomarker for detecting cancer in a subject.

16 Claims, 51 Drawing Sheets

Specification includes a Sequence Listing.

(56) References Cited

OTHER PUBLICATIONS

Gabriel E. Zentner, et al. "The Chromatin Fingerprint of Gene Enhancer Elements" Journal of Biological Chemistry, vol. 287, Issue 37, 30888-30896, Sep. 2012 (Year: 2012).*
Qamra et al., "Series GSE75898: Somatic Promoter Landscape of Primary Gastric Adenocarcinoma Delineated by Epigenomic Profiling", NCBI Gene Expression omnibus, Sep. 28, 2016, available online at <https://www.ncbi.nlm.nih.gov/geo/query/acc.cgi?token=kfoxgeamzfetpal&acc=GSE75898>.
The Extended European Search Report for Application No. 17753595.2 mailed Nov. 8, 2019, 6 pages.
Muratani, et al., "Nanoscale chromatin profiling of gastric adenocarcinoma reveals cancer-associated cryptic promoters and somatically acquired regulatory elements," Nature Communications, 2014, 14 pages, vol. 5, No. 4361, Macmillan Publishers Limited.
Previati, et al., "Next generation analysis of breast cancer genomes for precision medicine," Cancer Letters, 2013, pp. 1-7, vol. 339, Elsevier.
The Communication Pursuant to Article 94(3) EPC for European Application No. 17753595.2 mailed Jul. 9, 2020, 5 pages.
IP Office of Singapore—Notification of Transmittal of the International Search Report & the Written Opinion of the International Searching Authority, or the Declaration, with the International Search Report & Written Opinion mailed May 18, 2017 for International Application No. PCT/SG2017/050072 (19 pgs).
IP Office of Singapore—International Preliminary Report on Patentability mailed May 18, 2018 for International Application No. PCT/SG2017/050072, with the Chapter II Demand and Article 34 Amendment submitted Dec. 18, 2017 (35 pgs).
Chang, Q., et al., "Sustained JNK1 Activation is Associated with Altered Histone H3 Methylations in Human Liver Cancer." *J. Hepatol.*, Oct. 16, 2008, vol. 50, No. 2, pp. 323-333.
Cheng, J., et al., "A Role for H3K4 Mono-methylation in Gene Repression and Partitioning of Chromatin Readers." *Mol. Cell*, Mar. 20, 2014, vol. 53, No. 6, pp. 979-992.
Heintzman, N.D., et al., "Distinct and Predictive Chromatin Signatures of Transcriptional and Enhancers in the Human Genome." *Nature Genetics*, Feb. 4, 2007, vol. 39, No. 3, pp. 311-318.
Lu, T-Y., et al., "DNA Methylation and Histone Modification Regulate Silencing of OPG During Tumor Progression." *J. Cell. Biochem.*, Jun. 29, 2009, vol. 108, No. 1, pp. 315-325.
Messier, T.L., et al., "Histone H3 Lysine 4 Acetylation and Methylation Dynamics Define Breast Cancer Subtypes." *Oncotarget*, Jan. 15, 2016, vol. 7, No. 5, pp. 5094-5109.
Muratani, M., et al., "Nanoscale Chromatin Profiling of Gastric Adenocarcinoma Reveals Cancer-associated Cryptic Promoters and Somatically Acquired Regulatory Elements." *Nature Communications*, Jul. 10, 2014, vol. 5, pp. 4361:1-14.
Qamra, A., et al., "Epigenomic Promoter Alterations Amplify Gene Isoform and Immunogenic Diversity in Gastric Adenocarcinoma." *Cancer Discovery*, Mar. 20, 2017, Author Manuscript Published Online First: pp. 1-63.
Suzuki, A., et al., "Aberrant Transcription Regulations in Cancers: Genome Transcriptome and Epigenome Analysis of Lung Adenocarcinoma Cell Lines." *Nucleic Acids Research*, Nov. 6, 2014, vol. 42, No. 22, pp. 13557-13572.
Notice of Decision for Rejection of the Japanese Patent Office dated Aug. 17, 2021, for Japanese Patent Application No. 2018-543243.
Notice of Reasons for Rejection of the Japanese Patent Office dated Jan. 6, 2021, for Japanese Patent Application No. 2018-543243.
Choe et al., "Functional elements demarcated by histone modifications in breast cancer cells" Biochemical and Biophysical Research Communications, Feb. 17, 2012, vol. 418 Issue 3, pp. 475-482.
First Office Action for Chinese Application No. 201780023934.9 mailed Apr. 21, 2021, 11 pages.
Second Office Action for Chinese Application No. 201780023934.9 mailed Nov. 29, 2021, 8 pages.
Invitation to Respond to Written Opinion (Supplementary Examination) for Singapore Application No. 11201806946V mailed Sep. 5, 2022, 6 pages.
Notification to Grant Patent Right for Invention for Chinese Application No. 201780023934.9 mailed Mar. 8, 2022, 4 pages.
Cheng, Jemmie et al., "A Role for H3K4 Monomethylation in Gene Repression and Partitioning of Chromatin Readers," Molecular Cell 53, 979-992, Mar. 20, 2014.
Batool Akhtar-Zaidi et al., "Epigenomic Enhancer Profiling Defines a Signature of Colon Cancer," Science 336, 34 pages, Jan. 2012.
Notice of Non-Final Rejection with translation, mailed Jan. 20, 2024, for Korean Application No. 10-2018-7026650, filed Sep. 14, 2018, 31 pages.
Pre-Appeal Report issued Jan. 5, 2024, in Japanese Patent Application No. 2021-204616.
Reconsideration Report by Examiner before Appeal with English translation, for Japanese Application No. 2018-543243, drafted Feb. 4, 2022, 9 pages.
Notice of Final Rejection with English translation for Korean Application No. 10-2018-7026650, dated Sep. 26, 2024, 8 pages.
Qamra, et al., Epigenomic promoter alterations amplify gene isoform and immunogenic diversity in gastric adenocarcinoma, Cancer discovery, Jun. 1, 2017, pp. 630-651, 7(6).
Korean Patent Office, Korean Notice of Preliminary Rejection for Korean application No. 10-2021-7023202, May 30, 2025, 6 pages.
Korean Patent Office, Korean Notice of Preliminary Rejection for for Korean application No. 10-2021-7023202, May 30, 2025, 8 pages. [Not in English].

* cited by examiner

A)

B)

A)

B)

C)

D)

E)

F)

C)

D)

E)

F)

All H3K4me3 Promoters

A)

B)

C)

D)

E)

A)

C)

| | 0 | 50 | 100 | 150 |
|---|---|---|---|---|
| High | 44 | 8 | 6 | 1 |
| Low | 41 | 16 | 11 | 4 |

D) Mutation Count

A)

A)

SEQUENCE LISTING

<160> NUMBER OF SEQ ID NOS: 2068

<210> SEQ ID NO 1
<211> LENGTH: 22
<212> TYPE: PRT
<213> ORGANISM: Homo sapiens

<400> SEQUENCE: 1

Ile Asp Asn Ser Gln Val Glu Ser Gly Ser Leu Glu Asp Asp Trp Asp
1 5 10 15

Phe Leu Pro Pro Lys Lys
20

<210> SEQ ID NO 2
<211> LENGTH: 14
<212> TYPE: PRT
<213> ORGANISM: Homo sapiens

<400> SEQUENCE: 2

Phe Tyr Ala Leu Ser Ala Ser Phe Glu Pro Phe Ser Asn Lys
1 5 10

<210> SEQ ID NO 3
<211> LENGTH: 12
<212> TYPE: PRT
<213> ORGANISM: Homo sapiens

<400> SEQUENCE: 3

Glu Gln Phe Leu Asp Gly Asp Gly Trp Thr Ser Arg
1 5 10

<210> SEQ ID NO 4
<211> LENGTH: 15
<212> TYPE: PRT
<213> ORGANISM: Homo sapiens

<400> SEQUENCE: 4

Ile Lys Asp Pro Asp Ala Ser Lys Pro Glu Asp Trp Asp Glu Arg
1 5 10 15

<210> SEQ ID NO 5
<211> LENGTH: 14
<212> TYPE: PRT
<213> ORGANISM: Homo sapiens

<400> SEQUENCE: 5

Gly Asp Val Thr Ala Gln Ile Ala Leu Gln Pro Ala Leu Lys
1 5 10

<210> SEQ ID NO 6
<211> LENGTH: 13
<212> TYPE: PRT
<213> ORGANISM: Homo sapiens

<400> SEQUENCE: 6

Gly Ile Ser Leu Asn Pro Glu Gln Trp Ser Gln Leu Lys
1 5 10

<210> SEQ ID NO 7
<211> LENGTH: 17
<212> TYPE: PRT
<213> ORGANISM: Homo sapiens

<400> SEQUENCE: 7

Ala Tyr His Ser Phe Leu Val Glu Pro Ile Ser Cys His Ala Trp Asn
1 5 10 15

Lys

<210> SEQ ID NO 8
<211> LENGTH: 13
<212> TYPE: PRT
<213> ORGANISM: Homo sapiens

<400> SEQUENCE: 8

Ile Ala Val Gln Pro Gly Thr Val Gly Pro Gln Gly Arg
1 5 10

<210> SEQ ID NO 9
<211> LENGTH: 16
<212> TYPE: PRT
<213> ORGANISM: Homo sapiens

<400> SEQUENCE: 9

Val Leu Ala Gln Asn Ser Gly Phe Asp Leu Gln Glu Thr Leu Val Lys
1 5 10 15

<210> SEQ ID NO 10
<211> LENGTH: 23
<212> TYPE: PRT
<213> ORGANISM: Homo sapiens

<400> SEQUENCE: 10

Cys Lys Asp Asp Glu Phe Thr His Leu Tyr Thr Leu Ile Val Arg Pro
1 5 10 15

Asp Asn Thr Tyr Glu Val Lys
20

<210> SEQ ID NO 11
<211> LENGTH: 26
<212> TYPE: PRT
<213> ORGANISM: Homo sapiens

<400> SEQUENCE: 11

Ala Lys Ile Asp Asp Pro Thr Asp Ser Lys Pro Glu Asp Trp Asp Lys
1 5 10 15

Pro Glu His Ile Pro Asp Pro Asp Ala Lys
20 25

<210> SEQ ID NO 12
<211> LENGTH: 8
<212> TYPE: PRT
<213> ORGANISM: Homo sapiens

<400> SEQUENCE: 12

Val His Val Ile Phe Asn Tyr Lys
1 5

<210> SEQ ID NO 13
<211> LENGTH: 13
<212> TYPE: PRT
<213> ORGANISM: Homo sapiens

<400> SEQUENCE: 13

His Glu Gln Asn Ile Asp Cys Gly Gly Gly Tyr Val Lys
1 5 10

<210> SEQ ID NO 14

<211> LENGTH: 8
<212> TYPE: PRT
<213> ORGANISM: Homo sapiens

<400> SEQUENCE: 14

Leu Ile Asp Phe Gly Leu Ala Arg
1               5

<210> SEQ ID NO 15
<211> LENGTH: 10
<212> TYPE: PRT
<213> ORGANISM: Homo sapiens

<400> SEQUENCE: 15

Thr Trp Lys Pro Thr Leu Val Ile Leu Arg
1               5                   10

<210> SEQ ID NO 16
<211> LENGTH: 14
<212> TYPE: PRT
<213> ORGANISM: Homo sapiens

<400> SEQUENCE: 16

Ala Ile Trp Asn Val Ile Asn Trp Glu Asn Val Thr Glu Arg
1               5                   10

<210> SEQ ID NO 17
<211> LENGTH: 24
<212> TYPE: PRT
<213> ORGANISM: Homo sapiens

<400> SEQUENCE: 17

Ile Asp Asp Pro Thr Asp Ser Lys Pro Glu Asp Trp Asp Lys Pro Glu
1               5                   10                  15

His Ile Pro Asp Pro Asp Ala Lys
            20

<210> SEQ ID NO 18
<211> LENGTH: 8
<212> TYPE: PRT
<213> ORGANISM: Homo sapiens

<400> SEQUENCE: 18

Asn Val Arg Pro Asp Tyr Leu Lys
1               5

<210> SEQ ID NO 19
<211> LENGTH: 13
<212> TYPE: PRT
<213> ORGANISM: Homo sapiens

<400> SEQUENCE: 19

Asn Ser Val Ser Gln Ile Ser Val Leu Ser Gly Gly Lys
1               5                   10

<210> SEQ ID NO 20
<211> LENGTH: 21
<212> TYPE: PRT
<213> ORGANISM: Homo sapiens

<400> SEQUENCE: 20

Asp Gly Asn Val Leu Leu His Glu Met Gln Ile Gln His Pro Thr Ala
1               5                   10                  15

Ser Leu Ile Ala Lys

20

<210> SEQ ID NO 21
<211> LENGTH: 8
<212> TYPE: PRT
<213> ORGANISM: Homo sapiens

<400> SEQUENCE: 21

Ala Gly Ala Thr His Val Glu Arg
1 5

<210> SEQ ID NO 22
<211> LENGTH: 10
<212> TYPE: PRT
<213> ORGANISM: Homo sapiens

<400> SEQUENCE: 22

Leu Val Ala Leu Leu Asn Thr Leu Asp Arg
1 5 10

<210> SEQ ID NO 23
<211> LENGTH: 15
<212> TYPE: PRT
<213> ORGANISM: Homo sapiens

<400> SEQUENCE: 23

His His Ala Ala Tyr Val Asn Asn Leu Asn Val Thr Glu Glu Lys
1 5 10 15

<210> SEQ ID NO 24
<211> LENGTH: 18
<212> TYPE: PRT
<213> ORGANISM: Homo sapiens

<400> SEQUENCE: 24

Phe Tyr Gly Asp Glu Glu Lys Asp Lys Gly Leu Gln Thr Ser Gln Asp
1 5 10 15

Ala Arg

<210> SEQ ID NO 25
<211> LENGTH: 9
<212> TYPE: PRT
<213> ORGANISM: Homo sapiens

<400> SEQUENCE: 25

Lys Val His Val Ile Phe Asn Tyr Lys
1 5

<210> SEQ ID NO 26
<211> LENGTH: 13
<212> TYPE: PRT
<213> ORGANISM: Homo sapiens

<400> SEQUENCE: 26

Gly Pro Leu Pro Ala Ala Pro Pro Val Ala Pro Glu Arg
1 5 10

<210> SEQ ID NO 27
<211> LENGTH: 8
<212> TYPE: PRT
<213> ORGANISM: Homo sapiens

<400> SEQUENCE: 27

Val Leu Leu Ser Ala Leu Glu Arg 1 5

<210> SEQ ID NO 28
<211> LENGTH: 10
<212> TYPE: PRT
<213> ORGANISM: Homo sapiens

<400> SEQUENCE: 28

Ser Val Ser Ile Gly Tyr Leu Leu Val Lys
1 5 10

<210> SEQ ID NO 29
<211> LENGTH: 15
<212> TYPE: PRT
<213> ORGANISM: Homo sapiens

<400> SEQUENCE: 29

Ile Gln Gln Glu Ile Ala Val Gln Asn Pro Leu Val Ser Glu Arg
1 5 10 15

<210> SEQ ID NO 30
<211> LENGTH: 9
<212> TYPE: PRT
<213> ORGANISM: Homo sapiens

<400> SEQUENCE: 30

Gly Glu Leu Leu Glu Ala Ile Lys Arg
1 5

<210> SEQ ID NO 31
<211> LENGTH: 15
<212> TYPE: PRT
<213> ORGANISM: Homo sapiens

<400> SEQUENCE: 31

Ala His Asn Gln Asp Leu Gly Leu Ala Gly Ser Cys Leu Ala Arg
1 5 10 15

<210> SEQ ID NO 32
<211> LENGTH: 16
<212> TYPE: PRT
<213> ORGANISM: Homo sapiens

<400> SEQUENCE: 32

Tyr Val Val Val Thr Gly Ile Thr Pro Thr Pro Leu Gly Glu Gly Lys
1 5 10 15

<210> SEQ ID NO 33
<211> LENGTH: 24
<212> TYPE: PRT
<213> ORGANISM: Homo sapiens

<400> SEQUENCE: 33

Met Glu Asp Leu Asp Gln Ser Pro Leu Val Ser Ser Ser Asp Ser Pro
1 5 10 15

Pro Arg Pro Gln Pro Ala Phe Lys
20

<210> SEQ ID NO 34
<211> LENGTH: 15
<212> TYPE: PRT
<213> ORGANISM: Homo sapiens

<400> SEQUENCE: 34

Ala Ala Gln Ala Pro Ser Ser Phe Gln Leu Leu Tyr Asp Leu Lys
1 5 10 15

<210> SEQ ID NO 35
<211> LENGTH: 15
<212> TYPE: PRT
<213> ORGANISM: Homo sapiens

<400> SEQUENCE: 35

Leu Gln Ala Gln Leu Asn Glu Leu Gln Ala Gln Leu Ser Gln Lys
1 5 10 15

<210> SEQ ID NO 36
<211> LENGTH: 9
<212> TYPE: PRT
<213> ORGANISM: Homo sapiens

<400> SEQUENCE: 36

Ala Leu Gln Phe Leu Glu Glu Val Lys
1 5

<210> SEQ ID NO 37
<211> LENGTH: 9
<212> TYPE: PRT
<213> ORGANISM: Homo sapiens

<400> SEQUENCE: 37

Leu Leu Thr Ser Gly Tyr Leu Gln Arg
1 5

<210> SEQ ID NO 38
<211> LENGTH: 13
<212> TYPE: PRT
<213> ORGANISM: Homo sapiens

<400> SEQUENCE: 38

Gly Asp Leu Asn Asp Cys Phe Ile Pro Cys Thr Pro Lys
1 5 10

<210> SEQ ID NO 39
<211> LENGTH: 18
<212> TYPE: PRT
<213> ORGANISM: Homo sapiens

<400> SEQUENCE: 39

Ala Ser Ser Glu Gly Gly Thr Ala Ala Gly Ala Gly Leu Asp Ser Leu
1 5 10 15

His Lys

<210> SEQ ID NO 40
<211> LENGTH: 15
<212> TYPE: PRT
<213> ORGANISM: Homo sapiens

<400> SEQUENCE: 40

Glu Ala Val Thr Glu Ile Leu Gly Ile Glu Pro Asp Arg Glu Lys
1 5 10 15

<210> SEQ ID NO 41
<211> LENGTH: 14
<212> TYPE: PRT
<213> ORGANISM: Homo sapiens

<400> SEQUENCE: 41

Glu Val Glu Glu Arg Pro Ala Pro Thr Pro Trp Gly Ser Lys
1 5 10

<210> SEQ ID NO 42
<211> LENGTH: 10
<212> TYPE: PRT
<213> ORGANISM: Homo sapiens

<400> SEQUENCE: 42

Ile Ile Thr Glu Gly Phe Glu Ala Ala Lys
1 5 10

<210> SEQ ID NO 43
<211> LENGTH: 13
<212> TYPE: PRT
<213> ORGANISM: Homo sapiens

<400> SEQUENCE: 43

Tyr Leu Asn Ile Phe Gly Glu Ser Gln Pro Asn Pro Lys
1 5 10

<210> SEQ ID NO 44
<211> LENGTH: 20
<212> TYPE: PRT
<213> ORGANISM: Homo sapiens

<400> SEQUENCE: 44

Leu Thr Ala Ala Ser Val Gly Val Gln Gly Ser Gly Trp Gly Trp Leu
1 5 10 15

Gly Phe Asn Lys
20

<210> SEQ ID NO 45
<211> LENGTH: 18
<212> TYPE: PRT
<213> ORGANISM: Homo sapiens

<400> SEQUENCE: 45

Ile Ala Pro Leu Glu Glu Gly Thr Leu Pro Phe Asn Leu Ala Glu Ala
1 5 10 15

Gln Arg

<210> SEQ ID NO 46
<211> LENGTH: 11
<212> TYPE: PRT
<213> ORGANISM: Homo sapiens

<400> SEQUENCE: 46

Gly Gln Thr Leu Val Val Gln Phe Thr Val Lys
1 5 10

<210> SEQ ID NO 47
<211> LENGTH: 17
<212> TYPE: PRT
<213> ORGANISM: Homo sapiens

<400> SEQUENCE: 47

Ala Gln Leu Gly Val Gln Ala Phe Ala Asp Ala Leu Leu Ile Ile Pro
1 5 10 15

Lys

<210> SEQ ID NO 48
<211> LENGTH: 9

<212> TYPE: PRT
<213> ORGANISM: Homo sapiens

<400> SEQUENCE: 48

Gln Val Ala Pro Glu Lys Pro Val Lys
1 5

<210> SEQ ID NO 49
<211> LENGTH: 25
<212> TYPE: PRT
<213> ORGANISM: Homo sapiens

<400> SEQUENCE: 49

Val Ala Thr Ala Gln Asp Asp Ile Thr Gly Asp Gly Thr Thr Ser Asn
1 5 10 15

Val Leu Ile Ile Gly Glu Leu Leu Lys
20 25

<210> SEQ ID NO 50
<211> LENGTH: 13
<212> TYPE: PRT
<213> ORGANISM: Homo sapiens

<400> SEQUENCE: 50

Gly Leu Leu Pro Gln Leu Leu Gly Val Ala Pro Glu Lys
1 5 10

<210> SEQ ID NO 51
<211> LENGTH: 8
<212> TYPE: PRT
<213> ORGANISM: Homo sapiens

<400> SEQUENCE: 51

Asn Ala Tyr Val Trp Thr Leu Lys
1 5

<210> SEQ ID NO 52
<211> LENGTH: 16
<212> TYPE: PRT
<213> ORGANISM: Homo sapiens

<400> SEQUENCE: 52

Ile Tyr Gly Ala Asp Asp Ile Glu Leu Leu Pro Glu Ala Gln His Lys
1 5 10 15

<210> SEQ ID NO 53
<211> LENGTH: 13
<212> TYPE: PRT
<213> ORGANISM: Homo sapiens

<400> SEQUENCE: 53

Cys His Ala Ile Ile Asp Glu Gln Pro Leu Ile Phe Lys
1 5 10

<210> SEQ ID NO 54
<211> LENGTH: 14
<212> TYPE: PRT
<213> ORGANISM: Homo sapiens

<400> SEQUENCE: 54

Lys Gly Ile Ser Leu Asn Pro Glu Gln Trp Ser Gln Leu Lys
1 5 10

<210> SEQ ID NO 55

<211> LENGTH: 12
<212> TYPE: PRT
<213> ORGANISM: Homo sapiens

<400> SEQUENCE: 55

Gly Ile Asp Pro Phe Ser Leu Asp Ala Leu Ser Lys
1 5 10

<210> SEQ ID NO 56
<211> LENGTH: 14
<212> TYPE: PRT
<213> ORGANISM: Homo sapiens

<400> SEQUENCE: 56

Leu Leu Gln Cys Tyr Pro Pro Pro Glu Asp Ala Ala Val Lys
1 5 10

<210> SEQ ID NO 57
<211> LENGTH: 11
<212> TYPE: PRT
<213> ORGANISM: Homo sapiens

<400> SEQUENCE: 57

Gly Val Pro Thr Gly Phe Ile Leu Pro Ile Arg
1 5 10

<210> SEQ ID NO 58
<211> LENGTH: 8
<212> TYPE: PRT
<213> ORGANISM: Homo sapiens

<400> SEQUENCE: 58

Ile Val Thr Cys Gly Thr Asp Arg
1 5

<210> SEQ ID NO 59
<211> LENGTH: 11
<212> TYPE: PRT
<213> ORGANISM: Homo sapiens

<400> SEQUENCE: 59

Thr Pro Val Pro Ser Asp Ile Asp Ile Ser Arg
1 5 10

<210> SEQ ID NO 60
<211> LENGTH: 7
<212> TYPE: PRT
<213> ORGANISM: Homo sapiens

<400> SEQUENCE: 60

Tyr Gln Glu Ala Leu Ala Lys
1 5

<210> SEQ ID NO 61
<211> LENGTH: 18
<212> TYPE: PRT
<213> ORGANISM: Homo sapiens

<400> SEQUENCE: 61

Val Ala Trp Val Ser His Asp Ser Thr Val Cys Leu Ala Asp Ala Asp
1 5 10 15

Lys Lys

<210> SEQ ID NO 62

<211> LENGTH: 12
<212> TYPE: PRT
<213> ORGANISM: Homo sapiens

<400> SEQUENCE: 62

Leu Asp Ile Asp Pro Glu Thr Ile Thr Trp Gln Arg
1 5 10

<210> SEQ ID NO 63
<211> LENGTH: 21
<212> TYPE: PRT
<213> ORGANISM: Homo sapiens

<400> SEQUENCE: 63

Ile Asp Asn Ser Gln Val Glu Ser Gly Ser Leu Glu Asp Asp Trp Asp
1 5 10 15

Phe Leu Pro Pro Lys
20

<210> SEQ ID NO 64
<211> LENGTH: 9
<212> TYPE: PRT
<213> ORGANISM: Homo sapiens

<400> SEQUENCE: 64

Leu Ala Ile Leu Gln Val Gly Asn Arg
1 5

<210> SEQ ID NO 65
<211> LENGTH: 13
<212> TYPE: PRT
<213> ORGANISM: Homo sapiens

<400> SEQUENCE: 65

Ala Gln Ala Ala Leu Ala Val Asn Ile Ser Ala Ala Arg
1 5 10

<210> SEQ ID NO 66
<211> LENGTH: 11
<212> TYPE: PRT
<213> ORGANISM: Homo sapiens

<400> SEQUENCE: 66

Gly Ala Leu Ala Leu Ala Gln Ala Val Gln Arg
1 5 10

<210> SEQ ID NO 67
<211> LENGTH: 13
<212> TYPE: PRT
<213> ORGANISM: Homo sapiens

<400> SEQUENCE: 67

Thr Asp Pro Thr Thr Leu Thr Asp Glu Glu Ile Asn Arg
1 5 10

<210> SEQ ID NO 68
<211> LENGTH: 8
<212> TYPE: PRT
<213> ORGANISM: Homo sapiens

<400> SEQUENCE: 68

Leu Glu Leu Ser Val Leu Tyr Lys
1 5

<210> SEQ ID NO 69
<211> LENGTH: 12
<212> TYPE: PRT
<213> ORGANISM: Homo sapiens

<400> SEQUENCE: 69

Gly Leu Asp Gly Tyr Gln Gly Pro Asp Gly Pro Arg
1 5 10

<210> SEQ ID NO 70
<211> LENGTH: 14
<212> TYPE: PRT
<213> ORGANISM: Homo sapiens

<400> SEQUENCE: 70

Leu Ser Gly Leu Glu Gln Pro Gln Gly Ala Leu Gln Thr Arg
1 5 10

<210> SEQ ID NO 71
<211> LENGTH: 15
<212> TYPE: PRT
<213> ORGANISM: Homo sapiens

<400> SEQUENCE: 71

Ser Cys Gln Thr Ala Leu Val Glu Ile Leu Asp Val Ile Val Arg
1 5 10 15

<210> SEQ ID NO 72
<211> LENGTH: 9
<212> TYPE: PRT
<213> ORGANISM: Homo sapiens

<400> SEQUENCE: 72

Asp Asp Asn Met Phe Gln Ile Gly Lys
1 5

<210> SEQ ID NO 73
<211> LENGTH: 17
<212> TYPE: PRT
<213> ORGANISM: Homo sapiens

<400> SEQUENCE: 73

Glu His Asn Gly Gln Val Thr Gly Ile Asp Trp Ala Pro Glu Ser Asn
1 5 10 15

Arg

<210> SEQ ID NO 74
<211> LENGTH: 16
<212> TYPE: PRT
<213> ORGANISM: Homo sapiens

<400> SEQUENCE: 74

Lys Ile Lys Asp Pro Asp Ala Ser Lys Pro Glu Asp Trp Asp Glu Arg
1 5 10 15

<210> SEQ ID NO 75
<211> LENGTH: 14
<212> TYPE: PRT
<213> ORGANISM: Homo sapiens

<400> SEQUENCE: 75

Met Phe Gly Ile Pro Val Val Val Ala Val Asn Ala Phe Lys
1 5 10

<210> SEQ ID NO 76
<211> LENGTH: 10
<212> TYPE: PRT
<213> ORGANISM: Homo sapiens

<400> SEQUENCE: 76

Phe Phe Glu His Phe Ile Glu Gly Gly Arg
1 5 10

<210> SEQ ID NO 77
<211> LENGTH: 10
<212> TYPE: PRT
<213> ORGANISM: Homo sapiens

<400> SEQUENCE: 77

Ile Phe His Glu Leu Thr Gln Thr Asp Lys
1 5 10

<210> SEQ ID NO 78
<211> LENGTH: 9
<212> TYPE: PRT
<213> ORGANISM: Homo sapiens

<400> SEQUENCE: 78

Phe Ile Asn Leu Phe Pro Glu Thr Lys
1 5

<210> SEQ ID NO 79
<211> LENGTH: 9
<212> TYPE: PRT
<213> ORGANISM: Homo sapiens

<400> SEQUENCE: 79

Phe Tyr Gly Asp Glu Glu Lys Asp Lys
1 5

<210> SEQ ID NO 80
<211> LENGTH: 25
<212> TYPE: PRT
<213> ORGANISM: Homo sapiens

<400> SEQUENCE: 80

Phe Asn Gly Gly Gly His Ile Asn His Ser Ile Phe Trp Thr Asn Leu
1 5 10 15

Ser Pro Asn Gly Gly Gly Glu Pro Lys
20 25

<210> SEQ ID NO 81
<211> LENGTH: 13
<212> TYPE: PRT
<213> ORGANISM: Homo sapiens

<400> SEQUENCE: 81

Asp Pro Asp Ala Ser Lys Pro Glu Asp Trp Asp Glu Arg
1 5 10

<210> SEQ ID NO 82
<211> LENGTH: 22
<212> TYPE: PRT
<213> ORGANISM: Homo sapiens

<400> SEQUENCE: 82

Leu Gly Ser Pro Asp Tyr Gly Asn Ser Ala Leu Leu Ser Leu Pro Gly
1 5 10 15

Tyr Arg Pro Thr Thr Arg
20

<210> SEQ ID NO 83
<211> LENGTH: 19
<212> TYPE: PRT
<213> ORGANISM: Homo sapiens

<400> SEQUENCE: 83

Ala Ser Gly Asp Ser Ala Arg Pro Val Leu Leu Gln Val Ala Glu Ser
1 5 10 15

Ala Tyr Arg

<210> SEQ ID NO 84
<211> LENGTH: 12
<212> TYPE: PRT
<213> ORGANISM: Homo sapiens

<400> SEQUENCE: 84

Thr Asp Thr Glu Ser Glu Leu Asp Leu Ile Ser Arg
1 5 10

<210> SEQ ID NO 85
<211> LENGTH: 10
<212> TYPE: PRT
<213> ORGANISM: Homo sapiens

<400> SEQUENCE: 85

Leu Asp Phe Val Cys Ser Phe Leu Gln Lys
1 5 10

<210> SEQ ID NO 86
<211> LENGTH: 13
<212> TYPE: PRT
<213> ORGANISM: Homo sapiens

<400> SEQUENCE: 86

Trp Ile Asp Glu Thr Pro Pro Val Asp Gln Pro Ser Arg
1 5 10

<210> SEQ ID NO 87
<211> LENGTH: 19
<212> TYPE: PRT
<213> ORGANISM: Homo sapiens

<400> SEQUENCE: 87

Gly Leu Leu Gly Ala Leu Thr Ser Thr Pro Tyr Ser Pro Thr Gln His
1 5 10 15

Leu Glu Arg

<210> SEQ ID NO 88
<211> LENGTH: 24
<212> TYPE: PRT
<213> ORGANISM: Homo sapiens

<400> SEQUENCE: 88

Lys Pro Glu Asp Trp Asp Glu Glu Met Asp Gly Glu Trp Glu Pro Pro
1 5 10 15

Val Ile Gln Asn Pro Glu Tyr Lys
20

<210> SEQ ID NO 89
<211> LENGTH: 7

<212> TYPE: PRT
<213> ORGANISM: Homo sapiens

<400> SEQUENCE: 89

Phe Ser Asp Ile Gln Ile Arg
1               5

<210> SEQ ID NO 90
<211> LENGTH: 16
<212> TYPE: PRT
<213> ORGANISM: Homo sapiens

<400> SEQUENCE: 90

Ser Thr Ser Phe Asn Val Gln Asp Leu Leu Pro Asp His Glu Tyr Lys
1               5                   10                  15

<210> SEQ ID NO 91
<211> LENGTH: 18
<212> TYPE: PRT
<213> ORGANISM: Homo sapiens

<400> SEQUENCE: 91

Gly Glu Gln Gly Phe Met Gly Asn Thr Gly Pro Thr Gly Ala Val Gly
1               5                   10                  15

Asp Arg

<210> SEQ ID NO 92
<211> LENGTH: 11
<212> TYPE: PRT
<213> ORGANISM: Homo sapiens

<400> SEQUENCE: 92

Gln Pro Ser Gln Gly Pro Thr Phe Gly Ile Lys
1               5                   10

<210> SEQ ID NO 93
<211> LENGTH: 12
<212> TYPE: PRT
<213> ORGANISM: Homo sapiens

<400> SEQUENCE: 93

Thr His Leu Ser Leu Ser His Asn Pro Glu Gln Lys
1               5                   10

<210> SEQ ID NO 94
<211> LENGTH: 23
<212> TYPE: PRT
<213> ORGANISM: Homo sapiens

<400> SEQUENCE: 94

Ala Pro Val Pro Ser Thr Cys Ser Ser Thr Phe Pro Glu Glu Leu Ser
1               5                   10                  15

Pro Pro Ser His Gln Ala Lys
            20

<210> SEQ ID NO 95
<211> LENGTH: 18
<212> TYPE: PRT
<213> ORGANISM: Homo sapiens

<400> SEQUENCE: 95

Gly Glu Gly Gly Thr Thr Asn Pro His Ile Phe Pro Glu Gly Ser Glu
1               5                   10                  15

Pro Lys

<210> SEQ ID NO 96
<211> LENGTH: 17
<212> TYPE: PRT
<213> ORGANISM: Homo sapiens

<400> SEQUENCE: 96

Thr Ala Leu Ala Glu Ala Glu Leu Glu Tyr Asn Pro Glu His Val Ser
1 5 10 15

Arg

<210> SEQ ID NO 97
<211> LENGTH: 9
<212> TYPE: PRT
<213> ORGANISM: Homo sapiens

<400> SEQUENCE: 97

Phe Pro Leu Leu Lys Pro Ser Pro Lys
1 5

<210> SEQ ID NO 98
<211> LENGTH: 10
<212> TYPE: PRT
<213> ORGANISM: Homo sapiens

<400> SEQUENCE: 98

Asp Gln Ala Ala Asn Leu Met Ala Asn Arg
1 5 10

<210> SEQ ID NO 99
<211> LENGTH: 7
<212> TYPE: PRT
<213> ORGANISM: Homo sapiens

<400> SEQUENCE: 99

His Leu Thr Ala Gln Val Arg
1 5

<210> SEQ ID NO 100
<211> LENGTH: 7
<212> TYPE: PRT
<213> ORGANISM: Homo sapiens

<400> SEQUENCE: 100

Phe Val Leu Ser Ser Gly Lys
1 5

<210> SEQ ID NO 101
<211> LENGTH: 16
<212> TYPE: PRT
<213> ORGANISM: Homo sapiens

<400> SEQUENCE: 101

Ser Ser Leu Pro Pro Val Leu Gly Thr Glu Ser Asp Ala Thr Val Lys
1 5 10 15

<210> SEQ ID NO 102
<211> LENGTH: 11
<212> TYPE: PRT
<213> ORGANISM: Homo sapiens

<400> SEQUENCE: 102

Ala Trp Gly Ala Val Val Pro Leu Val Gly Lys 1 5 10

<210> SEQ ID NO 103
<211> LENGTH: 13
<212> TYPE: PRT
<213> ORGANISM: Homo sapiens

<400> SEQUENCE: 103

Ile Glu Gly Tyr Pro Asp Pro Glu Val Val Trp Phe Lys
1 5 10

<210> SEQ ID NO 104
<211> LENGTH: 8
<212> TYPE: PRT
<213> ORGANISM: Homo sapiens

<400> SEQUENCE: 104

Gly Lys Asn Val Leu Ile Asn Lys
1 5

<210> SEQ ID NO 105
<211> LENGTH: 9
<212> TYPE: PRT
<213> ORGANISM: Homo sapiens

<400> SEQUENCE: 105

Gly Leu Gln Thr Ser Gln Asp Ala Arg
1 5

<210> SEQ ID NO 106
<211> LENGTH: 7
<212> TYPE: PRT
<213> ORGANISM: Homo sapiens

<400> SEQUENCE: 106

His Thr Leu Thr Gln Ile Lys
1 5

<210> SEQ ID NO 107
<211> LENGTH: 21
<212> TYPE: PRT
<213> ORGANISM: Homo sapiens

<400> SEQUENCE: 107

Val His Ala Glu Leu Ala Asp Val Leu Thr Glu Ala Val Val Asp Ser
1 5 10 15

Ile Leu Ala Ile Lys
20

<210> SEQ ID NO 108
<211> LENGTH: 23
<212> TYPE: PRT
<213> ORGANISM: Homo sapiens

<400> SEQUENCE: 108

Tyr Val Ile His Thr Val Gly Pro Ile Ala Tyr Gly Glu Pro Ser Ala
1 5 10 15

Ser Gln Ala Ala Glu Leu Arg
20

<210> SEQ ID NO 109
<211> LENGTH: 14
<212> TYPE: PRT
<213> ORGANISM: Homo sapiens

<400> SEQUENCE: 109

Ile Gln Ser Ser His Asn Phe Gln Leu Glu Ser Val Asn Lys
1 5 10

<210> SEQ ID NO 110
<211> LENGTH: 8
<212> TYPE: PRT
<213> ORGANISM: Homo sapiens

<400> SEQUENCE: 110

Gln Ile Asp Asn Pro Asp Tyr Lys
1 5

<210> SEQ ID NO 111
<211> LENGTH: 13
<212> TYPE: PRT
<213> ORGANISM: Homo sapiens

<400> SEQUENCE: 111

Asp Ala Glu Gly Ile Leu Glu Asp Leu Gln Ser Tyr Arg
1 5 10

<210> SEQ ID NO 112
<211> LENGTH: 12
<212> TYPE: PRT
<213> ORGANISM: Homo sapiens

<400> SEQUENCE: 112

Tyr Thr Ala Glu Ser Ser Asp Thr Leu Cys Pro Arg
1 5 10

<210> SEQ ID NO 113
<211> LENGTH: 19
<212> TYPE: PRT
<213> ORGANISM: Homo sapiens

<400> SEQUENCE: 113

Glu Glu Ser Arg Glu Pro Ala Pro Ala Ser Pro Ala Pro Ala Gly Val
1 5 10 15

Glu Ile Arg

<210> SEQ ID NO 114
<211> LENGTH: 12
<212> TYPE: PRT
<213> ORGANISM: Homo sapiens

<400> SEQUENCE: 114

Glu Met Asp Arg Glu Thr Leu Ile Asp Val Ala Arg
1 5 10

<210> SEQ ID NO 115
<211> LENGTH: 15
<212> TYPE: PRT
<213> ORGANISM: Homo sapiens

<400> SEQUENCE: 115

Asn Glu Val Ser Phe Val Ile His Asn Leu Pro Val Leu Ala Lys
1 5 10 15

<210> SEQ ID NO 116
<211> LENGTH: 10
<212> TYPE: PRT
<213> ORGANISM: Homo sapiens

<400> SEQUENCE: 116

Gln Val Ala Pro Glu Lys Pro Val Lys Lys
1 5 10

<210> SEQ ID NO 117
<211> LENGTH: 11
<212> TYPE: PRT
<213> ORGANISM: Homo sapiens

<400> SEQUENCE: 117

Phe Leu Ile Asn Leu Glu Gly Gly Asp Ile Arg
1 5 10

<210> SEQ ID NO 118
<211> LENGTH: 13
<212> TYPE: PRT
<213> ORGANISM: Homo sapiens

<400> SEQUENCE: 118

Leu Ser Val Asn Ser Val Thr Ala Gly Asp Tyr Ser Arg
1 5 10

<210> SEQ ID NO 119
<211> LENGTH: 25
<212> TYPE: PRT
<213> ORGANISM: Homo sapiens

<400> SEQUENCE: 119

Gln Ala Gln Val Asn Leu Thr Val Val Asp Lys Pro Asp Pro Pro Ala
1 5 10 15

Gly Thr Pro Cys Ala Ser Asp Ile Arg
20 25

<210> SEQ ID NO 120
<211> LENGTH: 15
<212> TYPE: PRT
<213> ORGANISM: Homo sapiens

<400> SEQUENCE: 120

Ile Phe Asp Asp Val Ser Ser Gly Val Ser Gln Leu Ala Ser Lys
1 5 10 15

<210> SEQ ID NO 121
<211> LENGTH: 12
<212> TYPE: PRT
<213> ORGANISM: Homo sapiens

<400> SEQUENCE: 121

Pro Asp Ala Ser Lys Pro Glu Asp Trp Asp Glu Arg
1 5 10

<210> SEQ ID NO 122
<211> LENGTH: 11
<212> TYPE: PRT
<213> ORGANISM: Homo sapiens

<400> SEQUENCE: 122

Tyr Gly Gly Ala Pro Gln Ala Leu Thr Leu Lys
1 5 10

<210> SEQ ID NO 123
<211> LENGTH: 17
<212> TYPE: PRT

<213> ORGANISM: Homo sapiens

<400> SEQUENCE: 123

Leu Val Thr Pro Gly Glu Thr Pro Ser Trp Thr Gly Ser Gly Phe Val
1 5 10 15

Arg

<210> SEQ ID NO 124
<211> LENGTH: 11
<212> TYPE: PRT
<213> ORGANISM: Homo sapiens

<400> SEQUENCE: 124

Glu Gln Ile Ser Asp Ile Asp Asp Ala Val Arg
1 5 10

<210> SEQ ID NO 125
<211> LENGTH: 34
<212> TYPE: PRT
<213> ORGANISM: Homo sapiens

<400> SEQUENCE: 125

Lys Pro Ala Ala Gly Leu Ser Ala Ala Pro Val Pro Thr Ala Pro Ala
1 5 10 15

Ala Gly Ala Pro Leu Met Asp Phe Gly Asn Asp Phe Val Pro Pro Ala
20 25 30

Pro Arg

<210> SEQ ID NO 126
<211> LENGTH: 10
<212> TYPE: PRT
<213> ORGANISM: Homo sapiens

<400> SEQUENCE: 126

Ala Thr Ser Ser Thr Gln Ser Leu Ala Arg
1 5 10

<210> SEQ ID NO 127
<211> LENGTH: 14
<212> TYPE: PRT
<213> ORGANISM: Homo sapiens

<400> SEQUENCE: 127

Leu Leu Val Pro Thr Gln Phe Val Gly Ala Ile Ile Gly Lys
1 5 10

<210> SEQ ID NO 128
<211> LENGTH: 8
<212> TYPE: PRT
<213> ORGANISM: Homo sapiens

<400> SEQUENCE: 128

Gly Glu Leu Leu Glu Ala Ile Lys
1 5

<210> SEQ ID NO 129
<211> LENGTH: 15
<212> TYPE: PRT
<213> ORGANISM: Homo sapiens

<400> SEQUENCE: 129

Phe Phe Gln Pro Thr Glu Met Ala Ala Gln Asp Phe Phe Gln Arg
1 5 10 15

<210> SEQ ID NO 130
<211> LENGTH: 14
<212> TYPE: PRT
<213> ORGANISM: Homo sapiens

<400> SEQUENCE: 130

Gly Ser Gly Ser Arg Pro Gly Ile Glu Gly Asp Thr Pro Arg
1 5 10

<210> SEQ ID NO 131
<211> LENGTH: 25
<212> TYPE: PRT
<213> ORGANISM: Homo sapiens

<400> SEQUENCE: 131

Asn Ala Ile Asp Asp Gly Cys Val Val Pro Gly Ala Gly Ala Val Glu
1 5 10 15

Val Ala Met Ala Glu Ala Leu Ile Lys
20 25

<210> SEQ ID NO 132
<211> LENGTH: 35
<212> TYPE: PRT
<213> ORGANISM: Homo sapiens

<400> SEQUENCE: 132

Ala Ala Ala Ala Ala Ala Val Gly Pro Gly Ala Gly Gly Ala Gly Ser
1 5 10 15

Ala Val Pro Gly Gly Ala Gly Pro Cys Ala Thr Val Ser Val Phe Pro
20 25 30

Gly Ala Arg
35

<210> SEQ ID NO 133
<211> LENGTH: 11
<212> TYPE: PRT
<213> ORGANISM: Homo sapiens

<400> SEQUENCE: 133

Asp Phe Leu Thr Pro Pro Leu Leu Ser Val Arg
1 5 10

<210> SEQ ID NO 134
<211> LENGTH: 12
<212> TYPE: PRT
<213> ORGANISM: Homo sapiens

<400> SEQUENCE: 134

Leu Phe Val Val Pro Ala Asp Glu Ala Gln Ala Arg
1 5 10

<210> SEQ ID NO 135
<211> LENGTH: 11
<212> TYPE: PRT
<213> ORGANISM: Homo sapiens

<400> SEQUENCE: 135

Trp Met Ile Gln Tyr Asn Asn Leu Asn Leu Lys
1 5 10

<210> SEQ ID NO 136
<211> LENGTH: 13

<212> TYPE: PRT
<213> ORGANISM: Homo sapiens

<400> SEQUENCE: 136

Ser Leu Pro Ile Ser Leu Val Phe Leu Val Pro Val Arg
1 5 10

<210> SEQ ID NO 137
<211> LENGTH: 9
<212> TYPE: PRT
<213> ORGANISM: Homo sapiens

<400> SEQUENCE: 137

Ala Leu Gln Val Gly Cys Leu Leu Arg
1 5

<210> SEQ ID NO 138
<211> LENGTH: 12
<212> TYPE: PRT
<213> ORGANISM: Homo sapiens

<400> SEQUENCE: 138

Glu Ser Phe Asn Pro Glu Ser Tyr Glu Leu Asp Lys
1 5 10

<210> SEQ ID NO 139
<211> LENGTH: 11
<212> TYPE: PRT
<213> ORGANISM: Homo sapiens

<400> SEQUENCE: 139

Thr Gly Trp Ile Ser Thr Ser Ser Ile Trp Lys
1 5 10

<210> SEQ ID NO 140
<211> LENGTH: 12
<212> TYPE: PRT
<213> ORGANISM: Homo sapiens

<400> SEQUENCE: 140

Glu Tyr Ala Glu Asp Asp Asn Ile Tyr Gln Gln Lys
1 5 10

<210> SEQ ID NO 141
<211> LENGTH: 17
<212> TYPE: PRT
<213> ORGANISM: Homo sapiens

<400> SEQUENCE: 141

Thr Gln Ile Ala Ile Cys Pro Asn Asn His Glu Val His Ile Tyr Glu
1 5 10 15

Lys

<210> SEQ ID NO 142
<211> LENGTH: 14
<212> TYPE: PRT
<213> ORGANISM: Homo sapiens

<400> SEQUENCE: 142

Ser Leu Glu Ala Gln Val Ala His Ala Asp Gln Gln Leu Arg
1 5 10

<210> SEQ ID NO 143
<211> LENGTH: 7

<212> TYPE: PRT
<213> ORGANISM: Homo sapiens

<400> SEQUENCE: 143

Ser Val Thr Leu Leu Ile Lys
1 5

<210> SEQ ID NO 144
<211> LENGTH: 17
<212> TYPE: PRT
<213> ORGANISM: Homo sapiens

<400> SEQUENCE: 144

Ile His Phe Val Pro Gly Trp Asp Cys His Gly Leu Pro Ile Glu Ile
1 5 10 15

Lys

<210> SEQ ID NO 145
<211> LENGTH: 12
<212> TYPE: PRT
<213> ORGANISM: Homo sapiens

<400> SEQUENCE: 145

Gln Gln Pro Asp Thr Glu Leu Glu Ile Gln Gln Lys
1 5 10

<210> SEQ ID NO 146
<211> LENGTH: 21
<212> TYPE: PRT
<213> ORGANISM: Homo sapiens

<400> SEQUENCE: 146

Lys Gly Glu Pro Val Ser Ala Glu Asp Leu Gly Val Ser Gly Ala Leu
1 5 10 15

Thr Val Leu Met Lys
20

<210> SEQ ID NO 147
<211> LENGTH: 13
<212> TYPE: PRT
<213> ORGANISM: Homo sapiens

<400> SEQUENCE: 147

Leu Gly Ile Gly Met Asp Thr Cys Val Ile Pro Leu Arg
1 5 10

<210> SEQ ID NO 148
<211> LENGTH: 28
<212> TYPE: PRT
<213> ORGANISM: Homo sapiens

<400> SEQUENCE: 148

Gln Pro Ser Trp Asp Pro Ser Pro Val Ser Ser Thr Val Pro Ala Pro
1 5 10 15

Ser Pro Leu Ser Ala Ala Ala Val Ser Pro Ser Lys
20 25

<210> SEQ ID NO 149
<211> LENGTH: 11
<212> TYPE: PRT
<213> ORGANISM: Homo sapiens

<400> SEQUENCE: 149

Gln Ile Ser Glu Gly Val Glu Tyr Ile His Lys
1 5 10

<210> SEQ ID NO 150
<211> LENGTH: 16
<212> TYPE: PRT
<213> ORGANISM: Homo sapiens

<400> SEQUENCE: 150

Ser Glu Gly Gly Thr Ala Ala Gly Ala Gly Leu Asp Ser Leu His Lys
1 5 10 15

<210> SEQ ID NO 151
<211> LENGTH: 9
<212> TYPE: PRT
<213> ORGANISM: Homo sapiens

<400> SEQUENCE: 151

Pro Thr Gly Phe Ile Leu Pro Ile Arg
1 5

<210> SEQ ID NO 152
<211> LENGTH: 13
<212> TYPE: PRT
<213> ORGANISM: Homo sapiens

<400> SEQUENCE: 152

Ser Gln Ala Gly Val Ser Ser Gly Ala Pro Pro Gly Arg
1 5 10

<210> SEQ ID NO 153
<211> LENGTH: 15
<212> TYPE: PRT
<213> ORGANISM: Homo sapiens

<400> SEQUENCE: 153

Val Cys Gly Asp Ser Asp Lys Gly Phe Val Val Ile Asn Gln Lys
1 5 10 15

<210> SEQ ID NO 154
<211> LENGTH: 11
<212> TYPE: PRT
<213> ORGANISM: Homo sapiens

<400> SEQUENCE: 154

Leu Gly Ile Val Gln Gly Ile Val Gly Ala Arg
1 5 10

<210> SEQ ID NO 155
<211> LENGTH: 8
<212> TYPE: PRT
<213> ORGANISM: Homo sapiens

<400> SEQUENCE: 155

Phe Leu Ser Leu Pro Glu Val Arg
1 5

<210> SEQ ID NO 156
<211> LENGTH: 9
<212> TYPE: PRT
<213> ORGANISM: Homo sapiens

<400> SEQUENCE: 156

Gly Leu Val Leu Asp His Gly Ala Arg
1 5

<210> SEQ ID NO 157
<211> LENGTH: 9
<212> TYPE: PRT
<213> ORGANISM: Homo sapiens

<400> SEQUENCE: 157

Leu Lys Asn Gln Val Thr Gln Leu Lys
1               5

<210> SEQ ID NO 158
<211> LENGTH: 27
<212> TYPE: PRT
<213> ORGANISM: Homo sapiens

<400> SEQUENCE: 158

Thr Ser Val Gln Phe Gln Asn Phe Ser Pro Thr Val Val His Pro Gly
1               5                   10                  15

Asp Leu Gln Thr Gln Leu Ala Val Gln Thr Lys
            20                  25

<210> SEQ ID NO 159
<211> LENGTH: 10
<212> TYPE: PRT
<213> ORGANISM: Homo sapiens

<400> SEQUENCE: 159

Glu Pro Pro Tyr Gly Ala Asp Val Leu Arg
1               5                   10

<210> SEQ ID NO 160
<211> LENGTH: 11
<212> TYPE: PRT
<213> ORGANISM: Homo sapiens

<400> SEQUENCE: 160

Ala Ala Gly Pro Leu Leu Thr Asp Glu Cys Arg
1               5                   10

<210> SEQ ID NO 161
<211> LENGTH: 21
<212> TYPE: PRT
<213> ORGANISM: Homo sapiens

<400> SEQUENCE: 161

Ile Ile Glu Val Ala Pro Gln Val Ala Thr Gln Asn Val Asn Pro Thr
1               5                   10                  15

Pro Gly Ala Thr Ser
            20

<210> SEQ ID NO 162
<211> LENGTH: 11
<212> TYPE: PRT
<213> ORGANISM: Homo sapiens

<400> SEQUENCE: 162

Leu Phe Ser Gln Gly Gln Asp Val Ser Asn Lys
1               5                   10

<210> SEQ ID NO 163
<211> LENGTH: 15
<212> TYPE: PRT
<213> ORGANISM: Homo sapiens

<400> SEQUENCE: 163

Val Ser Gly Pro Trp Glu Glu Ala Asp Ala Glu Ala Val Ala Arg
1 5 10 15

<210> SEQ ID NO 164
<211> LENGTH: 13
<212> TYPE: PRT
<213> ORGANISM: Homo sapiens

<400> SEQUENCE: 164

Val Thr Gly Thr Gln Pro Ile Thr Cys Thr Trp Met Lys
1 5 10

<210> SEQ ID NO 165
<211> LENGTH: 6
<212> TYPE: PRT
<213> ORGANISM: Homo sapiens

<400> SEQUENCE: 165

Val Leu Ile Asp Ile Arg
1 5

<210> SEQ ID NO 166
<211> LENGTH: 12
<212> TYPE: PRT
<213> ORGANISM: Homo sapiens

<400> SEQUENCE: 166

Ala Val Leu Glu Glu Gly Thr Asp Val Val Ile Lys
1 5 10

<210> SEQ ID NO 167
<211> LENGTH: 11
<212> TYPE: PRT
<213> ORGANISM: Homo sapiens

<400> SEQUENCE: 167

Gln Phe Ala Glu Ile Leu His Phe Thr Leu Arg
1 5 10

<210> SEQ ID NO 168
<211> LENGTH: 23
<212> TYPE: PRT
<213> ORGANISM: Homo sapiens

<400> SEQUENCE: 168

Ile Val Gly Ala Pro Met His Asp Leu Leu Leu Trp Asn Asn Ala Thr
1 5 10 15

Val Thr Thr Cys His Ser Lys
20

<210> SEQ ID NO 169
<211> LENGTH: 12
<212> TYPE: PRT
<213> ORGANISM: Homo sapiens

<400> SEQUENCE: 169

Ala Tyr Ile Gln Glu Asn Leu Glu Leu Val Glu Lys
1 5 10

<210> SEQ ID NO 170
<211> LENGTH: 16
<212> TYPE: PRT
<213> ORGANISM: Homo sapiens

<400> SEQUENCE: 170

Glu Ile Gly Leu Leu Ser Glu Glu Val Glu Leu Tyr Gly Glu Thr Lys
1 5 10 15

<210> SEQ ID NO 171
<211> LENGTH: 10
<212> TYPE: PRT
<213> ORGANISM: Homo sapiens

<400> SEQUENCE: 171

Asp Ser Phe Leu Gly Ser Ile Pro Gly Lys
1 5 10

<210> SEQ ID NO 172
<211> LENGTH: 10
<212> TYPE: PRT
<213> ORGANISM: Homo sapiens

<400> SEQUENCE: 172

Gln Leu Asp Ala Leu Leu Glu Ala Leu Lys
1 5 10

<210> SEQ ID NO 173
<211> LENGTH: 11
<212> TYPE: PRT
<213> ORGANISM: Homo sapiens

<400> SEQUENCE: 173

Ile Ile Asp Glu Asp Phe Glu Leu Thr Glu Arg
1 5 10

<210> SEQ ID NO 174
<211> LENGTH: 9
<212> TYPE: PRT
<213> ORGANISM: Homo sapiens

<400> SEQUENCE: 174

Asp Thr Ile Asn Leu Leu Asp Gln Arg
1 5

<210> SEQ ID NO 175
<211> LENGTH: 10
<212> TYPE: PRT
<213> ORGANISM: Homo sapiens

<400> SEQUENCE: 175

Val Val Gln Ser Leu Glu Gln Thr Ala Arg
1 5 10

<210> SEQ ID NO 176
<211> LENGTH: 10
<212> TYPE: PRT
<213> ORGANISM: Homo sapiens

<400> SEQUENCE: 176

Asp Asp Ser Asn Leu Tyr Ile Asn Val Lys
1 5 10

<210> SEQ ID NO 177
<211> LENGTH: 14
<212> TYPE: PRT
<213> ORGANISM: Homo sapiens

<400> SEQUENCE: 177

Val Ser Gly Gln Pro Gln Ser Val Thr Ala Ser Ser Asp Lys
1 5 10

<210> SEQ ID NO 178
<211> LENGTH: 12
<212> TYPE: PRT
<213> ORGANISM: Homo sapiens

<400> SEQUENCE: 178

Glu Phe Cys Gln Gln Glu Val Glu Pro Met Cys Lys
1 5 10

<210> SEQ ID NO 179
<211> LENGTH: 20
<212> TYPE: PRT
<213> ORGANISM: Homo sapiens

<400> SEQUENCE: 179

Ala Gly Asn Ser Leu Ala Ala Ser Thr Ala Glu Glu Thr Ala Gly Ser
1 5 10 15

Ala Gln Gly Arg
20

<210> SEQ ID NO 180
<211> LENGTH: 14
<212> TYPE: PRT
<213> ORGANISM: Homo sapiens

<400> SEQUENCE: 180

Glu Tyr Trp Met Asp Pro Glu Gly Glu Met Lys Pro Gly Arg
1 5 10

<210> SEQ ID NO 181
<211> LENGTH: 10
<212> TYPE: PRT
<213> ORGANISM: Homo sapiens

<400> SEQUENCE: 181

Leu Gln Ser Gln Leu Leu Ser Ile Glu Lys
1 5 10

<210> SEQ ID NO 182
<211> LENGTH: 10
<212> TYPE: PRT
<213> ORGANISM: Homo sapiens

<400> SEQUENCE: 182

Ala Gly Glu Ser Val Glu Leu Phe Gly Lys
1 5 10

<210> SEQ ID NO 183
<211> LENGTH: 14
<212> TYPE: PRT
<213> ORGANISM: Homo sapiens

<400> SEQUENCE: 183

Asn Gly Glu Phe Phe Met Ser Pro Asn Asp Phe Val Thr Arg
1 5 10

<210> SEQ ID NO 184
<211> LENGTH: 15
<212> TYPE: PRT
<213> ORGANISM: Homo sapiens

<400> SEQUENCE: 184

Val Val Val Gly Ala Pro Gln Glu Ile Val Ala Ala Asn Gln Arg
1 5 10 15

<210> SEQ ID NO 185
<211> LENGTH: 22
<212> TYPE: PRT
<213> ORGANISM: Homo sapiens

<400> SEQUENCE: 185

Ser Gln Ala Pro Leu Glu Ser Ser Leu Asp Ser Leu Gly Asp Val Phe
1 5 10 15

Leu Asp Ser Gly Arg Lys
20

<210> SEQ ID NO 186
<211> LENGTH: 7
<212> TYPE: PRT
<213> ORGANISM: Homo sapiens

<400> SEQUENCE: 186

Gly Cys Leu Glu Leu Ile Lys
1 5

<210> SEQ ID NO 187
<211> LENGTH: 16
<212> TYPE: PRT
<213> ORGANISM: Homo sapiens

<400> SEQUENCE: 187

His Ser Gln Thr Asp Gln Glu Pro Met Cys Pro Val Gly Met Asn Lys
1 5 10 15

<210> SEQ ID NO 188
<211> LENGTH: 9
<212> TYPE: PRT
<213> ORGANISM: Homo sapiens

<400> SEQUENCE: 188

Asn Pro Gln Val Cys Gly Pro Gly Arg
1 5

<210> SEQ ID NO 189
<211> LENGTH: 16
<212> TYPE: PRT
<213> ORGANISM: Homo sapiens

<400> SEQUENCE: 189

Ser Arg Gly Pro Gly Ala Pro Cys Gln Asp Val Asp Glu Cys Ala Arg
1 5 10 15

<210> SEQ ID NO 190
<211> LENGTH: 17
<212> TYPE: PRT
<213> ORGANISM: Homo sapiens

<400> SEQUENCE: 190

Thr Lys Asp Glu Tyr Leu Ile Asn Ser Gln Thr Thr Glu His Ile Val
1 5 10 15

Lys

<210> SEQ ID NO 191
<211> LENGTH: 19

<212> TYPE: PRT
<213> ORGANISM: Homo sapiens

<400> SEQUENCE: 191

Ile Ala Thr Thr Thr Ala Ser Ala Ala Thr Ala Ala Ala Ile Gly Ala
1               5                   10                  15

Thr Pro Arg

<210> SEQ ID NO 192
<211> LENGTH: 11
<212> TYPE: PRT
<213> ORGANISM: Homo sapiens

<400> SEQUENCE: 192

Leu Gly His Glu Leu Gln Gln Ala Gly Leu Lys
1               5                   10

<210> SEQ ID NO 193
<211> LENGTH: 12
<212> TYPE: PRT
<213> ORGANISM: Homo sapiens

<400> SEQUENCE: 193

Thr Glu Val Pro Pro Leu Leu Leu Ile Leu Asp Arg
1               5                   10

<210> SEQ ID NO 194
<211> LENGTH: 8
<212> TYPE: PRT
<213> ORGANISM: Homo sapiens

<400> SEQUENCE: 194

Tyr Gly Asp Glu Glu Lys Asp Lys
1               5

<210> SEQ ID NO 195
<211> LENGTH: 11
<212> TYPE: PRT
<213> ORGANISM: Homo sapiens

<400> SEQUENCE: 195

Ser Glu Ser Gln Gly Thr Ala Pro Ala Phe Lys
1               5                   10

<210> SEQ ID NO 196
<211> LENGTH: 19
<212> TYPE: PRT
<213> ORGANISM: Homo sapiens

<400> SEQUENCE: 196

Leu Pro Gln Glu Pro Gly Arg Glu Gln Val Val Glu Asp Arg Pro Val
1               5                   10                  15

Gly Gly Arg

<210> SEQ ID NO 197
<211> LENGTH: 20
<212> TYPE: PRT
<213> ORGANISM: Homo sapiens

<400> SEQUENCE: 197

Leu Pro Tyr Gly Gly Gln Cys Arg Pro Cys Pro Cys Pro Glu Gly Pro
1               5                   10                  15

Gly Ser Gln Arg

20

<210> SEQ ID NO 198
<211> LENGTH: 15
<212> TYPE: PRT
<213> ORGANISM: Homo sapiens

<400> SEQUENCE: 198

Val Tyr Leu Leu Tyr Arg Pro Gly His Tyr Asp Ile Leu Tyr Lys
1 5 10 15

<210> SEQ ID NO 199
<211> LENGTH: 9
<212> TYPE: PRT
<213> ORGANISM: Homo sapiens

<400> SEQUENCE: 199

Phe Gln Val Ala Thr Asp Ala Leu Lys
1 5

<210> SEQ ID NO 200
<211> LENGTH: 16
<212> TYPE: PRT
<213> ORGANISM: Homo sapiens

<400> SEQUENCE: 200

Leu Gln Glu Gly Gln Thr Leu Glu Phe Leu Val Ala Ser Val Pro Lys
1 5 10 15

<210> SEQ ID NO 201
<211> LENGTH: 16
<212> TYPE: PRT
<213> ORGANISM: Homo sapiens

<400> SEQUENCE: 201

Leu Gln Gly Ala Val Cys Gly Val Ser Ser Gly Pro Pro Pro Pro Arg
1 5 10 15

<210> SEQ ID NO 202
<211> LENGTH: 12
<212> TYPE: PRT
<213> ORGANISM: Homo sapiens

<400> SEQUENCE: 202

Ile Gln Asn Val Val Thr Ser Phe Ala Pro Gln Arg
1 5 10

<210> SEQ ID NO 203
<211> LENGTH: 8
<212> TYPE: PRT
<213> ORGANISM: Homo sapiens

<400> SEQUENCE: 203

Val Ser Thr Leu Gln Asn Gln Arg
1 5

<210> SEQ ID NO 204
<211> LENGTH: 19
<212> TYPE: PRT
<213> ORGANISM: Homo sapiens

<400> SEQUENCE: 204

Leu Ser Gln Leu Glu Glu His Leu Ser Gln Leu Gln Asp Asn Pro Pro
1 5 10 15

Gln Glu Lys

<210> SEQ ID NO 205
<211> LENGTH: 21
<212> TYPE: PRT
<213> ORGANISM: Homo sapiens

<400> SEQUENCE: 205

Ser Gln Ala Pro Leu Glu Ser Ser Leu Asp Ser Leu Gly Asp Val Phe
1 5 10 15

Leu Asp Ser Gly Arg
20

<210> SEQ ID NO 206
<211> LENGTH: 15
<212> TYPE: PRT
<213> ORGANISM: Homo sapiens

<400> SEQUENCE: 206

Ala Gly Pro Asp Leu Ala Ser Cys Leu Asp Val Asp Glu Cys Arg
1 5 10 15

<210> SEQ ID NO 207
<211> LENGTH: 9
<212> TYPE: PRT
<213> ORGANISM: Homo sapiens

<400> SEQUENCE: 207

Gly Thr Cys His Tyr Tyr Ala Asn Lys
1 5

<210> SEQ ID NO 208
<211> LENGTH: 11
<212> TYPE: PRT
<213> ORGANISM: Homo sapiens

<400> SEQUENCE: 208

His Lys Ser Glu Thr Asp Thr Ser Leu Ile Arg
1 5 10

<210> SEQ ID NO 209
<211> LENGTH: 12
<212> TYPE: PRT
<213> ORGANISM: Homo sapiens

<400> SEQUENCE: 209

Lys Gln Gln Asn Gln Glu Leu Gln Glu Gln Leu Arg
1 5 10

<210> SEQ ID NO 210
<211> LENGTH: 11
<212> TYPE: PRT
<213> ORGANISM: Homo sapiens

<400> SEQUENCE: 210

Ser Gly Asp Leu Tyr Val Leu Ala Ala Asp Lys
1 5 10

<210> SEQ ID NO 211
<211> LENGTH: 15
<212> TYPE: PRT
<213> ORGANISM: Homo sapiens

<400> SEQUENCE: 211

Ala Phe Gly Phe Ser His Leu Glu Ala Leu Leu Asp Asp Ser Lys
1 5 10 15

<210> SEQ ID NO 212
<211> LENGTH: 20
<212> TYPE: PRT
<213> ORGANISM: Homo sapiens

<400> SEQUENCE: 212

Glu Ile Leu Thr Leu Leu Gln Gly Val His Gln Gly Ala Gly Phe Gln
1 5 10 15

Asp Ile Pro Lys
20

<210> SEQ ID NO 213
<211> LENGTH: 20
<212> TYPE: PRT
<213> ORGANISM: Homo sapiens

<400> SEQUENCE: 213

Ile Gln Gln Cys Pro Gly Thr Glu Thr Ala Glu Tyr Gln Ser Leu Cys
1 5 10 15

Pro His Gly Arg
20

<210> SEQ ID NO 214
<211> LENGTH: 14
<212> TYPE: PRT
<213> ORGANISM: Homo sapiens

<400> SEQUENCE: 214

Lys Asp Pro Asp Ala Ser Lys Pro Glu Asp Trp Asp Glu Arg
1 5 10

<210> SEQ ID NO 215
<211> LENGTH: 26
<212> TYPE: PRT
<213> ORGANISM: Homo sapiens

<400> SEQUENCE: 215

Ser Tyr Trp Leu Ser Thr Thr Ala Pro Leu Pro Met Met Pro Val Ala
1 5 10 15

Glu Asp Glu Ile Lys Pro Tyr Ile Ser Arg
20 25

<210> SEQ ID NO 216
<211> LENGTH: 8
<212> TYPE: PRT
<213> ORGANISM: Homo sapiens

<400> SEQUENCE: 216

Val Pro Gln Asp Val Leu Gln Lys
1 5

<210> SEQ ID NO 217
<211> LENGTH: 9
<212> TYPE: PRT
<213> ORGANISM: Homo sapiens

<400> SEQUENCE: 217

Asp Phe Gly Ser Phe Asp Lys Phe Lys
1 5

<210> SEQ ID NO 218
<211> LENGTH: 17
<212> TYPE: PRT
<213> ORGANISM: Homo sapiens

<400> SEQUENCE: 218

Phe Ile Ile Leu Ser Gln Glu Gly Ser Leu Cys Ser Val Ser Ile Glu
1 5 10 15

Lys

<210> SEQ ID NO 219
<211> LENGTH: 12
<212> TYPE: PRT
<213> ORGANISM: Homo sapiens

<400> SEQUENCE: 219

Leu Ala Val Ala Thr Phe Ala Gly Ile Glu Asn Lys
1 5 10

<210> SEQ ID NO 220
<211> LENGTH: 9
<212> TYPE: PRT
<213> ORGANISM: Homo sapiens

<400> SEQUENCE: 220

Arg Leu Glu Asn Ala Gly Ser Leu Lys
1 5

<210> SEQ ID NO 221
<211> LENGTH: 15
<212> TYPE: PRT
<213> ORGANISM: Homo sapiens

<400> SEQUENCE: 221

Ala Ala Met Pro Pro Gln Ile Ile Gln Phe Pro Glu Asp Gln Lys
1 5 10 15

<210> SEQ ID NO 222
<211> LENGTH: 11
<212> TYPE: PRT
<213> ORGANISM: Homo sapiens

<400> SEQUENCE: 222

Glu Ala Gln Asn Leu Ser Ala Met Glu Ile Arg
1 5 10

<210> SEQ ID NO 223
<211> LENGTH: 12
<212> TYPE: PRT
<213> ORGANISM: Homo sapiens

<400> SEQUENCE: 223

Ile Leu Val Ala Gly Asp Ser Met Asp Ser Val Lys
1 5 10

<210> SEQ ID NO 224
<211> LENGTH: 10
<212> TYPE: PRT
<213> ORGANISM: Homo sapiens

<400> SEQUENCE: 224

Leu Val His Ser Tyr Pro Tyr Asp Trp Arg
1 5 10

<210> SEQ ID NO 225
<211> LENGTH: 15
<212> TYPE: PRT
<213> ORGANISM: Homo sapiens

<400> SEQUENCE: 225

Ala Glu Ala Gly Asp Ala Ala Leu Ser Val Ala Glu Trp Leu Arg
1 5 10 15

<210> SEQ ID NO 226
<211> LENGTH: 11
<212> TYPE: PRT
<213> ORGANISM: Homo sapiens

<400> SEQUENCE: 226

Glu Leu Ser Asn Phe Tyr Phe Ser Ile Ile Lys
1 5 10

<210> SEQ ID NO 227
<211> LENGTH: 16
<212> TYPE: PRT
<213> ORGANISM: Homo sapiens

<400> SEQUENCE: 227

Ala Glu Ala Ala Ala Pro Tyr Thr Val Leu Ala Gln Ser Ala Pro Arg
1 5 10 15

<210> SEQ ID NO 228
<211> LENGTH: 14
<212> TYPE: PRT
<213> ORGANISM: Homo sapiens

<400> SEQUENCE: 228

Gly Pro Gly Ala Pro Cys Gln Asp Val Asp Glu Cys Ala Arg
1 5 10

<210> SEQ ID NO 229
<211> LENGTH: 10
<212> TYPE: PRT
<213> ORGANISM: Homo sapiens

<400> SEQUENCE: 229

Val Ser Asp Phe Tyr Asp Ile Glu Glu Arg
1 5 10

<210> SEQ ID NO 230
<211> LENGTH: 14
<212> TYPE: PRT
<213> ORGANISM: Homo sapiens

<400> SEQUENCE: 230

Asn Asn Asp Phe Tyr Val Thr Gly Glu Ser Tyr Ala Gly Lys
1 5 10

<210> SEQ ID NO 231
<211> LENGTH: 10
<212> TYPE: PRT
<213> ORGANISM: Homo sapiens

<400> SEQUENCE: 231

Gln Pro Val Val Asp Thr Phe Asp Ile Arg
1 5 10

<210> SEQ ID NO 232
<211> LENGTH: 12

<212> TYPE: PRT
<213> ORGANISM: Homo sapiens

<400> SEQUENCE: 232

Gln Gln Leu Gln Ala Leu Ser Glu Pro Gln Pro Arg
1 5 10

<210> SEQ ID NO 233
<211> LENGTH: 16
<212> TYPE: PRT
<213> ORGANISM: Homo sapiens

<400> SEQUENCE: 233

Ala Pro Ala Glu Ile Leu Asn Gly Lys Glu Ile Ser Ala Gln Ile Arg
1 5 10 15

<210> SEQ ID NO 234
<211> LENGTH: 18
<212> TYPE: PRT
<213> ORGANISM: Homo sapiens

<400> SEQUENCE: 234

Lys Leu Asp Val Glu Glu Pro Asp Ser Ala Asn Ser Ser Phe Tyr Ser
1 5 10 15

Thr Arg

<210> SEQ ID NO 235
<211> LENGTH: 21
<212> TYPE: PRT
<213> ORGANISM: Homo sapiens

<400> SEQUENCE: 235

Gln Pro Pro Pro Asp Ser Ser Glu Glu Ala Pro Pro Ala Thr Gln Asn
1 5 10 15

Phe Ile Ile Pro Lys
20

<210> SEQ ID NO 236
<211> LENGTH: 11
<212> TYPE: PRT
<213> ORGANISM: Homo sapiens

<400> SEQUENCE: 236

Ser Leu Ala Asp Val Asp Ala Ile Leu Ala Arg
1 5 10

<210> SEQ ID NO 237
<211> LENGTH: 26
<212> TYPE: PRT
<213> ORGANISM: Homo sapiens

<400> SEQUENCE: 237

Thr Gly Gly Ser Ala Gln Pro Glu Thr Pro Tyr Ser Gly Pro Gly Leu
1 5 10 15

Leu Ile Asp Ser Leu Val Leu Leu Pro Arg
20 25

<210> SEQ ID NO 238
<211> LENGTH: 15
<212> TYPE: PRT
<213> ORGANISM: Homo sapiens

<400> SEQUENCE: 238

Cys Asp Leu Cys Gln Glu Val Leu Ala Asp Ile Gly Phe Val Lys
1 5 10 15

<210> SEQ ID NO 239
<211> LENGTH: 10
<212> TYPE: PRT
<213> ORGANISM: Homo sapiens

<400> SEQUENCE: 239

Phe Ile Ala Gly Thr Gly Cys Leu Val Arg
1 5 10

<210> SEQ ID NO 240
<211> LENGTH: 22
<212> TYPE: PRT
<213> ORGANISM: Homo sapiens

<400> SEQUENCE: 240

His His Ala Ala Tyr Val Asn Asn Leu Asn Val Thr Glu Glu Lys Tyr
1 5 10 15

Gln Glu Ala Leu Ala Lys
20

<210> SEQ ID NO 241
<211> LENGTH: 18
<212> TYPE: PRT
<213> ORGANISM: Homo sapiens

<400> SEQUENCE: 241

Gln Gly Ile Val His Leu Asp Leu Lys Pro Glu Asn Ile Met Cys Val
1 5 10 15

Asn Lys

<210> SEQ ID NO 242
<211> LENGTH: 13
<212> TYPE: PRT
<213> ORGANISM: Homo sapiens

<400> SEQUENCE: 242

Thr Leu Gly Asp Gln Leu Ser Leu Leu Leu Gly Ala Arg
1 5 10

<210> SEQ ID NO 243
<211> LENGTH: 9
<212> TYPE: PRT
<213> ORGANISM: Homo sapiens

<400> SEQUENCE: 243

Cys Thr His Trp Ala Glu Gly Gly Lys
1 5

<210> SEQ ID NO 244
<211> LENGTH: 16
<212> TYPE: PRT
<213> ORGANISM: Homo sapiens

<400> SEQUENCE: 244

Phe Gly Leu Tyr Leu Pro Leu Phe Lys Pro Ser Val Ser Thr Ser Lys
1 5 10 15

<210> SEQ ID NO 245
<211> LENGTH: 14
<212> TYPE: PRT
<213> ORGANISM: Homo sapiens

<400> SEQUENCE: 245

Gly Ser Cys Tyr Pro Ala Thr Gly Asp Leu Leu Val Gly Arg
1 5 10

<210> SEQ ID NO 246
<211> LENGTH: 10
<212> TYPE: PRT
<213> ORGANISM: Homo sapiens

<400> SEQUENCE: 246

Val Met Pro Leu Ile Ile Gln Gly Phe Lys
1 5 10

<210> SEQ ID NO 247
<211> LENGTH: 14
<212> TYPE: PRT
<213> ORGANISM: Homo sapiens

<400> SEQUENCE: 247

Thr Pro Leu Trp Ile Gly Leu Ala Gly Glu Glu Gly Ser Arg
1 5 10

<210> SEQ ID NO 248
<211> LENGTH: 19
<212> TYPE: PRT
<213> ORGANISM: Homo sapiens

<400> SEQUENCE: 248

Thr Gln Pro Asp Gly Thr Ser Val Pro Gly Glu Pro Ala Ser Pro Ile
1 5 10 15

Ser Gln Arg

<210> SEQ ID NO 249
<211> LENGTH: 12
<212> TYPE: PRT
<213> ORGANISM: Homo sapiens

<400> SEQUENCE: 249

Val Trp Gly Val Pro Ile Pro Val Phe His His Lys
1 5 10

<210> SEQ ID NO 250
<211> LENGTH: 10
<212> TYPE: PRT
<213> ORGANISM: Homo sapiens

<400> SEQUENCE: 250

Ala Leu Leu Asn Val Val Asp Asn Ala Arg
1 5 10

<210> SEQ ID NO 251
<211> LENGTH: 16
<212> TYPE: PRT
<213> ORGANISM: Homo sapiens

<400> SEQUENCE: 251

Gly Gly Thr Thr Asn Pro His Ile Phe Pro Glu Gly Ser Glu Pro Lys
1 5 10 15

<210> SEQ ID NO 252
<211> LENGTH: 9
<212> TYPE: PRT
<213> ORGANISM: Homo sapiens

<400> SEQUENCE: 252

Tyr Thr Val Asn Phe Leu Glu Ala Lys
1 5

<210> SEQ ID NO 253
<211> LENGTH: 8
<212> TYPE: PRT
<213> ORGANISM: Homo sapiens

<400> SEQUENCE: 253

Ala Thr Ile Gln Gly Val Leu Arg
1 5

<210> SEQ ID NO 254
<211> LENGTH: 11
<212> TYPE: PRT
<213> ORGANISM: Homo sapiens

<400> SEQUENCE: 254

Gly Pro Leu Gly Asp Gln Tyr Gln Thr Val Lys
1 5 10

<210> SEQ ID NO 255
<211> LENGTH: 21
<212> TYPE: PRT
<213> ORGANISM: Homo sapiens

<400> SEQUENCE: 255

Val Ala Ala Gln Val Asp Gly Gly Ala Gln Val Gln Gln Val Leu Asn
1 5 10 15

Ile Glu Cys Leu Arg
20

<210> SEQ ID NO 256
<211> LENGTH: 9
<212> TYPE: PRT
<213> ORGANISM: Homo sapiens

<400> SEQUENCE: 256

Phe Thr Pro Val Val Cys Gly Leu Arg
1 5

<210> SEQ ID NO 257
<211> LENGTH: 31
<212> TYPE: PRT
<213> ORGANISM: Homo sapiens

<400> SEQUENCE: 257

Leu Phe Pro Asn Ser Leu Asp Gln Thr Asp Met His Gly Asp Ser Glu
1 5 10 15

Tyr Asn Ile Met Phe Gly Pro Asp Ile Cys Gly Pro Gly Thr Lys
20 25 30

<210> SEQ ID NO 258
<211> LENGTH: 20
<212> TYPE: PRT
<213> ORGANISM: Homo sapiens

<400> SEQUENCE: 258

Thr Ile Leu Leu Ser Thr Thr Asp Pro Ala Asp Phe Ala Val Ala Glu
1 5 10 15

Ala Leu Glu Lys

20

<210> SEQ ID NO 259
<211> LENGTH: 13
<212> TYPE: PRT
<213> ORGANISM: Homo sapiens

<400> SEQUENCE: 259

Leu Thr Tyr Leu Gly Cys Ala Ser Val Asn Ala Pro Arg
1 5 10

<210> SEQ ID NO 260
<211> LENGTH: 14
<212> TYPE: PRT
<213> ORGANISM: Homo sapiens

<400> SEQUENCE: 260

Ser Cys Tyr Leu Ser Ser Leu Asp Leu Leu Leu Glu His Arg
1 5 10

<210> SEQ ID NO 261
<211> LENGTH: 13
<212> TYPE: PRT
<213> ORGANISM: Homo sapiens

<400> SEQUENCE: 261

Val Val Ala Thr Thr Gln Met Gln Ala Ala Asp Ala Arg
1 5 10

<210> SEQ ID NO 262
<211> LENGTH: 27
<212> TYPE: PRT
<213> ORGANISM: Homo sapiens

<400> SEQUENCE: 262

Gly Val Gly Gly Ser Gln Pro Pro Asp Ile Asp Lys Thr Glu Leu Val
1 5 10 15

Glu Pro Thr Glu Tyr Leu Val Val His Leu Lys
20 25

<210> SEQ ID NO 263
<211> LENGTH: 11
<212> TYPE: PRT
<213> ORGANISM: Homo sapiens

<400> SEQUENCE: 263

Lys Glu Ile His Thr Val Pro Asp Met Gly Lys
1 5 10

<210> SEQ ID NO 264
<211> LENGTH: 10
<212> TYPE: PRT
<213> ORGANISM: Homo sapiens

<400> SEQUENCE: 264

Leu Phe Thr Ala Leu Phe Pro Phe Glu Lys
1 5 10

<210> SEQ ID NO 265
<211> LENGTH: 7
<212> TYPE: PRT
<213> ORGANISM: Homo sapiens

<400> SEQUENCE: 265

Ser Leu Glu Ser Ala Leu Lys
1 5

<210> SEQ ID NO 266
<211> LENGTH: 10
<212> TYPE: PRT
<213> ORGANISM: Homo sapiens

<400> SEQUENCE: 266

Val Asp Asp Gln Ile Ala Ile Val Phe Lys
1 5 10

<210> SEQ ID NO 267
<211> LENGTH: 15
<212> TYPE: PRT
<213> ORGANISM: Homo sapiens

<400> SEQUENCE: 267

Val Leu Asp Pro Ala Ile Pro Ile Pro Asp Pro Tyr Ser Ser Arg
1 5 10 15

<210> SEQ ID NO 268
<211> LENGTH: 11
<212> TYPE: PRT
<213> ORGANISM: Homo sapiens

<400> SEQUENCE: 268

Ala Thr Pro Phe Ile Glu Cys Asn Gly Gly Arg
1 5 10

<210> SEQ ID NO 269
<211> LENGTH: 28
<212> TYPE: PRT
<213> ORGANISM: Homo sapiens

<400> SEQUENCE: 269

Cys Ser Val Cys Glu Ala Pro Ala Ile Ala Ile Ala Val His Ser Gln
1 5 10 15

Asp Val Ser Ile Pro His Cys Pro Ala Gly Trp Arg
20 25

<210> SEQ ID NO 270
<211> LENGTH: 12
<212> TYPE: PRT
<213> ORGANISM: Homo sapiens

<400> SEQUENCE: 270

Glu Ala Gln Val Ala His Ala Asp Gln Gln Leu Arg
1 5 10

<210> SEQ ID NO 271
<211> LENGTH: 15
<212> TYPE: PRT
<213> ORGANISM: Homo sapiens

<400> SEQUENCE: 271

Glu Ile Ile Leu Asp Asp Asp Glu Cys Pro Leu Gln Ile Phe Arg
1 5 10 15

<210> SEQ ID NO 272
<211> LENGTH: 17
<212> TYPE: PRT
<213> ORGANISM: Homo sapiens

<400> SEQUENCE: 272

Thr Pro Ala Ala Ile Pro Ala Thr Pro Val Ala Val Ser Gln Pro Ile
1 5 10 15

Arg

<210> SEQ ID NO 273
<211> LENGTH: 9
<212> TYPE: PRT
<213> ORGANISM: Homo sapiens

<400> SEQUENCE: 273

Asp Leu Gly Phe Phe Gly Ile Tyr Lys
1 5

<210> SEQ ID NO 274
<211> LENGTH: 12
<212> TYPE: PRT
<213> ORGANISM: Homo sapiens

<400> SEQUENCE: 274

Glu Glu Arg Pro Ala Pro Thr Pro Trp Gly Ser Lys
1 5 10

<210> SEQ ID NO 275
<211> LENGTH: 12
<212> TYPE: PRT
<213> ORGANISM: Homo sapiens

<400> SEQUENCE: 275

Tyr Val Gly Phe Gly Asn Thr Pro Pro Pro Gln Lys
1 5 10

<210> SEQ ID NO 276
<211> LENGTH: 10
<212> TYPE: PRT
<213> ORGANISM: Homo sapiens

<400> SEQUENCE: 276

Cys Leu Phe Gln Ser Pro Leu Phe Ala Lys
1 5 10

<210> SEQ ID NO 277
<211> LENGTH: 9
<212> TYPE: PRT
<213> ORGANISM: Homo sapiens

<400> SEQUENCE: 277

Ser Glu Thr Asp Thr Ser Leu Ile Arg
1 5

<210> SEQ ID NO 278
<211> LENGTH: 11
<212> TYPE: PRT
<213> ORGANISM: Homo sapiens

<400> SEQUENCE: 278

Ile Leu Glu Thr Trp Gly Glu Leu Leu Ser Lys
1 5 10

<210> SEQ ID NO 279
<211> LENGTH: 16
<212> TYPE: PRT
<213> ORGANISM: Homo sapiens

<400> SEQUENCE: 279

Tyr Ser Gly Leu Cys Pro His Val Val Val Leu Val Ala Thr Val Arg
1 5 10 15

<210> SEQ ID NO 280
<211> LENGTH: 16
<212> TYPE: PRT
<213> ORGANISM: Homo sapiens

<400> SEQUENCE: 280

Glu Asn Ser Leu Leu Phe Asp Pro Leu Ser Ser Ser Ser Ser Asn Lys
1 5 10 15

<210> SEQ ID NO 281
<211> LENGTH: 12
<212> TYPE: PRT
<213> ORGANISM: Homo sapiens

<400> SEQUENCE: 281

Ile Lys Asn Glu Ala Glu Pro Glu Phe Ala Ser Arg
1 5 10

<210> SEQ ID NO 282
<211> LENGTH: 14
<212> TYPE: PRT
<213> ORGANISM: Homo sapiens

<400> SEQUENCE: 282

Val Ser Ala Pro Asp Gly Pro Cys Pro Thr Gly Phe Glu Arg
1 5 10

<210> SEQ ID NO 283
<211> LENGTH: 10
<212> TYPE: PRT
<213> ORGANISM: Homo sapiens

<400> SEQUENCE: 283

Ala Gln Gly Ile Ala Gln Gly Ala Ile Arg
1 5 10

<210> SEQ ID NO 284
<211> LENGTH: 16
<212> TYPE: PRT
<213> ORGANISM: Homo sapiens

<400> SEQUENCE: 284

Lys Val Cys Gly Asp Ser Asp Lys Gly Phe Val Val Ile Asn Gln Lys
1 5 10 15

<210> SEQ ID NO 285
<211> LENGTH: 15
<212> TYPE: PRT
<213> ORGANISM: Homo sapiens

<400> SEQUENCE: 285

Leu Trp Ser Gly Tyr Ser Leu Leu Tyr Phe Glu Gly Gln Glu Lys
1 5 10 15

<210> SEQ ID NO 286
<211> LENGTH: 16
<212> TYPE: PRT
<213> ORGANISM: Homo sapiens

<400> SEQUENCE: 286

Val Pro Ile Trp Asp Gln Asp Ile Gln Phe Leu Pro Gly Ser Gln Lys 1 5 10 15

<210> SEQ ID NO 287
<211> LENGTH: 12
<212> TYPE: PRT
<213> ORGANISM: Homo sapiens

<400> SEQUENCE: 287

Tyr Leu Ser Tyr Thr Leu Asn Pro Asp Leu Ile Arg
1 5 10

<210> SEQ ID NO 288
<211> LENGTH: 10
<212> TYPE: PRT
<213> ORGANISM: Homo sapiens

<400> SEQUENCE: 288

Tyr Val Ile Gly Val Gly Asp Ala Phe Arg
1 5 10

<210> SEQ ID NO 289
<211> LENGTH: 11
<212> TYPE: PRT
<213> ORGANISM: Homo sapiens

<400> SEQUENCE: 289

Asp Leu Glu Val Val Glu Gly Ser Ala Ala Arg
1 5 10

<210> SEQ ID NO 290
<211> LENGTH: 8
<212> TYPE: PRT
<213> ORGANISM: Homo sapiens

<400> SEQUENCE: 290

Phe Ala Val Gly Ser Gly Ser Arg
1 5

<210> SEQ ID NO 291
<211> LENGTH: 13
<212> TYPE: PRT
<213> ORGANISM: Homo sapiens

<400> SEQUENCE: 291

Gly Phe Gly Gln Ser Val Val Gln Leu Gln Gly Ser Arg
1 5 10

<210> SEQ ID NO 292
<211> LENGTH: 14
<212> TYPE: PRT
<213> ORGANISM: Homo sapiens

<400> SEQUENCE: 292

Gly Leu Pro Gly Glu Val Leu Gly Ala Gln Pro Gly Pro Arg
1 5 10

<210> SEQ ID NO 293
<211> LENGTH: 7
<212> TYPE: PRT
<213> ORGANISM: Homo sapiens

<400> SEQUENCE: 293

Leu Ala Glu Thr Leu Gly Arg
1 5

<210> SEQ ID NO 294
<211> LENGTH: 19
<212> TYPE: PRT
<213> ORGANISM: Homo sapiens

<400> SEQUENCE: 294

Leu Pro Pro Lys Val Glu Ser Leu Glu Ser Leu Tyr Phe Thr Pro Ile
1 5 10 15

Pro Ala Arg

<210> SEQ ID NO 295
<211> LENGTH: 21
<212> TYPE: PRT
<213> ORGANISM: Homo sapiens

<400> SEQUENCE: 295

Pro Thr Asp Ser Lys Pro Glu Asp Trp Asp Lys Pro Glu His Ile Pro
1 5 10 15

Asp Pro Asp Ala Lys
20

<210> SEQ ID NO 296
<211> LENGTH: 11
<212> TYPE: PRT
<213> ORGANISM: Homo sapiens

<400> SEQUENCE: 296

Gln Leu Ser Leu Pro Gln Gln Glu Ala Gln Lys
1 5 10

<210> SEQ ID NO 297
<211> LENGTH: 9
<212> TYPE: PRT
<213> ORGANISM: Homo sapiens

<400> SEQUENCE: 297

Asp Val Thr Thr Phe Phe Ser Gly Lys
1 5

<210> SEQ ID NO 298
<211> LENGTH: 18
<212> TYPE: PRT
<213> ORGANISM: Homo sapiens

<400> SEQUENCE: 298

Gly Gln Val Glu Gln Ala Asn Gln Glu Leu Gln Glu Leu Ile Gln Ser
1 5 10 15

Val Lys

<210> SEQ ID NO 299
<211> LENGTH: 16
<212> TYPE: PRT
<213> ORGANISM: Homo sapiens

<400> SEQUENCE: 299

Ile Asp Asp Val Leu His Thr Leu Thr Gly Ala Met Ser Leu Leu Arg
1 5 10 15

<210> SEQ ID NO 300
<211> LENGTH: 17
<212> TYPE: PRT
<213> ORGANISM: Homo sapiens

<400> SEQUENCE: 300

Leu Gln Leu Pro Asn Cys Ile Glu Asp Pro Val Ser Pro Ile Val Leu
1 5 10 15

Arg

<210> SEQ ID NO 301
<211> LENGTH: 15
<212> TYPE: PRT
<213> ORGANISM: Homo sapiens

<400> SEQUENCE: 301

Val Glu Ser Leu Glu Ser Leu Tyr Phe Thr Pro Ile Pro Ala Arg
1 5 10 15

<210> SEQ ID NO 302
<211> LENGTH: 21
<212> TYPE: PRT
<213> ORGANISM: Homo sapiens

<400> SEQUENCE: 302

Phe Gly Asp Pro Leu Gly Tyr Glu Asp Val Ile Pro Glu Ala Asp Arg
1 5 10 15

Glu Gly Val Ile Arg
20

<210> SEQ ID NO 303
<211> LENGTH: 11
<212> TYPE: PRT
<213> ORGANISM: Homo sapiens

<400> SEQUENCE: 303

Leu Glu Pro Asn Ala Gln Ala Gln Met Tyr Arg
1 5 10

<210> SEQ ID NO 304
<211> LENGTH: 15
<212> TYPE: PRT
<213> ORGANISM: Homo sapiens

<400> SEQUENCE: 304

Asp Ser Leu Glu Asp Cys Val Thr Ile Trp Gly Pro Glu Gly Arg
1 5 10 15

<210> SEQ ID NO 305
<211> LENGTH: 13
<212> TYPE: PRT
<213> ORGANISM: Homo sapiens

<400> SEQUENCE: 305

Glu Ala Val Thr Glu Ile Leu Gly Ile Glu Pro Asp Arg
1 5 10

<210> SEQ ID NO 306
<211> LENGTH: 7
<212> TYPE: PRT
<213> ORGANISM: Homo sapiens

<400> SEQUENCE: 306

Phe Gln Asn Leu Asp Lys Lys
1 5

<210> SEQ ID NO 307
<211> LENGTH: 12

<212> TYPE: PRT
<213> ORGANISM: Homo sapiens

<400> SEQUENCE: 307

Gly Gly Glu Cys Ala Ser Pro Leu Pro Gly Leu Arg
1               5                   10

<210> SEQ ID NO 308
<211> LENGTH: 26
<212> TYPE: PRT
<213> ORGANISM: Homo sapiens

<400> SEQUENCE: 308

Ile Ala Val Ser Lys Pro Ser Gly Pro Gln Pro Gln Ala Asp Leu Gln
1               5                   10                  15

Ala Leu Leu Gln Ser Gly Ala Gln Val Arg
            20                  25

<210> SEQ ID NO 309
<211> LENGTH: 23
<212> TYPE: PRT
<213> ORGANISM: Homo sapiens

<400> SEQUENCE: 309

Val Leu Glu Leu Ser Ile Pro Ala Ser Ala Glu Gln Ile Gln His Leu
1               5                   10                  15

Ala Gly Ala Ile Ala Glu Arg
            20

<210> SEQ ID NO 310
<211> LENGTH: 27
<212> TYPE: PRT
<213> ORGANISM: Homo sapiens

<400> SEQUENCE: 310

Ala Ala Pro Val Pro Thr Ala Pro Ala Ala Gly Ala Pro Leu Met Asp
1               5                   10                  15

Phe Gly Asn Asp Phe Val Pro Pro Ala Pro Arg
            20                  25

<210> SEQ ID NO 311
<211> LENGTH: 17
<212> TYPE: PRT
<213> ORGANISM: Homo sapiens

<400> SEQUENCE: 311

Gly Gly Tyr Thr Cys Val Cys Pro Asp Gly Phe Leu Leu Asp Ser Ser
1               5                   10                  15

Arg

<210> SEQ ID NO 312
<211> LENGTH: 21
<212> TYPE: PRT
<213> ORGANISM: Homo sapiens

<400> SEQUENCE: 312

Val Leu Leu Thr Arg Pro Gly Glu Gly Gly Thr Gly Leu Pro Gly Pro
1               5                   10                  15

Pro Leu Ile Thr Arg
            20

<210> SEQ ID NO 313

<211> LENGTH: 9
<212> TYPE: PRT
<213> ORGANISM: Homo sapiens

<400> SEQUENCE: 313

Glu Leu Gln Pro Gln Gln Gln Pro Arg
1               5

<210> SEQ ID NO 314
<211> LENGTH: 21
<212> TYPE: PRT
<213> ORGANISM: Homo sapiens

<400> SEQUENCE: 314

Phe Cys Gln Leu His Ser Ser Gly Ala Arg Pro Pro Ala Pro Ala Val
1               5                   10                  15

Pro Gly Leu Thr Arg
            20

<210> SEQ ID NO 315
<211> LENGTH: 13
<212> TYPE: PRT
<213> ORGANISM: Homo sapiens

<400> SEQUENCE: 315

Leu Ala Ala Gly Asp Gln Leu Leu Ser Val Asp Gly Arg
1               5                   10

<210> SEQ ID NO 316
<211> LENGTH: 13
<212> TYPE: PRT
<213> ORGANISM: Homo sapiens

<400> SEQUENCE: 316

Ser Leu Thr Leu Asp Thr Trp Glu Pro Glu Leu Leu Lys
1               5                   10

<210> SEQ ID NO 317
<211> LENGTH: 9
<212> TYPE: PRT
<213> ORGANISM: Homo sapiens

<400> SEQUENCE: 317

Glu Gln Val Pro Gly Phe Thr Pro Arg
1               5

<210> SEQ ID NO 318
<211> LENGTH: 9
<212> TYPE: PRT
<213> ORGANISM: Homo sapiens

<400> SEQUENCE: 318

Glu Thr Gly Val Pro Ile Ala Gly Arg
1               5

<210> SEQ ID NO 319
<211> LENGTH: 11
<212> TYPE: PRT
<213> ORGANISM: Homo sapiens

<400> SEQUENCE: 319

Lys Ile Thr Ile Gly Gln Ala Pro Thr Glu Lys
1               5                   10

<210> SEQ ID NO 320
<211> LENGTH: 20
<212> TYPE: PRT
<213> ORGANISM: Homo sapiens

<400> SEQUENCE: 320

Phe Ser Thr Met Pro Phe Leu Tyr Cys Asn Pro Gly Asp Val Cys Tyr
1 5 10 15

Tyr Ala Ser Arg
20

<210> SEQ ID NO 321
<211> LENGTH: 13
<212> TYPE: PRT
<213> ORGANISM: Homo sapiens

<400> SEQUENCE: 321

Leu Leu Thr Ile Gly Asp Ala Asn Gly Glu Ile Gln Arg
1 5 10

<210> SEQ ID NO 322
<211> LENGTH: 13
<212> TYPE: PRT
<213> ORGANISM: Homo sapiens

<400> SEQUENCE: 322

Leu Gln Ser Gln Val Ile Ser Glu Leu Asp Ala Cys Lys
1 5 10

<210> SEQ ID NO 323
<211> LENGTH: 7
<212> TYPE: PRT
<213> ORGANISM: Homo sapiens

<400> SEQUENCE: 323

Leu Thr Ile Leu Ala Ala Arg
1 5

<210> SEQ ID NO 324
<211> LENGTH: 11
<212> TYPE: PRT
<213> ORGANISM: Homo sapiens

<400> SEQUENCE: 324

Leu Val Glu Cys Leu Glu Thr Val Leu Asn Lys
1 5 10

<210> SEQ ID NO 325
<211> LENGTH: 17
<212> TYPE: PRT
<213> ORGANISM: Homo sapiens

<400> SEQUENCE: 325

Ser Ser Pro Gln Phe Gly Val Thr Leu Leu Thr Tyr Glu Leu Leu Gln
1 5 10 15

Arg

<210> SEQ ID NO 326
<211> LENGTH: 12
<212> TYPE: PRT
<213> ORGANISM: Homo sapiens

<400> SEQUENCE: 326

Tyr Gln Cys His Glu Glu Gly Leu Val Pro Ser Lys 1 5 10

<210> SEQ ID NO 327
<211> LENGTH: 14
<212> TYPE: PRT
<213> ORGANISM: Homo sapiens

<400> SEQUENCE: 327

Gly Cys Gln Leu Cys Pro Pro Phe Gly Ser Glu Gly Phe Arg
1 5 10

<210> SEQ ID NO 328
<211> LENGTH: 15
<212> TYPE: PRT
<213> ORGANISM: Homo sapiens

<400> SEQUENCE: 328

Lys Pro Gly Leu Glu Glu Ala Val Glu Ser Ala Cys Ala Met Arg
1 5 10 15

<210> SEQ ID NO 329
<211> LENGTH: 11
<212> TYPE: PRT
<213> ORGANISM: Homo sapiens

<400> SEQUENCE: 329

Leu Val Gln Cys Val Asp Ala Phe Glu Glu Lys
1 5 10

<210> SEQ ID NO 330
<211> LENGTH: 10
<212> TYPE: PRT
<213> ORGANISM: Homo sapiens

<400> SEQUENCE: 330

Gln Trp Phe Ile Asn Ile Thr Asp Ile Lys
1 5 10

<210> SEQ ID NO 331
<211> LENGTH: 9
<212> TYPE: PRT
<213> ORGANISM: Homo sapiens

<400> SEQUENCE: 331

Ser Gln Leu Glu Ala Ile Phe Leu Arg
1 5

<210> SEQ ID NO 332
<211> LENGTH: 11
<212> TYPE: PRT
<213> ORGANISM: Homo sapiens

<400> SEQUENCE: 332

Val Leu Glu Gly Ser Glu Leu Glu Leu Ala Lys
1 5 10

<210> SEQ ID NO 333
<211> LENGTH: 8
<212> TYPE: PRT
<213> ORGANISM: Homo sapiens

<400> SEQUENCE: 333

Val Val Gln Asp Leu Ala Ala Arg
1 5

<210> SEQ ID NO 334
<211> LENGTH: 8
<212> TYPE: PRT
<213> ORGANISM: Homo sapiens

<400> SEQUENCE: 334

Ala Ile Met Glu Phe Asn Pro Arg
1 5

<210> SEQ ID NO 335
<211> LENGTH: 11
<212> TYPE: PRT
<213> ORGANISM: Homo sapiens

<400> SEQUENCE: 335

Ala Leu Ala Glu Gly Gly Ser Ile Leu Ser Arg
1 5 10

<210> SEQ ID NO 336
<211> LENGTH: 17
<212> TYPE: PRT
<213> ORGANISM: Homo sapiens

<400> SEQUENCE: 336

Glu Ile Cys Pro Ala Gly Pro Gly Tyr His Tyr Ser Ala Ser Asp Leu
1 5 10 15

Arg

<210> SEQ ID NO 337
<211> LENGTH: 12
<212> TYPE: PRT
<213> ORGANISM: Homo sapiens

<400> SEQUENCE: 337

Glu Gln Val Val Glu Asp Arg Pro Val Gly Gly Arg
1 5 10

<210> SEQ ID NO 338
<211> LENGTH: 14
<212> TYPE: PRT
<213> ORGANISM: Homo sapiens

<400> SEQUENCE: 338

Leu Tyr Cys Asn Pro Gly Asp Val Cys Tyr Tyr Ala Ser Arg
1 5 10

<210> SEQ ID NO 339
<211> LENGTH: 18
<212> TYPE: PRT
<213> ORGANISM: Homo sapiens

<400> SEQUENCE: 339

Thr Gln Asp Ala Ser Gly Pro Glu Leu Ile Leu Pro Ala Ser Ile Glu
1 5 10 15

Phe Arg

<210> SEQ ID NO 340
<211> LENGTH: 15
<212> TYPE: PRT
<213> ORGANISM: Homo sapiens

<400> SEQUENCE: 340

Tyr Ser Glu Ile Glu Pro Ser Thr Glu Gly Glu Val Ile Tyr Arg 1 5 10 15

<210> SEQ ID NO 341
<211> LENGTH: 15
<212> TYPE: PRT
<213> ORGANISM: Homo sapiens

<400> SEQUENCE: 341

Ala Trp Cys Val Asn Cys Phe Ala Cys Ser Thr Cys Asn Thr Lys
1 5 10 15

<210> SEQ ID NO 342
<211> LENGTH: 23
<212> TYPE: PRT
<213> ORGANISM: Homo sapiens

<400> SEQUENCE: 342

Asp Asp Pro Thr Asp Ser Lys Pro Glu Asp Trp Asp Lys Pro Glu His
1 5 10 15

Ile Pro Asp Pro Asp Ala Lys
20

<210> SEQ ID NO 343
<211> LENGTH: 12
<212> TYPE: PRT
<213> ORGANISM: Homo sapiens

<400> SEQUENCE: 343

Ile Val Gln Ala Thr Thr Leu Leu Thr Met Asp Lys
1 5 10

<210> SEQ ID NO 344
<211> LENGTH: 10
<212> TYPE: PRT
<213> ORGANISM: Homo sapiens

<400> SEQUENCE: 344

Val Asp Leu Ser Thr Ser Thr Asp Trp Lys
1 5 10

<210> SEQ ID NO 345
<211> LENGTH: 8
<212> TYPE: PRT
<213> ORGANISM: Homo sapiens

<400> SEQUENCE: 345

Ala Gln Leu Leu Gln Gln Thr Arg
1 5

<210> SEQ ID NO 346
<211> LENGTH: 9
<212> TYPE: PRT
<213> ORGANISM: Homo sapiens

<400> SEQUENCE: 346

Asp Val Asp Glu Cys Gln Leu Phe Arg
1 5

<210> SEQ ID NO 347
<211> LENGTH: 19
<212> TYPE: PRT
<213> ORGANISM: Homo sapiens

<400> SEQUENCE: 347

Ile Glu Gly Tyr Pro Asp Pro Glu Val Val Trp Phe Lys Asp Asp Gln
1 5 10 15

Ser Ile Arg

<210> SEQ ID NO 348
<211> LENGTH: 13
<212> TYPE: PRT
<213> ORGANISM: Homo sapiens

<400> SEQUENCE: 348

Leu Ser Ser Met Ala Met Ile Ser Gly Leu Ser Gly Arg
1 5 10

<210> SEQ ID NO 349
<211> LENGTH: 16
<212> TYPE: PRT
<213> ORGANISM: Homo sapiens

<400> SEQUENCE: 349

Asn Asn Gly Val Leu Phe Glu Asn Gln Leu Leu Gln Ile Gly Val Lys
1 5 10 15

<210> SEQ ID NO 350
<211> LENGTH: 8
<212> TYPE: PRT
<213> ORGANISM: Homo sapiens

<400> SEQUENCE: 350

Arg Ala Asp Pro Ala Glu Leu Arg
1 5

<210> SEQ ID NO 351
<211> LENGTH: 10
<212> TYPE: PRT
<213> ORGANISM: Homo sapiens

<400> SEQUENCE: 351

Ser Ala Pro Ala Ser Gln Ala Ser Leu Arg
1 5 10

<210> SEQ ID NO 352
<211> LENGTH: 8
<212> TYPE: PRT
<213> ORGANISM: Homo sapiens

<400> SEQUENCE: 352

Asp Trp Glu Gln Phe Glu Tyr Lys
1 5

<210> SEQ ID NO 353
<211> LENGTH: 10
<212> TYPE: PRT
<213> ORGANISM: Homo sapiens

<400> SEQUENCE: 353

Ile Gln Ala Glu Leu Ala Val Ile Leu Lys
1 5 10

<210> SEQ ID NO 354
<211> LENGTH: 15
<212> TYPE: PRT
<213> ORGANISM: Homo sapiens

<400> SEQUENCE: 354

Ser Asn Arg Asp Glu Leu Glu Leu Glu Leu Ala Glu Asn Arg Lys
1 5 10 15

<210> SEQ ID NO 355
<211> LENGTH: 18
<212> TYPE: PRT
<213> ORGANISM: Homo sapiens

<400> SEQUENCE: 355

Thr Pro Val Pro Glu Lys Val Pro Pro Pro Lys Pro Ala Thr Pro Asp
1 5 10 15

Phe Arg

<210> SEQ ID NO 356
<211> LENGTH: 15
<212> TYPE: PRT
<213> ORGANISM: Homo sapiens

<400> SEQUENCE: 356

Val Ser Leu Glu Pro His Gln Gly Pro Gly Thr Pro Glu Ser Lys
1 5 10 15

<210> SEQ ID NO 357
<211> LENGTH: 12
<212> TYPE: PRT
<213> ORGANISM: Homo sapiens

<400> SEQUENCE: 357

Cys Thr Glu Pro Glu Asp Gln Leu Tyr Tyr Val Lys
1 5 10

<210> SEQ ID NO 358
<211> LENGTH: 18
<212> TYPE: PRT
<213> ORGANISM: Homo sapiens

<400> SEQUENCE: 358

Glu Cys Tyr Phe Asp Thr Ala Ala Pro Asp Ala Cys Asp Asn Ile Leu
1 5 10 15

Ala Arg

<210> SEQ ID NO 359
<211> LENGTH: 22
<212> TYPE: PRT
<213> ORGANISM: Homo sapiens

<400> SEQUENCE: 359

Phe Gly Leu Gly Ser Val Ala Gly Ala Val Gly Ala Thr Ala Val Tyr
1 5 10 15

Pro Ile Asp Leu Val Lys
20

<210> SEQ ID NO 360
<211> LENGTH: 14
<212> TYPE: PRT
<213> ORGANISM: Homo sapiens

<400> SEQUENCE: 360

Gly Gln Glu Asp Ala Ile Leu Ser Tyr Glu Pro Val Thr Arg
1 5 10

<210> SEQ ID NO 361
<211> LENGTH: 7

<212> TYPE: PRT
<213> ORGANISM: Homo sapiens

<400> SEQUENCE: 361

Ile Met Glu Leu Glu Gly Arg
1 5

<210> SEQ ID NO 362
<211> LENGTH: 9
<212> TYPE: PRT
<213> ORGANISM: Homo sapiens

<400> SEQUENCE: 362

Thr Cys Val Ser Leu Ala Val Ser Arg
1 5

<210> SEQ ID NO 363
<211> LENGTH: 15
<212> TYPE: PRT
<213> ORGANISM: Homo sapiens

<400> SEQUENCE: 363

Thr Ile Leu Thr Leu Thr Gly Val Ser Thr Leu Gly Asp Val Lys
1 5 10 15

<210> SEQ ID NO 364
<211> LENGTH: 17
<212> TYPE: PRT
<213> ORGANISM: Homo sapiens

<400> SEQUENCE: 364

Val Leu Gln Ile Val Thr Asn Arg Asp Asp Val Gln Gly Tyr Ala Ala
1 5 10 15

Lys

<210> SEQ ID NO 365
<211> LENGTH: 19
<212> TYPE: PRT
<213> ORGANISM: Homo sapiens

<400> SEQUENCE: 365

Ala Phe Gly Phe Ser His Leu Glu Ala Leu Leu Asp Asp Ser Lys Glu
1 5 10 15

Leu Gln Arg

<210> SEQ ID NO 366
<211> LENGTH: 20
<212> TYPE: PRT
<213> ORGANISM: Homo sapiens

<400> SEQUENCE: 366

Ala Gly Pro Asp Ser Ala Gly Ile Ala Leu Tyr Ser His Glu Asp Val
1 5 10 15

Cys Val Phe Lys
20

<210> SEQ ID NO 367
<211> LENGTH: 10
<212> TYPE: PRT
<213> ORGANISM: Homo sapiens

<400> SEQUENCE: 367

Ala Gln Gly Val Leu Ala Ala Gln Ala Arg 1 5 10

<210> SEQ ID NO 368
<211> LENGTH: 9
<212> TYPE: PRT
<213> ORGANISM: Homo sapiens

<400> SEQUENCE: 368

Leu Pro Ser Phe Gln Gln Ser Cys Arg
1 5

<210> SEQ ID NO 369
<211> LENGTH: 12
<212> TYPE: PRT
<213> ORGANISM: Homo sapiens

<400> SEQUENCE: 369

Met Leu Ser Ser Phe Leu Ser Glu Asp Val Phe Lys
1 5 10

<210> SEQ ID NO 370
<211> LENGTH: 12
<212> TYPE: PRT
<213> ORGANISM: Homo sapiens

<400> SEQUENCE: 370

Asp Thr Glu Gln Thr Leu Tyr Gln Val Gln Glu Arg
1 5 10

<210> SEQ ID NO 371
<211> LENGTH: 15
<212> TYPE: PRT
<213> ORGANISM: Homo sapiens

<400> SEQUENCE: 371

Asp Val Glu Val Thr Lys Glu Glu Phe Val Leu Ala Ala Gln Lys
1 5 10 15

<210> SEQ ID NO 372
<211> LENGTH: 14
<212> TYPE: PRT
<213> ORGANISM: Homo sapiens

<400> SEQUENCE: 372

Ile Asn Gln Leu Ser Glu Glu Asn Gly Asp Leu Ser Phe Lys
1 5 10

<210> SEQ ID NO 373
<211> LENGTH: 12
<212> TYPE: PRT
<213> ORGANISM: Homo sapiens

<400> SEQUENCE: 373

Leu Asn Ile Pro Ala Thr Asn Val Phe Ala Asn Arg
1 5 10

<210> SEQ ID NO 374
<211> LENGTH: 12
<212> TYPE: PRT
<213> ORGANISM: Homo sapiens

<400> SEQUENCE: 374

Ser Leu Val Lys Pro Ile Thr Gln Leu Leu Gly Arg
1 5 10

<210> SEQ ID NO 375
<211> LENGTH: 20
<212> TYPE: PRT
<213> ORGANISM: Homo sapiens

<400> SEQUENCE: 375

Tyr Leu Cys Glu Gly Thr Glu Ser Pro Tyr Gln Thr Gly Gln Leu His
1 5 10 15

Pro Ala Ile Arg
20

<210> SEQ ID NO 376
<211> LENGTH: 17
<212> TYPE: PRT
<213> ORGANISM: Homo sapiens

<400> SEQUENCE: 376

Ala Ser Met Gln Pro Ile Gln Ile Ala Glu Gly Thr Gly Ile Thr Thr
1 5 10 15

Arg

<210> SEQ ID NO 377
<211> LENGTH: 15
<212> TYPE: PRT
<213> ORGANISM: Homo sapiens

<400> SEQUENCE: 377

Ile Ala Gly Ala Leu Gly Gly Leu Leu Thr Pro Leu Phe Leu Arg
1 5 10 15

<210> SEQ ID NO 378
<211> LENGTH: 13
<212> TYPE: PRT
<213> ORGANISM: Homo sapiens

<400> SEQUENCE: 378

Leu Gly Ala Ser Ala Leu Asp Ser Ile Gln Glu Phe Arg
1 5 10

<210> SEQ ID NO 379
<211> LENGTH: 29
<212> TYPE: PRT
<213> ORGANISM: Homo sapiens

<400> SEQUENCE: 379

Ser Gly Thr Ile Phe Asp Asn Phe Leu Ile Thr Asn Asp Glu Ala Tyr
1 5 10 15

Ala Glu Glu Phe Gly Asn Glu Thr Trp Gly Val Thr Lys
20 25

<210> SEQ ID NO 380
<211> LENGTH: 17
<212> TYPE: PRT
<213> ORGANISM: Homo sapiens

<400> SEQUENCE: 380

Thr Val Leu Asp Leu Gln Ser Ser Leu Ala Gly Val Ser Glu Asn Leu
1 5 10 15

Lys

<210> SEQ ID NO 381
<211> LENGTH: 17

<212> TYPE: PRT
<213> ORGANISM: Homo sapiens

<400> SEQUENCE: 381

Ala Gly Pro Asp Leu Ala Ser Cys Leu Asp Val Asp Glu Cys Arg Glu
1 5 10 15

Arg

<210> SEQ ID NO 382
<211> LENGTH: 15
<212> TYPE: PRT
<213> ORGANISM: Homo sapiens

<400> SEQUENCE: 382

Glu Gly Gly Thr Ala Ala Gly Ala Gly Leu Asp Ser Leu His Lys
1 5 10 15

<210> SEQ ID NO 383
<211> LENGTH: 7
<212> TYPE: PRT
<213> ORGANISM: Homo sapiens

<400> SEQUENCE: 383

Phe Tyr Glu Phe Ser Gln Arg
1 5

<210> SEQ ID NO 384
<211> LENGTH: 22
<212> TYPE: PRT
<213> ORGANISM: Homo sapiens

<400> SEQUENCE: 384

Gly Glu Trp Ile Lys Pro Gly Ala Ile Val Ile Asp Cys Gly Ile Asn
1 5 10 15

Tyr Val Pro Asp Asp Lys
20

<210> SEQ ID NO 385
<211> LENGTH: 16
<212> TYPE: PRT
<213> ORGANISM: Homo sapiens

<400> SEQUENCE: 385

Asn Asp Pro Tyr His Pro Asp His Phe Asn Cys Ala Asn Cys Gly Lys
1 5 10 15

<210> SEQ ID NO 386
<211> LENGTH: 14
<212> TYPE: PRT
<213> ORGANISM: Homo sapiens

<400> SEQUENCE: 386

Ser Leu Glu Pro His Gln Gly Pro Gly Thr Pro Glu Ser Lys
1 5 10

<210> SEQ ID NO 387
<211> LENGTH: 11
<212> TYPE: PRT
<213> ORGANISM: Homo sapiens

<400> SEQUENCE: 387

Ser Leu Gly Glu Glu Asn Phe Glu Val Val Lys
1 5 10

<210> SEQ ID NO 388
<211> LENGTH: 11
<212> TYPE: PRT
<213> ORGANISM: Homo sapiens

<400> SEQUENCE: 388

Thr His Ile Asp Thr Val Ile Asn Ala Leu Lys
1               5                   10

<210> SEQ ID NO 389
<211> LENGTH: 22
<212> TYPE: PRT
<213> ORGANISM: Homo sapiens

<400> SEQUENCE: 389

Val His Ala Glu Leu Ala Asp Val Leu Thr Glu Ala Val Val Asp Ser
1               5                   10                  15

Ile Leu Ala Ile Lys Lys
            20

<210> SEQ ID NO 390
<211> LENGTH: 14
<212> TYPE: PRT
<213> ORGANISM: Homo sapiens

<400> SEQUENCE: 390

Val Met Gln His Gln Tyr Gln Val Ser Asn Leu Gly Gln Arg
1               5                   10

<210> SEQ ID NO 391
<211> LENGTH: 28
<212> TYPE: PRT
<213> ORGANISM: Homo sapiens

<400> SEQUENCE: 391

Ala Ser Phe Ile Thr Pro Val Pro Gly Gly Val Gly Pro Met Thr Val
1               5                   10                  15

Ala Met Leu Met Gln Ser Thr Val Glu Ser Ala Lys
            20                  25

<210> SEQ ID NO 392
<211> LENGTH: 9
<212> TYPE: PRT
<213> ORGANISM: Homo sapiens

<400> SEQUENCE: 392

Phe Glu His Phe Ile Glu Gly Gly Arg
1               5

<210> SEQ ID NO 393
<211> LENGTH: 16
<212> TYPE: PRT
<213> ORGANISM: Homo sapiens

<400> SEQUENCE: 393

Leu Gln Gln Ala Gln Leu Tyr Pro Ile Ala Ile Phe Ile Lys Pro Lys
1               5                   10                  15

<210> SEQ ID NO 394
<211> LENGTH: 8
<212> TYPE: PRT
<213> ORGANISM: Homo sapiens

<400> SEQUENCE: 394

Met Thr Leu Ala Asp Ile Glu Arg
1 5

<210> SEQ ID NO 395
<211> LENGTH: 13
<212> TYPE: PRT
<213> ORGANISM: Homo sapiens

<400> SEQUENCE: 395

Thr Val Glu Leu Leu Ser Gly Val Val Asp Gln Thr Lys
1 5 10

<210> SEQ ID NO 396
<211> LENGTH: 9
<212> TYPE: PRT
<213> ORGANISM: Homo sapiens

<400> SEQUENCE: 396

Ala Met Asp Tyr Asp Leu Leu Leu Arg
1 5

<210> SEQ ID NO 397
<211> LENGTH: 7
<212> TYPE: PRT
<213> ORGANISM: Homo sapiens

<400> SEQUENCE: 397

Asp Phe Gly Ser Phe Asp Lys
1 5

<210> SEQ ID NO 398
<211> LENGTH: 19
<212> TYPE: PRT
<213> ORGANISM: Homo sapiens

<400> SEQUENCE: 398

Glu Pro Ala Val Tyr Phe Lys Glu Gln Phe Leu Asp Gly Asp Gly Trp
1 5 10 15

Thr Ser Arg

<210> SEQ ID NO 399
<211> LENGTH: 17
<212> TYPE: PRT
<213> ORGANISM: Homo sapiens

<400> SEQUENCE: 399

Phe Leu Ile Asn Leu Glu Gly Gly Asp Ile Arg Glu Glu Ser Ser Tyr
1 5 10 15

Lys

<210> SEQ ID NO 400
<211> LENGTH: 27
<212> TYPE: PRT
<213> ORGANISM: Homo sapiens

<400> SEQUENCE: 400

Gly Glu Trp Ile Lys Pro Gly Ala Ile Val Ile Asp Cys Gly Ile Asn
1 5 10 15

Tyr Val Pro Asp Asp Lys Lys Pro Asn Gly Arg
20 25

<210> SEQ ID NO 401

<211> LENGTH: 7
<212> TYPE: PRT
<213> ORGANISM: Homo sapiens

<400> SEQUENCE: 401

His Ala Val Val Val Gly Arg
1 5

<210> SEQ ID NO 402
<211> LENGTH: 14
<212> TYPE: PRT
<213> ORGANISM: Homo sapiens

<400> SEQUENCE: 402

Leu Glu Gly Asp Thr Phe Leu Leu Leu Ile Gln Ser Leu Lys
1 5 10

<210> SEQ ID NO 403
<211> LENGTH: 11
<212> TYPE: PRT
<213> ORGANISM: Homo sapiens

<400> SEQUENCE: 403

Asn Thr Ser Val Val Asp Ser Glu Pro Val Arg
1 5 10

<210> SEQ ID NO 404
<211> LENGTH: 9
<212> TYPE: PRT
<213> ORGANISM: Homo sapiens

<400> SEQUENCE: 404

Pro Gly Thr Thr Asp Gln Val Pro Arg
1 5

<210> SEQ ID NO 405
<211> LENGTH: 10
<212> TYPE: PRT
<213> ORGANISM: Homo sapiens

<400> SEQUENCE: 405

Gln Leu Asp Gln His Leu Asp Leu Leu Lys
1 5 10

<210> SEQ ID NO 406
<211> LENGTH: 12
<212> TYPE: PRT
<213> ORGANISM: Homo sapiens

<400> SEQUENCE: 406

Thr Val Ile Val His Gly Phe Thr Leu Gly Glu Lys
1 5 10

<210> SEQ ID NO 407
<211> LENGTH: 15
<212> TYPE: PRT
<213> ORGANISM: Homo sapiens

<400> SEQUENCE: 407

Tyr Ala Pro Asp Asp Ile Pro Asn Ile Asn Ser Thr Cys Phe Lys
1 5 10 15

<210> SEQ ID NO 408
<211> LENGTH: 11
<212> TYPE: PRT

<213> ORGANISM: Homo sapiens

<400> SEQUENCE: 408

Ala Ala Asp Leu Leu Tyr Ala Met Cys Asp Arg
1 5 10

<210> SEQ ID NO 409
<211> LENGTH: 12
<212> TYPE: PRT
<213> ORGANISM: Homo sapiens

<400> SEQUENCE: 409

Glu Met Gly Glu Ala Phe Ala Ala Asp Ile Pro Arg
1 5 10

<210> SEQ ID NO 410
<211> LENGTH: 10
<212> TYPE: PRT
<213> ORGANISM: Homo sapiens

<400> SEQUENCE: 410

Ile Gln Gly Thr Leu Gln Pro His Ala Arg
1 5 10

<210> SEQ ID NO 411
<211> LENGTH: 17
<212> TYPE: PRT
<213> ORGANISM: Homo sapiens

<400> SEQUENCE: 411

Leu Pro Ile Ala Val Asn Gly Ser Leu Ile Tyr Gly Val Cys Ala Gly
1 5 10 15

Lys

<210> SEQ ID NO 412
<211> LENGTH: 12
<212> TYPE: PRT
<213> ORGANISM: Homo sapiens

<400> SEQUENCE: 412

Val Asn Asp Asp Leu Ile Ser Glu Phe Pro His Lys
1 5 10

<210> SEQ ID NO 413
<211> LENGTH: 10
<212> TYPE: PRT
<213> ORGANISM: Homo sapiens

<400> SEQUENCE: 413

Asp Gly Gly Cys Ser Leu Pro Ile Leu Arg
1 5 10

<210> SEQ ID NO 414
<211> LENGTH: 11
<212> TYPE: PRT
<213> ORGANISM: Homo sapiens

<400> SEQUENCE: 414

Glu Asn Val Asp Tyr Ile Ile Gln Glu Leu Arg
1 5 10

<210> SEQ ID NO 415
<211> LENGTH: 9
<212> TYPE: PRT

<213> ORGANISM: Homo sapiens

<400> SEQUENCE: 415

Gly Ala Ala Val Asp Glu Tyr Phe Arg
1 5

<210> SEQ ID NO 416
<211> LENGTH: 13
<212> TYPE: PRT
<213> ORGANISM: Homo sapiens

<400> SEQUENCE: 416

Gly Glu Thr Ala Val Pro Gly Ala Pro Glu Ala Leu Arg
1 5 10

<210> SEQ ID NO 417
<211> LENGTH: 10
<212> TYPE: PRT
<213> ORGANISM: Homo sapiens

<400> SEQUENCE: 417

Ile Leu Tyr Ser Phe Ala Thr Ala Phe Arg
1 5 10

<210> SEQ ID NO 418
<211> LENGTH: 11
<212> TYPE: PRT
<213> ORGANISM: Homo sapiens

<400> SEQUENCE: 418

Asn Val Phe Glu Cys Asn Asp Gln Val Val Lys
1 5 10

<210> SEQ ID NO 419
<211> LENGTH: 12
<212> TYPE: PRT
<213> ORGANISM: Homo sapiens

<400> SEQUENCE: 419

Ser Thr Gly Ser Phe Val Gly Glu Leu Met Tyr Lys
1 5 10

<210> SEQ ID NO 420
<211> LENGTH: 14
<212> TYPE: PRT
<213> ORGANISM: Homo sapiens

<400> SEQUENCE: 420

Thr Ile Arg Asp Leu Glu Val Val Glu Gly Ser Ala Ala Arg
1 5 10

<210> SEQ ID NO 421
<211> LENGTH: 17
<212> TYPE: PRT
<213> ORGANISM: Homo sapiens

<400> SEQUENCE: 421

Thr Val Phe Glu Ala Leu Gln Ala Pro Ala Cys His Glu Asn Met Val
1 5 10 15

Lys

<210> SEQ ID NO 422
<211> LENGTH: 11
<212> TYPE: PRT

<213> ORGANISM: Homo sapiens

<400> SEQUENCE: 422

Val Gly Leu Leu Gln Tyr Gly Ser Thr Val Lys
1 5 10

<210> SEQ ID NO 423
<211> LENGTH: 16
<212> TYPE: PRT
<213> ORGANISM: Homo sapiens

<400> SEQUENCE: 423

Tyr Val Leu Ser Asn Gln Tyr Arg Pro Asp Ile Ser Pro Thr Glu Arg
1 5 10 15

<210> SEQ ID NO 424
<211> LENGTH: 14
<212> TYPE: PRT
<213> ORGANISM: Homo sapiens

<400> SEQUENCE: 424

Ala Glu Ala Glu Leu Glu Tyr Asn Pro Glu His Val Ser Arg
1 5 10

<210> SEQ ID NO 425
<211> LENGTH: 14
<212> TYPE: PRT
<213> ORGANISM: Homo sapiens

<400> SEQUENCE: 425

Ala Ser Pro Asp Leu Val Pro Met Gly Glu Trp Thr Ala Arg
1 5 10

<210> SEQ ID NO 426
<211> LENGTH: 18
<212> TYPE: PRT
<213> ORGANISM: Homo sapiens

<400> SEQUENCE: 426

Cys Glu Ala Cys Ala Pro Gly His Phe Gly Asp Pro Ser Arg Pro Gly
1 5 10 15

Gly Arg

<210> SEQ ID NO 427
<211> LENGTH: 15
<212> TYPE: PRT
<213> ORGANISM: Homo sapiens

<400> SEQUENCE: 427

Glu Asp Gly Tyr Ser Asp Ala Ser Gly Phe Gly Tyr Cys Phe Arg
1 5 10 15

<210> SEQ ID NO 428
<211> LENGTH: 12
<212> TYPE: PRT
<213> ORGANISM: Homo sapiens

<400> SEQUENCE: 428

Gly Asp Leu Ile Gly Val Val Glu Ala Leu Thr Arg
1 5 10

<210> SEQ ID NO 429
<211> LENGTH: 19
<212> TYPE: PRT

<213> ORGANISM: Homo sapiens

<400> SEQUENCE: 429

Leu Ala Ile Leu Gln Val Gly Asn Arg Asp Asp Ser Asn Leu Tyr Ile
1 5 10 15

Asn Val Lys

<210> SEQ ID NO 430
<211> LENGTH: 24
<212> TYPE: PRT
<213> ORGANISM: Homo sapiens

<400> SEQUENCE: 430

Asn Asp Ala Gly Gln Ala Glu Cys Ser Cys Gln Val Thr Val Asp Asp
1 5 10 15

Ala Pro Ala Ser Glu Asn Thr Lys
20

<210> SEQ ID NO 431
<211> LENGTH: 12
<212> TYPE: PRT
<213> ORGANISM: Homo sapiens

<400> SEQUENCE: 431

Gln Asn Trp Phe Glu Ala Phe Glu Ile Leu Asp Lys
1 5 10

<210> SEQ ID NO 432
<211> LENGTH: 17
<212> TYPE: PRT
<213> ORGANISM: Homo sapiens

<400> SEQUENCE: 432

Ser Ser Glu Gly Leu Leu Ala Thr Ala Thr Val Pro Leu Asp Leu Phe
1 5 10 15

Lys

<210> SEQ ID NO 433
<211> LENGTH: 24
<212> TYPE: PRT
<213> ORGANISM: Homo sapiens

<400> SEQUENCE: 433

Ser Thr Thr Thr Ile Gly Leu Val Gln Ala Leu Gly Ala His Leu Tyr
1 5 10 15

Gln Asn Val Phe Ala Cys Val Arg
20

<210> SEQ ID NO 434
<211> LENGTH: 17
<212> TYPE: PRT
<213> ORGANISM: Homo sapiens

<400> SEQUENCE: 434

Val Leu Val Leu Glu Met Phe Ser Gly Gly Asp Ala Ala Ala Leu Glu
1 5 10 15

Arg

<210> SEQ ID NO 435
<211> LENGTH: 10
<212> TYPE: PRT
<213> ORGANISM: Homo sapiens

<400> SEQUENCE: 435

Lys Gln Val Ala Pro Glu Lys Pro Val Lys
1               5                   10

<210> SEQ ID NO 436
<211> LENGTH: 13
<212> TYPE: PRT
<213> ORGANISM: Homo sapiens

<400> SEQUENCE: 436

Leu Gln Glu Leu Glu Gly Thr Tyr Glu Glu Asn Glu Arg
1               5                   10

<210> SEQ ID NO 437
<211> LENGTH: 21
<212> TYPE: PRT
<213> ORGANISM: Homo sapiens

<400> SEQUENCE: 437

Leu Val Glu Gln His Gly Ser Asp Ile Trp Trp Thr Leu Pro Pro Glu
1               5                   10                  15

Gln Leu Leu Pro Lys
            20

<210> SEQ ID NO 438
<211> LENGTH: 18
<212> TYPE: PRT
<213> ORGANISM: Homo sapiens

<400> SEQUENCE: 438

Asn Pro Thr Phe Met Cys Leu Ala Leu His Cys Ile Ala Asn Val Gly
1               5                   10                  15

Ser Arg

<210> SEQ ID NO 439
<211> LENGTH: 13
<212> TYPE: PRT
<213> ORGANISM: Homo sapiens

<400> SEQUENCE: 439

Ser Ser Asp Gly Arg Pro Asp Ser Gly Gly Thr Leu Arg
1               5                   10

<210> SEQ ID NO 440
<211> LENGTH: 16
<212> TYPE: PRT
<213> ORGANISM: Homo sapiens

<400> SEQUENCE: 440

Ala Ala Pro Gln Pro Leu Asn Leu Val Ser Ser Val Thr Leu Ser Lys
1               5                   10                  15

<210> SEQ ID NO 441
<211> LENGTH: 15
<212> TYPE: PRT
<213> ORGANISM: Homo sapiens

<400> SEQUENCE: 441

Ala Val Gln Ala Gln Gly Gly Glu Ser Gln Gln Glu Ala Gln Arg
1               5                   10                  15

<210> SEQ ID NO 442

<211> LENGTH: 19
<212> TYPE: PRT
<213> ORGANISM: Homo sapiens

<400> SEQUENCE: 442

Asp Phe Leu Asn Gln Glu Gly Ala Asp Pro Asp Ser Ile Glu Met Val
1 5 10 15

Ala Thr Arg

<210> SEQ ID NO 443
<211> LENGTH: 9
<212> TYPE: PRT
<213> ORGANISM: Homo sapiens

<400> SEQUENCE: 443

Gly Gln Val Leu Asp Val Val Glu Arg
1 5

<210> SEQ ID NO 444
<211> LENGTH: 8
<212> TYPE: PRT
<213> ORGANISM: Homo sapiens

<400> SEQUENCE: 444

Leu Ala Leu Ile Gln Pro Ser Arg
1 5

<210> SEQ ID NO 445
<211> LENGTH: 10
<212> TYPE: PRT
<213> ORGANISM: Homo sapiens

<400> SEQUENCE: 445

Leu Gln Gln Asp Val Leu Gln Phe Gln Lys
1 5 10

<210> SEQ ID NO 446
<211> LENGTH: 8
<212> TYPE: PRT
<213> ORGANISM: Homo sapiens

<400> SEQUENCE: 446

Leu Thr Phe Glu Glu Leu Glu Arg
1 5

<210> SEQ ID NO 447
<211> LENGTH: 10
<212> TYPE: PRT
<213> ORGANISM: Homo sapiens

<400> SEQUENCE: 447

Gln Val Thr Pro Leu Phe Ile His Phe Arg
1 5 10

<210> SEQ ID NO 448
<211> LENGTH: 14
<212> TYPE: PRT
<213> ORGANISM: Homo sapiens

<400> SEQUENCE: 448

Ser Phe Asn Val Gln Asp Leu Leu Pro Asp His Glu Tyr Lys
1 5 10

<210> SEQ ID NO 449

<211> LENGTH: 13
<212> TYPE: PRT
<213> ORGANISM: Homo sapiens

<400> SEQUENCE: 449

Ser Ser Cys Ile Ser Gln His Val Ile Ser Glu Ala Lys
1 5 10

<210> SEQ ID NO 450
<211> LENGTH: 8
<212> TYPE: PRT
<213> ORGANISM: Homo sapiens

<400> SEQUENCE: 450

Val Leu Gln Ile Val Thr Asn Arg
1 5

<210> SEQ ID NO 451
<211> LENGTH: 11
<212> TYPE: PRT
<213> ORGANISM: Homo sapiens

<400> SEQUENCE: 451

Val Val Gly Asp Val Ala Tyr Asp Glu Ala Lys
1 5 10

<210> SEQ ID NO 452
<211> LENGTH: 10
<212> TYPE: PRT
<213> ORGANISM: Homo sapiens

<400> SEQUENCE: 452

Ala Leu Gln Ser Gly Pro Pro Gln Ser Arg
1 5 10

<210> SEQ ID NO 453
<211> LENGTH: 10
<212> TYPE: PRT
<213> ORGANISM: Homo sapiens

<400> SEQUENCE: 453

Ile Thr Ile Gly Gln Ala Pro Thr Glu Lys
1 5 10

<210> SEQ ID NO 454
<211> LENGTH: 11
<212> TYPE: PRT
<213> ORGANISM: Homo sapiens

<400> SEQUENCE: 454

Lys Ala Gln Gly Val Leu Ala Ala Gln Ala Arg
1 5 10

<210> SEQ ID NO 455
<211> LENGTH: 15
<212> TYPE: PRT
<213> ORGANISM: Homo sapiens

<400> SEQUENCE: 455

Leu Lys Glu Asn Leu Tyr Pro Tyr Leu Gly Pro Ser Thr Leu Arg
1 5 10 15

<210> SEQ ID NO 456
<211> LENGTH: 7
<212> TYPE: PRT

<213> ORGANISM: Homo sapiens

<400> SEQUENCE: 456

Leu Pro Val Thr Ile Asn Lys
1 5

<210> SEQ ID NO 457
<211> LENGTH: 17
<212> TYPE: PRT
<213> ORGANISM: Homo sapiens

<400> SEQUENCE: 457

Ser Ile Leu Thr Ala Ile Pro Asn Asp Asp Pro Tyr Phe His Ile Thr
1 5 10 15

Lys

<210> SEQ ID NO 458
<211> LENGTH: 20
<212> TYPE: PRT
<213> ORGANISM: Homo sapiens

<400> SEQUENCE: 458

Ser Leu Gly Asn Val Ile His Pro Asp Val Val Val Asn Gly Gly Gln
1 5 10 15

Asp Gln Ser Lys
20

<210> SEQ ID NO 459
<211> LENGTH: 11
<212> TYPE: PRT
<213> ORGANISM: Homo sapiens

<400> SEQUENCE: 459

Ala Val Gln Thr Ser Ile Ala Thr Ala Tyr Arg
1 5 10

<210> SEQ ID NO 460
<211> LENGTH: 11
<212> TYPE: PRT
<213> ORGANISM: Homo sapiens

<400> SEQUENCE: 460

Asp Ala Ser Lys Pro Glu Asp Trp Asp Glu Arg
1 5 10

<210> SEQ ID NO 461
<211> LENGTH: 10
<212> TYPE: PRT
<213> ORGANISM: Homo sapiens

<400> SEQUENCE: 461

Ile Pro Val Ser Gly Pro Phe Leu Val Lys
1 5 10

<210> SEQ ID NO 462
<211> LENGTH: 11
<212> TYPE: PRT
<213> ORGANISM: Homo sapiens

<400> SEQUENCE: 462

Leu Leu Gly Pro Ala Gly Leu Thr Trp Glu Arg
1 5 10

<210> SEQ ID NO 463
<211> LENGTH: 12
<212> TYPE: PRT
<213> ORGANISM: Homo sapiens

<400> SEQUENCE: 463

```
Leu Pro Val Glu Ala Phe Ser Ala Val Phe Thr Lys
1               5                   10
```

<210> SEQ ID NO 464
<211> LENGTH: 22
<212> TYPE: PRT
<213> ORGANISM: Homo sapiens

<400> SEQUENCE: 464

```
Ser Glu Glu Ser Thr Thr Val His Ser Ser Pro Gly Ala Thr Gly Thr
1               5                   10                  15

Ala Leu Phe Pro Thr Arg
            20
```

<210> SEQ ID NO 465
<211> LENGTH: 22
<212> TYPE: PRT
<213> ORGANISM: Homo sapiens

<400> SEQUENCE: 465

```
Ser Glu Glu Ser Thr Thr Val His Ser Ser Pro Gly Ala Thr Gly Thr
1               5                   10                  15

Ala Leu Phe Pro Thr Arg
            20
```

<210> SEQ ID NO 466
<211> LENGTH: 22
<212> TYPE: PRT
<213> ORGANISM: Homo sapiens

<400> SEQUENCE: 466

```
Ser Glu Glu Ser Thr Thr Val His Ser Ser Pro Gly Ala Thr Gly Thr
1               5                   10                  15

Ala Leu Phe Pro Thr Arg
            20
```

<210> SEQ ID NO 467
<211> LENGTH: 23
<212> TYPE: PRT
<213> ORGANISM: Homo sapiens

<400> SEQUENCE: 467

```
Thr Lys Val His Ala Glu Leu Ala Asp Val Leu Thr Glu Ala Val Val
1               5                   10                  15

Asp Ser Ile Leu Ala Ile Lys
            20
```

<210> SEQ ID NO 468
<211> LENGTH: 15
<212> TYPE: PRT
<213> ORGANISM: Homo sapiens

<400> SEQUENCE: 468

```
Tyr Gly Glu Gly His Gln Ala Trp Ile Ile Gly Ile Val Glu Lys
1               5                   10                  15
```

<210> SEQ ID NO 469

<211> LENGTH: 8
<212> TYPE: PRT
<213> ORGANISM: Homo sapiens

<400> SEQUENCE: 469

Ala Asp Leu Tyr Leu Glu Gly Lys
1               5

<210> SEQ ID NO 470
<211> LENGTH: 12
<212> TYPE: PRT
<213> ORGANISM: Homo sapiens

<400> SEQUENCE: 470

Cys Leu Glu Glu Lys Asn Glu Ile Leu Gln Gly Lys
1               5                   10

<210> SEQ ID NO 471
<211> LENGTH: 16
<212> TYPE: PRT
<213> ORGANISM: Homo sapiens

<400> SEQUENCE: 471

Phe Ile Phe Asp Cys Val Ser Gln Glu Tyr Gly Ile Asn Pro Glu Arg
1               5                   10                  15

<210> SEQ ID NO 472
<211> LENGTH: 12
<212> TYPE: PRT
<213> ORGANISM: Homo sapiens

<400> SEQUENCE: 472

Ile His Gly Thr Glu Glu Gly Gln Gln Ile Leu Lys
1               5                   10

<210> SEQ ID NO 473
<211> LENGTH: 8
<212> TYPE: PRT
<213> ORGANISM: Homo sapiens

<400> SEQUENCE: 473

Lys Ile Gln Thr Gln Leu Gln Arg
1               5

<210> SEQ ID NO 474
<211> LENGTH: 12
<212> TYPE: PRT
<213> ORGANISM: Homo sapiens

<400> SEQUENCE: 474

Lys Val Val Gly Asp Val Ala Tyr Asp Glu Ala Lys
1               5                   10

<210> SEQ ID NO 475
<211> LENGTH: 10
<212> TYPE: PRT
<213> ORGANISM: Homo sapiens

<400> SEQUENCE: 475

Leu Asp Ser Ile Ser Gly Asn Leu Gln Arg
1               5                   10

<210> SEQ ID NO 476
<211> LENGTH: 12
<212> TYPE: PRT

<213> ORGANISM: Homo sapiens

<400> SEQUENCE: 476

Leu Phe Glu Asp Leu Glu Phe Gln Gln Leu Glu Arg
1 5 10

<210> SEQ ID NO 477
<211> LENGTH: 30
<212> TYPE: PRT
<213> ORGANISM: Homo sapiens

<400> SEQUENCE: 477

Ser Leu Gly Asn Val Ile His Pro Asp Val Val Val Asn Gly Gly Gln
1 5 10 15

Asp Gln Ser Lys Glu Pro Pro Tyr Gly Ala Asp Val Leu Arg
20 25 30

<210> SEQ ID NO 478
<211> LENGTH: 10
<212> TYPE: PRT
<213> ORGANISM: Homo sapiens

<400> SEQUENCE: 478

Thr Glu Val Asn Ser Gly Phe Phe Tyr Lys
1 5 10

<210> SEQ ID NO 479
<211> LENGTH: 30
<212> TYPE: PRT
<213> ORGANISM: Homo sapiens

<400> SEQUENCE: 479

Thr Ser Ala Gly Thr Phe Pro Gly Ser Gln Pro Gln Ala Pro Ala Ser
1 5 10 15

Pro Val Leu Pro Ala Arg Pro Pro Pro Pro Pro Leu Pro Arg
20 25 30

<210> SEQ ID NO 480
<211> LENGTH: 10
<212> TYPE: PRT
<213> ORGANISM: Homo sapiens

<400> SEQUENCE: 480

Val His Ser Pro Gln Gln Val Asp Phe Arg
1 5 10

<210> SEQ ID NO 481
<211> LENGTH: 17
<212> TYPE: PRT
<213> ORGANISM: Homo sapiens

<400> SEQUENCE: 481

Val Leu Thr Gly Asn Thr Ile Ala Leu Val Leu Gly Gly Gly Gly Ala
1 5 10 15

Arg

<210> SEQ ID NO 482
<211> LENGTH: 8
<212> TYPE: PRT
<213> ORGANISM: Homo sapiens

<400> SEQUENCE: 482

Val Ser Ala Leu Ser Val Val Arg 1 5

<210> SEQ ID NO 483
<211> LENGTH: 15
<212> TYPE: PRT
<213> ORGANISM: Homo sapiens

<400> SEQUENCE: 483

Ala Ser Leu Glu Asn Gly Val Leu Leu Cys Asp Leu Ile Asn Lys
1 5 10 15

<210> SEQ ID NO 484
<211> LENGTH: 8
<212> TYPE: PRT
<213> ORGANISM: Homo sapiens

<400> SEQUENCE: 484

Glu Thr Leu Ile Asp Val Ala Arg
1 5

<210> SEQ ID NO 485
<211> LENGTH: 11
<212> TYPE: PRT
<213> ORGANISM: Homo sapiens

<400> SEQUENCE: 485

Phe Glu Ser Lys Pro Gln Ser Gln Glu Val Lys
1 5 10

<210> SEQ ID NO 486
<211> LENGTH: 38
<212> TYPE: PRT
<213> ORGANISM: Homo sapiens

<400> SEQUENCE: 486

Gly His Leu Gln Ile Ala Ala Cys Pro Asn Gln Asp Pro Leu Gln Gly
1 5 10 15

Thr Thr Gly Leu Ile Pro Leu Leu Gly Ile Asp Val Trp Glu His Ala
20 25 30

Tyr Tyr Leu Gln Tyr Lys
35

<210> SEQ ID NO 487
<211> LENGTH: 22
<212> TYPE: PRT
<213> ORGANISM: Homo sapiens

<400> SEQUENCE: 487

Gly Ile Cys Glu Ala Leu Glu Asp Ser Asp Gly Arg Gln Asp Ser Pro
1 5 10 15

Ala Gly Glu Leu Pro Lys
20

<210> SEQ ID NO 488
<211> LENGTH: 12
<212> TYPE: PRT
<213> ORGANISM: Homo sapiens

<400> SEQUENCE: 488

Gly Tyr Leu Ala Pro Ser Gly Asp Leu Ser Leu Arg
1 5 10

<210> SEQ ID NO 489

<211> LENGTH: 16
<212> TYPE: PRT
<213> ORGANISM: Homo sapiens

<400> SEQUENCE: 489

Leu Gln Ser Gln Leu Leu Ser Ile Glu Lys Glu Val Glu Glu Tyr Lys
1 5 10 15

<210> SEQ ID NO 490
<211> LENGTH: 21
<212> TYPE: PRT
<213> ORGANISM: Homo sapiens

<400> SEQUENCE: 490

Ser Gly Gln Gly Ser Asp Arg Gly Ser Gly Ser Arg Pro Gly Ile Glu
1 5 10 15

Gly Asp Thr Pro Arg
20

<210> SEQ ID NO 491
<211> LENGTH: 8
<212> TYPE: PRT
<213> ORGANISM: Homo sapiens

<400> SEQUENCE: 491

Val Ala Ile Ser Thr Phe Gln Lys
1 5

<210> SEQ ID NO 492
<211> LENGTH: 12
<212> TYPE: PRT
<213> ORGANISM: Homo sapiens

<400> SEQUENCE: 492

Gly Gln Asp Ile Phe Ile Ile Gln Thr Ile Pro Arg
1 5 10

<210> SEQ ID NO 493
<211> LENGTH: 18
<212> TYPE: PRT
<213> ORGANISM: Homo sapiens

<400> SEQUENCE: 493

Ile Thr Leu Asp Ala Gln Asp Val Leu Ala His Leu Val Gln Met Ala
1 5 10 15

Phe Lys

<210> SEQ ID NO 494
<211> LENGTH: 13
<212> TYPE: PRT
<213> ORGANISM: Homo sapiens

<400> SEQUENCE: 494

Arg Thr Glu Val Pro Pro Leu Leu Leu Ile Leu Asp Arg
1 5 10

<210> SEQ ID NO 495
<211> LENGTH: 13
<212> TYPE: PRT
<213> ORGANISM: Homo sapiens

<400> SEQUENCE: 495

Ser Ser Pro Pro Val Gln Phe Ser Leu Leu His Ser Lys
1 5 10

<210> SEQ ID NO 496
<211> LENGTH: 14
<212> TYPE: PRT
<213> ORGANISM: Homo sapiens

<400> SEQUENCE: 496

Ser Ser Thr Gly Ser Pro Thr Ser Pro Leu Asn Ala Glu Lys
1 5 10

<210> SEQ ID NO 497
<211> LENGTH: 10
<212> TYPE: PRT
<213> ORGANISM: Homo sapiens

<400> SEQUENCE: 497

Thr Lys Phe Pro Ala Glu Gln Tyr Tyr Arg
1 5 10

<210> SEQ ID NO 498
<211> LENGTH: 18
<212> TYPE: PRT
<213> ORGANISM: Homo sapiens

<400> SEQUENCE: 498

Ala Asn Phe Trp Tyr Gln Pro Ser Phe His Gly Val Asp Leu Ser Ala
1 5 10 15

Leu Arg

<210> SEQ ID NO 499
<211> LENGTH: 10
<212> TYPE: PRT
<213> ORGANISM: Homo sapiens

<400> SEQUENCE: 499

Asp Ala Gln Ile Ala Met Met Gln Gln Arg
1 5 10

<210> SEQ ID NO 500
<211> LENGTH: 9
<212> TYPE: PRT
<213> ORGANISM: Homo sapiens

<400> SEQUENCE: 500

Glu His Gly Ala Phe Asp Ala Val Lys
1 5

<210> SEQ ID NO 501
<211> LENGTH: 19
<212> TYPE: PRT
<213> ORGANISM: Homo sapiens

<400> SEQUENCE: 501

Gly Leu Ala Gln Ala Asp Gly Thr Leu Ile Thr Cys Val Asp Ser Gly
1 5 10 15

Ile Leu Arg

<210> SEQ ID NO 502
<211> LENGTH: 12
<212> TYPE: PRT
<213> ORGANISM: Homo sapiens

<400> SEQUENCE: 502

Gly Leu Asn Cys Glu Gln Cys Gln Asp Phe Tyr Arg
1 5 10

<210> SEQ ID NO 503
<211> LENGTH: 14
<212> TYPE: PRT
<213> ORGANISM: Homo sapiens

<400> SEQUENCE: 503

Lys Val Val Ala Thr Thr Gln Met Gln Ala Ala Asp Ala Arg
1 5 10

<210> SEQ ID NO 504
<211> LENGTH: 13
<212> TYPE: PRT
<213> ORGANISM: Homo sapiens

<400> SEQUENCE: 504

Met Lys Leu Thr His Ser Leu Gln Glu Glu Leu Glu Lys
1 5 10

<210> SEQ ID NO 505
<211> LENGTH: 12
<212> TYPE: PRT
<213> ORGANISM: Homo sapiens

<400> SEQUENCE: 505

Asn Ile Asp Val Phe Asn Val Glu Asp Gln Lys Arg
1 5 10

<210> SEQ ID NO 506
<211> LENGTH: 19
<212> TYPE: PRT
<213> ORGANISM: Homo sapiens

<400> SEQUENCE: 506

Gln Ala Ser Asp Lys Asp Asp Arg Pro Phe Gln Gly Glu Asp Val Glu
1 5 10 15

Asn Ser Arg

<210> SEQ ID NO 507
<211> LENGTH: 27
<212> TYPE: PRT
<213> ORGANISM: Homo sapiens

<400> SEQUENCE: 507

Ser Leu Asp Gln Thr Asp Met His Gly Asp Ser Glu Tyr Asn Ile Met
1 5 10 15

Phe Gly Pro Asp Ile Cys Gly Pro Gly Thr Lys
20 25

<210> SEQ ID NO 508
<211> LENGTH: 25
<212> TYPE: PRT
<213> ORGANISM: Homo sapiens

<400> SEQUENCE: 508

Ser Thr Ile Phe His Ser Ser Pro Asp Ala Ser Gly Thr Thr Pro Ser
1 5 10 15

Ser Ala His Ser Thr Thr Ser Gly Arg
20 25

<210> SEQ ID NO 509

<211> LENGTH: 25
<212> TYPE: PRT
<213> ORGANISM: Homo sapiens

<400> SEQUENCE: 509

Ser Thr Ile Phe His Ser Ser Pro Asp Ala Ser Gly Thr Thr Pro Ser
1               5                   10                  15

Ser Ala His Ser Thr Thr Ser Gly Arg
            20                  25

<210> SEQ ID NO 510
<211> LENGTH: 25
<212> TYPE: PRT
<213> ORGANISM: Homo sapiens

<400> SEQUENCE: 510

Ser Thr Ile Phe His Ser Ser Pro Asp Ala Ser Gly Thr Thr Pro Ser
1               5                   10                  15

Ser Ala His Ser Thr Thr Ser Gly Arg
            20                  25

<210> SEQ ID NO 511
<211> LENGTH: 25
<212> TYPE: PRT
<213> ORGANISM: Homo sapiens

<400> SEQUENCE: 511

Ser Thr Ile Phe His Ser Ser Pro Asp Ala Ser Gly Thr Thr Pro Ser
1               5                   10                  15

Ser Ala His Ser Thr Thr Ser Gly Arg
            20                  25

<210> SEQ ID NO 512
<211> LENGTH: 7
<212> TYPE: PRT
<213> ORGANISM: Homo sapiens

<400> SEQUENCE: 512

Val Cys Leu His Val Gln Lys
1               5

<210> SEQ ID NO 513
<211> LENGTH: 14
<212> TYPE: PRT
<213> ORGANISM: Homo sapiens

<400> SEQUENCE: 513

Val Ser Gln Phe Leu Gln Val Leu Glu Thr Asp Leu Tyr Arg
1               5                   10

<210> SEQ ID NO 514
<211> LENGTH: 17
<212> TYPE: PRT
<213> ORGANISM: Homo sapiens

<400> SEQUENCE: 514

Val Ser Ser Thr Ala Thr Thr Gln Asp Val Ile Glu Thr Leu Ala Glu
1               5                   10                  15

Lys

<210> SEQ ID NO 515
<211> LENGTH: 12
<212> TYPE: PRT

<213> ORGANISM: Homo sapiens

<400> SEQUENCE: 515

Tyr Asn Thr Arg Pro Leu Gly Gln Glu Pro Pro Arg
1 5 10

<210> SEQ ID NO 516
<211> LENGTH: 11
<212> TYPE: PRT
<213> ORGANISM: Homo sapiens

<400> SEQUENCE: 516

Ala Asn His Pro Met Asp Ala Glu Val Thr Lys
1 5 10

<210> SEQ ID NO 517
<211> LENGTH: 19
<212> TYPE: PRT
<213> ORGANISM: Homo sapiens

<400> SEQUENCE: 517

Ala Ser Glu Leu Gly His Ser Leu Asn Glu Asn Val Leu Lys Pro Ala
1 5 10 15

Gln Glu Lys

<210> SEQ ID NO 518
<211> LENGTH: 17
<212> TYPE: PRT
<213> ORGANISM: Homo sapiens

<400> SEQUENCE: 518

Ala Trp Val Ser His Asp Ser Thr Val Cys Leu Ala Asp Ala Asp Lys
1 5 10 15

Lys

<210> SEQ ID NO 519
<211> LENGTH: 13
<212> TYPE: PRT
<213> ORGANISM: Homo sapiens

<400> SEQUENCE: 519

Phe Ser Tyr Asp Leu Ser Gln Cys Ile Asn Gln Met Lys
1 5 10

<210> SEQ ID NO 520
<211> LENGTH: 10
<212> TYPE: PRT
<213> ORGANISM: Homo sapiens

<400> SEQUENCE: 520

Ile Tyr Gln Phe Thr Ala Ala Ser Pro Lys
1 5 10

<210> SEQ ID NO 521
<211> LENGTH: 17
<212> TYPE: PRT
<213> ORGANISM: Homo sapiens

<400> SEQUENCE: 521

Lys Gln Asp Glu Pro Ile Asp Leu Phe Met Ile Glu Ile Met Glu Met
1 5 10 15

Lys

<210> SEQ ID NO 522
<211> LENGTH: 13
<212> TYPE: PRT
<213> ORGANISM: Homo sapiens

<400> SEQUENCE: 522

Asn Ile Met Ala Gly Leu Gln Gln Thr Asn Ser Glu Lys
1               5                   10

<210> SEQ ID NO 523
<211> LENGTH: 6
<212> TYPE: PRT
<213> ORGANISM: Homo sapiens

<400> SEQUENCE: 523

Arg Pro Asp Tyr Leu Lys
1               5

<210> SEQ ID NO 524
<211> LENGTH: 22
<212> TYPE: PRT
<213> ORGANISM: Homo sapiens

<400> SEQUENCE: 524

Ser Glu Glu Ser Thr Thr Val His Ser Ser Pro Val Ala Thr Ala Thr
1               5                   10                  15

Thr Pro Ser Pro Ala Arg
            20

<210> SEQ ID NO 525
<211> LENGTH: 22
<212> TYPE: PRT
<213> ORGANISM: Homo sapiens

<400> SEQUENCE: 525

Ser Glu Glu Ser Thr Thr Val His Ser Ser Pro Val Ala Thr Ala Thr
1               5                   10                  15

Thr Pro Ser Pro Ala Arg
            20

<210> SEQ ID NO 526
<211> LENGTH: 22
<212> TYPE: PRT
<213> ORGANISM: Homo sapiens

<400> SEQUENCE: 526

Ser Glu Glu Ser Thr Thr Val His Ser Ser Pro Val Ala Thr Ala Thr
1               5                   10                  15

Thr Pro Ser Pro Ala Arg
            20

<210> SEQ ID NO 527
<211> LENGTH: 22
<212> TYPE: PRT
<213> ORGANISM: Homo sapiens

<400> SEQUENCE: 527

Ser Glu Glu Ser Thr Thr Val His Ser Ser Pro Val Ala Thr Ala Thr
1               5                   10                  15

Thr Pro Ser Pro Ala Arg
            20

<210> SEQ ID NO 528
<211> LENGTH: 7
<212> TYPE: PRT
<213> ORGANISM: Homo sapiens

<400> SEQUENCE: 528

Thr His Leu Thr Ser Leu Lys
1 5

<210> SEQ ID NO 529
<211> LENGTH: 9
<212> TYPE: PRT
<213> ORGANISM: Homo sapiens

<400> SEQUENCE: 529

Ala Gln Glu Ala Glu Gln Leu Leu Arg
1 5

<210> SEQ ID NO 530
<211> LENGTH: 15
<212> TYPE: PRT
<213> ORGANISM: Homo sapiens

<400> SEQUENCE: 530

Ala Gln Ile Ile Asn Asp Ala Phe Asn Leu Ala Ser Ala His Lys
1 5 10 15

<210> SEQ ID NO 531
<211> LENGTH: 18
<212> TYPE: PRT
<213> ORGANISM: Homo sapiens

<400> SEQUENCE: 531

Asp Gln Leu Gly Gly Trp Phe Gln Ser Ser Leu Leu Thr Ser Val Ala
1 5 10 15

Ala Arg

<210> SEQ ID NO 532
<211> LENGTH: 14
<212> TYPE: PRT
<213> ORGANISM: Homo sapiens

<400> SEQUENCE: 532

Gly Ala Asp Asp Ile Glu Leu Leu Pro Glu Ala Gln His Lys
1 5 10

<210> SEQ ID NO 533
<211> LENGTH: 13
<212> TYPE: PRT
<213> ORGANISM: Homo sapiens

<400> SEQUENCE: 533

Gly Phe Ser His Leu Glu Ala Leu Leu Asp Asp Ser Lys
1 5 10

<210> SEQ ID NO 534
<211> LENGTH: 16
<212> TYPE: PRT
<213> ORGANISM: Homo sapiens

<400> SEQUENCE: 534

Gly Leu Leu Thr Asp Ser Pro Ala Ala Thr Val Leu Ala Glu Ala Arg
1 5 10 15

<210> SEQ ID NO 535
<211> LENGTH: 12
<212> TYPE: PRT
<213> ORGANISM: Homo sapiens

<400> SEQUENCE: 535

His Ser Asn Phe Leu Gly Ala Tyr Asp Ser Ile Arg
1 5 10

<210> SEQ ID NO 536
<211> LENGTH: 10
<212> TYPE: PRT
<213> ORGANISM: Homo sapiens

<400> SEQUENCE: 536

Lys Asn Glu Phe Gln Gly Glu Leu Glu Lys
1 5 10

<210> SEQ ID NO 537
<211> LENGTH: 14
<212> TYPE: PRT
<213> ORGANISM: Homo sapiens

<400> SEQUENCE: 537

Ser Phe Leu Glu Glu Val Leu Ala Ser Gly Leu His Ser Arg
1 5 10

<210> SEQ ID NO 538
<211> LENGTH: 12
<212> TYPE: PRT
<213> ORGANISM: Homo sapiens

<400> SEQUENCE: 538

Thr Glu Ile Leu Gly Ile Glu Pro Asp Arg Glu Lys
1 5 10

<210> SEQ ID NO 539
<211> LENGTH: 12
<212> TYPE: PRT
<213> ORGANISM: Homo sapiens

<400> SEQUENCE: 539

Val Ile Leu Leu Asp Pro Ser Ile Ile Glu Ala Lys
1 5 10

<210> SEQ ID NO 540
<211> LENGTH: 13
<212> TYPE: PRT
<213> ORGANISM: Homo sapiens

<400> SEQUENCE: 540

Ala Glu Thr Val Gln Ala Ala Leu Glu Glu Ala Gln Arg
1 5 10

<210> SEQ ID NO 541
<211> LENGTH: 10
<212> TYPE: PRT
<213> ORGANISM: Homo sapiens

<400> SEQUENCE: 541

Ala Phe Val Glu Asn Tyr Pro Gln Phe Lys
1 5 10

<210> SEQ ID NO 542
<211> LENGTH: 8

<212> TYPE: PRT
<213> ORGANISM: Homo sapiens

<400> SEQUENCE: 542

Asp Phe Ile Ser Asn Leu Leu Lys
1 5

<210> SEQ ID NO 543
<211> LENGTH: 11
<212> TYPE: PRT
<213> ORGANISM: Homo sapiens

<400> SEQUENCE: 543

Asp Gly Phe Phe Gly Leu Ser Ile Ser Asp Arg
1 5 10

<210> SEQ ID NO 544
<211> LENGTH: 13
<212> TYPE: PRT
<213> ORGANISM: Homo sapiens

<400> SEQUENCE: 544

Asp His Val Phe Gln Val Asn Asn Phe Glu Ala Leu Lys
1 5 10

<210> SEQ ID NO 545
<211> LENGTH: 22
<212> TYPE: PRT
<213> ORGANISM: Homo sapiens

<400> SEQUENCE: 545

Asp Pro Thr Asp Ser Lys Pro Glu Asp Trp Asp Lys Pro Glu His Ile
1 5 10 15

Pro Asp Pro Asp Ala Lys
20

<210> SEQ ID NO 546
<211> LENGTH: 6
<212> TYPE: PRT
<213> ORGANISM: Homo sapiens

<400> SEQUENCE: 546

Lys Ile Ile Glu Leu Lys
1 5

<210> SEQ ID NO 547
<211> LENGTH: 21
<212> TYPE: PRT
<213> ORGANISM: Homo sapiens

<400> SEQUENCE: 547

Leu Cys Cys Pro Val Ala Leu Ala Gln Asp Val Thr Gly Ala Leu Glu
1 5 10 15

Asp Ala Leu Ala Lys
20

<210> SEQ ID NO 548
<211> LENGTH: 14
<212> TYPE: PRT
<213> ORGANISM: Homo sapiens

<400> SEQUENCE: 548

Pro Ala Ile Ala His Leu Ile His Ser Leu Asn Pro Val Arg
1 5 10

<210> SEQ ID NO 549
<211> LENGTH: 18
<212> TYPE: PRT
<213> ORGANISM: Homo sapiens

<400> SEQUENCE: 549

Pro Ser Ser Thr Pro Thr Thr His Phe Ser Ala Ser Ser Thr Thr Leu
1               5                   10                  15

Gly Arg

<210> SEQ ID NO 550
<211> LENGTH: 18
<212> TYPE: PRT
<213> ORGANISM: Homo sapiens

<400> SEQUENCE: 550

Pro Ser Ser Thr Pro Thr Thr His Phe Ser Ala Ser Ser Thr Thr Leu
1               5                   10                  15

Gly Arg

<210> SEQ ID NO 551
<211> LENGTH: 18
<212> TYPE: PRT
<213> ORGANISM: Homo sapiens

<400> SEQUENCE: 551

Pro Ser Ser Thr Pro Thr Thr His Phe Ser Ala Ser Ser Thr Thr Leu
1               5                   10                  15

Gly Arg

<210> SEQ ID NO 552
<211> LENGTH: 18
<212> TYPE: PRT
<213> ORGANISM: Homo sapiens

<400> SEQUENCE: 552

Pro Ser Ser Thr Pro Thr Thr His Phe Ser Ala Ser Ser Thr Thr Leu
1               5                   10                  15

Gly Arg

<210> SEQ ID NO 553
<211> LENGTH: 18
<212> TYPE: PRT
<213> ORGANISM: Homo sapiens

<400> SEQUENCE: 553

Pro Ser Ser Thr Pro Thr Thr His Phe Ser Ala Ser Ser Thr Thr Leu
1               5                   10                  15

Gly Arg

<210> SEQ ID NO 554
<211> LENGTH: 18
<212> TYPE: PRT
<213> ORGANISM: Homo sapiens

<400> SEQUENCE: 554

Pro Ser Ser Thr Pro Thr Thr His Phe Ser Ala Ser Ser Thr Thr Leu
1               5                   10                  15

Gly Arg

<210> SEQ ID NO 555
<211> LENGTH: 18
<212> TYPE: PRT
<213> ORGANISM: Homo sapiens

<400> SEQUENCE: 555

Pro Ser Ser Thr Pro Thr Thr His Phe Ser Ala Ser Ser Thr Thr Leu
1 5 10 15

Gly Arg

<210> SEQ ID NO 556
<211> LENGTH: 15
<212> TYPE: PRT
<213> ORGANISM: Homo sapiens

<400> SEQUENCE: 556

Gln Phe Val Thr Gly Ile Ile Asp Ser Leu Thr Ile Ser Pro Lys
1 5 10 15

<210> SEQ ID NO 557
<211> LENGTH: 14
<212> TYPE: PRT
<213> ORGANISM: Homo sapiens

<400> SEQUENCE: 557

Ser Glu Ala Val Leu Gln Ser Pro Glu Phe Ala Ile Phe Arg
1 5 10

<210> SEQ ID NO 558
<211> LENGTH: 13
<212> TYPE: PRT
<213> ORGANISM: Homo sapiens

<400> SEQUENCE: 558

Thr Thr Gln Gly Leu Thr Ala Leu Leu Leu Ser Leu Lys
1 5 10

<210> SEQ ID NO 559
<211> LENGTH: 18
<212> TYPE: PRT
<213> ORGANISM: Homo sapiens

<400> SEQUENCE: 559

Val Pro Leu Ser Val Gln Leu Lys Pro Glu Val Ser Pro Thr Gln Asp
1 5 10 15

Ile Arg

<210> SEQ ID NO 560
<211> LENGTH: 7
<212> TYPE: PRT
<213> ORGANISM: Homo sapiens

<400> SEQUENCE: 560

Val Thr Ala Ile Asp Phe Arg
1 5

<210> SEQ ID NO 561
<211> LENGTH: 17
<212> TYPE: PRT
<213> ORGANISM: Homo sapiens

<400> SEQUENCE: 561

Tyr Leu Ile Phe Pro Asn Pro Val Cys Leu Glu Pro Gly Ile Ser Tyr 1 5 10 15

Lys

<210> SEQ ID NO 562
<211> LENGTH: 13
<212> TYPE: PRT
<213> ORGANISM: Homo sapiens

<400> SEQUENCE: 562

Tyr Arg Leu Pro Asn Thr Leu Lys Pro Asp Ser Tyr Arg
1 5 10

<210> SEQ ID NO 563
<211> LENGTH: 10
<212> TYPE: PRT
<213> ORGANISM: Homo sapiens

<400> SEQUENCE: 563

Ala Phe Leu Leu Ser Leu Ala Ala Leu Arg
1 5 10

<210> SEQ ID NO 564
<211> LENGTH: 18
<212> TYPE: PRT
<213> ORGANISM: Homo sapiens

<400> SEQUENCE: 564

Asp Leu Ala Gln Tyr Ser Ser Asn Asp Ala Val Val Glu Thr Ser Leu
1 5 10 15

Thr Lys

<210> SEQ ID NO 565
<211> LENGTH: 21
<212> TYPE: PRT
<213> ORGANISM: Homo sapiens

<400> SEQUENCE: 565

Asp Arg Leu Pro Gln Glu Pro Gly Arg Glu Gln Val Val Glu Asp Arg
1 5 10 15

Pro Val Gly Gly Arg
20

<210> SEQ ID NO 566
<211> LENGTH: 14
<212> TYPE: PRT
<213> ORGANISM: Homo sapiens

<400> SEQUENCE: 566

Glu Ala Ile Gln His Pro Ala Asp Glu Lys Leu Gln Glu Lys
1 5 10

<210> SEQ ID NO 567
<211> LENGTH: 9
<212> TYPE: PRT
<213> ORGANISM: Homo sapiens

<400> SEQUENCE: 567

Glu Phe Gln Asn Asn Pro Asn Pro Arg
1 5

<210> SEQ ID NO 568
<211> LENGTH: 10
<212> TYPE: PRT

<213> ORGANISM: Homo sapiens

<400> SEQUENCE: 568

Glu Leu Ser Ala Ala Leu Gln Asp Lys Lys
1 5 10

<210> SEQ ID NO 569
<211> LENGTH: 9
<212> TYPE: PRT
<213> ORGANISM: Homo sapiens

<400> SEQUENCE: 569

Glu Leu Ser Gly Ser Gly Leu Glu Arg
1 5

<210> SEQ ID NO 570
<211> LENGTH: 7
<212> TYPE: PRT
<213> ORGANISM: Homo sapiens

<400> SEQUENCE: 570

Glu Leu Trp Ile Leu Asn Arg
1 5

<210> SEQ ID NO 571
<211> LENGTH: 15
<212> TYPE: PRT
<213> ORGANISM: Homo sapiens

<400> SEQUENCE: 571

Phe Ser Thr Glu Tyr Glu Leu Gln Gln Leu Glu Gln Phe Lys Lys
1 5 10 15

<210> SEQ ID NO 572
<211> LENGTH: 9
<212> TYPE: PRT
<213> ORGANISM: Homo sapiens

<400> SEQUENCE: 572

Gly Pro Ala Leu Cys Gly Ser Gln Arg
1 5

<210> SEQ ID NO 573
<211> LENGTH: 18
<212> TYPE: PRT
<213> ORGANISM: Homo sapiens

<400> SEQUENCE: 573

Gly Pro Leu Glu Pro Gly Pro Pro Lys Pro Gly Val Pro Gln Glu Pro
1 5 10 15

Gly Arg

<210> SEQ ID NO 574
<211> LENGTH: 17
<212> TYPE: PRT
<213> ORGANISM: Homo sapiens

<400> SEQUENCE: 574

Gly Ser Leu Tyr Gln Cys Asp Tyr Ser Thr Gly Ser Cys Glu Pro Ile
1 5 10 15

Arg

<210> SEQ ID NO 575

<211> LENGTH: 7
<212> TYPE: PRT
<213> ORGANISM: Homo sapiens

<400> SEQUENCE: 575

Ile Gln Thr Gln Leu Gln Arg
1               5

<210> SEQ ID NO 576
<211> LENGTH: 19
<212> TYPE: PRT
<213> ORGANISM: Homo sapiens

<400> SEQUENCE: 576

Lys Asn Ser Ser Ile Ile Gly Asp Tyr Lys Gln Ile Cys Ser Gln Leu
1               5                   10                  15

Ser Glu Arg

<210> SEQ ID NO 577
<211> LENGTH: 10
<212> TYPE: PRT
<213> ORGANISM: Homo sapiens

<400> SEQUENCE: 577

Leu Glu Ile Asn Phe Glu Glu Leu Leu Lys
1               5                   10

<210> SEQ ID NO 578
<211> LENGTH: 13
<212> TYPE: PRT
<213> ORGANISM: Homo sapiens

<400> SEQUENCE: 578

Leu Ile Val Pro Glu Pro Asp Val Asp Phe Asp Ala Lys
1               5                   10

<210> SEQ ID NO 579
<211> LENGTH: 22
<212> TYPE: PRT
<213> ORGANISM: Homo sapiens

<400> SEQUENCE: 579

Leu Val Gly Pro Glu Gly Phe Val Val Thr Glu Ala Gly Phe Gly Ala
1               5                   10                  15

Asp Ile Gly Met Glu Lys
            20

<210> SEQ ID NO 580
<211> LENGTH: 14
<212> TYPE: PRT
<213> ORGANISM: Homo sapiens

<400> SEQUENCE: 580

Gln Glu His Cys Gly Cys Tyr Thr Leu Leu Val Glu Asn Lys
1               5                   10

<210> SEQ ID NO 581
<211> LENGTH: 14
<212> TYPE: PRT
<213> ORGANISM: Homo sapiens

<400> SEQUENCE: 581

Arg Ser Gln Ala Gly Val Ser Ser Gly Ala Pro Pro Gly Arg
1               5                   10

<210> SEQ ID NO 582
<211> LENGTH: 22
<212> TYPE: PRT
<213> ORGANISM: Homo sapiens

<400> SEQUENCE: 582

Ser Pro Gly Ser Thr Pro Thr Thr His Phe Pro Ala Ser Ser Thr Thr
1 5 10 15

Ser Gly His Ser Glu Lys
20

<210> SEQ ID NO 583
<211> LENGTH: 22
<212> TYPE: PRT
<213> ORGANISM: Homo sapiens

<400> SEQUENCE: 583

Ser Pro Gly Ser Thr Pro Thr Thr His Phe Pro Ala Ser Ser Thr Thr
1 5 10 15

Ser Gly His Ser Glu Lys
20

<210> SEQ ID NO 584
<211> LENGTH: 22
<212> TYPE: PRT
<213> ORGANISM: Homo sapiens

<400> SEQUENCE: 584

Ser Pro Gly Ser Thr Pro Thr Thr His Phe Pro Ala Ser Ser Thr Thr
1 5 10 15

Ser Gly His Ser Glu Lys
20

<210> SEQ ID NO 585
<211> LENGTH: 22
<212> TYPE: PRT
<213> ORGANISM: Homo sapiens

<400> SEQUENCE: 585

Ser Pro Gly Ser Thr Pro Thr Thr His Phe Pro Ala Ser Ser Thr Thr
1 5 10 15

Ser Gly His Ser Glu Lys
20

<210> SEQ ID NO 586
<211> LENGTH: 10
<212> TYPE: PRT
<213> ORGANISM: Homo sapiens

<400> SEQUENCE: 586

Val Leu Ser Gln Ile Asp Val Ala Gln Lys
1 5 10

<210> SEQ ID NO 587
<211> LENGTH: 15
<212> TYPE: PRT
<213> ORGANISM: Homo sapiens

<400> SEQUENCE: 587

Tyr Gly Gly Met Phe Cys Asn Val Glu Gly Ala Phe Glu Ser Lys
1 5 10 15

<210> SEQ ID NO 588
<211> LENGTH: 30
<212> TYPE: PRT
<213> ORGANISM: Homo sapiens

<400> SEQUENCE: 588

Ala Thr Val Val Val Glu Ala Thr Glu Pro Glu Pro Ser Gly Ser Ile
1 5 10 15

Ala Asn Pro Ala Ala Ser Thr Ser Pro Ser Leu Ser His Arg
20 25 30

<210> SEQ ID NO 589
<211> LENGTH: 10
<212> TYPE: PRT
<213> ORGANISM: Homo sapiens

<400> SEQUENCE: 589

Glu Met Thr Ala Asp Val Ile Glu Leu Lys
1 5 10

<210> SEQ ID NO 590
<211> LENGTH: 21
<212> TYPE: PRT
<213> ORGANISM: Homo sapiens

<400> SEQUENCE: 590

Gly Glu Gln Gly Phe Met Gly Asn Thr Gly Pro Thr Gly Ala Val Gly
1 5 10 15

Asp Arg Gly Pro Lys
20

<210> SEQ ID NO 591
<211> LENGTH: 15
<212> TYPE: PRT
<213> ORGANISM: Homo sapiens

<400> SEQUENCE: 591

Leu Ala Glu Ala Glu Leu Glu Tyr Asn Pro Glu His Val Ser Arg
1 5 10 15

<210> SEQ ID NO 592
<211> LENGTH: 28
<212> TYPE: PRT
<213> ORGANISM: Homo sapiens

<400> SEQUENCE: 592

Leu Glu Ser Glu Glu Asp Val Ser Gln Ala Phe Leu Glu Ala Val Ala
1 5 10 15

Glu Glu Lys Pro His Val Lys Pro Tyr Phe Ser Lys
20 25

<210> SEQ ID NO 593
<211> LENGTH: 12
<212> TYPE: PRT
<213> ORGANISM: Homo sapiens

<400> SEQUENCE: 593

Leu Met Cys Glu Leu Gly Asn Asp Val Ile Asn Arg
1 5 10

<210> SEQ ID NO 594
<211> LENGTH: 11
<212> TYPE: PRT

<213> ORGANISM: Homo sapiens

<400> SEQUENCE: 594

Gln Gln Gln Asp Tyr Trp Leu Ile Asp Val Arg
1 5 10

<210> SEQ ID NO 595
<211> LENGTH: 17
<212> TYPE: PRT
<213> ORGANISM: Homo sapiens

<400> SEQUENCE: 595

Ser Ser Glu Gly Gly Thr Ala Ala Gly Ala Gly Leu Asp Ser Leu His
1 5 10 15

Lys

<210> SEQ ID NO 596
<211> LENGTH: 12
<212> TYPE: PRT
<213> ORGANISM: Homo sapiens

<400> SEQUENCE: 596

Ser Tyr Lys Pro Val Phe Trp Ser Pro Ser Ser Arg
1 5 10

<210> SEQ ID NO 597
<211> LENGTH: 25
<212> TYPE: PRT
<213> ORGANISM: Homo sapiens

<400> SEQUENCE: 597

Thr Ala His Leu Asp Glu Glu Val Asn Lys Gly Asp Ile Leu Val Val
1 5 10 15

Ala Thr Gly Gln Pro Glu Met Val Lys
20 25

<210> SEQ ID NO 598
<211> LENGTH: 10
<212> TYPE: PRT
<213> ORGANISM: Homo sapiens

<400> SEQUENCE: 598

Thr Arg Pro Asp Gly Asn Cys Phe Tyr Arg
1 5 10

<210> SEQ ID NO 599
<211> LENGTH: 8
<212> TYPE: PRT
<213> ORGANISM: Homo sapiens

<400> SEQUENCE: 599

Thr Ser Gly Gln Cys Leu Cys Arg
1 5

<210> SEQ ID NO 600
<211> LENGTH: 7
<212> TYPE: PRT
<213> ORGANISM: Homo sapiens

<400> SEQUENCE: 600

Ala Phe Cys Val Ala Asn Lys
1 5

<210> SEQ ID NO 601
<211> LENGTH: 9
<212> TYPE: PRT
<213> ORGANISM: Homo sapiens

<400> SEQUENCE: 601

Ala Met Ile Ser Gly Leu Ser Gly Arg
1 5

<210> SEQ ID NO 602
<211> LENGTH: 22
<212> TYPE: PRT
<213> ORGANISM: Homo sapiens

<400> SEQUENCE: 602

Ala Val Glu Ser Ser Lys Pro Leu Ser Asn Ala Gln Pro Ser Gly Pro
1 5 10 15

Leu Lys Pro Val Gly Asn
20

<210> SEQ ID NO 603
<211> LENGTH: 19
<212> TYPE: PRT
<213> ORGANISM: Homo sapiens

<400> SEQUENCE: 603

Ala Tyr His Ser Phe Leu Val Glu Pro Ile Ser Cys His Ala Trp Asn
1 5 10 15

Lys Asp Arg

<210> SEQ ID NO 604
<211> LENGTH: 11
<212> TYPE: PRT
<213> ORGANISM: Homo sapiens

<400> SEQUENCE: 604

Glu Gly Val Val Asp Ile Tyr Asn Cys Val Lys
1 5 10

<210> SEQ ID NO 605
<211> LENGTH: 36
<212> TYPE: PRT
<213> ORGANISM: Homo sapiens

<400> SEQUENCE: 605

Gly Thr Trp Ile His Pro Glu Ile Asp Asn Pro Glu Tyr Ser Pro Asp
1 5 10 15

Pro Ser Ile Tyr Ala Tyr Asp Asn Phe Gly Val Leu Gly Leu Asp Leu
20 25 30

Trp Gln Val Lys
35

<210> SEQ ID NO 606
<211> LENGTH: 10
<212> TYPE: PRT
<213> ORGANISM: Homo sapiens

<400> SEQUENCE: 606

His Leu Thr Gln Ala Val Cys Thr Val Lys
1 5 10

<210> SEQ ID NO 607
<211> LENGTH: 16

<212> TYPE: PRT
<213> ORGANISM: Homo sapiens

<400> SEQUENCE: 607

Ile Thr Ile Ser Pro Leu Gln Glu Leu Thr Leu Tyr Asn Pro Glu Arg
1 5 10 15

<210> SEQ ID NO 608
<211> LENGTH: 16
<212> TYPE: PRT
<213> ORGANISM: Homo sapiens

<400> SEQUENCE: 608

Leu Ala Cys Glu Ser Ala Ser Ser Thr Glu Val Ser Gly Ala Leu Lys
1 5 10 15

<210> SEQ ID NO 609
<211> LENGTH: 14
<212> TYPE: PRT
<213> ORGANISM: Homo sapiens

<400> SEQUENCE: 609

Leu Asp Cys Thr Gln Cys Leu Gln His Pro Trp Leu Met Lys
1 5 10

<210> SEQ ID NO 610
<211> LENGTH: 29
<212> TYPE: PRT
<213> ORGANISM: Homo sapiens

<400> SEQUENCE: 610

Leu Asp Glu Glu Ala Glu Asn Leu Val Ala Thr Val Val Pro Thr His
1 5 10 15

Leu Ala Ala Ala Val Pro Glu Val Ala Val Tyr Leu Lys
20 25

<210> SEQ ID NO 611
<211> LENGTH: 45
<212> TYPE: PRT
<213> ORGANISM: Homo sapiens

<400> SEQUENCE: 611

Leu Pro Glu Asp Asp Glu Pro Pro Ala Arg Pro Pro Pro Pro Pro Pro
1 5 10 15

Ala Ser Val Ser Pro Gln Ala Glu Pro Val Trp Thr Pro Pro Ala Pro
20 25 30

Ala Pro Ala Ala Pro Pro Ser Thr Pro Ala Ala Pro Lys
35 40 45

<210> SEQ ID NO 612
<211> LENGTH: 11
<212> TYPE: PRT
<213> ORGANISM: Homo sapiens

<400> SEQUENCE: 612

Leu Pro Asn Thr Leu Lys Pro Asp Ser Tyr Arg
1 5 10

<210> SEQ ID NO 613
<211> LENGTH: 11
<212> TYPE: PRT
<213> ORGANISM: Homo sapiens

<400> SEQUENCE: 613

Leu Ser Ser Thr Gln Gln Ser Leu Ala Glu Lys
1 5 10

<210> SEQ ID NO 614
<211> LENGTH: 10
<212> TYPE: PRT
<213> ORGANISM: Homo sapiens

<400> SEQUENCE: 614

Leu Val Ala Leu Glu Thr Gly Ile Gln Lys
1 5 10

<210> SEQ ID NO 615
<211> LENGTH: 16
<212> TYPE: PRT
<213> ORGANISM: Homo sapiens

<400> SEQUENCE: 615

Met His Gly Gly Gly Pro Thr Val Thr Ala Gly Leu Pro Leu Pro Lys
1 5 10 15

<210> SEQ ID NO 616
<211> LENGTH: 16
<212> TYPE: PRT
<213> ORGANISM: Homo sapiens

<400> SEQUENCE: 616

Gln Gln Ala Leu Glu Leu Val Val Gln Glu Val Ser Ser Val Leu Arg
1 5 10 15

<210> SEQ ID NO 617
<211> LENGTH: 12
<212> TYPE: PRT
<213> ORGANISM: Homo sapiens

<400> SEQUENCE: 617

Gln Ser Met Ala Phe Ser Ile Leu Asn Thr Pro Lys
1 5 10

<210> SEQ ID NO 618
<211> LENGTH: 8
<212> TYPE: PRT
<213> ORGANISM: Homo sapiens

<400> SEQUENCE: 618

Ser Ser Asn Leu Leu Asp Leu Lys
1 5

<210> SEQ ID NO 619
<211> LENGTH: 7
<212> TYPE: PRT
<213> ORGANISM: Homo sapiens

<400> SEQUENCE: 619

Val Leu Gln Asp Gln Leu Lys
1 5

<210> SEQ ID NO 620
<211> LENGTH: 16
<212> TYPE: PRT
<213> ORGANISM: Homo sapiens

<400> SEQUENCE: 620

Trp Val Ser His Asp Ser Thr Val Cys Leu Ala Asp Ala Asp Lys Lys 1 5 10 15

<210> SEQ ID NO 621
<211> LENGTH: 10
<212> TYPE: PRT
<213> ORGANISM: Homo sapiens

<400> SEQUENCE: 621

Ala Ala Gln Leu Asp Gly Leu Glu Ala Arg
1 5 10

<210> SEQ ID NO 622
<211> LENGTH: 11
<212> TYPE: PRT
<213> ORGANISM: Homo sapiens

<400> SEQUENCE: 622

Ala Asn Ala Leu Ala Ser Ala Thr Cys Glu Arg
1 5 10

<210> SEQ ID NO 623
<211> LENGTH: 13
<212> TYPE: PRT
<213> ORGANISM: Homo sapiens

<400> SEQUENCE: 623

Ala Thr Asp Asn Glu Pro Ser Gln Phe Ser Glu Pro Arg
1 5 10

<210> SEQ ID NO 624
<211> LENGTH: 11
<212> TYPE: PRT
<213> ORGANISM: Homo sapiens

<400> SEQUENCE: 624

Cys Gly Phe Ser Glu Leu Tyr Ser Trp Gln Arg
1 5 10

<210> SEQ ID NO 625
<211> LENGTH: 9
<212> TYPE: PRT
<213> ORGANISM: Homo sapiens

<400> SEQUENCE: 625

Asp Leu Leu Gln Ala Ala Gln Asp Lys
1 5

<210> SEQ ID NO 626
<211> LENGTH: 15
<212> TYPE: PRT
<213> ORGANISM: Homo sapiens

<400> SEQUENCE: 626

Glu Pro Ala Pro Ala Ser Pro Ala Pro Ala Gly Val Glu Ile Arg
1 5 10 15

<210> SEQ ID NO 627
<211> LENGTH: 8
<212> TYPE: PRT
<213> ORGANISM: Homo sapiens

<400> SEQUENCE: 627

Glu Tyr Glu Leu Phe Glu Phe Arg
1 5

<210> SEQ ID NO 628
<211> LENGTH: 27
<212> TYPE: PRT
<213> ORGANISM: Homo sapiens

<400> SEQUENCE: 628

His Lys Pro Gly Ile Val Gln Glu Thr Thr Phe Asp Leu Gly Gly Asp
1 5 10 15

Ile His Ser Gly Thr Ala Leu Pro Thr Ser Lys
20 25

<210> SEQ ID NO 629
<211> LENGTH: 13
<212> TYPE: PRT
<213> ORGANISM: Homo sapiens

<400> SEQUENCE: 629

Ile Trp Asp Leu Gln Gly Ser Glu Glu Pro Val Phe Arg
1 5 10

<210> SEQ ID NO 630
<211> LENGTH: 11
<212> TYPE: PRT
<213> ORGANISM: Homo sapiens

<400> SEQUENCE: 630

Leu Phe Gly Asp Val Glu Ala Ser Leu Gly Arg
1 5 10

<210> SEQ ID NO 631
<211> LENGTH: 12
<212> TYPE: PRT
<213> ORGANISM: Homo sapiens

<400> SEQUENCE: 631

Leu His Thr Leu Gly Asp Asn Leu Leu Asp Pro Arg
1 5 10

<210> SEQ ID NO 632
<211> LENGTH: 8
<212> TYPE: PRT
<213> ORGANISM: Homo sapiens

<400> SEQUENCE: 632

Arg Phe Ser Asp Ile Gln Ile Arg
1 5

<210> SEQ ID NO 633
<211> LENGTH: 8
<212> TYPE: PRT
<213> ORGANISM: Homo sapiens

<400> SEQUENCE: 633

Ser Glu Val Tyr Gly Pro Met Lys
1 5

<210> SEQ ID NO 634
<211> LENGTH: 9
<212> TYPE: PRT
<213> ORGANISM: Homo sapiens

<400> SEQUENCE: 634

Ser Leu Ser Glu Ser Ala Ala Thr Arg
1 5

<210> SEQ ID NO 635
<211> LENGTH: 15
<212> TYPE: PRT
<213> ORGANISM: Homo sapiens

<400> SEQUENCE: 635

Val Thr Cys Val Glu Met Glu Pro Leu Ala Glu Tyr Val Val Arg
1 5 10 15

<210> SEQ ID NO 636
<211> LENGTH: 10
<212> TYPE: PRT
<213> ORGANISM: Homo sapiens

<400> SEQUENCE: 636

Tyr Leu Phe Glu Glu Asp Asn Leu Leu Arg
1 5 10

<210> SEQ ID NO 637
<211> LENGTH: 12
<212> TYPE: PRT
<213> ORGANISM: Homo sapiens

<400> SEQUENCE: 637

Ala Ala Glu Cys Leu Asp Val Asp Glu Cys His Arg
1 5 10

<210> SEQ ID NO 638
<211> LENGTH: 8
<212> TYPE: PRT
<213> ORGANISM: Homo sapiens

<400> SEQUENCE: 638

Ala Gly Met Ser Ser Leu Lys Gly
1 5

<210> SEQ ID NO 639
<211> LENGTH: 9
<212> TYPE: PRT
<213> ORGANISM: Homo sapiens

<400> SEQUENCE: 639

Ala Leu Ala Ser Ala Thr Cys Glu Arg
1 5

<210> SEQ ID NO 640
<211> LENGTH: 17
<212> TYPE: PRT
<213> ORGANISM: Homo sapiens

<400> SEQUENCE: 640

Cys Asp Ser His Asp Asp Pro Ala Leu Gly Leu Val Ser Gly Gln Cys
1 5 10 15

Arg

<210> SEQ ID NO 641
<211> LENGTH: 11
<212> TYPE: PRT
<213> ORGANISM: Homo sapiens

<400> SEQUENCE: 641

Asp Cys Ser Ile Ala Leu Pro Tyr Val Cys Lys
1 5 10

<210> SEQ ID NO 642
<211> LENGTH: 20
<212> TYPE: PRT
<213> ORGANISM: Homo sapiens

<400> SEQUENCE: 642

Asp Ile Ser Leu Gln Gly Pro Gly Leu Ala Pro Glu His Cys Tyr Ile
1 5 10 15

Glu Asn Leu Arg
20

<210> SEQ ID NO 643
<211> LENGTH: 21
<212> TYPE: PRT
<213> ORGANISM: Homo sapiens

<400> SEQUENCE: 643

Phe Val Leu Asp His Glu Asp Gly Leu Asn Leu Asn Glu Asp Leu Glu
1 5 10 15

Asn Phe Leu Gln Lys
20

<210> SEQ ID NO 644
<211> LENGTH: 31
<212> TYPE: PRT
<213> ORGANISM: Homo sapiens

<400> SEQUENCE: 644

Gly Ala Asn Gln His Ala Thr Asp Glu Glu Gly Lys Asp Pro Leu Ser
1 5 10 15

Ile Ala Val Glu Ala Ala Asn Ala Asp Ile Val Thr Leu Leu Arg
20 25 30

<210> SEQ ID NO 645
<211> LENGTH: 17
<212> TYPE: PRT
<213> ORGANISM: Homo sapiens

<400> SEQUENCE: 645

Gly Phe Ser His Leu Glu Ala Leu Leu Asp Asp Ser Lys Glu Leu Gln
1 5 10 15

Arg

<210> SEQ ID NO 646
<211> LENGTH: 13
<212> TYPE: PRT
<213> ORGANISM: Homo sapiens

<400> SEQUENCE: 646

Gly Ser Gly Val Ser Asn Phe Ala Gln Leu Ile Val Arg
1 5 10

<210> SEQ ID NO 647
<211> LENGTH: 13
<212> TYPE: PRT
<213> ORGANISM: Homo sapiens

<400> SEQUENCE: 647

Ile Ile Asn Asp Ala Phe Asn Leu Ala Ser Ala His Lys
1 5 10

<210> SEQ ID NO 648
<211> LENGTH: 11
<212> TYPE: PRT
<213> ORGANISM: Homo sapiens

<400> SEQUENCE: 648

Lys Val Val Gln Ser Leu Glu Gln Thr Ala Arg
1               5                   10

<210> SEQ ID NO 649
<211> LENGTH: 18
<212> TYPE: PRT
<213> ORGANISM: Homo sapiens

<400> SEQUENCE: 649

Gln Pro Ala Val Glu Glu Pro Ala Glu Val Thr Ala Thr Val Leu Ala
1               5                   10                  15

Ser Arg

<210> SEQ ID NO 650
<211> LENGTH: 15
<212> TYPE: PRT
<213> ORGANISM: Homo sapiens

<400> SEQUENCE: 650

Gln Thr Gln Val Leu Gly Leu Thr Gln Thr Cys Glu Thr Leu Lys
1               5                   10                  15

<210> SEQ ID NO 651
<211> LENGTH: 18
<212> TYPE: PRT
<213> ORGANISM: Homo sapiens

<400> SEQUENCE: 651

Arg Val Glu Asp Ala Tyr Ile Leu Thr Cys Asn Val Ser Leu Glu Tyr
1               5                   10                  15

Glu Lys

<210> SEQ ID NO 652
<211> LENGTH: 12
<212> TYPE: PRT
<213> ORGANISM: Homo sapiens

<400> SEQUENCE: 652

Thr Leu Asp Phe Asp Ala Leu Ser Val Gly Gln Arg
1               5                   10

<210> SEQ ID NO 653
<211> LENGTH: 7
<212> TYPE: PRT
<213> ORGANISM: Homo sapiens

<400> SEQUENCE: 653

Val Val Asn Ala Met Gly Lys
1               5

<210> SEQ ID NO 654
<211> LENGTH: 22
<212> TYPE: PRT
<213> ORGANISM: Homo sapiens

<400> SEQUENCE: 654

Ala Lys Ile Asp Asp Pro Thr Asp Ser Lys Pro Glu Asp Trp Asp Lys
1               5                   10                  15

Pro Glu His Ile Pro Asp
20

<210> SEQ ID NO 655
<211> LENGTH: 14
<212> TYPE: PRT
<213> ORGANISM: Homo sapiens

<400> SEQUENCE: 655

Ala Leu Glu Gln Leu Leu Thr Glu Leu Asp Asp Phe Leu Lys
1 5 10

<210> SEQ ID NO 656
<211> LENGTH: 10
<212> TYPE: PRT
<213> ORGANISM: Homo sapiens

<400> SEQUENCE: 656

Ala Ser Lys Pro Glu Asp Trp Asp Glu Arg
1 5 10

<210> SEQ ID NO 657
<211> LENGTH: 13
<212> TYPE: PRT
<213> ORGANISM: Homo sapiens

<400> SEQUENCE: 657

Asp Leu Asn Gln Leu Phe Gln Gln Asp Ser Ser Ser Arg
1 5 10

<210> SEQ ID NO 658
<211> LENGTH: 37
<212> TYPE: PRT
<213> ORGANISM: Homo sapiens

<400> SEQUENCE: 658

Glu Thr Pro Gly Arg Pro Pro Asp Pro Thr Gly Ala Pro Leu Pro Gly
1 5 10 15

Pro Thr Gly Asp Pro Val Lys Pro Thr Ser Leu Glu Thr Pro Ser Ala
20 25 30

Pro Leu Leu Ser Arg
35

<210> SEQ ID NO 659
<211> LENGTH: 22
<212> TYPE: PRT
<213> ORGANISM: Homo sapiens

<400> SEQUENCE: 659

Gly Ser Ala Cys Glu Glu Asp Val Asp Glu Cys Ala Gln Glu Pro Pro
1 5 10 15

Pro Cys Gly Pro Gly Arg
20

<210> SEQ ID NO 660
<211> LENGTH: 19
<212> TYPE: PRT
<213> ORGANISM: Homo sapiens

<400> SEQUENCE: 660

Lys Ala Ser Ser Glu Gly Gly Thr Ala Ala Gly Ala Gly Leu Asp Ser
1 5 10 15

Leu His Lys

<210> SEQ ID NO 661
<211> LENGTH: 10
<212> TYPE: PRT
<213> ORGANISM: Homo sapiens

<400> SEQUENCE: 661

Leu Gly Phe Ile Thr Asn Asn Ser Ser Lys
1 5 10

<210> SEQ ID NO 662
<211> LENGTH: 12
<212> TYPE: PRT
<213> ORGANISM: Homo sapiens

<400> SEQUENCE: 662

Leu Pro Ser His Ser Asp Phe Leu Ala Glu Leu Arg
1 5 10

<210> SEQ ID NO 663
<211> LENGTH: 10
<212> TYPE: PRT
<213> ORGANISM: Homo sapiens

<400> SEQUENCE: 663

Leu Gln Asp Val His Val Ala Glu Gly Lys
1 5 10

<210> SEQ ID NO 664
<211> LENGTH: 11
<212> TYPE: PRT
<213> ORGANISM: Homo sapiens

<400> SEQUENCE: 664

Leu Val Thr Cys Thr Gly Tyr His Gln Val Arg
1 5 10

<210> SEQ ID NO 665
<211> LENGTH: 9
<212> TYPE: PRT
<213> ORGANISM: Homo sapiens

<400> SEQUENCE: 665

Ser Ile Gln Leu Pro Thr Thr Val Arg
1 5

<210> SEQ ID NO 666
<211> LENGTH: 7
<212> TYPE: PRT
<213> ORGANISM: Homo sapiens

<400> SEQUENCE: 666

Val Leu Ser Glu Leu Gly Arg
1 5

<210> SEQ ID NO 667
<211> LENGTH: 15
<212> TYPE: PRT
<213> ORGANISM: Homo sapiens

<400> SEQUENCE: 667

Trp Ala Pro Asn Glu Asn Lys Phe Ala Val Gly Ser Gly Ser Arg
1 5 10 15

<210> SEQ ID NO 668
<211> LENGTH: 23
<212> TYPE: PRT
<213> ORGANISM: Homo sapiens

<400> SEQUENCE: 668

Ala Gln Glu Leu Gln Gln Thr Gly Val Leu Gly Ala Phe Glu Ser Ser
1               5                   10                  15

Phe Trp His Met Gln Glu Lys
            20

<210> SEQ ID NO 669
<211> LENGTH: 28
<212> TYPE: PRT
<213> ORGANISM: Homo sapiens

<400> SEQUENCE: 669

Ala Ser Ala Ala Ala Ala Ala Gly Gly Gly Ala Thr Gly His Pro Gly
1               5                   10                  15

Gly Gly Gln Gly Ala Glu Asn Pro Ala Gly Leu Lys
            20                  25

<210> SEQ ID NO 670
<211> LENGTH: 17
<212> TYPE: PRT
<213> ORGANISM: Homo sapiens

<400> SEQUENCE: 670

Glu Ala Glu Asn Phe His Glu Glu Asp Asp Val Asp Val Arg Pro Ala
1               5                   10                  15

Arg

<210> SEQ ID NO 671
<211> LENGTH: 14
<212> TYPE: PRT
<213> ORGANISM: Homo sapiens

<400> SEQUENCE: 671

Glu Arg Leu Pro Ser His Ser Asp Phe Leu Ala Glu Leu Arg
1               5                   10

<210> SEQ ID NO 672
<211> LENGTH: 18
<212> TYPE: PRT
<213> ORGANISM: Homo sapiens

<400> SEQUENCE: 672

Glu Trp Ser Leu Glu Ser Ser Pro Ala Gln Asn Trp Thr Pro Pro Gln
1               5                   10                  15

Pro Arg

<210> SEQ ID NO 673
<211> LENGTH: 15
<212> TYPE: PRT
<213> ORGANISM: Homo sapiens

<400> SEQUENCE: 673

Phe Tyr Ala Leu Ser Ala Ser Phe Glu Pro Phe Ser Asn Lys Gly
1               5                   10                  15

<210> SEQ ID NO 674
<211> LENGTH: 24

<212> TYPE: PRT
<213> ORGANISM: Homo sapiens

<400> SEQUENCE: 674

Gly Ile Ser Leu Asn Pro Glu Gln Trp Ser Gln Leu Lys Glu Gln Ile
1 5 10 15

Ser Asp Ile Asp Asp Ala Val Arg
20

<210> SEQ ID NO 675
<211> LENGTH: 14
<212> TYPE: PRT
<213> ORGANISM: Homo sapiens

<400> SEQUENCE: 675

His Pro Leu Leu Val Gly His Met Pro Val Met Val Ala Lys
1 5 10

<210> SEQ ID NO 676
<211> LENGTH: 12
<212> TYPE: PRT
<213> ORGANISM: Homo sapiens

<400> SEQUENCE: 676

Ile Ala His Gly Asn Ser Ser Ile Ile Ala Asp Arg
1 5 10

<210> SEQ ID NO 677
<211> LENGTH: 13
<212> TYPE: PRT
<213> ORGANISM: Homo sapiens

<400> SEQUENCE: 677

Ile Tyr Ala Asp Ser Leu Lys Pro Asn Ile Pro Tyr Lys
1 5 10

<210> SEQ ID NO 678
<211> LENGTH: 12
<212> TYPE: PRT
<213> ORGANISM: Homo sapiens

<400> SEQUENCE: 678

Leu Ala Ile Leu Asp Ser Gln Ala Gly Gln Ile Arg
1 5 10

<210> SEQ ID NO 679
<211> LENGTH: 13
<212> TYPE: PRT
<213> ORGANISM: Homo sapiens

<400> SEQUENCE: 679

Asn Met Val Val Asp Asp Asp Ser Pro Glu Met Tyr Lys
1 5 10

<210> SEQ ID NO 680
<211> LENGTH: 16
<212> TYPE: PRT
<213> ORGANISM: Homo sapiens

<400> SEQUENCE: 680

Asn Arg Leu Asp Cys Thr Gln Cys Leu Gln His Pro Trp Leu Met Lys
1 5 10 15

<210> SEQ ID NO 681

<211> LENGTH: 12
<212> TYPE: PRT
<213> ORGANISM: Homo sapiens

<400> SEQUENCE: 681

Pro Val Leu Leu Gln Val Ala Glu Ser Ala Tyr Arg
1 5 10

<210> SEQ ID NO 682
<211> LENGTH: 26
<212> TYPE: PRT
<213> ORGANISM: Homo sapiens

<400> SEQUENCE: 682

Gln Glu Pro Leu Gly Ser Asp Ser Glu Gly Val Asn Cys Leu Ala Tyr
1 5 10 15

Asp Glu Ala Ile Met Ala Gln Gln Asp Arg
20 25

<210> SEQ ID NO 683
<211> LENGTH: 14
<212> TYPE: PRT
<213> ORGANISM: Homo sapiens

<400> SEQUENCE: 683

Gln Glu Val Glu Glu Leu Trp Ile Gly Leu Asn Asp Leu Lys
1 5 10

<210> SEQ ID NO 684
<211> LENGTH: 12
<212> TYPE: PRT
<213> ORGANISM: Homo sapiens

<400> SEQUENCE: 684

Ser Phe Val Ile His Asn Leu Pro Val Leu Ala Lys
1 5 10

<210> SEQ ID NO 685
<211> LENGTH: 9
<212> TYPE: PRT
<213> ORGANISM: Homo sapiens

<400> SEQUENCE: 685

Ser Thr Thr Phe His Ser Ser Pro Arg
1 5

<210> SEQ ID NO 686
<211> LENGTH: 9
<212> TYPE: PRT
<213> ORGANISM: Homo sapiens

<400> SEQUENCE: 686

Ser Thr Thr Phe His Ser Ser Pro Arg
1 5

<210> SEQ ID NO 687
<211> LENGTH: 9
<212> TYPE: PRT
<213> ORGANISM: Homo sapiens

<400> SEQUENCE: 687

Ser Thr Thr Phe His Ser Ser Pro Arg
1 5

<210> SEQ ID NO 688
<211> LENGTH: 31
<212> TYPE: PRT
<213> ORGANISM: Homo sapiens

<400> SEQUENCE: 688

Thr Ala Ala Gly Leu Met His Thr Phe Asn Ala His Ala Ala Thr Asp
1               5                   10                  15

Ile Thr Gly Phe Gly Ile Leu Gly His Ala Gln Asn Leu Ala Lys
            20                  25                  30

<210> SEQ ID NO 689
<211> LENGTH: 7
<212> TYPE: PRT
<213> ORGANISM: Homo sapiens

<400> SEQUENCE: 689

Thr Gly Ala Phe Gly Leu Arg
1               5

<210> SEQ ID NO 690
<211> LENGTH: 9
<212> TYPE: PRT
<213> ORGANISM: Homo sapiens

<400> SEQUENCE: 690

Thr Ser Leu Thr Val Val Leu Leu Arg
1               5

<210> SEQ ID NO 691
<211> LENGTH: 14
<212> TYPE: PRT
<213> ORGANISM: Homo sapiens

<400> SEQUENCE: 691

Val Pro Pro Leu Leu Ile Tyr Gly Pro Phe Gly Thr Gly Lys
1               5                   10

<210> SEQ ID NO 692
<211> LENGTH: 8
<212> TYPE: PRT
<213> ORGANISM: Homo sapiens

<400> SEQUENCE: 692

Val Pro Ser Phe Ala Ala Gly Arg
1               5

<210> SEQ ID NO 693
<211> LENGTH: 15
<212> TYPE: PRT
<213> ORGANISM: Homo sapiens

<400> SEQUENCE: 693

Val Pro Val Gly Asp Gln Pro Pro Asp Ile Glu Phe Gln Ile Arg
1               5                   10                  15

<210> SEQ ID NO 694
<211> LENGTH: 9
<212> TYPE: PRT
<213> ORGANISM: Homo sapiens

<400> SEQUENCE: 694

Val Tyr Asp Pro Ala Ser Pro Gln Arg
1               5

<210> SEQ ID NO 695
<211> LENGTH: 19
<212> TYPE: PRT
<213> ORGANISM: Homo sapiens

<400> SEQUENCE: 695

Trp Phe Tyr Ile Asp Phe Gly Gly Val Lys Pro Met Gly Ser Glu Pro
1 5 10 15

Val Pro Lys

<210> SEQ ID NO 696
<211> LENGTH: 19
<212> TYPE: PRT
<213> ORGANISM: Homo sapiens

<400> SEQUENCE: 696

Trp Thr Pro Pro Ala Pro Ala Pro Ala Ala Pro Pro Ser Thr Pro Ala
1 5 10 15

Ala Pro Lys

<210> SEQ ID NO 697
<211> LENGTH: 14
<212> TYPE: PRT
<213> ORGANISM: Homo sapiens

<400> SEQUENCE: 697

Tyr Asp Asn Gln Trp Phe His Gly Cys Thr Ser Thr Gly Arg
1 5 10

<210> SEQ ID NO 698
<211> LENGTH: 19
<212> TYPE: PRT
<213> ORGANISM: Homo sapiens

<400> SEQUENCE: 698

Tyr Phe Ser Tyr Asp Cys Gly Ala Asp Phe Pro Gly Val Pro Leu Ala
1 5 10 15

Pro Pro Arg

<210> SEQ ID NO 699
<211> LENGTH: 17
<212> TYPE: PRT
<213> ORGANISM: Homo sapiens

<400> SEQUENCE: 699

Tyr Gly Asp Glu Glu Lys Asp Lys Gly Leu Gln Thr Ser Gln Asp Ala
1 5 10 15

Arg

<210> SEQ ID NO 700
<211> LENGTH: 10
<212> TYPE: PRT
<213> ORGANISM: Homo sapiens

<400> SEQUENCE: 700

Tyr Leu Glu Thr Ala Asp Tyr Ala Ile Arg
1 5 10

<210> SEQ ID NO 701
<211> LENGTH: 31
<212> TYPE: PRT
<213> ORGANISM: Homo sapiens

<400> SEQUENCE: 701

Ala Lys Gln Pro Asp Leu Ala Pro Gly Leu Thr Thr Ile Gly Ala Ser
1               5                   10                  15

Pro Thr Gln Thr Val Thr Leu Val Thr Gln Pro Val Val Thr Lys
            20                  25                  30

<210> SEQ ID NO 702
<211> LENGTH: 14
<212> TYPE: PRT
<213> ORGANISM: Homo sapiens

<400> SEQUENCE: 702

Ala Ser Pro Leu Leu Pro Ala Asn His Val Thr Met Ala Lys
1               5                   10

<210> SEQ ID NO 703
<211> LENGTH: 13
<212> TYPE: PRT
<213> ORGANISM: Homo sapiens

<400> SEQUENCE: 703

Ala Val Leu Glu Leu Leu Gln Arg Pro Gly Asn Ala Arg
1               5                   10

<210> SEQ ID NO 704
<211> LENGTH: 12
<212> TYPE: PRT
<213> ORGANISM: Homo sapiens

<400> SEQUENCE: 704

Cys Phe Gln Val Gln Gly Gln Glu Pro Gln Ser Arg
1               5                   10

<210> SEQ ID NO 705
<211> LENGTH: 11
<212> TYPE: PRT
<213> ORGANISM: Homo sapiens

<400> SEQUENCE: 705

Asp Lys Gly Leu Gln Thr Ser Gln Asp Ala Arg
1               5                   10

<210> SEQ ID NO 706
<211> LENGTH: 11
<212> TYPE: PRT
<213> ORGANISM: Homo sapiens

<400> SEQUENCE: 706

Asp Leu Thr Ala Leu Ser Asn Met Leu Pro Lys
1               5                   10

<210> SEQ ID NO 707
<211> LENGTH: 10
<212> TYPE: PRT
<213> ORGANISM: Homo sapiens

<400> SEQUENCE: 707

Asp Pro Phe Ser Leu Asp Ala Leu Ser Lys
1               5                   10

<210> SEQ ID NO 708
<211> LENGTH: 16
<212> TYPE: PRT

<213> ORGANISM: Homo sapiens

<400> SEQUENCE: 708

Phe Gly Asp Pro Leu Gly Tyr Glu Asp Val Ile Pro Glu Ala Asp Arg
1 5 10 15

<210> SEQ ID NO 709
<211> LENGTH: 9
<212> TYPE: PRT
<213> ORGANISM: Homo sapiens

<400> SEQUENCE: 709

Phe Gly Leu Tyr Leu Pro Leu Phe Lys
1 5

<210> SEQ ID NO 710
<211> LENGTH: 14
<212> TYPE: PRT
<213> ORGANISM: Homo sapiens

<400> SEQUENCE: 710

Phe Ser Thr Glu Tyr Glu Leu Gln Gln Leu Glu Gln Phe Lys
1 5 10

<210> SEQ ID NO 711
<211> LENGTH: 21
<212> TYPE: PRT
<213> ORGANISM: Homo sapiens

<400> SEQUENCE: 711

Gly Ala Val Tyr Leu Phe His Gly Thr Ser Gly Ser Gly Ile Ser Pro
1 5 10 15

Ser His Ser Gln Arg
20

<210> SEQ ID NO 712
<211> LENGTH: 10
<212> TYPE: PRT
<213> ORGANISM: Homo sapiens

<400> SEQUENCE: 712

His Leu Cys Glu Leu Leu Ala Gln Gln Phe
1 5 10

<210> SEQ ID NO 713
<211> LENGTH: 14
<212> TYPE: PRT
<213> ORGANISM: Homo sapiens

<400> SEQUENCE: 713

Ile Leu Asp Gln Glu Asn Leu Ser Ser Thr Ala Leu Val Lys
1 5 10

<210> SEQ ID NO 714
<211> LENGTH: 12
<212> TYPE: PRT
<213> ORGANISM: Homo sapiens

<400> SEQUENCE: 714

Ile Ser Glu Thr Thr Met Leu Gln Ser Gly Met Lys
1 5 10

<210> SEQ ID NO 715
<211> LENGTH: 20

<212> TYPE: PRT
<213> ORGANISM: Homo sapiens

<400> SEQUENCE: 715

Ile Ser Tyr His Gly Ser Cys Pro Gln Gly Leu Ala Asp Ser Ala Trp
1               5                   10                  15

Ile Pro Phe Arg
            20

<210> SEQ ID NO 716
<211> LENGTH: 13
<212> TYPE: PRT
<213> ORGANISM: Homo sapiens

<400> SEQUENCE: 716

Lys Gln Asn Trp Phe Glu Ala Phe Glu Ile Leu Asp Lys
1               5                   10

<210> SEQ ID NO 717
<211> LENGTH: 11
<212> TYPE: PRT
<213> ORGANISM: Homo sapiens

<400> SEQUENCE: 717

Pro Ile Ser Leu Val Phe Leu Val Pro Val Arg
1               5                   10

<210> SEQ ID NO 718
<211> LENGTH: 10
<212> TYPE: PRT
<213> ORGANISM: Homo sapiens

<400> SEQUENCE: 718

Ser Lys Glu Ser Ser Gln Val Thr Ser Arg
1               5                   10

<210> SEQ ID NO 719
<211> LENGTH: 9
<212> TYPE: PRT
<213> ORGANISM: Homo sapiens

<400> SEQUENCE: 719

Ser Pro Pro Pro Cys Thr Tyr Gly Arg
1               5

<210> SEQ ID NO 720
<211> LENGTH: 11
<212> TYPE: PRT
<213> ORGANISM: Homo sapiens

<400> SEQUENCE: 720

Ser Gln Leu Asn Cys Leu Leu Leu Ser Gly Arg
1               5                   10

<210> SEQ ID NO 721
<211> LENGTH: 34
<212> TYPE: PRT
<213> ORGANISM: Homo sapiens

<400> SEQUENCE: 721

Thr Pro Leu Ser Ala Ala Ala His Thr His Pro Val Tyr Cys Val Asn
1               5                   10                  15

Val Val Gly Thr Gln Asn Ala His Asn Leu Ile Thr Val Ser Thr Asp
            20                  25                  30

Gly Lys

<210> SEQ ID NO 722
<211> LENGTH: 9
<212> TYPE: PRT
<213> ORGANISM: Homo sapiens

<400> SEQUENCE: 722

Val Asn Tyr Asp Glu Glu Asn Trp Arg
1 5

<210> SEQ ID NO 723
<211> LENGTH: 13
<212> TYPE: PRT
<213> ORGANISM: Homo sapiens

<400> SEQUENCE: 723

Val Ser Phe Val Ile His Asn Leu Pro Val Leu Ala Lys
1 5 10

<210> SEQ ID NO 724
<211> LENGTH: 12
<212> TYPE: PRT
<213> ORGANISM: Homo sapiens

<400> SEQUENCE: 724

Val Thr Leu Arg Pro Tyr Leu Thr Pro Asn Asp Arg
1 5 10

<210> SEQ ID NO 725
<211> LENGTH: 12
<212> TYPE: PRT
<213> ORGANISM: Homo sapiens

<400> SEQUENCE: 725

Trp Asn Val Ile Asn Trp Glu Asn Val Thr Glu Arg
1 5 10

<210> SEQ ID NO 726
<211> LENGTH: 10
<212> TYPE: PRT
<213> ORGANISM: Homo sapiens

<400> SEQUENCE: 726

Ala Asp Thr Asp Gly Gly Leu Ile Phe Arg
1 5 10

<210> SEQ ID NO 727
<211> LENGTH: 7
<212> TYPE: PRT
<213> ORGANISM: Homo sapiens

<400> SEQUENCE: 727

Ala Gly Tyr Thr Gly Leu Arg
1 5

<210> SEQ ID NO 728
<211> LENGTH: 24
<212> TYPE: PRT
<213> ORGANISM: Homo sapiens

<400> SEQUENCE: 728

Ala Val Glu Ser Ser Lys Pro Leu Ser Asn Ala Gln Pro Ser Gly Pro
1 5 10 15

Leu Lys Pro Val Gly Asn Ala Lys
20

<210> SEQ ID NO 729
<211> LENGTH: 13
<212> TYPE: PRT
<213> ORGANISM: Homo sapiens

<400> SEQUENCE: 729

Cys Ser Glu Gly Phe Val Leu Ala Glu Asp Gly Arg Arg
1 5 10

<210> SEQ ID NO 730
<211> LENGTH: 10
<212> TYPE: PRT
<213> ORGANISM: Homo sapiens

<400> SEQUENCE: 730

Asp Leu Met Val Leu Asn Asp Val Tyr Arg
1 5 10

<210> SEQ ID NO 731
<211> LENGTH: 8
<212> TYPE: PRT
<213> ORGANISM: Homo sapiens

<400> SEQUENCE: 731

Phe Pro Ala Glu Gln Tyr Tyr Arg
1 5

<210> SEQ ID NO 732
<211> LENGTH: 15
<212> TYPE: PRT
<213> ORGANISM: Homo sapiens

<400> SEQUENCE: 732

Phe Thr Gly His Cys Ser Cys Arg Pro Gly Val Ser Gly Val Arg
1 5 10 15

<210> SEQ ID NO 733
<211> LENGTH: 15
<212> TYPE: PRT
<213> ORGANISM: Homo sapiens

<400> SEQUENCE: 733

Gly Asp Pro Gly Asp Thr Gly Ala Pro Gly Pro Val Gly Met Lys
1 5 10 15

<210> SEQ ID NO 734
<211> LENGTH: 19
<212> TYPE: PRT
<213> ORGANISM: Homo sapiens

<400> SEQUENCE: 734

Gly Gly Pro Ser Leu Ser Ser Val Leu Asn Glu Leu Pro Ser Ala Ala
1 5 10 15

Thr Leu Arg

<210> SEQ ID NO 735
<211> LENGTH: 17
<212> TYPE: PRT
<213> ORGANISM: Homo sapiens

<400> SEQUENCE: 735

Ile Lys Asp Pro Asp Ala Ser Lys Pro Glu Asp Trp Asp Glu Arg Ala
1 5 10 15

Lys

<210> SEQ ID NO 736
<211> LENGTH: 13
<212> TYPE: PRT
<213> ORGANISM: Homo sapiens

<400> SEQUENCE: 736

Ile Leu Cys Ile Gly Ala Val Pro Gly Leu Gln Pro Arg
1 5 10

<210> SEQ ID NO 737
<211> LENGTH: 17
<212> TYPE: PRT
<213> ORGANISM: Homo sapiens

<400> SEQUENCE: 737

Ile Gln Ser Asp Leu Thr Ser His Glu Ile Ser Leu Glu Glu Met Lys
1 5 10 15

Lys

<210> SEQ ID NO 738
<211> LENGTH: 13
<212> TYPE: PRT
<213> ORGANISM: Homo sapiens

<400> SEQUENCE: 738

Ile Thr Gly His Phe Tyr Ala Cys Gln Val Ala Gln Arg
1 5 10

<210> SEQ ID NO 739
<211> LENGTH: 14
<212> TYPE: PRT
<213> ORGANISM: Homo sapiens

<400> SEQUENCE: 739

Lys Val Val Gly Asp Val Ala Tyr Asp Glu Ala Lys Glu Arg
1 5 10

<210> SEQ ID NO 740
<211> LENGTH: 14
<212> TYPE: PRT
<213> ORGANISM: Homo sapiens

<400> SEQUENCE: 740

Leu Asp Thr Asp Ile Leu Leu Gly Ala Thr Cys Gly Leu Lys
1 5 10

<210> SEQ ID NO 741
<211> LENGTH: 11
<212> TYPE: PRT
<213> ORGANISM: Homo sapiens

<400> SEQUENCE: 741

Leu Val Ser Ala Val Val Glu Tyr Gly Gly Lys
1 5 10

<210> SEQ ID NO 742
<211> LENGTH: 24
<212> TYPE: PRT
<213> ORGANISM: Homo sapiens

<400> SEQUENCE: 742

Met Leu Gly Val Ala Ala Gly Met Thr His Ser Asn Met Ala Asn Ala
1 5 10 15

Leu Ala Ser Ala Thr Cys Glu Arg
20

<210> SEQ ID NO 743
<211> LENGTH: 16
<212> TYPE: PRT
<213> ORGANISM: Homo sapiens

<400> SEQUENCE: 743

Asn Ile Pro Asn Gly Leu Gln Glu Phe Leu Asp Pro Leu Cys Gln Arg
1 5 10 15

<210> SEQ ID NO 744
<211> LENGTH: 10
<212> TYPE: PRT
<213> ORGANISM: Homo sapiens

<400> SEQUENCE: 744

Gln Ala Asp Ile Ile Gly Lys Pro Ser Arg
1 5 10

<210> SEQ ID NO 745
<211> LENGTH: 13
<212> TYPE: PRT
<213> ORGANISM: Homo sapiens

<400> SEQUENCE: 745

Gln Glu Ile Ser Ile Met Asn Cys Leu His His Pro Lys
1 5 10

<210> SEQ ID NO 746
<211> LENGTH: 8
<212> TYPE: PRT
<213> ORGANISM: Homo sapiens

<400> SEQUENCE: 746

Gln Ile Val Ser Glu Met Leu Arg
1 5

<210> SEQ ID NO 747
<211> LENGTH: 10
<212> TYPE: PRT
<213> ORGANISM: Homo sapiens

<400> SEQUENCE: 747

Arg Ala Glu Gln Leu Leu Gln Asp Ala Arg
1 5 10

<210> SEQ ID NO 748
<211> LENGTH: 10
<212> TYPE: PRT
<213> ORGANISM: Homo sapiens

<400> SEQUENCE: 748

Arg Phe Glu Asn Ala Pro Asp Ser Ala Lys
1 5 10

<210> SEQ ID NO 749
<211> LENGTH: 7
<212> TYPE: PRT

<213> ORGANISM: Homo sapiens

<400> SEQUENCE: 749

Ser Gly Ala Pro Trp Phe Lys
1               5

<210> SEQ ID NO 750
<211> LENGTH: 9
<212> TYPE: PRT
<213> ORGANISM: Homo sapiens

<400> SEQUENCE: 750

Ser Ile Val Glu His Val Ala Ser Lys
1               5

<210> SEQ ID NO 751
<211> LENGTH: 9
<212> TYPE: PRT
<213> ORGANISM: Homo sapiens

<400> SEQUENCE: 751

Ser Leu Val Gly Leu Ser Gln Glu Arg
1               5

<210> SEQ ID NO 752
<211> LENGTH: 17
<212> TYPE: PRT
<213> ORGANISM: Homo sapiens

<400> SEQUENCE: 752

Thr Val Asn Glu Leu Gln Asn Leu Ser Ser Ala Glu Val Val Val Pro
1               5                   10                  15

Arg

<210> SEQ ID NO 753
<211> LENGTH: 7
<212> TYPE: PRT
<213> ORGANISM: Homo sapiens

<400> SEQUENCE: 753

Val Ile Ala Val Val Asn Lys
1               5

<210> SEQ ID NO 754
<211> LENGTH: 7
<212> TYPE: PRT
<213> ORGANISM: Homo sapiens

<400> SEQUENCE: 754

Val Ser His Ser Glu Leu Arg
1               5

<210> SEQ ID NO 755
<211> LENGTH: 14
<212> TYPE: PRT
<213> ORGANISM: Homo sapiens

<400> SEQUENCE: 755

Trp Ser Asp Gly Val Gly Phe Ser Tyr His Asn Phe Asp Arg
1               5                   10

<210> SEQ ID NO 756
<211> LENGTH: 15
<212> TYPE: PRT

<213> ORGANISM: Homo sapiens

<400> SEQUENCE: 756

Tyr Gly Ala Asp Asp Ile Glu Leu Leu Pro Glu Ala Gln His Lys
1 5 10 15

<210> SEQ ID NO 757
<211> LENGTH: 12
<212> TYPE: PRT
<213> ORGANISM: Homo sapiens

<400> SEQUENCE: 757

Ala Lys Pro Glu Ala Ser Phe Gln Val Trp Asn Lys
1 5 10

<210> SEQ ID NO 758
<211> LENGTH: 16
<212> TYPE: PRT
<213> ORGANISM: Homo sapiens

<400> SEQUENCE: 758

Ala Leu Gln Leu Ser Asn Ser Pro Gly Ala Ser Ser Ala Phe Leu Lys
1 5 10 15

<210> SEQ ID NO 759
<211> LENGTH: 31
<212> TYPE: PRT
<213> ORGANISM: Homo sapiens

<400> SEQUENCE: 759

Ala Ser Ser Glu Gly Gly Thr Ala Ala Gly Ala Gly Leu Asp Ser Leu
1 5 10 15

His Lys Asn Ser Val Ser Gln Ile Ser Val Leu Ser Gly Gly Lys
20 25 30

<210> SEQ ID NO 760
<211> LENGTH: 8
<212> TYPE: PRT
<213> ORGANISM: Homo sapiens

<400> SEQUENCE: 760

Ala Val Glu Met Ala Ala Gln Arg
1 5

<210> SEQ ID NO 761
<211> LENGTH: 8
<212> TYPE: PRT
<213> ORGANISM: Homo sapiens

<400> SEQUENCE: 761

Ala Val Leu Glu Leu Leu Gln Arg
1 5

<210> SEQ ID NO 762
<211> LENGTH: 11
<212> TYPE: PRT
<213> ORGANISM: Homo sapiens

<400> SEQUENCE: 762

Ala Tyr Ala Gln Gln Leu Ala Asp Trp Ala Arg
1 5 10

<210> SEQ ID NO 763
<211> LENGTH: 10

<212> TYPE: PRT
<213> ORGANISM: Homo sapiens

<400> SEQUENCE: 763

Asp His Ser Ala Ile Pro Val Ile Asn Arg
1 5 10

<210> SEQ ID NO 764
<211> LENGTH: 9
<212> TYPE: PRT
<213> ORGANISM: Homo sapiens

<400> SEQUENCE: 764

Asp Leu Arg Asp Pro Ala Val Cys Arg
1 5

<210> SEQ ID NO 765
<211> LENGTH: 12
<212> TYPE: PRT
<213> ORGANISM: Homo sapiens

<400> SEQUENCE: 765

Phe Gly Ser Cys Val Pro His Thr Thr Arg Pro Arg
1 5 10

<210> SEQ ID NO 766
<211> LENGTH: 9
<212> TYPE: PRT
<213> ORGANISM: Homo sapiens

<400> SEQUENCE: 766

Gly Pro Gln Tyr Gly Thr Leu Glu Lys
1 5

<210> SEQ ID NO 767
<211> LENGTH: 10
<212> TYPE: PRT
<213> ORGANISM: Homo sapiens

<400> SEQUENCE: 767

His Trp Asp Asp Val Val Cys Glu Ser Arg
1 5 10

<210> SEQ ID NO 768
<211> LENGTH: 16
<212> TYPE: PRT
<213> ORGANISM: Homo sapiens

<400> SEQUENCE: 768

Ile Val Leu Tyr Gln Thr Asp Ala Ser Leu Thr Pro Trp Thr Val Arg
1 5 10 15

<210> SEQ ID NO 769
<211> LENGTH: 11
<212> TYPE: PRT
<213> ORGANISM: Homo sapiens

<400> SEQUENCE: 769

Lys Val His Ser Pro Gln Gln Val Asp Phe Arg
1 5 10

<210> SEQ ID NO 770
<211> LENGTH: 15
<212> TYPE: PRT
<213> ORGANISM: Homo sapiens

<400> SEQUENCE: 770

Leu Cys Thr Asp His Gly Ser Gln Leu Val Thr Ile Thr Asn Arg
1 5 10 15

<210> SEQ ID NO 771
<211> LENGTH: 12
<212> TYPE: PRT
<213> ORGANISM: Homo sapiens

<400> SEQUENCE: 771

Leu Asp Phe Leu Pro Asp Met Met Val Glu Gly Arg
1 5 10

<210> SEQ ID NO 772
<211> LENGTH: 17
<212> TYPE: PRT
<213> ORGANISM: Homo sapiens

<400> SEQUENCE: 772

Leu Glu Ala Val Ala Glu Glu Lys Pro His Val Lys Pro Tyr Phe Ser
1 5 10 15

Lys

<210> SEQ ID NO 773
<211> LENGTH: 26
<212> TYPE: PRT
<213> ORGANISM: Homo sapiens

<400> SEQUENCE: 773

Leu Glu Val Asp Ala Ile Val Asn Ala Ala Asn Ser Ser Leu Leu Gly
1 5 10 15

Gly Gly Gly Val Asp Gly Cys Ile His Arg
20 25

<210> SEQ ID NO 774
<211> LENGTH: 17
<212> TYPE: PRT
<213> ORGANISM: Homo sapiens

<400> SEQUENCE: 774

Leu Leu His Glu Met Gln Ile Gln His Pro Thr Ala Ser Leu Ile Ala
1 5 10 15

Lys

<210> SEQ ID NO 775
<211> LENGTH: 9
<212> TYPE: PRT
<213> ORGANISM: Homo sapiens

<400> SEQUENCE: 775

Leu Leu Val Glu Glu Leu Pro Leu Arg
1 5

<210> SEQ ID NO 776
<211> LENGTH: 11
<212> TYPE: PRT
<213> ORGANISM: Homo sapiens

<400> SEQUENCE: 776

Leu Met Asn Ser Gln Leu Val Thr Thr Glu Lys
1 5 10

<210> SEQ ID NO 777
<211> LENGTH: 20
<212> TYPE: PRT
<213> ORGANISM: Homo sapiens

<400> SEQUENCE: 777

Leu Ser Asn Pro Pro Ser Ala Gly Pro Ile Val Val His Cys Ser Ala
1 5 10 15

Gly Ala Gly Arg
20

<210> SEQ ID NO 778
<211> LENGTH: 23
<212> TYPE: PRT
<213> ORGANISM: Homo sapiens

<400> SEQUENCE: 778

Leu Ser Pro Ser Ser Thr Glu Thr Thr Thr Leu Pro Gly Ser Pro Thr
1 5 10 15

Thr Pro Ser Leu Ser Glu Lys
20

<210> SEQ ID NO 779
<211> LENGTH: 23
<212> TYPE: PRT
<213> ORGANISM: Homo sapiens

<400> SEQUENCE: 779

Leu Ser Pro Ser Ser Thr Glu Thr Thr Thr Leu Pro Gly Ser Pro Thr
1 5 10 15

Thr Pro Ser Leu Ser Glu Lys
20

<210> SEQ ID NO 780
<211> LENGTH: 23
<212> TYPE: PRT
<213> ORGANISM: Homo sapiens

<400> SEQUENCE: 780

Leu Ser Pro Ser Ser Thr Glu Thr Thr Thr Leu Pro Gly Ser Pro Thr
1 5 10 15

Thr Pro Ser Leu Ser Glu Lys
20

<210> SEQ ID NO 781
<211> LENGTH: 23
<212> TYPE: PRT
<213> ORGANISM: Homo sapiens

<400> SEQUENCE: 781

Leu Ser Pro Ser Ser Thr Glu Thr Thr Thr Leu Pro Gly Ser Pro Thr
1 5 10 15

Thr Pro Ser Leu Ser Glu Lys
20

<210> SEQ ID NO 782
<211> LENGTH: 8
<212> TYPE: PRT
<213> ORGANISM: Homo sapiens

<400> SEQUENCE: 782

Met Tyr Leu Phe Tyr Gly Asn Lys 1 5

<210> SEQ ID NO 783
<211> LENGTH: 9
<212> TYPE: PRT
<213> ORGANISM: Homo sapiens

<400> SEQUENCE: 783

Pro Pro Leu Leu Leu Ile Leu Asp Arg
1 5

<210> SEQ ID NO 784
<211> LENGTH: 14
<212> TYPE: PRT
<213> ORGANISM: Homo sapiens

<400> SEQUENCE: 784

Pro Ser Leu Ser Leu Gly Thr Ile Thr Asp Glu Glu Met Lys
1 5 10

<210> SEQ ID NO 785
<211> LENGTH: 10
<212> TYPE: PRT
<213> ORGANISM: Homo sapiens

<400> SEQUENCE: 785

Gln Cys His Glu Cys Ile Glu His Ile Arg
1 5 10

<210> SEQ ID NO 786
<211> LENGTH: 11
<212> TYPE: PRT
<213> ORGANISM: Homo sapiens

<400> SEQUENCE: 786

Gln Gln Asn Gln Glu Leu Gln Glu Gln Leu Arg
1 5 10

<210> SEQ ID NO 787
<211> LENGTH: 19
<212> TYPE: PRT
<213> ORGANISM: Homo sapiens

<400> SEQUENCE: 787

Ser Phe Ala Pro Ile Leu Pro His Leu Ala Glu Glu Val Phe Gln His
1 5 10 15

Ile Pro Tyr

<210> SEQ ID NO 788
<211> LENGTH: 15
<212> TYPE: PRT
<213> ORGANISM: Homo sapiens

<400> SEQUENCE: 788

Ser Gly Leu Cys Pro His Val Val Val Leu Val Ala Thr Val Arg
1 5 10 15

<210> SEQ ID NO 789
<211> LENGTH: 16
<212> TYPE: PRT
<213> ORGANISM: Homo sapiens

<400> SEQUENCE: 789

Ser Ile Thr Ile Leu Ser Thr Pro Glu Gly Thr Ser Ala Ala Cys Lys 1 5 10 15

<210> SEQ ID NO 790
<211> LENGTH: 13
<212> TYPE: PRT
<213> ORGANISM: Homo sapiens

<400> SEQUENCE: 790

Ser Leu Glu Gly Ser Asp Asp Ala Val Leu Leu Gln Arg
1 5 10

<210> SEQ ID NO 791
<211> LENGTH: 12
<212> TYPE: PRT
<213> ORGANISM: Homo sapiens

<400> SEQUENCE: 791

Ser Met Asp Ala Glu Thr Tyr Val Glu Gly Gln Arg
1 5 10

<210> SEQ ID NO 792
<211> LENGTH: 14
<212> TYPE: PRT
<213> ORGANISM: Homo sapiens

<400> SEQUENCE: 792

Ser Thr Thr Ser Gly Leu Val Gly Glu Ser Thr Pro Ser Arg
1 5 10

<210> SEQ ID NO 793
<211> LENGTH: 14
<212> TYPE: PRT
<213> ORGANISM: Homo sapiens

<400> SEQUENCE: 793

Ser Thr Thr Ser Gly Leu Val Gly Glu Ser Thr Pro Ser Arg
1 5 10

<210> SEQ ID NO 794
<211> LENGTH: 14
<212> TYPE: PRT
<213> ORGANISM: Homo sapiens

<400> SEQUENCE: 794

Ser Thr Thr Ser Gly Leu Val Gly Glu Ser Thr Pro Ser Arg
1 5 10

<210> SEQ ID NO 795
<211> LENGTH: 14
<212> TYPE: PRT
<213> ORGANISM: Homo sapiens

<400> SEQUENCE: 795

Ser Thr Thr Ser Gly Leu Val Gly Glu Ser Thr Pro Ser Arg
1 5 10

<210> SEQ ID NO 796
<211> LENGTH: 23
<212> TYPE: PRT
<213> ORGANISM: Homo sapiens

<400> SEQUENCE: 796

Thr Gln Gly Ser Ser Thr Ser Trp Phe Gly Ser Asn Gln Ser Lys Pro
1 5 10 15

Glu Phe Thr Val Asp Leu Lys
20

<210> SEQ ID NO 797
<211> LENGTH: 20
<212> TYPE: PRT
<213> ORGANISM: Homo sapiens

<400> SEQUENCE: 797

Val Ile Met Ile Val Thr Asp Gly Arg Pro Gln Asp Ser Val Ala Glu
1 5 10 15

Val Ala Ala Lys
20

<210> SEQ ID NO 798
<211> LENGTH: 12
<212> TYPE: PRT
<213> ORGANISM: Homo sapiens

<400> SEQUENCE: 798

Val Pro Pro Pro Lys Pro Ala Thr Pro Asp Phe Arg
1 5 10

<210> SEQ ID NO 799
<211> LENGTH: 7
<212> TYPE: PRT
<213> ORGANISM: Homo sapiens

<400> SEQUENCE: 799

Trp Gly Phe Cys Pro Ile Lys
1 5

<210> SEQ ID NO 800
<211> LENGTH: 16
<212> TYPE: PRT
<213> ORGANISM: Homo sapiens

<400> SEQUENCE: 800

Tyr Ala Val Gln Val Ala Glu Gly Met Gly Tyr Leu Glu Ser Lys Arg
1 5 10 15

<210> SEQ ID NO 801
<211> LENGTH: 16
<212> TYPE: PRT
<213> ORGANISM: Homo sapiens

<400> SEQUENCE: 801

Ala Ala Glu Glu Ile Gly Ile Lys Ala Thr His Ile Lys Leu Pro Arg
1 5 10 15

<210> SEQ ID NO 802
<211> LENGTH: 13
<212> TYPE: PRT
<213> ORGANISM: Homo sapiens

<400> SEQUENCE: 802

Ala Gly Asp Ala Val Asn Val Val Val Thr Gly Gly Lys
1 5 10

<210> SEQ ID NO 803
<211> LENGTH: 15
<212> TYPE: PRT
<213> ORGANISM: Homo sapiens

<400> SEQUENCE: 803

Ala Gly Asp Thr Leu Ser Gly Thr Cys Leu Leu Ile Ala Asn Lys
1 5 10 15

<210> SEQ ID NO 804
<211> LENGTH: 16
<212> TYPE: PRT
<213> ORGANISM: Homo sapiens

<400> SEQUENCE: 804

Ala Gly Asp Thr Leu Ser Gly Thr Cys Leu Leu Ile Ala Asn Lys Arg
1 5 10 15

<210> SEQ ID NO 805
<211> LENGTH: 8
<212> TYPE: PRT
<213> ORGANISM: Homo sapiens

<400> SEQUENCE: 805

Ala Ile Asp Tyr Glu Ile Gln Arg
1 5

<210> SEQ ID NO 806
<211> LENGTH: 8
<212> TYPE: PRT
<213> ORGANISM: Homo sapiens

<400> SEQUENCE: 806

Ala Leu Glu Gln Ala Leu Glu Lys
1 5

<210> SEQ ID NO 807
<211> LENGTH: 8
<212> TYPE: PRT
<213> ORGANISM: Homo sapiens

<400> SEQUENCE: 807

Ala Leu Ser Ser Ala Gly Glu Arg
1 5

<210> SEQ ID NO 808
<211> LENGTH: 7
<212> TYPE: PRT
<213> ORGANISM: Homo sapiens

<400> SEQUENCE: 808

Cys Phe Leu Cys Asp Ser Arg
1 5

<210> SEQ ID NO 809
<211> LENGTH: 10
<212> TYPE: PRT
<213> ORGANISM: Homo sapiens

<400> SEQUENCE: 809

Asp Ala Glu Glu Trp Val Gln Gln Leu Lys
1 5 10

<210> SEQ ID NO 810
<211> LENGTH: 21
<212> TYPE: PRT
<213> ORGANISM: Homo sapiens

<400> SEQUENCE: 810

Asp Asp Glu Phe Thr His Leu Tyr Thr Leu Ile Val Arg Pro Asp Asn 1 5 10 15

Thr Tyr Glu Val Lys
20

<210> SEQ ID NO 811
<211> LENGTH: 11
<212> TYPE: PRT
<213> ORGANISM: Homo sapiens

<400> SEQUENCE: 811

Asp Phe Gly Ser Phe Asp Lys Phe Lys Glu Lys
1 5 10

<210> SEQ ID NO 812
<211> LENGTH: 14
<212> TYPE: PRT
<213> ORGANISM: Homo sapiens

<400> SEQUENCE: 812

Asp Gly Asp Val Gln Ala Gly Ala Asn Leu Ser Phe Asn Arg
1 5 10

<210> SEQ ID NO 813
<211> LENGTH: 22
<212> TYPE: PRT
<213> ORGANISM: Homo sapiens

<400> SEQUENCE: 813

Glu Phe Ala Ser His Leu Gln Gln Leu Gln Asp Ala Leu Asn Glu Leu
1 5 10 15

Thr Glu Glu His Ser Lys
20

<210> SEQ ID NO 814
<211> LENGTH: 11
<212> TYPE: PRT
<213> ORGANISM: Homo sapiens

<400> SEQUENCE: 814

Glu Thr Leu Pro Glu Leu Pro Ser Val Thr Arg
1 5 10

<210> SEQ ID NO 815
<211> LENGTH: 21
<212> TYPE: PRT
<213> ORGANISM: Homo sapiens

<400> SEQUENCE: 815

Gly Ala Pro Met His Asp Leu Leu Leu Trp Asn Asn Ala Thr Val Thr
1 5 10 15

Thr Cys His Ser Lys
20

<210> SEQ ID NO 816
<211> LENGTH: 7
<212> TYPE: PRT
<213> ORGANISM: Homo sapiens

<400> SEQUENCE: 816

His Lys Ser Asp Phe Gly Lys
1 5

<210> SEQ ID NO 817

<211> LENGTH: 9
<212> TYPE: PRT
<213> ORGANISM: Homo sapiens

<400> SEQUENCE: 817

Ile Ala Leu Glu Thr Ser Leu Ser Lys
1               5

<210> SEQ ID NO 818
<211> LENGTH: 8
<212> TYPE: PRT
<213> ORGANISM: Homo sapiens

<400> SEQUENCE: 818

Ile Gly Asp Phe Gly Leu Met Arg
1               5

<210> SEQ ID NO 819
<211> LENGTH: 8
<212> TYPE: PRT
<213> ORGANISM: Homo sapiens

<400> SEQUENCE: 819

Ile Leu Arg Glu Glu Gly Pro Lys
1               5

<210> SEQ ID NO 820
<211> LENGTH: 9
<212> TYPE: PRT
<213> ORGANISM: Homo sapiens

<400> SEQUENCE: 820

Lys Ser Glu Ala Pro Phe Thr His Lys
1               5

<210> SEQ ID NO 821
<211> LENGTH: 12
<212> TYPE: PRT
<213> ORGANISM: Homo sapiens

<400> SEQUENCE: 821

Leu Cys Gly Asp Leu Val Ser Cys Phe Gln Glu Arg
1               5                   10

<210> SEQ ID NO 822
<211> LENGTH: 12
<212> TYPE: PRT
<213> ORGANISM: Homo sapiens

<400> SEQUENCE: 822

Leu Leu Asp Leu Leu Glu Gly Leu Thr Gly Gln Lys
1               5                   10

<210> SEQ ID NO 823
<211> LENGTH: 14
<212> TYPE: PRT
<213> ORGANISM: Homo sapiens

<400> SEQUENCE: 823

Leu Leu Glu Gln Ser Ile Gln Ser Ala Gln Glu Thr Glu Lys
1               5                   10

<210> SEQ ID NO 824
<211> LENGTH: 13
<212> TYPE: PRT

<213> ORGANISM: Homo sapiens

<400> SEQUENCE: 824

Leu Gln Ala Glu Asp Cys Ser Ile Ala Cys Leu Pro Arg
1 5 10

<210> SEQ ID NO 825
<211> LENGTH: 8
<212> TYPE: PRT
<213> ORGANISM: Homo sapiens

<400> SEQUENCE: 825

Met Asn Val Val Phe Ala Val Lys
1 5

<210> SEQ ID NO 826
<211> LENGTH: 9
<212> TYPE: PRT
<213> ORGANISM: Homo sapiens

<400> SEQUENCE: 826

Asn Pro Pro Ala Ala Tyr Ile Gln Lys
1 5

<210> SEQ ID NO 827
<211> LENGTH: 11
<212> TYPE: PRT
<213> ORGANISM: Homo sapiens

<400> SEQUENCE: 827

Asn Thr Ser Leu Asn Pro Gln Glu Leu Gln Arg
1 5 10

<210> SEQ ID NO 828
<211> LENGTH: 9
<212> TYPE: PRT
<213> ORGANISM: Homo sapiens

<400> SEQUENCE: 828

Asn Val Leu Ile Asn Lys Asp Ile Arg
1 5

<210> SEQ ID NO 829
<211> LENGTH: 10
<212> TYPE: PRT
<213> ORGANISM: Homo sapiens

<400> SEQUENCE: 829

Pro Ala Glu Thr Leu Lys Pro Met Gly Asn
1 5 10

<210> SEQ ID NO 830
<211> LENGTH: 10
<212> TYPE: PRT
<213> ORGANISM: Homo sapiens

<400> SEQUENCE: 830

Pro Ala Glu Thr Leu Lys Pro Met Gly Asn
1 5 10

<210> SEQ ID NO 831
<211> LENGTH: 9
<212> TYPE: PRT
<213> ORGANISM: Homo sapiens

<400> SEQUENCE: 831

Pro Phe Ser Leu Asp Ala Leu Ser Lys
1               5

<210> SEQ ID NO 832
<211> LENGTH: 12
<212> TYPE: PRT
<213> ORGANISM: Homo sapiens

<400> SEQUENCE: 832

Pro Leu Leu Pro Ala Asn His Val Thr Met Ala Lys
1               5                   10

<210> SEQ ID NO 833
<211> LENGTH: 13
<212> TYPE: PRT
<213> ORGANISM: Homo sapiens

<400> SEQUENCE: 833

Pro Ser Gly Tyr Thr Cys Ala Cys Asp Ser Gly Phe Arg
1               5                   10

<210> SEQ ID NO 834
<211> LENGTH: 14
<212> TYPE: PRT
<213> ORGANISM: Homo sapiens

<400> SEQUENCE: 834

Pro Ser Val Val Leu Ser Ala Ala His Thr Val Ala Ala Arg
1               5                   10

<210> SEQ ID NO 835
<211> LENGTH: 9
<212> TYPE: PRT
<213> ORGANISM: Homo sapiens

<400> SEQUENCE: 835

Gln Ala Ser Asn Gly Val Leu Ile Arg
1               5

<210> SEQ ID NO 836
<211> LENGTH: 13
<212> TYPE: PRT
<213> ORGANISM: Homo sapiens

<400> SEQUENCE: 836

Gln Gly Leu Glu Leu Ala Ala Asp Cys His Leu Ser Arg
1               5                   10

<210> SEQ ID NO 837
<211> LENGTH: 11
<212> TYPE: PRT
<213> ORGANISM: Homo sapiens

<400> SEQUENCE: 837

Gln Val Glu Glu Leu Leu Met Ala Met Glu Lys
1               5                   10

<210> SEQ ID NO 838
<211> LENGTH: 19
<212> TYPE: PRT
<213> ORGANISM: Homo sapiens

<400> SEQUENCE: 838

Gln Val Glu Lys Glu Glu Thr Asn Glu Ile Gln Val Val Asn Glu Glu
1 5 10 15

Pro Gln Arg

<210> SEQ ID NO 839
<211> LENGTH: 16
<212> TYPE: PRT
<213> ORGANISM: Homo sapiens

<400> SEQUENCE: 839

Arg Leu Glu Ala Glu Phe Pro Pro His His Ser Gln Ser Thr Phe Arg
1 5 10 15

<210> SEQ ID NO 840
<211> LENGTH: 16
<212> TYPE: PRT
<213> ORGANISM: Homo sapiens

<400> SEQUENCE: 840

Ser Trp Asp Thr Asn Leu Ile Glu Cys Asn Leu Asp Gln Glu Leu Lys
1 5 10 15

<210> SEQ ID NO 841
<211> LENGTH: 16
<212> TYPE: PRT
<213> ORGANISM: Homo sapiens

<400> SEQUENCE: 841

Thr Gly Glu Pro Cys Val Ala Glu Leu Thr Glu Glu Asn Phe Gln Arg
1 5 10 15

<210> SEQ ID NO 842
<211> LENGTH: 16
<212> TYPE: PRT
<213> ORGANISM: Homo sapiens

<400> SEQUENCE: 842

Val Glu Cys Glu Pro Ser Trp Gln Pro Phe Gln Gly His Cys Tyr Arg
1 5 10 15

<210> SEQ ID NO 843
<211> LENGTH: 11
<212> TYPE: PRT
<213> ORGANISM: Homo sapiens

<400> SEQUENCE: 843

Val Arg Phe Thr Pro Val Val Cys Gly Leu Arg
1 5 10

<210> SEQ ID NO 844
<211> LENGTH: 7
<212> TYPE: PRT
<213> ORGANISM: Homo sapiens

<400> SEQUENCE: 844

Val Ser Leu Ser Gln Pro Arg
1 5

<210> SEQ ID NO 845
<211> LENGTH: 17
<212> TYPE: PRT
<213> ORGANISM: Homo sapiens

<400> SEQUENCE: 845

Ala Ala Glu Gly Tyr Thr Gln Phe Tyr Tyr Val Asp Val Leu Asp Gly
1 5 10 15

Lys

<210> SEQ ID NO 846
<211> LENGTH: 16
<212> TYPE: PRT
<213> ORGANISM: Homo sapiens

<400> SEQUENCE: 846

Ala Ala Leu Glu Glu Val Glu Gly Asp Val Ala Glu Leu Glu Leu Lys
1 5 10 15

<210> SEQ ID NO 847
<211> LENGTH: 13
<212> TYPE: PRT
<213> ORGANISM: Homo sapiens

<400> SEQUENCE: 847

Ala Glu Glu Phe Gly Asn Glu Thr Trp Gly Val Thr Lys
1 5 10

<210> SEQ ID NO 848
<211> LENGTH: 20
<212> TYPE: PRT
<213> ORGANISM: Homo sapiens

<400> SEQUENCE: 848

Ala Phe Glu Asp Trp Leu Asn Asp Asp Leu Gly Ser Tyr Gln Gly Ala
1 5 10 15

Gln Gly Asn Arg
20

<210> SEQ ID NO 849
<211> LENGTH: 8
<212> TYPE: PRT
<213> ORGANISM: Homo sapiens

<400> SEQUENCE: 849

Ala Thr Gln Glu Trp Leu Glu Lys
1 5

<210> SEQ ID NO 850
<211> LENGTH: 19
<212> TYPE: PRT
<213> ORGANISM: Homo sapiens

<400> SEQUENCE: 850

Cys Ser Gln Phe Cys Thr Thr Gly Met Asp Gly Gly Met Ser Ile Trp
1 5 10 15

Asp Val Lys

<210> SEQ ID NO 851
<211> LENGTH: 20
<212> TYPE: PRT
<213> ORGANISM: Homo sapiens

<400> SEQUENCE: 851

Asp Gln Leu Val Ile Pro Asp Gly Gln Glu Glu Glu Gln Glu Ala Ala
1 5 10 15

Gly Glu Gly Arg
20

<210> SEQ ID NO 852
<211> LENGTH: 13
<212> TYPE: PRT
<213> ORGANISM: Homo sapiens

<400> SEQUENCE: 852

Glu Ala Gln Glu Ala Glu Ala Phe Ala Leu Tyr His Lys
1               5                   10

<210> SEQ ID NO 853
<211> LENGTH: 13
<212> TYPE: PRT
<213> ORGANISM: Homo sapiens

<400> SEQUENCE: 853

Glu Gly Asn Cys Ser Gly Cys Ile Gln Asp Cys Asn Arg
1               5                   10

<210> SEQ ID NO 854
<211> LENGTH: 22
<212> TYPE: PRT
<213> ORGANISM: Homo sapiens

<400> SEQUENCE: 854

Glu Gly Gln Ile Gln Ser Val Val Thr Tyr Asp Leu Ala Leu Asp Ser
1               5                   10                  15

Gly Arg Pro His Ser Arg
            20

<210> SEQ ID NO 855
<211> LENGTH: 9
<212> TYPE: PRT
<213> ORGANISM: Homo sapiens

<400> SEQUENCE: 855

Glu Ile Asp Ala Ala Leu Gln Lys Lys
1               5

<210> SEQ ID NO 856
<211> LENGTH: 9
<212> TYPE: PRT
<213> ORGANISM: Homo sapiens

<400> SEQUENCE: 856

Glu Arg Phe Gln Asn Leu Asp Lys Lys
1               5

<210> SEQ ID NO 857
<211> LENGTH: 25
<212> TYPE: PRT
<213> ORGANISM: Homo sapiens

<400> SEQUENCE: 857

Glu Thr Gln Pro Pro Asp Leu Pro Thr Thr Ala Leu Gly Gly Cys Pro
1               5                   10                  15

Ser Asp Trp Ile Gln Phe Leu Asn Lys
            20                  25

<210> SEQ ID NO 858
<211> LENGTH: 20
<212> TYPE: PRT
<213> ORGANISM: Homo sapiens

<400> SEQUENCE: 858

```
Phe Arg Glu Phe Leu Glu Ser Gln Glu Asp Tyr Asp Pro Cys Trp Ser
1               5                   10                  15

Leu Gln Glu Lys
            20


<210> SEQ ID NO 859
<211> LENGTH: 14
<212> TYPE: PRT
<213> ORGANISM: Homo sapiens

<400> SEQUENCE: 859

Gly Gly Thr Ala Ala Gly Ala Gly Leu Asp Ser Leu His Lys
1               5                   10


<210> SEQ ID NO 860
<211> LENGTH: 12
<212> TYPE: PRT
<213> ORGANISM: Homo sapiens

<400> SEQUENCE: 860

Gly Leu Asn Pro Gly Thr Leu Asn Ile Leu Val Arg
1               5                   10


<210> SEQ ID NO 861
<211> LENGTH: 9
<212> TYPE: PRT
<213> ORGANISM: Homo sapiens

<400> SEQUENCE: 861

Gly Gln Leu Ala Pro Val Phe Gln Arg
1               5


<210> SEQ ID NO 862
<211> LENGTH: 14
<212> TYPE: PRT
<213> ORGANISM: Homo sapiens

<400> SEQUENCE: 862

Gly Ser Ala Ala Ser Thr Cys Ile Leu Thr Ile Glu Ser Lys
1               5                   10


<210> SEQ ID NO 863
<211> LENGTH: 13
<212> TYPE: PRT
<213> ORGANISM: Homo sapiens

<400> SEQUENCE: 863

Ile Cys Gly Val Glu Asp Ala Val Ser Glu Met Thr Arg
1               5                   10


<210> SEQ ID NO 864
<211> LENGTH: 12
<212> TYPE: PRT
<213> ORGANISM: Homo sapiens

<400> SEQUENCE: 864

Ile Ile Thr Glu Gly Phe Glu Ala Ala Lys Glu Lys
1               5                   10


<210> SEQ ID NO 865
<211> LENGTH: 8
<212> TYPE: PRT
<213> ORGANISM: Homo sapiens
```

<400> SEQUENCE: 865

Ile Leu Lys Asp Ile Ala Asn Arg
1 5

<210> SEQ ID NO 866
<211> LENGTH: 19
<212> TYPE: PRT
<213> ORGANISM: Homo sapiens

<400> SEQUENCE: 866

Ile Gln Asp Leu Glu His His Leu Gly Leu Ala Leu Asn Glu Val Gln
1 5 10 15

Ala Ala Lys

<210> SEQ ID NO 867
<211> LENGTH: 10
<212> TYPE: PRT
<213> ORGANISM: Homo sapiens

<400> SEQUENCE: 867

Ile Val Asp Ala Val Ile Glu Gln Val Lys
1 5 10

<210> SEQ ID NO 868
<211> LENGTH: 7
<212> TYPE: PRT
<213> ORGANISM: Homo sapiens

<400> SEQUENCE: 868

Lys Val Asn Val Leu Gln Lys
1 5

<210> SEQ ID NO 869
<211> LENGTH: 22
<212> TYPE: PRT
<213> ORGANISM: Homo sapiens

<400> SEQUENCE: 869

Leu Leu Leu Gln Cys Gln Val Ser Ser Asp Pro Pro Ala Thr Ile Ile
1 5 10 15

Trp Thr Leu Asn Gly Lys
20

<210> SEQ ID NO 870
<211> LENGTH: 8
<212> TYPE: PRT
<213> ORGANISM: Homo sapiens

<400> SEQUENCE: 870

Leu Ser Phe Glu Glu Met Glu Arg
1 5

<210> SEQ ID NO 871
<211> LENGTH: 20
<212> TYPE: PRT
<213> ORGANISM: Homo sapiens

<400> SEQUENCE: 871

Leu Ser Pro Ile Pro Ala Val Pro Ala Ser Val Pro Leu Gln Ala Trp
1 5 10 15

His Pro Ala Lys
20

<210> SEQ ID NO 872
<211> LENGTH: 17
<212> TYPE: PRT
<213> ORGANISM: Homo sapiens

<400> SEQUENCE: 872

Asn Gln Asp Asn Glu Asp Glu Trp Pro Leu Ala Glu Ile Leu Ser Val
1 5 10 15

Lys

<210> SEQ ID NO 873
<211> LENGTH: 11
<212> TYPE: PRT
<213> ORGANISM: Homo sapiens

<400> SEQUENCE: 873

Pro Thr Thr Leu Thr Asp Glu Glu Ile Asn Arg
1 5 10

<210> SEQ ID NO 874
<211> LENGTH: 19
<212> TYPE: PRT
<213> ORGANISM: Homo sapiens

<400> SEQUENCE: 874

Gln Ile Ile Glu Asp Gln Ser Gly His Tyr Ile Trp Val Pro Ser Pro
1 5 10 15

Glu Lys Leu

<210> SEQ ID NO 875
<211> LENGTH: 9
<212> TYPE: PRT
<213> ORGANISM: Homo sapiens

<400> SEQUENCE: 875

Gln Ile Gln Glu Ser Glu His Met Lys
1 5

<210> SEQ ID NO 876
<211> LENGTH: 8
<212> TYPE: PRT
<213> ORGANISM: Homo sapiens

<400> SEQUENCE: 876

Arg Asp Phe Gly Ser Phe Asp Lys
1 5

<210> SEQ ID NO 877
<211> LENGTH: 15
<212> TYPE: PRT
<213> ORGANISM: Homo sapiens

<400> SEQUENCE: 877

Arg Pro Gln Leu Glu Glu Leu Ile Thr Ala Ala Gln Asn Leu Lys
1 5 10 15

<210> SEQ ID NO 878
<211> LENGTH: 8
<212> TYPE: PRT
<213> ORGANISM: Homo sapiens

<400> SEQUENCE: 878

Arg Pro Tyr Trp Cys Ile Ser Arg 1 5

<210> SEQ ID NO 879
<211> LENGTH: 22
<212> TYPE: PRT
<213> ORGANISM: Homo sapiens

<400> SEQUENCE: 879

Ser Glu Glu Ser Thr Ala Ser His Ser Ser Gln Asp Ala Thr Gly Thr
1 5 10 15

Ile Val Leu Pro Ala Arg
20

<210> SEQ ID NO 880
<211> LENGTH: 22
<212> TYPE: PRT
<213> ORGANISM: Homo sapiens

<400> SEQUENCE: 880

Ser Glu Glu Ser Thr Ala Ser His Ser Ser Gln Asp Ala Thr Gly Thr
1 5 10 15

Ile Val Leu Pro Ala Arg
20

<210> SEQ ID NO 881
<211> LENGTH: 22
<212> TYPE: PRT
<213> ORGANISM: Homo sapiens

<400> SEQUENCE: 881

Ser Glu Glu Ser Thr Ala Ser His Ser Ser Gln Asp Ala Thr Gly Thr
1 5 10 15

Ile Val Leu Pro Ala Arg
20

<210> SEQ ID NO 882
<211> LENGTH: 22
<212> TYPE: PRT
<213> ORGANISM: Homo sapiens

<400> SEQUENCE: 882

Ser Glu Glu Ser Thr Ala Ser His Ser Ser Gln Asp Ala Thr Gly Thr
1 5 10 15

Ile Val Leu Pro Ala Arg
20

<210> SEQ ID NO 883
<211> LENGTH: 16
<212> TYPE: PRT
<213> ORGANISM: Homo sapiens

<400> SEQUENCE: 883

Ser Gly Thr Ile Phe Asp Asn Phe Leu Ile Thr Asn Asp Glu Ala Tyr
1 5 10 15

<210> SEQ ID NO 884
<211> LENGTH: 19
<212> TYPE: PRT
<213> ORGANISM: Homo sapiens

<400> SEQUENCE: 884

Ser Gln Asp Ala Asp Ser Pro Gly Ser Ser Gly Ala Pro Glu Asn Leu
1 5 10 15

Thr Phe Lys

<210> SEQ ID NO 885
<211> LENGTH: 22
<212> TYPE: PRT
<213> ORGANISM: Homo sapiens

<400> SEQUENCE: 885

Thr Cys Tyr Pro Leu Glu Ser Arg Pro Ser Leu Ser Leu Gly Thr Ile
1 5 10 15

Thr Asp Glu Glu Met Lys
20

<210> SEQ ID NO 886
<211> LENGTH: 15
<212> TYPE: PRT
<213> ORGANISM: Homo sapiens

<400> SEQUENCE: 886

Thr Gly Leu Phe Thr Pro Asp Met Ala Phe Glu Thr Ile Val Lys
1 5 10 15

<210> SEQ ID NO 887
<211> LENGTH: 16
<212> TYPE: PRT
<213> ORGANISM: Homo sapiens

<400> SEQUENCE: 887

Val Ala Thr Glu Ala Glu Phe Ser Pro Glu Asp Ser Pro Ser Val Arg
1 5 10 15

<210> SEQ ID NO 888
<211> LENGTH: 9
<212> TYPE: PRT
<213> ORGANISM: Homo sapiens

<400> SEQUENCE: 888

Val Pro Pro Pro Cys Asp Leu Gly Arg
1 5

<210> SEQ ID NO 889
<211> LENGTH: 25
<212> TYPE: PRT
<213> ORGANISM: Homo sapiens

<400> SEQUENCE: 889

Val Val Ser Asn Phe Ile Leu Gln Ala Leu Gln Gly Glu Pro Leu Thr
1 5 10 15

Val Tyr Gly Ser Gly Ser Gln Thr Arg
20 25

<210> SEQ ID NO 890
<211> LENGTH: 9
<212> TYPE: PRT
<213> ORGANISM: Homo sapiens

<400> SEQUENCE: 890

Ala Ala Ile Val Phe Thr Asp Gly Arg
1 5

<210> SEQ ID NO 891
<211> LENGTH: 12
<212> TYPE: PRT

<213> ORGANISM: Homo sapiens

<400> SEQUENCE: 891

Ala Gly Lys Gly Glu Val Thr Phe Glu Asp Val Lys
1 5 10

<210> SEQ ID NO 892
<211> LENGTH: 7
<212> TYPE: PRT
<213> ORGANISM: Homo sapiens

<400> SEQUENCE: 892

Ala Ile Asp Leu Glu Ile Lys
1 5

<210> SEQ ID NO 893
<211> LENGTH: 16
<212> TYPE: PRT
<213> ORGANISM: Homo sapiens

<400> SEQUENCE: 893

Ala Ile Glu Glu Glu Leu Gln Glu Ile Ala Ser Glu Pro Thr Asn Lys
1 5 10 15

<210> SEQ ID NO 894
<211> LENGTH: 29
<212> TYPE: PRT
<213> ORGANISM: Homo sapiens

<400> SEQUENCE: 894

Ala Ser Phe Ile Thr Pro Val Pro Gly Gly Val Gly Pro Met Thr Val
1 5 10 15

Ala Met Leu Met Gln Ser Thr Val Glu Ser Ala Lys Arg
20 25

<210> SEQ ID NO 895
<211> LENGTH: 11
<212> TYPE: PRT
<213> ORGANISM: Homo sapiens

<400> SEQUENCE: 895

Cys Ala Val Val Ser Ser Ala Gly Ser Leu Lys
1 5 10

<210> SEQ ID NO 896
<211> LENGTH: 7
<212> TYPE: PRT
<213> ORGANISM: Homo sapiens

<400> SEQUENCE: 896

Cys His Tyr Tyr Ala Asn Lys
1 5

<210> SEQ ID NO 897
<211> LENGTH: 10
<212> TYPE: PRT
<213> ORGANISM: Homo sapiens

<400> SEQUENCE: 897

Cys Leu Thr Ala Leu Pro Tyr Ile Cys Lys
1 5 10

<210> SEQ ID NO 898
<211> LENGTH: 13

<212> TYPE: PRT
<213> ORGANISM: Homo sapiens

<400> SEQUENCE: 898

Asp Glu Glu Leu Pro Thr Leu Leu His Phe Ala Ala Lys
1 5 10

<210> SEQ ID NO 899
<211> LENGTH: 12
<212> TYPE: PRT
<213> ORGANISM: Homo sapiens

<400> SEQUENCE: 899

Asp Lys Val Met Pro Leu Ile Ile Gln Gly Phe Lys
1 5 10

<210> SEQ ID NO 900
<211> LENGTH: 10
<212> TYPE: PRT
<213> ORGANISM: Homo sapiens

<400> SEQUENCE: 900

Asp Lys Val Val Ala Leu Ala Glu Gly Arg
1 5 10

<210> SEQ ID NO 901
<211> LENGTH: 14
<212> TYPE: PRT
<213> ORGANISM: Homo sapiens

<400> SEQUENCE: 901

Asp Gln Val Phe Gly Ser Asn Leu Ala Asn Leu Cys Gln Arg
1 5 10

<210> SEQ ID NO 902
<211> LENGTH: 10
<212> TYPE: PRT
<213> ORGANISM: Homo sapiens

<400> SEQUENCE: 902

Asp Val Phe Asn Val Glu Asp Gln Lys Arg
1 5 10

<210> SEQ ID NO 903
<211> LENGTH: 13
<212> TYPE: PRT
<213> ORGANISM: Homo sapiens

<400> SEQUENCE: 903

Glu Ala Glu Leu Glu Tyr Asn Pro Glu His Val Ser Arg
1 5 10

<210> SEQ ID NO 904
<211> LENGTH: 11
<212> TYPE: PRT
<213> ORGANISM: Homo sapiens

<400> SEQUENCE: 904

Glu Ala Thr Asp Val Ile Ile Ile His Ser Lys
1 5 10

<210> SEQ ID NO 905
<211> LENGTH: 10
<212> TYPE: PRT
<213> ORGANISM: Homo sapiens

<400> SEQUENCE: 905

Glu Gln Tyr Asp Val Pro Gln Glu Trp Arg
1 5 10

<210> SEQ ID NO 906
<211> LENGTH: 10
<212> TYPE: PRT
<213> ORGANISM: Homo sapiens

<400> SEQUENCE: 906

Glu Ser Pro Gln Asp Ser Ala Ile Thr Arg
1 5 10

<210> SEQ ID NO 907
<211> LENGTH: 12
<212> TYPE: PRT
<213> ORGANISM: Homo sapiens

<400> SEQUENCE: 907

Glu Val Val Leu Gln Trp Phe Thr Glu Asn Ser Lys
1 5 10

<210> SEQ ID NO 908
<211> LENGTH: 9
<212> TYPE: PRT
<213> ORGANISM: Homo sapiens

<400> SEQUENCE: 908

Glu Tyr Phe Thr Phe Pro Ala Ser Lys
1 5

<210> SEQ ID NO 909
<211> LENGTH: 18
<212> TYPE: PRT
<213> ORGANISM: Homo sapiens

<400> SEQUENCE: 909

Phe Phe Asp Ser Ala Cys Thr Met Gly Ala Tyr His Pro Leu Leu Tyr
1 5 10 15

Glu Lys

<210> SEQ ID NO 910
<211> LENGTH: 8
<212> TYPE: PRT
<213> ORGANISM: Homo sapiens

<400> SEQUENCE: 910

Phe Gly Ser Phe Asp Lys Phe Lys
1 5

<210> SEQ ID NO 911
<211> LENGTH: 20
<212> TYPE: PRT
<213> ORGANISM: Homo sapiens

<400> SEQUENCE: 911

Phe Ile Glu Ala Gly Gln Phe Asn Asp Asn Leu Tyr Gly Thr Ser Ile
1 5 10 15

Gln Ser Val Arg
20

<210> SEQ ID NO 912

<211> LENGTH: 16
<212> TYPE: PRT
<213> ORGANISM: Homo sapiens

<400> SEQUENCE: 912

Phe Ile Pro Gly Ser Ala Leu Asn Gly Met Val Glu Met Met Asp Arg
1 5 10 15

<210> SEQ ID NO 913
<211> LENGTH: 12
<212> TYPE: PRT
<213> ORGANISM: Homo sapiens

<400> SEQUENCE: 913

Gly His Leu Gln Ile Ala Ala Cys Pro Asn Gln Asp
1 5 10

<210> SEQ ID NO 914
<211> LENGTH: 20
<212> TYPE: PRT
<213> ORGANISM: Homo sapiens

<400> SEQUENCE: 914

Gly Ser Trp Gln Pro Val Gly Asp Leu Leu Ile Asp Ser Leu Gln Asp
1 5 10 15

His Leu Glu Lys
20

<210> SEQ ID NO 915
<211> LENGTH: 8
<212> TYPE: PRT
<213> ORGANISM: Homo sapiens

<400> SEQUENCE: 915

His Val Val Pro Gly Val Glu Arg
1 5

<210> SEQ ID NO 916
<211> LENGTH: 20
<212> TYPE: PRT
<213> ORGANISM: Homo sapiens

<400> SEQUENCE: 916

Ile Asp Tyr Gly Thr Gly His Glu Ala Ala Phe Ala Ala Phe Leu Cys
1 5 10 15

Cys Leu Cys Lys
20

<210> SEQ ID NO 917
<211> LENGTH: 12
<212> TYPE: PRT
<213> ORGANISM: Homo sapiens

<400> SEQUENCE: 917

Ile Val Gly Asn Gly Ser Glu Gln Gln Leu Gln Lys
1 5 10

<210> SEQ ID NO 918
<211> LENGTH: 21
<212> TYPE: PRT
<213> ORGANISM: Homo sapiens

<400> SEQUENCE: 918

Lys Glu Ser Glu Glu Thr Ile Ile Gln Thr Asp Glu Asp Val Pro Gly 1 5 10 15

Pro Val Pro Val Lys
20

<210> SEQ ID NO 919
<211> LENGTH: 13
<212> TYPE: PRT
<213> ORGANISM: Homo sapiens

<400> SEQUENCE: 919

Leu Glu Pro Ala Gly Pro Ala Cys Pro Glu Gly Gly Arg
1 5 10

<210> SEQ ID NO 920
<211> LENGTH: 12
<212> TYPE: PRT
<213> ORGANISM: Homo sapiens

<400> SEQUENCE: 920

Leu Glu Thr Leu Thr Asn Gln Phe Ser Asp Ser Lys
1 5 10

<210> SEQ ID NO 921
<211> LENGTH: 8
<212> TYPE: PRT
<213> ORGANISM: Homo sapiens

<400> SEQUENCE: 921

Leu Phe Ser Gly Ser Gln Val Arg
1 5

<210> SEQ ID NO 922
<211> LENGTH: 6
<212> TYPE: PRT
<213> ORGANISM: Homo sapiens

<400> SEQUENCE: 922

Leu Leu Glu Ile Leu Lys
1 5

<210> SEQ ID NO 923
<211> LENGTH: 11
<212> TYPE: PRT
<213> ORGANISM: Homo sapiens

<400> SEQUENCE: 923

Leu Leu Gln Gln Phe Pro Leu Asp Leu Glu Lys
1 5 10

<210> SEQ ID NO 924
<211> LENGTH: 23
<212> TYPE: PRT
<213> ORGANISM: Homo sapiens

<400> SEQUENCE: 924

Leu Leu Thr Glu Ser Val Asn Ser Val Ile Ala Gln Ala Pro Pro Val
1 5 10 15

Ala Gln Glu Ala Leu Lys Lys
20

<210> SEQ ID NO 925
<211> LENGTH: 8
<212> TYPE: PRT
<213> ORGANISM: Homo sapiens

<400> SEQUENCE: 925

Leu Pro Val Glu Asp Lys Ile Arg
1               5

<210> SEQ ID NO 926
<211> LENGTH: 8
<212> TYPE: PRT
<213> ORGANISM: Homo sapiens

<400> SEQUENCE: 926

Leu Pro Tyr Gly Gly Gln Cys Arg
1               5

<210> SEQ ID NO 927
<211> LENGTH: 14
<212> TYPE: PRT
<213> ORGANISM: Homo sapiens

<400> SEQUENCE: 927

Leu Ser Thr Ala Ile Thr Leu Leu Pro Leu Glu Glu Gly Arg
1               5                   10

<210> SEQ ID NO 928
<211> LENGTH: 26
<212> TYPE: PRT
<213> ORGANISM: Homo sapiens

<400> SEQUENCE: 928

Leu Thr Ala Ser Ser Thr Cys Gly Leu Asn Gly Pro Gln Pro Tyr Cys
1               5                   10                  15

Ile Val Ser His Leu Gln Asp Glu Lys Lys
            20                  25

<210> SEQ ID NO 929
<211> LENGTH: 17
<212> TYPE: PRT
<213> ORGANISM: Homo sapiens

<400> SEQUENCE: 929

Leu Val Thr Pro His Gly Glu Ser Glu Gln Ile Gly Val Ile Pro Ser
1               5                   10                  15

Lys

<210> SEQ ID NO 930
<211> LENGTH: 15
<212> TYPE: PRT
<213> ORGANISM: Homo sapiens

<400> SEQUENCE: 930

Asn Ala Glu Val Arg Pro Pro Phe Thr Tyr Ala Ser Leu Ile Arg
1               5                   10                  15

<210> SEQ ID NO 931
<211> LENGTH: 18
<212> TYPE: PRT
<213> ORGANISM: Homo sapiens

<400> SEQUENCE: 931

Pro Ala Glu Thr Leu Lys Pro Met Gly Asn Ala Lys Pro Asp Glu Asn
1               5                   10                  15

Leu Lys

<210> SEQ ID NO 932
<211> LENGTH: 17
<212> TYPE: PRT
<213> ORGANISM: Homo sapiens

<400> SEQUENCE: 932

Pro Gly Gly Ala Gly Pro Cys Ala Thr Val Ser Val Phe Pro Gly Ala
1 5 10 15

Arg

<210> SEQ ID NO 933
<211> LENGTH: 12
<212> TYPE: PRT
<213> ORGANISM: Homo sapiens

<400> SEQUENCE: 933

Gln Glu Leu Asn Thr Ile Ala Ser Lys Pro Pro Arg
1 5 10

<210> SEQ ID NO 934
<211> LENGTH: 16
<212> TYPE: PRT
<213> ORGANISM: Homo sapiens

<400> SEQUENCE: 934

Arg Phe Ser Thr Glu Tyr Glu Leu Gln Gln Leu Glu Gln Phe Lys Lys
1 5 10 15

<210> SEQ ID NO 935
<211> LENGTH: 10
<212> TYPE: PRT
<213> ORGANISM: Homo sapiens

<400> SEQUENCE: 935

Arg Val Pro Pro Pro Cys Ala Pro Gly Arg
1 5 10

<210> SEQ ID NO 936
<211> LENGTH: 22
<212> TYPE: PRT
<213> ORGANISM: Homo sapiens

<400> SEQUENCE: 936

Ser Cys His Ala Gly Phe Gly Ser Pro Ala Gly Trp Asp Val Pro Val
1 5 10 15

Gly Ala Leu Ile Gln Arg
20

<210> SEQ ID NO 937
<211> LENGTH: 15
<212> TYPE: PRT
<213> ORGANISM: Homo sapiens

<400> SEQUENCE: 937

Ser Phe Gly His Phe Pro Gly Pro Glu Phe Leu Asp Val Glu Lys
1 5 10 15

<210> SEQ ID NO 938
<211> LENGTH: 10
<212> TYPE: PRT
<213> ORGANISM: Homo sapiens

<400> SEQUENCE: 938

Ser Ile Thr Glu Val Gly Glu Ala Leu Lys
1 5 10

<210> SEQ ID NO 939
<211> LENGTH: 25
<212> TYPE: PRT
<213> ORGANISM: Homo sapiens

<400> SEQUENCE: 939

Ser Leu Gln Ala Asp Thr Thr Asn Thr Asp Thr Ala Leu Thr Thr Leu
1 5 10 15

Glu Glu Ala Leu Ala Glu Lys Glu Arg
20 25

<210> SEQ ID NO 940
<211> LENGTH: 13
<212> TYPE: PRT
<213> ORGANISM: Homo sapiens

<400> SEQUENCE: 940

Ser Ser Asn Leu Leu Asp Leu Lys Asn Pro Phe Phe Arg
1 5 10

<210> SEQ ID NO 941
<211> LENGTH: 16
<212> TYPE: PRT
<213> ORGANISM: Homo sapiens

<400> SEQUENCE: 941

Thr Gly Tyr Ala Phe Val Asp Cys Pro Asp Glu Ser Trp Ala Leu Lys
1 5 10 15

<210> SEQ ID NO 942
<211> LENGTH: 14
<212> TYPE: PRT
<213> ORGANISM: Homo sapiens

<400> SEQUENCE: 942

Thr Gln Val Thr Phe Phe Phe Pro Leu Asp Leu Ser Tyr Arg
1 5 10

<210> SEQ ID NO 943
<211> LENGTH: 16
<212> TYPE: PRT
<213> ORGANISM: Homo sapiens

<400> SEQUENCE: 943

Thr Ser Lys Asp Asp Leu Leu Leu Thr Asp Phe Glu Gly Ala Leu Lys
1 5 10 15

<210> SEQ ID NO 944
<211> LENGTH: 9
<212> TYPE: PRT
<213> ORGANISM: Homo sapiens

<400> SEQUENCE: 944

Thr Val Thr Ile Asn Thr Glu Gln Lys
1 5

<210> SEQ ID NO 945
<211> LENGTH: 12
<212> TYPE: PRT
<213> ORGANISM: Homo sapiens

<400> SEQUENCE: 945

Val Ala Asp Leu Leu Gln His Ile Asn Leu Met Lys
1 5 10

<210> SEQ ID NO 946
<211> LENGTH: 17
<212> TYPE: PRT
<213> ORGANISM: Homo sapiens

<400> SEQUENCE: 946

Val Asp Ala Asn Ile Ser Val His His Pro Gly Glu Pro Leu Gly Val
1 5 10 15

Arg

<210> SEQ ID NO 947
<211> LENGTH: 15
<212> TYPE: PRT
<213> ORGANISM: Homo sapiens

<400> SEQUENCE: 947

Val Met Val Gly Asp Leu Glu Asp Ile Asn Glu Met Ile Ile Lys
1 5 10 15

<210> SEQ ID NO 948
<211> LENGTH: 13
<212> TYPE: PRT
<213> ORGANISM: Homo sapiens

<400> SEQUENCE: 948

Val Val Gly Asp Val Ala Tyr Asp Glu Ala Lys Glu Arg
1 5 10

<210> SEQ ID NO 949
<211> LENGTH: 6
<212> TYPE: PRT
<213> ORGANISM: Homo sapiens

<400> SEQUENCE: 949

Val Tyr Leu Leu Tyr Arg
1 5

<210> SEQ ID NO 950
<211> LENGTH: 15
<212> TYPE: PRT
<213> ORGANISM: Homo sapiens

<400> SEQUENCE: 950

Trp Ala Asn Gly Leu Ser Glu Glu Lys Pro Leu Ser Val Pro Arg
1 5 10 15

<210> SEQ ID NO 951
<211> LENGTH: 7
<212> TYPE: PRT
<213> ORGANISM: Homo sapiens

<400> SEQUENCE: 951

Trp Ala Pro Asn Glu Asn Lys
1 5

<210> SEQ ID NO 952
<211> LENGTH: 11
<212> TYPE: PRT
<213> ORGANISM: Homo sapiens

<400> SEQUENCE: 952

Trp Cys Val Leu Ser Thr Pro Glu Ile Gln Lys
1 5 10

<210> SEQ ID NO 953
<211> LENGTH: 12
<212> TYPE: PRT
<213> ORGANISM: Homo sapiens

<400> SEQUENCE: 953

Trp Met Asp Pro Glu Gly Glu Met Lys Pro Gly Arg
1 5 10

<210> SEQ ID NO 954
<211> LENGTH: 10
<212> TYPE: PRT
<213> ORGANISM: Homo sapiens

<400> SEQUENCE: 954

Trp Val Leu Leu Gln Asp Ile Leu Leu Lys
1 5 10

<210> SEQ ID NO 955
<211> LENGTH: 9
<212> TYPE: PRT
<213> ORGANISM: Homo sapiens

<400> SEQUENCE: 955

Tyr Glu Glu Gln Arg Pro Ser Leu Lys
1 5

<210> SEQ ID NO 956
<211> LENGTH: 8
<212> TYPE: PRT
<213> ORGANISM: Homo sapiens

<400> SEQUENCE: 956

Tyr Gly Leu Leu Asn Val Thr Lys
1 5

<210> SEQ ID NO 957
<211> LENGTH: 11
<212> TYPE: PRT
<213> ORGANISM: Homo sapiens

<400> SEQUENCE: 957

Tyr Gln His Ile Gly Leu Val Ala Met Phe Arg
1 5 10

<210> SEQ ID NO 958
<211> LENGTH: 16
<212> TYPE: PRT
<213> ORGANISM: Homo sapiens

<400> SEQUENCE: 958

Tyr Val Pro Ala Ile Ala His Leu Ile His Ser Leu Asn Pro Val Arg
1 5 10 15

<210> SEQ ID NO 959
<211> LENGTH: 12
<212> TYPE: PRT
<213> ORGANISM: Homo sapiens

<400> SEQUENCE: 959

Ala Ala Ile Leu Gln Thr Glu Val Asp Ala Leu Arg 1 5 10

<210> SEQ ID NO 960
<211> LENGTH: 25
<212> TYPE: PRT
<213> ORGANISM: Homo sapiens

<400> SEQUENCE: 960

Ala Asp Gly Gly Pro Glu Ala Gly Glu Leu Pro Ser Ile Gly Glu Ala
1 5 10 15

Thr Ala Ala Leu Ala Leu Ala Gly Arg
20 25

<210> SEQ ID NO 961
<211> LENGTH: 7
<212> TYPE: PRT
<213> ORGANISM: Homo sapiens

<400> SEQUENCE: 961

Ala Glu Asn Tyr Trp Trp Arg
1 5

<210> SEQ ID NO 962
<211> LENGTH: 12
<212> TYPE: PRT
<213> ORGANISM: Homo sapiens

<400> SEQUENCE: 962

Ala Glu Gln Pro Pro His Leu Thr Pro Gly Ile Arg
1 5 10

<210> SEQ ID NO 963
<211> LENGTH: 8
<212> TYPE: PRT
<213> ORGANISM: Homo sapiens

<400> SEQUENCE: 963

Ala Ile Glu Ala Leu Ser Gly Lys
1 5

<210> SEQ ID NO 964
<211> LENGTH: 10
<212> TYPE: PRT
<213> ORGANISM: Homo sapiens

<400> SEQUENCE: 964

Ala Ile Gly Asn Ile Glu Leu Gly Ile Arg
1 5 10

<210> SEQ ID NO 965
<211> LENGTH: 12
<212> TYPE: PRT
<213> ORGANISM: Homo sapiens

<400> SEQUENCE: 965

Ala Met Asn Asn Ser Trp His Pro Glu Cys Phe Arg
1 5 10

<210> SEQ ID NO 966
<211> LENGTH: 12
<212> TYPE: PRT
<213> ORGANISM: Homo sapiens

<400> SEQUENCE: 966

Ala Pro Asn Leu Ser Ser Gly Asn Val Ser Leu Lys
1 5 10

<210> SEQ ID NO 967
<211> LENGTH: 11
<212> TYPE: PRT
<213> ORGANISM: Homo sapiens

<400> SEQUENCE: 967

Ala Gln Val Ala His Ala Asp Gln Gln Leu Arg
1 5 10

<210> SEQ ID NO 968
<211> LENGTH: 9
<212> TYPE: PRT
<213> ORGANISM: Homo sapiens

<400> SEQUENCE: 968

Ala Arg Glu His Phe Gly Thr Val Lys
1 5

<210> SEQ ID NO 969
<211> LENGTH: 12
<212> TYPE: PRT
<213> ORGANISM: Homo sapiens

<400> SEQUENCE: 969

Ala Arg Phe Glu Gln Met Ala Lys Ala Arg Glu Glu
1 5 10

<210> SEQ ID NO 970
<211> LENGTH: 37
<212> TYPE: PRT
<213> ORGANISM: Homo sapiens

<400> SEQUENCE: 970

Ala Ser Phe Ala Asn Glu Asp Gly Gln Val Ser Pro Gly Ser Leu Leu
1 5 10 15

Leu Ala Gly Ala Ile Ala Gly Met Pro Ala Ala Ser Leu Val Thr Pro
20 25 30

Ala Asp Val Ile Lys
35

<210> SEQ ID NO 971
<211> LENGTH: 14
<212> TYPE: PRT
<213> ORGANISM: Homo sapiens

<400> SEQUENCE: 971

Ala Val Val Val Gly Phe Asp Pro His Phe Ser Tyr Met Lys
1 5 10

<210> SEQ ID NO 972
<211> LENGTH: 13
<212> TYPE: PRT
<213> ORGANISM: Homo sapiens

<400> SEQUENCE: 972

Asp Asp Leu Leu Leu Thr Asp Phe Glu Gly Ala Leu Lys
1 5 10

<210> SEQ ID NO 973
<211> LENGTH: 12
<212> TYPE: PRT

<213> ORGANISM: Homo sapiens

<400> SEQUENCE: 973

Asp Asn Glu Glu Thr Gly Phe Gly Ser Gly Thr Arg
1 5 10

<210> SEQ ID NO 974
<211> LENGTH: 12
<212> TYPE: PRT
<213> ORGANISM: Homo sapiens

<400> SEQUENCE: 974

Asp Val Asp Gly Leu Thr Ser Ile Asn Ala Gly Lys
1 5 10

<210> SEQ ID NO 975
<211> LENGTH: 12
<212> TYPE: PRT
<213> ORGANISM: Homo sapiens

<400> SEQUENCE: 975

Glu Ala Gly Ile Gln Pro Ser Leu Leu Cys Val Arg
1 5 10

<210> SEQ ID NO 976
<211> LENGTH: 16
<212> TYPE: PRT
<213> ORGANISM: Homo sapiens

<400> SEQUENCE: 976

Glu Asp Phe Asn Ser Lys His Met Ala Asn Gln Arg Ala Leu Gly Lys
1 5 10 15

<210> SEQ ID NO 977
<211> LENGTH: 14
<212> TYPE: PRT
<213> ORGANISM: Homo sapiens

<400> SEQUENCE: 977

Glu Glu Gly Asp Leu Gly Pro Val Tyr Gly Phe Gln Trp Arg
1 5 10

<210> SEQ ID NO 978
<211> LENGTH: 15
<212> TYPE: PRT
<213> ORGANISM: Homo sapiens

<400> SEQUENCE: 978

Glu Glu Leu Ser Ser Gly Asp Ser Leu Ser Pro Asp Pro Trp Lys
1 5 10 15

<210> SEQ ID NO 979
<211> LENGTH: 10
<212> TYPE: PRT
<213> ORGANISM: Homo sapiens

<400> SEQUENCE: 979

Glu Leu Gln Lys Ala Val Glu Glu Met Lys
1 5 10

<210> SEQ ID NO 980
<211> LENGTH: 23
<212> TYPE: PRT
<213> ORGANISM: Homo sapiens

<400> SEQUENCE: 980

Glu Asn Ser Met Leu Arg Glu Glu Met His Arg Arg Phe Glu Asn Ala
1 5 10 15

Pro Asp Ser Ala Lys Thr Lys
20

<210> SEQ ID NO 981
<211> LENGTH: 12
<212> TYPE: PRT
<213> ORGANISM: Homo sapiens

<400> SEQUENCE: 981

Glu Gln Ile Ser Asp Ile Asp Asp Ala Val Arg Lys
1 5 10

<210> SEQ ID NO 982
<211> LENGTH: 12
<212> TYPE: PRT
<213> ORGANISM: Homo sapiens

<400> SEQUENCE: 982

Glu Val Val Asp Ala Gly Leu Val Gly Leu Glu Arg
1 5 10

<210> SEQ ID NO 983
<211> LENGTH: 15
<212> TYPE: PRT
<213> ORGANISM: Homo sapiens

<400> SEQUENCE: 983

Phe Glu Ala Leu Gln Ala Pro Ala Cys His Glu Asn Met Val Lys
1 5 10 15

<210> SEQ ID NO 984
<211> LENGTH: 9
<212> TYPE: PRT
<213> ORGANISM: Homo sapiens

<400> SEQUENCE: 984

Phe His Leu Cys Ser Val Ala Thr Arg
1 5

<210> SEQ ID NO 985
<211> LENGTH: 16
<212> TYPE: PRT
<213> ORGANISM: Homo sapiens

<400> SEQUENCE: 985

Phe Asn Leu Asp Thr Glu Asn Ala Met Thr Phe Gln Glu Asn Ala Arg
1 5 10 15

<210> SEQ ID NO 986
<211> LENGTH: 8
<212> TYPE: PRT
<213> ORGANISM: Homo sapiens

<400> SEQUENCE: 986

Phe Thr Glu Glu Ile Pro Leu Lys
1 5

<210> SEQ ID NO 987
<211> LENGTH: 16
<212> TYPE: PRT
<213> ORGANISM: Homo sapiens

<400> SEQUENCE: 987

```
Gly Ala Leu Thr Ser Thr Pro Tyr Ser Pro Thr Gln His Leu Glu Arg
1               5                   10                  15
```

<210> SEQ ID NO 988
<211> LENGTH: 20
<212> TYPE: PRT
<213> ORGANISM: Homo sapiens

<400> SEQUENCE: 988

```
Gly Asp Glu Gly Pro Ile Gly His Gln Gly Pro Ile Gly Gln Glu Gly
1               5                   10                  15

Ala Pro Gly Arg
            20
```

<210> SEQ ID NO 989
<211> LENGTH: 17
<212> TYPE: PRT
<213> ORGANISM: Homo sapiens

<400> SEQUENCE: 989

```
Gly Asp Ser Gly Gln Pro Leu Phe Leu Thr Pro Tyr Ile Glu Ala Gly
1               5                   10                  15

Lys
```

<210> SEQ ID NO 990
<211> LENGTH: 20
<212> TYPE: PRT
<213> ORGANISM: Homo sapiens

<400> SEQUENCE: 990

```
Gly Glu Pro Val Ser Ala Glu Asp Leu Gly Val Ser Gly Ala Leu Thr
1               5                   10                  15

Val Leu Met Lys
            20
```

<210> SEQ ID NO 991
<211> LENGTH: 21
<212> TYPE: PRT
<213> ORGANISM: Homo sapiens

<400> SEQUENCE: 991

```
Gly Phe Ser Gly Ile Phe Pro Ala Cys His Pro Cys His Ala Cys Phe
1               5                   10                  15

Gly Asp Trp Asp Arg
            20
```

<210> SEQ ID NO 992
<211> LENGTH: 9
<212> TYPE: PRT
<213> ORGANISM: Homo sapiens

<400> SEQUENCE: 992

```
Gly Ile Asp Thr Pro Gln Cys His Arg
1               5
```

<210> SEQ ID NO 993
<211> LENGTH: 16
<212> TYPE: PRT
<213> ORGANISM: Homo sapiens

<400> SEQUENCE: 993

Gly Trp Asp Ser Ser His Glu Asp Asp Leu Pro Val Tyr Leu Ala Arg
1 5 10 15

<210> SEQ ID NO 994
<211> LENGTH: 12
<212> TYPE: PRT
<213> ORGANISM: Homo sapiens

<400> SEQUENCE: 994

His Glu Gln Asn Ile Asp Cys Gly Gly Gly Tyr Val
1 5 10

<210> SEQ ID NO 995
<211> LENGTH: 15
<212> TYPE: PRT
<213> ORGANISM: Homo sapiens

<400> SEQUENCE: 995

His Leu Asn Gln Gly Thr Asp Glu Asp Ile Tyr Leu Leu Gly Lys
1 5 10 15

<210> SEQ ID NO 996
<211> LENGTH: 7
<212> TYPE: PRT
<213> ORGANISM: Homo sapiens

<400> SEQUENCE: 996

Ile Ala Glu Leu Gln Gln Arg
1 5

<210> SEQ ID NO 997
<211> LENGTH: 10
<212> TYPE: PRT
<213> ORGANISM: Homo sapiens

<400> SEQUENCE: 997

Ile Leu Val Val Ile Thr Asp Gly Glu Lys
1 5 10

<210> SEQ ID NO 998
<211> LENGTH: 12
<212> TYPE: PRT
<213> ORGANISM: Homo sapiens

<400> SEQUENCE: 998

Ile Asn Asp Ala Phe Asn Leu Ala Ser Ala His Lys
1 5 10

<210> SEQ ID NO 999
<211> LENGTH: 15
<212> TYPE: PRT
<213> ORGANISM: Homo sapiens

<400> SEQUENCE: 999

Ile Asn Leu Pro Ala Pro Asn Pro Asp His Val Gly Gly Tyr Lys
1 5 10 15

<210> SEQ ID NO 1000
<211> LENGTH: 9
<212> TYPE: PRT
<213> ORGANISM: Homo sapiens

<400> SEQUENCE: 1000

Ile Gln Glu Ile Leu Thr Gln Val Lys 1 5

<210> SEQ ID NO 1001
<211> LENGTH: 13
<212> TYPE: PRT
<213> ORGANISM: Homo sapiens

<400> SEQUENCE: 1001

Ile Gln Pro Thr Thr Pro Ser Glu Pro Thr Ala Ile Lys
1 5 10

<210> SEQ ID NO 1002
<211> LENGTH: 32
<212> TYPE: PRT
<213> ORGANISM: Homo sapiens

<400> SEQUENCE: 1002

Ile Ser Pro Gly Ser Thr Glu Ile Thr Thr Leu Pro Gly Ser Thr Thr
1 5 10 15

Thr Pro Gly Leu Ser Glu Ala Ser Thr Thr Phe Tyr Ser Ser Pro Arg
20 25 30

<210> SEQ ID NO 1003
<211> LENGTH: 32
<212> TYPE: PRT
<213> ORGANISM: Homo sapiens

<400> SEQUENCE: 1003

Ile Ser Pro Gly Ser Thr Glu Ile Thr Thr Leu Pro Gly Ser Thr Thr
1 5 10 15

Thr Pro Gly Leu Ser Glu Ala Ser Thr Thr Phe Tyr Ser Ser Pro Arg
20 25 30

<210> SEQ ID NO 1004
<211> LENGTH: 32
<212> TYPE: PRT
<213> ORGANISM: Homo sapiens

<400> SEQUENCE: 1004

Ile Ser Pro Gly Ser Thr Glu Ile Thr Thr Leu Pro Gly Ser Thr Thr
1 5 10 15

Thr Pro Gly Leu Ser Glu Ala Ser Thr Thr Phe Tyr Ser Ser Pro Arg
20 25 30

<210> SEQ ID NO 1005
<211> LENGTH: 32
<212> TYPE: PRT
<213> ORGANISM: Homo sapiens

<400> SEQUENCE: 1005

Ile Ser Pro Gly Ser Thr Glu Ile Thr Thr Leu Pro Gly Ser Thr Thr
1 5 10 15

Thr Pro Gly Leu Ser Glu Ala Ser Thr Thr Phe Tyr Ser Ser Pro Arg
20 25 30

<210> SEQ ID NO 1006
<211> LENGTH: 9
<212> TYPE: PRT
<213> ORGANISM: Homo sapiens

<400> SEQUENCE: 1006

Ile Ser Ser Met Glu Arg Gly Leu Arg
1 5

<210> SEQ ID NO 1007
<211> LENGTH: 22
<212> TYPE: PRT
<213> ORGANISM: Homo sapiens

<400> SEQUENCE: 1007

Ile Val Leu Asp Val Gly Cys Gly Ser Gly Ile Leu Ser Phe Phe Ala
1 5 10 15

Ala Gln Ala Gly Ala Arg
20

<210> SEQ ID NO 1008
<211> LENGTH: 22
<212> TYPE: PRT
<213> ORGANISM: Homo sapiens

<400> SEQUENCE: 1008

Ile Tyr Gly Ala Asp Asp Ile Glu Leu Leu Pro Glu Ala Gln His Lys
1 5 10 15

Ala Glu Val Tyr Thr Lys
20

<210> SEQ ID NO 1009
<211> LENGTH: 7
<212> TYPE: PRT
<213> ORGANISM: Homo sapiens

<400> SEQUENCE: 1009

Lys Asp Val Lys Leu Asp Lys
1 5

<210> SEQ ID NO 1010
<211> LENGTH: 11
<212> TYPE: PRT
<213> ORGANISM: Homo sapiens

<400> SEQUENCE: 1010

Lys Phe Gln Glu Thr Glu Gln Thr Ile Gln Lys
1 5 10

<210> SEQ ID NO 1011
<211> LENGTH: 14
<212> TYPE: PRT
<213> ORGANISM: Homo sapiens

<400> SEQUENCE: 1011

Lys Phe Ser Tyr Asp Leu Ser Gln Cys Ile Asn Gln Met Lys
1 5 10

<210> SEQ ID NO 1012
<211> LENGTH: 17
<212> TYPE: PRT
<213> ORGANISM: Homo sapiens

<400> SEQUENCE: 1012

Lys Leu Pro Ala Glu Asn Gly Ser Ser Ser Ala Glu Thr Leu Asn Ala
1 5 10 15

Lys

<210> SEQ ID NO 1013
<211> LENGTH: 12
<212> TYPE: PRT

<213> ORGANISM: Homo sapiens

<400> SEQUENCE: 1013

Lys Leu Thr Glu Leu Glu Asn Glu Leu Asn Thr Lys
1 5 10

<210> SEQ ID NO 1014
<211> LENGTH: 7
<212> TYPE: PRT
<213> ORGANISM: Homo sapiens

<400> SEQUENCE: 1014

Lys Gln Thr Glu Asn Pro Lys
1 5

<210> SEQ ID NO 1015
<211> LENGTH: 11
<212> TYPE: PRT
<213> ORGANISM: Homo sapiens

<400> SEQUENCE: 1015

Lys Gln Val Thr Pro Leu Phe Ile His Phe Arg
1 5 10

<210> SEQ ID NO 1016
<211> LENGTH: 19
<212> TYPE: PRT
<213> ORGANISM: Homo sapiens

<400> SEQUENCE: 1016

Lys Arg Val Glu Asp Ala Tyr Ile Leu Thr Cys Asn Val Ser Leu Glu
1 5 10 15

Tyr Glu Lys

<210> SEQ ID NO 1017
<211> LENGTH: 13
<212> TYPE: PRT
<213> ORGANISM: Homo sapiens

<400> SEQUENCE: 1017

Lys Val Pro Phe Ala Trp Cys Ala Pro Glu Ser Leu Lys
1 5 10

<210> SEQ ID NO 1018
<211> LENGTH: 8
<212> TYPE: PRT
<213> ORGANISM: Homo sapiens

<400> SEQUENCE: 1018

Leu Ala Gly Ala Pro Ala Pro Lys
1 5

<210> SEQ ID NO 1019
<211> LENGTH: 15
<212> TYPE: PRT
<213> ORGANISM: Homo sapiens

<400> SEQUENCE: 1019

Leu His Glu Leu Tyr Glu Lys Val Phe Ser Arg Arg Ala Asp Arg
1 5 10 15

<210> SEQ ID NO 1020
<211> LENGTH: 15
<212> TYPE: PRT

<213> ORGANISM: Homo sapiens

<400> SEQUENCE: 1020

Leu Leu Asp Pro Glu Asp Val Asp Thr Thr Tyr Pro Asp Lys Lys
1 5 10 15

<210> SEQ ID NO 1021
<211> LENGTH: 23
<212> TYPE: PRT
<213> ORGANISM: Homo sapiens

<400> SEQUENCE: 1021

Leu Leu Glu Ser Leu Gln Glu Asn His Phe Gln Glu Asp Glu Gln Phe
1 5 10 15

Leu Gly Ala Val Met Pro Arg
20

<210> SEQ ID NO 1022
<211> LENGTH: 9
<212> TYPE: PRT
<213> ORGANISM: Homo sapiens

<400> SEQUENCE: 1022

Leu Leu Gln Val Ala Val Glu Asp Arg
1 5

<210> SEQ ID NO 1023
<211> LENGTH: 22
<212> TYPE: PRT
<213> ORGANISM: Homo sapiens

<400> SEQUENCE: 1023

Leu Leu Val Ser Asp Ile Gln Thr Ile Gln Pro Ser Leu Asn Ser Val
1 5 10 15

Asn Glu Gly Gly Gln Lys
20

<210> SEQ ID NO 1024
<211> LENGTH: 10
<212> TYPE: PRT
<213> ORGANISM: Homo sapiens

<400> SEQUENCE: 1024

Leu Asn Leu His Ser Ala Asp Trp Gln Arg
1 5 10

<210> SEQ ID NO 1025
<211> LENGTH: 16
<212> TYPE: PRT
<213> ORGANISM: Homo sapiens

<400> SEQUENCE: 1025

Leu Pro Ala Glu Asn Gly Ser Ser Ser Ala Glu Thr Leu Asn Ala Lys
1 5 10 15

<210> SEQ ID NO 1026
<211> LENGTH: 10
<212> TYPE: PRT
<213> ORGANISM: Homo sapiens

<400> SEQUENCE: 1026

Leu Pro Leu Glu Asp Ala Asp Ile Ile Lys
1 5 10

<210> SEQ ID NO 1027
<211> LENGTH: 16
<212> TYPE: PRT
<213> ORGANISM: Homo sapiens

<400> SEQUENCE: 1027

Leu Pro Leu Gln Met Ala Leu Thr Glu Leu Glu Thr Leu Ala Glu Lys
1 5 10 15

<210> SEQ ID NO 1028
<211> LENGTH: 20
<212> TYPE: PRT
<213> ORGANISM: Homo sapiens

<400> SEQUENCE: 1028

Leu Pro Thr Glu Trp Asn Val Leu Gly Thr Asp Gln Ser Leu His Asp
1 5 10 15

Ala Gly Pro Arg
20

<210> SEQ ID NO 1029
<211> LENGTH: 14
<212> TYPE: PRT
<213> ORGANISM: Homo sapiens

<400> SEQUENCE: 1029

Leu Gln Glu Ala Leu Ser Gln Leu Asp Phe Gln Trp Glu Lys
1 5 10

<210> SEQ ID NO 1030
<211> LENGTH: 24
<212> TYPE: PRT
<213> ORGANISM: Homo sapiens

<400> SEQUENCE: 1030

Leu Gln Glu Pro Ser Ala Gln Ala Asn Cys Cys Asp Ser Glu Lys Asn
1 5 10 15

Gly Asp Ile Gly Gln Gln Ile Lys
20

<210> SEQ ID NO 1031
<211> LENGTH: 21
<212> TYPE: PRT
<213> ORGANISM: Homo sapiens

<400> SEQUENCE: 1031

Leu Gln Ser Gln Val Ile Ser Glu Leu Asp Ala Cys Lys Glu Cys Thr
1 5 10 15

Gln Gly Val Gln Arg
20

<210> SEQ ID NO 1032
<211> LENGTH: 20
<212> TYPE: PRT
<213> ORGANISM: Homo sapiens

<400> SEQUENCE: 1032

Leu Tyr Ile Gly Asn Leu Ser Glu Asn Ala Ala Pro Ser Asp Leu Glu
1 5 10 15

Ser Ile Phe Lys
20

<210> SEQ ID NO 1033
<211> LENGTH: 9
<212> TYPE: PRT
<213> ORGANISM: Homo sapiens

<400> SEQUENCE: 1033

Met Leu Glu Ser Tyr Leu His Ala Lys
1 5

<210> SEQ ID NO 1034
<211> LENGTH: 7
<212> TYPE: PRT
<213> ORGANISM: Homo sapiens

<400> SEQUENCE: 1034

Asn Leu Leu Leu Ala Thr Arg
1 5

<210> SEQ ID NO 1035
<211> LENGTH: 19
<212> TYPE: PRT
<213> ORGANISM: Homo sapiens

<400> SEQUENCE: 1035

Asn Val Leu Leu His Glu Met Gln Ile Gln His Pro Thr Ala Ser Leu
1 5 10 15

Ile Ala Lys

<210> SEQ ID NO 1036
<211> LENGTH: 9
<212> TYPE: PRT
<213> ORGANISM: Homo sapiens

<400> SEQUENCE: 1036

Gln Lys Pro Cys Asp Leu Pro Leu Arg
1 5

<210> SEQ ID NO 1037
<211> LENGTH: 17
<212> TYPE: PRT
<213> ORGANISM: Homo sapiens

<400> SEQUENCE: 1037

Gln Pro Ala Ala Phe Ile Val Thr Gln Tyr Pro Leu Pro Asn Thr Val
1 5 10 15

Lys

<210> SEQ ID NO 1038
<211> LENGTH: 12
<212> TYPE: PRT
<213> ORGANISM: Homo sapiens

<400> SEQUENCE: 1038

Gln Gln Leu Gly His Ile Glu Ala Trp Ala Glu Lys
1 5 10

<210> SEQ ID NO 1039
<211> LENGTH: 9
<212> TYPE: PRT
<213> ORGANISM: Homo sapiens

<400> SEQUENCE: 1039

Gln Arg Glu Glu His Tyr Phe Cys Lys
1 5

<210> SEQ ID NO 1040
<211> LENGTH: 12
<212> TYPE: PRT
<213> ORGANISM: Homo sapiens

<400> SEQUENCE: 1040

Gln Val Phe His Ala Leu Glu Asp Glu Leu Gln Lys
1 5 10

<210> SEQ ID NO 1041
<211> LENGTH: 16
<212> TYPE: PRT
<213> ORGANISM: Homo sapiens

<400> SEQUENCE: 1041

Gln Trp Met Glu Asn Pro Asn Asn Asn Pro Ile His Pro Asn Leu Arg
1 5 10 15

<210> SEQ ID NO 1042
<211> LENGTH: 20
<212> TYPE: PRT
<213> ORGANISM: Homo sapiens

<400> SEQUENCE: 1042

Ser Ala Gln Ala Leu Val Glu Gln Met Val Asn Glu Gly Val Asn Ala
1 5 10 15

Asp Ser Ile Lys
20

<210> SEQ ID NO 1043
<211> LENGTH: 37
<212> TYPE: PRT
<213> ORGANISM: Homo sapiens

<400> SEQUENCE: 1043

Ser Ala Thr Ser Val Leu Val Gly Glu Pro Thr Thr Ser Pro Ile Ser
1 5 10 15

Ser Gly Ser Thr Glu Thr Thr Ala Leu Pro Gly Ser Thr Thr Thr Ala
20 25 30

Gly Leu Ser Glu Lys
35

<210> SEQ ID NO 1044
<211> LENGTH: 37
<212> TYPE: PRT
<213> ORGANISM: Homo sapiens

<400> SEQUENCE: 1044

Ser Ala Thr Ser Val Leu Val Gly Glu Pro Thr Thr Ser Pro Ile Ser
1 5 10 15

Ser Gly Ser Thr Glu Thr Thr Ala Leu Pro Gly Ser Thr Thr Thr Ala
20 25 30

Gly Leu Ser Glu Lys
35

<210> SEQ ID NO 1045
<211> LENGTH: 37
<212> TYPE: PRT
<213> ORGANISM: Homo sapiens

<400> SEQUENCE: 1045

Ser Ala Thr Ser Val Leu Val Gly Glu Pro Thr Thr Ser Pro Ile Ser
1 5 10 15

Ser Gly Ser Thr Glu Thr Thr Ala Leu Pro Gly Ser Thr Thr Thr Ala
20 25 30

Gly Leu Ser Glu Lys
35

<210> SEQ ID NO 1046
<211> LENGTH: 18
<212> TYPE: PRT
<213> ORGANISM: Homo sapiens

<400> SEQUENCE: 1046

Ser Ala Val Glu Gly Met Pro Ser Asn Leu Asp Ser Glu Val Ala Trp
1 5 10 15

Gly Lys

<210> SEQ ID NO 1047
<211> LENGTH: 17
<212> TYPE: PRT
<213> ORGANISM: Homo sapiens

<400> SEQUENCE: 1047

Ser Glu Asp Ser Thr Ile Tyr Asp Leu Leu Lys Asp Pro Val Ser Leu
1 5 10 15

Arg

<210> SEQ ID NO 1048
<211> LENGTH: 10
<212> TYPE: PRT
<213> ORGANISM: Homo sapiens

<400> SEQUENCE: 1048

Ser Leu Glu Ser Ala Leu Lys Asp Leu Lys
1 5 10

<210> SEQ ID NO 1049
<211> LENGTH: 11
<212> TYPE: PRT
<213> ORGANISM: Homo sapiens

<400> SEQUENCE: 1049

Ser Pro Asn Pro Ala Leu Thr Phe Cys Val Lys
1 5 10

<210> SEQ ID NO 1050
<211> LENGTH: 9
<212> TYPE: PRT
<213> ORGANISM: Homo sapiens

<400> SEQUENCE: 1050

Ser Thr Thr Phe Tyr Thr Ser Pro Arg
1 5

<210> SEQ ID NO 1051
<211> LENGTH: 9
<212> TYPE: PRT
<213> ORGANISM: Homo sapiens

<400> SEQUENCE: 1051

Ser Thr Thr Phe Tyr Thr Ser Pro Arg
1 5

<210> SEQ ID NO 1052
<211> LENGTH: 9
<212> TYPE: PRT
<213> ORGANISM: Homo sapiens

<400> SEQUENCE: 1052

Ser Thr Thr Phe Tyr Thr Ser Pro Arg
1 5

<210> SEQ ID NO 1053
<211> LENGTH: 9
<212> TYPE: PRT
<213> ORGANISM: Homo sapiens

<400> SEQUENCE: 1053

Ser Thr Thr Phe Tyr Thr Ser Pro Arg
1 5

<210> SEQ ID NO 1054
<211> LENGTH: 8
<212> TYPE: PRT
<213> ORGANISM: Homo sapiens

<400> SEQUENCE: 1054

Thr Cys His Tyr Tyr Ala Asn Lys
1 5

<210> SEQ ID NO 1055
<211> LENGTH: 25
<212> TYPE: PRT
<213> ORGANISM: Homo sapiens

<400> SEQUENCE: 1055

Thr Cys Ser Glu Cys Gln Glu Leu His Trp Gly Asp Pro Gly Leu Gln
1 5 10 15

Cys His Ala Cys Asp Cys Asp Ser Arg
20 25

<210> SEQ ID NO 1056
<211> LENGTH: 8
<212> TYPE: PRT
<213> ORGANISM: Homo sapiens

<400> SEQUENCE: 1056

Thr Cys Tyr Pro Leu Glu Ser Arg
1 5

<210> SEQ ID NO 1057
<211> LENGTH: 10
<212> TYPE: PRT
<213> ORGANISM: Homo sapiens

<400> SEQUENCE: 1057

Thr Glu Phe Gln Leu Glu Leu Pro Val Lys
1 5 10

<210> SEQ ID NO 1058
<211> LENGTH: 14
<212> TYPE: PRT
<213> ORGANISM: Homo sapiens

<400> SEQUENCE: 1058

Thr Lys Glu Pro Val Ile Met Ser Thr Leu Glu Thr Val Arg
1 5 10

<210> SEQ ID NO 1059
<211> LENGTH: 15
<212> TYPE: PRT
<213> ORGANISM: Homo sapiens

<400> SEQUENCE: 1059

Thr Pro Leu Trp Ile Gly Leu Ala Gly Glu Glu Gly Ser Arg Arg
1 5 10 15

<210> SEQ ID NO 1060
<211> LENGTH: 34
<212> TYPE: PRT
<213> ORGANISM: Homo sapiens

<400> SEQUENCE: 1060

Thr Gln Ser Leu Asn Pro Ala Pro Phe Ser Pro Leu Thr Ala Gln Gln
1 5 10 15

Met Lys Pro Glu Lys Pro Ser Thr Leu Gln Arg Pro Gln Glu Thr Val
20 25 30

Ile Arg

<210> SEQ ID NO 1061
<211> LENGTH: 16
<212> TYPE: PRT
<213> ORGANISM: Homo sapiens

<400> SEQUENCE: 1061

Thr Val Gly Trp Asn Val Pro Val Gly Tyr Leu Val Glu Ser Gly Arg
1 5 10 15

<210> SEQ ID NO 1062
<211> LENGTH: 31
<212> TYPE: PRT
<213> ORGANISM: Homo sapiens

<400> SEQUENCE: 1062

Val Ala Ser Ser Ser Ser Gly Asn Asn Phe Leu Ser Gly Ser Pro Ala
1 5 10 15

Ser Pro Met Gly Asp Ile Leu Gln Thr Pro Gln Phe Gln Met Arg
20 25 30

<210> SEQ ID NO 1063
<211> LENGTH: 17
<212> TYPE: PRT
<213> ORGANISM: Homo sapiens

<400> SEQUENCE: 1063

Val Ala Trp Val Ser His Asp Ser Thr Val Cys Leu Ala Asp Ala Asp
1 5 10 15

Lys

<210> SEQ ID NO 1064
<211> LENGTH: 8
<212> TYPE: PRT
<213> ORGANISM: Homo sapiens

<400> SEQUENCE: 1064

Val Glu Gln Gln Pro Asp Tyr Arg
1 5

<210> SEQ ID NO 1065

<211> LENGTH: 25
<212> TYPE: PRT
<213> ORGANISM: Homo sapiens

<400> SEQUENCE: 1065

Val Ile Gln Glu Val Ser Gly Leu Pro Ser Glu Gly Ala Ser Glu Gly
1 5 10 15

Asn Gln Tyr Thr Pro Asp Ala Gln Arg
20 25

<210> SEQ ID NO 1066
<211> LENGTH: 15
<212> TYPE: PRT
<213> ORGANISM: Homo sapiens

<400> SEQUENCE: 1066

Val Leu Asp Leu Leu Asp Pro Ala Ser Gly Asp Leu Val Ile Arg
1 5 10 15

<210> SEQ ID NO 1067
<211> LENGTH: 18
<212> TYPE: PRT
<213> ORGANISM: Homo sapiens

<400> SEQUENCE: 1067

Val Leu Leu His Glu Met Gln Ile Gln His Pro Thr Ala Ser Leu Ile
1 5 10 15

Ala Lys

<210> SEQ ID NO 1068
<211> LENGTH: 11
<212> TYPE: PRT
<213> ORGANISM: Homo sapiens

<400> SEQUENCE: 1068

Val Met Asp Lys Val Thr Ser Asp Glu Thr Arg
1 5 10

<210> SEQ ID NO 1069
<211> LENGTH: 9
<212> TYPE: PRT
<213> ORGANISM: Homo sapiens

<400> SEQUENCE: 1069

Val Pro Arg Tyr Glu Leu Leu Leu Lys
1 5

<210> SEQ ID NO 1070
<211> LENGTH: 10
<212> TYPE: PRT
<213> ORGANISM: Homo sapiens

<400> SEQUENCE: 1070

Val Gln Phe Gly Ala Ser His Val Phe Lys
1 5 10

<210> SEQ ID NO 1071
<211> LENGTH: 9
<212> TYPE: PRT
<213> ORGANISM: Homo sapiens

<400> SEQUENCE: 1071

Val Ser Cys Ile Val Ser Ala Ala Lys
1 5

<210> SEQ ID NO 1072
<211> LENGTH: 13
<212> TYPE: PRT
<213> ORGANISM: Homo sapiens

<400> SEQUENCE: 1072

Val Thr Glu Ile Leu Gly Ile Glu Pro Asp Arg Glu Lys
1               5                   10

<210> SEQ ID NO 1073
<211> LENGTH: 11
<212> TYPE: PRT
<213> ORGANISM: Homo sapiens

<400> SEQUENCE: 1073

Val Val Asp Ala Leu Asn Gln Gly Leu Pro Arg
1               5                   10

<210> SEQ ID NO 1074
<211> LENGTH: 19
<212> TYPE: PRT
<213> ORGANISM: Homo sapiens

<400> SEQUENCE: 1074

Trp Lys Thr Pro Ala Ala Ile Pro Ala Thr Pro Val Ala Val Ser Gln
1               5                   10                  15

Pro Ile Arg

<210> SEQ ID NO 1075
<211> LENGTH: 16
<212> TYPE: PRT
<213> ORGANISM: Homo sapiens

<400> SEQUENCE: 1075

Tyr Leu Glu Thr Ala Asp Tyr Ala Ile Arg Glu Glu Ile Val Leu Lys
1               5                   10                  15

<210> SEQ ID NO 1076
<211> LENGTH: 21
<212> TYPE: PRT
<213> ORGANISM: Homo sapiens

<400> SEQUENCE: 1076

Tyr Leu Asn Trp Glu Ser Asp Gln Pro Asp Asn Pro Ser Glu Glu Asn
1               5                   10                  15

Cys Gly Val Ile Arg
            20

<210> SEQ ID NO 1077
<211> LENGTH: 13
<212> TYPE: PRT
<213> ORGANISM: Homo sapiens

<400> SEQUENCE: 1077

Tyr Val Gly Phe Gly Asn Thr Pro Pro Pro Gln Lys Lys
1               5                   10

<210> SEQ ID NO 1078
<211> LENGTH: 8
<212> TYPE: PRT
<213> ORGANISM: Homo sapiens

<400> SEQUENCE: 1078

Ala Ala Gly Asn Phe Ala Thr Lys
1               5

<210> SEQ ID NO 1079
<211> LENGTH: 26
<212> TYPE: PRT
<213> ORGANISM: Homo sapiens

<400> SEQUENCE: 1079

Ala Glu Gly Glu Arg Gln Pro Pro Pro Asp Ser Ser Glu Glu Ala Pro
1               5                   10                  15

Pro Ala Thr Gln Asn Phe Ile Ile Pro Lys
            20                  25

<210> SEQ ID NO 1080
<211> LENGTH: 18
<212> TYPE: PRT
<213> ORGANISM: Homo sapiens

<400> SEQUENCE: 1080

Ala Gly Leu Val Val Glu Asp Ala Leu Phe Glu Thr Leu Pro Ser Asp
1               5                   10                  15

Val Arg

<210> SEQ ID NO 1081
<211> LENGTH: 30
<212> TYPE: PRT
<213> ORGANISM: Homo sapiens

<400> SEQUENCE: 1081

Ala His Cys Gly Asp Pro Val Ser Leu Ala Ala Ala Gly Asp Gly Ser
1               5                   10                  15

Pro Asp Ile Gly Pro Thr Gly Glu Leu Ser Gly Ser Leu Lys
            20                  25                  30

<210> SEQ ID NO 1082
<211> LENGTH: 12
<212> TYPE: PRT
<213> ORGANISM: Homo sapiens

<400> SEQUENCE: 1082

Ala Ile Leu Gln Asn His Thr Asp Phe Lys Asp Lys
1               5                   10

<210> SEQ ID NO 1083
<211> LENGTH: 27
<212> TYPE: PRT
<213> ORGANISM: Homo sapiens

<400> SEQUENCE: 1083

Ala Ile Asn Val Tyr Gly Thr Ser Glu Pro Ser Gln Glu Ser Glu Leu
1               5                   10                  15

Thr Thr Val Gly Glu Lys Pro Glu Glu Pro Lys
            20                  25

<210> SEQ ID NO 1084
<211> LENGTH: 22
<212> TYPE: PRT
<213> ORGANISM: Homo sapiens

<400> SEQUENCE: 1084

Ala Leu Gly Glu Asp Gln Val Ala Glu Thr Ser Ala Met Ser Asp Val 1 5 10 15

Leu Lys Asp Ile Leu Lys
20

<210> SEQ ID NO 1085
<211> LENGTH: 18
<212> TYPE: PRT
<213> ORGANISM: Homo sapiens

<400> SEQUENCE: 1085

Ala Asn Ile Val Met Val Leu Glu Ile Val Ser Gly Gly Glu Leu Phe
1 5 10 15

Glu Arg

<210> SEQ ID NO 1086
<211> LENGTH: 22
<212> TYPE: PRT
<213> ORGANISM: Homo sapiens

<400> SEQUENCE: 1086

Ala Pro Glu Glu Gln Gly Leu Leu Pro Asn Gly Glu Pro Ser Gln His
1 5 10 15

Ser Ser Ala Pro Gln Lys
20

<210> SEQ ID NO 1087
<211> LENGTH: 14
<212> TYPE: PRT
<213> ORGANISM: Homo sapiens

<400> SEQUENCE: 1087

Ala Pro Gly Leu Gly Val Leu Ser Pro Ser Gly Glu Glu Arg
1 5 10

<210> SEQ ID NO 1088
<211> LENGTH: 11
<212> TYPE: PRT
<213> ORGANISM: Homo sapiens

<400> SEQUENCE: 1088

Ala Gln Asp Asp Val Ser Glu Trp Ala Ser Lys
1 5 10

<210> SEQ ID NO 1089
<211> LENGTH: 18
<212> TYPE: PRT
<213> ORGANISM: Homo sapiens

<400> SEQUENCE: 1089

Ala Ser Ser Ile Ser Glu Glu Val Ala Val Gly Ser Ile Ala Ala Thr
1 5 10 15

Leu Lys

<210> SEQ ID NO 1090
<211> LENGTH: 14
<212> TYPE: PRT
<213> ORGANISM: Homo sapiens

<400> SEQUENCE: 1090

Ala Thr Leu Ala Leu Asp Ser Val Leu Thr Glu Glu Gly Lys
1 5 10

<210> SEQ ID NO 1091
<211> LENGTH: 49
<212> TYPE: PRT
<213> ORGANISM: Homo sapiens

<400> SEQUENCE: 1091

```
Ala Val Gly Gly Asp Arg Gln Glu Ala Ile Gln Pro Gly Cys Ile Gly
1               5                   10                  15

Gly Pro Lys Gly Leu Pro Gly Leu Pro Gly Pro Pro Gly Pro Thr Gly
            20                  25                  30

Ala Lys Gly Leu Arg Gly Ile Pro Gly Phe Ala Gly Ala Asp Gly Gly
        35                  40                  45

Pro
```

<210> SEQ ID NO 1092
<211> LENGTH: 11
<212> TYPE: PRT
<213> ORGANISM: Homo sapiens

<400> SEQUENCE: 1092

```
Ala Val Gly Leu Val Ser Thr Trp Thr Gln Arg
1               5                   10
```

<210> SEQ ID NO 1093
<211> LENGTH: 8
<212> TYPE: PRT
<213> ORGANISM: Homo sapiens

<400> SEQUENCE: 1093

```
Ala Val Ser Ser Ala Asp Pro Arg
1               5
```

<210> SEQ ID NO 1094
<211> LENGTH: 11
<212> TYPE: PRT
<213> ORGANISM: Homo sapiens

<400> SEQUENCE: 1094

```
Ala Trp His Ala Phe Phe Thr Ala Ala Glu Arg
1               5                   10
```

<210> SEQ ID NO 1095
<211> LENGTH: 13
<212> TYPE: PRT
<213> ORGANISM: Homo sapiens

<400> SEQUENCE: 1095

```
Asp Cys Thr Gln Cys Leu Gln His Pro Trp Leu Met Lys
1               5                   10
```

<210> SEQ ID NO 1096
<211> LENGTH: 16
<212> TYPE: PRT
<213> ORGANISM: Homo sapiens

<400> SEQUENCE: 1096

```
Asp Glu Ile Ser Asp Asp Ala Lys Asp Phe Ile Ser Asn Leu Leu Lys
1               5                   10                  15
```

<210> SEQ ID NO 1097
<211> LENGTH: 20
<212> TYPE: PRT
<213> ORGANISM: Homo sapiens

<400> SEQUENCE: 1097

Asp Phe Gly Pro Ala Ser Gln His Phe Leu Ser Thr Ser Val Gln Gly
1 5 10 15

Pro Trp Glu Arg
20

<210> SEQ ID NO 1098
<211> LENGTH: 11
<212> TYPE: PRT
<213> ORGANISM: Homo sapiens

<400> SEQUENCE: 1098

Asp Phe Leu Asp Ser Leu Gly Phe Ser Thr Arg
1 5 10

<210> SEQ ID NO 1099
<211> LENGTH: 15
<212> TYPE: PRT
<213> ORGANISM: Homo sapiens

<400> SEQUENCE: 1099

Asp Gly Glu Trp Glu Pro Pro Val Ile Gln Asn Pro Glu Tyr Lys
1 5 10 15

<210> SEQ ID NO 1100
<211> LENGTH: 15
<212> TYPE: PRT
<213> ORGANISM: Homo sapiens

<400> SEQUENCE: 1100

Asp Thr Ser Pro Ala Pro Ser Gly Thr Thr Ser Ala Phe Val Lys
1 5 10 15

<210> SEQ ID NO 1101
<211> LENGTH: 13
<212> TYPE: PRT
<213> ORGANISM: Homo sapiens

<400> SEQUENCE: 1101

Glu Ala Glu Asp Arg Ala Arg Gln Glu Glu Glu Arg Arg
1 5 10

<210> SEQ ID NO 1102
<211> LENGTH: 8
<212> TYPE: PRT
<213> ORGANISM: Homo sapiens

<400> SEQUENCE: 1102

Glu Ala Pro Tyr Gly Ala Pro Arg
1 5

<210> SEQ ID NO 1103
<211> LENGTH: 8
<212> TYPE: PRT
<213> ORGANISM: Homo sapiens

<400> SEQUENCE: 1103

Glu Cys Ala Ile Tyr Thr Asn Arg
1 5

<210> SEQ ID NO 1104
<211> LENGTH: 8
<212> TYPE: PRT
<213> ORGANISM: Homo sapiens

<400> SEQUENCE: 1104

Glu Gly Ile Val Ala Leu Arg Arg
1 5

<210> SEQ ID NO 1105
<211> LENGTH: 11
<212> TYPE: PRT
<213> ORGANISM: Homo sapiens

<400> SEQUENCE: 1105

Glu Gly Pro Tyr Thr Val Asp Ala Ile Gln Lys
1 5 10

<210> SEQ ID NO 1106
<211> LENGTH: 15
<212> TYPE: PRT
<213> ORGANISM: Homo sapiens

<400> SEQUENCE: 1106

Glu Lys Glu Leu Gln Thr Ile Phe Asp Thr Leu Pro Pro Met Arg
1 5 10 15

<210> SEQ ID NO 1107
<211> LENGTH: 11
<212> TYPE: PRT
<213> ORGANISM: Homo sapiens

<400> SEQUENCE: 1107

Glu Leu Glu Gln Gln Leu Gln Glu Ser Ala Arg
1 5 10

<210> SEQ ID NO 1108
<211> LENGTH: 19
<212> TYPE: PRT
<213> ORGANISM: Homo sapiens

<400> SEQUENCE: 1108

Glu Gln Leu Asp Lys Ile Gln Ser Ser His Asn Phe Gln Leu Glu Ser
1 5 10 15

Val Asn Lys

<210> SEQ ID NO 1109
<211> LENGTH: 13
<212> TYPE: PRT
<213> ORGANISM: Homo sapiens

<400> SEQUENCE: 1109

Glu Val Thr Lys Glu Glu Phe Val Leu Ala Ala Gln Lys
1 5 10

<210> SEQ ID NO 1110
<211> LENGTH: 26
<212> TYPE: PRT
<213> ORGANISM: Homo sapiens

<400> SEQUENCE: 1110

Glu Val Val Pro Gly Asp Ser Val Asn Ser Leu Leu Ser Ile Leu Asp
1 5 10 15

Val Ile Thr Gly His Gln His Pro Gln Arg
20 25

<210> SEQ ID NO 1111

<211> LENGTH: 15
<212> TYPE: PRT
<213> ORGANISM: Homo sapiens

<400> SEQUENCE: 1111

Glu Tyr Trp Met Asp Pro Glu Gly Glu Met Lys Pro Gly Arg Lys
1 5 10 15

<210> SEQ ID NO 1112
<211> LENGTH: 14
<212> TYPE: PRT
<213> ORGANISM: Homo sapiens

<400> SEQUENCE: 1112

Phe Gly Phe Ser His Leu Glu Ala Leu Leu Asp Asp Ser Lys
1 5 10

<210> SEQ ID NO 1113
<211> LENGTH: 8
<212> TYPE: PRT
<213> ORGANISM: Homo sapiens

<400> SEQUENCE: 1113

Phe Gly Ser Gln Ala Ser Gln Lys
1 5

<210> SEQ ID NO 1114
<211> LENGTH: 9
<212> TYPE: PRT
<213> ORGANISM: Homo sapiens

<400> SEQUENCE: 1114

Phe His Glu Leu Thr Gln Thr Asp Lys
1 5

<210> SEQ ID NO 1115
<211> LENGTH: 12
<212> TYPE: PRT
<213> ORGANISM: Homo sapiens

<400> SEQUENCE: 1115

Phe Leu Asp Leu Gly Ile Ser Ile Ala Glu Asn Arg
1 5 10

<210> SEQ ID NO 1116
<211> LENGTH: 8
<212> TYPE: PRT
<213> ORGANISM: Homo sapiens

<400> SEQUENCE: 1116

Phe Leu Leu Asp Cys Gly Ile Arg
1 5

<210> SEQ ID NO 1117
<211> LENGTH: 12
<212> TYPE: PRT
<213> ORGANISM: Homo sapiens

<400> SEQUENCE: 1117

Phe Val Asp Pro Ser Gln Asp His Ala Leu Ala Lys
1 5 10

<210> SEQ ID NO 1118
<211> LENGTH: 7
<212> TYPE: PRT

<213> ORGANISM: Homo sapiens

<400> SEQUENCE: 1118

Phe Tyr Gly Asp Glu Glu Lys
1 5

<210> SEQ ID NO 1119
<211> LENGTH: 11
<212> TYPE: PRT
<213> ORGANISM: Homo sapiens

<400> SEQUENCE: 1119

Gly Ala Trp Leu Gly Met Asn Phe Asn Pro Lys
1 5 10

<210> SEQ ID NO 1120
<211> LENGTH: 8
<212> TYPE: PRT
<213> ORGANISM: Homo sapiens

<400> SEQUENCE: 1120

Gly Ile Leu Val Phe Gln Leu Lys
1 5

<210> SEQ ID NO 1121
<211> LENGTH: 12
<212> TYPE: PRT
<213> ORGANISM: Homo sapiens

<400> SEQUENCE: 1121

Gly Ile Ser Leu Asn Pro Glu Gln Trp Ser Gln Leu
1 5 10

<210> SEQ ID NO 1122
<211> LENGTH: 15
<212> TYPE: PRT
<213> ORGANISM: Homo sapiens

<400> SEQUENCE: 1122

Gly Leu Tyr Leu Pro Leu Phe Lys Pro Ser Val Ser Thr Ser Lys
1 5 10 15

<210> SEQ ID NO 1123
<211> LENGTH: 11
<212> TYPE: PRT
<213> ORGANISM: Homo sapiens

<400> SEQUENCE: 1123

Gly Met Glu Asp Leu Ile Pro Leu Val Asn Arg
1 5 10

<210> SEQ ID NO 1124
<211> LENGTH: 17
<212> TYPE: PRT
<213> ORGANISM: Homo sapiens

<400> SEQUENCE: 1124

Gly Pro Ile Gly His Gln Gly Pro Ile Gly Gln Glu Gly Ala Pro Gly
1 5 10 15

Arg

<210> SEQ ID NO 1125
<211> LENGTH: 11
<212> TYPE: PRT

<213> ORGANISM: Homo sapiens

<400> SEQUENCE: 1125

Gly Pro Asn Lys His Thr Leu Thr Gln Ile Lys
1 5 10

<210> SEQ ID NO 1126
<211> LENGTH: 14
<212> TYPE: PRT
<213> ORGANISM: Homo sapiens

<400> SEQUENCE: 1126

Gly Pro Thr Cys Asn Glu Phe Thr Gly Gln Cys His Cys Arg
1 5 10

<210> SEQ ID NO 1127
<211> LENGTH: 9
<212> TYPE: PRT
<213> ORGANISM: Homo sapiens

<400> SEQUENCE: 1127

Gly Ser Glu Gly Glu Pro Gly Ile Arg
1 5

<210> SEQ ID NO 1128
<211> LENGTH: 14
<212> TYPE: PRT
<213> ORGANISM: Homo sapiens

<400> SEQUENCE: 1128

Gly Thr Asp Val Arg Glu Pro Asp Asp Ser Pro Gln Gly Arg
1 5 10

<210> SEQ ID NO 1129
<211> LENGTH: 11
<212> TYPE: PRT
<213> ORGANISM: Homo sapiens

<400> SEQUENCE: 1129

Gly Trp Ala Gly Asp Ser Gly Pro Gln Gly Arg
1 5 10

<210> SEQ ID NO 1130
<211> LENGTH: 14
<212> TYPE: PRT
<213> ORGANISM: Homo sapiens

<400> SEQUENCE: 1130

His Ala Gln Glu Glu Leu Pro Pro Pro Pro Pro Gln Lys Lys
1 5 10

<210> SEQ ID NO 1131
<211> LENGTH: 11
<212> TYPE: PRT
<213> ORGANISM: Homo sapiens

<400> SEQUENCE: 1131

His Ser Thr Val Leu Glu Asn Thr Asp Gly Lys
1 5 10

<210> SEQ ID NO 1132
<211> LENGTH: 9
<212> TYPE: PRT
<213> ORGANISM: Homo sapiens

<400> SEQUENCE: 1132

Ile Glu Glu Leu Glu Glu Ala Leu Arg
1 5

<210> SEQ ID NO 1133
<211> LENGTH: 18
<212> TYPE: PRT
<213> ORGANISM: Homo sapiens

<400> SEQUENCE: 1133

Ile Glu Gly Ser Gly Asp Gln Ile Asp Thr Tyr Glu Leu Ser Gly Gly
1 5 10 15

Ala Arg

<210> SEQ ID NO 1134
<211> LENGTH: 16
<212> TYPE: PRT
<213> ORGANISM: Homo sapiens

<400> SEQUENCE: 1134

Ile Glu Leu His Gly Lys Pro Ile Glu Val Glu His Ser Val Pro Lys
1 5 10 15

<210> SEQ ID NO 1135
<211> LENGTH: 15
<212> TYPE: PRT
<213> ORGANISM: Homo sapiens

<400> SEQUENCE: 1135

Ile Ile Asp Glu Asp Phe Glu Leu Thr Glu Arg Glu Cys Ile Lys
1 5 10 15

<210> SEQ ID NO 1136
<211> LENGTH: 10
<212> TYPE: PRT
<213> ORGANISM: Homo sapiens

<400> SEQUENCE: 1136

Ile Lys Leu Ile Asp Phe Gly Leu Ala Arg
1 5 10

<210> SEQ ID NO 1137
<211> LENGTH: 11
<212> TYPE: PRT
<213> ORGANISM: Homo sapiens

<400> SEQUENCE: 1137

Ile Leu Asp Leu Leu Asn Glu Gly Ser Ala Arg
1 5 10

<210> SEQ ID NO 1138
<211> LENGTH: 11
<212> TYPE: PRT
<213> ORGANISM: Homo sapiens

<400> SEQUENCE: 1138

Ile Leu Met Glu Leu Asp Gly Pro Asn Trp Arg
1 5 10

<210> SEQ ID NO 1139
<211> LENGTH: 14
<212> TYPE: PRT
<213> ORGANISM: Homo sapiens

<400> SEQUENCE: 1139

Ile Pro Gln Ala Val Val Asp Val Ser Ser His Leu Gln Lys
1 5 10

<210> SEQ ID NO 1140
<211> LENGTH: 21
<212> TYPE: PRT
<213> ORGANISM: Homo sapiens

<400> SEQUENCE: 1140

Ile Gln Ala Glu Gln Val Asp Ala Val Thr Leu Ser Gly Glu Asp Ile
1 5 10 15

Tyr Thr Ala Gly Lys
20

<210> SEQ ID NO 1141
<211> LENGTH: 11
<212> TYPE: PRT
<213> ORGANISM: Homo sapiens

<400> SEQUENCE: 1141

Ile Val Ile Tyr Val Gln Gln Thr Thr Asn Lys
1 5 10

<210> SEQ ID NO 1142
<211> LENGTH: 10
<212> TYPE: PRT
<213> ORGANISM: Homo sapiens

<400> SEQUENCE: 1142

Ile Val Ser Glu Phe Asp Tyr Val Glu Lys
1 5 10

<210> SEQ ID NO 1143
<211> LENGTH: 7
<212> TYPE: PRT
<213> ORGANISM: Homo sapiens

<400> SEQUENCE: 1143

Lys Ala Asp Thr Leu Pro Arg
1 5

<210> SEQ ID NO 1144
<211> LENGTH: 15
<212> TYPE: PRT
<213> ORGANISM: Homo sapiens

<400> SEQUENCE: 1144

Lys Ile Asn Gln Leu Ser Glu Glu Asn Gly Asp Leu Ser Phe Lys
1 5 10 15

<210> SEQ ID NO 1145
<211> LENGTH: 10
<212> TYPE: PRT
<213> ORGANISM: Homo sapiens

<400> SEQUENCE: 1145

Lys Ile Gln Glu Ile Leu Thr Gln Val Lys
1 5 10

<210> SEQ ID NO 1146
<211> LENGTH: 18
<212> TYPE: PRT
<213> ORGANISM: Homo sapiens

<400> SEQUENCE: 1146

Lys Lys Leu Pro Ala Glu Asn Gly Ser Ser Ser Ala Glu Thr Leu Asn
1 5 10 15

Ala Lys

<210> SEQ ID NO 1147
<211> LENGTH: 23
<212> TYPE: PRT
<213> ORGANISM: Homo sapiens

<400> SEQUENCE: 1147

Lys Leu Leu Leu Gln Cys Gln Val Ser Ser Asp Pro Pro Ala Thr Ile
1 5 10 15

Ile Trp Thr Leu Asn Gly Lys
20

<210> SEQ ID NO 1148
<211> LENGTH: 21
<212> TYPE: PRT
<213> ORGANISM: Homo sapiens

<400> SEQUENCE: 1148

Lys Pro Ala Ala Gly Leu Ser Ala Ala Pro Val Pro Thr Ala Pro Ala
1 5 10 15

Ala Gly Ala Pro Leu
20

<210> SEQ ID NO 1149
<211> LENGTH: 17
<212> TYPE: PRT
<213> ORGANISM: Homo sapiens

<400> SEQUENCE: 1149

Lys Ser Pro Ser Ser Asp Ser Trp Thr Cys Ala Asp Thr Ser Thr Glu
1 5 10 15

Arg

<210> SEQ ID NO 1150
<211> LENGTH: 15
<212> TYPE: PRT
<213> ORGANISM: Homo sapiens

<400> SEQUENCE: 1150

Lys Ser Ser Thr Gly Ser Pro Thr Ser Pro Leu Asn Ala Glu Lys
1 5 10 15

<210> SEQ ID NO 1151
<211> LENGTH: 7
<212> TYPE: PRT
<213> ORGANISM: Homo sapiens

<400> SEQUENCE: 1151

Leu Ala Leu Leu Asn Glu Lys
1 5

<210> SEQ ID NO 1152
<211> LENGTH: 6
<212> TYPE: PRT
<213> ORGANISM: Homo sapiens

<400> SEQUENCE: 1152

Leu Asp Ile Asp Glu Lys
1 5

<210> SEQ ID NO 1153
<211> LENGTH: 10
<212> TYPE: PRT
<213> ORGANISM: Homo sapiens

<400> SEQUENCE: 1153

Leu Ile Ala Pro Leu Glu Gly Tyr Thr Arg
1 5 10

<210> SEQ ID NO 1154
<211> LENGTH: 9
<212> TYPE: PRT
<213> ORGANISM: Homo sapiens

<400> SEQUENCE: 1154

Leu Lys Glu Glu Glu Glu Asp Lys Lys
1 5

<210> SEQ ID NO 1155
<211> LENGTH: 18
<212> TYPE: PRT
<213> ORGANISM: Homo sapiens

<400> SEQUENCE: 1155

Leu Lys Asn Gln Val Thr Gln Leu Lys Glu Gln Val Pro Gly Phe Thr
1 5 10 15

Pro Arg

<210> SEQ ID NO 1156
<211> LENGTH: 17
<212> TYPE: PRT
<213> ORGANISM: Homo sapiens

<400> SEQUENCE: 1156

Leu Leu Asp Pro Gln Thr Asn Thr Glu Ile Ala Asn Tyr Pro Ile Tyr
1 5 10 15

Lys

<210> SEQ ID NO 1157
<211> LENGTH: 13
<212> TYPE: PRT
<213> ORGANISM: Homo sapiens

<400> SEQUENCE: 1157

Leu Leu Asp Arg Leu Pro Ser Phe Gln Gln Ser Cys Arg
1 5 10

<210> SEQ ID NO 1158
<211> LENGTH: 7
<212> TYPE: PRT
<213> ORGANISM: Homo sapiens

<400> SEQUENCE: 1158

Leu Leu Glu Ala Ile Lys Arg
1 5

<210> SEQ ID NO 1159
<211> LENGTH: 28
<212> TYPE: PRT
<213> ORGANISM: Homo sapiens

<400> SEQUENCE: 1159

Leu Leu Gly Phe Gly Ser Ala Leu Leu Asp Asn Val Asp Pro Asn Pro
1 5 10 15

Glu Asn Phe Val Gly Ala Gly Ile Ile Gln Thr Lys
20 25

<210> SEQ ID NO 1160
<211> LENGTH: 23
<212> TYPE: PRT
<213> ORGANISM: Homo sapiens

<400> SEQUENCE: 1160

Leu Gln Ala Gln Leu Asn Glu Leu Gln Ala Gln Leu Ser Gln Lys Glu
1 5 10 15

Gln Ala Ala Glu His Tyr Lys
20

<210> SEQ ID NO 1161
<211> LENGTH: 11
<212> TYPE: PRT
<213> ORGANISM: Homo sapiens

<400> SEQUENCE: 1161

Leu Gln Asp Val His Val Ala Glu Gly Lys Lys
1 5 10

<210> SEQ ID NO 1162
<211> LENGTH: 12
<212> TYPE: PRT
<213> ORGANISM: Homo sapiens

<400> SEQUENCE: 1162

Leu Gln Gly Glu Val Leu Ala Leu Glu Glu Glu Arg
1 5 10

<210> SEQ ID NO 1163
<211> LENGTH: 9
<212> TYPE: PRT
<213> ORGANISM: Homo sapiens

<400> SEQUENCE: 1163

Leu Ser Ala Leu His Leu Glu Val Arg
1 5

<210> SEQ ID NO 1164
<211> LENGTH: 11
<212> TYPE: PRT
<213> ORGANISM: Homo sapiens

<400> SEQUENCE: 1164

Leu Ser Ser Gln Leu Val Glu His Cys Gln Lys
1 5 10

<210> SEQ ID NO 1165
<211> LENGTH: 10
<212> TYPE: PRT
<213> ORGANISM: Homo sapiens

<400> SEQUENCE: 1165

Leu Ser Val Met Gly Cys Asp Val Leu Lys
1 5 10

<210> SEQ ID NO 1166

<211> LENGTH: 22
<212> TYPE: PRT
<213> ORGANISM: Homo sapiens

<400> SEQUENCE: 1166

Leu Thr Ala Ala Ser Val Gly Val Gln Gly Ser Gly Trp Gly Trp Leu
1 5 10 15

Gly Phe Asn Lys Glu Arg
20

<210> SEQ ID NO 1167
<211> LENGTH: 15
<212> TYPE: PRT
<213> ORGANISM: Homo sapiens

<400> SEQUENCE: 1167

Leu Thr Asp Val Ala Ile Gly Ala Pro Gly Glu Glu Asp Asn Arg
1 5 10 15

<210> SEQ ID NO 1168
<211> LENGTH: 9
<212> TYPE: PRT
<213> ORGANISM: Homo sapiens

<400> SEQUENCE: 1168

Leu Thr His Gly Val Leu His Thr Lys
1 5

<210> SEQ ID NO 1169
<211> LENGTH: 19
<212> TYPE: PRT
<213> ORGANISM: Homo sapiens

<400> SEQUENCE: 1169

Leu Val Thr Asp Pro Asp Ser Gly Leu Cys Ser His Tyr Trp Gly Ala
1 5 10 15

Ile Ile Arg

<210> SEQ ID NO 1170
<211> LENGTH: 11
<212> TYPE: PRT
<213> ORGANISM: Homo sapiens

<400> SEQUENCE: 1170

Met Asp Pro Glu Gly Glu Met Lys Pro Gly Arg
1 5 10

<210> SEQ ID NO 1171
<211> LENGTH: 6
<212> TYPE: PRT
<213> ORGANISM: Homo sapiens

<400> SEQUENCE: 1171

Met Glu Leu Leu Val Lys
1 5

<210> SEQ ID NO 1172
<211> LENGTH: 11
<212> TYPE: PRT
<213> ORGANISM: Homo sapiens

<400> SEQUENCE: 1172

Met Val Ser Met Met Glu Gly Val Ile Gln Lys
1 5 10

<210> SEQ ID NO 1173
<211> LENGTH: 7
<212> TYPE: PRT
<213> ORGANISM: Homo sapiens

<400> SEQUENCE: 1173

Met Val Val Ala Ser Ser Lys
1               5

<210> SEQ ID NO 1174
<211> LENGTH: 29
<212> TYPE: PRT
<213> ORGANISM: Homo sapiens

<400> SEQUENCE: 1174

Asn Asp Ala Gly Gln Ala Glu Cys Ser Cys Gln Val Thr Val Asp Asp
1               5                   10                  15

Ala Pro Ala Ser Glu Asn Thr Lys Ala Pro Glu Met Lys
            20                  25

<210> SEQ ID NO 1175
<211> LENGTH: 8
<212> TYPE: PRT
<213> ORGANISM: Homo sapiens

<400> SEQUENCE: 1175

Asn Ile Leu Ser Glu Phe Gln Arg
1               5

<210> SEQ ID NO 1176
<211> LENGTH: 26
<212> TYPE: PRT
<213> ORGANISM: Homo sapiens

<400> SEQUENCE: 1176

Asn Leu Leu Glu Val Ser Glu Val Glu Gln Glu Leu Ala Cys Gln Asn
1               5                   10                  15

Asp His Ser Ser Ala Leu Gln Asn Ile Lys
            20                  25

<210> SEQ ID NO 1177
<211> LENGTH: 12
<212> TYPE: PRT
<213> ORGANISM: Homo sapiens

<400> SEQUENCE: 1177

Asn Leu Val Asp Ser Tyr Met Ala Ile Val Asn Lys
1               5                   10

<210> SEQ ID NO 1178
<211> LENGTH: 10
<212> TYPE: PRT
<213> ORGANISM: Homo sapiens

<400> SEQUENCE: 1178

Asn Val Asn Val Phe Phe Pro His Phe Lys
1               5                   10

<210> SEQ ID NO 1179
<211> LENGTH: 17
<212> TYPE: PRT
<213> ORGANISM: Homo sapiens

<400> SEQUENCE: 1179

Pro Ala Ser Ala Glu Gln Ile Gln His Leu Ala Gly Ala Ile Ala Glu
1 5 10 15

Arg

<210> SEQ ID NO 1180
<211> LENGTH: 16
<212> TYPE: PRT
<213> ORGANISM: Homo sapiens

<400> SEQUENCE: 1180

Pro Ala Val Pro Ala Ser Val Pro Leu Gln Ala Trp His Pro Ala Lys
1 5 10 15

<210> SEQ ID NO 1181
<211> LENGTH: 14
<212> TYPE: PRT
<213> ORGANISM: Homo sapiens

<400> SEQUENCE: 1181

Pro Phe Ser Ala Ile Tyr Phe Pro Cys Tyr Ala His Val Lys
1 5 10

<210> SEQ ID NO 1182
<211> LENGTH: 16
<212> TYPE: PRT
<213> ORGANISM: Homo sapiens

<400> SEQUENCE: 1182

Pro Gly Pro Val Pro Ala His Ser Leu Cys Gly His Leu Val Pro Lys
1 5 10 15

<210> SEQ ID NO 1183
<211> LENGTH: 26
<212> TYPE: PRT
<213> ORGANISM: Homo sapiens

<400> SEQUENCE: 1183

Pro Leu Gln Gly Thr Thr Gly Leu Ile Pro Leu Leu Gly Ile Asp Val
1 5 10 15

Trp Glu His Ala Tyr Tyr Leu Gln Tyr Lys
20 25

<210> SEQ ID NO 1184
<211> LENGTH: 13
<212> TYPE: PRT
<213> ORGANISM: Homo sapiens

<400> SEQUENCE: 1184

Pro Asn Glu Asn Lys Phe Ala Val Gly Ser Gly Ser Arg
1 5 10

<210> SEQ ID NO 1185
<211> LENGTH: 11
<212> TYPE: PRT
<213> ORGANISM: Homo sapiens

<400> SEQUENCE: 1185

Pro Pro Val Gln Phe Ser Leu Leu His Ser Lys
1 5 10

<210> SEQ ID NO 1186
<211> LENGTH: 13

<212> TYPE: PRT
<213> ORGANISM: Homo sapiens

<400> SEQUENCE: 1186

Gln Ala Pro Ile Gly Gly Asp Phe Pro Ala Val Gln Lys
1 5 10

<210> SEQ ID NO 1187
<211> LENGTH: 12
<212> TYPE: PRT
<213> ORGANISM: Homo sapiens

<400> SEQUENCE: 1187

Gln Lys Leu Gln Asp Val His Val Ala Glu Gly Lys
1 5 10

<210> SEQ ID NO 1188
<211> LENGTH: 21
<212> TYPE: PRT
<213> ORGANISM: Homo sapiens

<400> SEQUENCE: 1188

Gln Leu Ala Ala Tyr Ile Ala Asp Lys Val Asp Ala Ala Gln Met Pro
1 5 10 15

Gln Glu Ala Gln Lys
20

<210> SEQ ID NO 1189
<211> LENGTH: 9
<212> TYPE: PRT
<213> ORGANISM: Homo sapiens

<400> SEQUENCE: 1189

Gln Leu Ser Glu Ser Ser Lys Leu Lys
1 5

<210> SEQ ID NO 1190
<211> LENGTH: 11
<212> TYPE: PRT
<213> ORGANISM: Homo sapiens

<400> SEQUENCE: 1190

Gln Gln Thr Ala Asn Lys Val Glu Ile Glu Lys
1 5 10

<210> SEQ ID NO 1191
<211> LENGTH: 15
<212> TYPE: PRT
<213> ORGANISM: Homo sapiens

<400> SEQUENCE: 1191

Gln Ser Ser Ser Ser Arg Asp Asp Asn Met Phe Gln Ile Gly Lys
1 5 10 15

<210> SEQ ID NO 1192
<211> LENGTH: 13
<212> TYPE: PRT
<213> ORGANISM: Homo sapiens

<400> SEQUENCE: 1192

Gln Tyr Thr Tyr Gly Leu Val Ser Cys Gly Leu Asp Arg
1 5 10

<210> SEQ ID NO 1193

<211> LENGTH: 21
<212> TYPE: PRT
<213> ORGANISM: Homo sapiens

<400> SEQUENCE: 1193

Arg Ala Gly Asn Ser Leu Ala Ala Ser Thr Ala Glu Glu Thr Ala Gly
1 5 10 15

Ser Ala Gln Gly Arg
20

<210> SEQ ID NO 1194
<211> LENGTH: 9
<212> TYPE: PRT
<213> ORGANISM: Homo sapiens

<400> SEQUENCE: 1194

Arg Glu Ala Pro Tyr Gly Ala Pro Arg
1 5

<210> SEQ ID NO 1195
<211> LENGTH: 19
<212> TYPE: PRT
<213> ORGANISM: Homo sapiens

<400> SEQUENCE: 1195

Arg Glu Pro Ala Pro Asn Ala Pro Gly Asp Ile Ala Ala Ala Phe Pro
1 5 10 15

Ala Glu Arg

<210> SEQ ID NO 1196
<211> LENGTH: 17
<212> TYPE: PRT
<213> ORGANISM: Homo sapiens

<400> SEQUENCE: 1196

Arg Gly Trp Asp Ser Ser His Glu Asp Asp Leu Pro Val Tyr Leu Ala
1 5 10 15

Arg

<210> SEQ ID NO 1197
<211> LENGTH: 10
<212> TYPE: PRT
<213> ORGANISM: Homo sapiens

<400> SEQUENCE: 1197

Arg Leu Glu Glu Glu Ser Ala Gln Leu Lys
1 5 10

<210> SEQ ID NO 1198
<211> LENGTH: 20
<212> TYPE: PRT
<213> ORGANISM: Homo sapiens

<400> SEQUENCE: 1198

Arg Gln Val Glu Lys Glu Glu Thr Asn Glu Ile Gln Val Val Asn Glu
1 5 10 15

Glu Pro Gln Arg
20

<210> SEQ ID NO 1199
<211> LENGTH: 12
<212> TYPE: PRT
<213> ORGANISM: Homo sapiens

<400> SEQUENCE: 1199

Arg Ser Glu Ser Gln Gly Thr Ala Pro Ala Phe Lys
1               5                   10

<210> SEQ ID NO 1200
<211> LENGTH: 13
<212> TYPE: PRT
<213> ORGANISM: Homo sapiens

<400> SEQUENCE: 1200

Ser Cys Thr Glu Glu Thr His Gly Phe Ile Cys Gln Lys
1               5                   10

<210> SEQ ID NO 1201
<211> LENGTH: 12
<212> TYPE: PRT
<213> ORGANISM: Homo sapiens

<400> SEQUENCE: 1201

Ser Asp Phe Gly Lys Phe Val Leu Ser Ser Gly Lys
1               5                   10

<210> SEQ ID NO 1202
<211> LENGTH: 9
<212> TYPE: PRT
<213> ORGANISM: Homo sapiens

<400> SEQUENCE: 1202

Ser Glu Tyr Met Glu Gly Asn Val Arg
1               5

<210> SEQ ID NO 1203
<211> LENGTH: 21
<212> TYPE: PRT
<213> ORGANISM: Homo sapiens

<400> SEQUENCE: 1203

Ser Phe Ala Pro Ile Leu Pro His Leu Ala Glu Glu Val Phe Gln His
1               5                   10                  15

Ile Pro Tyr Ile Lys
            20

<210> SEQ ID NO 1204
<211> LENGTH: 14
<212> TYPE: PRT
<213> ORGANISM: Homo sapiens

<400> SEQUENCE: 1204

Ser Lys Val Pro Gln Glu Thr Gln Ser Gly Gly Gly Ser Arg
1               5                   10

<210> SEQ ID NO 1205
<211> LENGTH: 26
<212> TYPE: PRT
<213> ORGANISM: Homo sapiens

<400> SEQUENCE: 1205

Ser Pro Ala Thr Thr Leu Ser Pro Ala Ser Thr Thr Ser Ser Gly Val
1               5                   10                  15

Ser Glu Glu Ser Thr Thr Ser His Ser Arg
            20                  25

<210> SEQ ID NO 1206
<211> LENGTH: 26
<212> TYPE: PRT
<213> ORGANISM: Homo sapiens

<400> SEQUENCE: 1206

```
Ser Pro Ala Thr Thr Leu Ser Pro Ala Ser Thr Thr Ser Ser Gly Val
1               5                   10                  15

Ser Glu Glu Ser Thr Thr Ser His Ser Arg
            20                  25
```

<210> SEQ ID NO 1207
<211> LENGTH: 46
<212> TYPE: PRT
<213> ORGANISM: Homo sapiens

<400> SEQUENCE: 1207

```
Ser Pro Ala Thr Thr Leu Ser Pro Ala Ser Thr Thr Ser Ser Gly Val
1               5                   10                  15

Ser Glu Glu Ser Thr Thr Ser His Ser Arg Pro Gly Ser Thr His Thr
            20                  25                  30

Thr Ala Phe Pro Asp Ser Thr Thr Thr Pro Gly Leu Ser Arg
        35                  40                  45
```

<210> SEQ ID NO 1208
<211> LENGTH: 46
<212> TYPE: PRT
<213> ORGANISM: Homo sapiens

<400> SEQUENCE: 1208

```
Ser Pro Ala Thr Thr Leu Ser Pro Ala Ser Thr Thr Ser Ser Gly Val
1               5                   10                  15

Ser Glu Glu Ser Thr Thr Ser His Ser Arg Pro Gly Ser Thr His Thr
            20                  25                  30

Thr Ala Phe Pro Asp Ser Thr Thr Thr Pro Gly Leu Ser Arg
        35                  40                  45
```

<210> SEQ ID NO 1209
<211> LENGTH: 16
<212> TYPE: PRT
<213> ORGANISM: Homo sapiens

<400> SEQUENCE: 1209

```
Ser Gln Asp Leu Gln Val Ile Asp Leu Leu Thr Val Gly Glu Ser Arg
1               5                   10                  15
```

<210> SEQ ID NO 1210
<211> LENGTH: 32
<212> TYPE: PRT
<213> ORGANISM: Homo sapiens

<400> SEQUENCE: 1210

```
Ser Arg Glu Pro Gln Ala Lys Pro Gln Leu Asp Leu Ser Ile Asp Ser
1               5                   10                  15

Leu Asp Leu Ser Cys Glu Glu Gly Thr Pro Leu Ser Ile Thr Ser Lys
            20                  25                  30
```

<210> SEQ ID NO 1211
<211> LENGTH: 22
<212> TYPE: PRT
<213> ORGANISM: Homo sapiens

<400> SEQUENCE: 1211

```
Ser Arg Gln Glu Leu Ala Ser Gly Leu Pro Ser Pro Ala Ala Thr Gln
1               5                   10                  15

Glu Leu Pro Val Glu Arg
            20


<210> SEQ ID NO 1212
<211> LENGTH: 10
<212> TYPE: PRT
<213> ORGANISM: Homo sapiens

<400> SEQUENCE: 1212

Ser Ser Ala Ala Ala Gly Ala Pro Ser Arg
1               5                   10


<210> SEQ ID NO 1213
<211> LENGTH: 15
<212> TYPE: PRT
<213> ORGANISM: Homo sapiens

<400> SEQUENCE: 1213

Ser Ser Pro Asn Val Ala Asn Gln Pro Pro Ser Pro Gly Gly Lys
1               5                   10                  15


<210> SEQ ID NO 1214
<211> LENGTH: 16
<212> TYPE: PRT
<213> ORGANISM: Homo sapiens

<400> SEQUENCE: 1214

Ser Ser Ser Glu Val Leu Val Leu Ala Glu Thr Leu Asp Gly Val Arg
1               5                   10                  15


<210> SEQ ID NO 1215
<211> LENGTH: 17
<212> TYPE: PRT
<213> ORGANISM: Homo sapiens

<400> SEQUENCE: 1215

Ser Val Gln Glu Ile Ala Glu Gln Leu Leu Leu Glu Asn His Pro Ala
1               5                   10                  15

Arg


<210> SEQ ID NO 1216
<211> LENGTH: 9
<212> TYPE: PRT
<213> ORGANISM: Homo sapiens

<400> SEQUENCE: 1216

Thr Cys Thr Gly Tyr His Gln Val Arg
1               5


<210> SEQ ID NO 1217
<211> LENGTH: 6
<212> TYPE: PRT
<213> ORGANISM: Homo sapiens

<400> SEQUENCE: 1217

Thr Gly Glu Thr Ser Arg
1               5


<210> SEQ ID NO 1218
<211> LENGTH: 7
<212> TYPE: PRT
```

<213> ORGANISM: Homo sapiens

<400> SEQUENCE: 1218

Thr Ile Gln Asn Gln Leu Arg
1 5

<210> SEQ ID NO 1219
<211> LENGTH: 13
<212> TYPE: PRT
<213> ORGANISM: Homo sapiens

<400> SEQUENCE: 1219

Thr Leu Phe Ser Leu Met Gln Tyr Ser Glu Glu Phe Arg
1 5 10

<210> SEQ ID NO 1220
<211> LENGTH: 8
<212> TYPE: PRT
<213> ORGANISM: Homo sapiens

<400> SEQUENCE: 1220

Thr Pro Ala Pro Asp Gly Pro Arg
1 5

<210> SEQ ID NO 1221
<211> LENGTH: 9
<212> TYPE: PRT
<213> ORGANISM: Homo sapiens

<400> SEQUENCE: 1221

Thr Pro Gly Gln Ile Val Ser Glu Lys
1 5

<210> SEQ ID NO 1222
<211> LENGTH: 6
<212> TYPE: PRT
<213> ORGANISM: Homo sapiens

<400> SEQUENCE: 1222

Thr Pro Val Pro Glu Lys
1 5

<210> SEQ ID NO 1223
<211> LENGTH: 10
<212> TYPE: PRT
<213> ORGANISM: Homo sapiens

<400> SEQUENCE: 1223

Thr Thr Leu Leu Asp Pro Asp Ser Cys Arg
1 5 10

<210> SEQ ID NO 1224
<211> LENGTH: 9
<212> TYPE: PRT
<213> ORGANISM: Homo sapiens

<400> SEQUENCE: 1224

Thr Thr Thr Glu Ser Glu Val Met Lys
1 5

<210> SEQ ID NO 1225
<211> LENGTH: 18
<212> TYPE: PRT
<213> ORGANISM: Homo sapiens

<400> SEQUENCE: 1225

Thr Val Leu Gln Ile Asp Cys Gly Leu Gln Leu Ala Asn Asp Ser Val
1 5 10 15

Asn Arg

<210> SEQ ID NO 1226
<211> LENGTH: 26
<212> TYPE: PRT
<213> ORGANISM: Homo sapiens

<400> SEQUENCE: 1226

Val Ala Gln Gln Pro Leu Ser Leu Val Gly Cys Glu Val Val Pro Asp
1 5 10 15

Pro Ser Pro Asp His Leu Tyr Ser Phe Arg
20 25

<210> SEQ ID NO 1227
<211> LENGTH: 9
<212> TYPE: PRT
<213> ORGANISM: Homo sapiens

<400> SEQUENCE: 1227

Val His Ala Leu Asn Asn Val Asn Lys
1 5

<210> SEQ ID NO 1228
<211> LENGTH: 8
<212> TYPE: PRT
<213> ORGANISM: Homo sapiens

<400> SEQUENCE: 1228

Val Ile Val Met Pro Thr Thr Lys
1 5

<210> SEQ ID NO 1229
<211> LENGTH: 12
<212> TYPE: PRT
<213> ORGANISM: Homo sapiens

<400> SEQUENCE: 1229

Val Leu Gln Glu Asp Leu Glu Gln Glu Gln Val Arg
1 5 10

<210> SEQ ID NO 1230
<211> LENGTH: 9
<212> TYPE: PRT
<213> ORGANISM: Homo sapiens

<400> SEQUENCE: 1230

Val Pro Ala His Ala Val Val Val Arg
1 5

<210> SEQ ID NO 1231
<211> LENGTH: 8
<212> TYPE: PRT
<213> ORGANISM: Homo sapiens

<400> SEQUENCE: 1231

Trp Leu Asn Glu Val Glu Phe Lys
1 5

<210> SEQ ID NO 1232
<211> LENGTH: 16

<212> TYPE: PRT
<213> ORGANISM: Homo sapiens

<400> SEQUENCE: 1232

Trp Thr Asp Gly Ser Ile Ile Asn Phe Ile Ser Trp Ala Pro Gly Lys
1               5                   10                  15

<210> SEQ ID NO 1233
<211> LENGTH: 18
<212> TYPE: PRT
<213> ORGANISM: Homo sapiens

<400> SEQUENCE: 1233

Trp Thr Asp Gly Ser Ile Ile Asn Phe Ile Ser Trp Ala Pro Gly Lys
1               5                   10                  15

Pro Arg

<210> SEQ ID NO 1234
<211> LENGTH: 8
<212> TYPE: PRT
<213> ORGANISM: Homo sapiens

<400> SEQUENCE: 1234

Trp Val Asn Ala Gln Phe Ser Lys
1               5

<210> SEQ ID NO 1235
<211> LENGTH: 15
<212> TYPE: PRT
<213> ORGANISM: Homo sapiens

<400> SEQUENCE: 1235

Tyr Asp Asn Phe Gly Val Leu Gly Leu Asp Leu Trp Gln Val Lys
1               5                   10                  15

<210> SEQ ID NO 1236
<211> LENGTH: 14
<212> TYPE: PRT
<213> ORGANISM: Homo sapiens

<400> SEQUENCE: 1236

Tyr Leu Leu Tyr Arg Pro Gly His Tyr Asp Ile Leu Tyr Lys
1               5                   10

<210> SEQ ID NO 1237
<211> LENGTH: 12
<212> TYPE: PRT
<213> ORGANISM: Homo sapiens

<400> SEQUENCE: 1237

Tyr Leu Ser Ser Leu Asp Leu Leu Leu Glu His Arg
1               5                   10

<210> SEQ ID NO 1238
<211> LENGTH: 30
<212> TYPE: PRT
<213> ORGANISM: Homo sapiens

<400> SEQUENCE: 1238

Tyr Leu Val His Cys Leu Gln Ser Glu Leu Asn Asn Tyr Met Pro Ala
1               5                   10                  15

Phe Leu Asp Asp Pro Glu Glu Asn Ser Leu Gln Arg Pro Lys
            20                  25                  30

<210> SEQ ID NO 1239
<211> LENGTH: 21
<212> TYPE: PRT
<213> ORGANISM: Homo sapiens

<400> SEQUENCE: 1239

Tyr Arg Asp Pro Gly Val Leu Pro Trp Gly Ala Leu Glu Glu Glu Glu
1 5 10 15

Glu Asp Gly Gly Arg
20

<210> SEQ ID NO 1240
<211> LENGTH: 34
<212> TYPE: PRT
<213> ORGANISM: Homo sapiens

<400> SEQUENCE: 1240

Ala Ala Ala Ala Ala Val Gly Pro Gly Ala Gly Gly Ala Gly Ser Ala
1 5 10 15

Val Pro Gly Gly Ala Gly Pro Cys Ala Thr Val Ser Val Phe Pro Gly
20 25 30

Ala Arg

<210> SEQ ID NO 1241
<211> LENGTH: 17
<212> TYPE: PRT
<213> ORGANISM: Homo sapiens

<400> SEQUENCE: 1241

Ala Ala Ala Lys Val Ala Leu Thr Lys Arg Ala Asp Pro Ala Glu Leu
1 5 10 15

Arg

<210> SEQ ID NO 1242
<211> LENGTH: 15
<212> TYPE: PRT
<213> ORGANISM: Homo sapiens

<400> SEQUENCE: 1242

Ala Ala Ala Thr Glu Glu Pro Glu Val Ile Pro Asp Pro Ala Lys
1 5 10 15

<210> SEQ ID NO 1243
<211> LENGTH: 9
<212> TYPE: PRT
<213> ORGANISM: Homo sapiens

<400> SEQUENCE: 1243

Ala Ala Glu Glu Pro Gln Gln Gln Lys
1 5

<210> SEQ ID NO 1244
<211> LENGTH: 24
<212> TYPE: PRT
<213> ORGANISM: Homo sapiens

<400> SEQUENCE: 1244

Ala Ala Gly Asp Gly Ser Pro Asp Ile Gly Pro Thr Gly Glu Leu Ser
1 5 10 15

Gly Ser Leu Lys Ile Pro Asn Arg
20

<210> SEQ ID NO 1245
<211> LENGTH: 12
<212> TYPE: PRT
<213> ORGANISM: Homo sapiens

<400> SEQUENCE: 1245

Ala Ala Gly Leu Gln Ala Glu Ile Gly Gln Val Lys
1 5 10

<210> SEQ ID NO 1246
<211> LENGTH: 7
<212> TYPE: PRT
<213> ORGANISM: Homo sapiens

<400> SEQUENCE: 1246

Ala Ala Ser Gly Val Pro Arg
1 5

<210> SEQ ID NO 1247
<211> LENGTH: 26
<212> TYPE: PRT
<213> ORGANISM: Homo sapiens

<400> SEQUENCE: 1247

Ala Cys Gly Asn Met Phe Gly Leu Met His Gly Thr Cys Pro Glu Thr
1 5 10 15

Ser Gly Gly Leu Leu Ile Cys Leu Pro Arg
20 25

<210> SEQ ID NO 1248
<211> LENGTH: 11
<212> TYPE: PRT
<213> ORGANISM: Homo sapiens

<400> SEQUENCE: 1248

Ala Asp Ser Ala Val Ser Gln Glu Gln Leu Arg
1 5 10

<210> SEQ ID NO 1249
<211> LENGTH: 13
<212> TYPE: PRT
<213> ORGANISM: Homo sapiens

<400> SEQUENCE: 1249

Ala Glu Glu Lys Pro His Val Lys Pro Tyr Phe Ser Lys
1 5 10

<210> SEQ ID NO 1250
<211> LENGTH: 12
<212> TYPE: PRT
<213> ORGANISM: Homo sapiens

<400> SEQUENCE: 1250

Ala Glu Leu Glu Tyr Asn Pro Glu His Val Ser Arg
1 5 10

<210> SEQ ID NO 1251
<211> LENGTH: 9
<212> TYPE: PRT
<213> ORGANISM: Homo sapiens

<400> SEQUENCE: 1251

Ala Glu Gln Leu Leu Gln Asp Ala Arg
1 5

<210> SEQ ID NO 1252
<211> LENGTH: 20
<212> TYPE: PRT
<213> ORGANISM: Homo sapiens

<400> SEQUENCE: 1252

Ala Glu Tyr Met Arg Ile Gln Ala Gln Gln Gln Ala Thr Lys Pro Ser
1               5                   10                  15

Lys Glu Met Ser
            20

<210> SEQ ID NO 1253
<211> LENGTH: 12
<212> TYPE: PRT
<213> ORGANISM: Homo sapiens

<400> SEQUENCE: 1253

Ala Phe Cys Gly Leu Gly Thr Thr Gly Met Trp Arg
1               5                   10

<210> SEQ ID NO 1254
<211> LENGTH: 19
<212> TYPE: PRT
<213> ORGANISM: Homo sapiens

<400> SEQUENCE: 1254

Ala Phe Leu Glu Ala Val Ala Glu Glu Lys Pro His Val Lys Pro Tyr
1               5                   10                  15

Phe Ser Lys

<210> SEQ ID NO 1255
<211> LENGTH: 11
<212> TYPE: PRT
<213> ORGANISM: Homo sapiens

<400> SEQUENCE: 1255

Ala His Lys Gln Cys Ala Leu Lys Leu Leu Arg
1               5                   10

<210> SEQ ID NO 1256
<211> LENGTH: 10
<212> TYPE: PRT
<213> ORGANISM: Homo sapiens

<400> SEQUENCE: 1256

Ala Leu Met Asp Leu Leu Gln Leu Thr Arg
1               5                   10

<210> SEQ ID NO 1257
<211> LENGTH: 10
<212> TYPE: PRT
<213> ORGANISM: Homo sapiens

<400> SEQUENCE: 1257

Ala Leu Gln Asp Phe Glu Glu Pro Asp Lys
1               5                   10

<210> SEQ ID NO 1258
<211> LENGTH: 12
<212> TYPE: PRT
<213> ORGANISM: Homo sapiens

<400> SEQUENCE: 1258

Ala Leu Gln Phe Leu Glu Glu Val Lys Val Ser Arg
1 5 10

<210> SEQ ID NO 1259
<211> LENGTH: 32
<212> TYPE: PRT
<213> ORGANISM: Homo sapiens

<400> SEQUENCE: 1259

Ala Leu Gln His Met Ala Ala Met Ser Ser Ala Gln Ile Val Ser Ala
1 5 10 15

Thr Ala Ile His Asn Lys Leu Gly Leu Pro Gly Ile Pro Arg Pro Thr
20 25 30

<210> SEQ ID NO 1260
<211> LENGTH: 12
<212> TYPE: PRT
<213> ORGANISM: Homo sapiens

<400> SEQUENCE: 1260

Ala Met Ala Tyr Glu Thr Leu Glu Gln Tyr Gly Lys
1 5 10

<210> SEQ ID NO 1261
<211> LENGTH: 23
<212> TYPE: PRT
<213> ORGANISM: Homo sapiens

<400> SEQUENCE: 1261

Ala Met Leu Ala Ala Val Leu Glu Gln Glu Leu Pro Ala Leu Ala Glu
1 5 10 15

Asn Leu His Gln Glu Gln Lys
20

<210> SEQ ID NO 1262
<211> LENGTH: 23
<212> TYPE: PRT
<213> ORGANISM: Homo sapiens

<400> SEQUENCE: 1262

Ala Met Leu Ala Ala Val Leu Glu Gln Glu Leu Pro Ala Leu Ala Glu
1 5 10 15

Asn Leu His Gln Glu Gln Lys
20

<210> SEQ ID NO 1263
<211> LENGTH: 29
<212> TYPE: PRT
<213> ORGANISM: Homo sapiens

<400> SEQUENCE: 1263

Ala Asn Gly Ile Thr Met Tyr Ala Val Gly Val Gly Lys Ala Ile Glu
1 5 10 15

Glu Glu Leu Gln Glu Ile Ala Ser Glu Pro Thr Asn Lys
20 25

<210> SEQ ID NO 1264
<211> LENGTH: 11
<212> TYPE: PRT
<213> ORGANISM: Homo sapiens

<400> SEQUENCE: 1264

Ala Pro Ala Pro Asp Val Pro Gly Cys Ser Arg
1               5                   10

<210> SEQ ID NO 1265
<211> LENGTH: 19
<212> TYPE: PRT
<213> ORGANISM: Homo sapiens

<400> SEQUENCE: 1265

Ala Pro Ile Leu Pro His Leu Ala Glu Glu Val Phe Gln His Ile Pro
1               5                   10                  15

Tyr Ile Lys

<210> SEQ ID NO 1266
<211> LENGTH: 21
<212> TYPE: PRT
<213> ORGANISM: Homo sapiens

<400> SEQUENCE: 1266

Ala Gln Ala Leu Leu Ala Asp Val Asp Thr Leu Leu Phe Asp Cys Asp
1               5                   10                  15

Gly Val Leu Trp Arg
            20

<210> SEQ ID NO 1267
<211> LENGTH: 14
<212> TYPE: PRT
<213> ORGANISM: Homo sapiens

<400> SEQUENCE: 1267

Ala Gln Asn Ser Gly Phe Asp Leu Gln Glu Thr Leu Val Lys
1               5                   10

<210> SEQ ID NO 1268
<211> LENGTH: 8
<212> TYPE: PRT
<213> ORGANISM: Homo sapiens

<400> SEQUENCE: 1268

Ala Arg Phe Glu Gln Met Ala Lys
1               5

<210> SEQ ID NO 1269
<211> LENGTH: 19
<212> TYPE: PRT
<213> ORGANISM: Homo sapiens

<400> SEQUENCE: 1269

Ala Arg Pro Glu Ala Tyr Gln Val Pro Ala Ser Tyr Gln Pro Asp Glu
1               5                   10                  15

Glu Glu Arg

<210> SEQ ID NO 1270
<211> LENGTH: 22
<212> TYPE: PRT
<213> ORGANISM: Homo sapiens

<400> SEQUENCE: 1270

Ala Arg Thr Ser Ala Gly Val Gly Ala Trp Gly Ala Ala Ala Val Gly
1               5                   10                  15

Arg Thr Ala Gly Val Arg
            20

<210> SEQ ID NO 1271
<211> LENGTH: 17
<212> TYPE: PRT
<213> ORGANISM: Homo sapiens

<400> SEQUENCE: 1271

Ala Ser Ile Pro Leu Lys Glu Leu Glu Gln Phe Asn Ser Asp Ile Gln
1               5                   10                  15

Lys

<210> SEQ ID NO 1272
<211> LENGTH: 14
<212> TYPE: PRT
<213> ORGANISM: Homo sapiens

<400> SEQUENCE: 1272

Ala Thr Ser Cys Phe Pro Arg Pro Met Thr Pro Arg Asp Arg
1               5                   10

<210> SEQ ID NO 1273
<211> LENGTH: 13
<212> TYPE: PRT
<213> ORGANISM: Homo sapiens

<400> SEQUENCE: 1273

Ala Val Thr Ser Val Ser Gly Pro Gly Glu His Leu Arg
1               5                   10

<210> SEQ ID NO 1274
<211> LENGTH: 8
<212> TYPE: PRT
<213> ORGANISM: Homo sapiens

<400> SEQUENCE: 1274

Cys Ala Glu Val Val Ser Gly Lys
1               5

<210> SEQ ID NO 1275
<211> LENGTH: 10
<212> TYPE: PRT
<213> ORGANISM: Homo sapiens

<400> SEQUENCE: 1275

Cys Phe Gly Leu Leu Leu Ser Pro Gly Lys
1               5                   10

<210> SEQ ID NO 1276
<211> LENGTH: 14
<212> TYPE: PRT
<213> ORGANISM: Homo sapiens

<400> SEQUENCE: 1276

Cys Gly Asp Ser Asp Lys Gly Phe Val Val Ile Asn Gln Lys
1               5                   10

<210> SEQ ID NO 1277
<211> LENGTH: 19
<212> TYPE: PRT
<213> ORGANISM: Homo sapiens

<400> SEQUENCE: 1277

Cys Gly Gly Leu Ser Cys Asn Gly Ala Ala Ala Thr Ala Asp Leu Ala
1               5                   10                  15

Leu Gly Arg

<210> SEQ ID NO 1278
<211> LENGTH: 10
<212> TYPE: PRT
<213> ORGANISM: Homo sapiens

<400> SEQUENCE: 1278

Cys Leu Cys Pro Pro Asp Phe Ala Gly Lys
1 5 10

<210> SEQ ID NO 1279
<211> LENGTH: 9
<212> TYPE: PRT
<213> ORGANISM: Homo sapiens

<400> SEQUENCE: 1279

Cys Leu Gln His Pro Trp Leu Met Lys
1 5

<210> SEQ ID NO 1280
<211> LENGTH: 13
<212> TYPE: PRT
<213> ORGANISM: Homo sapiens

<400> SEQUENCE: 1280

Cys Leu Val Glu Asn Ala Gly Asp Val Ala Phe Val Arg
1 5 10

<210> SEQ ID NO 1281
<211> LENGTH: 22
<212> TYPE: PRT
<213> ORGANISM: Homo sapiens

<400> SEQUENCE: 1281

Cys Ser Gly Asn Ile Asp Pro Met Asp Pro Asp Ala Cys Asp Pro His
1 5 10 15

Thr Gly Gln Cys Leu Arg
20

<210> SEQ ID NO 1282
<211> LENGTH: 16
<212> TYPE: PRT
<213> ORGANISM: Homo sapiens

<400> SEQUENCE: 1282

Cys Thr Glu Gly Pro Ile Asp Leu Val Phe Val Ile Asp Gly Ser Lys
1 5 10 15

<210> SEQ ID NO 1283
<211> LENGTH: 12
<212> TYPE: PRT
<213> ORGANISM: Homo sapiens

<400> SEQUENCE: 1283

Cys Thr Gln Cys Leu Gln His Pro Trp Leu Met Lys
1 5 10

<210> SEQ ID NO 1284
<211> LENGTH: 10
<212> TYPE: PRT
<213> ORGANISM: Homo sapiens

<400> SEQUENCE: 1284

Cys Val Arg Trp Ala Pro Asn Glu Asn Lys
1 5 10

<210> SEQ ID NO 1285
<211> LENGTH: 8
<212> TYPE: PRT
<213> ORGANISM: Homo sapiens

<400> SEQUENCE: 1285

Asp Ala Leu Leu Glu Ala Leu Lys
1 5

<210> SEQ ID NO 1286
<211> LENGTH: 12
<212> TYPE: PRT
<213> ORGANISM: Homo sapiens

<400> SEQUENCE: 1286

Asp Cys Cys Phe Glu Ile Ser Ala Pro Asp Lys Arg
1 5 10

<210> SEQ ID NO 1287
<211> LENGTH: 21
<212> TYPE: PRT
<213> ORGANISM: Homo sapiens

<400> SEQUENCE: 1287

Asp Asp Arg Thr Gly Thr Gly Thr Leu Ser Val Phe Gly Met Gln Ala
1 5 10 15

Arg Tyr Ser Leu Arg
20

<210> SEQ ID NO 1288
<211> LENGTH: 13
<212> TYPE: PRT
<213> ORGANISM: Homo sapiens

<400> SEQUENCE: 1288

Asp Glu Asp Phe Glu Leu Thr Glu Arg Glu Cys Ile Lys
1 5 10

<210> SEQ ID NO 1289
<211> LENGTH: 12
<212> TYPE: PRT
<213> ORGANISM: Homo sapiens

<400> SEQUENCE: 1289

Asp Ile Ser Leu Gln Gly Pro Gly Leu Ala Pro Glu
1 5 10

<210> SEQ ID NO 1290
<211> LENGTH: 10
<212> TYPE: PRT
<213> ORGANISM: Homo sapiens

<400> SEQUENCE: 1290

Asp Ile Thr Ala Ala Leu Ala Ala Glu Arg
1 5 10

<210> SEQ ID NO 1291
<211> LENGTH: 10
<212> TYPE: PRT
<213> ORGANISM: Homo sapiens

<400> SEQUENCE: 1291

Asp Leu Asn Val Ile Ser Ser Leu Leu Lys
1 5 10

<210> SEQ ID NO 1292
<211> LENGTH: 16
<212> TYPE: PRT
<213> ORGANISM: Homo sapiens

<400> SEQUENCE: 1292

Asp Gln Arg Glu Pro Leu Pro Pro Ala Pro Ala Glu Asn Glu Met Lys
1 5 10 15

<210> SEQ ID NO 1293
<211> LENGTH: 20
<212> TYPE: PRT
<213> ORGANISM: Homo sapiens

<400> SEQUENCE: 1293

Asp Gln Ser Pro Leu Val Ser Ser Ser Asp Ser Pro Pro Arg Pro Gln
1 5 10 15

Pro Ala Phe Lys
20

<210> SEQ ID NO 1294
<211> LENGTH: 9
<212> TYPE: PRT
<213> ORGANISM: Homo sapiens

<400> SEQUENCE: 1294

Asp Arg Arg Gly Ser Gly Lys Pro Arg
1 5

<210> SEQ ID NO 1295
<211> LENGTH: 12
<212> TYPE: PRT
<213> ORGANISM: Homo sapiens

<400> SEQUENCE: 1295

Asp Ser Ser His Ala Phe Thr Leu Asp Glu Leu Arg
1 5 10

<210> SEQ ID NO 1296
<211> LENGTH: 22
<212> TYPE: PRT
<213> ORGANISM: Homo sapiens

<400> SEQUENCE: 1296

Asp Trp Asp Ser Pro Tyr Ser His Asp Leu Asp Thr Ser Ala Asp Ser
1 5 10 15

Val Gly Asn Ala Cys Arg
20

<210> SEQ ID NO 1297
<211> LENGTH: 18
<212> TYPE: PRT
<213> ORGANISM: Homo sapiens

<400> SEQUENCE: 1297

Glu Ala Glu Gln Leu Leu Arg Gly Pro Leu Gly Asp Gln Tyr Gln Thr
1 5 10 15

Val Lys

<210> SEQ ID NO 1298
<211> LENGTH: 15
<212> TYPE: PRT
<213> ORGANISM: Homo sapiens

<400> SEQUENCE: 1298

Glu Ala Glu Val Gln Thr Trp Leu Gln Gln Ile Gly Phe Ser Lys
1               5                   10                  15

<210> SEQ ID NO 1299
<211> LENGTH: 8
<212> TYPE: PRT
<213> ORGANISM: Homo sapiens

<400> SEQUENCE: 1299

Glu Asp Thr Val Gln Ser Val Lys
1               5

<210> SEQ ID NO 1300
<211> LENGTH: 11
<212> TYPE: PRT
<213> ORGANISM: Homo sapiens

<400> SEQUENCE: 1300

Glu Glu Ala Glu Gln Val Leu Gly Gln Ala Arg
1               5                   10

<210> SEQ ID NO 1301
<211> LENGTH: 7
<212> TYPE: PRT
<213> ORGANISM: Homo sapiens

<400> SEQUENCE: 1301

Glu Gly Ile Val Ala Leu Arg
1               5

<210> SEQ ID NO 1302
<211> LENGTH: 11
<212> TYPE: PRT
<213> ORGANISM: Homo sapiens

<400> SEQUENCE: 1302

Glu Gly Thr Glu Ala Glu Pro Leu Pro Leu Arg
1               5                   10

<210> SEQ ID NO 1303
<211> LENGTH: 11
<212> TYPE: PRT
<213> ORGANISM: Homo sapiens

<400> SEQUENCE: 1303

Glu Gly Thr Glu Ala Glu Pro Leu Pro Leu Arg
1               5                   10

<210> SEQ ID NO 1304
<211> LENGTH: 9
<212> TYPE: PRT
<213> ORGANISM: Homo sapiens

<400> SEQUENCE: 1304

Glu Gly Thr Pro Gly Ile Phe Gln Lys
1               5

<210> SEQ ID NO 1305
<211> LENGTH: 8

<212> TYPE: PRT
<213> ORGANISM: Homo sapiens

<400> SEQUENCE: 1305

Glu Gly Val Ile Gln Asn Phe Lys
1               5

<210> SEQ ID NO 1306
<211> LENGTH: 8
<212> TYPE: PRT
<213> ORGANISM: Homo sapiens

<400> SEQUENCE: 1306

Glu Ile Asp Ala Ala Leu Gln Lys
1               5

<210> SEQ ID NO 1307
<211> LENGTH: 13
<212> TYPE: PRT
<213> ORGANISM: Homo sapiens

<400> SEQUENCE: 1307

Glu Ile His Thr Val Pro Asp Met Gly Lys Trp Lys Arg
1               5                   10

<210> SEQ ID NO 1308
<211> LENGTH: 22
<212> TYPE: PRT
<213> ORGANISM: Homo sapiens

<400> SEQUENCE: 1308

Glu Lys Leu Thr Ala Ala Ser Val Gly Val Gln Gly Ser Gly Trp Gly
1               5                   10                  15

Trp Leu Gly Phe Asn Lys
            20

<210> SEQ ID NO 1309
<211> LENGTH: 23
<212> TYPE: PRT
<213> ORGANISM: Homo sapiens

<400> SEQUENCE: 1309

Glu Leu Glu Ala Lys Met Leu Ala Gln Lys Ala Glu Glu Lys Glu Asn
1               5                   10                  15

His Cys Pro Thr Met Leu Arg
            20

<210> SEQ ID NO 1310
<211> LENGTH: 19
<212> TYPE: PRT
<213> ORGANISM: Homo sapiens

<400> SEQUENCE: 1310

Glu Leu Glu Glu Lys Asp Gly Asp Val Gln Ala Gly Ala Asn Leu Ser
1               5                   10                  15

Phe Asn Arg

<210> SEQ ID NO 1311
<211> LENGTH: 15
<212> TYPE: PRT
<213> ORGANISM: Homo sapiens

<400> SEQUENCE: 1311

Glu Leu Glu Thr Leu Thr Thr Asn Tyr Gln Trp Leu Cys Thr Arg
1 5 10 15

<210> SEQ ID NO 1312
<211> LENGTH: 26
<212> TYPE: PRT
<213> ORGANISM: Homo sapiens

<400> SEQUENCE: 1312

Glu Leu Leu Leu Ser Gly Pro Pro Glu Val Ala Ala Pro Asp Thr Pro
1 5 10 15

Tyr Leu His Val Asp Ser Ala Ala Gln Arg
20 25

<210> SEQ ID NO 1313
<211> LENGTH: 9
<212> TYPE: PRT
<213> ORGANISM: Homo sapiens

<400> SEQUENCE: 1313

Glu Leu Gln Asp Gly Ile Gly Gln Arg
1 5

<210> SEQ ID NO 1314
<211> LENGTH: 13
<212> TYPE: PRT
<213> ORGANISM: Homo sapiens

<400> SEQUENCE: 1314

Glu Met Ser Lys Lys Ala Pro Ser Glu Ile Ser Arg Lys
1 5 10

<210> SEQ ID NO 1315
<211> LENGTH: 17
<212> TYPE: PRT
<213> ORGANISM: Homo sapiens

<400> SEQUENCE: 1315

Glu Asn Ile Arg Gln Glu Ile Ser Ile Met Asn Cys Leu His His Pro
1 5 10 15

Lys

<210> SEQ ID NO 1316
<211> LENGTH: 22
<212> TYPE: PRT
<213> ORGANISM: Homo sapiens

<400> SEQUENCE: 1316

Glu Pro Met Lys Ala Pro Leu Cys Gly Glu Gly Asp Gln Pro Gly Gly
1 5 10 15

Phe Glu Ser Gln Glu Lys
20

<210> SEQ ID NO 1317
<211> LENGTH: 18
<212> TYPE: PRT
<213> ORGANISM: Homo sapiens

<400> SEQUENCE: 1317

Glu Pro Tyr Ala Arg Glu Met Leu Ala Ile Ser Phe Ile Ser Ala Val
1 5 10 15

Asn Arg

<210> SEQ ID NO 1318
<211> LENGTH: 25
<212> TYPE: PRT
<213> ORGANISM: Homo sapiens

<400> SEQUENCE: 1318

Glu Arg Ala Arg Lys Phe Ser Gly Ser Gly Leu Ala Met Gly Leu Gly
1 5 10 15

Ser Ala Ser Ala Ser Ala Trp Arg Arg
20 25

<210> SEQ ID NO 1319
<211> LENGTH: 25
<212> TYPE: PRT
<213> ORGANISM: Homo sapiens

<400> SEQUENCE: 1319

Glu Arg Ala Arg Lys Phe Ser Gly Ser Gly Leu Ala Met Gly Leu Gly
1 5 10 15

Ser Ala Ser Ala Ser Ala Trp Arg Arg
20 25

<210> SEQ ID NO 1320
<211> LENGTH: 19
<212> TYPE: PRT
<213> ORGANISM: Homo sapiens

<400> SEQUENCE: 1320

Glu Arg Val Leu Ser Leu Ser Gln Ala Leu Ala Thr Glu Ala Ser Gln
1 5 10 15

Trp His Arg

<210> SEQ ID NO 1321
<211> LENGTH: 30
<212> TYPE: PRT
<213> ORGANISM: Homo sapiens

<400> SEQUENCE: 1321

Glu Ser Gly Arg Gly Ser Ser Thr Pro Pro Gly Pro Ile Ala Ala Leu
1 5 10 15

Gly Met Pro Asp Thr Gly Pro Gly Ser Ser Ser Leu Gly Lys
20 25 30

<210> SEQ ID NO 1322
<211> LENGTH: 16
<212> TYPE: PRT
<213> ORGANISM: Homo sapiens

<400> SEQUENCE: 1322

Glu Ser Gly Ser Leu Glu Asp Asp Trp Asp Phe Leu Pro Pro Lys Lys
1 5 10 15

<210> SEQ ID NO 1323
<211> LENGTH: 15
<212> TYPE: PRT
<213> ORGANISM: Homo sapiens

<400> SEQUENCE: 1323

Glu Val Ala Arg Asn Val Phe Glu Cys Asn Asp Gln Val Val Lys
1 5 10 15

<210> SEQ ID NO 1324

<211> LENGTH: 12
<212> TYPE: PRT
<213> ORGANISM: Homo sapiens

<400> SEQUENCE: 1324

Glu Val Pro Glu Glu Gly Pro Gly Ala Pro Ala Arg
1 5 10

<210> SEQ ID NO 1325
<211> LENGTH: 9
<212> TYPE: PRT
<213> ORGANISM: Homo sapiens

<400> SEQUENCE: 1325

Glu Tyr Gln Glu Asp Leu Ala Leu Arg
1 5

<210> SEQ ID NO 1326
<211> LENGTH: 7
<212> TYPE: PRT
<213> ORGANISM: Homo sapiens

<400> SEQUENCE: 1326

Phe Ala Gly Asp Ser Leu Lys
1 5

<210> SEQ ID NO 1327
<211> LENGTH: 8
<212> TYPE: PRT
<213> ORGANISM: Homo sapiens

<400> SEQUENCE: 1327

Phe Gly Pro Gly Asp Gln Val Arg
1 5

<210> SEQ ID NO 1328
<211> LENGTH: 12
<212> TYPE: PRT
<213> ORGANISM: Homo sapiens

<400> SEQUENCE: 1328

Phe Gly Val Leu Gly Leu Asp Leu Trp Gln Val Lys
1 5 10

<210> SEQ ID NO 1329
<211> LENGTH: 13
<212> TYPE: PRT
<213> ORGANISM: Homo sapiens

<400> SEQUENCE: 1329

Phe Lys Asp Asn Pro Thr Val Val Val Glu Asp Leu Arg
1 5 10

<210> SEQ ID NO 1330
<211> LENGTH: 16
<212> TYPE: PRT
<213> ORGANISM: Homo sapiens

<400> SEQUENCE: 1330

Phe Asn Gly Ala Pro Thr Ala Asn Phe Gln Gln Asp Val Gly Thr Lys
1 5 10 15

<210> SEQ ID NO 1331
<211> LENGTH: 11
<212> TYPE: PRT

<213> ORGANISM: Homo sapiens

<400> SEQUENCE: 1331

Phe Asn His Pro Ala Glu Ala Lys Trp Met Lys
1 5 10

<210> SEQ ID NO 1332
<211> LENGTH: 14
<212> TYPE: PRT
<213> ORGANISM: Homo sapiens

<400> SEQUENCE: 1332

Phe Asn Arg Ala Leu Asn Cys Met Asn Leu Pro Pro Asp Lys
1 5 10

<210> SEQ ID NO 1333
<211> LENGTH: 9
<212> TYPE: PRT
<213> ORGANISM: Homo sapiens

<400> SEQUENCE: 1333

Phe Arg Leu Ala Glu Asp Gly Lys Arg
1 5

<210> SEQ ID NO 1334
<211> LENGTH: 7
<212> TYPE: PRT
<213> ORGANISM: Homo sapiens

<400> SEQUENCE: 1334

Phe Ser Ala Glu Ala Leu Arg
1 5

<210> SEQ ID NO 1335
<211> LENGTH: 9
<212> TYPE: PRT
<213> ORGANISM: Homo sapiens

<400> SEQUENCE: 1335

Phe Ser Pro Glu Val Pro Gly Gln Lys
1 5

<210> SEQ ID NO 1336
<211> LENGTH: 8
<212> TYPE: PRT
<213> ORGANISM: Homo sapiens

<400> SEQUENCE: 1336

Phe Thr Asp Phe Glu Glu Val Arg
1 5

<210> SEQ ID NO 1337
<211> LENGTH: 14
<212> TYPE: PRT
<213> ORGANISM: Homo sapiens

<400> SEQUENCE: 1337

Phe Val Pro Ile Ile Gly Ile Ala Met Pro Leu Ser Ser Arg
1 5 10

<210> SEQ ID NO 1338
<211> LENGTH: 11
<212> TYPE: PRT
<213> ORGANISM: Homo sapiens

<400> SEQUENCE: 1338

Phe Trp Pro Ala Ile Asp Asp Gly Leu Arg Arg
1 5 10

<210> SEQ ID NO 1339
<211> LENGTH: 19
<212> TYPE: PRT
<213> ORGANISM: Homo sapiens

<400> SEQUENCE: 1339

Phe Trp Val Val Asp Gln Thr His Phe Tyr Leu Gly Ser Ala Asn Met
1 5 10 15

Asp Trp Arg

<210> SEQ ID NO 1340
<211> LENGTH: 19
<212> TYPE: PRT
<213> ORGANISM: Homo sapiens

<400> SEQUENCE: 1340

Gly Ala Ala Val Asp Glu Tyr Phe Arg Gln Pro Val Val Asp Thr Phe
1 5 10 15

Asp Ile Arg

<210> SEQ ID NO 1341
<211> LENGTH: 12
<212> TYPE: PRT
<213> ORGANISM: Homo sapiens

<400> SEQUENCE: 1341

Gly Ala Phe His Arg Pro Val Leu Gly Gly Phe Arg
1 5 10

<210> SEQ ID NO 1342
<211> LENGTH: 17
<212> TYPE: PRT
<213> ORGANISM: Homo sapiens

<400> SEQUENCE: 1342

Gly Ala Gly Leu Ala Trp Gly Val His Asp Cys Gln Leu Cys Ser Glu
1 5 10 15

Arg

<210> SEQ ID NO 1343
<211> LENGTH: 19
<212> TYPE: PRT
<213> ORGANISM: Homo sapiens

<400> SEQUENCE: 1343

Gly Ala Pro Ile Ser Ala Tyr Gln Ile Val Val Glu Glu Leu His Pro
1 5 10 15

His Arg Thr

<210> SEQ ID NO 1344
<211> LENGTH: 27
<212> TYPE: PRT
<213> ORGANISM: Homo sapiens

<400> SEQUENCE: 1344

Gly Ala Thr Gly His Pro Gly Gly Gly Gln Gly Ala Glu Asn Pro Ala
1 5 10 15

Gly Leu Lys Ser Gln Gly Asn Glu Leu Phe Arg
20 25

<210> SEQ ID NO 1345
<211> LENGTH: 16
<212> TYPE: PRT
<213> ORGANISM: Homo sapiens

<400> SEQUENCE: 1345

Gly Cys Leu Glu Leu Ile Lys Glu Thr Gly Val Pro Ile Ala Gly Arg
1 5 10 15

<210> SEQ ID NO 1346
<211> LENGTH: 25
<212> TYPE: PRT
<213> ORGANISM: Homo sapiens

<400> SEQUENCE: 1346

Gly Cys Pro Gln Glu Asp Ser Asp Ile Ala Phe Leu Ile Asp Gly Ser
1 5 10 15

Gly Ser Ile Ile Pro His Asp Phe Arg
20 25

<210> SEQ ID NO 1347
<211> LENGTH: 32
<212> TYPE: PRT
<213> ORGANISM: Homo sapiens

<400> SEQUENCE: 1347

Gly Asp Glu Gly Pro Ile Gly His Gln Gly Pro Ile Gly Gln Glu Gly
1 5 10 15

Ala Pro Gly Arg Pro Gly Ser Pro Gly Leu Pro Gly Met Pro Gly Arg
20 25 30

<210> SEQ ID NO 1348
<211> LENGTH: 15
<212> TYPE: PRT
<213> ORGANISM: Homo sapiens

<400> SEQUENCE: 1348

Gly Asp Lys Gly Glu Arg Gly Ala Pro Gly Val Thr Gly Pro Lys
1 5 10 15

<210> SEQ ID NO 1349
<211> LENGTH: 14
<212> TYPE: PRT
<213> ORGANISM: Homo sapiens

<400> SEQUENCE: 1349

Gly Asp Asn Val Leu Ile Asn Thr Phe Ser Gly Leu Leu Lys
1 5 10

<210> SEQ ID NO 1350
<211> LENGTH: 14
<212> TYPE: PRT
<213> ORGANISM: Homo sapiens

<400> SEQUENCE: 1350

Gly Asp Asn Val Leu Ile Asn Thr Phe Ser Gly Leu Leu Lys
1 5 10

<210> SEQ ID NO 1351
<211> LENGTH: 27
<212> TYPE: PRT

<213> ORGANISM: Homo sapiens

<400> SEQUENCE: 1351

Gly Asp Thr Gly Asn Pro Gly Ala Pro Gly Thr Pro Gly Thr Lys Gly
1 5 10 15

Trp Ala Gly Asp Ser Gly Pro Gln Gly Arg Pro
20 25

<210> SEQ ID NO 1352
<211> LENGTH: 11
<212> TYPE: PRT
<213> ORGANISM: Homo sapiens

<400> SEQUENCE: 1352

Gly Glu Phe Ala Ile Asp Gly Tyr Ser Val Arg
1 5 10

<210> SEQ ID NO 1353
<211> LENGTH: 16
<212> TYPE: PRT
<213> ORGANISM: Homo sapiens

<400> SEQUENCE: 1353

Gly Glu Gly Leu Tyr Ala Asp Pro Tyr Gly Leu Leu His Glu Gly Arg
1 5 10 15

<210> SEQ ID NO 1354
<211> LENGTH: 18
<212> TYPE: PRT
<213> ORGANISM: Homo sapiens

<400> SEQUENCE: 1354

Gly Glu Ile Ala Pro Leu Lys Glu Asn Val Ser His Val Asn Asp Leu
1 5 10 15

Ala Arg

<210> SEQ ID NO 1355
<211> LENGTH: 14
<212> TYPE: PRT
<213> ORGANISM: Homo sapiens

<400> SEQUENCE: 1355

Gly Glu Trp Lys Pro Arg Gln Ile Asp Asn Pro Asp Tyr Lys
1 5 10

<210> SEQ ID NO 1356
<211> LENGTH: 18
<212> TYPE: PRT
<213> ORGANISM: Homo sapiens

<400> SEQUENCE: 1356

Gly Gly Cys Val Ala Leu Ala Thr Gly Ser Ala Met Gly Leu Trp Glu
1 5 10 15

Val Lys

<210> SEQ ID NO 1357
<211> LENGTH: 14
<212> TYPE: PRT
<213> ORGANISM: Homo sapiens

<400> SEQUENCE: 1357

Gly Gly His Asp Ile Ile Leu Ala Ala Phe Asp Asn Phe Lys
1 5 10

<210> SEQ ID NO 1358
<211> LENGTH: 25
<212> TYPE: PRT
<213> ORGANISM: Homo sapiens

<400> SEQUENCE: 1358

Gly Gly Ser Gln Pro Pro Asp Ile Asp Lys Thr Glu Leu Val Glu Pro
1 5 10 15

Thr Glu Tyr Leu Val Val His Leu Lys
20 25

<210> SEQ ID NO 1359
<211> LENGTH: 10
<212> TYPE: PRT
<213> ORGANISM: Homo sapiens

<400> SEQUENCE: 1359

Gly Gly Val Ser Ala Val Pro Gly Phe Arg
1 5 10

<210> SEQ ID NO 1360
<211> LENGTH: 33
<212> TYPE: PRT
<213> ORGANISM: Homo sapiens

<400> SEQUENCE: 1360

Gly His Leu Gln Ile Ala Ala Cys Pro Asn Gln Asp Pro Leu Gln Gly
1 5 10 15

Thr Thr Gly Leu Ile Pro Leu Leu Gly Ile Asp Val Trp Glu His Ala
20 25 30

Tyr

<210> SEQ ID NO 1361
<211> LENGTH: 21
<212> TYPE: PRT
<213> ORGANISM: Homo sapiens

<400> SEQUENCE: 1361

Gly His Pro Asp Arg Leu Pro Leu Gln Met Ala Leu Thr Glu Leu Glu
1 5 10 15

Thr Leu Ala Glu Lys
20

<210> SEQ ID NO 1362
<211> LENGTH: 8
<212> TYPE: PRT
<213> ORGANISM: Homo sapiens

<400> SEQUENCE: 1362

Gly Lys Glu Ala Gly Glu Val Arg
1 5

<210> SEQ ID NO 1363
<211> LENGTH: 11
<212> TYPE: PRT
<213> ORGANISM: Homo sapiens

<400> SEQUENCE: 1363

Gly Lys Asn Val Leu Ile Asn Lys Asp Ile Arg
1 5 10

<210> SEQ ID NO 1364
<211> LENGTH: 11
<212> TYPE: PRT
<213> ORGANISM: Homo sapiens

<400> SEQUENCE: 1364

Gly Leu Cys Phe Leu Phe Gly Ser Asn Leu Arg
1 5 10

<210> SEQ ID NO 1365
<211> LENGTH: 13
<212> TYPE: PRT
<213> ORGANISM: Homo sapiens

<400> SEQUENCE: 1365

Gly Leu Glu Glu Ala Val Glu Ser Ala Cys Ala Met Arg
1 5 10

<210> SEQ ID NO 1366
<211> LENGTH: 19
<212> TYPE: PRT
<213> ORGANISM: Homo sapiens

<400> SEQUENCE: 1366

Gly Leu Gly Lys Tyr Ile Cys Gln Lys Cys His Ala Ile Ile Asp Glu
1 5 10 15

Gln Pro Leu

<210> SEQ ID NO 1367
<211> LENGTH: 33
<212> TYPE: PRT
<213> ORGANISM: Homo sapiens

<400> SEQUENCE: 1367

Gly Asn Cys Phe Cys Tyr Gly His Ala Ser Glu Cys Ala Pro Ala Pro
1 5 10 15

Gly Ala Pro Ala His Ala Glu Gly Met Val His Gly Ala Cys Ile Cys
20 25 30

Lys

<210> SEQ ID NO 1368
<211> LENGTH: 31
<212> TYPE: PRT
<213> ORGANISM: Homo sapiens

<400> SEQUENCE: 1368

Gly Pro Ala Pro Ala Arg Pro Lys Met Leu Val Ile Ser Gly Gly Asp
1 5 10 15

Gly Tyr Glu Asp Phe Arg Leu Ser Ser Gly Gly Gly Ser Ser Ser
20 25 30

<210> SEQ ID NO 1369
<211> LENGTH: 13
<212> TYPE: PRT
<213> ORGANISM: Homo sapiens

<400> SEQUENCE: 1369

Gly Pro Gly Ala Gly Ser Ala Leu Asp Asp Gly Arg Arg
1 5 10

<210> SEQ ID NO 1370
<211> LENGTH: 8
<212> TYPE: PRT

<213> ORGANISM: Homo sapiens

<400> SEQUENCE: 1370

Gly Pro Pro Ser Ser Val Pro Lys
1 5

<210> SEQ ID NO 1371
<211> LENGTH: 12
<212> TYPE: PRT
<213> ORGANISM: Homo sapiens

<400> SEQUENCE: 1371

Gly Gln Leu Gln Asp Glu Leu Glu Lys Gly Glu Arg
1 5 10

<210> SEQ ID NO 1372
<211> LENGTH: 32
<212> TYPE: PRT
<213> ORGANISM: Homo sapiens

<400> SEQUENCE: 1372

Gly Gln Thr Pro Glu Ala Gly Ala Asp Lys Arg Ser Pro Arg Arg Ala
1 5 10 15

Ser Ala Ala Ala Ala Ala Gly Gly Gly Ala Thr Gly His Pro Gly Gly
20 25 30

<210> SEQ ID NO 1373
<211> LENGTH: 24
<212> TYPE: PRT
<213> ORGANISM: Homo sapiens

<400> SEQUENCE: 1373

Gly Arg Glu Pro Ala Ser Cys Glu Asp Leu Cys Gly Gly Gly Val Gly
1 5 10 15

Ala Asp Gly Gly Gly Ser Asp Arg
20

<210> SEQ ID NO 1374
<211> LENGTH: 21
<212> TYPE: PRT
<213> ORGANISM: Homo sapiens

<400> SEQUENCE: 1374

Gly Arg Ile Ser Val Ser Leu Gln Glu Glu Ala Ser Gly Gly Ser Leu
1 5 10 15

Ala Ala Pro Ala Arg
20

<210> SEQ ID NO 1375
<211> LENGTH: 16
<212> TYPE: PRT
<213> ORGANISM: Homo sapiens

<400> SEQUENCE: 1375

Gly Ser Asp Gly Met Asp Ala Val Arg Ser Ala Pro Thr Leu Ile Arg
1 5 10 15

<210> SEQ ID NO 1376
<211> LENGTH: 12
<212> TYPE: PRT
<213> ORGANISM: Homo sapiens

<400> SEQUENCE: 1376

Gly Ser Arg Pro Gly Ile Glu Gly Asp Thr Pro Arg
1 5 10

<210> SEQ ID NO 1377
<211> LENGTH: 11
<212> TYPE: PRT
<213> ORGANISM: Homo sapiens

<400> SEQUENCE: 1377

Gly Thr Ile Ser Phe Phe Glu Ile Asp Gly Arg
1 5 10

<210> SEQ ID NO 1378
<211> LENGTH: 16
<212> TYPE: PRT
<213> ORGANISM: Homo sapiens

<400> SEQUENCE: 1378

Gly Thr Trp Ile His Pro Glu Ile Asp Asn Pro Glu Tyr Ser Pro Asp
1 5 10 15

<210> SEQ ID NO 1379
<211> LENGTH: 10
<212> TYPE: PRT
<213> ORGANISM: Homo sapiens

<400> SEQUENCE: 1379

Gly Val Thr Asp Thr Leu Ala Gln Ile Arg
1 5 10

<210> SEQ ID NO 1380
<211> LENGTH: 12
<212> TYPE: PRT
<213> ORGANISM: Homo sapiens

<400> SEQUENCE: 1380

Gly Trp Asp Cys His Gly Leu Pro Ile Glu Ile Lys
1 5 10

<210> SEQ ID NO 1381
<211> LENGTH: 11
<212> TYPE: PRT
<213> ORGANISM: Homo sapiens

<400> SEQUENCE: 1381

His Cys Glu Leu Cys Arg Pro Phe Phe Tyr Arg
1 5 10

<210> SEQ ID NO 1382
<211> LENGTH: 26
<212> TYPE: PRT
<213> ORGANISM: Homo sapiens

<400> SEQUENCE: 1382

His Phe Gln Ile Asp Tyr Asp Glu Asp Gly Asn Cys Ser Leu Ile Ile
1 5 10 15

Ser Asp Val Cys Gly Asp Asp Asp Ala Lys
20 25

<210> SEQ ID NO 1383
<211> LENGTH: 25
<212> TYPE: PRT
<213> ORGANISM: Homo sapiens

<400> SEQUENCE: 1383

His Gly Gly Leu Ser Leu Val Gln Thr Thr Asp Tyr Ile Tyr Pro Ile
1 5 10 15

Val Asp Asp Pro Tyr Met Met Gly Arg
20 25

<210> SEQ ID NO 1384
<211> LENGTH: 11
<212> TYPE: PRT
<213> ORGANISM: Homo sapiens

<400> SEQUENCE: 1384

His Leu Asp Thr Leu His Asn Phe Val Ser Arg
1 5 10

<210> SEQ ID NO 1385
<211> LENGTH: 10
<212> TYPE: PRT
<213> ORGANISM: Homo sapiens

<400> SEQUENCE: 1385

His Leu Asn Pro Gly Leu Gln Leu Tyr Arg
1 5 10

<210> SEQ ID NO 1386
<211> LENGTH: 19
<212> TYPE: PRT
<213> ORGANISM: Homo sapiens

<400> SEQUENCE: 1386

His Thr Glu Ile Leu Glu Ile Leu Glu Ile Pro Gln Leu Met Asp Thr
1 5 10 15

Cys Val Arg

<210> SEQ ID NO 1387
<211> LENGTH: 11
<212> TYPE: PRT
<213> ORGANISM: Homo sapiens

<400> SEQUENCE: 1387

His Thr Leu Thr Gln Ile Lys Asp Ala Val Arg
1 5 10

<210> SEQ ID NO 1388
<211> LENGTH: 19
<212> TYPE: PRT
<213> ORGANISM: Homo sapiens

<400> SEQUENCE: 1388

Ile Ala Ala Leu Asn Ala Ser Ser Thr Ile Glu Asp Asp His Glu Gly
1 5 10 15

Ser Phe Lys

<210> SEQ ID NO 1389
<211> LENGTH: 7
<212> TYPE: PRT
<213> ORGANISM: Homo sapiens

<400> SEQUENCE: 1389

Ile Ala Glu Ile Gln Ala Arg
1 5

<210> SEQ ID NO 1390

<211> LENGTH: 14
<212> TYPE: PRT
<213> ORGANISM: Homo sapiens

<400> SEQUENCE: 1390

Ile Asp Ala Leu Arg Glu Glu Leu Met Glu Gly Met Asp Arg
1 5 10

<210> SEQ ID NO 1391
<211> LENGTH: 10
<212> TYPE: PRT
<213> ORGANISM: Homo sapiens

<400> SEQUENCE: 1391

Ile Phe Glu Glu Gln Pro Cys Leu Arg Lys
1 5 10

<210> SEQ ID NO 1392
<211> LENGTH: 13
<212> TYPE: PRT
<213> ORGANISM: Homo sapiens

<400> SEQUENCE: 1392

Ile Phe Leu Thr Glu Gln Pro Leu Glu Gly Leu Glu Lys
1 5 10

<210> SEQ ID NO 1393
<211> LENGTH: 7
<212> TYPE: PRT
<213> ORGANISM: Homo sapiens

<400> SEQUENCE: 1393

Ile Phe Ser Ala Tyr Ile Lys
1 5

<210> SEQ ID NO 1394
<211> LENGTH: 16
<212> TYPE: PRT
<213> ORGANISM: Homo sapiens

<400> SEQUENCE: 1394

Ile Ile Asp Arg Ile His Gly Thr Glu Glu Gly Gln Gln Ile Leu Lys
1 5 10 15

<210> SEQ ID NO 1395
<211> LENGTH: 10
<212> TYPE: PRT
<213> ORGANISM: Homo sapiens

<400> SEQUENCE: 1395

Ile Leu His Lys Gly Glu Glu Leu Ala Lys
1 5 10

<210> SEQ ID NO 1396
<211> LENGTH: 20
<212> TYPE: PRT
<213> ORGANISM: Homo sapiens

<400> SEQUENCE: 1396

Ile Asn Glu Leu Glu Asn Gly Gly Glu Ile Leu Asn Glu Thr Arg Ser
1 5 10 15

Phe His His Lys
20

<210> SEQ ID NO 1397
<211> LENGTH: 18
<212> TYPE: PRT
<213> ORGANISM: Homo sapiens

<400> SEQUENCE: 1397

Ile Pro Ala Ser Ala Glu Gln Ile Gln His Leu Ala Gly Ala Ile Ala
1               5                   10                  15

Glu Arg

<210> SEQ ID NO 1398
<211> LENGTH: 8
<212> TYPE: PRT
<213> ORGANISM: Homo sapiens

<400> SEQUENCE: 1398

Ile Gln Gly Thr Leu Gln Pro His
1               5

<210> SEQ ID NO 1399
<211> LENGTH: 15
<212> TYPE: PRT
<213> ORGANISM: Homo sapiens

<400> SEQUENCE: 1399

Ile Gln Asn Gln Trp Asp Glu Val Gln Glu His Leu Gln Asn Arg
1               5                   10                  15

<210> SEQ ID NO 1400
<211> LENGTH: 25
<212> TYPE: PRT
<213> ORGANISM: Homo sapiens

<400> SEQUENCE: 1400

Ile Gln Asn Val Val Thr Ser Phe Ala Pro Gln Arg Arg Ala Ala Trp
1               5                   10                  15

Trp Gln Ser Glu Asn Gly Ile Pro Ala
            20                  25

<210> SEQ ID NO 1401
<211> LENGTH: 12
<212> TYPE: PRT
<213> ORGANISM: Homo sapiens

<400> SEQUENCE: 1401

Ile Arg Gln Lys Val Asp Asp Cys Glu Arg Cys Arg
1               5                   10

<210> SEQ ID NO 1402
<211> LENGTH: 8
<212> TYPE: PRT
<213> ORGANISM: Homo sapiens

<400> SEQUENCE: 1402

Ile Thr Glu Gln Glu Lys Leu Lys
1               5

<210> SEQ ID NO 1403
<211> LENGTH: 32
<212> TYPE: PRT
<213> ORGANISM: Homo sapiens

<400> SEQUENCE: 1403

Ile Thr Ser Val Ser Thr Gly Asn Leu Cys Thr Glu Glu Gln Thr Pro 1 5 10 15

Pro Pro Arg Pro Glu Ala Tyr Pro Ile Pro Thr Gln Thr Tyr Thr Arg
20 25 30

<210> SEQ ID NO 1404
<211> LENGTH: 12
<212> TYPE: PRT
<213> ORGANISM: Homo sapiens

<400> SEQUENCE: 1404

Ile Val Leu Gly Gly Thr Thr Val His Asn Thr Lys
1 5 10

<210> SEQ ID NO 1405
<211> LENGTH: 7
<212> TYPE: PRT
<213> ORGANISM: Homo sapiens

<400> SEQUENCE: 1405

Ile Val Thr Thr His Ile Arg
1 5

<210> SEQ ID NO 1406
<211> LENGTH: 14
<212> TYPE: PRT
<213> ORGANISM: Homo sapiens

<400> SEQUENCE: 1406

Lys Asp Ala Glu Gly Ile Leu Glu Asp Leu Gln Ser Tyr Arg
1 5 10

<210> SEQ ID NO 1407
<211> LENGTH: 16
<212> TYPE: PRT
<213> ORGANISM: Homo sapiens

<400> SEQUENCE: 1407

Lys Asp Val Glu Val Thr Lys Glu Glu Phe Val Leu Ala Ala Gln Lys
1 5 10 15

<210> SEQ ID NO 1408
<211> LENGTH: 8
<212> TYPE: PRT
<213> ORGANISM: Homo sapiens

<400> SEQUENCE: 1408

Lys Glu Ala Asp Met Gln Gln Lys
1 5

<210> SEQ ID NO 1409
<211> LENGTH: 14
<212> TYPE: PRT
<213> ORGANISM: Homo sapiens

<400> SEQUENCE: 1409

Lys His Pro Ser Ser Pro Glu Cys Leu Val Ser Ala Gln Lys
1 5 10

<210> SEQ ID NO 1410
<211> LENGTH: 10
<212> TYPE: PRT
<213> ORGANISM: Homo sapiens

<400> SEQUENCE: 1410

Lys Ile Gln Asn His Ile Gln Thr Leu Lys
1 5 10

<210> SEQ ID NO 1411
<211> LENGTH: 13
<212> TYPE: PRT
<213> ORGANISM: Homo sapiens

<400> SEQUENCE: 1411

Lys Ile Ser Glu Glu Ser Gly Glu Thr Ala Lys Arg Arg
1 5 10

<210> SEQ ID NO 1412
<211> LENGTH: 19
<212> TYPE: PRT
<213> ORGANISM: Homo sapiens

<400> SEQUENCE: 1412

Lys Ile Tyr Ala Val Glu Ala Ser Thr Met Ala Gln His Ala Glu Val
1 5 10 15

Leu Val Lys

<210> SEQ ID NO 1413
<211> LENGTH: 9
<212> TYPE: PRT
<213> ORGANISM: Homo sapiens

<400> SEQUENCE: 1413

Lys Lys Glu Glu Leu Asn Ala Val Arg
1 5

<210> SEQ ID NO 1414
<211> LENGTH: 14
<212> TYPE: PRT
<213> ORGANISM: Homo sapiens

<400> SEQUENCE: 1414

Lys Lys Gly Pro Gly Ala Gly Ser Ala Leu Asp Asp Gly Arg
1 5 10

<210> SEQ ID NO 1415
<211> LENGTH: 6
<212> TYPE: PRT
<213> ORGANISM: Homo sapiens

<400> SEQUENCE: 1415

Lys Leu Met Gln Ile Arg
1 5

<210> SEQ ID NO 1416
<211> LENGTH: 12
<212> TYPE: PRT
<213> ORGANISM: Homo sapiens

<400> SEQUENCE: 1416

Lys Leu Ser Ser Gln Leu Val Glu His Cys Gln Lys
1 5 10

<210> SEQ ID NO 1417
<211> LENGTH: 7
<212> TYPE: PRT
<213> ORGANISM: Homo sapiens

<400> SEQUENCE: 1417

Lys Leu Thr Phe Glu Tyr Arg
1 5

<210> SEQ ID NO 1418
<211> LENGTH: 16
<212> TYPE: PRT
<213> ORGANISM: Homo sapiens

<400> SEQUENCE: 1418

Lys Met Glu Glu Glu Pro Leu Gly Pro Asp Leu Glu Asp Leu Lys Arg
1 5 10 15

<210> SEQ ID NO 1419
<211> LENGTH: 8
<212> TYPE: PRT
<213> ORGANISM: Homo sapiens

<400> SEQUENCE: 1419

Lys Met Ser Gly Thr Val Ser Lys
1 5

<210> SEQ ID NO 1420
<211> LENGTH: 11
<212> TYPE: PRT
<213> ORGANISM: Homo sapiens

<400> SEQUENCE: 1420

Lys Gln Val Ala Pro Glu Lys Pro Val Lys Lys
1 5 10

<210> SEQ ID NO 1421
<211> LENGTH: 26
<212> TYPE: PRT
<213> ORGANISM: Homo sapiens

<400> SEQUENCE: 1421

Lys Ser Ser Thr Gly Ser Pro Thr Ser Pro Leu Asn Ala Glu Lys Leu
1 5 10 15

Glu Ser Glu Glu Asp Val Ser Gln Ala Phe
20 25

<210> SEQ ID NO 1422
<211> LENGTH: 11
<212> TYPE: PRT
<213> ORGANISM: Homo sapiens

<400> SEQUENCE: 1422

Lys Thr Arg Pro Asp Gly Asn Cys Phe Tyr Arg
1 5 10

<210> SEQ ID NO 1423
<211> LENGTH: 9
<212> TYPE: PRT
<213> ORGANISM: Homo sapiens

<400> SEQUENCE: 1423

Lys Val Ser Thr Leu Gln Asn Gln Arg
1 5

<210> SEQ ID NO 1424
<211> LENGTH: 9
<212> TYPE: PRT
<213> ORGANISM: Homo sapiens

<400> SEQUENCE: 1424

Leu Ala Gly Glu Glu Glu Ala Leu Arg
1               5

<210> SEQ ID NO 1425
<211> LENGTH: 15
<212> TYPE: PRT
<213> ORGANISM: Homo sapiens

<400> SEQUENCE: 1425

Leu Cys Asp Asn Ile Val Ser Glu Ser Glu Ser Thr Thr Ala Arg
1               5                   10                  15

<210> SEQ ID NO 1426
<211> LENGTH: 18
<212> TYPE: PRT
<213> ORGANISM: Homo sapiens

<400> SEQUENCE: 1426

Leu Cys Ile Glu His Val Glu Glu His Gly Leu Asp Ile Asp Gly Ile
1               5                   10                  15

Tyr Arg

<210> SEQ ID NO 1427
<211> LENGTH: 23
<212> TYPE: PRT
<213> ORGANISM: Homo sapiens

<400> SEQUENCE: 1427

Leu Cys Gln Phe Glu Glu Ala Lys Gln Asp Cys Asp Gln Ala Leu Gln
1               5                   10                  15

Leu Ala Asp Gly Asn Val Lys
            20

<210> SEQ ID NO 1428
<211> LENGTH: 21
<212> TYPE: PRT
<213> ORGANISM: Homo sapiens

<400> SEQUENCE: 1428

Leu Asp Ala Trp Glu Glu Ala Gln Val Glu Phe Met Ala Ser His Gly
1               5                   10                  15

Asn Asp Ala Ala Arg
            20

<210> SEQ ID NO 1429
<211> LENGTH: 13
<212> TYPE: PRT
<213> ORGANISM: Homo sapiens

<400> SEQUENCE: 1429

Leu Asp Glu Asp Leu Thr Thr Leu Gly Gln Met Ser Lys
1               5                   10

<210> SEQ ID NO 1430
<211> LENGTH: 20
<212> TYPE: PRT
<213> ORGANISM: Homo sapiens

<400> SEQUENCE: 1430

Leu Asp Leu Phe Glu Ile Ser Gln Pro Thr Glu Asp Leu Glu Phe His
1               5                   10                  15

Gly Val Met Arg

20

<210> SEQ ID NO 1431
<211> LENGTH: 6
<212> TYPE: PRT
<213> ORGANISM: Homo sapiens

<400> SEQUENCE: 1431

Leu Glu Ala Ile Lys Arg
1               5

<210> SEQ ID NO 1432
<211> LENGTH: 10
<212> TYPE: PRT
<213> ORGANISM: Homo sapiens

<400> SEQUENCE: 1432

Leu Glu Met Leu Gln Gln Ile Ala Asn Arg
1               5                   10

<210> SEQ ID NO 1433
<211> LENGTH: 23
<212> TYPE: PRT
<213> ORGANISM: Homo sapiens

<400> SEQUENCE: 1433

Leu Glu Ser Glu Glu Asp Val Ser Gln Ala Phe Leu Glu Ala Val Ala
1               5                   10                  15

Glu Glu Lys Pro His Val Lys
            20

<210> SEQ ID NO 1434
<211> LENGTH: 25
<212> TYPE: PRT
<213> ORGANISM: Homo sapiens

<400> SEQUENCE: 1434

Leu Glu Ser Glu Glu Asp Val Ser Gln Ala Phe Leu Glu Ala Val Ala
1               5                   10                  15

Glu Glu Lys Pro His Val Lys Pro Tyr
            20                  25

<210> SEQ ID NO 1435
<211> LENGTH: 16
<212> TYPE: PRT
<213> ORGANISM: Homo sapiens

<400> SEQUENCE: 1435

Leu Glu Thr Met Ala Arg Asn Glu Val Ile Ala Asp Ile Asn Cys Lys
1               5                   10                  15

<210> SEQ ID NO 1436
<211> LENGTH: 19
<212> TYPE: PRT
<213> ORGANISM: Homo sapiens

<400> SEQUENCE: 1436

Leu Glu Tyr Asn Val Asp Ala Ala Asn Gly Ile Val Met Glu Gly Tyr
1               5                   10                  15

Leu Phe Lys

<210> SEQ ID NO 1437
<211> LENGTH: 32

<212> TYPE: PRT
<213> ORGANISM: Homo sapiens

<400> SEQUENCE: 1437

Leu Phe Pro Asn Ser Leu Asp Gln Thr Asp Met His Gly Asp Ser Glu
1 5 10 15

Tyr Asn Ile Met Phe Gly Pro Asp Ile Cys Gly Pro Gly Thr Lys Lys
20 25 30

<210> SEQ ID NO 1438
<211> LENGTH: 8
<212> TYPE: PRT
<213> ORGANISM: Homo sapiens

<400> SEQUENCE: 1438

Leu Gly Cys Thr Met Ser Met Arg
1 5

<210> SEQ ID NO 1439
<211> LENGTH: 18
<212> TYPE: PRT
<213> ORGANISM: Homo sapiens

<400> SEQUENCE: 1439

Leu Gly Ile Glu Lys Thr Asp Pro Thr Thr Leu Thr Asp Glu Glu Ile
1 5 10 15

Asn Arg

<210> SEQ ID NO 1440
<211> LENGTH: 14
<212> TYPE: PRT
<213> ORGANISM: Homo sapiens

<400> SEQUENCE: 1440

Leu Gly Ile Val Asn Val Asp Glu Ala Val Leu His Phe Lys
1 5 10

<210> SEQ ID NO 1441
<211> LENGTH: 16
<212> TYPE: PRT
<213> ORGANISM: Homo sapiens

<400> SEQUENCE: 1441

Leu Gly Tyr Thr Pro Leu Ile Val Ala Cys His Tyr Gly Asn Val Lys
1 5 10 15

<210> SEQ ID NO 1442
<211> LENGTH: 16
<212> TYPE: PRT
<213> ORGANISM: Homo sapiens

<400> SEQUENCE: 1442

Leu His Glu Met Gln Ile Gln His Pro Thr Ala Ser Leu Ile Ala Lys
1 5 10 15

<210> SEQ ID NO 1443
<211> LENGTH: 9
<212> TYPE: PRT
<213> ORGANISM: Homo sapiens

<400> SEQUENCE: 1443

Leu His Tyr Asn Glu Leu Gly Ala Lys
1 5

<210> SEQ ID NO 1444
<211> LENGTH: 17
<212> TYPE: PRT
<213> ORGANISM: Homo sapiens

<400> SEQUENCE: 1444

Leu Lys Ala Val Gln Ala Gln Gly Gly Glu Ser Gln Gln Glu Ala Gln
1 5 10 15

Arg

<210> SEQ ID NO 1445
<211> LENGTH: 17
<212> TYPE: PRT
<213> ORGANISM: Homo sapiens

<400> SEQUENCE: 1445

Leu Lys Glu Asp Met Lys Lys Ile Val Ala Val Pro Leu Asn Glu Gln
1 5 10 15

Lys

<210> SEQ ID NO 1446
<211> LENGTH: 10
<212> TYPE: PRT
<213> ORGANISM: Homo sapiens

<400> SEQUENCE: 1446

Leu Lys Glu Glu Glu Glu Asp Lys Lys Arg
1 5 10

<210> SEQ ID NO 1447
<211> LENGTH: 10
<212> TYPE: PRT
<213> ORGANISM: Homo sapiens

<400> SEQUENCE: 1447

Leu Lys Glu Leu Asn Asp Trp Leu Thr Lys
1 5 10

<210> SEQ ID NO 1448
<211> LENGTH: 10
<212> TYPE: PRT
<213> ORGANISM: Homo sapiens

<400> SEQUENCE: 1448

Leu Lys Leu Ser Phe Glu Glu Met Glu Arg
1 5 10

<210> SEQ ID NO 1449
<211> LENGTH: 10
<212> TYPE: PRT
<213> ORGANISM: Homo sapiens

<400> SEQUENCE: 1449

Leu Lys Leu Thr Phe Glu Glu Leu Glu Arg
1 5 10

<210> SEQ ID NO 1450
<211> LENGTH: 11
<212> TYPE: PRT
<213> ORGANISM: Homo sapiens

<400> SEQUENCE: 1450

Leu Lys Pro Glu Ile Gln Cys Val Ser Ala Lys 1 5 10

<210> SEQ ID NO 1451
<211> LENGTH: 14
<212> TYPE: PRT
<213> ORGANISM: Homo sapiens

<400> SEQUENCE: 1451

Leu Leu Glu Ala Thr Pro Thr Asp Ser Cys Gly Tyr Phe Arg
1 5 10

<210> SEQ ID NO 1452
<211> LENGTH: 14
<212> TYPE: PRT
<213> ORGANISM: Homo sapiens

<400> SEQUENCE: 1452

Leu Leu Glu Ala Thr Pro Thr Asp Ser Cys Gly Tyr Phe Arg
1 5 10

<210> SEQ ID NO 1453
<211> LENGTH: 10
<212> TYPE: PRT
<213> ORGANISM: Homo sapiens

<400> SEQUENCE: 1453

Leu Leu Lys Gly Glu Ser Ala Leu Gln Arg
1 5 10

<210> SEQ ID NO 1454
<211> LENGTH: 7
<212> TYPE: PRT
<213> ORGANISM: Homo sapiens

<400> SEQUENCE: 1454

Leu Leu Asn Glu Gly Gln Arg
1 5

<210> SEQ ID NO 1455
<211> LENGTH: 12
<212> TYPE: PRT
<213> ORGANISM: Homo sapiens

<400> SEQUENCE: 1455

Leu Asn Gly Phe Gln Leu Glu Asn Phe Thr Leu Lys
1 5 10

<210> SEQ ID NO 1456
<211> LENGTH: 6
<212> TYPE: PRT
<213> ORGANISM: Homo sapiens

<400> SEQUENCE: 1456

Leu Asn Lys Ile Leu Lys
1 5

<210> SEQ ID NO 1457
<211> LENGTH: 12
<212> TYPE: PRT
<213> ORGANISM: Homo sapiens

<400> SEQUENCE: 1457

Leu Asn Arg Glu Val Ala Glu Ser Pro Arg Pro Arg
1 5 10

<210> SEQ ID NO 1458
<211> LENGTH: 32
<212> TYPE: PRT
<213> ORGANISM: Homo sapiens

<400> SEQUENCE: 1458

Leu Pro Pro Ser Ser Pro Gln Lys Leu Ala Asp Val Ala Ala Pro Pro
1 5 10 15

Gly Gly Pro Pro Pro Pro His Ser Pro Tyr Ser Gly Pro Pro Ser Arg
20 25 30

<210> SEQ ID NO 1459
<211> LENGTH: 29
<212> TYPE: PRT
<213> ORGANISM: Homo sapiens

<400> SEQUENCE: 1459

Leu Gln Asp Ala Phe Ser Ala Ile Gly Gln Asn Ala Asp Leu Asp Leu
1 5 10 15

Pro Gln Ile Ala Val Val Gly Gly Gln Ser Ala Gly Lys
20 25

<210> SEQ ID NO 1460
<211> LENGTH: 18
<212> TYPE: PRT
<213> ORGANISM: Homo sapiens

<400> SEQUENCE: 1460

Leu Gln Glu Leu Glu Gly Thr Tyr Glu Glu Asn Glu Arg Ala Leu Glu
1 5 10 15

Ser Lys

<210> SEQ ID NO 1461
<211> LENGTH: 22
<212> TYPE: PRT
<213> ORGANISM: Homo sapiens

<400> SEQUENCE: 1461

Leu Gln Gln Gln Cys Asp Asp Tyr Gly Ser Ser Tyr Leu Gly Val Ile
1 5 10 15

Glu Leu Ile Gly Glu Lys
20

<210> SEQ ID NO 1462
<211> LENGTH: 37
<212> TYPE: PRT
<213> ORGANISM: Homo sapiens

<400> SEQUENCE: 1462

Leu Ser Ala His Thr His Thr Leu Ser Leu Thr Asp Ile Asn Glu Leu
1 5 10 15

Val Cys Gly Ala Pro Gly Asp Ala Pro Cys Ala Thr Ser Pro Cys Gly
20 25 30

Gly Ala Gly Cys Arg
35

<210> SEQ ID NO 1463
<211> LENGTH: 11
<212> TYPE: PRT
<213> ORGANISM: Homo sapiens

<400> SEQUENCE: 1463

Leu Ser Phe Glu Glu Met Glu Arg Gln Arg Arg
1 5 10

<210> SEQ ID NO 1464
<211> LENGTH: 13
<212> TYPE: PRT
<213> ORGANISM: Homo sapiens

<400> SEQUENCE: 1464

Leu Ser Gly Trp Leu Ala Gln Gln Glu Asp Ala His Arg
1 5 10

<210> SEQ ID NO 1465
<211> LENGTH: 14
<212> TYPE: PRT
<213> ORGANISM: Homo sapiens

<400> SEQUENCE: 1465

Leu Ser His Phe Glu Tyr Val Lys Asn Glu Asp Leu Glu Lys
1 5 10

<210> SEQ ID NO 1466
<211> LENGTH: 14
<212> TYPE: PRT
<213> ORGANISM: Homo sapiens

<400> SEQUENCE: 1466

Leu Ser Ile Pro Gln Leu Ser Val Thr Asp Tyr Glu Ile Met
1 5 10

<210> SEQ ID NO 1467
<211> LENGTH: 17
<212> TYPE: PRT
<213> ORGANISM: Homo sapiens

<400> SEQUENCE: 1467

Leu Ser Ile Pro Gln Leu Ser Val Thr Asp Tyr Glu Ile Met Glu Gln
1 5 10 15

Arg

<210> SEQ ID NO 1468
<211> LENGTH: 23
<212> TYPE: PRT
<213> ORGANISM: Homo sapiens

<400> SEQUENCE: 1468

Leu Ser Pro Ala Tyr Ser Leu Gly Ser Leu Thr Gly Ala Ser Pro Cys
1 5 10 15

Gln Ser Pro Cys Val Gln Arg
20

<210> SEQ ID NO 1469
<211> LENGTH: 14
<212> TYPE: PRT
<213> ORGANISM: Homo sapiens

<400> SEQUENCE: 1469

Leu Ser Ser Gly Gly Gly Ser Ser Ser Glu Thr Val Gly Arg
1 5 10

<210> SEQ ID NO 1470
<211> LENGTH: 21
<212> TYPE: PRT

<213> ORGANISM: Homo sapiens

<400> SEQUENCE: 1470

Leu Thr Glu Glu Gln Cys Leu Phe Ser Ala Trp Leu Ser Glu Lys Glu
1 5 10 15

Asp Ala Val Asn Lys
20

<210> SEQ ID NO 1471
<211> LENGTH: 15
<212> TYPE: PRT
<213> ORGANISM: Homo sapiens

<400> SEQUENCE: 1471

Leu Val Ala Ala Gly Gly Leu Asp Ala Val Leu Tyr Trp Cys Arg
1 5 10 15

<210> SEQ ID NO 1472
<211> LENGTH: 12
<212> TYPE: PRT
<213> ORGANISM: Homo sapiens

<400> SEQUENCE: 1472

Leu Val Glu Phe Ser Ala Phe Leu Glu Gln Gln Arg
1 5 10

<210> SEQ ID NO 1473
<211> LENGTH: 9
<212> TYPE: PRT
<213> ORGANISM: Homo sapiens

<400> SEQUENCE: 1473

Leu Val Pro Ser Val Asn Gly Val Arg
1 5

<210> SEQ ID NO 1474
<211> LENGTH: 18
<212> TYPE: PRT
<213> ORGANISM: Homo sapiens

<400> SEQUENCE: 1474

Leu Val Thr Pro His Gly Glu Ser Glu Gln Ile Gly Val Ile Pro Ser
1 5 10 15

Lys Lys

<210> SEQ ID NO 1475
<211> LENGTH: 31
<212> TYPE: PRT
<213> ORGANISM: Homo sapiens

<400> SEQUENCE: 1475

Leu Val Val Thr Gln Glu Asp Val Glu Leu Ala Tyr Gln Glu Ala Met
1 5 10 15

Met Asn Met Ala Arg Leu Asn Arg Thr Ala Ala Gly Leu Met His
20 25 30

<210> SEQ ID NO 1476
<211> LENGTH: 12
<212> TYPE: PRT
<213> ORGANISM: Homo sapiens

<400> SEQUENCE: 1476

Met Ala Ala Ala Glu Ala Gly Gly Asp Asp Ala Arg 1 5 10

<210> SEQ ID NO 1477
<211> LENGTH: 14
<212> TYPE: PRT
<213> ORGANISM: Homo sapiens

<400> SEQUENCE: 1477

Met Ala Val Trp Glu Ala Glu Gln Leu Gly Gly Leu Gln Arg
1 5 10

<210> SEQ ID NO 1478
<211> LENGTH: 7
<212> TYPE: PRT
<213> ORGANISM: Homo sapiens

<400> SEQUENCE: 1478

Met Glu Ala Leu Glu Asn Arg
1 5

<210> SEQ ID NO 1479
<211> LENGTH: 10
<212> TYPE: PRT
<213> ORGANISM: Homo sapiens

<400> SEQUENCE: 1479

Met Glu Phe Asp Glu Lys Glu Leu Arg Arg
1 5 10

<210> SEQ ID NO 1480
<211> LENGTH: 25
<212> TYPE: PRT
<213> ORGANISM: Homo sapiens

<400> SEQUENCE: 1480

Met Glu Ser Gly Arg Gly Ser Ser Thr Pro Pro Gly Pro Ile Ala Ala
1 5 10 15

Leu Gly Met Pro Asp Thr Gly Pro Gly
20 25

<210> SEQ ID NO 1481
<211> LENGTH: 31
<212> TYPE: PRT
<213> ORGANISM: Homo sapiens

<400> SEQUENCE: 1481

Met Glu Ser Gly Arg Gly Ser Ser Thr Pro Pro Gly Pro Ile Ala Ala
1 5 10 15

Leu Gly Met Pro Asp Thr Gly Pro Gly Ser Ser Ser Leu Gly Lys
20 25 30

<210> SEQ ID NO 1482
<211> LENGTH: 6
<212> TYPE: PRT
<213> ORGANISM: Homo sapiens

<400> SEQUENCE: 1482

Met Glu Ser Gln Leu Lys
1 5

<210> SEQ ID NO 1483
<211> LENGTH: 11
<212> TYPE: PRT
<213> ORGANISM: Homo sapiens

<400> SEQUENCE: 1483

Met Gly Met Ser Phe Gly Leu Glu Ser Gly Lys
1 5 10

<210> SEQ ID NO 1484
<211> LENGTH: 20
<212> TYPE: PRT
<213> ORGANISM: Homo sapiens

<400> SEQUENCE: 1484

Met Gly Asn Ala Ala Gly Ser Ala Glu Gln Pro Ala Gly Pro Ala Ala
1 5 10 15

Pro Pro Pro Lys
20

<210> SEQ ID NO 1485
<211> LENGTH: 34
<212> TYPE: PRT
<213> ORGANISM: Homo sapiens

<400> SEQUENCE: 1485

Met Ile Ile Ser Thr Pro Gln Arg Leu Thr Ser Ser Gly Ser Val Leu
1 5 10 15

Ile Gly Ser Pro Tyr Thr Pro Ala Pro Ala Met Val Thr Gln Thr His
20 25 30

Ile Ala

<210> SEQ ID NO 1486
<211> LENGTH: 9
<212> TYPE: PRT
<213> ORGANISM: Homo sapiens

<400> SEQUENCE: 1486

Met Ile Leu Thr Asn Pro Glu Gly Arg
1 5

<210> SEQ ID NO 1487
<211> LENGTH: 14
<212> TYPE: PRT
<213> ORGANISM: Homo sapiens

<400> SEQUENCE: 1487

Met Lys Ala Ala Lys Ser Gly Thr Lys Asp Gly Leu Glu Lys
1 5 10

<210> SEQ ID NO 1488
<211> LENGTH: 15
<212> TYPE: PRT
<213> ORGANISM: Homo sapiens

<400> SEQUENCE: 1488

Met Leu Glu Asp Leu Gly Phe Lys Asp Leu Thr Leu Gln Pro Arg
1 5 10 15

<210> SEQ ID NO 1489
<211> LENGTH: 8
<212> TYPE: PRT
<213> ORGANISM: Homo sapiens

<400> SEQUENCE: 1489

Met Asn Ser Leu Thr Leu Asn Arg
1 5

<210> SEQ ID NO 1490
<211> LENGTH: 13
<212> TYPE: PRT
<213> ORGANISM: Homo sapiens

<400> SEQUENCE: 1490

Met Ser Asp Lys Ser Asp Leu Lys Ala Glu Leu Glu Arg
1 5 10

<210> SEQ ID NO 1491
<211> LENGTH: 32
<212> TYPE: PRT
<213> ORGANISM: Homo sapiens

<400> SEQUENCE: 1491

Met Ser Gly Ser Ser Gly Gly Ala Ala Ala Pro Ala Ala Ser Ser Gly
1 5 10 15

Pro Ala Ala Ala Ala Ser Ala Ala Gly Ser Gly Cys Gly Gly Gly Ala
20 25 30

<210> SEQ ID NO 1492
<211> LENGTH: 11
<212> TYPE: PRT
<213> ORGANISM: Homo sapiens

<400> SEQUENCE: 1492

Met Ser Lys Ser Leu Gly Asn Val Ile His Pro
1 5 10

<210> SEQ ID NO 1493
<211> LENGTH: 11
<212> TYPE: PRT
<213> ORGANISM: Homo sapiens

<400> SEQUENCE: 1493

Met Val Ser Thr Ser Ala Thr Asp Glu Pro Arg
1 5 10

<210> SEQ ID NO 1494
<211> LENGTH: 31
<212> TYPE: PRT
<213> ORGANISM: Homo sapiens

<400> SEQUENCE: 1494

Asn Ala Asn Ser Ser Pro Val Ala Ser Thr Thr Pro Ser Ala Ser Ala
1 5 10 15

Thr Thr Asn Pro Ala Ser Ala Thr Thr Leu Asp Gln Ser Lys Ala
20 25 30

<210> SEQ ID NO 1495
<211> LENGTH: 12
<212> TYPE: PRT
<213> ORGANISM: Homo sapiens

<400> SEQUENCE: 1495

Asn Ala Thr Leu Val Asn Glu Ala Asp Lys Leu Arg
1 5 10

<210> SEQ ID NO 1496
<211> LENGTH: 20
<212> TYPE: PRT
<213> ORGANISM: Homo sapiens

<400> SEQUENCE: 1496

Asn Ala Val Leu Glu His Met Glu Glu Leu Gln Glu Gln Val Ala Leu
1               5                   10                  15

Leu Thr Glu Arg
            20

<210> SEQ ID NO 1497
<211> LENGTH: 29
<212> TYPE: PRT
<213> ORGANISM: Homo sapiens

<400> SEQUENCE: 1497

Asn Asp Lys Ser Tyr Trp Leu Ser Thr Thr Ala Pro Leu Pro Met Met
1               5                   10                  15

Pro Val Ala Glu Asp Glu Ile Lys Pro Tyr Ile Ser Arg
            20                  25

<210> SEQ ID NO 1498
<211> LENGTH: 14
<212> TYPE: PRT
<213> ORGANISM: Homo sapiens

<400> SEQUENCE: 1498

Asn Phe Val Lys Glu Ala Glu Glu Ile Ser Ser Asn Arg Arg
1               5                   10

<210> SEQ ID NO 1499
<211> LENGTH: 14
<212> TYPE: PRT
<213> ORGANISM: Homo sapiens

<400> SEQUENCE: 1499

Asn Ile Leu Val Ser Asp Met Glu Met Asn Glu Gln Gln Glu
1               5                   10

<210> SEQ ID NO 1500
<211> LENGTH: 12
<212> TYPE: PRT
<213> ORGANISM: Homo sapiens

<400> SEQUENCE: 1500

Asn Leu Ala Ala Thr Leu Gln Asp Ile Glu Thr Lys
1               5                   10

<210> SEQ ID NO 1501
<211> LENGTH: 17
<212> TYPE: PRT
<213> ORGANISM: Homo sapiens

<400> SEQUENCE: 1501

Asn Leu Glu Glu Leu Tyr Leu Val Gly Ser Leu Ser His Asp Ile Ser
1               5                   10                  15

Arg

<210> SEQ ID NO 1502
<211> LENGTH: 27
<212> TYPE: PRT
<213> ORGANISM: Homo sapiens

<400> SEQUENCE: 1502

Asn Leu Leu Glu Val Ser Glu Val Glu Gln Glu Leu Ala Cys Gln Asn
1               5                   10                  15

Asp His Ser Ser Ala Leu Gln Asn Ile Lys Arg
20 25

<210> SEQ ID NO 1503
<211> LENGTH: 22
<212> TYPE: PRT
<213> ORGANISM: Homo sapiens

<400> SEQUENCE: 1503

Asn Leu Val Gly Ser Gly Ser Glu Ile Gln Phe Leu Ser Glu Ala Gln
1 5 10 15

Asp Asp Pro Gln Lys Arg
20

<210> SEQ ID NO 1504
<211> LENGTH: 9
<212> TYPE: PRT
<213> ORGANISM: Homo sapiens

<400> SEQUENCE: 1504

Asn Arg Thr Glu Ala Glu Val Lys Arg
1 5

<210> SEQ ID NO 1505
<211> LENGTH: 9
<212> TYPE: PRT
<213> ORGANISM: Homo sapiens

<400> SEQUENCE: 1505

Asn Ser Leu Ser Val Leu Ser Pro Lys
1 5

<210> SEQ ID NO 1506
<211> LENGTH: 19
<212> TYPE: PRT
<213> ORGANISM: Homo sapiens

<400> SEQUENCE: 1506

Asn Thr Ser Ala Ala Ser Thr Ala Gln Leu Val Glu Ala Thr Glu Glu
1 5 10 15

Leu Arg Arg

<210> SEQ ID NO 1507
<211> LENGTH: 12
<212> TYPE: PRT
<213> ORGANISM: Homo sapiens

<400> SEQUENCE: 1507

Asn Val Gln Val Phe Leu Ile Ser Gly Gly Phe Arg
1 5 10

<210> SEQ ID NO 1508
<211> LENGTH: 17
<212> TYPE: PRT
<213> ORGANISM: Homo sapiens

<400> SEQUENCE: 1508

Asn Tyr Pro Ser Ser Leu Cys Ala Leu Cys Val Gly Asp Glu Gln Gly
1 5 10 15

Arg

<210> SEQ ID NO 1509
<211> LENGTH: 12

<212> TYPE: PRT
<213> ORGANISM: Homo sapiens

<400> SEQUENCE: 1509

Pro Cys Pro Cys Pro Glu Gly Pro Gly Ser Gln Arg
1 5 10

<210> SEQ ID NO 1510
<211> LENGTH: 10
<212> TYPE: PRT
<213> ORGANISM: Homo sapiens

<400> SEQUENCE: 1510

Pro Cys Gln Asp Val Asp Glu Cys Ala Arg
1 5 10

<210> SEQ ID NO 1511
<211> LENGTH: 15
<212> TYPE: PRT
<213> ORGANISM: Homo sapiens

<400> SEQUENCE: 1511

Pro Asp Glu Asn Leu Lys Ser Ala Ser Lys Glu Glu Leu Lys Lys
1 5 10 15

<210> SEQ ID NO 1512
<211> LENGTH: 19
<212> TYPE: PRT
<213> ORGANISM: Homo sapiens

<400> SEQUENCE: 1512

Pro Glu Ala Tyr Gln Val Pro Ala Ser Tyr Gln Pro Asp Glu Glu Glu
1 5 10 15

Arg Ala Arg

<210> SEQ ID NO 1513
<211> LENGTH: 9
<212> TYPE: PRT
<213> ORGANISM: Homo sapiens

<400> SEQUENCE: 1513

Pro Glu Gly Glu Met Lys Pro Gly Arg
1 5

<210> SEQ ID NO 1514
<211> LENGTH: 20
<212> TYPE: PRT
<213> ORGANISM: Homo sapiens

<400> SEQUENCE: 1514

Pro Glu Thr Pro Tyr Ser Gly Pro Gly Leu Leu Ile Asp Ser Leu Val
1 5 10 15

Leu Leu Pro Arg
20

<210> SEQ ID NO 1515
<211> LENGTH: 7
<212> TYPE: PRT
<213> ORGANISM: Homo sapiens

<400> SEQUENCE: 1515

Pro Glu Val Val Trp Phe Lys
1 5

<210> SEQ ID NO 1516
<211> LENGTH: 16
<212> TYPE: PRT
<213> ORGANISM: Homo sapiens

<400> SEQUENCE: 1516

```
Pro Gly Ala Gly Ala Val Glu Val Ala Met Ala Glu Ala Leu Ile Lys
1               5                   10                  15
```

<210> SEQ ID NO 1517
<211> LENGTH: 21
<212> TYPE: PRT
<213> ORGANISM: Homo sapiens

<400> SEQUENCE: 1517

```
Pro Gly Glu Met Gly Pro Gln Gly Pro Pro Gly Glu Pro Gly Phe Arg
1               5                   10                  15

Gly Ala Pro Gly Lys
            20
```

<210> SEQ ID NO 1518
<211> LENGTH: 14
<212> TYPE: PRT
<213> ORGANISM: Homo sapiens

<400> SEQUENCE: 1518

```
Pro Gly Glu Thr Pro Ser Trp Thr Gly Ser Gly Phe Val Arg
1               5                   10
```

<210> SEQ ID NO 1519
<211> LENGTH: 9
<212> TYPE: PRT
<213> ORGANISM: Homo sapiens

<400> SEQUENCE: 1519

```
Pro Gly Phe His Gly Gln Ala Ala Arg
1               5
```

<210> SEQ ID NO 1520
<211> LENGTH: 25
<212> TYPE: PRT
<213> ORGANISM: Homo sapiens

<400> SEQUENCE: 1520

```
Pro Gly His Val Gly Gln Met Gly Pro Val Gly Ala Pro Gly Arg Pro
1               5                   10                  15

Gly Pro Pro Gly Pro Pro Gly Pro Lys
            20                  25
```

<210> SEQ ID NO 1521
<211> LENGTH: 18
<212> TYPE: PRT
<213> ORGANISM: Homo sapiens

<400> SEQUENCE: 1521

```
Pro Ile Leu Pro His Leu Ala Glu Glu Val Phe Gln His Ile Pro Tyr
1               5                   10                  15

Ile Lys
```

<210> SEQ ID NO 1522
<211> LENGTH: 19
<212> TYPE: PRT
<213> ORGANISM: Homo sapiens

<400> SEQUENCE: 1522

Pro Lys Ile Asp Asp Val Leu His Thr Leu Thr Gly Ala Met Ser Leu
1 5 10 15

Leu Arg Arg

<210> SEQ ID NO 1523
<211> LENGTH: 16
<212> TYPE: PRT
<213> ORGANISM: Homo sapiens

<400> SEQUENCE: 1523

Pro Lys Met Leu Val Ile Ser Gly Gly Asp Gly Tyr Glu Asp Phe Arg
1 5 10 15

<210> SEQ ID NO 1524
<211> LENGTH: 21
<212> TYPE: PRT
<213> ORGANISM: Homo sapiens

<400> SEQUENCE: 1524

Pro Pro Asp Ile Asp Lys Thr Glu Leu Val Glu Pro Thr Glu Tyr Leu
1 5 10 15

Val Val His Leu Lys
20

<210> SEQ ID NO 1525
<211> LENGTH: 10
<212> TYPE: PRT
<213> ORGANISM: Homo sapiens

<400> SEQUENCE: 1525

Pro Pro Lys Pro Ala Thr Pro Asp Phe Arg
1 5 10

<210> SEQ ID NO 1526
<211> LENGTH: 10
<212> TYPE: PRT
<213> ORGANISM: Homo sapiens

<400> SEQUENCE: 1526

Pro Pro Val Ile Gln Asn Pro Glu Tyr Lys
1 5 10

<210> SEQ ID NO 1527
<211> LENGTH: 13
<212> TYPE: PRT
<213> ORGANISM: Homo sapiens

<400> SEQUENCE: 1527

Pro Pro Val Leu Gly Thr Glu Ser Asp Ala Thr Val Lys
1 5 10

<210> SEQ ID NO 1528
<211> LENGTH: 10
<212> TYPE: PRT
<213> ORGANISM: Homo sapiens

<400> SEQUENCE: 1528

Pro Gln Leu Leu Gly Val Ala Pro Glu Lys
1 5 10

<210> SEQ ID NO 1529

<211> LENGTH: 13
<212> TYPE: PRT
<213> ORGANISM: Homo sapiens

<400> SEQUENCE: 1529

Pro Arg Met Ser Ala Gln Glu Gln Leu Glu Arg Met Arg
1 5 10

<210> SEQ ID NO 1530
<211> LENGTH: 19
<212> TYPE: PRT
<213> ORGANISM: Homo sapiens

<400> SEQUENCE: 1530

Pro Ser Gly Pro Ala Thr Ala Glu Asp Pro Gly Arg Arg Pro Val Leu
1 5 10 15

Pro Gln Arg

<210> SEQ ID NO 1531
<211> LENGTH: 14
<212> TYPE: PRT
<213> ORGANISM: Homo sapiens

<400> SEQUENCE: 1531

Pro Thr Pro Arg Pro Val Pro Met Lys Arg His Ile Phe Arg
1 5 10

<210> SEQ ID NO 1532
<211> LENGTH: 9
<212> TYPE: PRT
<213> ORGANISM: Homo sapiens

<400> SEQUENCE: 1532

Pro Val Ala Gly Ser Glu Leu Pro Arg
1 5

<210> SEQ ID NO 1533
<211> LENGTH: 7
<212> TYPE: PRT
<213> ORGANISM: Homo sapiens

<400> SEQUENCE: 1533

Pro Tyr Trp Cys Ile Ser Arg
1 5

<210> SEQ ID NO 1534
<211> LENGTH: 9
<212> TYPE: PRT
<213> ORGANISM: Homo sapiens

<400> SEQUENCE: 1534

Gln Ala Ala Ser Pro Leu Glu Pro Lys
1 5

<210> SEQ ID NO 1535
<211> LENGTH: 11
<212> TYPE: PRT
<213> ORGANISM: Homo sapiens

<400> SEQUENCE: 1535

Gln Ala Glu Glu Val Asn Thr Glu Trp Glu Lys
1 5 10

<210> SEQ ID NO 1536

<211> LENGTH: 23
<212> TYPE: PRT
<213> ORGANISM: Homo sapiens

<400> SEQUENCE: 1536

Gln Ala Glu Gly Leu Ser Glu Asp Gly Ala Ala Met Ala Val Glu Pro
1 5 10 15

Thr Gln Ile Gln Leu Ser Lys
20

<210> SEQ ID NO 1537
<211> LENGTH: 13
<212> TYPE: PRT
<213> ORGANISM: Homo sapiens

<400> SEQUENCE: 1537

Gln Ala Pro Ser Ser Phe Gln Leu Leu Tyr Asp Leu Lys
1 5 10

<210> SEQ ID NO 1538
<211> LENGTH: 16
<212> TYPE: PRT
<213> ORGANISM: Homo sapiens

<400> SEQUENCE: 1538

Gln Ala Gln Leu Glu Lys Glu Leu Ser Ala Ala Leu Gln Asp Lys Lys
1 5 10 15

<210> SEQ ID NO 1539
<211> LENGTH: 13
<212> TYPE: PRT
<213> ORGANISM: Homo sapiens

<400> SEQUENCE: 1539

Gln Ala Gln Val Asn Leu Thr Val Val Asp Lys Pro Asp
1 5 10

<210> SEQ ID NO 1540
<211> LENGTH: 15
<212> TYPE: PRT
<213> ORGANISM: Homo sapiens

<400> SEQUENCE: 1540

Gln Asp Cys Asp Gln Ala Leu Gln Leu Ala Asp Gly Asn Val Lys
1 5 10 15

<210> SEQ ID NO 1541
<211> LENGTH: 14
<212> TYPE: PRT
<213> ORGANISM: Homo sapiens

<400> SEQUENCE: 1541

Gln Glu Met Val Ile Glu Val Lys Ala Ile Gly Gly Lys Lys
1 5 10

<210> SEQ ID NO 1542
<211> LENGTH: 32
<212> TYPE: PRT
<213> ORGANISM: Homo sapiens

<400> SEQUENCE: 1542

Gln Glu Thr Pro Pro Pro Arg Ser Pro Pro Val Ala Asn Ser Gly Ser
1 5 10 15

Thr Gly Phe Ser Arg Arg Gly Ser Gly Arg Gly Gly Gly Pro Thr Pro 20 25 30

<210> SEQ ID NO 1543
<211> LENGTH: 10
<212> TYPE: PRT
<213> ORGANISM: Homo sapiens

<400> SEQUENCE: 1543

Gln Gly Pro Met Thr Gln Ala Ile Asn Arg
1 5 10

<210> SEQ ID NO 1544
<211> LENGTH: 15
<212> TYPE: PRT
<213> ORGANISM: Homo sapiens

<400> SEQUENCE: 1544

Gln His Glu Val Glu Glu Ala Thr Asn Ile Leu Thr Ala Thr Arg
1 5 10 15

<210> SEQ ID NO 1545
<211> LENGTH: 15
<212> TYPE: PRT
<213> ORGANISM: Homo sapiens

<400> SEQUENCE: 1545

Gln Ile Ala Ser Leu Thr Gly Leu Val Gln Ser Ala Leu Leu Arg
1 5 10 15

<210> SEQ ID NO 1546
<211> LENGTH: 9
<212> TYPE: PRT
<213> ORGANISM: Homo sapiens

<400> SEQUENCE: 1546

Gln Ile Cys Ser Gln Leu Ser Glu Arg
1 5

<210> SEQ ID NO 1547
<211> LENGTH: 9
<212> TYPE: PRT
<213> ORGANISM: Homo sapiens

<400> SEQUENCE: 1547

Gln Lys Ala Ser Gly Asp Ser Ala Arg
1 5

<210> SEQ ID NO 1548
<211> LENGTH: 14
<212> TYPE: PRT
<213> ORGANISM: Homo sapiens

<400> SEQUENCE: 1548

Gln Lys Met Glu Glu Glu Lys Arg Arg Thr Glu Glu Glu Arg
1 5 10

<210> SEQ ID NO 1549
<211> LENGTH: 16
<212> TYPE: PRT
<213> ORGANISM: Homo sapiens

<400> SEQUENCE: 1549

Gln Leu Glu Leu Ala Cys Glu Thr Gln Glu Glu Val Asp Ser Trp Lys
1 5 10 15

<210> SEQ ID NO 1550
<211> LENGTH: 26
<212> TYPE: PRT
<213> ORGANISM: Homo sapiens

<400> SEQUENCE: 1550

Gln Leu Asn Glu Thr Gly Gly Pro Val Leu Val Ser Ala Pro Ile Ser
1 5 10 15

Pro Glu Glu Gln Asp Lys Leu Glu Asn Lys
20 25

<210> SEQ ID NO 1551
<211> LENGTH: 15
<212> TYPE: PRT
<213> ORGANISM: Homo sapiens

<400> SEQUENCE: 1551

Gln Leu Pro Lys Pro Asn Gln Asp Thr Met Gln Ile Leu Phe Arg
1 5 10 15

<210> SEQ ID NO 1552
<211> LENGTH: 8
<212> TYPE: PRT
<213> ORGANISM: Homo sapiens

<400> SEQUENCE: 1552

Gln Leu Gln Thr Leu Ala Pro Lys
1 5

<210> SEQ ID NO 1553
<211> LENGTH: 14
<212> TYPE: PRT
<213> ORGANISM: Homo sapiens

<400> SEQUENCE: 1553

Gln Asn Gly Asp Ser Ala Tyr Leu Tyr Leu Leu Ser Ala Arg
1 5 10

<210> SEQ ID NO 1554
<211> LENGTH: 10
<212> TYPE: PRT
<213> ORGANISM: Homo sapiens

<400> SEQUENCE: 1554

Gln Pro Asp Val Glu Glu Ile Leu Ser Lys
1 5 10

<210> SEQ ID NO 1555
<211> LENGTH: 26
<212> TYPE: PRT
<213> ORGANISM: Homo sapiens

<400> SEQUENCE: 1555

Gln Gln Asn Leu Ala Val Ser Glu Ser Pro Val Thr Pro Ser Ala Leu
1 5 10 15

Ala Glu Leu Leu Asp Leu Leu Asp Ser Arg
20 25

<210> SEQ ID NO 1556
<211> LENGTH: 12
<212> TYPE: PRT
<213> ORGANISM: Homo sapiens

<400> SEQUENCE: 1556

Gln Gln Gln Met His Ile Val Asp Met Leu Ser Lys
1 5 10

<210> SEQ ID NO 1557
<211> LENGTH: 13
<212> TYPE: PRT
<213> ORGANISM: Homo sapiens

<400> SEQUENCE: 1557

Gln Ser Ser His Asn Phe Gln Leu Glu Ser Val Asn Lys
1 5 10

<210> SEQ ID NO 1558
<211> LENGTH: 16
<212> TYPE: PRT
<213> ORGANISM: Homo sapiens

<400> SEQUENCE: 1558

Gln Thr Leu Leu Ala Glu Ser Glu Ala Leu Thr Ser Tyr Ser His Arg
1 5 10 15

<210> SEQ ID NO 1559
<211> LENGTH: 25
<212> TYPE: PRT
<213> ORGANISM: Homo sapiens

<400> SEQUENCE: 1559

Gln Thr Ser Val Ala Asp Leu Leu Ala Ser Phe Asn Asp Gln Ser Thr
1 5 10 15

Ser Asp Tyr Leu Val Val Tyr Leu Arg
20 25

<210> SEQ ID NO 1560
<211> LENGTH: 27
<212> TYPE: PRT
<213> ORGANISM: Homo sapiens

<400> SEQUENCE: 1560

Gln Val Phe Gly Gln Thr Thr Ile His Gln His Ile Pro Phe Asn Trp
1 5 10 15

Asp Ser Glu Phe Val Gln Leu His Phe Gly Lys
20 25

<210> SEQ ID NO 1561
<211> LENGTH: 8
<212> TYPE: PRT
<213> ORGANISM: Homo sapiens

<400> SEQUENCE: 1561

Gln Val Val Gln Asp Leu Leu Lys
1 5

<210> SEQ ID NO 1562
<211> LENGTH: 29
<212> TYPE: PRT
<213> ORGANISM: Homo sapiens

<400> SEQUENCE: 1562

Arg Ala Ser Ala Ala Ala Ala Ala Gly Gly Gly Ala Thr Gly His Pro
1 5 10 15

Gly Gly Gly Gln Gly Ala Glu Asn Pro Ala Gly Leu Lys
20 25

<210> SEQ ID NO 1563
<211> LENGTH: 34
<212> TYPE: PRT
<213> ORGANISM: Homo sapiens

<400> SEQUENCE: 1563

Arg Cys Asp Leu Cys Ala Pro Gly Tyr Tyr Gly Phe Gly Pro Thr Gly
1 5 10 15

Cys Gln Ala Cys Gln Cys Ser His Glu Gly Ala Leu Ser Ser Leu Cys
20 25 30

Glu Lys

<210> SEQ ID NO 1564
<211> LENGTH: 11
<212> TYPE: PRT
<213> ORGANISM: Homo sapiens

<400> SEQUENCE: 1564

Arg Cys Glu Gln Val Gln Pro Gly Tyr Phe Arg
1 5 10

<210> SEQ ID NO 1565
<211> LENGTH: 16
<212> TYPE: PRT
<213> ORGANISM: Homo sapiens

<400> SEQUENCE: 1565

Arg Asp Asn Glu Val Asp Gly Gln Asp Tyr His Phe Val Val Ser Arg
1 5 10 15

<210> SEQ ID NO 1566
<211> LENGTH: 32
<212> TYPE: PRT
<213> ORGANISM: Homo sapiens

<400> SEQUENCE: 1566

Arg Asp Pro Ser Ser Asn Asp Ile Asn Gly Gly Met Glu Pro Thr Pro
1 5 10 15

Ser Thr Val Ser Thr Pro Ser Pro Ser Ala Asp Leu Leu Gly Leu Arg
20 25 30

<210> SEQ ID NO 1567
<211> LENGTH: 16
<212> TYPE: PRT
<213> ORGANISM: Homo sapiens

<400> SEQUENCE: 1567

Arg Glu Met Ala Ala Ala Ser Ala Ala Ala Ile Ser Gly Ala Gly Arg
1 5 10 15

<210> SEQ ID NO 1568
<211> LENGTH: 29
<212> TYPE: PRT
<213> ORGANISM: Homo sapiens

<400> SEQUENCE: 1568

Arg Glu Thr Leu Phe Thr Leu Asp Asp Gln Ala Leu Gly Pro Glu Leu
1 5 10 15

Thr Ala Pro Ala Pro Glu Pro Pro Ala Glu Glu Pro Arg
20 25

<210> SEQ ID NO 1569

<211> LENGTH: 15
<212> TYPE: PRT
<213> ORGANISM: Homo sapiens

<400> SEQUENCE: 1569

Arg Phe Ser Thr Glu Tyr Glu Leu Gln Gln Leu Glu Gln Phe Lys
1               5                   10                  15

<210> SEQ ID NO 1570
<211> LENGTH: 12
<212> TYPE: PRT
<213> ORGANISM: Homo sapiens

<400> SEQUENCE: 1570

Arg Gly Ser Asp Glu Leu Thr Val Pro Arg Tyr Arg
1               5                   10

<210> SEQ ID NO 1571
<211> LENGTH: 19
<212> TYPE: PRT
<213> ORGANISM: Homo sapiens

<400> SEQUENCE: 1571

Arg Ile Glu Gly Ser Gly Asp Gln Ile Asp Thr Tyr Glu Leu Ser Gly
1               5                   10                  15

Gly Ala Arg

<210> SEQ ID NO 1572
<211> LENGTH: 10
<212> TYPE: PRT
<213> ORGANISM: Homo sapiens

<400> SEQUENCE: 1572

Arg Lys Glu Glu Glu Glu Ala Glu Asp Lys
1               5                   10

<210> SEQ ID NO 1573
<211> LENGTH: 20
<212> TYPE: PRT
<213> ORGANISM: Homo sapiens

<400> SEQUENCE: 1573

Arg Leu Asp Ile Asp Glu Lys Pro Leu Val Val Gln Leu Asn Trp Asn
1               5                   10                  15

Lys Asp Asp Arg
            20

<210> SEQ ID NO 1574
<211> LENGTH: 22
<212> TYPE: PRT
<213> ORGANISM: Homo sapiens

<400> SEQUENCE: 1574

Arg Pro Pro Glu Pro Glu Lys Ala Pro Pro Ala Ala Pro Thr Arg Pro
1               5                   10                  15

Ser Ala Leu Glu Leu Lys
            20

<210> SEQ ID NO 1575
<211> LENGTH: 13
<212> TYPE: PRT
<213> ORGANISM: Homo sapiens

<400> SEQUENCE: 1575

Arg Pro Arg Pro Gln Gly Arg Ser Val Ser Glu Pro Arg
1 5 10

<210> SEQ ID NO 1576
<211> LENGTH: 24
<212> TYPE: PRT
<213> ORGANISM: Homo sapiens

<400> SEQUENCE: 1576

Arg Gln Ala Glu Gly Leu Ser Glu Asp Gly Ala Ala Met Ala Val Glu
1 5 10 15

Pro Thr Gln Ile Gln Leu Ser Lys
20

<210> SEQ ID NO 1577
<211> LENGTH: 24
<212> TYPE: PRT
<213> ORGANISM: Homo sapiens

<400> SEQUENCE: 1577

Arg Arg Lys Val Pro Pro Ser Gly Ser Gly Gly Ser Glu Leu Ser Asn
1 5 10 15

Gly Glu Ala Gly Glu Ala Tyr Arg
20

<210> SEQ ID NO 1578
<211> LENGTH: 14
<212> TYPE: PRT
<213> ORGANISM: Homo sapiens

<400> SEQUENCE: 1578

Arg Ser Leu Glu Leu Gln Thr Arg Thr Glu Glu Glu Lys Lys
1 5 10

<210> SEQ ID NO 1579
<211> LENGTH: 14
<212> TYPE: PRT
<213> ORGANISM: Homo sapiens

<400> SEQUENCE: 1579

Arg Ser Ser Tyr Leu Leu Ala Ile Thr Thr Glu Arg Ser Lys
1 5 10

<210> SEQ ID NO 1580
<211> LENGTH: 22
<212> TYPE: PRT
<213> ORGANISM: Homo sapiens

<400> SEQUENCE: 1580

Arg Val Ala Ala Gln Val Asp Gly Gly Ala Gln Val Gln Gln Val Leu
1 5 10 15

Asn Ile Glu Cys Leu Arg
20

<210> SEQ ID NO 1581
<211> LENGTH: 9
<212> TYPE: PRT
<213> ORGANISM: Homo sapiens

<400> SEQUENCE: 1581

Ser Ala Glu Glu Ser Asp Arg Leu Arg
1 5

<210> SEQ ID NO 1582
<211> LENGTH: 14
<212> TYPE: PRT
<213> ORGANISM: Homo sapiens

<400> SEQUENCE: 1582

Ser Cys Asp Cys Asp Pro Met Gly Ser Gln Asp Gly Gly Arg
1 5 10

<210> SEQ ID NO 1583
<211> LENGTH: 22
<212> TYPE: PRT
<213> ORGANISM: Homo sapiens

<400> SEQUENCE: 1583

Ser Asp Val Leu Glu Thr Val Val Leu Ile Asn Pro Ser Asp Glu Ala
1 5 10 15

Val Ser Thr Glu Val Arg
20

<210> SEQ ID NO 1584
<211> LENGTH: 13
<212> TYPE: PRT
<213> ORGANISM: Homo sapiens

<400> SEQUENCE: 1584

Ser Glu Asp Tyr Glu Leu Leu Cys Pro Asn Gly Ala Arg
1 5 10

<210> SEQ ID NO 1585
<211> LENGTH: 15
<212> TYPE: PRT
<213> ORGANISM: Homo sapiens

<400> SEQUENCE: 1585

Ser Phe Gly Ser Ser Leu Met Glu Ser Glu Val Asn Leu Asp Arg
1 5 10 15

<210> SEQ ID NO 1586
<211> LENGTH: 20
<212> TYPE: PRT
<213> ORGANISM: Homo sapiens

<400> SEQUENCE: 1586

Ser Gly His Asp Gln Val Val Glu Leu Leu Leu Glu Arg Gly Ala Pro
1 5 10 15

Leu Leu Ala Arg
20

<210> SEQ ID NO 1587
<211> LENGTH: 23
<212> TYPE: PRT
<213> ORGANISM: Homo sapiens

<400> SEQUENCE: 1587

Ser Gly Leu Thr Ser Leu His Leu Ala Ala Gln Glu Asp Lys Val Asn
1 5 10 15

Val Ala Asp Ile Leu Thr Lys
20

<210> SEQ ID NO 1588
<211> LENGTH: 18
<212> TYPE: PRT

<213> ORGANISM: Homo sapiens

<400> SEQUENCE: 1588

Ser Gly Arg Pro Ser Cys Leu Tyr Ser Ala Ala Arg Pro Ser Gly Ser
1 5 10 15

Tyr Arg

<210> SEQ ID NO 1589
<211> LENGTH: 15
<212> TYPE: PRT
<213> ORGANISM: Homo sapiens

<400> SEQUENCE: 1589

Ser Gly Thr Ile Phe Asp Asn Phe Leu Ile Thr Asn Asp Glu Ala
1 5 10 15

<210> SEQ ID NO 1590
<211> LENGTH: 18
<212> TYPE: PRT
<213> ORGANISM: Homo sapiens

<400> SEQUENCE: 1590

Ser Gly Thr Leu Ala Leu Val Glu Pro Leu Val Ala Ser Leu Asp Pro
1 5 10 15

Gly Arg

<210> SEQ ID NO 1591
<211> LENGTH: 25
<212> TYPE: PRT
<213> ORGANISM: Homo sapiens

<400> SEQUENCE: 1591

Ser Lys Ile Val Gly Ala Pro Met His Asp Leu Leu Leu Trp Asn Asn
1 5 10 15

Ala Thr Val Thr Thr Cys His Ser Lys
20 25

<210> SEQ ID NO 1592
<211> LENGTH: 9
<212> TYPE: PRT
<213> ORGANISM: Homo sapiens

<400> SEQUENCE: 1592

Ser Lys Pro Glu Asp Trp Asp Glu Arg
1 5

<210> SEQ ID NO 1593
<211> LENGTH: 26
<212> TYPE: PRT
<213> ORGANISM: Homo sapiens

<400> SEQUENCE: 1593

Ser Leu Glu Gly Ser Asp Asp Ala Val Leu Leu Gln Arg Arg Leu Asp
1 5 10 15

Asn Met Asn Phe Lys Trp Ser Glu Leu Arg
20 25

<210> SEQ ID NO 1594
<211> LENGTH: 11
<212> TYPE: PRT
<213> ORGANISM: Homo sapiens

<400> SEQUENCE: 1594

Ser Leu Asn Pro Glu Gln Trp Ser Gln Leu Lys
1 5 10

<210> SEQ ID NO 1595
<211> LENGTH: 27
<212> TYPE: PRT
<213> ORGANISM: Homo sapiens

<400> SEQUENCE: 1595

Ser Leu Ser Asp Pro Ser Arg Arg Gly Glu Leu Ala Gly Pro Gly Phe
1 5 10 15

Glu Gly Pro Gly Gly Glu Pro Ile Arg Glu Val
20 25

<210> SEQ ID NO 1596
<211> LENGTH: 14
<212> TYPE: PRT
<213> ORGANISM: Homo sapiens

<400> SEQUENCE: 1596

Ser Asn Arg Asp Glu Leu Glu Leu Glu Leu Ala Glu Asn Arg
1 5 10

<210> SEQ ID NO 1597
<211> LENGTH: 22
<212> TYPE: PRT
<213> ORGANISM: Homo sapiens

<400> SEQUENCE: 1597

Ser Pro Ala Arg Pro Gln Pro Gly Glu Gly Pro Gly Gly Pro Gly Gly
1 5 10 15

Pro Pro Glu Val Ser Arg
20

<210> SEQ ID NO 1598
<211> LENGTH: 22
<212> TYPE: PRT
<213> ORGANISM: Homo sapiens

<400> SEQUENCE: 1598

Ser Pro Ala Arg Pro Gln Pro Gly Glu Gly Pro Gly Gly Pro Gly Gly
1 5 10 15

Pro Pro Glu Val Ser Arg
20

<210> SEQ ID NO 1599
<211> LENGTH: 26
<212> TYPE: PRT
<213> ORGANISM: Homo sapiens

<400> SEQUENCE: 1599

Ser Pro Asp Thr Thr Leu Ser Pro Ala Ser Thr Thr Ser Ser Gly Val
1 5 10 15

Ser Glu Glu Ser Thr Thr Ser His Ser Arg
20 25

<210> SEQ ID NO 1600
<211> LENGTH: 26
<212> TYPE: PRT
<213> ORGANISM: Homo sapiens

<400> SEQUENCE: 1600

Ser Pro Asp Thr Thr Leu Ser Pro Ala Ser Thr Thr Ser Ser Gly Val
1 5 10 15

Ser Glu Glu Ser Thr Thr Ser His Ser Arg
20 25

<210> SEQ ID NO 1601
<211> LENGTH: 26
<212> TYPE: PRT
<213> ORGANISM: Homo sapiens

<400> SEQUENCE: 1601

Ser Pro Asp Thr Thr Leu Ser Pro Ala Ser Thr Thr Ser Ser Gly Val
1 5 10 15

Ser Glu Glu Ser Thr Thr Ser His Ser Arg
20 25

<210> SEQ ID NO 1602
<211> LENGTH: 14
<212> TYPE: PRT
<213> ORGANISM: Homo sapiens

<400> SEQUENCE: 1602

Ser Pro Phe Pro Ser Gln His Leu Glu Ala Pro Glu Asp Lys
1 5 10

<210> SEQ ID NO 1603
<211> LENGTH: 20
<212> TYPE: PRT
<213> ORGANISM: Homo sapiens

<400> SEQUENCE: 1603

Ser Pro Gly Pro Pro Gln Val Asp Gly Thr Pro Thr Met Ser Leu Glu
1 5 10 15

Arg Pro Pro Arg
20

<210> SEQ ID NO 1604
<211> LENGTH: 24
<212> TYPE: PRT
<213> ORGANISM: Homo sapiens

<400> SEQUENCE: 1604

Ser Pro Thr Thr Thr Leu Ser Pro Ala Ser Met Thr Ser Leu Gly Val
1 5 10 15

Gly Glu Glu Ser Thr Thr Ser Arg
20

<210> SEQ ID NO 1605
<211> LENGTH: 24
<212> TYPE: PRT
<213> ORGANISM: Homo sapiens

<400> SEQUENCE: 1605

Ser Pro Thr Thr Thr Leu Ser Pro Ala Ser Met Thr Ser Leu Gly Val
1 5 10 15

Gly Glu Glu Ser Thr Thr Ser Arg
20

<210> SEQ ID NO 1606
<211> LENGTH: 24
<212> TYPE: PRT
<213> ORGANISM: Homo sapiens

<400> SEQUENCE: 1606

Ser Pro Thr Thr Thr Leu Ser Pro Ala Ser Met Thr Ser Leu Gly Val
1 5 10 15

Gly Glu Glu Ser Thr Thr Ser Arg
20

<210> SEQ ID NO 1607
<211> LENGTH: 24
<212> TYPE: PRT
<213> ORGANISM: Homo sapiens

<400> SEQUENCE: 1607

Ser Pro Thr Thr Thr Leu Ser Pro Ala Ser Met Thr Ser Leu Gly Val
1 5 10 15

Gly Glu Glu Ser Thr Thr Ser Arg
20

<210> SEQ ID NO 1608
<211> LENGTH: 19
<212> TYPE: PRT
<213> ORGANISM: Homo sapiens

<400> SEQUENCE: 1608

Ser Gln Ala Tyr Ala Asp Tyr Ile Gly Phe Ile Leu Thr Leu Asn Glu
1 5 10 15

Gly Val Lys

<210> SEQ ID NO 1609
<211> LENGTH: 14
<212> TYPE: PRT
<213> ORGANISM: Homo sapiens

<400> SEQUENCE: 1609

Ser Gln Met Asn Cys Asn Leu Gly Thr Cys Gln Leu Gln Arg
1 5 10

<210> SEQ ID NO 1610
<211> LENGTH: 14
<212> TYPE: PRT
<213> ORGANISM: Homo sapiens

<400> SEQUENCE: 1610

Ser Arg Gln Glu Leu Asn Thr Ile Ala Ser Lys Pro Pro Arg
1 5 10

<210> SEQ ID NO 1611
<211> LENGTH: 10
<212> TYPE: PRT
<213> ORGANISM: Homo sapiens

<400> SEQUENCE: 1611

Ser Ser His Val Thr Ile Asp Thr Leu Lys
1 5 10

<210> SEQ ID NO 1612
<211> LENGTH: 27
<212> TYPE: PRT
<213> ORGANISM: Homo sapiens

<400> SEQUENCE: 1612

Ser Ser Gln Asn Asp Ser Pro Gly Asp Ala Ser Glu Gly Pro Glu Tyr
1 5 10 15

Leu Ala Ile Gly Asn Leu Asp Pro Arg Gly Arg
20 25

<210> SEQ ID NO 1613
<211> LENGTH: 14
<212> TYPE: PRT
<213> ORGANISM: Homo sapiens

<400> SEQUENCE: 1613

Ser Thr Glu Tyr Glu Leu Gln Gln Leu Glu Gln Phe Lys Lys
1 5 10

<210> SEQ ID NO 1614
<211> LENGTH: 18
<212> TYPE: PRT
<213> ORGANISM: Homo sapiens

<400> SEQUENCE: 1614

Ser Thr Ser Phe Asn Val Gln Asp Leu Leu Pro Asp His Glu Tyr Lys
1 5 10 15

Phe Arg

<210> SEQ ID NO 1615
<211> LENGTH: 19
<212> TYPE: PRT
<213> ORGANISM: Homo sapiens

<400> SEQUENCE: 1615

Ser Val Glu Gln Glu Val Val Gln Ser Gln Leu Asn His Cys Val Asn
1 5 10 15

Leu Tyr Lys

<210> SEQ ID NO 1616
<211> LENGTH: 11
<212> TYPE: PRT
<213> ORGANISM: Homo sapiens

<400> SEQUENCE: 1616

Ser Val Tyr Thr Met Pro Leu Ala Asn His Arg
1 5 10

<210> SEQ ID NO 1617
<211> LENGTH: 22
<212> TYPE: PRT
<213> ORGANISM: Homo sapiens

<400> SEQUENCE: 1617

Ser Trp Ala Glu Asp Glu Lys Gln Lys Ala Glu Thr Val Gln Ala Ala
1 5 10 15

Leu Glu Glu Ala Gln Arg
20

<210> SEQ ID NO 1618
<211> LENGTH: 13
<212> TYPE: PRT
<213> ORGANISM: Homo sapiens

<400> SEQUENCE: 1618

Ser Trp Cys Ser Gly His Leu His Leu Arg Cys Pro Arg
1 5 10

<210> SEQ ID NO 1619
<211> LENGTH: 10

<212> TYPE: PRT
<213> ORGANISM: Homo sapiens

<400> SEQUENCE: 1619

Ser Tyr Val Asp Thr Gly Gly Val Ser Arg
1 5 10

<210> SEQ ID NO 1620
<211> LENGTH: 11
<212> TYPE: PRT
<213> ORGANISM: Homo sapiens

<400> SEQUENCE: 1620

Ser Tyr Val Ile Thr Gly Ser Trp Asn Pro Lys
1 5 10

<210> SEQ ID NO 1621
<211> LENGTH: 10
<212> TYPE: PRT
<213> ORGANISM: Homo sapiens

<400> SEQUENCE: 1621

Thr Ala Ile Trp Glu Asp Gln Asn Leu Arg
1 5 10

<210> SEQ ID NO 1622
<211> LENGTH: 16
<212> TYPE: PRT
<213> ORGANISM: Homo sapiens

<400> SEQUENCE: 1622

Thr Ala Leu Leu Thr Ala Gly Asp Ile Tyr Leu Leu Ser Thr Phe Arg
1 5 10 15

<210> SEQ ID NO 1623
<211> LENGTH: 15
<212> TYPE: PRT
<213> ORGANISM: Homo sapiens

<400> SEQUENCE: 1623

Thr Glu Ala Leu Met Asp Ala Gln Lys Glu Asp Phe Asn Ser Lys
1 5 10 15

<210> SEQ ID NO 1624
<211> LENGTH: 24
<212> TYPE: PRT
<213> ORGANISM: Homo sapiens

<400> SEQUENCE: 1624

Thr Glu Phe Cys Leu His Asp Gly Pro Pro Tyr Ala Asn Gly Asp Pro
1 5 10 15

His Val Gly His Ala Leu Asn Lys
20

<210> SEQ ID NO 1625
<211> LENGTH: 10
<212> TYPE: PRT
<213> ORGANISM: Homo sapiens

<400> SEQUENCE: 1625

Thr Glu Ser Ser Gly Gly Trp Gln Asn Arg
1 5 10

<210> SEQ ID NO 1626

<211> LENGTH: 24
<212> TYPE: PRT
<213> ORGANISM: Homo sapiens

<400> SEQUENCE: 1626

Thr His Ile Glu Ser Ser Gly His Gly Val Asp Thr Cys Leu His Val
1 5 10 15

Val Leu Ser Ser Lys Val Cys Arg
20

<210> SEQ ID NO 1627
<211> LENGTH: 24
<212> TYPE: PRT
<213> ORGANISM: Homo sapiens

<400> SEQUENCE: 1627

Thr Lys Val His Ala Glu Leu Ala Asp Val Leu Thr Glu Ala Val Val
1 5 10 15

Asp Ser Ile Leu Ala Ile Lys Lys
20

<210> SEQ ID NO 1628
<211> LENGTH: 15
<212> TYPE: PRT
<213> ORGANISM: Homo sapiens

<400> SEQUENCE: 1628

Thr Leu Glu Ile Ala Leu Glu Gln Lys Lys Glu Glu Cys Leu Lys
1 5 10 15

<210> SEQ ID NO 1629
<211> LENGTH: 15
<212> TYPE: PRT
<213> ORGANISM: Homo sapiens

<400> SEQUENCE: 1629

Thr Leu Asn Ala Thr Gly Glu Glu Ile Ile Gln Gln Ser Ser Lys
1 5 10 15

<210> SEQ ID NO 1630
<211> LENGTH: 8
<212> TYPE: PRT
<213> ORGANISM: Homo sapiens

<400> SEQUENCE: 1630

Thr Leu Pro Ser Met Val His Arg
1 5

<210> SEQ ID NO 1631
<211> LENGTH: 7
<212> TYPE: PRT
<213> ORGANISM: Homo sapiens

<400> SEQUENCE: 1631

Thr Met Asn Gly Asp Met Arg
1 5

<210> SEQ ID NO 1632
<211> LENGTH: 16
<212> TYPE: PRT
<213> ORGANISM: Homo sapiens

<400> SEQUENCE: 1632

Thr Asn His Ile Gly Trp Val Gln Glu Phe Leu Asn Glu Glu Asn Arg 1 5 10 15

<210> SEQ ID NO 1633
<211> LENGTH: 10
<212> TYPE: PRT
<213> ORGANISM: Homo sapiens

<400> SEQUENCE: 1633

Thr Asn Ile Gln Leu Pro Ala Cys Leu Arg
1 5 10

<210> SEQ ID NO 1634
<211> LENGTH: 7
<212> TYPE: PRT
<213> ORGANISM: Homo sapiens

<400> SEQUENCE: 1634

Thr Pro Asp Glu Leu Gln Lys
1 5

<210> SEQ ID NO 1635
<211> LENGTH: 14
<212> TYPE: PRT
<213> ORGANISM: Homo sapiens

<400> SEQUENCE: 1635

Thr Pro Leu Glu Arg Asp Asp Leu His Glu Ser Val Phe Arg
1 5 10

<210> SEQ ID NO 1636
<211> LENGTH: 12
<212> TYPE: PRT
<213> ORGANISM: Homo sapiens

<400> SEQUENCE: 1636

Thr Ser Gly Asn Gln Asp Glu Ile Leu Val Ile Arg
1 5 10

<210> SEQ ID NO 1637
<211> LENGTH: 49
<212> TYPE: PRT
<213> ORGANISM: Homo sapiens

<400> SEQUENCE: 1637

Thr Thr Leu Ser Pro Ala Ser Ser Thr Ser Pro Gly Leu Gln Gly Glu
1 5 10 15

Ser Thr Ala Phe Gln Thr His Pro Ala Ser Thr His Thr Thr Pro Ser
20 25 30

Pro Pro Ser Thr Ala Thr Ala Pro Val Glu Glu Ser Thr Thr Tyr His
35 40 45

Arg

<210> SEQ ID NO 1638
<211> LENGTH: 49
<212> TYPE: PRT
<213> ORGANISM: Homo sapiens

<400> SEQUENCE: 1638

Thr Thr Leu Ser Pro Ala Ser Ser Thr Ser Pro Gly Leu Gln Gly Glu
1 5 10 15

Ser Thr Ala Phe Gln Thr His Pro Ala Ser Thr His Thr Thr Pro Ser
20 25 30

Pro Pro Ser Thr Ala Thr Ala Pro Val Glu Glu Ser Thr Thr Tyr His
35 40 45

Arg

<210> SEQ ID NO 1639
<211> LENGTH: 49
<212> TYPE: PRT
<213> ORGANISM: Homo sapiens

<400> SEQUENCE: 1639

Thr Thr Leu Ser Pro Ala Ser Ser Thr Ser Pro Gly Leu Gln Gly Glu
1 5 10 15

Ser Thr Ala Phe Gln Thr His Pro Ala Ser Thr His Thr Thr Pro Ser
20 25 30

Pro Pro Ser Thr Ala Thr Ala Pro Val Glu Glu Ser Thr Thr Tyr His
35 40 45

Arg

<210> SEQ ID NO 1640
<211> LENGTH: 14
<212> TYPE: PRT
<213> ORGANISM: Homo sapiens

<400> SEQUENCE: 1640

Thr Thr Gln Gly Leu Thr Ala Leu Leu Leu Ser Leu Lys Lys
1 5 10

<210> SEQ ID NO 1641
<211> LENGTH: 11
<212> TYPE: PRT
<213> ORGANISM: Homo sapiens

<400> SEQUENCE: 1641

Thr Thr Gln Ile Ile Asn Ile Thr Met Thr Lys
1 5 10

<210> SEQ ID NO 1642
<211> LENGTH: 9
<212> TYPE: PRT
<213> ORGANISM: Homo sapiens

<400> SEQUENCE: 1642

Thr Trp Val Gln Gln Ser Glu Thr Lys
1 5

<210> SEQ ID NO 1643
<211> LENGTH: 12
<212> TYPE: PRT
<213> ORGANISM: Homo sapiens

<400> SEQUENCE: 1643

Val Ala Ile Gly Pro Ser Val Leu Asn Ala Ala Arg
1 5 10

<210> SEQ ID NO 1644
<211> LENGTH: 19
<212> TYPE: PRT
<213> ORGANISM: Homo sapiens

<400> SEQUENCE: 1644

Val Ala Tyr Ile Pro Asp Glu Met Ala Ala Gln Gln Asn Pro Leu Gln
1 5 10 15

Gln Pro Arg

<210> SEQ ID NO 1645
<211> LENGTH: 19
<212> TYPE: PRT
<213> ORGANISM: Homo sapiens

<400> SEQUENCE: 1645

Val Asp Ser Asp Met Asn Asp Ala Tyr Leu Gly Tyr Ala Ala Ala Ile
1               5                   10                  15

Ile Leu Arg

<210> SEQ ID NO 1646
<211> LENGTH: 17
<212> TYPE: PRT
<213> ORGANISM: Homo sapiens

<400> SEQUENCE: 1646

Val Glu Asp Ala Tyr Ile Leu Thr Cys Asn Val Ser Leu Glu Tyr Glu
1               5                   10                  15

Lys

<210> SEQ ID NO 1647
<211> LENGTH: 22
<212> TYPE: PRT
<213> ORGANISM: Homo sapiens

<400> SEQUENCE: 1647

Val Gly Ala Pro Met His Asp Leu Leu Leu Trp Asn Asn Ala Thr Val
1               5                   10                  15

Thr Thr Cys His Ser Lys
            20

<210> SEQ ID NO 1648
<211> LENGTH: 11
<212> TYPE: PRT
<213> ORGANISM: Homo sapiens

<400> SEQUENCE: 1648

Val His Leu Phe Asp Ile Ile Thr Gln Tyr Arg
1               5                   10

<210> SEQ ID NO 1649
<211> LENGTH: 10
<212> TYPE: PRT
<213> ORGANISM: Homo sapiens

<400> SEQUENCE: 1649

Val Ile Glu Cys Phe Asn Val Glu Ser Arg
1               5                   10

<210> SEQ ID NO 1650
<211> LENGTH: 15
<212> TYPE: PRT
<213> ORGANISM: Homo sapiens

<400> SEQUENCE: 1650

Val Leu Gly His Phe Glu Lys Pro Leu Phe Leu Glu Leu Cys Arg
1               5                   10                  15

<210> SEQ ID NO 1651
<211> LENGTH: 9
<212> TYPE: PRT

<213> ORGANISM: Homo sapiens

<400> SEQUENCE: 1651

Val Leu Met Asp Leu Gln Asn Gln Lys
1 5

<210> SEQ ID NO 1652
<211> LENGTH: 8
<212> TYPE: PRT
<213> ORGANISM: Homo sapiens

<400> SEQUENCE: 1652

Val Leu Thr Thr Ser Pro Ser Arg
1 5

<210> SEQ ID NO 1653
<211> LENGTH: 13
<212> TYPE: PRT
<213> ORGANISM: Homo sapiens

<400> SEQUENCE: 1653

Val Met Leu Pro Pro Gly Ala Gln His Ser Asp Glu Lys
1 5 10

<210> SEQ ID NO 1654
<211> LENGTH: 35
<212> TYPE: PRT
<213> ORGANISM: Homo sapiens

<400> SEQUENCE: 1654

Val Asn Phe Arg Pro Arg Tyr Val Thr Arg Tyr Lys Thr Val Thr Gln
1 5 10 15

Leu Glu Trp Arg Cys Cys Pro Gly Phe Arg Gly Gly Asp Cys Gln Glu
20 25 30

Gly Pro Lys
35

<210> SEQ ID NO 1655
<211> LENGTH: 10
<212> TYPE: PRT
<213> ORGANISM: Homo sapiens

<400> SEQUENCE: 1655

Val Pro Asp Met Ala Glu Ile Gln Ser Arg
1 5 10

<210> SEQ ID NO 1656
<211> LENGTH: 11
<212> TYPE: PRT
<213> ORGANISM: Homo sapiens

<400> SEQUENCE: 1656

Val Gln Leu Leu Ser Gln Tyr Asp Asn Glu Lys
1 5 10

<210> SEQ ID NO 1657
<211> LENGTH: 20
<212> TYPE: PRT
<213> ORGANISM: Homo sapiens

<400> SEQUENCE: 1657

Val Ser Arg Ala Ser Ser Pro Glu Gly Arg His Leu Pro Ser Pro Gln
1 5 10 15

Leu Gly Thr Lys
20

<210> SEQ ID NO 1658
<211> LENGTH: 10
<212> TYPE: PRT
<213> ORGANISM: Homo sapiens

<400> SEQUENCE: 1658

Val Thr Cys Thr Gly Tyr His Gln Val Arg
1 5 10

<210> SEQ ID NO 1659
<211> LENGTH: 8
<212> TYPE: PRT
<213> ORGANISM: Homo sapiens

<400> SEQUENCE: 1659

Val Thr Glu Phe Asp Ala Ala Arg
1 5

<210> SEQ ID NO 1660
<211> LENGTH: 21
<212> TYPE: PRT
<213> ORGANISM: Homo sapiens

<400> SEQUENCE: 1660

Val Val Gln Glu Glu Asn Gln His Met Gln Met Thr Ile Gln Ala Leu
1 5 10 15

Gln Asp Glu Leu Arg
20

<210> SEQ ID NO 1661
<211> LENGTH: 9
<212> TYPE: PRT
<213> ORGANISM: Homo sapiens

<400> SEQUENCE: 1661

Val Tyr Leu Asp Leu Thr Pro Val Lys
1 5

<210> SEQ ID NO 1662
<211> LENGTH: 11
<212> TYPE: PRT
<213> ORGANISM: Homo sapiens

<400> SEQUENCE: 1662

Trp Cys Ala Thr Ser Asp Pro Glu Gln His Lys
1 5 10

<210> SEQ ID NO 1663
<211> LENGTH: 13
<212> TYPE: PRT
<213> ORGANISM: Homo sapiens

<400> SEQUENCE: 1663

Trp Phe Ser Ile Gln Asn Asn Gln Leu Val Tyr Gln Lys
1 5 10

<210> SEQ ID NO 1664
<211> LENGTH: 11
<212> TYPE: PRT
<213> ORGANISM: Homo sapiens

<400> SEQUENCE: 1664

Trp Ile Glu Phe Cys Gln Leu Leu Ser Glu Arg
1 5 10

<210> SEQ ID NO 1665
<211> LENGTH: 14
<212> TYPE: PRT
<213> ORGANISM: Homo sapiens

<400> SEQUENCE: 1665

Trp Tyr Gln Asn Pro Asp Tyr Asn Phe Phe Asn Asn Tyr Lys
1 5 10

<210> SEQ ID NO 1666
<211> LENGTH: 12
<212> TYPE: PRT
<213> ORGANISM: Homo sapiens

<400> SEQUENCE: 1666

Tyr Ala Asp Ser Leu Lys Pro Asn Ile Pro Tyr Lys
1 5 10

<210> SEQ ID NO 1667
<211> LENGTH: 12
<212> TYPE: PRT
<213> ORGANISM: Homo sapiens

<400> SEQUENCE: 1667

Tyr Glu Asn His Ser Ala Thr Ala Glu Ser Ser Arg
1 5 10

<210> SEQ ID NO 1668
<211> LENGTH: 11
<212> TYPE: PRT
<213> ORGANISM: Homo sapiens

<400> SEQUENCE: 1668

Tyr Leu Ile Thr Ala Thr Leu Thr Pro Glu Arg
1 5 10

<210> SEQ ID NO 1669
<211> LENGTH: 17
<212> TYPE: PRT
<213> ORGANISM: Homo sapiens

<400> SEQUENCE: 1669

Tyr Leu Gln Gln Pro Gly Cys Leu Leu Val Gly Thr Asn Met Asp Asn
1 5 10 15

Arg

<210> SEQ ID NO 1670
<211> LENGTH: 12
<212> TYPE: PRT
<213> ORGANISM: Homo sapiens

<400> SEQUENCE: 1670

Tyr Leu Arg Glu Leu Ser Gly Ser Gly Leu Glu Arg
1 5 10

<210> SEQ ID NO 1671
<211> LENGTH: 21
<212> TYPE: PRT
<213> ORGANISM: Homo sapiens

<400> SEQUENCE: 1671

Tyr Leu Ser Ala Ser Glu Tyr Gly Ser Ser Val Asp Gly His Pro Glu
1 5 10 15

Val Pro Glu Thr Lys
20

<210> SEQ ID NO 1672
<211> LENGTH: 9
<212> TYPE: PRT
<213> ORGANISM: Homo sapiens

<400> SEQUENCE: 1672

Tyr Asn Ala Ser Ser Gln Gln Gln Arg
1 5

<210> SEQ ID NO 1673
<211> LENGTH: 9
<212> TYPE: PRT
<213> ORGANISM: Homo sapiens

<400> SEQUENCE: 1673

Tyr Gln Glu Thr Met Ser Ala Ile Arg
1 5

<210> SEQ ID NO 1674
<211> LENGTH: 23
<212> TYPE: PRT
<213> ORGANISM: Homo sapiens

<400> SEQUENCE: 1674

Tyr Ser Phe Trp Leu Thr Thr Ile Pro Glu Gln Ser Phe Gln Gly Ser
1 5 10 15

Pro Ser Ala Asp Thr Leu Lys
20

<210> SEQ ID NO 1675
<211> LENGTH: 15
<212> TYPE: PRT
<213> ORGANISM: Homo sapiens

<400> SEQUENCE: 1675

Tyr Thr Lys Gln Gly Phe Gly Asn Leu Pro Ile Cys Met Ala Lys
1 5 10 15

<210> SEQ ID NO 1676
<211> LENGTH: 13
<212> TYPE: PRT
<213> ORGANISM: Homo sapiens

<400> SEQUENCE: 1676

Tyr Val Pro Ala Ile Ala His Leu Ile His Ser Leu Asn
1 5 10

<210> SEQ ID NO 1677
<211> LENGTH: 21
<212> TYPE: PRT
<213> ORGANISM: Homo sapiens

<400> SEQUENCE: 1677

Ala Ala Glu Cys Leu Asp Val Asp Glu Cys His Arg Val Pro Pro Pro
1 5 10 15

Cys Asp Leu Gly Arg
20

<210> SEQ ID NO 1678
<211> LENGTH: 9
<212> TYPE: PRT
<213> ORGANISM: Homo sapiens

<400> SEQUENCE: 1678

Ala Glu Gly Gly Lys Arg Pro Ala Arg
1 5

<210> SEQ ID NO 1679
<211> LENGTH: 23
<212> TYPE: PRT
<213> ORGANISM: Homo sapiens

<400> SEQUENCE: 1679

Ala Glu Pro Val Trp Thr Pro Pro Ala Pro Ala Pro Ala Ala Pro Pro
1 5 10 15

Ser Thr Pro Ala Ala Pro Lys
20

<210> SEQ ID NO 1680
<211> LENGTH: 19
<212> TYPE: PRT
<213> ORGANISM: Homo sapiens

<400> SEQUENCE: 1680

Ala Phe Leu Cys Pro Leu Ile Cys His Asn Gly Gly Val Cys Val Lys
1 5 10 15

Pro Asp Arg

<210> SEQ ID NO 1681
<211> LENGTH: 11
<212> TYPE: PRT
<213> ORGANISM: Homo sapiens

<400> SEQUENCE: 1681

Ala His Leu Ile His Ser Leu Asn Pro Val Arg
1 5 10

<210> SEQ ID NO 1682
<211> LENGTH: 13
<212> TYPE: PRT
<213> ORGANISM: Homo sapiens

<400> SEQUENCE: 1682

Ala Ile Ala His Leu Ile His Ser Leu Asn Pro Val Arg
1 5 10

<210> SEQ ID NO 1683
<211> LENGTH: 8
<212> TYPE: PRT
<213> ORGANISM: Homo sapiens

<400> SEQUENCE: 1683

Ala Ile Trp Asn Val Ile Asn Trp
1 5

<210> SEQ ID NO 1684
<211> LENGTH: 11
<212> TYPE: PRT
<213> ORGANISM: Homo sapiens

<400> SEQUENCE: 1684

Ala Ile Trp Asn Val Ile Asn Trp Glu Asn Val
1 5 10

<210> SEQ ID NO 1685
<211> LENGTH: 13
<212> TYPE: PRT
<213> ORGANISM: Homo sapiens

<400> SEQUENCE: 1685

Ala Asn Gly Ile Thr Met Tyr Ala Val Gly Val Gly Lys
1 5 10

<210> SEQ ID NO 1686
<211> LENGTH: 34
<212> TYPE: PRT
<213> ORGANISM: Homo sapiens

<400> SEQUENCE: 1686

Ala Gln Pro Val Pro Phe Val Pro Gln Val Leu Gly Val Met Ile Gly
1 5 10 15

Ala Gly Val Ala Val Val Val Thr Ala Val Leu Ile Leu Leu Val Val
20 25 30

Arg Arg

<210> SEQ ID NO 1687
<211> LENGTH: 8
<212> TYPE: PRT
<213> ORGANISM: Homo sapiens

<400> SEQUENCE: 1687

Ala Arg Ile Leu Thr Ala Ala Arg
1 5

<210> SEQ ID NO 1688
<211> LENGTH: 30
<212> TYPE: PRT
<213> ORGANISM: Homo sapiens

<400> SEQUENCE: 1688

Ala Val Gly Pro Gly Ala Gly Gly Ala Gly Ser Ala Val Pro Gly Gly
1 5 10 15

Ala Gly Pro Cys Ala Thr Val Ser Val Phe Pro Gly Ala Arg
20 25 30

<210> SEQ ID NO 1689
<211> LENGTH: 16
<212> TYPE: PRT
<213> ORGANISM: Homo sapiens

<400> SEQUENCE: 1689

Ala Tyr Asp Asn Phe Gly Val Leu Gly Leu Asp Leu Trp Gln Val Lys
1 5 10 15

<210> SEQ ID NO 1690
<211> LENGTH: 8
<212> TYPE: PRT
<213> ORGANISM: Homo sapiens

<400> SEQUENCE: 1690

Cys Val Cys Pro Ala Gly Phe Arg
1 5

<210> SEQ ID NO 1691

<211> LENGTH: 9
<212> TYPE: PRT
<213> ORGANISM: Homo sapiens

<400> SEQUENCE: 1691

Cys Val His Gly Pro Thr Gly Ser Arg
1               5

<210> SEQ ID NO 1692
<211> LENGTH: 27
<212> TYPE: PRT
<213> ORGANISM: Homo sapiens

<400> SEQUENCE: 1692

Cys Val Pro Pro Arg Thr Ser Ala Gly Thr Phe Pro Gly Ser Gln Pro
1               5                   10                  15

Gln Ala Pro Ala Ser Pro Val Leu Pro Ala Arg
            20                  25

<210> SEQ ID NO 1693
<211> LENGTH: 12
<212> TYPE: PRT
<213> ORGANISM: Homo sapiens

<400> SEQUENCE: 1693

Asp His Pro Ser Ser His Ser Ala Gln Pro Pro Arg
1               5                   10

<210> SEQ ID NO 1694
<211> LENGTH: 20
<212> TYPE: PRT
<213> ORGANISM: Homo sapiens

<400> SEQUENCE: 1694

Asp Lys Glu Arg Leu Gln Ala Met Met Thr His Leu His Val Lys Ser
1               5                   10                  15

Thr Glu Pro Lys
            20

<210> SEQ ID NO 1695
<211> LENGTH: 14
<212> TYPE: PRT
<213> ORGANISM: Homo sapiens

<400> SEQUENCE: 1695

Asp Leu Asp Asn Ala Glu Glu Lys Ala Asp Ala Leu Asn Lys
1               5                   10

<210> SEQ ID NO 1696
<211> LENGTH: 17
<212> TYPE: PRT
<213> ORGANISM: Homo sapiens

<400> SEQUENCE: 1696

Asp Leu Tyr Ser Ala Leu Ile Gln Phe Phe Gln Ile Phe Pro Glu Tyr
1               5                   10                  15

Lys

<210> SEQ ID NO 1697
<211> LENGTH: 36
<212> TYPE: PRT
<213> ORGANISM: Homo sapiens

<400> SEQUENCE: 1697

Asp Pro Ala Ser Asp Lys Leu Leu Gly Pro Ala Gly Leu Thr Trp Glu
1 5 10 15

Arg Asn Leu Pro Gly Ala Gly Val Gly Lys Glu Met Ala Gly Val Pro
20 25 30

Pro Thr Leu Arg
35

<210> SEQ ID NO 1698
<211> LENGTH: 21
<212> TYPE: PRT
<213> ORGANISM: Homo sapiens

<400> SEQUENCE: 1698

Asp Ser Ala Val Met Asp Asp Ser Val Val Ile Pro Ser His Gln Val
1 5 10 15

Ser Thr Leu Ala Lys
20

<210> SEQ ID NO 1699
<211> LENGTH: 17
<212> TYPE: PRT
<213> ORGANISM: Homo sapiens

<400> SEQUENCE: 1699

Asp Ser Ser Thr Pro Tyr Gln Glu Ile Ala Ala Val Pro Ser Ala Gly
1 5 10 15

Arg

<210> SEQ ID NO 1700
<211> LENGTH: 12
<212> TYPE: PRT
<213> ORGANISM: Homo sapiens

<400> SEQUENCE: 1700

Asp Trp Asp Ser Pro Tyr Ser His Asp Leu Asp Thr
1 5 10

<210> SEQ ID NO 1701
<211> LENGTH: 13
<212> TYPE: PRT
<213> ORGANISM: Homo sapiens

<400> SEQUENCE: 1701

Asp Trp Asp Ser Pro Tyr Ser His Asp Leu Asp Thr Ser
1 5 10

<210> SEQ ID NO 1702
<211> LENGTH: 23
<212> TYPE: PRT
<213> ORGANISM: Homo sapiens

<400> SEQUENCE: 1702

Glu Asp Leu Asp Gln Ser Pro Leu Val Ser Ser Ser Asp Ser Pro Pro
1 5 10 15

Arg Pro Gln Pro Ala Phe Lys
20

<210> SEQ ID NO 1703
<211> LENGTH: 14
<212> TYPE: PRT
<213> ORGANISM: Homo sapiens

<400> SEQUENCE: 1703

Glu Glu Ser Arg Glu Pro Ala Pro Ala Ser Pro Ala Pro Ala
1 5 10

<210> SEQ ID NO 1704
<211> LENGTH: 8
<212> TYPE: PRT
<213> ORGANISM: Homo sapiens

<400> SEQUENCE: 1704

Glu Leu Ser Ser Lys Gly Val Lys
1 5

<210> SEQ ID NO 1705
<211> LENGTH: 14
<212> TYPE: PRT
<213> ORGANISM: Homo sapiens

<400> SEQUENCE: 1705

Glu Met Glu Leu Arg Arg Gln Ala Leu Glu Glu Glu Arg Arg
1 5 10

<210> SEQ ID NO 1706
<211> LENGTH: 7
<212> TYPE: PRT
<213> ORGANISM: Homo sapiens

<400> SEQUENCE: 1706

Glu Asn Gly Thr Val Pro Lys
1 5

<210> SEQ ID NO 1707
<211> LENGTH: 15
<212> TYPE: PRT
<213> ORGANISM: Homo sapiens

<400> SEQUENCE: 1707

Glu Asn Lys Glu Val Val Leu Gln Trp Phe Thr Glu Asn Ser Lys
1 5 10 15

<210> SEQ ID NO 1708
<211> LENGTH: 9
<212> TYPE: PRT
<213> ORGANISM: Homo sapiens

<400> SEQUENCE: 1708

Glu Val Ala Glu Ser Pro Arg Pro Arg
1 5

<210> SEQ ID NO 1709
<211> LENGTH: 7
<212> TYPE: PRT
<213> ORGANISM: Homo sapiens

<400> SEQUENCE: 1709

Phe Ile Leu Asp Asn Leu Lys
1 5

<210> SEQ ID NO 1710
<211> LENGTH: 18
<212> TYPE: PRT
<213> ORGANISM: Homo sapiens

<400> SEQUENCE: 1710

Phe Leu Glu Ala Val Ala Glu Glu Lys Pro His Val Lys Pro Tyr Phe
1 5 10 15

Ser Lys

<210> SEQ ID NO 1711
<211> LENGTH: 11
<212> TYPE: PRT
<213> ORGANISM: Homo sapiens

<400> SEQUENCE: 1711

Phe Pro Ile Glu Gly Gly Gln Lys Asp Pro Lys
1 5 10

<210> SEQ ID NO 1712
<211> LENGTH: 27
<212> TYPE: PRT
<213> ORGANISM: Homo sapiens

<400> SEQUENCE: 1712

Phe Ser Thr Glu Tyr Glu Leu Gln Gln Leu Glu Gln Phe Lys Lys Asp
1 5 10 15

Asn Glu Glu Thr Gly Phe Gly Ser Gly Thr Arg
20 25

<210> SEQ ID NO 1713
<211> LENGTH: 10
<212> TYPE: PRT
<213> ORGANISM: Homo sapiens

<400> SEQUENCE: 1713

Phe Trp Pro Ala Ile Asp Asp Gly Leu Arg
1 5 10

<210> SEQ ID NO 1714
<211> LENGTH: 20
<212> TYPE: PRT
<213> ORGANISM: Homo sapiens

<400> SEQUENCE: 1714

Phe Tyr Ile Asp Phe Gly Gly Val Lys Pro Met Gly Ser Glu Pro Val
1 5 10 15

Pro Lys Ser Arg
20

<210> SEQ ID NO 1715
<211> LENGTH: 31
<212> TYPE: PRT
<213> ORGANISM: Homo sapiens

<400> SEQUENCE: 1715

Gly Ala Asp Leu Ile Glu Glu Ala Ala Ser Arg Ile Val Asp Ala Val
1 5 10 15

Ile Glu Gln Val Lys Ala Ala Gly Ala Leu Leu Thr Glu Gly Glu
20 25 30

<210> SEQ ID NO 1716
<211> LENGTH: 12
<212> TYPE: PRT
<213> ORGANISM: Homo sapiens

<400> SEQUENCE: 1716

Gly Ala Asp Tyr Ala Glu Pro Thr Trp Asn Leu Lys
1 5 10

<210> SEQ ID NO 1717
<211> LENGTH: 16
<212> TYPE: PRT
<213> ORGANISM: Homo sapiens

<400> SEQUENCE: 1717

Gly Asp Glu Glu Lys Asp Lys Gly Leu Gln Thr Ser Gln Asp Ala Arg
1 5 10 15

<210> SEQ ID NO 1718
<211> LENGTH: 12
<212> TYPE: PRT
<213> ORGANISM: Homo sapiens

<400> SEQUENCE: 1718

Gly Asp Ile Leu Gln Thr Pro Gln Phe Gln Met Arg
1 5 10

<210> SEQ ID NO 1719
<211> LENGTH: 8
<212> TYPE: PRT
<213> ORGANISM: Homo sapiens

<400> SEQUENCE: 1719

Gly Asp Asn Leu Pro Gln Tyr Arg
1 5

<210> SEQ ID NO 1720
<211> LENGTH: 8
<212> TYPE: PRT
<213> ORGANISM: Homo sapiens

<400> SEQUENCE: 1720

Gly Asn Glu Ala Val Ala Ser Arg
1 5

<210> SEQ ID NO 1721
<211> LENGTH: 15
<212> TYPE: PRT
<213> ORGANISM: Homo sapiens

<400> SEQUENCE: 1721

Gly Pro Asn Lys His Thr Leu Thr Gln Ile Lys Asp Ala Val Arg
1 5 10 15

<210> SEQ ID NO 1722
<211> LENGTH: 19
<212> TYPE: PRT
<213> ORGANISM: Homo sapiens

<400> SEQUENCE: 1722

Gly Gln Gly Pro Met Phe Leu Asp Ala Asp Phe Val Ala Phe Thr Asn
1 5 10 15

His Phe Lys

<210> SEQ ID NO 1723
<211> LENGTH: 14
<212> TYPE: PRT
<213> ORGANISM: Homo sapiens

<400> SEQUENCE: 1723

Gly Thr Ala Thr Pro Glu Leu His Thr Ala Thr Asp Tyr Arg
1 5 10

<210> SEQ ID NO 1724
<211> LENGTH: 21
<212> TYPE: PRT
<213> ORGANISM: Homo sapiens

<400> SEQUENCE: 1724

Gly Trp Ala Gly Asp Ser Gly Pro Gln Gly Arg Pro Gly Val Phe Gly
1 5 10 15

Leu Pro Gly Glu Lys
20

<210> SEQ ID NO 1725
<211> LENGTH: 13
<212> TYPE: PRT
<213> ORGANISM: Homo sapiens

<400> SEQUENCE: 1725

Gly Tyr Leu Ala Pro Ser Gly Asp Leu Ser Leu Arg Arg
1 5 10

<210> SEQ ID NO 1726
<211> LENGTH: 8
<212> TYPE: PRT
<213> ORGANISM: Homo sapiens

<400> SEQUENCE: 1726

His Ala Glu Gln Gln Ala Leu Arg
1 5

<210> SEQ ID NO 1727
<211> LENGTH: 10
<212> TYPE: PRT
<213> ORGANISM: Homo sapiens

<400> SEQUENCE: 1727

Ile Glu Asp Pro Ser Leu Leu Asn Ser Arg
1 5 10

<210> SEQ ID NO 1728
<211> LENGTH: 17
<212> TYPE: PRT
<213> ORGANISM: Homo sapiens

<400> SEQUENCE: 1728

Ile Phe Met Glu Glu Val Pro Gly Gly Ser Leu Ser Ser Leu Leu Arg
1 5 10 15

Ser

<210> SEQ ID NO 1729
<211> LENGTH: 17
<212> TYPE: PRT
<213> ORGANISM: Homo sapiens

<400> SEQUENCE: 1729

Ile Phe Met Glu Glu Val Pro Gly Gly Ser Leu Ser Ser Leu Leu Arg
1 5 10 15

Ser

<210> SEQ ID NO 1730
<211> LENGTH: 20
<212> TYPE: PRT
<213> ORGANISM: Homo sapiens

<400> SEQUENCE: 1730

Ile Ile Glu Val Ala Pro Gln Val Ala Thr Gln Asn Val Asn Pro Thr
1 5 10 15

Pro Gly Ala Thr
20

<210> SEQ ID NO 1731
<211> LENGTH: 10
<212> TYPE: PRT
<213> ORGANISM: Homo sapiens

<400> SEQUENCE: 1731

Ile Leu Asn Ser Asp Gln Thr Thr Cys Arg
1 5 10

<210> SEQ ID NO 1732
<211> LENGTH: 12
<212> TYPE: PRT
<213> ORGANISM: Homo sapiens

<400> SEQUENCE: 1732

Ile Ser Cys Trp Gly His Ser Glu Pro Ser Met Arg
1 5 10

<210> SEQ ID NO 1733
<211> LENGTH: 12
<212> TYPE: PRT
<213> ORGANISM: Homo sapiens

<400> SEQUENCE: 1733

Ile Val Val His Ser Val Glu Asn Met Asn Phe Arg
1 5 10

<210> SEQ ID NO 1734
<211> LENGTH: 7
<212> TYPE: PRT
<213> ORGANISM: Homo sapiens

<400> SEQUENCE: 1734

Lys Ala Val Ala His Met Lys
1 5

<210> SEQ ID NO 1735
<211> LENGTH: 11
<212> TYPE: PRT
<213> ORGANISM: Homo sapiens

<400> SEQUENCE: 1735

Lys Asp Ile Thr Ala Ala Leu Ala Ala Glu Arg
1 5 10

<210> SEQ ID NO 1736
<211> LENGTH: 13
<212> TYPE: PRT
<213> ORGANISM: Homo sapiens

<400> SEQUENCE: 1736

Lys Asp Asn Glu Glu Thr Gly Phe Gly Ser Gly Thr Arg
1 5 10

<210> SEQ ID NO 1737
<211> LENGTH: 13
<212> TYPE: PRT

<213> ORGANISM: Homo sapiens

<400> SEQUENCE: 1737

Lys His Gln Gly His Phe Leu Leu Gly Thr Leu Ser Arg
1 5 10

<210> SEQ ID NO 1738
<211> LENGTH: 9
<212> TYPE: PRT
<213> ORGANISM: Homo sapiens

<400> SEQUENCE: 1738

Lys Ile Ala Glu Ile Gln Ala Arg Arg
1 5

<210> SEQ ID NO 1739
<211> LENGTH: 9
<212> TYPE: PRT
<213> ORGANISM: Homo sapiens

<400> SEQUENCE: 1739

Lys Lys Glu Ala Asp Met Gln Gln Lys
1 5

<210> SEQ ID NO 1740
<211> LENGTH: 10
<212> TYPE: PRT
<213> ORGANISM: Homo sapiens

<400> SEQUENCE: 1740

Lys Leu Phe Gly Gly Pro Gly Ser Arg Arg
1 5 10

<210> SEQ ID NO 1741
<211> LENGTH: 20
<212> TYPE: PRT
<213> ORGANISM: Homo sapiens

<400> SEQUENCE: 1741

Lys Pro Ala Ala Gly Leu Ser Ala Ala Pro Val Pro Thr Ala Pro Ala
1 5 10 15

Ala Gly Ala Pro
20

<210> SEQ ID NO 1742
<211> LENGTH: 25
<212> TYPE: PRT
<213> ORGANISM: Homo sapiens

<400> SEQUENCE: 1742

Lys Ser Ser Thr Gly Ser Pro Thr Ser Pro Leu Asn Ala Glu Lys Leu
1 5 10 15

Glu Ser Glu Glu Asp Val Ser Gln Ala
20 25

<210> SEQ ID NO 1743
<211> LENGTH: 15
<212> TYPE: PRT
<213> ORGANISM: Homo sapiens

<400> SEQUENCE: 1743

Lys Val Val Ala Thr Thr Gln Met Gln Ala Ala Asp Ala Arg Lys
1 5 10 15

<210> SEQ ID NO 1744
<211> LENGTH: 14
<212> TYPE: PRT
<213> ORGANISM: Homo sapiens

<400> SEQUENCE: 1744

Leu Ala Asp Ser Asp Gln Ala Ser Lys Val Gln Gln Gln Lys
1               5                   10

<210> SEQ ID NO 1745
<211> LENGTH: 8
<212> TYPE: PRT
<213> ORGANISM: Homo sapiens

<400> SEQUENCE: 1745

Leu Ala Tyr Val Ser Cys Val Arg
1               5

<210> SEQ ID NO 1746
<211> LENGTH: 33
<212> TYPE: PRT
<213> ORGANISM: Homo sapiens

<400> SEQUENCE: 1746

Leu Gly Ile Val Gln Gly Ile Val Gly Ala Arg Asn Thr Ser Ala Ala
1               5                   10                  15

Ser Thr Ala Gln Leu Val Glu Ala Thr Glu Glu Leu Arg Arg Glu Ile
            20                  25                  30

Gly

<210> SEQ ID NO 1747
<211> LENGTH: 16
<212> TYPE: PRT
<213> ORGANISM: Homo sapiens

<400> SEQUENCE: 1747

Leu His Tyr Asn Glu Leu Gly Ala Lys Val Thr Glu Arg Lys Gln Gln
1               5                   10                  15

<210> SEQ ID NO 1748
<211> LENGTH: 14
<212> TYPE: PRT
<213> ORGANISM: Homo sapiens

<400> SEQUENCE: 1748

Leu Ile Glu Val Gly Pro Ser Gly Ala Gln Phe Leu Gly Lys
1               5                   10

<210> SEQ ID NO 1749
<211> LENGTH: 10
<212> TYPE: PRT
<213> ORGANISM: Homo sapiens

<400> SEQUENCE: 1749

Leu Lys Gln Thr Asn Leu Gln Trp Ile Lys
1               5                   10

<210> SEQ ID NO 1750
<211> LENGTH: 7
<212> TYPE: PRT
<213> ORGANISM: Homo sapiens

<400> SEQUENCE: 1750

Leu Lys Thr Val Phe Tyr Arg
1 5

<210> SEQ ID NO 1751
<211> LENGTH: 14
<212> TYPE: PRT
<213> ORGANISM: Homo sapiens

<400> SEQUENCE: 1751

Leu Leu Ile Ser Cys Trp Gly His Ser Glu Pro Ser Met Arg
1 5 10

<210> SEQ ID NO 1752
<211> LENGTH: 13
<212> TYPE: PRT
<213> ORGANISM: Homo sapiens

<400> SEQUENCE: 1752

Leu Met Phe Asp Arg Ser Glu Val Tyr Gly Pro Met Lys
1 5 10

<210> SEQ ID NO 1753
<211> LENGTH: 9
<212> TYPE: PRT
<213> ORGANISM: Homo sapiens

<400> SEQUENCE: 1753

Leu Met Leu Glu Trp Gln Phe Gln Lys
1 5

<210> SEQ ID NO 1754
<211> LENGTH: 11
<212> TYPE: PRT
<213> ORGANISM: Homo sapiens

<400> SEQUENCE: 1754

Leu Pro Ala Ala Pro Pro Val Ala Pro Glu Arg
1 5 10

<210> SEQ ID NO 1755
<211> LENGTH: 14
<212> TYPE: PRT
<213> ORGANISM: Homo sapiens

<400> SEQUENCE: 1755

Leu Pro Pro Val Leu Gly Thr Glu Ser Asp Ala Thr Val Lys
1 5 10

<210> SEQ ID NO 1756
<211> LENGTH: 7
<212> TYPE: PRT
<213> ORGANISM: Homo sapiens

<400> SEQUENCE: 1756

Leu Pro Gln Glu Pro Gly Arg
1 5

<210> SEQ ID NO 1757
<211> LENGTH: 14
<212> TYPE: PRT
<213> ORGANISM: Homo sapiens

<400> SEQUENCE: 1757

Leu Gln Gly Gln Asp Ser Glu Arg Val Arg Ala Trp Gln Arg
1 5 10

<210> SEQ ID NO 1758
<211> LENGTH: 9
<212> TYPE: PRT
<213> ORGANISM: Homo sapiens

<400> SEQUENCE: 1758

Leu Ser Arg Lys Gly Gly His Glu Arg
1 5

<210> SEQ ID NO 1759
<211> LENGTH: 11
<212> TYPE: PRT
<213> ORGANISM: Homo sapiens

<400> SEQUENCE: 1759

Leu Thr Glu Leu Glu Asn Glu Leu Asn Thr Lys
1 5 10

<210> SEQ ID NO 1760
<211> LENGTH: 9
<212> TYPE: PRT
<213> ORGANISM: Homo sapiens

<400> SEQUENCE: 1760

Leu Thr Gly Lys Ala Glu Gly Gly Lys
1 5

<210> SEQ ID NO 1761
<211> LENGTH: 8
<212> TYPE: PRT
<213> ORGANISM: Homo sapiens

<400> SEQUENCE: 1761

Leu Trp Glu Ala Val Lys Arg Arg
1 5

<210> SEQ ID NO 1762
<211> LENGTH: 13
<212> TYPE: PRT
<213> ORGANISM: Homo sapiens

<400> SEQUENCE: 1762

Leu Trp His Leu Asp Pro Asp Thr Glu Tyr Glu Ile Arg
1 5 10

<210> SEQ ID NO 1763
<211> LENGTH: 11
<212> TYPE: PRT
<213> ORGANISM: Homo sapiens

<400> SEQUENCE: 1763

Leu Tyr Gly Val Val Leu Thr Pro Pro Met Lys
1 5 10

<210> SEQ ID NO 1764
<211> LENGTH: 15
<212> TYPE: PRT
<213> ORGANISM: Homo sapiens

<400> SEQUENCE: 1764

Met Glu Leu Glu Glu Val Thr Arg Leu Leu Asn Leu Lys Asp Lys
1 5 10 15

<210> SEQ ID NO 1765
<211> LENGTH: 13
<212> TYPE: PRT
<213> ORGANISM: Homo sapiens

<400> SEQUENCE: 1765

Met Ile Glu Asp Ser Gly Pro Gly Met Lys Val Leu Leu
1 5 10

<210> SEQ ID NO 1766
<211> LENGTH: 10
<212> TYPE: PRT
<213> ORGANISM: Homo sapiens

<400> SEQUENCE: 1766

Met Pro Val Ala Gly Ser Glu Leu Pro Arg
1 5 10

<210> SEQ ID NO 1767
<211> LENGTH: 13
<212> TYPE: PRT
<213> ORGANISM: Homo sapiens

<400> SEQUENCE: 1767

Asn Phe Val Leu Val Leu Ser Pro Gly Ala Leu Asp Lys
1 5 10

<210> SEQ ID NO 1768
<211> LENGTH: 14
<212> TYPE: PRT
<213> ORGANISM: Homo sapiens

<400> SEQUENCE: 1768

Asn Ile Met Phe Gly Pro Asp Ile Cys Gly Pro Gly Thr Lys
1 5 10

<210> SEQ ID NO 1769
<211> LENGTH: 24
<212> TYPE: PRT
<213> ORGANISM: Homo sapiens

<400> SEQUENCE: 1769

Asn Ile Thr Ile Ile Val Glu Asp Pro Ile Ala Glu Ser Cys Asn Asp
1 5 10 15

Lys Ala Lys Leu Arg Gly Pro Leu
20

<210> SEQ ID NO 1770
<211> LENGTH: 34
<212> TYPE: PRT
<213> ORGANISM: Homo sapiens

<400> SEQUENCE: 1770

Asn Pro Lys Ala Glu Val Ala Arg Ala Gln Ala Ala Leu Ala Val Asn
1 5 10 15

Ile Ser Ala Ala Arg Gly Leu Gln Asp Val Leu Arg Thr Asn Leu Gly
20 25 30

Pro Lys

<210> SEQ ID NO 1771
<211> LENGTH: 7
<212> TYPE: PRT
<213> ORGANISM: Homo sapiens

<400> SEQUENCE: 1771

Asn Gln Val Thr Gln Leu Lys
1 5

<210> SEQ ID NO 1772
<211> LENGTH: 11
<212> TYPE: PRT
<213> ORGANISM: Homo sapiens

<400> SEQUENCE: 1772

Asn Val Ile Asn Trp Glu Asn Val Thr Glu Arg
1 5 10

<210> SEQ ID NO 1773
<211> LENGTH: 9
<212> TYPE: PRT
<213> ORGANISM: Homo sapiens

<400> SEQUENCE: 1773

Pro Gly His Tyr Asp Ile Leu Tyr Lys
1 5

<210> SEQ ID NO 1774
<211> LENGTH: 12
<212> TYPE: PRT
<213> ORGANISM: Homo sapiens

<400> SEQUENCE: 1774

Pro Gly Ser Pro Gly Leu Pro Gly Met Pro Gly Arg
1 5 10

<210> SEQ ID NO 1775
<211> LENGTH: 14
<212> TYPE: PRT
<213> ORGANISM: Homo sapiens

<400> SEQUENCE: 1775

Pro Leu Glu Glu Gly Leu Asn Lys Ala Ile His Tyr Phe Arg
1 5 10

<210> SEQ ID NO 1776
<211> LENGTH: 8
<212> TYPE: PRT
<213> ORGANISM: Homo sapiens

<400> SEQUENCE: 1776

Pro Leu Ser Thr Arg Val Pro Arg
1 5

<210> SEQ ID NO 1777
<211> LENGTH: 10
<212> TYPE: PRT
<213> ORGANISM: Homo sapiens

<400> SEQUENCE: 1777

Pro Ser Ala Gly Phe Leu Pro Thr His Arg
1 5 10

<210> SEQ ID NO 1778
<211> LENGTH: 21
<212> TYPE: PRT
<213> ORGANISM: Homo sapiens

<400> SEQUENCE: 1778

Pro Ser Gly Pro Gln Pro Gln Ala Asp Leu Gln Ala Leu Leu Gln Ser
1 5 10 15

Gly Ala Gln Val Arg
20

<210> SEQ ID NO 1779
<211> LENGTH: 29
<212> TYPE: PRT
<213> ORGANISM: Homo sapiens

<400> SEQUENCE: 1779

Pro Ser Ser Ser Gly Ser Thr Gly Thr Lys Leu Ser Pro Ala Arg Ser
1 5 10 15

Thr Thr Ser Gly Leu Val Gly Glu Ser Thr Pro Ser Arg
20 25

<210> SEQ ID NO 1780
<211> LENGTH: 29
<212> TYPE: PRT
<213> ORGANISM: Homo sapiens

<400> SEQUENCE: 1780

Pro Ser Ser Ser Gly Ser Thr Gly Thr Lys Leu Ser Pro Ala Arg Ser
1 5 10 15

Thr Thr Ser Gly Leu Val Gly Glu Ser Thr Pro Ser Arg
20 25

<210> SEQ ID NO 1781
<211> LENGTH: 13
<212> TYPE: PRT
<213> ORGANISM: Homo sapiens

<400> SEQUENCE: 1781

Gln Gly Tyr Ile Leu Asn Ser Asp Gln Thr Thr Cys Arg
1 5 10

<210> SEQ ID NO 1782
<211> LENGTH: 8
<212> TYPE: PRT
<213> ORGANISM: Homo sapiens

<400> SEQUENCE: 1782

Gln Val Phe Glu Glu Leu Trp Lys
1 5

<210> SEQ ID NO 1783
<211> LENGTH: 14
<212> TYPE: PRT
<213> ORGANISM: Homo sapiens

<400> SEQUENCE: 1783

Gln Val Lys Pro Lys Thr Val Ser Glu Glu Glu Arg Lys Val
1 5 10

<210> SEQ ID NO 1784
<211> LENGTH: 15
<212> TYPE: PRT
<213> ORGANISM: Homo sapiens

<400> SEQUENCE: 1784

Gln Tyr Ile Ser Lys Met Ile Glu Asp Ser Gly Pro Gly Met Lys
1 5 10 15

<210> SEQ ID NO 1785
<211> LENGTH: 16
<212> TYPE: PRT
<213> ORGANISM: Homo sapiens

<400> SEQUENCE: 1785

Gln Tyr Met Pro Trp Glu Ala Ala Leu Ser Ser Leu Ser Tyr Phe Lys
1 5 10 15

<210> SEQ ID NO 1786
<211> LENGTH: 21
<212> TYPE: PRT
<213> ORGANISM: Homo sapiens

<400> SEQUENCE: 1786

Arg Ala Asp Val Leu Ala Phe Pro Ser Ser Gly Phe Thr Asp Leu Ala
1 5 10 15

Glu Ile Val Ser Arg
20

<210> SEQ ID NO 1787
<211> LENGTH: 11
<212> TYPE: PRT
<213> ORGANISM: Homo sapiens

<400> SEQUENCE: 1787

Arg Ala Val Ala Ala Gln Pro Gly Arg Lys Arg
1 5 10

<210> SEQ ID NO 1788
<211> LENGTH: 20
<212> TYPE: PRT
<213> ORGANISM: Homo sapiens

<400> SEQUENCE: 1788

Arg Asp Glu Gly Ser Gln Asp Gln Thr Gly Ser Leu Ser Arg Ala Arg
1 5 10 15

Pro Ser Ser Arg
20

<210> SEQ ID NO 1789
<211> LENGTH: 20
<212> TYPE: PRT
<213> ORGANISM: Homo sapiens

<400> SEQUENCE: 1789

Arg Asp Pro Glu Val Gly Lys Asp Glu Leu Ser Lys Pro Ser Ser Asp
1 5 10 15

Ala Glu Ser Arg
20

<210> SEQ ID NO 1790
<211> LENGTH: 19
<212> TYPE: PRT
<213> ORGANISM: Homo sapiens

<400> SEQUENCE: 1790

Arg Met Gln Ser Ser Ala Asp Leu Ile Ile Gln Glu Phe Met Asp Leu
1 5 10 15

Arg Thr Arg

<210> SEQ ID NO 1791
<211> LENGTH: 10

<212> TYPE: PRT
<213> ORGANISM: Homo sapiens

<400> SEQUENCE: 1791

Ser Ala Ser Phe Glu Pro Phe Ser Asn Lys
1               5                   10

<210> SEQ ID NO 1792
<211> LENGTH: 23
<212> TYPE: PRT
<213> ORGANISM: Homo sapiens

<400> SEQUENCE: 1792

Ser Asp Gln Ile Gly Leu Pro Asp Phe Asn Ala Gly Ala Met Glu Asn
1               5                   10                  15

Trp Gly Leu Val Thr Tyr Arg
            20

<210> SEQ ID NO 1793
<211> LENGTH: 13
<212> TYPE: PRT
<213> ORGANISM: Homo sapiens

<400> SEQUENCE: 1793

Ser Phe Ala Cys Gln Cys Pro Glu Gly His Val Leu Arg
1               5                   10

<210> SEQ ID NO 1794
<211> LENGTH: 33
<212> TYPE: PRT
<213> ORGANISM: Homo sapiens

<400> SEQUENCE: 1794

Ser Phe Leu Lys Leu Ile Leu Gln Val Glu Lys Trp Gln Glu Glu Cys
1               5                   10                  15

Glu Glu Gly Glu Gly Arg Thr Ile Ile His Cys Leu Asn Gly Gly Gly
            20                  25                  30

Arg

<210> SEQ ID NO 1795
<211> LENGTH: 35
<212> TYPE: PRT
<213> ORGANISM: Homo sapiens

<400> SEQUENCE: 1795

Ser Phe Pro Ala Ala Gln Ile Pro Ile Ala Val Glu Glu Pro Gly Ser
1               5                   10                  15

Ser Ser Arg Glu Ser Val Ser Lys Ala Gly Met Pro Val Ser Ala Asp
            20                  25                  30

Ala Ala Lys
        35

<210> SEQ ID NO 1796
<211> LENGTH: 9
<212> TYPE: PRT
<213> ORGANISM: Homo sapiens

<400> SEQUENCE: 1796

Ser Phe Thr Gln Gly Glu Gly Ala Arg
1               5

<210> SEQ ID NO 1797

<211> LENGTH: 14
<212> TYPE: PRT
<213> ORGANISM: Homo sapiens

<400> SEQUENCE: 1797

Ser Phe Thr Gln Gly Glu Gly Ala Arg Pro Leu Ser Thr Arg
1 5 10

<210> SEQ ID NO 1798
<211> LENGTH: 11
<212> TYPE: PRT
<213> ORGANISM: Homo sapiens

<400> SEQUENCE: 1798

Ser His Thr Leu Ser His Ala Ser Tyr Leu Arg
1 5 10

<210> SEQ ID NO 1799
<211> LENGTH: 7
<212> TYPE: PRT
<213> ORGANISM: Homo sapiens

<400> SEQUENCE: 1799

Ser Leu Glu Gln Leu Gln Lys
1 5

<210> SEQ ID NO 1800
<211> LENGTH: 14
<212> TYPE: PRT
<213> ORGANISM: Homo sapiens

<400> SEQUENCE: 1800

Ser Pro His Thr Thr Leu Ser Pro Ala Gly Ser Thr Thr Arg
1 5 10

<210> SEQ ID NO 1801
<211> LENGTH: 14
<212> TYPE: PRT
<213> ORGANISM: Homo sapiens

<400> SEQUENCE: 1801

Ser Pro His Thr Thr Leu Ser Pro Ala Gly Ser Thr Thr Arg
1 5 10

<210> SEQ ID NO 1802
<211> LENGTH: 14
<212> TYPE: PRT
<213> ORGANISM: Homo sapiens

<400> SEQUENCE: 1802

Ser Pro His Thr Thr Leu Ser Pro Ala Gly Ser Thr Thr Arg
1 5 10

<210> SEQ ID NO 1803
<211> LENGTH: 14
<212> TYPE: PRT
<213> ORGANISM: Homo sapiens

<400> SEQUENCE: 1803

Ser Pro His Thr Thr Leu Ser Pro Ala Gly Ser Thr Thr Arg
1 5 10

<210> SEQ ID NO 1804
<211> LENGTH: 9
<212> TYPE: PRT

<213> ORGANISM: Homo sapiens

<400> SEQUENCE: 1804

Ser Gln Thr Leu Ile Asp Leu Asn Arg
1 5

<210> SEQ ID NO 1805
<211> LENGTH: 12
<212> TYPE: PRT
<213> ORGANISM: Homo sapiens

<400> SEQUENCE: 1805

Ser Ser His Asn Phe Gln Leu Glu Ser Val Asn Lys
1 5 10

<210> SEQ ID NO 1806
<211> LENGTH: 9
<212> TYPE: PRT
<213> ORGANISM: Homo sapiens

<400> SEQUENCE: 1806

Ser Thr Cys Ala Pro Ser Pro Gln Arg
1 5

<210> SEQ ID NO 1807
<211> LENGTH: 9
<212> TYPE: PRT
<213> ORGANISM: Homo sapiens

<400> SEQUENCE: 1807

Ser Thr Thr Phe Tyr Ser Ser Pro Arg
1 5

<210> SEQ ID NO 1808
<211> LENGTH: 9
<212> TYPE: PRT
<213> ORGANISM: Homo sapiens

<400> SEQUENCE: 1808

Ser Thr Thr Phe Tyr Ser Ser Pro Arg
1 5

<210> SEQ ID NO 1809
<211> LENGTH: 9
<212> TYPE: PRT
<213> ORGANISM: Homo sapiens

<400> SEQUENCE: 1809

Ser Thr Thr Phe Tyr Ser Ser Pro Arg
1 5

<210> SEQ ID NO 1810
<211> LENGTH: 9
<212> TYPE: PRT
<213> ORGANISM: Homo sapiens

<400> SEQUENCE: 1810

Ser Thr Thr Phe Tyr Ser Ser Pro Arg
1 5

<210> SEQ ID NO 1811
<211> LENGTH: 9
<212> TYPE: PRT
<213> ORGANISM: Homo sapiens

<400> SEQUENCE: 1811

Ser Thr Thr Phe Tyr Ser Ser Pro Arg
1               5

<210> SEQ ID NO 1812
<211> LENGTH: 9
<212> TYPE: PRT
<213> ORGANISM: Homo sapiens

<400> SEQUENCE: 1812

Ser Thr Thr Phe Tyr Ser Ser Pro Arg
1               5

<210> SEQ ID NO 1813
<211> LENGTH: 9
<212> TYPE: PRT
<213> ORGANISM: Homo sapiens

<400> SEQUENCE: 1813

Ser Thr Thr Phe Tyr Ser Ser Pro Arg
1               5

<210> SEQ ID NO 1814
<211> LENGTH: 9
<212> TYPE: PRT
<213> ORGANISM: Homo sapiens

<400> SEQUENCE: 1814

Ser Thr Thr Phe Tyr Ser Ser Pro Arg
1               5

<210> SEQ ID NO 1815
<211> LENGTH: 9
<212> TYPE: PRT
<213> ORGANISM: Homo sapiens

<400> SEQUENCE: 1815

Ser Thr Thr Phe Tyr Ser Ser Pro Arg
1               5

<210> SEQ ID NO 1816
<211> LENGTH: 16
<212> TYPE: PRT
<213> ORGANISM: Homo sapiens

<400> SEQUENCE: 1816

Thr Ala Thr Ala Gly Ala Ile Ser Glu Leu Thr Glu Ser Arg Leu Arg
1               5                   10                  15

<210> SEQ ID NO 1817
<211> LENGTH: 14
<212> TYPE: PRT
<213> ORGANISM: Homo sapiens

<400> SEQUENCE: 1817

Thr Glu Val Ala Ile Gly Pro Ser Val Leu Asn Ala Ala Arg
1               5                   10

<210> SEQ ID NO 1818
<211> LENGTH: 10
<212> TYPE: PRT
<213> ORGANISM: Homo sapiens

<400> SEQUENCE: 1818

Thr Gly Asp Pro Gln Glu Thr Leu Arg Arg
1 5 10

<210> SEQ ID NO 1819
<211> LENGTH: 26
<212> TYPE: PRT
<213> ORGANISM: Homo sapiens

<400> SEQUENCE: 1819

Thr His Leu Ser Leu Ser His Asn Pro Glu Gln Lys Gly Val Pro Thr
1 5 10 15

Gly Phe Ile Leu Pro Ile Arg Asp Ile Arg
20 25

<210> SEQ ID NO 1820
<211> LENGTH: 8
<212> TYPE: PRT
<213> ORGANISM: Homo sapiens

<400> SEQUENCE: 1820

Thr His Thr Ala Thr Gly Ile Arg
1 5

<210> SEQ ID NO 1821
<211> LENGTH: 10
<212> TYPE: PRT
<213> ORGANISM: Homo sapiens

<400> SEQUENCE: 1821

Thr Leu Ala Thr Gln Leu Asn Gln Gln Lys
1 5 10

<210> SEQ ID NO 1822
<211> LENGTH: 17
<212> TYPE: PRT
<213> ORGANISM: Homo sapiens

<400> SEQUENCE: 1822

Thr Pro Val Pro Glu Lys Val Pro Pro Pro Lys Pro Ala Thr Pro Asp
1 5 10 15

Phe

<210> SEQ ID NO 1823
<211> LENGTH: 10
<212> TYPE: PRT
<213> ORGANISM: Homo sapiens

<400> SEQUENCE: 1823

Thr Val Gln Gln Pro Thr Val Gln His Arg
1 5 10

<210> SEQ ID NO 1824
<211> LENGTH: 13
<212> TYPE: PRT
<213> ORGANISM: Homo sapiens

<400> SEQUENCE: 1824

Thr Tyr Gln Gly Phe Trp Asn Pro Pro Leu Ala Pro Arg
1 5 10

<210> SEQ ID NO 1825
<211> LENGTH: 37
<212> TYPE: PRT
<213> ORGANISM: Homo sapiens

<400> SEQUENCE: 1825

Val Leu Cys Gly Asp Ala Gly Leu Leu Arg Gly Leu Ala Asp Gly Leu
1               5                   10                  15

Val Gln Ala Gly Val Gly Thr Glu Ala Leu Leu Thr Pro Leu Val Gly
            20                  25                  30

Arg Leu Ala Arg Leu
        35

<210> SEQ ID NO 1826
<211> LENGTH: 37
<212> TYPE: PRT
<213> ORGANISM: Homo sapiens

<400> SEQUENCE: 1826

Val Leu Cys Gly Asp Ala Gly Leu Leu Arg Gly Leu Ala Asp Gly Leu
1               5                   10                  15

Val Gln Ala Gly Val Gly Thr Glu Ala Leu Leu Thr Pro Leu Val Gly
            20                  25                  30

Arg Leu Ala Arg Leu
        35

<210> SEQ ID NO 1827
<211> LENGTH: 10
<212> TYPE: PRT
<213> ORGANISM: Homo sapiens

<400> SEQUENCE: 1827

Val Asn Tyr Asp Glu Glu Asn Trp Arg Lys
1               5                   10

<210> SEQ ID NO 1828
<211> LENGTH: 8
<212> TYPE: PRT
<213> ORGANISM: Homo sapiens

<400> SEQUENCE: 1828

Val Pro Glu Gly Phe Thr Cys Arg
1               5

<210> SEQ ID NO 1829
<211> LENGTH: 12
<212> TYPE: PRT
<213> ORGANISM: Homo sapiens

<400> SEQUENCE: 1829

Trp Ser Glu Leu Arg Lys Lys Ser Leu Asn Ile Arg
1               5                   10

<210> SEQ ID NO 1830
<211> LENGTH: 25
<212> TYPE: PRT
<213> ORGANISM: Homo sapiens

<400> SEQUENCE: 1830

Trp Ser Ser Arg Gly Ser Gly Gly Trp Gly Val Tyr Arg Ser Pro Ser
1               5                   10                  15

Phe Gly Ala Gly Glu Gly Leu Leu Arg
            20                  25

<210> SEQ ID NO 1831
<211> LENGTH: 15

<212> TYPE: PRT
<213> ORGANISM: Homo sapiens

<400> SEQUENCE: 1831

Trp Tyr Gln Pro Ser Phe His Gly Val Asp Leu Ser Ala Leu Arg
1 5 10 15

<210> SEQ ID NO 1832
<211> LENGTH: 13
<212> TYPE: PRT
<213> ORGANISM: Homo sapiens

<400> SEQUENCE: 1832

Tyr Cys Asn Pro Gly Asp Val Cys Tyr Tyr Ala Ser Arg
1 5 10

<210> SEQ ID NO 1833
<211> LENGTH: 22
<212> TYPE: PRT
<213> ORGANISM: Homo sapiens

<400> SEQUENCE: 1833

Tyr Gly Asn Leu Gly His Val Asn Ile Gly Ala Ile Gln Glu Pro Leu
1 5 10 15

Ala Phe Ile Leu Pro Lys
20

<210> SEQ ID NO 1834
<211> LENGTH: 8
<212> TYPE: PRT
<213> ORGANISM: Homo sapiens

<400> SEQUENCE: 1834

Tyr Ile Thr Ile Ser Gly Asn Arg
1 5

<210> SEQ ID NO 1835
<211> LENGTH: 13
<212> TYPE: PRT
<213> ORGANISM: Homo sapiens

<400> SEQUENCE: 1835

Tyr Leu Ser Tyr Thr Leu Asn Pro Asp Leu Ile Arg Lys
1 5 10

<210> SEQ ID NO 1836
<211> LENGTH: 6
<212> TYPE: PRT
<213> ORGANISM: Homo sapiens

<400> SEQUENCE: 1836

Tyr Met Val Thr Glu Arg
1 5

<210> SEQ ID NO 1837
<211> LENGTH: 18
<212> TYPE: DNA
<213> ORGANISM: Artifical Sequence
<220> FEATURE:
<223> OTHER INFORMATION: Primer

<400> SEQUENCE: 1837
ggagtagata cgctccgt 18

<210> SEQ ID NO 1838
<211> LENGTH: 23
<212> TYPE: DNA
<213> ORGANISM: Artifical Sequence
<220> FEATURE:
<223> OTHER INFORMATION: Primer

<400> SEQUENCE: 1838
cacagccagt ggccgctcag gta 23

<210> SEQ ID NO 1839
<211> LENGTH: 21
<212> TYPE: DNA
<213> ORGANISM: Artifical Sequence
<220> FEATURE:
<223> OTHER INFORMATION: Primer

<400> SEQUENCE: 1839
cttctccact gccaggatgt t 21

<210> SEQ ID NO 1840
<211> LENGTH: 18
<212> TYPE: DNA
<213> ORGANISM: Artifical Sequence
<220> FEATURE:
<223> OTHER INFORMATION: Primer

<400> SEQUENCE: 1840
taggagaatg tactgtat 18

<210> SEQ ID NO 1841
<211> LENGTH: 20
<212> TYPE: DNA
<213> ORGANISM: Artifical Sequence
<220> FEATURE:
<223> OTHER INFORMATION: Primer

<400> SEQUENCE: 1841
ggagacactg gatgggagtc 20

<210> SEQ ID NO 1842
<211> LENGTH: 20
<212> TYPE: DNA
<213> ORGANISM: Artifical Sequence
<220> FEATURE:
<223> OTHER INFORMATION: Primer

<400> SEQUENCE: 1842
cgagaaacca caacctgcat 20

<210> SEQ ID NO 1843
<211> LENGTH: 19
<212> TYPE: DNA
<213> ORGANISM: Artifical Sequence
<220> FEATURE:
<223> OTHER INFORMATION: Primer

<400> SEQUENCE: 1843
tccctggaga agagctacg 19

<210> SEQ ID NO 1844
<211> LENGTH: 20
<212> TYPE: DNA
<213> ORGANISM: Artifical Sequence
<220> FEATURE:
<223> OTHER INFORMATION: Primer

<400> SEQUENCE: 1844
gtagtttcgt ggatgccaca 20

<210> SEQ ID NO 1845
<211> LENGTH: 20
<212> TYPE: DNA
<213> ORGANISM: Artifical Sequence
<220> FEATURE:
<223> OTHER INFORMATION: Primer

<400> SEQUENCE: 1845
ttgtgagtgg ttcagcggta 20

<210> SEQ ID NO 1846
<211> LENGTH: 21
<212> TYPE: DNA
<213> ORGANISM: Artifical Sequence
<220> FEATURE:
<223> OTHER INFORMATION: Primer

<400> SEQUENCE: 1846
tcaagcgaaa ccatctcttc t 21

<210> SEQ ID NO 1847
<211> LENGTH: 222
<212> TYPE: PRT
<213> ORGANISM: Homo sapiens

<400> SEQUENCE: 1847

```
Met Ala Cys Pro Trp Lys Phe Leu Phe Lys Thr Lys Phe His Gln Tyr
1               5                   10                  15

Ala Met Asn Gly Glu Lys Asp Ile Asn Asn Asn Val Glu Lys Ala Pro
            20                  25                  30

Cys Ala Thr Ser Ser Pro Val Thr Gln Asp Asp Leu Gln Tyr His Asn
        35                  40                  45

Leu Ser Lys Gln Gln Asn Glu Ser Pro Gln Pro Leu Val Glu Thr Gly
    50                  55                  60

Lys Lys Ser Pro Glu Ser Leu Val Lys Leu Asp Ala Thr Pro Leu Ser
65                  70                  75                  80

Ser Pro Arg His Val Arg Ile Lys Asn Trp Gly Ser Gly Met Thr Phe
                85                  90                  95

Gln Asp Thr Leu His His Lys Ala Lys Gly Ile Leu Thr Cys Arg Ser
            100                 105                 110

Lys Ser Cys Leu Gly Ser Ile Met Thr Pro Lys Ser Leu Thr Arg Gly
        115                 120                 125

Pro Arg Asp Lys Pro Thr Pro Pro Asp Glu Leu Leu Pro Gln Ala Ile
    130                 135                 140

Glu Phe Val Asn Gln Tyr Tyr Gly Ser Phe Lys Glu Ala Lys Ile Glu
145                 150                 155                 160

Glu His Leu Ala Arg Val Glu Ala Val Thr Lys Glu Ile Glu Thr Thr
                165                 170                 175

Gly Thr Tyr Gln Leu Thr Gly Asp Glu Leu Ile Phe Ala Thr Lys Gln
            180                 185                 190

Ala Trp Arg Asn Ala Pro Arg Cys Ile Gly Arg Ile Gln Trp Ser Asn
        195                 200                 205

Leu Gln Val Phe Asp Ala Arg Ser Cys Ser Thr Ala Arg Glu
    210                 215                 220
```

<210> SEQ ID NO 1848
<211> LENGTH: 255
<212> TYPE: PRT
<213> ORGANISM: Homo sapiens

<400> SEQUENCE: 1848

Met Gly Pro Gly Arg Pro Ala Pro Ala Pro Trp Pro Arg His Leu Leu
1 5 10 15

Arg Cys Val Leu Leu Leu Gly Cys Leu His Leu Gly Arg Pro Gly Ala
20 25 30

Pro Gly Asp Ala Ala Leu Pro Glu Pro Asn Val Phe Leu Ile Phe Ser
35 40 45

His Gly Leu Gln Gly Cys Leu Glu Ala Gln Gly Gly Gln Val Arg Val
50 55 60

Thr Pro Ala Cys Asn Thr Ser Leu Pro Ala Gln Arg Trp Lys Trp Val
65 70 75 80

Ser Arg Asn Arg Leu Phe Asn Leu Gly Thr Met Gln Cys Leu Gly Thr
85 90 95

Gly Trp Pro Gly Thr Asn Thr Thr Ala Ser Leu Gly Met Tyr Glu Cys
100 105 110

Asp Arg Glu Ala Leu Asn Leu Arg Trp His Cys Arg Thr Leu Gly Asp
115 120 125

Gln Leu Ser Leu Leu Leu Gly Ala Arg Thr Ser Asn Ile Ser Lys Pro
130 135 140

Gly Thr Leu Glu Arg Gly Asp Gln Thr Arg Ser Gly Gln Trp Arg Ile
145 150 155 160

Tyr Gly Ser Glu Glu Asp Leu Cys Ala Leu Pro Tyr His Glu Val Tyr
165 170 175

Thr Ile Gln Gly Asn Ser His Gly Lys Pro Cys Thr Ile Pro Phe Lys
180 185 190

Tyr Asp Asn Gln Trp Phe His Gly Cys Thr Ser Thr Gly Arg Glu Asp
195 200 205

Gly His Leu Trp Cys Ala Thr Thr Gln Asp Tyr Gly Lys Asp Glu Arg
210 215 220

Trp Gly Phe Cys Pro Ile Lys Ser Asn Asp Cys Glu Thr Phe Trp Asp
225 230 235 240

Lys Asp Gln Leu Thr Asp Ser Cys Tyr Gln Phe Asn Phe Gln Ser
245 250 255

<210> SEQ ID NO 1849
<211> LENGTH: 110
<212> TYPE: PRT
<213> ORGANISM: Homo sapiens

<400> SEQUENCE: 1849

Met Asn Ala Ser Ser Glu Gly Glu Ser Phe Ala Gly Ser Val Gln Ile
1 5 10 15

Pro Gly Gly Thr Thr Val Leu Val Glu Leu Thr Pro Asp Ile His Ile
20 25 30

Cys Gly Ile Cys Lys Gln Gln Phe Asn Asn Leu Asp Ala Phe Val Ala
35 40 45

His Lys Gln Ser Gly Cys Gln Leu Thr Gly Thr Ser Ala Ala Ala Pro
50 55 60

Ser Thr Val Gln Phe Val Ser Glu Glu Thr Val Pro Ala Thr Gln Thr
65 70 75 80

Gln Thr Thr Thr Arg Thr Ile Thr Ser Glu Thr Gln Thr Ile Thr Val

```
                85                  90                  95

Ser Ala Pro Glu Phe Val Phe Glu His Gly Tyr Gln Thr Tyr
            100                 105                 110


<210> SEQ ID NO 1850
<211> LENGTH: 134
<212> TYPE: PRT
<213> ORGANISM: Homo sapiens

<400> SEQUENCE: 1850

Met Glu Asp Asp Ala Pro Val Ile Tyr Gly Leu Glu Phe Gln Ala Arg
1               5                   10                  15

Ala Leu Thr Pro Gln Thr Ala Glu Thr Asp Ala Ile Arg Phe Leu Val
            20                  25                  30

Gly Thr Gln Ser Leu Lys Tyr Asp Asn Gln Ile His Ile Ile Asp Phe
        35                  40                  45

Asp Asp Glu Asn Asn Ile Ile Asn Lys Asn Val Leu Leu His Gln Ala
    50                  55                  60

Gly Glu Ile Trp His Ile Ser Ala Ser Pro Ala Asp Arg Gly Val Leu
65                  70                  75                  80

Thr Thr Cys Tyr Asn Arg Arg Asp Ile Ile Glu Ser Phe Gly Ile Leu
                85                  90                  95

Pro Val Ala Gln Ser Pro Thr Ile Val Phe Val Asn Thr Leu His Gln
            100                 105                 110

Val Phe Phe Arg Gly Gln Val Ala Ala Ser Asp Ser Lys Val Leu Thr
        115                 120                 125

Cys Ala Ala Val Trp Arg
    130


<210> SEQ ID NO 1851
<211> LENGTH: 65
<212> TYPE: PRT
<213> ORGANISM: Homo sapiens

<400> SEQUENCE: 1851

Met Leu Glu Ala Ile Leu Gly Gly Gly Gly Leu Pro Val Glu Gly Arg
1               5                   10                  15

Gly Ser Thr Glu Phe Glu Ala Phe Arg Leu Ile Leu Phe Gly Ser Glu
            20                  25                  30

Asp Ser Val Leu Pro Ser Pro Leu Leu Tyr Lys Met Ala His Met Gly
        35                  40                  45

Ser Asp Gly Gly Val Leu Pro Val His Tyr Ala Thr Ile Leu Phe Ser
    50                  55                  60

Leu
65


<210> SEQ ID NO 1852
<211> LENGTH: 255
<212> TYPE: PRT
<213> ORGANISM: Homo sapiens

<400> SEQUENCE: 1852

Met Ala Ala Ala Ala Arg Pro Arg Gly Arg Ala Leu Gly Pro Val Leu
1               5                   10                  15

Pro Pro Thr Pro Leu Leu Leu Leu Val Leu Arg Val Leu Pro Ala Cys
            20                  25                  30

Gly Ala Thr Ala Arg Asp Pro Gly Ala Ala Ala Gly Leu Ser Leu His
        35                  40                  45
```

```
Pro Thr Tyr Phe Asn Leu Ala Glu Ala Ala Arg Ile Trp Ala Thr Ala
    50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
                85                  90                  95

Ile Gln Gly Gln Phe Cys Asp Tyr Cys Asn Ser Glu Asp Pro Arg Lys
            100                 105                 110

Ala His Pro Val Thr Asn Ala Ile Asp Gly Ser Glu Arg Trp Trp Gln
        115                 120                 125

Ser Pro Pro Leu Ser Ser Gly Thr Gln Tyr Asn Arg Val Asn Leu Thr
    130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
        195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala
                245                 250                 255


<210> SEQ ID NO 1853
<211> LENGTH: 255
<212> TYPE: PRT
<213> ORGANISM: Homo sapiens

<400> SEQUENCE: 1853

Met Pro Ser Val Ser Lys Ala Ala Ala Ala Ala Leu Ser Gly Ser Pro
1               5                   10                  15

Pro Gln Thr Glu Lys Pro Thr His Tyr Arg Tyr Leu Lys Glu Phe Arg
            20                  25                  30

Thr Glu Gln Cys Pro Leu Phe Ser Gln His Lys Cys Ala Gln His Arg
        35                  40                  45

Pro Phe Thr Cys Phe His Trp His Phe Leu Asn Gln Arg Arg Arg Arg
    50                  55                  60

Pro Leu Arg Arg Arg Asp Gly Thr Phe Asn Tyr Ser Pro Asp Val Tyr
65                  70                  75                  80

Cys Ser Lys Tyr Asn Glu Ala Thr Gly Val Cys Pro Asp Gly Asp Glu
                85                  90                  95

Cys Pro Tyr Leu His Arg Thr Thr Gly Asp Thr Glu Arg Lys Tyr His
            100                 105                 110

Leu Arg Tyr Tyr Lys Thr Gly Thr Cys Ile His Glu Thr Asp Ala Arg
        115                 120                 125

Gly His Cys Val Lys Asn Gly Leu His Cys Ala Phe Ala His Gly Pro
    130                 135                 140

Leu Asp Leu Arg Pro Pro Val Cys Asp Val Arg Glu Leu Gln Ala Gln
145                 150                 155                 160

Glu Ala Leu Gln Asn Gly Gln Leu Gly Gly Gly Glu Gly Val Pro Asp
```

```
                165                 170                 175

Leu Gln Pro Gly Val Leu Ala Ser Gln Ala Met Ile Glu Lys Ile Leu
            180                 185                 190

Ser Glu Asp Pro Arg Trp Gln Asp Ala Asn Phe Val Leu Gly Ser Tyr
        195                 200                 205

Lys Thr Glu Gln Cys Pro Lys Pro Pro Arg Leu Cys Arg Gln Gly Tyr
    210                 215                 220

Ala Cys Pro His Tyr His Asn Ser Arg Asp Arg Arg Arg Asn Pro Arg
225                 230                 235                 240

Arg Phe Gln Tyr Arg Ser Thr Pro Cys Pro Ser Val Lys His Gly
                245                 250                 255


<210> SEQ ID NO 1854
<211> LENGTH: 255
<212> TYPE: PRT
<213> ORGANISM: Homo sapiens

<400> SEQUENCE: 1854

Met Ala Arg Ala Gln Ala Leu Val Leu Ala Leu Thr Phe Gln Leu Cys
1               5                   10                  15

Ala Pro Glu Thr Glu Thr Pro Ala Ala Gly Cys Thr Phe Glu Glu Ala
            20                  25                  30

Ser Asp Pro Ala Val Pro Cys Glu Tyr Ser Gln Ala Gln Tyr Asp Asp
        35                  40                  45

Phe Gln Trp Glu Gln Val Arg Ile His Pro Gly Thr Arg Ala Pro Ala
    50                  55                  60

Asp Leu Pro His Gly Ser Tyr Leu Met Val Asn Thr Ser Gln His Ala
65                  70                  75                  80

Pro Gly Gln Arg Ala His Val Ile Phe Gln Ser Leu Ser Glu Asn Asp
                85                  90                  95

Thr His Cys Val Gln Phe Ser Tyr Phe Leu Tyr Ser Arg Asp Gly His
            100                 105                 110

Ser Pro Gly Thr Leu Gly Val Tyr Val Arg Val Asn Gly Gly Pro Leu
        115                 120                 125

Gly Ser Ala Val Trp Asn Met Thr Gly Ser His Gly Arg Gln Trp His
    130                 135                 140

Gln Ala Glu Leu Ala Val Ser Thr Phe Trp Pro Asn Glu Tyr Gln Val
145                 150                 155                 160

Leu Phe Glu Ala Leu Ile Ser Pro Asp Arg Arg Gly Tyr Met Gly Leu
                165                 170                 175

Asp Asp Ile Leu Leu Leu Ser Tyr Pro Cys Ala Lys Ala Pro His Phe
            180                 185                 190

Ser Arg Leu Gly Asp Val Glu Val Asn Ala Gly Gln Asn Ala Ser Phe
        195                 200                 205

Gln Cys Met Ala Ala Gly Arg Ala Ala Glu Ala Glu Arg Phe Leu Leu
    210                 215                 220

Gln Arg Gln Ser Gly Ala Leu Val Pro Ala Ala Gly Val Arg His Ile
225                 230                 235                 240

Ser His Arg Arg Phe Leu Ala Thr Phe Pro Leu Ala Ala Val Ser
                245                 250                 255


<210> SEQ ID NO 1855
<211> LENGTH: 116
<212> TYPE: PRT
<213> ORGANISM: Homo sapiens
```

<400> SEQUENCE: 1855

Met Glu Thr Arg Glu Ser Glu Asp Leu Glu Lys Thr Arg Arg Lys Ser
1               5                   10                  15

Ala Ser Asp Gln Trp Asn Thr Asp Asn Glu Pro Ala Lys Val Lys Pro
            20                  25                  30

Glu Leu Leu Pro Glu Lys Glu Glu Thr Ser Gln Ala Asp Gln Asp Ile
        35                  40                  45

Gln Asp Lys Glu Pro His Cys His Ile Pro Ile Lys Arg Asn Ser Ile
    50                  55                  60

Phe Asn Arg Ser Ile Arg Arg Lys Ser Lys Ala Lys Ala Arg Asp Asn
65                  70                  75                  80

Pro Glu Arg Asn Ala Ser Cys Leu Ala Asp Ser Gln Asp Asn Gly Lys
                85                  90                  95

Ser Val Asn Glu Pro Leu Thr Leu Asn Ile Pro Trp Ser Arg Met Pro
            100                 105                 110

Pro Cys Arg Thr
        115

<210> SEQ ID NO 1856
<211> LENGTH: 65
<212> TYPE: PRT
<213> ORGANISM: Homo sapiens

<400> SEQUENCE: 1856

Met Thr Thr Ser Gly His Ala Cys Pro Val Pro Ala Val Asn Gly His
1               5                   10                  15

Met Thr His Tyr Pro Ala Thr Pro Tyr Pro Leu Leu Phe Pro Pro Val
            20                  25                  30

Ile Gly Gly Leu Ser Leu Pro Pro Leu His Gly Leu His Gly His Pro
        35                  40                  45

Pro Pro Ser Gly Cys Ser Thr Pro Ser Pro Ala Thr Ile Glu Thr Gln
    50                  55                  60

Ser
65

<210> SEQ ID NO 1857
<211> LENGTH: 146
<212> TYPE: PRT
<213> ORGANISM: Homo sapiens

<400> SEQUENCE: 1857

Met Thr Arg Leu Ser Trp Cys Phe Ser Cys Val Ile Arg Trp Gly Lys
1               5                   10                  15

Tyr Leu Phe Ser Cys Leu Leu Pro Leu Arg Phe Cys Leu Arg Ser Gln
            20                  25                  30

Pro Glu Asp Leu Glu Ala Pro Lys Thr His Arg Phe Lys Val Lys Thr
        35                  40                  45

Phe Lys Lys Val Lys Pro Cys Gly Ile Cys Arg Gln Val Ile Thr Gln
    50                  55                  60

Glu Gly Cys Thr Cys Lys Val Cys Ser Phe Ser Cys His Arg Lys Cys
65                  70                  75                  80

Gln Ala Lys Val Ala Ala Pro Cys Val Pro Pro Ser Asn His Glu Leu
                85                  90                  95

Val Pro Ile Thr Thr Glu Asn Ala Pro Lys Asn Val Val Asp Lys Gly
            100                 105                 110

Glu Gly Ala Ser Arg Gly Gly Asn Thr Arg Lys Ser Leu Glu Asp Asn

```
        115                 120                 125

Gly Ser Thr Arg Val Thr Pro Ser Val Gln Pro His Leu Gln Pro Ile
    130                 135                 140

Arg Asn
145


<210> SEQ ID NO 1858
<211> LENGTH: 145
<212> TYPE: PRT
<213> ORGANISM: Homo sapiens

<400> SEQUENCE: 1858

Met Lys Asn Tyr Lys Ala Ile Gly Lys Ile Gly Glu Gly Thr Phe Ser
1               5                   10                  15

Glu Val Met Lys Met Gln Ser Leu Arg Asp Gly Asn Tyr Tyr Ala Cys
            20                  25                  30

Lys Gln Met Lys Gln Arg Phe Glu Ser Ile Glu Gln Val Asn Asn Leu
        35                  40                  45

Arg Glu Ile Gln Ala Leu Arg Arg Leu Asn Pro His Pro Asn Ile Leu
    50                  55                  60

Met Leu His Glu Val Val Phe Asp Arg Lys Ser Gly Ser Leu Ala Leu
65                  70                  75                  80

Ile Cys Glu Leu Met Asp Met Asn Ile Tyr Glu Leu Ile Arg Gly Arg
                85                  90                  95

Arg Tyr Pro Leu Ser Glu Lys Lys Ile Met His Tyr Met Tyr Gln Leu
            100                 105                 110

Cys Lys Ser Leu Asp His Ile His Arg Asn Gly Ile Phe His Arg Asp
        115                 120                 125

Val Lys Pro Glu Asn Ile Leu Ile Lys Gln Asp Val Leu Lys Leu Gly
    130                 135                 140

Asp
145


<210> SEQ ID NO 1859
<211> LENGTH: 32
<212> TYPE: PRT
<213> ORGANISM: Homo sapiens

<400> SEQUENCE: 1859

Met Ala Arg Pro Gly Leu Ile His Ser Ala Pro Gly Leu Pro Asp Thr
1               5                   10                  15

Cys Ala Leu Leu Gln Pro Pro Ala Ala Ser Ala Ala Ala Ala Pro Ser
            20                  25                  30


<210> SEQ ID NO 1860
<211> LENGTH: 255
<212> TYPE: PRT
<213> ORGANISM: Homo sapiens

<400> SEQUENCE: 1860

Met Pro Thr Trp Gly Ala Arg Pro Ala Ser Pro Asp Arg Phe Ala Val
1               5                   10                  15

Ser Ala Glu Ala Glu Asn Lys Val Arg Glu Gln Gln Pro His Val Glu
            20                  25                  30

Arg Ile Phe Ser Val Gly Val Ser Val Leu Pro Lys Asp Cys Pro Asp
        35                  40                  45

Asn Pro His Ile Trp Leu Gln Leu Glu Gly Pro Lys Glu Asn Ala Ser
    50                  55                  60
```

Arg Ala Lys Glu Tyr Leu Lys Gly Leu Cys Ser Pro Glu Leu Gln Asp
65 70 75 80

Glu Ile His Tyr Pro Pro Lys Leu His Cys Ile Phe Leu Gly Ala Gln
85 90 95

Gly Phe Phe Leu Asp Cys Leu Ala Trp Ser Thr Ser Ala His Leu Val
100 105 110

Pro Arg Ala Pro Gly Ser Leu Met Ile Ser Gly Leu Thr Glu Ala Phe
115 120 125

Val Met Ala Gln Ser Arg Val Glu Glu Leu Ala Glu Arg Leu Ser Trp
130 135 140

Asp Phe Thr Pro Gly Pro Ser Ser Gly Ala Ser Gln Cys Thr Gly Val
145 150 155 160

Leu Arg Asp Phe Ser Ala Leu Leu Gln Ser Pro Gly Asp Ala His Arg
165 170 175

Glu Ala Leu Leu Gln Leu Pro Leu Ala Val Gln Glu Glu Leu Leu Ser
180 185 190

Leu Val Gln Glu Ala Ser Ser Gly Gln Gly Pro Gly Ala Leu Ala Ser
195 200 205

Trp Glu Gly Arg Ser Ser Ala Leu Leu Gly Ala Gln Cys Gln Gly Val
210 215 220

Arg Ala Pro Pro Ser Asp Gly Arg Glu Ser Leu Asp Thr Gly Ser Met
225 230 235 240

Gly Pro Gly Asp Cys Arg Gly Ala Arg Gly Asp Thr Tyr Ala Val
245 250 255

<210> SEQ ID NO 1861
<211> LENGTH: 255
<212> TYPE: PRT
<213> ORGANISM: Homo sapiens

<400> SEQUENCE: 1861

Met Val Leu Tyr Thr Thr Pro Phe Pro Asn Ser Cys Leu Ser Ala Leu
1 5 10 15

His Cys Val Ser Trp Ala Leu Ile Phe Pro Cys Tyr Trp Leu Val Asp
20 25 30

Arg Leu Ala Ala Ser Phe Ile Pro Thr Thr Tyr Glu Lys Arg Gln Arg
35 40 45

Ala Asp Asp Pro Cys Cys Leu Gln Leu Leu Cys Thr Ala Leu Phe Thr
50 55 60

Pro Ile Tyr Leu Ala Leu Leu Val Ala Ser Leu Pro Phe Ala Phe Leu
65 70 75 80

Gly Phe Leu Phe Trp Ser Pro Leu Gln Ser Ala Arg Arg Pro Tyr Ile
85 90 95

Tyr Ser Arg Leu Glu Asp Lys Gly Leu Ala Gly Gly Ala Ala Leu Leu
100 105 110

Ser Glu Trp Lys Gly Thr Gly Pro Gly Lys Ser Phe Cys Phe Ala Thr
115 120 125

Ala Asn Val Cys Leu Leu Pro Asp Ser Leu Ala Arg Val Asn Asn Leu
130 135 140

Phe Asn Thr Gln Ala Arg Ala Lys Glu Ile Gly Gln Arg Ile Arg Asn
145 150 155 160

Gly Ala Ala Arg Pro Gln Ile Lys Ile Tyr Ile Asp Ser Pro Thr Asn
165 170 175

Thr Ser Ile Ser Ala Ala Ser Phe Ser Ser Leu Val Ser Pro Gln Gly 180 185 190

Gly Asp Gly Val Ala Arg Ala Val Pro Gly Ser Ile Lys Arg Thr Ala
195 200 205

Ser Val Glu Tyr Lys Gly Asp Gly Gly Arg His Pro Gly Asp Glu Ala
210 215 220

Ala Asn Gly Pro Ala Ser Gly Asp Pro Val Asp Ser Ser Ser Pro Glu
225 230 235 240

Asp Ala Cys Ile Val Arg Ile Gly Gly Glu Glu Gly Gly Arg Pro
245 250 255

<210> SEQ ID NO 1862
<211> LENGTH: 255
<212> TYPE: PRT
<213> ORGANISM: Homo sapiens

<400> SEQUENCE: 1862

Met Leu Gly Ala Gly Leu Ile Lys Ile Arg Gly Asp Arg Cys Trp Arg
1 5 10 15

Asp Leu Thr Cys Met Asp Phe His Tyr Glu Thr Gln Pro Met Pro Asn
20 25 30

Pro Val Ala Tyr Tyr Leu His His Ser Pro Trp Trp Phe His Arg Phe
35 40 45

Glu Thr Leu Ser Asn His Phe Ile Glu Leu Leu Val Pro Phe Phe Leu
50 55 60

Phe Leu Gly Arg Arg Ala Cys Ile Ile His Gly Val Leu Gln Ile Leu
65 70 75 80

Phe Gln Ala Val Leu Ile Val Ser Gly Asn Leu Ser Phe Leu Asn Trp
85 90 95

Leu Thr Met Val Pro Ser Leu Ala Cys Phe Asp Asp Ala Thr Leu Gly
100 105 110

Phe Leu Phe Pro Ser Gly Pro Gly Ser Leu Lys Asp Arg Val Leu Gln
115 120 125

Met Gln Arg Asp Ile Arg Gly Ala Arg Pro Glu Pro Arg Phe Gly Ser
130 135 140

Val Val Arg Arg Ala Ala Asn Val Ser Leu Gly Val Leu Leu Ala Trp
145 150 155 160

Leu Ser Val Pro Val Val Leu Asn Leu Leu Ser Ser Arg Gln Val Met
165 170 175

Asn Thr His Phe Asn Ser Leu His Ile Val Asn Thr Tyr Gly Ala Phe
180 185 190

Gly Ser Ile Thr Lys Glu Arg Ala Glu Val Ile Leu Gln Gly Thr Ala
195 200 205

Ser Ser Asn Ala Ser Ala Pro Asp Ala Met Trp Glu Asp Tyr Glu Phe
210 215 220

Lys Cys Lys Pro Gly Asp Pro Ser Arg Arg Pro Cys Leu Ile Ser Pro
225 230 235 240

Tyr His Tyr Arg Leu Asp Trp Leu Met Trp Phe Ala Ala Phe Gln
245 250 255

<210> SEQ ID NO 1863
<211> LENGTH: 255
<212> TYPE: PRT
<213> ORGANISM: Homo sapiens

<400> SEQUENCE: 1863

Met Glu Gly Ser Arg Pro Arg Ser Ser Leu Ser Leu Ala Ser Ser Ala

```
1               5                   10                  15

Ser Thr Ile Ser Ser Leu Ser Ser Leu Ser Pro Lys Lys Pro Thr Arg
            20                  25                  30

Ala Val Asn Lys Ile His Ala Phe Gly Lys Arg Gly Asn Ala Leu Arg
        35                  40                  45

Arg Asp Pro Asn Leu Pro Val His Ile Arg Gly Trp Leu His Lys Gln
    50                  55                  60

Asp Ser Ser Gly Leu Arg Leu Trp Lys Arg Arg Trp Phe Val Leu Ser
65                  70                  75                  80

Gly His Cys Leu Phe Tyr Tyr Lys Asp Ser Arg Glu Glu Ser Val Leu
                85                  90                  95

Gly Ser Val Leu Leu Pro Ser Tyr Asn Ile Arg Pro Asp Gly Pro Gly
            100                 105                 110

Ala Pro Arg Gly Arg Arg Phe Thr Phe Thr Ala Glu His Pro Gly Met
        115                 120                 125

Arg Thr Tyr Val Leu Ala Ala Asp Thr Leu Glu Asp Leu Arg Gly Trp
    130                 135                 140

Leu Arg Ala Leu Gly Arg Ala Ser Arg Ala Glu Gly Asp Asp Tyr Gly
145                 150                 155                 160

Gln Pro Arg Ser Pro Ala Arg Pro Gln Pro Gly Glu Gly Pro Gly Gly
                165                 170                 175

Pro Gly Gly Pro Pro Glu Val Ser Arg Gly Glu Glu Gly Arg Ile Ser
            180                 185                 190

Glu Ser Pro Glu Val Thr Arg Leu Ser Arg Gly Arg Gly Arg Pro Arg
        195                 200                 205

Leu Leu Thr Pro Ser Pro Thr Thr Asp Leu His Ser Gly Leu Gln Met
    210                 215                 220

Arg Arg Ala Arg Ser Pro Asp Leu Phe Thr Pro Leu Ser Arg Pro Pro
225                 230                 235                 240

Ser Pro Leu Ser Leu Pro Arg Pro Arg Ser Ala Pro Ala Arg Arg
                245                 250                 255
```

<210> SEQ ID NO 1864
<211> LENGTH: 255
<212> TYPE: PRT
<213> ORGANISM: Homo sapiens

<400> SEQUENCE: 1864

```
Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125
```

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His
                245                 250                 255

<210> SEQ ID NO 1865
<211> LENGTH: 82
<212> TYPE: PRT
<213> ORGANISM: Homo sapiens

<400> SEQUENCE: 1865

Met Gln Ala Pro Val Pro His Ser Gln Arg Arg Glu Ser Phe Leu Tyr
1               5                   10                  15

Arg Ser Asp Ser Asp Tyr Glu Leu Ser Pro Lys Ala Met Ser Arg Asn
            20                  25                  30

Ser Ser Val Ala Ser Asp Leu His Gly Glu Asp Met Ile Val Thr Pro
        35                  40                  45

Phe Ala Gln Val Leu Ala Ser Leu Arg Thr Val Arg Ser Asn Val Ala
    50                  55                  60

Ala Leu Ala Arg Gln Gln Cys Leu Gly Ala Ala Lys Gln Gly Pro Val
65                  70                  75                  80

Gly Asn

<210> SEQ ID NO 1866
<211> LENGTH: 98
<212> TYPE: PRT
<213> ORGANISM: Homo sapiens

<400> SEQUENCE: 1866

Met Ala Lys Glu Arg Arg Arg Ala Val Leu Glu Leu Leu Gln Arg Pro
1               5                   10                  15

Gly Asn Ala Arg Cys Ala Asp Cys Gly Ala Pro Asp Pro Asp Trp Ala
            20                  25                  30

Ser Tyr Thr Leu Gly Val Phe Ile Cys Leu Ser Cys Ser Gly Ile His
        35                  40                  45

Arg Asn Ile Pro Gln Val Ser Lys Val Lys Ser Val Arg Leu Asp Ala
    50                  55                  60

Trp Glu Glu Ala Gln Val Glu Phe Met Ala Ser His Gly Asn Asp Ala
65                  70                  75                  80

Ala Arg Ala Arg Phe Glu Ser Lys Val Pro Ser Phe Tyr Tyr Arg Pro
                85                  90                  95

Thr Pro

<210> SEQ ID NO 1867

<211> LENGTH: 255
<212> TYPE: PRT
<213> ORGANISM: Homo sapiens

<400> SEQUENCE: 1867

Met Lys Ala Pro Ala Val Leu Ala Pro Gly Ile Leu Val Leu Leu Phe
1 5 10 15

Thr Leu Val Gln Arg Ser Asn Gly Glu Cys Lys Glu Ala Leu Ala Lys
20 25 30

Ser Glu Met Asn Val Asn Met Lys Tyr Gln Leu Pro Asn Phe Thr Ala
35 40 45

Glu Thr Pro Ile Gln Asn Val Ile Leu His Glu His His Ile Phe Leu
50 55 60

Gly Ala Thr Asn Tyr Ile Tyr Val Leu Asn Glu Glu Asp Leu Gln Lys
65 70 75 80

Val Ala Glu Tyr Lys Thr Gly Pro Val Leu Glu His Pro Asp Cys Phe
85 90 95

Pro Cys Gln Asp Cys Ser Ser Lys Ala Asn Leu Ser Gly Gly Val Trp
100 105 110

Lys Asp Asn Ile Asn Met Ala Leu Val Val Asp Thr Tyr Tyr Asp Asp
115 120 125

Gln Leu Ile Ser Cys Gly Ser Val Asn Arg Gly Thr Cys Gln Arg His
130 135 140

Val Phe Pro His Asn His Thr Ala Asp Ile Gln Ser Glu Val His Cys
145 150 155 160

Ile Phe Ser Pro Gln Ile Glu Glu Pro Ser Gln Cys Pro Asp Cys Val
165 170 175

Val Ser Ala Leu Gly Ala Lys Val Leu Ser Ser Val Lys Asp Arg Phe
180 185 190

Ile Asn Phe Phe Val Gly Asn Thr Ile Asn Ser Ser Tyr Phe Pro Asp
195 200 205

His Pro Leu His Ser Ile Ser Val Arg Arg Leu Lys Glu Thr Lys Asp
210 215 220

Gly Phe Met Phe Leu Thr Asp Gln Ser Tyr Ile Asp Val Leu Pro Glu
225 230 235 240

Phe Arg Asp Ser Tyr Pro Ile Lys Tyr Val His Ala Phe Glu Ser
245 250 255

<210> SEQ ID NO 1868
<211> LENGTH: 37
<212> TYPE: PRT
<213> ORGANISM: Homo sapiens

<400> SEQUENCE: 1868

Met Ala Thr His His Thr Leu Trp Met Gly Leu Ala Leu Leu Gly Val
1 5 10 15

Leu Gly Asp Leu Gln Ala Ala Pro Glu Ala Gln Val Ser Val Gln Pro
20 25 30

Asn Phe Gln Gln Asp
35

<210> SEQ ID NO 1869
<211> LENGTH: 28
<212> TYPE: PRT
<213> ORGANISM: Homo sapiens

<400> SEQUENCE: 1869

```
Met Asp Gln His Gln His Leu Asn Lys Thr Ala Glu Ser Ala Ser Ser
1               5                   10                  15

Glu Lys Lys Lys Thr Arg Arg Cys Asn Gly Phe Lys
            20                  25


<210> SEQ ID NO 1870
<211> LENGTH: 255
<212> TYPE: PRT
<213> ORGANISM: Homo sapiens

<400> SEQUENCE: 1870

Met Trp Gly Arg Phe Leu Ala Pro Glu Ala Ser Gly Arg Asp Ser Pro
1               5                   10                  15

Gly Gly Ala Arg Ser Phe Pro Ala Gly Pro Asp Tyr Ser Ser Ala Trp
            20                  25                  30

Leu Pro Ala Asn Glu Ser Leu Trp Gln Ala Thr Thr Val Pro Ser Asn
        35                  40                  45

His Arg Asn Asn His Ile Arg Arg His Ser Ile Ala Ser Asp Ser Gly
    50                  55                  60

Asp Thr Gly Ile Gly Thr Ser Cys Ser Asp Ser Val Glu Asp His Ser
65                  70                  75                  80

Thr Ser Ser Gly Thr Leu Ser Phe Lys Pro Ser Gln Ser Leu Ile Thr
                85                  90                  95

Leu Pro Thr Ala His Val Met Pro Ser Asn Ser Ser Ala Ser Ile Ser
            100                 105                 110

Lys Leu Arg Glu Ser Leu Thr Pro Asp Gly Ser Lys Trp Ser Thr Ser
        115                 120                 125

Leu Met Gln Thr Leu Gly Asn His Ser Arg Gly Glu Gln Asp Ser Ser
    130                 135                 140

Leu Asp Met Lys Asp Phe Arg Pro Leu Arg Lys Trp Ser Ser Leu Ser
145                 150                 155                 160

Lys Leu Thr Ala Pro Asp Asn Cys Gly Gln Gly Gly Thr Val Cys Arg
                165                 170                 175

Glu Glu Ser Arg Asn Gly Leu Glu Lys Ile Gly Lys Ala Lys Ala Leu
            180                 185                 190

Thr Ser Gln Leu Arg Thr Ile Gly Pro Ser Cys Leu His Asp Ser Met
        195                 200                 205

Glu Met Leu Arg Leu Glu Asp Lys Glu Ile Asn Lys Lys Arg Ser Ser
    210                 215                 220

Thr Leu Asp Cys Lys Tyr Lys Phe Glu Ser Cys Ser Lys Glu Asp Phe
225                 230                 235                 240

Arg Ala Ser Ser Ser Thr Leu Arg Arg Gln Pro Val Asp Met Thr
                245                 250                 255


<210> SEQ ID NO 1871
<211> LENGTH: 237
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1871

Xaa Glu Lys Thr Cys Ser Ser Leu Glu Arg Glu Pro His Phe Ser Leu
1               5                   10                  15

Leu Thr Met Arg Gly Gln Arg Leu Pro Leu Asp Ile Gln Ile Phe Tyr
            20                  25                  30
```

```
Cys Ala Arg Pro Asp Glu Glu Pro Phe Val Lys Ile Ile Thr Val Glu
        35                  40                  45

Glu Ala Lys Arg Arg Lys Ser Thr Cys Ser Tyr Tyr Glu Asp Glu Asp
    50                  55                  60

Glu Glu Val Leu Pro Val Leu Arg Pro His Ser Ala Leu Leu Glu Asn
65                  70                  75                  80

Met His Ile Glu Gln Leu Ala Arg Arg Leu Pro Ala Arg Val Gln Gly
                85                  90                  95

Tyr Pro Trp Arg Leu Ala Tyr Ser Thr Leu Glu His Gly Thr Ser Leu
            100                 105                 110

Lys Thr Leu Tyr Arg Lys Ser Ala Ser Leu Asp Ser Pro Val Leu Leu
        115                 120                 125

Val Ile Lys Asp Met Asp Asn Gln Ile Phe Gly Ala Tyr Ala Thr His
    130                 135                 140

Pro Phe Lys Phe Ser Asp His Tyr Tyr Gly Thr Gly Glu Thr Phe Leu
145                 150                 155                 160

Tyr Thr Phe Ser Pro His Phe Lys Val Phe Lys Trp Ser Gly Glu Asn
                165                 170                 175

Ser Tyr Phe Ile Asn Gly Asp Ile Ser Ser Leu Glu Leu Gly Gly Gly
            180                 185                 190

Gly Gly Arg Phe Gly Leu Trp Leu Asp Ala Asp Leu Tyr His Gly Arg
        195                 200                 205

Ser Asn Ser Cys Ser Thr Phe Asn Asn Asp Ile Leu Ser Lys Lys Glu
    210                 215                 220

Asp Phe Ile Val Gln Asp Leu Glu Val Trp Ala Phe Asp
225                 230                 235


<210> SEQ ID NO 1872
<211> LENGTH: 255
<212> TYPE: PRT
<213> ORGANISM: Homo sapiens

<400> SEQUENCE: 1872

Met Glu Gln Pro Gln Glu Glu Ala Pro Glu Val Arg Glu Glu Glu Glu
1               5                   10                  15

Lys Glu Glu Val Ala Glu Ala Glu Gly Ala Pro Glu Leu Asn Gly Gly
            20                  25                  30

Pro Gln His Ala Leu Pro Ser Ser Ser Tyr Thr Asp Leu Ser Arg Ser
        35                  40                  45

Ser Ser Pro Pro Ser Leu Leu Asp Gln Leu Gln Met Gly Cys Asp Gly
    50                  55                  60

Ala Ser Cys Gly Ser Leu Asn Met Glu Cys Arg Val Cys Gly Asp Lys
65                  70                  75                  80

Ala Ser Gly Phe His Tyr Gly Val His Ala Cys Glu Gly Cys Lys Gly
                85                  90                  95

Phe Phe Arg Arg Thr Ile Arg Met Lys Leu Glu Tyr Glu Lys Cys Glu
            100                 105                 110

Arg Ser Cys Lys Ile Gln Lys Lys Asn Arg Asn Lys Cys Gln Tyr Cys
        115                 120                 125

Arg Phe Gln Lys Cys Leu Ala Leu Gly Met Ser His Asn Ala Ile Arg
    130                 135                 140

Phe Gly Arg Met Pro Glu Ala Glu Lys Arg Lys Leu Val Ala Gly Leu
145                 150                 155                 160

Thr Ala Asn Glu Gly Ser Gln Tyr Asn Pro Gln Val Ala Asp Leu Lys
```

```
                165                 170                 175

Ala Phe Ser Lys His Ile Tyr Asn Ala Tyr Leu Lys Asn Phe Asn Met
            180                 185                 190

Thr Lys Lys Lys Ala Arg Ser Ile Leu Thr Gly Lys Ala Ser His Thr
        195                 200                 205

Ala Pro Phe Val Ile His Asp Ile Glu Thr Leu Trp Gln Ala Glu Lys
    210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu
                245                 250                 255


<210> SEQ ID NO 1873
<211> LENGTH: 255
<212> TYPE: PRT
<213> ORGANISM: Homo sapiens

<400> SEQUENCE: 1873

Met Met Asp Ile Tyr Val Cys Leu Lys Arg Pro Ser Trp Met Val Asp
1               5                   10                  15

Asn Lys Arg Met Arg Thr Ala Ser Asn Phe Gln Trp Leu Leu Ser Thr
            20                  25                  30

Phe Ile Leu Leu Tyr Leu Met Asn Gln Val Asn Ser Gln Lys Lys Gly
        35                  40                  45

Ala Pro His Asp Leu Lys Cys Val Thr Asn Asn Leu Gln Val Trp Asn
    50                  55                  60

Cys Ser Trp Lys Ala Pro Ser Gly Thr Gly Arg Gly Thr Asp Tyr Glu
65                  70                  75                  80

Val Cys Ile Glu Asn Arg Ser Arg Ser Cys Tyr Gln Leu Glu Lys Thr
                85                  90                  95

Ser Ile Lys Ile Pro Ala Leu Ser His Gly Asp Tyr Glu Ile Thr Ile
            100                 105                 110

Asn Ser Leu His Asp Phe Gly Ser Ser Thr Ser Lys Phe Thr Leu Asn
        115                 120                 125

Glu Gln Asn Val Ser Leu Ile Pro Asp Thr Pro Glu Ile Leu Asn Leu
    130                 135                 140

Ser Ala Asp Phe Ser Thr Ser Thr Leu Tyr Leu Lys Trp Asn Asp Arg
145                 150                 155                 160

Gly Ser Val Phe Pro His Arg Ser Asn Val Ile Trp Glu Ile Lys Val
                165                 170                 175

Leu Arg Lys Glu Ser Met Glu Leu Val Lys Leu Val Thr His Asn Thr
            180                 185                 190

Thr Leu Asn Gly Lys Asp Thr Leu His His Trp Ser Trp Ala Ser Asp
        195                 200                 205

Met Pro Leu Glu Cys Ala Ile His Phe Val Glu Ile Arg Cys Tyr Ile
    210                 215                 220

Asp Asn Leu His Phe Ser Gly Leu Glu Glu Trp Ser Asp Trp Ser Pro
225                 230                 235                 240

Val Lys Asn Ile Ser Trp Ile Pro Asp Ser Gln Thr Lys Val Phe
                245                 250                 255


<210> SEQ ID NO 1874
<211> LENGTH: 245
<212> TYPE: PRT
<213> ORGANISM: Homo sapiens
```

<400> SEQUENCE: 1874

Met Ala Ser Val Phe Met Cys Gly Val Glu Asp Leu Leu Phe Ser Gly
1 5 10 15

Ser Arg Phe Val Trp Asn Leu Thr Val Ser Thr Leu Arg Arg Trp Tyr
20 25 30

Thr Glu Arg Leu Arg Ala Cys His Gln Val Leu Arg Thr Trp Cys Gly
35 40 45

Leu Gln Asp Val Tyr Gln Met Thr Glu Gly Arg His Cys Gln Val His
50 55 60

Leu Leu Asp Asp Arg Arg Leu Glu Leu Leu Val Gln Pro Lys Leu Leu
65 70 75 80

Ala Arg Glu Leu Leu Asp Leu Val Ala Ser His Phe Asn Leu Lys Glu
85 90 95

Lys Glu Tyr Phe Gly Ile Thr Phe Ile Asp Asp Thr Gly Gln Gln Asn
100 105 110

Trp Leu Gln Leu Asp His Arg Val Leu Asp His Asp Leu Pro Lys Lys
115 120 125

Pro Gly Pro Thr Ile Leu His Phe Ala Val Arg Phe Tyr Ile Glu Ser
130 135 140

Ile Ser Phe Leu Lys Asp Lys Thr Thr Val Glu Leu Phe Phe Leu Asn
145 150 155 160

Ala Lys Ala Cys Val His Lys Gly Gln Ile Glu Val Glu Ser Glu Thr
165 170 175

Ile Phe Lys Leu Ala Ala Phe Ile Leu Gln Glu Ala Lys Gly Asp Tyr
180 185 190

Thr Ser Asp Glu Asn Ala Arg Lys Asp Leu Lys Thr Leu Pro Ala Phe
195 200 205

Pro Thr Lys Thr Leu Gln Glu His Pro Ser Leu Ala Tyr Cys Glu Asp
210 215 220

Arg Val Ile Glu His Tyr Leu Lys Ile Lys Gly Leu Thr Arg Gly Gln
225 230 235 240

Ala Val Val Gln Tyr
245

<210> SEQ ID NO 1875
<211> LENGTH: 255
<212> TYPE: PRT
<213> ORGANISM: Homo sapiens

<400> SEQUENCE: 1875

Met Lys Lys Phe Phe Asp Ser Arg Arg Glu Gln Gly Gly Ser Gly Leu
1 5 10 15

Gly Ser Gly Ser Ser Gly Gly Gly Gly Ser Thr Ser Gly Leu Gly Ser
20 25 30

Gly Tyr Ile Gly Arg Val Phe Gly Ile Gly Arg Gln Gln Val Thr Val
35 40 45

Asp Glu Val Leu Ala Glu Gly Gly Phe Ala Ile Val Phe Leu Val Arg
50 55 60

Thr Ser Asn Gly Met Lys Cys Ala Leu Lys Arg Met Phe Val Asn Asn
65 70 75 80

Glu His Asp Leu Gln Val Cys Lys Arg Glu Ile Gln Ile Met Arg Asp
85 90 95

Leu Ser Gly His Lys Asn Ile Val Gly Tyr Ile Asp Ser Ser Ile Asn
100 105 110

Asn Val Ser Ser Gly Asp Val Trp Glu Val Leu Ile Leu Met Asp Phe
        115                 120                 125

Cys Arg Gly Gly Gln Val Val Asn Leu Met Asn Gln Arg Leu Gln Thr
    130                 135                 140

Gly Phe Thr Glu Asn Glu Val Leu Gln Ile Phe Cys Asp Thr Cys Glu
145                 150                 155                 160

Ala Val Ala Arg Leu His Gln Cys Lys Thr Pro Ile Ile His Arg Asp
                165                 170                 175

Leu Lys Val Glu Asn Ile Leu Leu His Asp Arg Gly His Tyr Val Leu
            180                 185                 190

Cys Asp Phe Gly Ser Ala Thr Asn Lys Phe Gln Asn Pro Gln Thr Glu
        195                 200                 205

Gly Val Asn Ala Val Glu Asp Glu Ile Lys Lys Tyr Thr Thr Leu Ser
    210                 215                 220

Tyr Arg Ala Pro Glu Met Val Asn Leu Tyr Ser Gly Lys Ile Ile Thr
225                 230                 235                 240

Thr Lys Ala Asp Ile Trp Ala Leu Gly Cys Leu Leu Tyr Lys Leu
                245                 250                 255

<210> SEQ ID NO 1876
<211> LENGTH: 40
<212> TYPE: PRT
<213> ORGANISM: Homo sapiens

<400> SEQUENCE: 1876

Met Ser Ser Asn Ser Asp Thr Gly Asp Leu Gln Glu Ser Leu Lys His
1               5                   10                  15

Gly Leu Thr Pro Ile Gly Ala Gly Leu Pro Asp Arg His Gly Ser Pro
            20                  25                  30

Ile Pro Ala Arg Gly Arg Leu Val
        35                  40

<210> SEQ ID NO 1877
<211> LENGTH: 36
<212> TYPE: PRT
<213> ORGANISM: Homo sapiens

<400> SEQUENCE: 1877

Met Asp Ala Gly Lys Leu Ala Arg His Pro Thr Asp Thr Gly Ser Glu
1               5                   10                  15

Arg Ala Val Pro Ala Leu Ala Glu Ile Arg Pro Trp Trp Ala Pro Pro
            20                  25                  30

Leu Arg Pro Gln
        35

<210> SEQ ID NO 1878
<211> LENGTH: 255
<212> TYPE: PRT
<213> ORGANISM: Homo sapiens

<400> SEQUENCE: 1878

Met Lys Ala Ala Tyr Thr Ala Tyr Arg Cys Leu Thr Lys Asp Leu Glu
1               5                   10                  15

Gly Cys Ala Met Asn Pro Glu Leu Thr Met Glu Ser Leu Gly Thr Leu
            20                  25                  30

His Gly Pro Ala Gly Gly Gly Ser Gly Gly Gly Gly Gly Gly Gly Gly
        35                  40                  45

Gly Gly Gly Gly Gly Gly Pro Gly His Glu Gln Glu Leu Leu Ala Ser

```
    50                  55                  60

Pro Ser Pro His His Ala Gly Arg Gly Ala Ala Gly Ser Leu Arg Gly
65                  70                  75                  80

Pro Pro Pro Pro Pro Thr Ala His Gln Glu Leu Gly Thr Ala Ala Ala
                85                  90                  95

Ala Ala Ala Ala Ala Ser Arg Ser Ala Met Val Thr Ser Met Ala Ser
            100                 105                 110

Ile Leu Asp Gly Gly Asp Tyr Arg Pro Glu Leu Ser Ile Pro Leu His
        115                 120                 125

His Ala Met Ser Met Ser Cys Asp Ser Ser Pro Pro Gly Met Gly Met
    130                 135                 140

Ser Asn Thr Tyr Thr Thr Leu Thr Pro Leu Gln Pro Leu Pro Pro Ile
145                 150                 155                 160

Ser Thr Val Ser Asp Lys Phe His His Pro His Pro His His His Pro
                165                 170                 175

His His His His His His His His Gln Arg Leu Ser Gly Asn Val Ser
            180                 185                 190

Gly Ser Phe Thr Leu Met Arg Asp Glu Arg Gly Leu Pro Ala Met Asn
        195                 200                 205

Asn Leu Tyr Ser Pro Tyr Lys Glu Met Pro Gly Met Ser Gln Ser Leu
    210                 215                 220

Ser Pro Leu Ala Ala Thr Pro Leu Gly Asn Gly Leu Gly Gly Leu His
225                 230                 235                 240

Asn Ala Gln Gln Ser Leu Pro Asn Tyr Gly Pro Pro Gly His Asp
                245                 250                 255


<210> SEQ ID NO 1879
<211> LENGTH: 255
<212> TYPE: PRT
<213> ORGANISM: Homo sapiens

<400> SEQUENCE: 1879

Met Asp Glu Lys Thr Lys Lys Ala Glu Glu Met Ala Leu Ser Leu Thr
1               5                   10                  15

Arg Ala Val Ala Gly Gly Asp Glu Gln Val Ala Met Lys Cys Ala Ile
            20                  25                  30

Trp Leu Ala Glu Gln Arg Val Pro Leu Ser Val Gln Leu Lys Pro Glu
        35                  40                  45

Val Ser Pro Thr Gln Asp Ile Arg Leu Trp Val Ser Val Glu Asp Ala
    50                  55                  60

Gln Met His Thr Val Thr Ile Trp Leu Thr Val Arg Pro Asp Met Thr
65                  70                  75                  80

Val Ala Ser Leu Lys Asp Met Val Phe Leu Asp Tyr Gly Phe Pro Pro
                85                  90                  95

Val Leu Gln Gln Trp Val Ile Gly Gln Arg Leu Ala Arg Asp Gln Glu
            100                 105                 110

Thr Leu His Ser His Gly Val Arg Gln Asn Gly Asp Ser Ala Tyr Leu
        115                 120                 125

Tyr Leu Leu Ser Ala Arg Asn Thr Ser Leu Asn Pro Gln Glu Leu Gln
    130                 135                 140

Arg Glu Arg Gln Leu Arg Met Leu Glu Asp Leu Gly Phe Lys Asp Leu
145                 150                 155                 160

Thr Leu Gln Pro Arg Gly Pro Leu Glu Pro Gly Pro Pro Lys Pro Gly
                165                 170                 175
```

Val Pro Gln Glu Pro Gly Arg Gly Gln Pro Asp Ala Val Pro Glu Pro
180 185 190

Pro Pro Val Gly Trp Gln Cys Pro Gly Cys Thr Phe Ile Asn Lys Pro
195 200 205

Thr Arg Pro Gly Cys Glu Met Cys Cys Arg Ala Arg Pro Glu Ala Tyr
210 215 220

Gln Val Pro Ala Ser Tyr Gln Pro Asp Glu Glu Glu Arg Ala Arg Leu
225 230 235 240

Ala Gly Glu Glu Glu Ala Leu Arg Gln Tyr Gln Gln Arg Lys Gln
245 250 255

<210> SEQ ID NO 1880
<211> LENGTH: 255
<212> TYPE: PRT
<213> ORGANISM: Homo sapiens

<400> SEQUENCE: 1880

Met Ser Ala Leu Ala Ser Arg Ser Ala Pro Ala Met Gln Ser Ser Gly
1 5 10 15

Ser Phe Asn Tyr Ala Arg Pro Lys Gln Phe Ile Ala Ala Gln Asn Leu
20 25 30

Gly Pro Ala Ser Gly His Gly Thr Pro Ala Ser Ser Pro Ser Ser Ser
35 40 45

Ser Leu Pro Ser Pro Met Ser Pro Thr Pro Arg Gln Phe Gly Arg Ala
50 55 60

Pro Val Pro Pro Phe Ala Gln Pro Phe Gly Ala Glu Pro Glu Ala Pro
65 70 75 80

Trp Gly Ser Ser Ser Pro Ser Pro Pro Pro Pro Pro Pro Pro Val Phe
85 90 95

Ser Pro Thr Ala Ala Phe Pro Val Pro Asp Val Phe Pro Leu Pro Pro
100 105 110

Pro Pro Pro Pro Leu Pro Ser Pro Gly Gln Ala Ser His Cys Ser Ser
115 120 125

Pro Ala Thr Arg Phe Gly His Ser Gln Thr Pro Ala Ala Phe Leu Ser
130 135 140

Ala Leu Leu Pro Ser Gln Pro Pro Pro Ala Ala Val Asn Ala Leu Gly
145 150 155 160

Leu Pro Lys Gly Val Thr Pro Ala Gly Phe Pro Lys Lys Ala Ser Arg
165 170 175

Thr Ala Arg Ile Ala Ser Asp Glu Glu Ile Gln Gly Thr Lys Asp Ala
180 185 190

Val Ile Gln Asp Leu Glu Arg Lys Leu Arg Phe Lys Glu Asp Leu Leu
195 200 205

Asn Asn Gly Gln Pro Arg Leu Thr Tyr Glu Glu Arg Met Ala Arg Arg
210 215 220

Leu Leu Gly Ala Asp Ser Ala Thr Val Phe Asn Ile Gln Glu Pro Glu
225 230 235 240

Glu Glu Thr Ala Asn Gln Glu Tyr Lys Val Ser Ser Cys Glu Gln
245 250 255

<210> SEQ ID NO 1881
<211> LENGTH: 134
<212> TYPE: PRT
<213> ORGANISM: Homo sapiens

<400> SEQUENCE: 1881

Met Ser Gly Lys Val Thr Lys Pro Lys Glu Glu Lys Asp Ala Ser Lys
1               5                   10                  15

Val Leu Asp Asp Ala Pro Pro Gly Thr Gln Glu Tyr Ile Met Leu Arg
            20                  25                  30

Gln Asp Ser Ile Gln Ser Ala Glu Leu Lys Lys Lys Glu Ser Pro Phe
        35                  40                  45

Arg Ala Lys Cys His Glu Ile Phe Cys Cys Pro Leu Lys Gln Val His
    50                  55                  60

His Lys Glu Asn Thr Glu Pro Glu Glu Pro Gln Leu Lys Gly Ile Val
65                  70                  75                  80

Thr Lys Leu Tyr Ser Arg Gln Gly Tyr His Leu Gln Leu Gln Ala Asp
                85                  90                  95

Gly Thr Ile Asp Gly Thr Lys Asp Glu Asp Ser Thr Tyr Thr Leu Phe
            100                 105                 110

Asn Leu Ile Pro Val Gly Leu Arg Val Val Ala Ile Gln Gly Val Gln
        115                 120                 125

Thr Lys Leu Tyr Leu Ala
    130

<210> SEQ ID NO 1882
<211> LENGTH: 136
<212> TYPE: PRT
<213> ORGANISM: Homo sapiens

<400> SEQUENCE: 1882

Met Tyr His Ser Leu Ser Glu Thr Arg His Pro Leu Gln Pro Glu Glu
1               5                   10                  15

Gln Glu Val Gly Ile Asp Pro Leu Ser Ser Tyr Ser Asn Lys Ser Gly
            20                  25                  30

Gly Asp Ser Asn Lys Asn Gly Arg Arg Thr Ser Ser Thr Leu Asp Ser
        35                  40                  45

Glu Gly Thr Phe Asn Ser Tyr Arg Lys Glu Trp Glu Glu Leu Phe Val
    50                  55                  60

Asn Asn Asn Tyr Leu Ala Thr Ile Arg Gln Lys Gly Ile Asn Gly Gln
65                  70                  75                  80

Leu Arg Ser Ser Arg Phe Arg Ser Ile Cys Trp Lys Leu Phe Leu Cys
                85                  90                  95

Val Leu Pro Gln Asp Lys Ser Gln Trp Ile Ser Arg Ile Glu Glu Leu
            100                 105                 110

Arg Ala Trp Tyr Ser Asn Ile Lys Glu Ile His Ile Thr Asn Pro Arg
        115                 120                 125

Lys Val Val Gly Gln Gln Asp Leu
    130                 135

<210> SEQ ID NO 1883
<211> LENGTH: 165
<212> TYPE: PRT
<213> ORGANISM: Homo sapiens

<400> SEQUENCE: 1883

Met Trp Glu Ala Ser Gly Met Glu Glu Arg Ala Leu Glu Glu Leu Ala
1               5                   10                  15

Met Glu Glu Thr Ala Leu Asp Pro Leu Leu Ala Glu Ala Ala Gly Ala
            20                  25                  30

Val Asp Gly Glu Gly Ala Pro Pro Gly Gly Pro Ser Ala Gln Ala Ala
        35                  40                  45

```
Thr Met Arg Val Asn Glu Lys Tyr Ser Thr Leu Pro Ala Glu Asp Arg
    50                  55                  60

Ser Val His Ile Ile Asn Ile Cys Ala Ile Glu Asp Ile Gly Tyr Leu
65                  70                  75                  80

Pro Ser Glu Gly Thr Leu Leu Asn Ser Leu Ser Val Asp Pro Asp Ala
                85                  90                  95

Glu Cys Lys Tyr Gly Leu Tyr Phe Arg Asp Gly Arg Arg Lys Val Asp
            100                 105                 110

Tyr Ile Leu Val Tyr His His Lys Arg Pro Ser Gly Asn Arg Thr Leu
        115                 120                 125

Val Arg Arg Val Gln His Ser Asp Thr Pro Ser Gly Ala Arg Ser Val
    130                 135                 140

Lys Gln Asp His Pro Leu Pro Gly Lys Gly Ala Ser Leu Asp Ala Gly
145                 150                 155                 160

Ser Gly Glu Pro Pro
                165


<210> SEQ ID NO 1884
<211> LENGTH: 255
<212> TYPE: PRT
<213> ORGANISM: Homo sapiens

<400> SEQUENCE: 1884

Met Ala Thr Gln Ala Tyr Thr Glu Leu Gln Ala Ala Pro Pro Pro Ser
1               5                   10                  15

Gln Pro Pro Gln Ala Pro Pro Gln Ala Gln Pro Gln Pro Pro Pro Pro
            20                  25                  30

Pro Pro Pro Ala Ala Pro Gln Pro Pro Gln Pro Pro Thr Ala Ala Ala
        35                  40                  45

Thr Pro Gln Pro Gln Tyr Val Thr Glu Leu Gln Ser Pro Gln Pro Gln
    50                  55                  60

Ala Gln Pro Pro Gly Gly Gln Lys Gln Tyr Val Thr Glu Leu Pro Ala
65                  70                  75                  80

Val Pro Ala Pro Ser Gln Pro Thr Gly Ala Pro Thr Pro Ser Pro Ala
                85                  90                  95

Pro Gln Gln Tyr Ile Val Val Thr Val Ser Glu Gly Ala Met Arg Ala
            100                 105                 110

Ser Glu Thr Val Ser Glu Ala Ser Pro Gly Ser Thr Ala Ser Gln Thr
        115                 120                 125

Gly Val Pro Thr Gln Val Val Gln Gln Val Gln Gly Thr Gln Gln Arg
    130                 135                 140

Leu Leu Val Gln Thr Ser Val Gln Ala Lys Pro Gly His Val Ser Pro
145                 150                 155                 160

Leu Gln Leu Thr Asn Ile Gln Val Pro Gln Gln Ala Leu Pro Thr Gln
                165                 170                 175

Arg Leu Val Val Gln Ser Ala Ala Pro Gly Ser Lys Gly Gly Gln Val
            180                 185                 190

Ser Leu Thr Val His Gly Thr Gln Gln Val His Ser Pro Pro Glu Gln
        195                 200                 205

Ser Pro Val Gln Ala Asn Ser Ser Ser Ser Lys Thr Ala Gly Ala Pro
    210                 215                 220

Thr Gly Thr Val Pro Gln Gln Leu Gln Val His Gly Val Gln Gln Ser
225                 230                 235                 240

Val Pro Val Thr Gln Glu Arg Ser Val Val Gln Ala Thr Pro Gln
                245                 250                 255
```

<210> SEQ ID NO 1885
<211> LENGTH: 246
<212> TYPE: PRT
<213> ORGANISM: Homo sapiens

<400> SEQUENCE: 1885

Met Phe Gly Arg Lys Arg Ser Val Ser Phe Gly Gly Phe Gly Trp Ile
1               5                   10                  15

Asp Lys Thr Met Leu Ala Ser Leu Lys Val Lys Lys Gln Glu Leu Ala
            20                  25                  30

Asn Ser Ser Asp Ala Thr Leu Pro Asp Arg Pro Leu Ser Pro Pro Leu
        35                  40                  45

Thr Ala Pro Pro Thr Met Lys Ser Ser Glu Phe Phe Glu Met Leu Glu
    50                  55                  60

Lys Met Gln Gly Ile Lys Leu Glu Glu Gln Lys Pro Gly Pro Gln Lys
65                  70                  75                  80

Asn Lys Asp Asp Tyr Ile Pro Tyr Pro Ser Ile Asp Glu Val Val Glu
                85                  90                  95

Lys Gly Gly Pro Tyr Pro Gln Val Ile Leu Pro Gln Phe Gly Gly Tyr
            100                 105                 110

Trp Ile Glu Asp Pro Glu Asn Val Gly Thr Pro Thr Ser Leu Gly Ser
        115                 120                 125

Ser Ile Cys Glu Glu Glu Glu Glu Asp Asn Leu Ser Pro Asn Thr Phe
    130                 135                 140

Gly Tyr Lys Leu Glu Cys Lys Gly Glu Ala Arg Ala Tyr Arg Arg His
145                 150                 155                 160

Phe Leu Gly Lys Asp His Leu Asn Phe Tyr Cys Thr Gly Ser Ser Leu
                165                 170                 175

Gly Asn Leu Ile Leu Ser Val Lys Cys Glu Glu Ala Glu Gly Ile Glu
            180                 185                 190

Tyr Leu Arg Val Ile Leu Arg Ser Lys Leu Lys Thr Val His Glu Arg
        195                 200                 205

Ile Pro Leu Ala Gly Leu Ser Lys Leu Pro Ser Val Pro Gln Ile Ala
    210                 215                 220

Lys Ala Phe Cys Asp Asp Ala Val Gly Leu Arg Phe Asn Pro Val Leu
225                 230                 235                 240

Tyr Pro Lys Ala Ser Gln
                245

<210> SEQ ID NO 1886
<211> LENGTH: 255
<212> TYPE: PRT
<213> ORGANISM: Homo sapiens

<400> SEQUENCE: 1886

Met Cys Val Arg Arg Ser Leu Val Gly Leu Thr Phe Cys Thr Cys Tyr
1               5                   10                  15

Leu Ala Ser Tyr Leu Thr Asn Lys Tyr Val Leu Ser Val Leu Lys Phe
            20                  25                  30

Thr Tyr Pro Thr Leu Phe Gln Gly Trp Gln Thr Leu Ile Gly Gly Leu
        35                  40                  45

Leu Leu His Val Ser Trp Lys Leu Gly Trp Val Glu Ile Asn Ser Ser
    50                  55                  60

Ser Arg Ser His Val Leu Val Trp Leu Pro Ala Ser Val Leu Phe Val
65                  70                  75                  80

```
Gly Ile Ile Tyr Ala Gly Ser Arg Ala Leu Ser Arg Leu Ala Ile Pro
                85                  90                  95

Val Phe Leu Thr Leu His Asn Val Ala Glu Val Ile Ile Cys Gly Tyr
            100                 105                 110

Gln Lys Cys Phe Gln Lys Glu Lys Thr Ser Pro Ala Lys Ile Cys Ser
        115                 120                 125

Ala Leu Leu Leu Leu Ala Ala Ala Gly Cys Leu Pro Phe Asn Asp Ser
    130                 135                 140

Gln Phe Asn Pro Asp Gly Tyr Phe Trp Ala Ile Ile His Leu Leu Cys
145                 150                 155                 160

Val Gly Ala Tyr Lys Ile Leu Gln Lys Ser Gln Lys Pro Ser Ala Leu
                165                 170                 175

Ser Asp Ile Asp Gln Gln Tyr Leu Asn Tyr Ile Phe Ser Val Val Leu
            180                 185                 190

Leu Ala Phe Ala Ser His Pro Thr Gly Asp Leu Phe Ser Val Leu Asp
        195                 200                 205

Phe Pro Phe Leu Tyr Phe Tyr Arg Phe His Gly Ser Cys Cys Ala Ser
    210                 215                 220

Gly Phe Leu Gly Phe Phe Leu Met Phe Ser Thr Val Lys Leu Lys Asn
225                 230                 235                 240

Leu Leu Ala Pro Gly Gln Cys Ala Ala Trp Ile Phe Phe Ala Lys
                245                 250                 255


<210> SEQ ID NO 1887
<211> LENGTH: 231
<212> TYPE: PRT
<213> ORGANISM: Homo sapiens

<400> SEQUENCE: 1887

Met Leu Ser Ser Arg Ala Glu Ala Ala Met Thr Ala Ala Asp Arg Ala
1               5                   10                  15

Ile Gln Arg Phe Leu Arg Thr Gly Ala Ala Val Arg Tyr Lys Val Met
            20                  25                  30

Lys Asn Trp Gly Val Ile Gly Gly Ile Ala Ala Ala Leu Ala Ala Gly
        35                  40                  45

Ile Tyr Val Ile Trp Gly Pro Ile Thr Glu Arg Lys Lys Arg Arg Lys
    50                  55                  60

Gly Leu Val Pro Gly Leu Val Asn Leu Gly Asn Thr Cys Phe Met Asn
65                  70                  75                  80

Ser Leu Leu Gln Gly Leu Ser Ala Cys Pro Ala Phe Ile Arg Trp Leu
                85                  90                  95

Glu Glu Phe Thr Ser Gln Tyr Ser Arg Asp Gln Lys Glu Pro Pro Ser
            100                 105                 110

His Gln Tyr Leu Ser Leu Thr Leu Leu His Leu Leu Lys Ala Leu Ser
        115                 120                 125

Cys Gln Glu Val Thr Asp Asp Glu Val Leu Asp Ala Ser Cys Leu Leu
    130                 135                 140

Asp Val Leu Arg Met Tyr Arg Trp Gln Ile Ser Ser Phe Glu Glu Gln
145                 150                 155                 160

Asp Ala His Glu Leu Phe His Val Ile Thr Ser Ser Leu Glu Asp Glu
                165                 170                 175

Arg Asp Arg Gln Pro Arg Val Thr His Leu Phe Asp Val His Ser Leu
            180                 185                 190

Glu Gln Gln Ser Glu Ile Thr Pro Lys Gln Ile Thr Cys Arg Thr Arg
```

```
        195                 200                 205

Gly Ser Pro His Pro Thr Ser Asn His Trp Lys Ser Gln His Pro Phe
    210                 215                 220

His Gly Arg Leu Thr Ser Asn
225                 230


<210> SEQ ID NO 1888
<211> LENGTH: 255
<212> TYPE: PRT
<213> ORGANISM: Homo sapiens

<400> SEQUENCE: 1888

Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala
                245                 250                 255


<210> SEQ ID NO 1889
<211> LENGTH: 77
<212> TYPE: PRT
<213> ORGANISM: Homo sapiens

<400> SEQUENCE: 1889

Met Glu Pro Asp Ser Leu Leu Asp Gln Asp Asp Ser Tyr Glu Ser Pro
1               5                   10                  15

Gln Glu Arg Pro Gly Ser Arg Arg Ser Leu Pro Gly Ser Leu Ser Glu
            20                  25                  30

Lys Ser Pro Ser Met Glu Pro Ser Ala Ala Thr Pro Phe Arg Val Thr
```

```
        35                  40                  45

Gly Phe Leu Ser Arg Arg Leu Lys Gly Ser Ile Lys Arg Thr Lys Ser
    50                  55                  60

Gln Pro Lys Leu Asp Arg Asn His Ser Phe Arg His Ile
65                  70                  75


<210> SEQ ID NO 1890
<211> LENGTH: 226
<212> TYPE: PRT
<213> ORGANISM: Homo sapiens

<400> SEQUENCE: 1890

Met Leu Trp Lys Leu Thr Asp Asn Ile Lys Tyr Glu Asp Cys Glu Asp
1               5                   10                  15

Arg His Asp Gly Thr Ser Asn Gly Thr Ala Arg Leu Pro Gln Leu Gly
            20                  25                  30

Thr Val Gly Gln Ser Pro Tyr Thr Ser Ala Pro Pro Leu Ser His Thr
        35                  40                  45

Pro Asn Ala Asp Phe Gln Pro Pro Tyr Phe Pro Pro Pro Tyr Gln Pro
    50                  55                  60

Ile Tyr Pro Gln Ser Gln Asp Pro Tyr Ser His Val Asn Asp Pro Tyr
65                  70                  75                  80

Ser Leu Asn Pro Leu His Ala Gln Pro Gln Pro Gln His Pro Gly Trp
                85                  90                  95

Pro Gly Gln Arg Gln Ser Gln Glu Ser Gly Leu Leu His Thr His Arg
            100                 105                 110

Gly Leu Pro His Gln Leu Ser Gly Leu Asp Pro Arg Arg Asp Tyr Arg
        115                 120                 125

Arg His Glu Asp Leu Leu His Gly Pro His Ala Leu Ser Ser Gly Leu
    130                 135                 140

Gly Asp Leu Ser Ile His Ser Leu Pro His Ala Ile Glu Glu Val Pro
145                 150                 155                 160

His Val Glu Asp Pro Gly Ile Asn Ile Pro Asp Gln Thr Val Ile Lys
                165                 170                 175

Lys Gly Pro Val Ser Leu Ser Lys Ser Asn Ser Asn Ala Val Ser Ala
            180                 185                 190

Ile Pro Ile Asn Lys Asp Asn Leu Phe Gly Gly Val Val Asn Pro Asn
        195                 200                 205

Glu Val Phe Cys Ser Val Pro Gly Arg Leu Ser Leu Leu Ser Ser Thr
    210                 215                 220

Ser Lys
225


<210> SEQ ID NO 1891
<211> LENGTH: 255
<212> TYPE: PRT
<213> ORGANISM: Homo sapiens

<400> SEQUENCE: 1891

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
```

```
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe
                245                 250                 255


<210> SEQ ID NO 1892
<211> LENGTH: 255
<212> TYPE: PRT
<213> ORGANISM: Homo sapiens

<400> SEQUENCE: 1892

Met Gly Asp Leu Ser Ser Leu Thr Pro Gly Gly Ser Met Gly Leu Gln
1               5                   10                  15

Val Asn Arg Gly Ser Gln Ser Ser Leu Glu Gly Ala Pro Ala Thr Ala
            20                  25                  30

Pro Glu Pro His Ser Leu Gly Ile Leu His Ala Ser Tyr Ser Val Ser
        35                  40                  45

His Arg Val Arg Pro Trp Trp Asp Ile Thr Ser Cys Arg Gln Gln Trp
    50                  55                  60

Thr Arg Gln Ile Leu Lys Asp Val Ser Leu Tyr Val Glu Ser Gly Gln
65                  70                  75                  80

Ile Met Cys Ile Leu Gly Ser Ser Gly Ser Gly Lys Thr Thr Leu Leu
                85                  90                  95

Asp Ala Met Ser Gly Arg Leu Gly Arg Ala Gly Thr Phe Leu Gly Glu
            100                 105                 110

Val Tyr Val Asn Gly Arg Ala Leu Arg Arg Glu Gln Phe Gln Asp Cys
        115                 120                 125

Phe Ser Tyr Val Leu Gln Ser Asp Thr Leu Leu Ser Ser Leu Thr Val
    130                 135                 140

Arg Glu Thr Leu His Tyr Thr Ala Leu Leu Ala Ile Arg Arg Gly Asn
145                 150                 155                 160

Pro Gly Ser Phe Gln Lys Lys Val Glu Ala Val Met Ala Glu Leu Ser
                165                 170                 175
```

```
Leu Ser His Val Ala Asp Arg Leu Ile Gly Asn Tyr Ser Leu Gly Gly
            180                 185                 190

Ile Ser Thr Gly Glu Arg Arg Arg Val Ser Ile Ala Ala Gln Leu Leu
        195                 200                 205

Gln Asp Pro Lys Val Met Leu Phe Asp Glu Pro Thr Thr Gly Leu Asp
    210                 215                 220

Cys Met Thr Ala Asn Gln Ile Val Val Leu Leu Val Glu Leu Ala Arg
225                 230                 235                 240

Arg Asn Arg Ile Val Val Leu Thr Ile His Gln Pro Arg Ser Glu
                245                 250                 255


<210> SEQ ID NO 1893
<211> LENGTH: 255
<212> TYPE: PRT
<213> ORGANISM: Homo sapiens

<400> SEQUENCE: 1893

Met Glu Pro Ser Ala Leu Arg Lys Ala Gly Ser Glu Gln Glu Glu Gly
1               5                   10                  15

Phe Glu Gly Leu Pro Arg Arg Val Thr Asp Leu Gly Met Val Ser Asn
            20                  25                  30

Leu Arg Arg Ser Asn Ser Ser Leu Phe Lys Ser Trp Arg Leu Gln Cys
        35                  40                  45

Pro Phe Gly Asn Asn Asp Lys Gln Glu Ser Leu Ser Ser Trp Ile Pro
    50                  55                  60

Glu Asn Ile Lys Lys Lys Glu Cys Val Tyr Phe Val Glu Ser Ser Lys
65                  70                  75                  80

Leu Ser Asp Ala Gly Lys Val Val Cys Gln Cys Gly Tyr Thr His Glu
                85                  90                  95

Gln His Leu Glu Glu Ala Thr Lys Pro His Thr Phe Gln Gly Thr Gln
            100                 105                 110

Trp Asp Pro Lys Lys His Val Gln Glu Met Pro Thr Asp Ala Phe Gly
        115                 120                 125

Asp Ile Val Phe Thr Gly Leu Ser Gln Lys Val Lys Lys Tyr Val Arg
    130                 135                 140

Val Ser Gln Asp Thr Pro Ser Ser Val Ile Tyr His Leu Met Thr Gln
145                 150                 155                 160

His Trp Gly Leu Asp Val Pro Asn Leu Leu Ile Ser Val Thr Gly Gly
                165                 170                 175

Ala Lys Asn Phe Asn Met Lys Pro Arg Leu Lys Ser Ile Phe Arg Arg
            180                 185                 190

Gly Leu Val Lys Val Ala Gln Thr Thr Gly Ala Trp Ile Ile Thr Gly
        195                 200                 205

Gly Ser His Thr Gly Val Met Lys Gln Val Gly Glu Ala Val Arg Asp
    210                 215                 220

Phe Ser Leu Ser Ser Ser Tyr Lys Glu Gly Glu Leu Ile Thr Ile Gly
225                 230                 235                 240

Val Ala Thr Trp Gly Thr Val His Arg Arg Glu Gly Leu Ile His
                245                 250                 255


<210> SEQ ID NO 1894
<211> LENGTH: 255
<212> TYPE: PRT
<213> ORGANISM: Homo sapiens

<400> SEQUENCE: 1894
```

Met Arg Gln Val Leu Trp Leu Cys Asn Val Cys Val Thr Ala Arg Glu
1 5 10 15

Thr Arg His His Leu His Leu Pro Ala Ile Leu Asp Lys Met Pro Ala
20 25 30

Pro Gly Ala Leu Ile Leu Leu Ala Ala Val Ser Ala Ser Gly Cys Leu
35 40 45

Ala Ser Pro Ala His Pro Asp Gly Phe Ala Leu Gly Arg Ala Pro Leu
50 55 60

Ala Pro Pro Tyr Ala Val Val Leu Ile Ser Cys Ser Gly Leu Leu Ala
65 70 75 80

Phe Ile Phe Leu Leu Leu Thr Cys Leu Cys Cys Lys Arg Gly Asp Val
85 90 95

Gly Phe Lys Glu Phe Glu Asn Pro Glu Gly Glu Asp Cys Ser Gly Glu
100 105 110

Tyr Thr Pro Pro Ala Glu Glu Thr Ser Ser Ser Gln Ser Leu Pro Asp
115 120 125

Val Tyr Ile Leu Pro Leu Ala Glu Val Ser Leu Pro Met Pro Ala Pro
130 135 140

Gln Pro Ser His Ser Asp Met Thr Thr Pro Leu Gly Leu Ser Arg Gln
145 150 155 160

His Leu Ser Tyr Leu Gln Glu Ile Gly Ser Gly Trp Phe Gly Lys Val
165 170 175

Ile Leu Gly Glu Ile Phe Ser Asp Tyr Thr Pro Ala Gln Val Val Val
180 185 190

Lys Glu Leu Arg Ala Ser Ala Gly Pro Leu Glu Gln Arg Lys Phe Ile
195 200 205

Ser Glu Ala Gln Pro Tyr Arg Ser Leu Gln His Pro Asn Val Leu Gln
210 215 220

Cys Leu Gly Leu Cys Val Glu Thr Leu Pro Phe Leu Leu Ile Met Glu
225 230 235 240

Phe Cys Gln Leu Gly Asp Leu Lys Arg Tyr Leu Arg Ala Gln Arg
245 250 255

<210> SEQ ID NO 1895
<211> LENGTH: 255
<212> TYPE: PRT
<213> ORGANISM: Homo sapiens

<400> SEQUENCE: 1895

Met Thr Leu Pro His Ser Leu Gly Gly Ala Gly Asp Pro Arg Pro Pro
1 5 10 15

Gln Ala Met Glu Val His Arg Leu Glu His Arg Gln Glu Glu Glu Gln
20 25 30

Lys Glu Glu Arg Gln His Ser Leu Arg Met Gly Ser Ser Val Arg Arg
35 40 45

Arg Thr Phe Arg Ser Ser Glu Glu Glu His Glu Phe Ser Ala Ala Asp
50 55 60

Tyr Ala Leu Ala Ala Ala Leu Ala Leu Thr Ala Ser Ser Glu Leu Ser
65 70 75 80

Trp Glu Ala Gln Leu Arg Arg Gln Thr Ser Ala Val Glu Leu Glu Glu
85 90 95

Arg Gly Gln Lys Arg Val Gly Phe Gly Asn Asp Trp Glu Arg Thr Glu
100 105 110

Ile Ala Phe Leu Gln Thr His Arg Leu Leu Arg Gln Arg Arg Asp Trp
115 120 125

```
Lys Thr Leu Arg Arg Arg Thr Glu Glu Lys Val Gln Glu Ala Lys Glu
    130                 135                 140

Leu Arg Glu Leu Cys Tyr Gly Arg Gly Pro Trp Phe Trp Ile Pro Leu
145                 150                 155                 160

Arg Ser His Ala Val Trp Glu His Thr Thr Val Leu Leu Thr Cys Thr
                165                 170                 175

Val Gln Ala Ser Pro Pro Pro Gln Val Thr Trp Tyr Lys Asn Asp Thr
            180                 185                 190

Arg Ile Asp Pro Arg Leu Phe Arg Ala Gly Lys Tyr Arg Ile Thr Asn
        195                 200                 205

Asn Tyr Gly Leu Leu Ser Leu Glu Ile Arg Arg Cys Ala Ile Glu Asp
    210                 215                 220

Ser Ala Thr Tyr Thr Val Arg Val Lys Asn Ala His Gly Gln Ala Ser
225                 230                 235                 240

Ser Phe Ala Lys Val Leu Val Arg Thr Tyr Leu Gly Lys Asp Ala
                245                 250                 255


<210> SEQ ID NO 1896
<211> LENGTH: 255
<212> TYPE: PRT
<213> ORGANISM: Homo sapiens

<400> SEQUENCE: 1896

Met Ser Thr Asp Ser Asn Ser Leu Ala Arg Glu Phe Leu Thr Asp Val
1               5                   10                  15

Asn Arg Leu Cys Asn Ala Val Val Gln Arg Val Glu Ala Arg Glu Glu
            20                  25                  30

Glu Glu Glu Glu Thr His Met Ala Thr Leu Gly Gln Tyr Leu Val His
        35                  40                  45

Gly Arg Gly Phe Leu Leu Leu Thr Lys Leu Asn Ser Ile Ile Asp Gln
    50                  55                  60

Ala Leu Thr Cys Arg Glu Glu Leu Leu Thr Leu Leu Leu Ser Leu Leu
65                  70                  75                  80

Pro Leu Val Trp Lys Ile Pro Val Gln Glu Glu Lys Ala Thr Asp Phe
                85                  90                  95

Asn Leu Pro Leu Ser Ala Asp Ile Ile Leu Thr Lys Glu Lys Asn Ser
            100                 105                 110

Ser Ser Gln Arg Ser Thr Gln Glu Lys Leu His Leu Glu Gly Ser Ala
        115                 120                 125

Leu Ser Ser Gln Val Ser Ala Lys Val Asn Val Phe Arg Lys Ser Arg
    130                 135                 140

Arg Gln Arg Lys Ile Thr His Arg Tyr Ser Val Arg Asp Ala Arg Lys
145                 150                 155                 160

Thr Gln Leu Ser Thr Ser Asp Ser Glu Ala Asn Ser Asp Glu Lys Gly
                165                 170                 175

Ile Ala Met Asn Lys His Arg Arg Pro His Leu Leu His His Phe Leu
            180                 185                 190

Thr Ser Phe Pro Lys Gln Asp His Pro Lys Ala Lys Leu Asp Arg Leu
        195                 200                 205

Ala Thr Lys Glu Gln Thr Pro Pro Asp Ala Met Ala Leu Glu Asn Ser
    210                 215                 220

Arg Glu Ile Ile Pro Arg Gln Gly Ser Asn Thr Asp Ile Leu Ser Glu
225                 230                 235                 240

Pro Ala Ala Leu Ser Val Ile Ser Asn Met Asn Asn Ser Pro Phe
```

245 250 255

<210> SEQ ID NO 1897
<211> LENGTH: 107
<212> TYPE: PRT
<213> ORGANISM: Homo sapiens

<400> SEQUENCE: 1897

Met Ser Glu Phe Trp Leu Ile Ser Ala Pro Gly Asp Lys Glu Asn Leu
1 5 10 15

Gln Ala Leu Glu Arg Met Asn Thr Val Thr Ser Lys Ser Asn Leu Ser
20 25 30

Tyr Asn Thr Lys Phe Ala Ile Pro Asp Phe Lys Val Gly Thr Leu Asp
35 40 45

Ser Leu Val Gly Leu Ser Asp Glu Leu Gly Lys Leu Asp Thr Phe Ala
50 55 60

Glu Ser Leu Ile Arg Arg Met Ala Gln Ser Val Val Glu Val Met Glu
65 70 75 80

Asp Ser Lys Gly Lys Val Gln Glu His Leu Leu Ala Asn Gly Val Asp
85 90 95

Leu Thr Ser Phe Val Thr His Phe Glu Trp Asp
100 105

<210> SEQ ID NO 1898
<211> LENGTH: 255
<212> TYPE: PRT
<213> ORGANISM: Homo sapiens

<400> SEQUENCE: 1898

Met Ala Ala Ala Ala Glu Pro Gly Ala Arg Ala Trp Leu Gly Gly Gly
1 5 10 15

Ser Pro Arg Pro Gly Ser Pro Ala Cys Ser Pro Val Leu Gly Ser Gly
20 25 30

Gly Arg Ala Arg Pro Gly Pro Gly Pro Gly Pro Gly Pro Glu Arg Ala
35 40 45

Gly Val Arg Ala Pro Gly Pro Ala Ala Ala Pro Gly His Ser Phe Arg
50 55 60

Lys Val Thr Leu Thr Lys Pro Thr Phe Cys His Leu Cys Ser Asp Phe
65 70 75 80

Ile Trp Gly Leu Ala Gly Phe Leu Cys Asp Val Cys Asn Phe Met Ser
85 90 95

His Glu Lys Cys Leu Lys His Val Arg Ile Pro Cys Thr Ser Val Ala
100 105 110

Pro Ser Leu Val Arg Val Pro Val Ala His Cys Phe Gly Pro Arg Gly
115 120 125

Leu His Lys Arg Lys Phe Cys Ala Val Cys Arg Lys Val Leu Glu Ala
130 135 140

Pro Ala Leu His Cys Glu Val Cys Glu Leu His Leu His Pro Asp Cys
145 150 155 160

Val Pro Phe Ala Cys Ser Asp Cys Arg Gln Cys His Gln Asp Gly His
165 170 175

Gln Asp His Asp Thr His His His His Trp Arg Glu Gly Asn Leu Pro
180 185 190

Ser Gly Ala Arg Cys Glu Val Cys Arg Lys Thr Cys Gly Ser Ser Asp
195 200 205

Val Leu Ala Gly Val Arg Cys Glu Trp Cys Gly Val Gln Ala His Ser

```
    210                 215                 220

Leu Cys Ser Ala Ala Leu Ala Pro Glu Cys Gly Phe Gly Arg Leu Arg
225                 230                 235                 240

Ser Leu Val Leu Pro Pro Ala Cys Val Arg Leu Leu Pro Gly Gly
                245                 250                 255


<210> SEQ ID NO 1899
<211> LENGTH: 255
<212> TYPE: PRT
<213> ORGANISM: Homo sapiens

<400> SEQUENCE: 1899

Met Gly Ala Met Ala Tyr Pro Leu Leu Leu Cys Leu Leu Leu Ala Gln
1               5                   10                  15

Leu Gly Leu Gly Ala Val Gly Ala Ser Arg Asp Pro Gln Gly Arg Pro
            20                  25                  30

Asp Ser Pro Arg Glu Arg Thr Pro Lys Gly Lys Pro His Ala Gln Gln
        35                  40                  45

Pro Gly Arg Ala Ser Ala Ser Asp Ser Ser Ala Pro Trp Ser Arg Ser
    50                  55                  60

Thr Asp Gly Thr Ile Leu Ala Gln Lys Leu Ala Glu Glu Val Pro Met
65                  70                  75                  80

Asp Val Ala Ser Tyr Leu Tyr Thr Gly Asp Ser His Gln Leu Lys Arg
                85                  90                  95

Ala Asn Cys Ser Gly Arg Tyr Glu Leu Ala Gly Leu Pro Gly Lys Trp
            100                 105                 110

Pro Ala Leu Ala Ser Ala His Pro Ser Leu His Arg Ala Leu Asp Thr
        115                 120                 125

Leu Thr His Ala Thr Asn Phe Leu Asn Val Met Leu Gln Ser Asn Lys
    130                 135                 140

Ser Arg Glu Gln Asn Leu Gln Asp Asp Leu Asp Trp Tyr Gln Ala Leu
145                 150                 155                 160

Val Trp Ser Leu Leu Glu Gly Glu Pro Ser Ile Ser Arg Ala Ala Ile
                165                 170                 175

Thr Phe Ser Thr Asp Ser Leu Ser Ala Pro Ala Pro Gln Val Phe Leu
            180                 185                 190

Gln Ala Thr Arg Glu Glu Ser Arg Ile Leu Leu Gln Asp Leu Ser Ser
        195                 200                 205

Ser Ala Pro His Leu Ala Asn Ala Thr Leu Glu Thr Glu Trp Phe His
    210                 215                 220

Gly Leu Arg Arg Lys Trp Arg Pro His Leu His Arg Arg Gly Pro Asn
225                 230                 235                 240

Gln Gly Pro Arg Gly Leu Gly His Ser Trp Arg Arg Lys Asp Gly
                245                 250                 255


<210> SEQ ID NO 1900
<211> LENGTH: 238
<212> TYPE: PRT
<213> ORGANISM: Homo sapiens

<400> SEQUENCE: 1900

Met Ser Arg Lys Ala Ser Glu Asn Val Glu Tyr Thr Leu Arg Ser Leu
1               5                   10                  15

Ser Ser Leu Met Gly Glu Arg Arg Arg Lys Gln Pro Glu Pro Asp Ala
            20                  25                  30

Ala Ser Ala Ala Gly Glu Cys Ser Leu Leu Ala Ala Ala Glu Ser Ser
```

```
        35                  40                  45

Thr Ser Leu Gln Ser Ala Gly Ala Gly Gly Gly Gly Val Gly Asp Leu
    50                  55                  60

Glu Arg Ala Ala Arg Arg Gln Phe Gln Gln Asp Glu Thr Pro Ala Phe
65                  70                  75                  80

Val Tyr Val Val Ala Val Phe Ser Ala Leu Gly Gly Phe Leu Phe Gly
                85                  90                  95

Tyr Asp Thr Gly Val Val Ser Gly Ala Met Leu Leu Leu Lys Arg Gln
            100                 105                 110

Leu Ser Leu Asp Ala Leu Trp Gln Glu Leu Leu Val Ser Ser Thr Val
        115                 120                 125

Gly Ala Ala Ala Val Ser Ala Leu Ala Gly Gly Ala Leu Asn Gly Val
    130                 135                 140

Phe Gly Arg Arg Ala Ala Ile Leu Leu Ala Ser Ala Leu Phe Thr Ala
145                 150                 155                 160

Gly Ser Ala Val Leu Ala Ala Ala Asn Asn Lys Glu Thr Leu Leu Ala
                165                 170                 175

Gly Arg Leu Val Val Gly Leu Gly Ile Gly Ile Ala Ser Met Thr Val
            180                 185                 190

Pro Val Tyr Ile Ala Glu Val Ser Pro Pro Asn Leu Arg Gly Arg Leu
        195                 200                 205

Val Thr Ile Asn Thr Leu Phe Ile Thr Gly Gly Gln Phe Phe Ala Ser
    210                 215                 220

Val Val Asp Gly Ala Phe Ser Tyr Leu Gln Lys Asp Gly Trp
225                 230                 235


<210> SEQ ID NO 1901
<211> LENGTH: 255
<212> TYPE: PRT
<213> ORGANISM: Homo sapiens

<400> SEQUENCE: 1901

Met Ala Gly Tyr Leu Ser Pro Ala Ala Tyr Leu Tyr Val Glu Glu Gln
1               5                   10                  15

Glu Tyr Leu Gln Ala Tyr Glu Asp Val Leu Glu Arg Tyr Lys Asp Glu
            20                  25                  30

Arg Asp Lys Val Gln Lys Lys Thr Phe Thr Lys Trp Ile Asn Gln His
        35                  40                  45

Leu Met Lys Val Arg Lys His Val Asn Asp Leu Tyr Glu Asp Leu Arg
    50                  55                  60

Asp Gly His Asn Leu Ile Ser Leu Leu Glu Val Leu Ser Gly Asp Thr
65                  70                  75                  80

Leu Pro Arg Glu Lys Gly Arg Met Arg Phe His Arg Leu Gln Asn Val
                85                  90                  95

Gln Ile Ala Leu Asp Tyr Leu Lys Arg Arg Gln Val Lys Leu Val Asn
            100                 105                 110

Ile Arg Asn Asp Asp Ile Thr Asp Gly Asn Pro Lys Leu Thr Leu Gly
        115                 120                 125

Leu Ile Trp Thr Ile Ile Leu His Phe Gln Ile Ser Asp Ile His Val
    130                 135                 140

Thr Gly Glu Ser Glu Asp Met Ser Ala Lys Glu Arg Leu Leu Leu Trp
145                 150                 155                 160

Thr Gln Gln Ala Thr Glu Gly Tyr Ala Gly Ile Arg Cys Glu Asn Phe
                165                 170                 175
```

Thr Thr Cys Trp Arg Asp Gly Lys Leu Phe Asn Ala Ile Ile His Lys
180 185 190

Tyr Arg Pro Asp Leu Ile Asp Met Asn Thr Val Ala Val Gln Ser Asn
195 200 205

Leu Ala Asn Leu Glu His Ala Phe Tyr Val Ala Glu Lys Ile Gly Val
210 215 220

Ile Arg Leu Leu Asp Pro Glu Asp Val Asp Val Ser Ser Pro Asp Glu
225 230 235 240

Lys Ser Val Ile Thr Tyr Val Ser Ser Leu Tyr Asp Ala Phe Pro
245 250 255

<210> SEQ ID NO 1902
<211> LENGTH: 255
<212> TYPE: PRT
<213> ORGANISM: Homo sapiens

<400> SEQUENCE: 1902

Met Ser Ser Asp Glu Glu Lys Tyr Ser Leu Pro Val Val Gln Asn Asp
1 5 10 15

Ser Ser Arg Gly Ser Ser Val Ser Ser Asn Leu Gln Glu Glu Tyr Glu
20 25 30

Glu Leu Leu His Tyr Ala Ile Val Thr Pro Asn Ile Glu Pro Cys Ala
35 40 45

Ser Gln Ser Ser His Pro Lys Gly Glu Leu Val Pro Asp Val Arg Ile
50 55 60

Ser Thr Ile His Asp Ile Leu His Ser Gln Gly Asn Asn Ser Glu Val
65 70 75 80

Arg Glu Thr Ala Ile Glu Val Gly Lys Gly Cys Asp Phe His Ile Ser
85 90 95

Ser His Ser Lys Thr Asp Glu Ser Ser Pro Val Leu Ser Pro Arg Lys
100 105 110

Pro Ser His Pro Val Met Asp Phe Phe Ser Ser His Leu Leu Ala Asp
115 120 125

Ser Ser Ser Pro Ala Thr Asn Ser Ser His Thr Asp Ala His Glu Ile
130 135 140

Leu Val Ser Asp Phe Leu Val Ser Asp Glu Asn Leu Gln Lys Met Glu
145 150 155 160

Asn Val Leu Asp Leu Trp Ser Ser Gly Leu Lys Thr Asn Ile Ile Ser
165 170 175

Glu Leu Ser Lys Trp Arg Leu Asn Phe Ile Asp Trp His Arg Met Glu
180 185 190

Met Arg Lys Glu Lys Glu Lys His Ala Ala His Leu Lys Gln Leu Cys
195 200 205

Asn Gln Ile Asn Glu Leu Lys Glu Leu Gln Lys Thr Phe Glu Ile Ser
210 215 220

Ile Gly Arg Lys Asp Glu Val Ile Ser Ser Leu Ser His Ala Ile Gly
225 230 235 240

Lys Gln Lys Glu Lys Ile Glu Leu Met Arg Thr Phe Phe His Trp
245 250 255

<210> SEQ ID NO 1903
<211> LENGTH: 132
<212> TYPE: PRT
<213> ORGANISM: Homo sapiens

<400> SEQUENCE: 1903

```
Met Ala Ser Glu Glu Leu Tyr Glu Val Glu Arg Ile Val Asp Lys Arg
1               5                   10                  15

Lys Asn Lys Lys Gly Lys Thr Glu Tyr Leu Val Arg Trp Lys Gly Tyr
            20                  25                  30

Asp Ser Glu Asp Asp Thr Trp Glu Pro Glu Gln His Leu Val Asn Cys
        35                  40                  45

Glu Glu Tyr Ile His Asp Phe Asn Arg Arg His Thr Glu Lys Gln Lys
    50                  55                  60

Glu Ser Thr Leu Thr Arg Thr Asn Arg Thr Ser Pro Asn Asn Ala Arg
65                  70                  75                  80

Lys Gln Ile Ser Arg Ser Thr Asn Ser Asn Phe Ser Lys Thr Ser Pro
                85                  90                  95

Lys Ala Leu Val Ile Gly Lys Asp His Glu Ser Lys Asn Ser Gln Leu
            100                 105                 110

Phe Ala Ala Ser Gln Lys Phe Arg Lys Asn Thr Ala Pro Ser Leu Ser
        115                 120                 125

Ser Arg Lys Asn
    130


<210> SEQ ID NO 1904
<211> LENGTH: 255
<212> TYPE: PRT
<213> ORGANISM: Homo sapiens

<400> SEQUENCE: 1904

Met Ser Tyr Tyr Gln Arg Pro Phe Ser Pro Ser Ala Tyr Ser Leu Pro
1               5                   10                  15

Ala Ser Leu Asn Ser Ser Ile Val Met Gln His Gly Thr Ser Leu Asp
            20                  25                  30

Ser Thr Asp Thr Tyr Pro Gln His Ala Gln Ser Leu Asp Gly Thr Thr
        35                  40                  45

Ser Ser Ser Ile Pro Leu Tyr Arg Ser Ser Glu Glu Glu Lys Arg Val
    50                  55                  60

Thr Val Ile Lys Ala Pro His Tyr Pro Gly Ile Gly Pro Val Asp Glu
65                  70                  75                  80

Ser Gly Ile Pro Thr Ala Ile Arg Thr Thr Val Asp Arg Pro Lys Asp
                85                  90                  95

Trp Tyr Lys Thr Met Phe Lys Gln Ile His Met Val His Lys Pro Asp
            100                 105                 110

Asp Asp Thr Asp Met Tyr Asn Thr Pro Tyr Thr Tyr Asn Ala Gly Leu
        115                 120                 125

Tyr Asn Pro Pro Tyr Ser Ala Gln Ser His Pro Ala Ala Lys Thr Gln
    130                 135                 140

Thr Tyr Arg Pro Leu Ser Lys Ser His Ser Asp Asn Ser Pro Asn Ala
145                 150                 155                 160

Phe Lys Asp Ala Ser Ser Pro Val Pro Pro Pro His Val Pro Pro Pro
                165                 170                 175

Val Pro Pro Leu Arg Pro Arg Asp Arg Ser Ser Thr Glu Lys His Asp
            180                 185                 190

Trp Asp Pro Pro Asp Arg Lys Val Asp Thr Arg Lys Phe Arg Ser Glu
        195                 200                 205

Pro Arg Ser Ile Phe Glu Tyr Glu Pro Gly Lys Ser Ser Ile Leu Gln
    210                 215                 220

His Glu Arg Pro Ala Ser Leu Tyr Gln Ser Ser Ile Asp Arg Ser Leu
225                 230                 235                 240
```

Glu Arg Pro Met Ser Ser Ala Ser Met Ala Ser Asp Phe Arg Lys
245 250 255

<210> SEQ ID NO 1905
<211> LENGTH: 255
<212> TYPE: PRT
<213> ORGANISM: Homo sapiens

<400> SEQUENCE: 1905

Met Ala Glu Val Gly Arg Thr Gly Ile Ser Tyr Pro Gly Ala Leu Leu
1 5 10 15

Pro Gln Gly Phe Trp Ala Ala Val Glu Val Trp Leu Glu Arg Pro Gln
20 25 30

Val Ala Asn Lys Arg Leu Cys Gly Ala Arg Leu Glu Ala Arg Trp Ser
35 40 45

Ala Ala Leu Pro Cys Ala Glu Ala Arg Gly Pro Gly Thr Ser Ala Gly
50 55 60

Ser Glu Gln Lys Glu Arg Gly Pro Gly Pro Gly Gln Gly Ser Pro Gly
65 70 75 80

Gly Gly Pro Gly Pro Arg Ser Leu Ser Gly Pro Glu Gln Gly Thr Ala
85 90 95

Cys Cys Glu Leu Glu Glu Ala Gln Gly Gln Cys Gln Gln Glu Glu Ala
100 105 110

Gln Arg Glu Ala Ala Ser Val Pro Leu Arg Asp Ser Gly His Pro Gly
115 120 125

His Ala Glu Gly Arg Glu Gly Asp Phe Pro Ala Ala Asp Leu Asp Ser
130 135 140

Leu Trp Glu Asp Phe Ser Gln Ser Leu Ala Arg Gly Asn Ser Glu Leu
145 150 155 160

Leu Ala Phe Leu Thr Ser Ser Gly Ala Gly Ser Gln Pro Glu Ala Gln
165 170 175

Arg Glu Leu Asp Val Val Leu Arg Thr Val Ile Pro Lys Thr Ser Pro
180 185 190

His Cys Pro Leu Thr Thr Pro Arg Arg Glu Ile Val Val Gln Asp Val
195 200 205

Leu Asn Gly Thr Ile Thr Phe Leu Pro Leu Glu Glu Asp Asp Glu Gly
210 215 220

Asn Leu Lys Val Lys Met Ser Asn Val Tyr Gln Ile Gln Leu Ser His
225 230 235 240

Ser Lys Glu Glu Trp Phe Ile Ser Val Leu Ile Phe Cys Pro Glu
245 250 255

<210> SEQ ID NO 1906
<211> LENGTH: 142
<212> TYPE: PRT
<213> ORGANISM: Homo sapiens

<400> SEQUENCE: 1906

Met Ala Thr Gln Val Glu Pro Leu Leu Pro Gly Gly Ala Thr Leu Leu
1 5 10 15

Gln Ala Glu Glu His Gly Gly Leu Val Arg Lys Lys Pro Pro Pro Ala
20 25 30

Pro Glu Gly Lys Gly Glu Pro Gly Pro Asn Asp Val Arg Gly Gly Glu
35 40 45

Pro Asp Gly Ser Ala Arg Arg Pro Arg Pro Pro Cys Ala Lys Pro His
50 55 60

```
Lys Glu Gly Thr Gly Gln Gln Glu Arg Glu Ser Pro Arg Pro Leu Gln
65                  70                  75                  80

Leu Pro Gly Ala Glu Gly Pro Ala Ile Ser Asp Gly Glu Glu Gly Gly
                85                  90                  95

Gly Glu Pro Gly Ala Gly Gly Gly Ala Ala Gly Ala Ala Gly Ala Gly
            100                 105                 110

Arg Arg Asp Phe Val Glu Ala Pro Pro Pro Lys Val Asn Pro Trp Thr
        115                 120                 125

Lys Asn Ala Leu Pro Pro Val Leu Thr Thr Val Asn Gly Gln
    130                 135                 140


<210> SEQ ID NO 1907
<211> LENGTH: 39
<212> TYPE: PRT
<213> ORGANISM: Homo sapiens

<400> SEQUENCE: 1907

Met Asn Thr Glu Met Tyr Gln Thr Pro Met Glu Val Ala Val Tyr Gln
1               5                   10                  15

Leu His Asn Phe Ser Ile Ser Phe Phe Ser Ser Leu Leu Gly Gly Asp
            20                  25                  30

Val Val Ser Val Lys Leu Asp
        35


<210> SEQ ID NO 1908
<211> LENGTH: 255
<212> TYPE: PRT
<213> ORGANISM: Homo sapiens

<400> SEQUENCE: 1908

Met Asp Gly Pro Thr Arg Gly His Gly Leu Arg Lys Lys Arg Arg Ser
1               5                   10                  15

Arg Ser Gln Arg Asp Arg Glu Arg Arg Ser Arg Gly Gly Leu Gly Ala
            20                  25                  30

Gly Ala Ala Gly Gly Gly Gly Ala Gly Arg Thr Arg Ala Leu Ser Leu
        35                  40                  45

Ala Ser Ser Ser Gly Ser Asp Lys Glu Asp Asn Gly Lys Pro Pro Ser
    50                  55                  60

Ser Ala Pro Ser Arg Pro Arg Pro Pro Arg Arg Lys Arg Arg Glu Ser
65                  70                  75                  80

Thr Ser Ala Glu Glu Asp Ile Ile Asp Gly Phe Ala Met Thr Ser Phe
                85                  90                  95

Val Thr Phe Glu Ala Leu Glu Lys Asp Val Ala Leu Lys Pro Gln Glu
            100                 105                 110

Arg Val Glu Lys Arg Gln Thr Pro Leu Thr Lys Lys Lys Arg Glu Ala
        115                 120                 125

Leu Thr Asn Gly Leu Ser Phe His Ser Lys Lys Ser Arg Leu Ser His
    130                 135                 140

Pro His His Tyr Ser Ser Asp Arg Glu Asn Asp Arg Asn Leu Cys Gln
145                 150                 155                 160

His Leu Gly Lys Arg Lys Lys Met Pro Lys Ala Leu Arg Gln Leu Lys
                165                 170                 175

Pro Gly Gln Asn Ser Cys Arg Asp Ser Asp Ser Glu Ser Ala Ser Gly
            180                 185                 190

Glu Ser Lys Gly Phe His Arg Ser Ser Ser Arg Glu Arg Leu Ser Asp
        195                 200                 205
```

Ser Ser Ala Pro Ser Ser Leu Gly Thr Gly Tyr Phe Cys Asp Ser Asp
    210                 215                 220

Ser Asp Gln Glu Glu Lys Ala Ser Asp Ala Ser Ser Glu Lys Leu Phe
225                 230                 235                 240

Asn Thr Val Ile Val Asn Lys Asp Pro Glu Leu Gly Val Gly Thr
                245                 250                 255

<210> SEQ ID NO 1909
<211> LENGTH: 255
<212> TYPE: PRT
<213> ORGANISM: Homo sapiens

<400> SEQUENCE: 1909

Met Gly Ala Thr Gly Arg Leu Glu Leu Thr Leu Ala Ala Pro Pro His
1               5                   10                  15

Pro Gly Pro Ala Phe Gln Arg Ser Lys Ala Arg Glu Thr Gln Gly Glu
            20                  25                  30

Glu Glu Gly Ser Glu Met Gln Ile Ala Lys Ser Asp Ser Ile His His
        35                  40                  45

Met Ser His Ser Gln Gly Gln Pro Glu Leu Pro Pro Leu Pro Ala Ser
    50                  55                  60

Ala Asn Glu Glu Pro Ser Gly Leu Tyr Gln Thr Val Met Ser His Ser
65                  70                  75                  80

Phe Tyr Pro Pro Leu Met Gln Arg Thr Ser Trp Thr Leu Ala Ala Pro
                85                  90                  95

Phe Lys Glu Gln His His His Arg Gly Pro Ser Asp Ser Ile Ala Asn
            100                 105                 110

Asn Tyr Ser Leu Met Ala Gln Asp Leu Lys Leu Lys Asp Leu Leu Lys
        115                 120                 125

Val Tyr Gln Pro Ala Thr Ile Ser Val Pro Arg Asp Arg Thr Gly Gln
    130                 135                 140

Gly Leu Pro Ser Ser Gly Asn Arg Ser Ser Ser Glu Pro Met Arg Lys
145                 150                 155                 160

Lys Thr Lys Phe Ser Ser Arg Asn Lys Glu Asp Ser Thr Arg Ile Lys
                165                 170                 175

Leu Ala Phe Lys Thr Ser Ile Phe Ser Pro Met Lys Lys Glu Val Lys
            180                 185                 190

Thr Ser Leu Thr Phe Pro Gly Ser Arg Pro Met Ser Pro Glu Gln Gln
        195                 200                 205

Leu Asp Val Met Leu Gln Gln Glu Met Glu Met Glu Ser Lys Glu Lys
    210                 215                 220

Lys Pro Ser Glu Ser Asp Leu Glu Arg Tyr Tyr Tyr Tyr Leu Thr Asn
225                 230                 235                 240

Gly Ile Arg Lys Asp Met Ile Ala Pro Glu Glu Gly Glu Val Met
                245                 250                 255

<210> SEQ ID NO 1910
<211> LENGTH: 63
<212> TYPE: PRT
<213> ORGANISM: Homo sapiens

<400> SEQUENCE: 1910

Met Lys Glu Lys Ser Lys Asn Ala Ala Lys Thr Arg Arg Glu Lys Glu
1               5                   10                  15

Asn Gly Glu Phe Tyr Glu Leu Ala Lys Leu Leu Pro Leu Pro Ser Ala
            20                  25                  30

```
Ile Thr Ser Gln Leu Asp Lys Ala Ser Ile Ile Arg Leu Thr Thr Ser
        35                  40                  45

Tyr Leu Lys Met Arg Ala Val Phe Pro Glu Gly Leu Gly Asp Ala
    50                  55                  60


<210> SEQ ID NO 1911
<211> LENGTH: 255
<212> TYPE: PRT
<213> ORGANISM: Homo sapiens

<400> SEQUENCE: 1911

Met Phe Arg Ala Gly Glu Ala Ser Lys Arg Pro Leu Pro Gly Pro Ser
1               5                   10                  15

Pro Pro Arg Val Arg Ser Val Glu Val Ala Arg Gly Arg Ala Gly Tyr
            20                  25                  30

Gly Phe Thr Leu Ser Gly Gln Ala Pro Cys Val Leu Ser Cys Val Met
        35                  40                  45

Arg Gly Ser Pro Ala Asp Phe Val Gly Leu Arg Ala Gly Asp Gln Ile
    50                  55                  60

Leu Ala Val Asn Glu Ile Asn Val Lys Lys Ala Ser His Glu Asp Val
65                  70                  75                  80

Val Lys Leu Ile Gly Lys Cys Ser Gly Val Leu His Met Val Ile Ala
                85                  90                  95

Glu Gly Val Gly Arg Phe Glu Ser Cys Ser Ser Asp Glu Glu Gly Gly
            100                 105                 110

Leu Tyr Glu Gly Lys Gly Trp Leu Lys Pro Lys Leu Asp Ser Lys Ala
        115                 120                 125

Leu Gly Ile Asn Arg Ala Glu Arg Val Val Glu Glu Met Gln Ser Gly
    130                 135                 140

Gly Ile Phe Asn Met Ile Phe Glu Asn Pro Ser Leu Cys Ala Ser Asn
145                 150                 155                 160

Ser Glu Pro Leu Lys Leu Lys Gln Arg Ser Leu Ser Glu Ser Ala Ala
                165                 170                 175

Thr Arg Phe Asp Val Gly His Glu Ser Ile Asn Asn Pro Asn Pro Asn
            180                 185                 190

Met Leu Ser Lys Glu Glu Ile Ser Lys Val Ile His Asp Asp Ser Val
        195                 200                 205

Phe Ser Ile Gly Leu Glu Ser His Asp Asp Phe Ala Leu Asp Ala Ser
    210                 215                 220

Ile Leu Asn Val Ala Met Ile Val Gly Tyr Leu Gly Ser Ile Glu Leu
225                 230                 235                 240

Pro Ser Thr Ser Ser Asn Leu Glu Ser Asp Ser Leu Gln Ala Ile
                245                 250                 255


<210> SEQ ID NO 1912
<211> LENGTH: 255
<212> TYPE: PRT
<213> ORGANISM: Homo sapiens

<400> SEQUENCE: 1912

Met Pro Ser Glu Thr Pro Gln Ala Glu Val Gly Pro Thr Gly Cys Pro
1               5                   10                  15

His Arg Ser Gly Pro His Ser Ala Lys Gly Ser Leu Glu Lys Gly Ser
            20                  25                  30

Pro Glu Asp Lys Glu Ala Lys Glu Pro Leu Trp Ile Arg Pro Asp Ala
        35                  40                  45
```

Pro Ser Arg Cys Thr Trp Gln Leu Gly Arg Pro Ala Ser Glu Ser Pro
50 55 60

His His His Thr Ala Pro Ala Lys Ser Pro Lys Ile Leu Pro Asp Ile
65 70 75 80

Leu Lys Lys Ile Gly Asp Thr Pro Met Val Arg Ile Asn Lys Ile Gly
85 90 95

Lys Lys Phe Gly Leu Lys Cys Glu Leu Leu Ala Lys Cys Glu Phe Phe
100 105 110

Asn Ala Gly Gly Ser Val Lys Asp Arg Ile Ser Leu Arg Met Ile Glu
115 120 125

Asp Ala Glu Arg Asp Gly Thr Leu Lys Pro Gly Asp Thr Ile Ile Glu
130 135 140

Pro Thr Ser Gly Asn Thr Gly Ile Gly Leu Ala Leu Ala Ala Ala Val
145 150 155 160

Arg Gly Tyr Arg Cys Ile Ile Val Met Pro Glu Lys Met Ser Ser Glu
165 170 175

Lys Val Asp Val Leu Arg Ala Leu Gly Ala Glu Ile Val Arg Thr Pro
180 185 190

Thr Asn Ala Arg Phe Asp Ser Pro Glu Ser His Val Gly Val Ala Trp
195 200 205

Arg Leu Lys Asn Glu Ile Pro Asn Ser His Ile Leu Asp Gln Tyr Arg
210 215 220

Asn Ala Ser Asn Pro Leu Ala His Tyr Asp Thr Thr Ala Asp Glu Ile
225 230 235 240

Leu Gln Gln Cys Asp Gly Lys Leu Asp Met Leu Val Ala Ser Val
245 250 255

<210> SEQ ID NO 1913
<211> LENGTH: 43
<212> TYPE: PRT
<213> ORGANISM: Homo sapiens

<400> SEQUENCE: 1913

Met Gln Asp Gly Arg Lys Gly Gly Ala Tyr Ala Gly Lys Met Glu Ala
1 5 10 15

Thr Thr Ala Gly Val Gly Arg Leu Glu Glu Glu Ala Leu Arg Arg Lys
20 25 30

Glu Arg Leu Lys Ala Leu Arg Glu Lys Thr Gly
35 40

<210> SEQ ID NO 1914
<211> LENGTH: 215
<212> TYPE: PRT
<213> ORGANISM: Homo sapiens

<400> SEQUENCE: 1914

Met Ser Ser Glu Gln Ser Ala Pro Gly Ala Ser Pro Arg Ala Pro Arg
1 5 10 15

Pro Gly Thr Gln Lys Ser Ser Gly Ala Val Thr Lys Lys Gly Glu Arg
20 25 30

Ala Ala Lys Glu Lys Pro Ala Thr Val Leu Pro Pro Val Gly Glu Glu
35 40 45

Glu Pro Lys Ser Pro Glu Glu Tyr Gln Cys Ser Gly Val Leu Glu Thr
50 55 60

Asp Phe Ala Glu Leu Cys Thr Arg Trp Gly Tyr Thr Asp Phe Pro Lys
65 70 75 80

Val Val Asn Arg Pro Arg Pro His Pro Pro Phe Val Pro Ser Ala Ser
85 90 95

Leu Ser Glu Lys Ala Thr Leu Asp Asp Pro Arg Leu Ser Gly Ser Cys
100 105 110

Ser Leu Asn Ser Leu Glu Ser Lys Tyr Val Phe Phe Arg Pro Thr Ile
115 120 125

Gln Val Glu Leu Glu Gln Glu Asp Ser Lys Ser Val Lys Glu Ile Tyr
130 135 140

Ile Arg Gly Trp Lys Val Glu Glu Arg Ile Leu Gly Val Phe Ser Lys
145 150 155 160

Cys Leu Pro Pro Leu Thr Gln Leu Gln Ala Ile Asn Leu Trp Lys Val
165 170 175

Gly Leu Thr Asp Lys Thr Leu Thr Thr Phe Ile Glu Leu Leu Pro Leu
180 185 190

Cys Ser Ser Thr Leu Arg Lys Val Ser Leu Glu Gly Asn Pro Leu Pro
195 200 205

Glu Gln Ser Tyr His Lys Leu
210 215

<210> SEQ ID NO 1915
<211> LENGTH: 57
<212> TYPE: PRT
<213> ORGANISM: Homo sapiens

<400> SEQUENCE: 1915

Met Glu Thr Asn Cys Arg Lys Leu Val Ser Ala Cys Val Gln Leu Gly
1 5 10 15

Val Gln Pro Ala Ala Val Glu Cys Leu Phe Ser Lys Asp Ser Glu Ile
20 25 30

Lys Lys Val Glu Phe Thr Asp Ser Pro Glu Ser Arg Lys Glu Ala Ala
35 40 45

Ser Ser Lys Phe Phe Pro Arg Gln His
50 55

<210> SEQ ID NO 1916
<211> LENGTH: 255
<212> TYPE: PRT
<213> ORGANISM: Homo sapiens

<400> SEQUENCE: 1916

Met Arg Thr Leu Trp Met Ala Leu Cys Ala Leu Ser Arg Leu Trp Pro
1 5 10 15

Gly Ala Gln Ala Gly Cys Ala Glu Ala Gly Arg Cys Cys Pro Gly Arg
20 25 30

Asp Pro Ala Cys Phe Ala Arg Gly Trp Arg Leu Asp Arg Val Tyr Gly
35 40 45

Thr Cys Phe Cys Asp Gln Ala Cys Arg Phe Thr Gly Asp Cys Cys Phe
50 55 60

Asp Tyr Asp Arg Ala Cys Pro Ala Arg Pro Cys Phe Val Gly Glu Trp
65 70 75 80

Ser Pro Trp Ser Gly Cys Ala Asp Gln Cys Lys Pro Thr Thr Arg Val
85 90 95

Arg Arg Arg Ser Val Gln Gln Glu Pro Gln Asn Gly Gly Ala Pro Cys
100 105 110

Pro Pro Leu Glu Glu Arg Ala Gly Cys Leu Glu Tyr Ser Thr Pro Gln
115 120 125

Gly Gln Asp Cys Gly His Thr Tyr Val Pro Ala Phe Ile Thr Thr Ser
    130                 135                 140

Ala Phe Asn Lys Glu Arg Thr Arg Gln Ala Thr Ser Pro His Trp Ser
145                 150                 155                 160

Thr His Thr Glu Asp Ala Gly Tyr Cys Met Glu Phe Lys Thr Glu Ser
                165                 170                 175

Leu Thr Pro His Cys Ala Leu Glu Asn Trp Pro Leu Thr Arg Trp Met
            180                 185                 190

Gln Tyr Leu Arg Glu Gly Tyr Thr Val Cys Val Asp Cys Gln Pro Pro
        195                 200                 205

Ala Met Asn Ser Val Ser Leu Arg Cys Ser Gly Asp Gly Leu Asp Ser
    210                 215                 220

Asp Gly Asn Gln Thr Leu His Trp Gln Ala Ile Gly Asn Pro Arg Cys
225                 230                 235                 240

Gln Gly Thr Trp Lys Lys Val Arg Arg Val Asp Gln Cys Ser Cys
                245                 250                 255

<210> SEQ ID NO 1917
<211> LENGTH: 66
<212> TYPE: PRT
<213> ORGANISM: Homo sapiens

<400> SEQUENCE: 1917

Met Asp Tyr Leu Thr Thr Phe Thr Glu Lys Ser Gly Arg Leu Leu Arg
1               5                   10                  15

Gly Thr Ala Asn Arg Leu Leu Gly Phe Gly Gly Gly Gly Glu Ala Arg
            20                  25                  30

Gln Val Arg Phe Glu Asp Tyr Leu Arg Glu Pro Ala Gln Gly Asp Leu
        35                  40                  45

Gly Cys Gly Ser Pro Pro His Arg Pro Pro Ala Pro Ser Ser Pro Glu
    50                  55                  60

Gly Pro
65

<210> SEQ ID NO 1918
<211> LENGTH: 62
<212> TYPE: PRT
<213> ORGANISM: Homo sapiens

<400> SEQUENCE: 1918

Met Ala Ala Ala Thr Val Gly Arg Asp Thr Leu Pro Glu His Trp Ser
1               5                   10                  15

Tyr Gly Val Cys Arg Asp Gly Arg Val Phe Phe Ile Asn Asp Gln Leu
            20                  25                  30

Arg Cys Thr Thr Trp Leu His Pro Arg Thr Gly Glu Pro Val Asn Ser
        35                  40                  45

Gly His Met Ile Arg Ser Asp Leu Pro Arg Gly Trp Glu Glu
    50                  55                  60

<210> SEQ ID NO 1919
<211> LENGTH: 85
<212> TYPE: PRT
<213> ORGANISM: Homo sapiens

<400> SEQUENCE: 1919

Met Asp Ser Ala Ala Ala Ala Phe Ala Leu Asp Lys Pro Ala Leu Gly
1               5                   10                  15

```
Pro Gly Pro Pro Pro Pro Pro Pro Ala Leu Gly Pro Gly Asp Cys Ala
            20                  25                  30

Gln Ala Arg Lys Asn Phe Ser Val Ser His Leu Leu Asp Leu Glu Glu
        35                  40                  45

Val Ala Ala Ala Gly Arg Leu Ala Ala Arg Pro Gly Ala Arg Ala Glu
    50                  55                  60

Ala Arg Glu Gly Ala Ala Arg Glu Pro Ser Gly Gly Ser Ser Gly Ser
65                  70                  75                  80

Glu Ala Ala Pro Gln
                85


<210> SEQ ID NO 1920
<211> LENGTH: 255
<212> TYPE: PRT
<213> ORGANISM: Homo sapiens

<400> SEQUENCE: 1920

Met Ser Val Pro Asp Tyr Met Gln Cys Ala Glu Asp His Gln Thr Leu
1               5                   10                  15

Leu Val Val Val Gln Pro Val Gly Ile Val Ser Glu Glu Asn Phe Phe
            20                  25                  30

Arg Ile Tyr Lys Arg Ile Cys Ser Val Ser Gln Ile Ser Val Arg Asp
        35                  40                  45

Ser Gln Arg Val Leu Tyr Ile Arg Tyr Arg His His Tyr Pro Pro Glu
    50                  55                  60

Asn Asn Glu Trp Gly Asp Phe Gln Thr His Arg Lys Val Val Gly Leu
65                  70                  75                  80

Ile Thr Ile Thr Asp Cys Phe Ser Ala Lys Asp Trp Pro Gln Thr Phe
                85                  90                  95

Glu Lys Phe His Val Gln Lys Glu Ile Tyr Gly Ser Thr Leu Tyr Asp
            100                 105                 110

Ser Arg Leu Phe Val Phe Gly Leu Gln Gly Glu Ile Val Glu Gln Pro
        115                 120                 125

Arg Thr Asp Val Ala Phe Tyr Pro Asn Tyr Glu Asp Cys Gln Thr Val
    130                 135                 140

Glu Lys Arg Ile Glu Asp Phe Ile Glu Ser Leu Phe Ile Val Leu Glu
145                 150                 155                 160

Ser Lys Arg Leu Asp Arg Ala Thr Asp Lys Ser Gly Asp Lys Ile Pro
                165                 170                 175

Leu Leu Cys Val Pro Phe Glu Lys Lys Asp Phe Val Gly Leu Asp Thr
            180                 185                 190

Asp Ser Arg His Tyr Lys Lys Arg Cys Gln Gly Arg Met Arg Lys His
        195                 200                 205

Val Gly Asp Leu Cys Leu Gln Ala Gly Met Leu Gln Asp Ser Leu Val
    210                 215                 220

His Tyr His Met Ser Val Glu Leu Leu Arg Ser Val Asn Asp Phe Leu
225                 230                 235                 240

Trp Leu Gly Ala Ala Leu Glu Gly Leu Cys Ser Ala Ser Val Ile
                245                 250                 255


<210> SEQ ID NO 1921
<211> LENGTH: 255
<212> TYPE: PRT
<213> ORGANISM: Homo sapiens

<400> SEQUENCE: 1921
```

```
Met Asp His Ala Glu Glu Asn Glu Ile Leu Ala Ala Thr Gln Arg Tyr
1               5                   10                  15

Tyr Val Glu Arg Pro Ile Phe Ser His Pro Val Leu Gln Glu Arg Leu
            20                  25                  30

His Thr Lys Asp Lys Val Pro Asp Ser Ile Ala Asp Lys Leu Lys Gln
        35                  40                  45

Ala Phe Thr Cys Thr Pro Lys Lys Ile Arg Asn Ile Ile Tyr Met Phe
    50                  55                  60

Leu Pro Ile Thr Lys Trp Leu Pro Ala Tyr Lys Phe Lys Glu Tyr Val
65                  70                  75                  80

Leu Gly Asp Leu Val Ser Gly Ile Ser Thr Gly Val Leu Gln Leu Pro
                85                  90                  95

Gln Gly Leu Ala Phe Ala Met Leu Ala Ala Val Pro Pro Ile Phe Gly
            100                 105                 110

Leu Tyr Ser Ser Phe Tyr Pro Val Ile Met Tyr Cys Phe Leu Gly Thr
        115                 120                 125

Ser Arg His Ile Ser Ile Gly Pro Phe Ala Val Ile Ser Leu Met Ile
    130                 135                 140

Gly Gly Val Ala Val Arg Leu Val Pro Asp Asp Ile Val Ile Pro Gly
145                 150                 155                 160

Gly Val Asn Ala Thr Asn Gly Thr Glu Ala Arg Asp Ala Leu Arg Val
                165                 170                 175

Lys Val Ala Met Ser Val Thr Leu Leu Ser Gly Ile Ile Gln Phe Cys
            180                 185                 190

Leu Gly Val Cys Arg Phe Gly Phe Val Ala Ile Tyr Leu Thr Glu Pro
        195                 200                 205

Leu Val Arg Gly Phe Thr Thr Ala Ala Ala Val His Val Phe Thr Ser
    210                 215                 220

Met Leu Lys Tyr Leu Phe Gly Val Lys Thr Lys Arg Tyr Ser Gly Ile
225                 230                 235                 240

Phe Ser Val Val Tyr Ser Thr Val Ala Val Leu Gln Asn Val Lys
                245                 250                 255
```

<210> SEQ ID NO 1922
<211> LENGTH: 255
<212> TYPE: PRT
<213> ORGANISM: Homo sapiens

<400> SEQUENCE: 1922

```
Met His Tyr Asp Gly His Val Arg Phe Asp Leu Pro Pro Gln Gly Ser
1               5                   10                  15

Val Leu Ala Arg Asn Val Ser Thr Arg Ser Cys Pro Pro Arg Thr Ser
            20                  25                  30

Pro Ala Val Asp Leu Glu Glu Glu Glu Glu Glu Ser Ser Val Asp Gly
        35                  40                  45

Lys Gly Asp Arg Lys Ser Thr Gly Leu Lys Leu Ser Lys Lys Lys Ala
    50                  55                  60

Arg Arg Arg His Thr Asp Asp Pro Ser Lys Glu Cys Phe Thr Leu Lys
65                  70                  75                  80

Phe Asp Leu Asn Val Asp Ile Glu Thr Glu Ile Val Pro Ala Met Lys
                85                  90                  95

Lys Lys Ser Leu Gly Glu Val Leu Leu Pro Val Phe Glu Arg Lys Gly
            100                 105                 110

Ile Ala Leu Gly Lys Val Asp Ile Tyr Leu Asp Gln Ser Asn Thr Pro
        115                 120                 125
```

```
Leu Ser Leu Thr Phe Glu Ala Tyr Arg Phe Gly Gly His Tyr Leu Arg
    130                 135                 140

Val Lys Ala Pro Ala Lys Pro Gly Asp Glu Gly Lys Val Glu Gln Gly
145                 150                 155                 160

Met Lys Asp Ser Lys Ser Leu Ser Leu Pro Ile Leu Arg Pro Ala Gly
                165                 170                 175

Thr Gly Pro Pro Ala Leu Glu Arg Val Asp Ala Gln Ser Arg Arg Glu
            180                 185                 190

Ser Leu Asp Ile Leu Ala Pro Gly Arg Arg Arg Lys Asn Met Ser Glu
        195                 200                 205

Phe Leu Gly Glu Ala Ser Ile Pro Gly Gln Glu Pro Pro Thr Pro Ser
    210                 215                 220

Ser Cys Ser Leu Pro Ser Gly Ser Ser Gly Ser Thr Asn Thr Gly Asp
225                 230                 235                 240

Ser Trp Lys Asn Arg Ala Ala Ser Arg Phe Ser Gly Phe Phe Ser
                245                 250                 255
```

<210> SEQ ID NO 1923
<211> LENGTH: 205
<212> TYPE: PRT
<213> ORGANISM: Homo sapiens

<400> SEQUENCE: 1923

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser
        195                 200                 205
```

<210> SEQ ID NO 1924
<211> LENGTH: 77
<212> TYPE: PRT
<213> ORGANISM: Homo sapiens

<400> SEQUENCE: 1924

Met Lys Arg Gly Thr Ser Leu His Ser Arg Arg Gly Lys Pro Glu Ala
1 5 10 15

Pro Lys Gly Ser Pro Gln Ile Asn Arg Lys Ser Gly Gln Glu Met Thr
20 25 30

Ala Val Met Gln Ser Gly Arg Pro Arg Ser Ser Ser Thr Thr Asp Ala
35 40 45

Pro Thr Ser Ser Ala Met Met Glu Ile Ala Cys Ala Ala Ala Ala Ala
50 55 60

Ala Ala Ala Cys Leu Pro Gly Glu Glu Gly Thr Ala Glu
65 70 75

<210> SEQ ID NO 1925
<211> LENGTH: 255
<212> TYPE: PRT
<213> ORGANISM: Homo sapiens

<400> SEQUENCE: 1925

Met Thr Ser Thr Gly Lys Asp Gly Gly Ala Gln His Ala Gln Tyr Val
1 5 10 15

Gly Pro Tyr Arg Leu Glu Lys Thr Leu Gly Lys Gly Gln Thr Gly Leu
20 25 30

Val Lys Leu Gly Val His Cys Val Thr Cys Gln Lys Val Ala Ile Lys
35 40 45

Ile Val Asn Arg Glu Lys Leu Ser Glu Ser Val Leu Met Lys Val Glu
50 55 60

Arg Glu Ile Ala Ile Leu Lys Leu Ile Glu His Pro His Val Leu Lys
65 70 75 80

Leu His Asp Val Tyr Glu Asn Lys Lys Tyr Leu Tyr Leu Val Leu Glu
85 90 95

His Val Ser Gly Gly Glu Leu Phe Asp Tyr Leu Val Lys Lys Gly Arg
100 105 110

Leu Thr Pro Lys Glu Ala Arg Lys Phe Phe Arg Gln Ile Ile Ser Ala
115 120 125

Leu Asp Phe Cys His Ser His Ser Ile Cys His Arg Asp Leu Lys Pro
130 135 140

Glu Asn Leu Leu Leu Asp Glu Lys Asn Asn Ile Arg Ile Ala Asp Phe
145 150 155 160

Gly Met Ala Ser Leu Gln Val Gly Asp Ser Leu Leu Glu Thr Ser Cys
165 170 175

Gly Ser Pro His Tyr Ala Cys Pro Glu Val Ile Arg Gly Glu Lys Tyr
180 185 190

Asp Gly Arg Lys Ala Asp Val Trp Ser Cys Gly Val Ile Leu Phe Ala
195 200 205

Leu Leu Val Gly Ala Leu Pro Phe Asp Asp Asp Asn Leu Arg Gln Leu
210 215 220

Leu Glu Lys Val Lys Arg Gly Val Phe His Met Pro His Phe Ile Pro
225 230 235 240

Pro Asp Cys Gln Ser Leu Leu Arg Gly Met Ile Glu Val Asp Ala
245 250 255

<210> SEQ ID NO 1926
<211> LENGTH: 255
<212> TYPE: PRT
<213> ORGANISM: Homo sapiens

<400> SEQUENCE: 1926

Met Met Cys Glu Val Met Pro Thr Ile Ser Glu Asp Gly Arg Arg Gly
1 5 10 15

Ser Ala Leu Gly Pro Asp Glu Ala Gly Gly Glu Leu Glu Arg Leu Met
20 25 30

Val Thr Met Leu Thr Glu Arg Glu Arg Leu Leu Glu Thr Leu Arg Glu
35 40 45

Ala Gln Asp Gly Leu Ala Thr Ala Gln Leu Arg Leu Arg Glu Leu Gly
50 55 60

His Glu Lys Asp Ser Leu Gln Arg Gln Leu Ser Ile Ala Leu Pro Gln
65 70 75 80

Glu Phe Ala Ala Leu Thr Lys Glu Leu Asn Leu Cys Arg Glu Gln Leu
85 90 95

Leu Glu Arg Glu Glu Glu Ile Ala Glu Leu Lys Ala Glu Arg Asn Asn
100 105 110

Thr Arg Leu Leu Leu Glu His Leu Glu Cys Leu Val Ser Arg His Glu
115 120 125

Arg Ser Leu Arg Met Thr Val Val Lys Arg Gln Ala Gln Ser Pro Gly
130 135 140

Gly Val Ser Ser Glu Val Glu Val Leu Lys Ala Leu Lys Ser Leu Phe
145 150 155 160

Glu His His Lys Ala Leu Asp Glu Lys Val Arg Glu Arg Leu Arg Met
165 170 175

Ala Leu Glu Arg Val Ala Val Leu Glu Glu Glu Leu Glu Leu Ser Asn
180 185 190

Gln Glu Thr Leu Asn Leu Arg Glu Gln Leu Ser Arg Arg Arg Ser Gly
195 200 205

Leu Glu Glu Pro Gly Lys Asp Gly Asp Gly Gln Thr Leu Ala Asn Gly
210 215 220

Leu Gly Pro Gly Gly Asp Ser Asn Arg Arg Thr Ala Glu Leu Glu Glu
225 230 235 240

Ala Leu Glu Arg Gln Arg Ala Glu Val Cys Gln Leu Arg Glu Arg
245 250 255

<210> SEQ ID NO 1927
<211> LENGTH: 255
<212> TYPE: PRT
<213> ORGANISM: Homo sapiens

<400> SEQUENCE: 1927

Met Pro Pro Pro Arg Leu Leu Phe Phe Leu Leu Phe Leu Thr Pro Met
1 5 10 15

Glu Val Arg Pro Glu Glu Pro Leu Val Val Lys Val Glu Glu Gly Asp
20 25 30

Asn Ala Val Leu Gln Cys Leu Lys Gly Thr Ser Asp Gly Pro Thr Gln
35 40 45

Gln Leu Thr Trp Ser Arg Glu Ser Pro Leu Lys Pro Phe Leu Lys Leu
50 55 60

Ser Leu Gly Leu Pro Gly Leu Gly Ile His Met Arg Pro Leu Ala Ile
65 70 75 80

Trp Leu Phe Ile Phe Asn Val Ser Gln Gln Met Gly Gly Phe Tyr Leu
85 90 95

Cys Gln Pro Gly Pro Pro Ser Glu Lys Ala Trp Gln Pro Gly Trp Thr
100 105 110

Val Asn Val Glu Gly Ser Gly Glu Leu Phe Arg Trp Asn Val Ser Asp 115 120 125

Leu Gly Gly Leu Gly Cys Gly Leu Lys Asn Arg Ser Ser Glu Gly Pro
130 135 140

Ser Ser Pro Ser Gly Lys Leu Met Ser Pro Lys Leu Tyr Val Trp Ala
145 150 155 160

Lys Asp Arg Pro Glu Ile Trp Glu Gly Glu Pro Pro Cys Leu Pro Pro
165 170 175

Arg Asp Ser Leu Asn Gln Ser Leu Ser Gln Asp Leu Thr Met Ala Pro
180 185 190

Gly Ser Thr Leu Trp Leu Ser Cys Gly Val Pro Pro Asp Ser Val Ser
195 200 205

Arg Gly Pro Leu Ser Trp Thr His Val His Pro Lys Gly Pro Lys Ser
210 215 220

Leu Leu Ser Leu Glu Leu Lys Asp Asp Arg Pro Ala Arg Asp Met Trp
225 230 235 240

Val Met Glu Thr Gly Leu Leu Leu Pro Arg Ala Thr Ala Gln Asp
245 250 255

<210> SEQ ID NO 1928
<211> LENGTH: 174
<212> TYPE: PRT
<213> ORGANISM: Homo sapiens

<400> SEQUENCE: 1928

Met Val Ala Gly Met Leu Met Pro Arg Asp Gln Leu Arg Ala Ile Tyr
1 5 10 15

Glu Val Leu Phe Arg Glu Gly Val Met Val Ala Lys Lys Asp Arg Arg
20 25 30

Pro Arg Ser Leu His Pro His Val Pro Gly Val Thr Asn Leu Gln Val
35 40 45

Met Arg Ala Met Ala Ser Leu Arg Ala Arg Gly Leu Val Arg Glu Thr
50 55 60

Phe Ala Trp Cys His Phe Tyr Trp Tyr Leu Thr Asn Glu Gly Ile Ala
65 70 75 80

His Leu Arg Gln Tyr Leu His Leu Pro Pro Glu Ile Val Pro Ala Ser
85 90 95

Leu Gln Arg Val Arg Arg Pro Val Ala Met Val Met Pro Ala Arg Arg
100 105 110

Thr Pro His Val Gln Ala Val Gln Gly Pro Leu Gly Ser Pro Pro Lys
115 120 125

Arg Gly Pro Leu Pro Thr Glu Glu Gln Arg Val Tyr Arg Arg Lys Glu
130 135 140

Leu Glu Glu Val Ser Pro Glu Thr Pro Val Val Pro Ala Thr Thr Gln
145 150 155 160

Arg Thr Leu Ala Arg Pro Gly Pro Glu Pro Ala Pro Ala Thr
165 170

<210> SEQ ID NO 1929
<211> LENGTH: 255
<212> TYPE: PRT
<213> ORGANISM: Homo sapiens

<400> SEQUENCE: 1929

Met Gly Asn Gly Val Lys Glu Gly Pro Val Arg Leu His Glu Asp Ala
1 5 10 15

Glu Ala Val Leu Ser Ser Ser Val Ser Ser Lys Arg Asp His Arg Gln

```
            20                  25                  30

Val Leu Ser Ser Leu Leu Ser Gly Ala Leu Ala Gly Ala Leu Ala Lys
        35                  40                  45

Thr Ala Val Ala Pro Leu Asp Arg Thr Lys Ile Ile Phe Gln Val Ser
    50                  55                  60

Ser Lys Arg Phe Ser Ala Lys Glu Ala Phe Arg Val Leu Tyr Tyr Thr
65                  70                  75                  80

Tyr Leu Asn Glu Gly Phe Leu Ser Leu Trp Arg Gly Asn Ser Ala Thr
                85                  90                  95

Met Val Arg Val Val Pro Tyr Ala Ala Ile Gln Phe Ser Ala His Glu
            100                 105                 110

Glu Tyr Lys Arg Ile Leu Gly Ser Tyr Tyr Gly Phe Arg Gly Glu Ala
        115                 120                 125

Leu Pro Pro Trp Pro Arg Leu Phe Ala Gly Ala Leu Ala Gly Thr Thr
    130                 135                 140

Ala Ala Ser Leu Thr Tyr Pro Leu Asp Leu Val Arg Ala Arg Met Ala
145                 150                 155                 160

Val Thr Pro Lys Glu Met Tyr Ser Asn Ile Phe His Val Phe Ile Arg
                165                 170                 175

Ile Ser Arg Glu Glu Gly Leu Lys Thr Leu Tyr His Gly Phe Met Pro
            180                 185                 190

Thr Val Leu Gly Val Ile Pro Tyr Ala Gly Leu Ser Phe Phe Thr Tyr
        195                 200                 205

Glu Thr Leu Lys Ser Leu His Arg Glu Tyr Ser Gly Arg Arg Gln Pro
    210                 215                 220

Tyr Pro Phe Glu Arg Met Ile Phe Gly Ala Cys Ala Gly Leu Ile Gly
225                 230                 235                 240

Gln Ser Ala Ser Tyr Pro Leu Asp Val Val Arg Arg Arg Met Gln
                245                 250                 255
```

<210> SEQ ID NO 1930
<211> LENGTH: 87
<212> TYPE: PRT
<213> ORGANISM: Homo sapiens

<400> SEQUENCE: 1930

```
Met Ala Gly Gly Gly Ser Asp Leu Ser Thr Arg Gly Leu Asn Gly Gly
1               5                   10                  15

Val Ser Gln Val Ala Asn Glu Met Asn His Leu Pro Ala His Ser Gln
            20                  25                  30

Ser Leu Gln Arg Leu Phe Thr Glu Asp Gln Asp Val Asp Glu Gly Leu
        35                  40                  45

Val Tyr Asp Thr Val Phe Lys His Phe Lys Arg His Lys Leu Glu Ile
    50                  55                  60

Ser Asn Ala Ile Lys Lys Thr Phe Pro Phe Leu Glu Gly Leu Arg Asp
65                  70                  75                  80

Arg Glu Leu Ile Thr Asn Lys
                85
```

<210> SEQ ID NO 1931
<211> LENGTH: 255
<212> TYPE: PRT
<213> ORGANISM: Homo sapiens

<400> SEQUENCE: 1931

```
Met Glu Arg Arg Arg Leu Trp Gly Ser Ile Gln Ser Arg Tyr Ile Ser
```

```
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr
                245                 250                 255


<210> SEQ ID NO 1932
<211> LENGTH: 255
<212> TYPE: PRT
<213> ORGANISM: Homo sapiens

<400> SEQUENCE: 1932

Met Ala Val Glu Asp Glu Gly Leu Arg Val Phe Gln Ser Val Lys Ile
1               5                   10                  15

Lys Ile Gly Glu Ala Lys Asn Leu Pro Ser Tyr Pro Gly Pro Ser Lys
            20                  25                  30

Met Arg Asp Cys Tyr Cys Thr Val Asn Leu Asp Gln Glu Glu Val Phe
        35                  40                  45

Arg Thr Lys Ile Val Glu Lys Ser Leu Cys Pro Phe Tyr Gly Glu Asp
    50                  55                  60

Phe Tyr Cys Glu Ile Pro Arg Ser Phe Arg His Leu Ser Phe Tyr Ile
65                  70                  75                  80

Phe Asp Arg Asp Val Phe Arg Arg Asp Ser Ile Ile Gly Lys Val Ala
                85                  90                  95

Ile Gln Lys Glu Asp Leu Gln Lys Tyr His Asn Arg Asp Thr Trp Phe
            100                 105                 110

Gln Leu Gln His Val Asp Ala Asp Ser Glu Val Gln Gly Lys Val His
        115                 120                 125
```

Leu Glu Leu Arg Leu Ser Glu Val Ile Thr Asp Thr Gly Val Val Cys
    130                 135                 140

His Lys Leu Ala Thr Arg Ile Val Glu Cys Gln Gly Leu Pro Ile Val
145                 150                 155                 160

Asn Gly Gln Cys Asp Pro Tyr Ala Thr Val Thr Leu Ala Gly Pro Phe
                165                 170                 175

Arg Ser Glu Ala Lys Lys Thr Lys Val Lys Arg Lys Thr Asn Asn Pro
            180                 185                 190

Gln Phe Asp Glu Val Phe Tyr Phe Glu Val Thr Arg Pro Cys Ser Tyr
        195                 200                 205

Ser Lys Lys Ser His Phe Asp Phe Glu Glu Glu Asp Val Asp Lys Leu
    210                 215                 220

Glu Ile Arg Val Asp Leu Trp Asn Ala Ser Asn Leu Lys Phe Gly Asp
225                 230                 235                 240

Glu Phe Leu Gly Glu Leu Arg Ile Pro Leu Lys Val Leu Arg Gln
                245                 250                 255

<210> SEQ ID NO 1933
<211> LENGTH: 255
<212> TYPE: PRT
<213> ORGANISM: Homo sapiens

<400> SEQUENCE: 1933

Met Pro Ala Val Ser Lys Gly Asp Gly Met Arg Gly Leu Ala Val Phe
1               5                   10                  15

Ile Ser Asp Ile Arg Asn Cys Lys Ser Lys Glu Ala Glu Ile Lys Arg
            20                  25                  30

Ile Asn Lys Glu Leu Ala Asn Ile Arg Ser Lys Phe Lys Gly Asp Lys
        35                  40                  45

Ala Leu Asp Gly Tyr Ser Lys Lys Lys Tyr Val Cys Lys Leu Leu Phe
    50                  55                  60

Ile Phe Leu Leu Gly His Asp Ile Asp Phe Gly His Met Glu Ala Val
65                  70                  75                  80

Asn Leu Leu Ser Ser Asn Lys Tyr Thr Glu Lys Gln Ile Gly Tyr Leu
                85                  90                  95

Phe Ile Ser Val Leu Val Asn Ser Asn Ser Glu Leu Ile Arg Leu Ile
            100                 105                 110

Asn Asn Ala Ile Lys Asn Asp Leu Ala Ser Arg Asn Pro Thr Phe Met
        115                 120                 125

Cys Leu Ala Leu His Cys Ile Ala Asn Val Gly Ser Arg Glu Met Gly
    130                 135                 140

Glu Ala Phe Ala Ala Asp Ile Pro Arg Ile Leu Val Ala Gly Asp Ser
145                 150                 155                 160

Met Asp Ser Val Lys Gln Ser Ala Ala Leu Cys Leu Leu Arg Leu Tyr
                165                 170                 175

Lys Ala Ser Pro Asp Leu Val Pro Met Gly Glu Trp Thr Ala Arg Val
            180                 185                 190

Val His Leu Leu Asn Asp Gln His Met Gly Val Val Thr Ala Ala Val
        195                 200                 205

Ser Leu Ile Thr Cys Leu Cys Lys Lys Asn Pro Asp Asp Phe Lys Thr
    210                 215                 220

Cys Val Ser Leu Ala Val Ser Arg Leu Ser Arg Ile Val Ser Ser Ala
225                 230                 235                 240

Ser Thr Asp Leu Gln Asp Tyr Thr Tyr Tyr Phe Val Pro Ala Pro
                245                 250                 255

<210> SEQ ID NO 1934
<211> LENGTH: 255
<212> TYPE: PRT
<213> ORGANISM: Homo sapiens

<400> SEQUENCE: 1934

```
Met Ala Gly Ala Leu Arg Arg Gly Arg Ala Leu Gly Ser Arg Pro Ser
1               5                   10                  15

Gly Pro Thr Val Ser Ser Arg Arg Ser Pro Gln Cys Pro Val Ala Gln
            20                  25                  30

Glu Gly Leu Gly Ala Arg Ser Arg Pro Arg Val Ala Pro Arg Ser Leu
        35                  40                  45

Ala Arg Cys Gly Pro Ser Ser Arg Leu Met Gly Trp Lys Pro Ser Glu
    50                  55                  60

Ala Arg Gly Gln Ser Gln Ser Phe Gln Ala Ser Gly Leu Gln Pro Arg
65                  70                  75                  80

Ser Leu Lys Ala Ala Arg Arg Ala Thr Gly Arg Pro Asp Arg Ser Arg
                85                  90                  95

Ala Ala Pro Pro Asn Met Asp Pro Asp Pro Gln Ala Gly Val Gln Val
            100                 105                 110

Gly Met Arg Val Val Arg Gly Val Asp Trp Lys Trp Gly Gln Gln Asp
        115                 120                 125

Gly Gly Glu Gly Gly Val Gly Thr Val Val Glu Leu Gly Arg His Gly
    130                 135                 140

Ser Pro Ser Thr Pro Asp Arg Thr Val Val Val Gln Trp Asp Gln Gly
145                 150                 155                 160

Thr Arg Thr Asn Tyr Arg Ala Gly Tyr Gln Gly Ala His Asp Leu Leu
                165                 170                 175

Leu Tyr Asp Asn Ala Gln Ile Gly Val Arg His Pro Asn Ile Ile Cys
            180                 185                 190

Asp Cys Cys Lys Lys His Gly Leu Arg Gly Met Arg Trp Lys Cys Arg
        195                 200                 205

Val Cys Leu Asp Tyr Asp Leu Cys Thr Gln Cys Tyr Met His Asn Lys
    210                 215                 220

His Glu Leu Ala His Ala Phe Asp Arg Tyr Glu Thr Ala His Ser Arg
225                 230                 235                 240

Pro Val Thr Leu Ser Pro Arg Gln Gly Leu Pro Arg Ile Pro Leu
                245                 250                 255
```

<210> SEQ ID NO 1935
<211> LENGTH: 255
<212> TYPE: PRT
<213> ORGANISM: Homo sapiens

<400> SEQUENCE: 1935

```
Met Ala Gly Gly Val Trp Gly Arg Ser Arg Ala Arg Glu Ala Pro Val
1               5                   10                  15

Gly Ala Leu Thr Leu Thr Ala Leu Thr Glu Gly Ile Arg Ala Arg Gln
            20                  25                  30

Gly Gln Pro Gln Gly Pro Pro Ser Ala Gly Pro Gln Pro Lys Ser Trp
        35                  40                  45

Glu Val Lys Pro Glu Ala Glu Pro Gln Thr Gln Ala Leu Thr Ala Pro
    50                  55                  60

Ser Glu Ala Glu Pro Gly Arg Gly Ala Thr Val Pro Glu Ala Gly Ser
65                  70                  75                  80
```

```
Glu Pro Cys Ser Leu Asn Ser Ala Leu Glu Pro Ala Pro Glu Gly Pro
                85                  90                  95

His Gln Val Pro Gln Ser Ser Trp Glu Glu Gly Val Leu Ala Asp Leu
            100                 105                 110

Ala Leu Tyr Thr Ala Ala Cys Leu Glu Glu Ala Gly Phe Ala Gly Thr
        115                 120                 125

Gln Ala Thr Val Leu Thr Leu Ser Ser Ala Leu Glu Ala Arg Gly Glu
    130                 135                 140

Arg Leu Glu Asp Gln Val His Ala Leu Val Arg Gly Leu Leu Ala Gln
145                 150                 155                 160

Val Pro Ser Leu Ala Glu Gly Arg Pro Trp Arg Ala Ala Leu Arg Val
                165                 170                 175

Leu Ser Ala Leu Ala Leu Glu His Ala Arg Asp Val Val Cys Ala Leu
            180                 185                 190

Leu Pro Arg Ser Leu Pro Ala Asp Arg Val Ala Ala Glu Leu Trp Arg
        195                 200                 205

Ser Leu Ser Arg Asn Gln Arg Val Asn Gly Gln Val Leu Val Gln Leu
    210                 215                 220

Leu Trp Ala Leu Lys Gly Ala Ser Gly Pro Glu Pro Gln Ala Leu Ala
225                 230                 235                 240

Ala Thr Arg Ala Leu Gly Glu Met Leu Ala Val Ser Gly Cys Val
                245                 250                 255


<210> SEQ ID NO 1936
<211> LENGTH: 255
<212> TYPE: PRT
<213> ORGANISM: Homo sapiens

<400> SEQUENCE: 1936

Met Leu Val Ile Trp Ile Leu Thr Leu Ala Leu Arg Leu Cys Ala Ser
1               5                   10                  15

Val Thr Thr Val Thr Pro Gly Ser Thr Val Asn Thr Ser Ile Gly Gly
            20                  25                  30

Asn Thr Thr Ser Ala Ser Thr Pro Ser Ser Ser Asp Pro Phe Thr Thr
        35                  40                  45

Phe Ser Asp Tyr Gly Val Ser Val Thr Phe Ile Thr Gly Ser Thr Ala
    50                  55                  60

Thr Lys His Phe Leu Asp Ser Ser Thr Asn Ser Gly His Ser Glu Glu
65                  70                  75                  80

Ser Thr Val Ser His Ser Gly Pro Gly Ala Thr Gly Thr Thr Leu Phe
                85                  90                  95

Pro Ser His Ser Ala Thr Ser Val Phe Val Gly Glu Pro Lys Thr Ser
            100                 105                 110

Pro Ile Thr Ser Ala Ser Met Glu Thr Thr Ala Leu Pro Gly Ser Thr
        115                 120                 125

Thr Thr Ala Gly Leu Ser Glu Lys Ser Thr Thr Phe Tyr Ser Ser Pro
    130                 135                 140

Arg Ser Pro Asp Arg Thr Leu Ser Pro Ala Arg Thr Thr Ser Ser Gly
145                 150                 155                 160

Val Ser Glu Lys Ser Thr Thr Ser His Ser Arg Pro Gly Pro Thr His
                165                 170                 175

Thr Ile Ala Phe Pro Asp Ser Thr Thr Met Pro Gly Val Ser Gln Glu
            180                 185                 190

Ser Thr Ala Ser His Ser Ile Pro Gly Ser Thr Asp Thr Thr Leu Ser
```

```
        195                 200                 205

Pro Gly Thr Thr Thr Pro Ser Ser Leu Gly Pro Glu Ser Thr Thr Phe
    210                 215                 220

His Ser Ser Pro Gly Tyr Thr Lys Thr Thr Arg Leu Pro Asp Asn Thr
225                 230                 235                 240

Thr Thr Ser Gly Leu Leu Glu Ala Ser Thr Pro Val His Ser Ser
                245                 250                 255


<210> SEQ ID NO 1937
<211> LENGTH: 255
<212> TYPE: PRT
<213> ORGANISM: Homo sapiens

<400> SEQUENCE: 1937

Met Glu Ser Arg Ala Glu Gly Gly Ser Pro Ala Val Phe Asp Trp Phe
1               5                   10                  15

Phe Glu Ala Ala Cys Pro Ala Ser Leu Gln Glu Asp Pro Pro Ile Leu
            20                  25                  30

Arg Gln Phe Pro Pro Asp Phe Arg Asp Gln Glu Ala Met Gln Met Val
        35                  40                  45

Pro Lys Phe Cys Phe Pro Phe Asp Val Glu Arg Glu Pro Pro Ser Pro
    50                  55                  60

Ala Val Gln His Phe Thr Phe Ala Leu Thr Asp Leu Ala Gly Asn Arg
65                  70                  75                  80

Arg Phe Gly Phe Cys Arg Leu Arg Ala Gly Thr Gln Ser Cys Leu Cys
                85                  90                  95

Ile Leu Ser His Leu Pro Trp Phe Glu Val Phe Tyr Lys Leu Leu Asn
            100                 105                 110

Thr Val Gly Asp Leu Leu Ala Gln Asp Gln Val Thr Glu Ala Glu Glu
        115                 120                 125

Leu Leu Gln Asn Leu Phe Gln Gln Ser Leu Ser Gly Pro Gln Ala Ser
    130                 135                 140

Val Gly Leu Glu Leu Gly Ser Gly Val Thr Val Ser Ser Gly Gln Gly
145                 150                 155                 160

Ile Pro Pro Pro Thr Arg Gly Asn Ser Lys Pro Leu Ser Cys Phe Val
                165                 170                 175

Ala Pro Asp Ser Gly Arg Leu Pro Ser Ile Pro Glu Asn Arg Asn Leu
            180                 185                 190

Thr Glu Leu Val Val Ala Val Thr Asp Glu Asn Ile Val Gly Leu Phe
        195                 200                 205

Ala Ala Leu Leu Ala Glu Arg Arg Val Leu Leu Thr Ala Ser Lys Leu
    210                 215                 220

Ser Thr Leu Thr Ser Cys Val His Ala Ser Cys Ala Leu Leu Tyr Pro
225                 230                 235                 240

Met Arg Trp Glu His Val Leu Ile Pro Thr Leu Pro Pro His Leu
                245                 250                 255


<210> SEQ ID NO 1938
<211> LENGTH: 255
<212> TYPE: PRT
<213> ORGANISM: Homo sapiens

<400> SEQUENCE: 1938

Met Ser Ala Leu Arg Pro Leu Leu Leu Leu Leu Leu Pro Leu Cys Pro
1               5                   10                  15

Gly Pro Gly Pro Gly Pro Gly Ser Glu Ala Lys Val Thr Arg Ser Cys
```

```
            20                  25                  30

Ala Glu Thr Arg Gln Val Leu Gly Ala Arg Gly Tyr Ser Leu Asn Leu
        35                  40                  45

Ile Pro Pro Ala Leu Ile Ser Gly Glu His Leu Arg Val Cys Pro Gln
    50                  55                  60

Glu Tyr Thr Cys Cys Ser Ser Glu Thr Glu Gln Arg Leu Ile Arg Glu
65                  70                  75                  80

Thr Glu Ala Thr Phe Arg Gly Leu Val Glu Asp Ser Gly Ser Phe Leu
                85                  90                  95

Val His Thr Leu Ala Ala Arg His Arg Lys Phe Asp Glu Phe Phe Leu
            100                 105                 110

Glu Met Leu Ser Val Ala Gln His Ser Leu Thr Gln Leu Phe Ser His
        115                 120                 125

Ser Tyr Gly Arg Leu Tyr Ala Gln His Ala Leu Ile Phe Asn Gly Leu
    130                 135                 140

Phe Ser Arg Leu Arg Asp Phe Tyr Gly Glu Ser Gly Glu Gly Leu Asp
145                 150                 155                 160

Asp Thr Leu Ala Asp Phe Trp Ala Gln Leu Leu Glu Arg Val Phe Pro
                165                 170                 175

Leu Leu His Pro Gln Tyr Ser Phe Pro Pro Asp Tyr Leu Leu Cys Leu
            180                 185                 190

Ser Arg Leu Ala Ser Ser Thr Asp Gly Ser Leu Gln Pro Phe Gly Asp
        195                 200                 205

Ser Pro Arg Arg Leu Arg Leu Gln Ile Thr Arg Thr Leu Val Ala Ala
    210                 215                 220

Arg Ala Phe Val Gln Gly Leu Glu Thr Gly Arg Asn Val Val Ser Glu
225                 230                 235                 240

Ala Leu Lys Val Pro Val Ser Glu Gly Cys Ser Gln Ala Leu Met
                245                 250                 255


<210> SEQ ID NO 1939
<211> LENGTH: 255
<212> TYPE: PRT
<213> ORGANISM: Homo sapiens

<400> SEQUENCE: 1939

Met Asn Gly Val Ala Phe Cys Leu Val Gly Ile Pro Pro Arg Pro Glu
1               5                   10                  15

Pro Arg Pro Pro Gln Leu Pro Leu Gly Pro Arg Asp Gly Cys Ser Pro
            20                  25                  30

Arg Arg Pro Phe Pro Trp Gln Gly Pro Arg Thr Leu Leu Leu Tyr Lys
        35                  40                  45

Ser Pro Gln Asp Gly Phe Gly Phe Thr Leu Arg His Phe Ile Val Tyr
    50                  55                  60

Pro Pro Glu Ser Ala Val His Cys Ser Leu Lys Glu Glu Glu Asn Gly
65                  70                  75                  80

Gly Arg Gly Gly Gly Pro Ser Pro Arg Tyr Arg Leu Glu Pro Met Asp
                85                  90                  95

Thr Ile Phe Val Lys Asn Val Lys Glu Asp Gly Pro Ala His Arg Ala
            100                 105                 110

Gly Leu Arg Thr Gly Asp Arg Leu Val Lys Val Asn Gly Glu Ser Val
        115                 120                 125

Ile Gly Lys Thr Tyr Ser Gln Val Ile Ala Leu Ile Gln Asn Ser Asp
    130                 135                 140
```

Asp Thr Leu Glu Leu Ser Ile Met Pro Lys Asp Glu Asp Ile Leu Gln
145 150 155 160

Leu Ala Tyr Ser Gln Asp Ala Tyr Leu Lys Gly Asn Glu Pro Tyr Ser
165 170 175

Gly Glu Ala Arg Ser Ile Pro Glu Pro Pro Pro Ile Cys Tyr Pro Arg
180 185 190

Lys Thr Tyr Ala Pro Pro Ala Arg Ala Ser Thr Arg Ala Thr Met Val
195 200 205

Pro Glu Pro Thr Ser Ala Leu Pro Ser Asp Pro Arg Ser Pro Ala Ala
210 215 220

Trp Ser Asp Pro Gly Leu Arg Val Pro Pro Ala Ala Arg Ala His Leu
225 230 235 240

Asp Asn Ser Ser Leu Gly Met Ser Gln Pro Arg Pro Ser Pro Gly
245 250 255

<210> SEQ ID NO 1940
<211> LENGTH: 75
<212> TYPE: PRT
<213> ORGANISM: Homo sapiens

<400> SEQUENCE: 1940

Met Phe Arg Ala Ala Leu Glu Asp Ser Val Glu Lys Lys Ser Ser Leu
1 5 10 15

Lys Glu Thr Glu Thr Thr Ser Lys Gly Thr Ser Lys Tyr Asp Arg Glu
20 25 30

Arg Glu Thr Glu Met Lys Thr Val Met Gly Met Lys Met His Phe Trp
35 40 45

Val Arg Thr Pro Ala Ser Gly Arg Gly Arg Gly Gly Ser Asp His Ala
50 55 60

Arg Ser Arg Ala Ala Pro Leu Pro Leu Leu Ala
65 70 75

<210> SEQ ID NO 1941
<211> LENGTH: 167
<212> TYPE: PRT
<213> ORGANISM: Homo sapiens

<400> SEQUENCE: 1941

Met Asp Arg Gly Arg Pro Ala Gly Ser Pro Leu Ser Ala Ser Ala Glu
1 5 10 15

Pro Ala Pro Leu Ala Ala Ala Ile Arg Asp Ser Arg Pro Gly Arg Thr
20 25 30

Gly Pro Gly Pro Ala Gly Pro Gly Gly Gly Ser Arg Ser Gly Ser Gly
35 40 45

Arg Pro Ala Ala Ala Asn Ala Ala Arg Glu Arg Ser Arg Val Gln Thr
50 55 60

Leu Arg His Ala Phe Leu Glu Leu Gln Arg Thr Leu Pro Ser Val Pro
65 70 75 80

Pro Asp Thr Lys Leu Ser Lys Leu Asp Val Leu Leu Leu Ala Thr Thr
85 90 95

Tyr Ile Ala His Leu Thr Arg Ser Leu Gln Asp Asp Ala Glu Ala Pro
100 105 110

Ala Asp Ala Gly Leu Gly Ala Leu Arg Gly Asp Gly Tyr Leu His Pro
115 120 125

Val Lys Lys Trp Pro Met Arg Ser Arg Leu Tyr Ile Gly Ala Thr Gly
130 135 140

Gln Phe Leu Lys His Ser Val Ser Gly Glu Lys Thr Asn His Asp Asn
145 150 155 160

Thr Pro Thr Asp Ser Gln Pro
165

<210> SEQ ID NO 1942
<211> LENGTH: 15
<212> TYPE: PRT
<213> ORGANISM: Homo sapiens

<400> SEQUENCE: 1942

Met Ala Glu Lys Leu Gln Glu Ala Asn Phe Leu Leu Glu Asp Ile
1 5 10 15

<210> SEQ ID NO 1943
<211> LENGTH: 15
<212> TYPE: PRT
<213> ORGANISM: Homo sapiens

<400> SEQUENCE: 1943

Gln Tyr Ser His Ile Ala Asp Lys Val Ser Glu Val Pro Ala Asn
1 5 10 15

<210> SEQ ID NO 1944
<211> LENGTH: 15
<212> TYPE: PRT
<213> ORGANISM: Homo sapiens

<400> SEQUENCE: 1944

Phe Leu Lys Lys Ser Ser Ala Val Thr Val Phe Lys Leu Arg Arg
1 5 10 15

<210> SEQ ID NO 1945
<211> LENGTH: 15
<212> TYPE: PRT
<213> ORGANISM: Homo sapiens

<400> SEQUENCE: 1945

Pro Lys Leu Lys Tyr Ile Pro Leu Lys Phe Ser Phe Thr Ala Ala
1 5 10 15

<210> SEQ ID NO 1946
<211> LENGTH: 15
<212> TYPE: PRT
<213> ORGANISM: Homo sapiens

<400> SEQUENCE: 1946

Glu His Leu His Thr Val Asn Pro Met Met Leu Arg Leu Lys Glu
1 5 10 15

<210> SEQ ID NO 1947
<211> LENGTH: 15
<212> TYPE: PRT
<213> ORGANISM: Homo sapiens

<400> SEQUENCE: 1947

Val Ser Asp Phe Leu Ile Gln Thr Phe Lys Val Phe Gln Lys Asn
1 5 10 15

<210> SEQ ID NO 1948
<211> LENGTH: 15
<212> TYPE: PRT
<213> ORGANISM: Homo sapiens

<400> SEQUENCE: 1948

Asp Asn Thr Ala Glu Gln Asn Ile Ala Ala Phe Leu Lys Glu Asn
1 5 10 15

<210> SEQ ID NO 1949
<211> LENGTH: 15
<212> TYPE: PRT
<213> ORGANISM: Homo sapiens

<400> SEQUENCE: 1949

Val Asn Pro Met Met Leu Arg Leu Lys Glu Leu Trp Phe Ala Glu
1 5 10 15

<210> SEQ ID NO 1950
<211> LENGTH: 15
<212> TYPE: PRT
<213> ORGANISM: Homo sapiens

<400> SEQUENCE: 1950

Lys Thr Ser Leu Thr Phe Pro Gly Ser Arg Pro Met Ser Pro Glu
1 5 10 15

<210> SEQ ID NO 1951
<211> LENGTH: 15
<212> TYPE: PRT
<213> ORGANISM: Homo sapiens

<400> SEQUENCE: 1951

Ile Glu Glu Tyr Phe Ala Ser Val Ala Ser Phe Met Ser Leu Gln
1 5 10 15

<210> SEQ ID NO 1952
<211> LENGTH: 15
<212> TYPE: PRT
<213> ORGANISM: Homo sapiens

<400> SEQUENCE: 1952

Asn Glu Ile Ala Ser Met Asn Ile Thr Val Pro Leu Ala Met Phe
1 5 10 15

<210> SEQ ID NO 1953
<211> LENGTH: 15
<212> TYPE: PRT
<213> ORGANISM: Homo sapiens

<400> SEQUENCE: 1953

Asn Pro Lys Leu Thr Leu Gly Leu Ile Trp Thr Ile Ile Leu His
1 5 10 15

<210> SEQ ID NO 1954
<211> LENGTH: 15
<212> TYPE: PRT
<213> ORGANISM: Homo sapiens

<400> SEQUENCE: 1954

Phe Thr Lys Trp Ile Asn Gln His Leu Met Lys Val Arg Lys His
1 5 10 15

<210> SEQ ID NO 1955
<211> LENGTH: 15
<212> TYPE: PRT
<213> ORGANISM: Homo sapiens

<400> SEQUENCE: 1955

Glu Arg Asp Lys Val Gln Lys Lys Thr Phe Thr Lys Trp Ile Asn 1 5 10 15

<210> SEQ ID NO 1956
<211> LENGTH: 15
<212> TYPE: PRT
<213> ORGANISM: Homo sapiens

<400> SEQUENCE: 1956

Ile Ser Leu Leu Glu Val Leu Ser Gly Asp Thr Leu Pro Arg Glu
1 5 10 15

<210> SEQ ID NO 1957
<211> LENGTH: 15
<212> TYPE: PRT
<213> ORGANISM: Homo sapiens

<400> SEQUENCE: 1957

Met Ala Gly Tyr Leu Ser Pro Ala Ala Tyr Leu Tyr Val Glu Glu
1 5 10 15

<210> SEQ ID NO 1958
<211> LENGTH: 14
<212> TYPE: PRT
<213> ORGANISM: Homo sapiens

<400> SEQUENCE: 1958

Met Ala Gly Tyr Leu Ser Pro Ala Ala Tyr Leu Tyr Val Glu
1 5 10

<210> SEQ ID NO 1959
<211> LENGTH: 15
<212> TYPE: PRT
<213> ORGANISM: Homo sapiens

<400> SEQUENCE: 1959

Ala Asp Val Ser Gln Tyr Pro Val Asn His Leu Val Thr Phe Cys
1 5 10 15

<210> SEQ ID NO 1960
<211> LENGTH: 15
<212> TYPE: PRT
<213> ORGANISM: Homo sapiens

<400> SEQUENCE: 1960

Glu Val Asp Ile Leu Asn His Val Phe Asp Asp Val Glu Ser Phe
1 5 10 15

<210> SEQ ID NO 1961
<211> LENGTH: 15
<212> TYPE: PRT
<213> ORGANISM: Homo sapiens

<400> SEQUENCE: 1961

Met Ser Thr Ala Thr Gly Pro Glu Ala Ala Pro Lys Pro Ser Ala
1 5 10 15

<210> SEQ ID NO 1962
<211> LENGTH: 15
<212> TYPE: PRT
<213> ORGANISM: Homo sapiens

<400> SEQUENCE: 1962

Ala Gln Pro Asp Val His Phe Phe Gln Gly Leu Arg Leu Gly Ala
1 5 10 15

<210> SEQ ID NO 1963
<211> LENGTH: 15
<212> TYPE: PRT
<213> ORGANISM: Homo sapiens

<400> SEQUENCE: 1963

Ile Leu Asn His Val Phe Asp Asp Val Glu Ser Phe Val Ser Arg
1 5 10 15

<210> SEQ ID NO 1964
<211> LENGTH: 15
<212> TYPE: PRT
<213> ORGANISM: Homo sapiens

<400> SEQUENCE: 1964

Val Ser Gln Tyr Pro Val Asn His Leu Val Thr Phe Cys Leu Gly
1 5 10 15

<210> SEQ ID NO 1965
<211> LENGTH: 15
<212> TYPE: PRT
<213> ORGANISM: Homo sapiens

<400> SEQUENCE: 1965

Pro Ala Ser Lys Glu Glu Leu Glu Ser Tyr Pro Leu Gly Ala Ile
1 5 10 15

<210> SEQ ID NO 1966
<211> LENGTH: 15
<212> TYPE: PRT
<213> ORGANISM: Homo sapiens

<400> SEQUENCE: 1966

Glu Pro Glu Arg Ala Gln Pro Asp Val His Phe Phe Gln Gly Leu
1 5 10 15

<210> SEQ ID NO 1967
<211> LENGTH: 15
<212> TYPE: PRT
<213> ORGANISM: Homo sapiens

<400> SEQUENCE: 1967

Val Glu Asp Leu Leu Phe Ser Gly Ser Arg Phe Val Trp Asn Leu
1 5 10 15

<210> SEQ ID NO 1968
<211> LENGTH: 15
<212> TYPE: PRT
<213> ORGANISM: Homo sapiens

<400> SEQUENCE: 1968

Leu Leu Asp Leu Val Ala Ser His Phe Asn Leu Lys Glu Lys Glu
1 5 10 15

<210> SEQ ID NO 1969
<211> LENGTH: 15
<212> TYPE: PRT
<213> ORGANISM: Homo sapiens

<400> SEQUENCE: 1969

Thr Val Ser Thr Leu Arg Arg Trp Tyr Thr Glu Arg Leu Arg Ala
1 5 10 15

<210> SEQ ID NO 1970

<211> LENGTH: 15
<212> TYPE: PRT
<213> ORGANISM: Homo sapiens

<400> SEQUENCE: 1970

Gln Ile Glu Val Glu Ser Glu Thr Ile Phe Lys Leu Ala Ala Phe
1 5 10 15

<210> SEQ ID NO 1971
<211> LENGTH: 15
<212> TYPE: PRT
<213> ORGANISM: Homo sapiens

<400> SEQUENCE: 1971

Val Trp Asn Leu Thr Val Ser Thr Leu Arg Arg Trp Tyr Thr Glu
1 5 10 15

<210> SEQ ID NO 1972
<211> LENGTH: 15
<212> TYPE: PRT
<213> ORGANISM: Homo sapiens

<400> SEQUENCE: 1972

Ala Val Arg Phe Tyr Ile Glu Ser Ile Ser Phe Leu Lys Asp Lys
1 5 10 15

<210> SEQ ID NO 1973
<211> LENGTH: 15
<212> TYPE: PRT
<213> ORGANISM: Homo sapiens

<400> SEQUENCE: 1973

Ala Glu Gly Val Leu Leu Asp Tyr Leu Val Leu Leu Pro Arg Asp
1 5 10 15

<210> SEQ ID NO 1974
<211> LENGTH: 15
<212> TYPE: PRT
<213> ORGANISM: Homo sapiens

<400> SEQUENCE: 1974

Ser Arg Ile Ala Met Tyr Glu Leu Leu Ala Asp Ala Asp Ile Gln
1 5 10 15

<210> SEQ ID NO 1975
<211> LENGTH: 15
<212> TYPE: PRT
<213> ORGANISM: Homo sapiens

<400> SEQUENCE: 1975

Arg Thr Asn Thr Leu Leu Gly His Leu Ile Ser Lys Ala Gln Arg
1 5 10 15

<210> SEQ ID NO 1976
<211> LENGTH: 15
<212> TYPE: PRT
<213> ORGANISM: Homo sapiens

<400> SEQUENCE: 1976

Val Ile His Phe Tyr Gln Ala Ala His Pro Thr Phe Pro Ala Gln
1 5 10 15

<210> SEQ ID NO 1977
<211> LENGTH: 15
<212> TYPE: PRT

<213> ORGANISM: Homo sapiens

<400> SEQUENCE: 1977

Thr Lys Ala Thr Asn Ile Arg Leu Arg Phe Leu Arg Thr Asn Thr
1 5 10 15

<210> SEQ ID NO 1978
<211> LENGTH: 15
<212> TYPE: PRT
<213> ORGANISM: Homo sapiens

<400> SEQUENCE: 1978

Tyr Ala Gln Met Thr Ser Val Gln Asn Asp Val Arg Ile Thr Leu
1 5 10 15

<210> SEQ ID NO 1979
<211> LENGTH: 15
<212> TYPE: PRT
<213> ORGANISM: Homo sapiens

<400> SEQUENCE: 1979

Cys Leu Leu Tyr Gln His Leu Pro Val Thr Arg Phe Pro Cys Thr
1 5 10 15

<210> SEQ ID NO 1980
<211> LENGTH: 15
<212> TYPE: PRT
<213> ORGANISM: Homo sapiens

<400> SEQUENCE: 1980

Asp Lys Val Ser Ser Tyr Gly Gly Tyr Leu Thr Tyr Gln Ala Lys
1 5 10 15

<210> SEQ ID NO 1981
<211> LENGTH: 15
<212> TYPE: PRT
<213> ORGANISM: Homo sapiens

<400> SEQUENCE: 1981

Leu Ser Gly Arg Glu Val Glu Leu His Leu Arg Leu Arg Ile Pro
1 5 10 15

<210> SEQ ID NO 1982
<211> LENGTH: 15
<212> TYPE: PRT
<213> ORGANISM: Homo sapiens

<400> SEQUENCE: 1982

Leu His Lys Lys Ser Met Asp Lys Ser Leu Glu Phe Ile Thr Asn
1 5 10 15

<210> SEQ ID NO 1983
<211> LENGTH: 15
<212> TYPE: PRT
<213> ORGANISM: Homo sapiens

<400> SEQUENCE: 1983

Asp Gly Tyr Phe Ala Leu Glu Lys Ser Asn Tyr Phe Gly Cys Gln
1 5 10 15

<210> SEQ ID NO 1984
<211> LENGTH: 15
<212> TYPE: PRT
<213> ORGANISM: Homo sapiens

<400> SEQUENCE: 1984

Glu Asn Asn Tyr Tyr Phe Pro Asp Leu His His Met Lys Tyr Glu
1 5 10 15

<210> SEQ ID NO 1985
<211> LENGTH: 15
<212> TYPE: PRT
<213> ORGANISM: Homo sapiens

<400> SEQUENCE: 1985

Ile Leu Arg Tyr Val Asn Pro Gly Thr Glu Ala Val Ser Gly His
1 5 10 15

<210> SEQ ID NO 1986
<211> LENGTH: 15
<212> TYPE: PRT
<213> ORGANISM: Homo sapiens

<400> SEQUENCE: 1986

Ala Asp Pro Phe Ser Ile Thr Pro Gly Ile Trp Val Ala Cys Ile
1 5 10 15

<210> SEQ ID NO 1987
<211> LENGTH: 15
<212> TYPE: PRT
<213> ORGANISM: Homo sapiens

<400> SEQUENCE: 1987

Gln Asn Val Ile Leu His Glu His His Ile Phe Leu Gly Ala Thr
1 5 10 15

<210> SEQ ID NO 1988
<211> LENGTH: 15
<212> TYPE: PRT
<213> ORGANISM: Homo sapiens

<400> SEQUENCE: 1988

Cys Lys Glu Ala Leu Ala Lys Ser Glu Met Asn Val Asn Met Lys
1 5 10 15

<210> SEQ ID NO 1989
<211> LENGTH: 15
<212> TYPE: PRT
<213> ORGANISM: Homo sapiens

<400> SEQUENCE: 1989

Met Asp Arg Ser Ala Met Cys Ala Phe Pro Ile Lys Tyr Val Asn
1 5 10 15

<210> SEQ ID NO 1990
<211> LENGTH: 15
<212> TYPE: PRT
<213> ORGANISM: Homo sapiens

<400> SEQUENCE: 1990

Thr Asp Gln Ser Tyr Ile Asp Val Leu Pro Glu Phe Arg Asp Ser
1 5 10 15

<210> SEQ ID NO 1991
<211> LENGTH: 15
<212> TYPE: PRT
<213> ORGANISM: Homo sapiens

<400> SEQUENCE: 1991

Leu Asp Ala Gln Thr Phe His Thr Arg Ile Ile Arg Phe Cys Ser
1 5 10 15

<210> SEQ ID NO 1992
<211> LENGTH: 15
<212> TYPE: PRT
<213> ORGANISM: Homo sapiens

<400> SEQUENCE: 1992

Ser Asn Asn Phe Ile Tyr Phe Leu Thr Val Gln Arg Glu Thr Leu
1 5 10 15

<210> SEQ ID NO 1993
<211> LENGTH: 15
<212> TYPE: PRT
<213> ORGANISM: Homo sapiens

<400> SEQUENCE: 1993

Lys Asp Gly Phe Met Phe Leu Thr Asp Gln Ser Tyr Ile Asp Val
1 5 10 15

<210> SEQ ID NO 1994
<211> LENGTH: 15
<212> TYPE: PRT
<213> ORGANISM: Homo sapiens

<400> SEQUENCE: 1994

Arg Asp Ser Tyr Pro Ile Lys Tyr Val His Ala Phe Glu Ser Asn
1 5 10 15

<210> SEQ ID NO 1995
<211> LENGTH: 15
<212> TYPE: PRT
<213> ORGANISM: Homo sapiens

<400> SEQUENCE: 1995

Gln Lys Val Ala Glu Tyr Lys Thr Gly Pro Val Leu Glu His Pro
1 5 10 15

<210> SEQ ID NO 1996
<211> LENGTH: 15
<212> TYPE: PRT
<213> ORGANISM: Homo sapiens

<400> SEQUENCE: 1996

Cys Ser Ser Lys Ala Asn Leu Ser Gly Gly Val Trp Lys Asp Asn
1 5 10 15

<210> SEQ ID NO 1997
<211> LENGTH: 15
<212> TYPE: PRT
<213> ORGANISM: Homo sapiens

<400> SEQUENCE: 1997

Arg Asp Glu Tyr Arg Thr Glu Phe Thr Thr Ala Leu Gln Arg Val
1 5 10 15

<210> SEQ ID NO 1998
<211> LENGTH: 15
<212> TYPE: PRT
<213> ORGANISM: Homo sapiens

<400> SEQUENCE: 1998

Thr Ile Asn Ser Ser Tyr Phe Pro Asp His Pro Leu His Ser Ile
1 5 10 15

<210> SEQ ID NO 1999
<211> LENGTH: 15
<212> TYPE: PRT
<213> ORGANISM: Homo sapiens

<400> SEQUENCE: 1999

Pro Met Asp Arg Ser Ala Met Cys Ala Phe Pro Ile Lys Tyr Val
1 5 10 15

<210> SEQ ID NO 2000
<211> LENGTH: 15
<212> TYPE: PRT
<213> ORGANISM: Homo sapiens

<400> SEQUENCE: 2000

Gly Ala Ser Gly Ile Val Glu Val Leu Thr Glu Val Pro Asn Ile
1 5 10 15

<210> SEQ ID NO 2001
<211> LENGTH: 15
<212> TYPE: PRT
<213> ORGANISM: Homo sapiens

<400> SEQUENCE: 2001

Gln Gly Phe Thr Leu Leu His His Ala Ser Leu Lys Gly His Ala
1 5 10 15

<210> SEQ ID NO 2002
<211> LENGTH: 15
<212> TYPE: PRT
<213> ORGANISM: Homo sapiens

<400> SEQUENCE: 2002

Glu Asn Lys Ser Ser Leu Ser Val Ala Leu Asp Lys Leu Arg Ala
1 5 10 15

<210> SEQ ID NO 2003
<211> LENGTH: 15
<212> TYPE: PRT
<213> ORGANISM: Homo sapiens

<400> SEQUENCE: 2003

Gln Val Ala Ala Tyr Leu Gly Gln Val Glu Leu Ile Arg Leu Leu
1 5 10 15

<210> SEQ ID NO 2004
<211> LENGTH: 15
<212> TYPE: PRT
<213> ORGANISM: Homo sapiens

<400> SEQUENCE: 2004

Thr Ala Leu His Leu Ala Ala Leu Asn Asn His Arg Glu Val Ala
1 5 10 15

<210> SEQ ID NO 2005
<211> LENGTH: 15
<212> TYPE: PRT
<213> ORGANISM: Homo sapiens

<400> SEQUENCE: 2005

Cys Val Gly Glu Ala Ala Gly Gly Phe Tyr Tyr Lys Asp His Leu
1 5 10 15

<210> SEQ ID NO 2006
<211> LENGTH: 15
<212> TYPE: PRT
<213> ORGANISM: Homo sapiens

<400> SEQUENCE: 2006

Leu Gln Arg Arg Val Ser Ala Asp Ser Gln Pro Phe Gln His Gly
1 5 10 15

<210> SEQ ID NO 2007
<211> LENGTH: 15
<212> TYPE: PRT
<213> ORGANISM: Homo sapiens

<400> SEQUENCE: 2007

Gly Asn Leu Arg Val Ala Val Ala Gly Gln Arg Trp Thr Phe Ser
1 5 10 15

<210> SEQ ID NO 2008
<211> LENGTH: 15
<212> TYPE: PRT
<213> ORGANISM: Homo sapiens

<400> SEQUENCE: 2008

Glu Asp Gly Phe Thr Ala Leu His Leu Ala Ala Leu Asn Asn His
1 5 10 15

<210> SEQ ID NO 2009
<211> LENGTH: 15
<212> TYPE: PRT
<213> ORGANISM: Homo sapiens

<400> SEQUENCE: 2009

Gly Gly Phe Tyr Tyr Lys Asp His Leu Pro Arg Leu Gly Lys Pro
1 5 10 15

<210> SEQ ID NO 2010
<211> LENGTH: 15
<212> TYPE: PRT
<213> ORGANISM: Homo sapiens

<400> SEQUENCE: 2010

Asp Ser Cys Tyr Gln Phe Asn Phe Gln Ser Thr Leu Ser Trp Arg
1 5 10 15

<210> SEQ ID NO 2011
<211> LENGTH: 15
<212> TYPE: PRT
<213> ORGANISM: Homo sapiens

<400> SEQUENCE: 2011

Thr Asp Gly Ser Ile Ile Asn Phe Ile Ser Trp Ala Pro Gly Lys
1 5 10 15

<210> SEQ ID NO 2012
<211> LENGTH: 15
<212> TYPE: PRT
<213> ORGANISM: Homo sapiens

<400> SEQUENCE: 2012

Arg Asp Cys Ser Ile Ala Leu Pro Tyr Val Cys Lys Lys Lys Pro
1 5 10 15

<210> SEQ ID NO 2013
<211> LENGTH: 15

<212> TYPE: PRT
<213> ORGANISM: Homo sapiens

<400> SEQUENCE: 2013

Glu Trp Leu Arg Phe Gln Glu Ala Glu Tyr Lys Phe Phe Glu His
1 5 10 15

<210> SEQ ID NO 2014
<211> LENGTH: 15
<212> TYPE: PRT
<213> ORGANISM: Homo sapiens

<400> SEQUENCE: 2014

Ser Gly Asp Glu Val Met Tyr Thr His Trp Asn Arg Asp Gln Pro
1 5 10 15

<210> SEQ ID NO 2015
<211> LENGTH: 15
<212> TYPE: PRT
<213> ORGANISM: Homo sapiens

<400> SEQUENCE: 2015

Arg Phe Glu Gln Ala Phe Val Ser Ser Leu Ile Tyr Asn Trp Glu
1 5 10 15

<210> SEQ ID NO 2016
<211> LENGTH: 15
<212> TYPE: PRT
<213> ORGANISM: Homo sapiens

<400> SEQUENCE: 2016

Gly Trp Thr Trp His Ser Pro Ser Cys Tyr Trp Leu Gly Glu Asp
1 5 10 15

<210> SEQ ID NO 2017
<211> LENGTH: 15
<212> TYPE: PRT
<213> ORGANISM: Homo sapiens

<400> SEQUENCE: 2017

Thr Asn Arg Phe Glu Gln Ala Phe Val Ser Ser Leu Ile Tyr Asn
1 5 10 15

<210> SEQ ID NO 2018
<211> LENGTH: 15
<212> TYPE: PRT
<213> ORGANISM: Homo sapiens

<400> SEQUENCE: 2018

Gln Gly Arg Arg Glu Trp Leu Arg Phe Gln Glu Ala Glu Tyr Lys
1 5 10 15

<210> SEQ ID NO 2019
<211> LENGTH: 15
<212> TYPE: PRT
<213> ORGANISM: Homo sapiens

<400> SEQUENCE: 2019

Leu Cys Ala Leu Pro Tyr His Glu Val Tyr Thr Ile Gln Gly Asn
1 5 10 15

<210> SEQ ID NO 2020
<211> LENGTH: 15
<212> TYPE: PRT
<213> ORGANISM: Homo sapiens

<400> SEQUENCE: 2020

Cys Pro Ile Lys Ser Asn Asp Cys Glu Thr Phe Trp Asp Lys Asp
1 5 10 15

<210> SEQ ID NO 2021
<211> LENGTH: 15
<212> TYPE: PRT
<213> ORGANISM: Homo sapiens

<400> SEQUENCE: 2021

Gly Gly Cys Val Ala Leu Ala Thr Gly Ser Ala Met Gly Leu Trp
1 5 10 15

<210> SEQ ID NO 2022
<211> LENGTH: 15
<212> TYPE: PRT
<213> ORGANISM: Homo sapiens

<400> SEQUENCE: 2022

Glu Gly Glu Tyr Phe Trp Thr Ala Leu Gln Asp Leu Asn Ser Thr
1 5 10 15

<210> SEQ ID NO 2023
<211> LENGTH: 15
<212> TYPE: PRT
<213> ORGANISM: Homo sapiens

<400> SEQUENCE: 2023

Pro Asp Glu Leu Leu Pro Gln Ala Ile Glu Phe Val Asn Gln Tyr
1 5 10 15

<210> SEQ ID NO 2024
<211> LENGTH: 15
<212> TYPE: PRT
<213> ORGANISM: Homo sapiens

<400> SEQUENCE: 2024

Ser Lys Ser Cys Leu Gly Ser Ile Met Thr Pro Lys Ser Leu Thr
1 5 10 15

<210> SEQ ID NO 2025
<211> LENGTH: 15
<212> TYPE: PRT
<213> ORGANISM: Homo sapiens

<400> SEQUENCE: 2025

Val Lys Leu Asp Ala Thr Pro Leu Ser Ser Pro Arg His Val Arg
1 5 10 15

<210> SEQ ID NO 2026
<211> LENGTH: 15
<212> TYPE: PRT
<213> ORGANISM: Homo sapiens

<400> SEQUENCE: 2026

Ile Gly Arg Ile Gln Trp Ser Asn Leu Gln Val Phe Asp Ala Arg
1 5 10 15

<210> SEQ ID NO 2027
<211> LENGTH: 15
<212> TYPE: PRT
<213> ORGANISM: Homo sapiens

<400> SEQUENCE: 2027

Ala Ile Glu Phe Val Asn Gln Tyr Tyr Gly Ser Phe Lys Glu Ala
1 5 10 15

<210> SEQ ID NO 2028
<211> LENGTH: 15
<212> TYPE: PRT
<213> ORGANISM: Homo sapiens

<400> SEQUENCE: 2028

Thr Lys Glu Ile Glu Thr Thr Gly Thr Tyr Gln Leu Thr Gly Asp
1 5 10 15

<210> SEQ ID NO 2029
<211> LENGTH: 12
<212> TYPE: PRT
<213> ORGANISM: Homo sapiens

<400> SEQUENCE: 2029

Met Ala Cys Pro Trp Lys Phe Leu Phe Lys Thr Lys
1 5 10

<210> SEQ ID NO 2030
<211> LENGTH: 15
<212> TYPE: PRT
<213> ORGANISM: Homo sapiens

<400> SEQUENCE: 2030

Arg Pro Arg Ser Leu His Pro His Val Pro Gly Val Thr Asn Leu
1 5 10 15

<210> SEQ ID NO 2031
<211> LENGTH: 12
<212> TYPE: PRT
<213> ORGANISM: Homo sapiens

<400> SEQUENCE: 2031

Met Val Ala Gly Met Leu Met Pro Arg Asp Gln Leu
1 5 10

<210> SEQ ID NO 2032
<211> LENGTH: 15
<212> TYPE: PRT
<213> ORGANISM: Homo sapiens

<400> SEQUENCE: 2032

His Leu Arg Gln Tyr Leu His Leu Pro Pro Glu Ile Val Pro Ala
1 5 10 15

<210> SEQ ID NO 2033
<211> LENGTH: 15
<212> TYPE: PRT
<213> ORGANISM: Homo sapiens

<400> SEQUENCE: 2033

Arg Glu Thr Phe Ala Trp Cys His Phe Tyr Trp Tyr Leu Thr Asn
1 5 10 15

<210> SEQ ID NO 2034
<211> LENGTH: 15
<212> TYPE: PRT
<213> ORGANISM: Homo sapiens

<400> SEQUENCE: 2034

Lys Lys Lys Ser Leu Gly Glu Val Leu Leu Pro Val Phe Glu Arg 1 5 10 15

<210> SEQ ID NO 2035
<211> LENGTH: 15
<212> TYPE: PRT
<213> ORGANISM: Homo sapiens

<400> SEQUENCE: 2035

Leu Trp Ala Ser Val Met Ala Pro Val Leu Glu Lys Ala Arg Arg
1 5 10 15

<210> SEQ ID NO 2036
<211> LENGTH: 15
<212> TYPE: PRT
<213> ORGANISM: Homo sapiens

<400> SEQUENCE: 2036

Leu His Thr Glu Ala Ser Tyr Ile Arg Lys Leu Arg Val Ile Ile
1 5 10 15

<210> SEQ ID NO 2037
<211> LENGTH: 15
<212> TYPE: PRT
<213> ORGANISM: Homo sapiens

<400> SEQUENCE: 2037

Ser Leu Gly Glu Val Leu Leu Pro Val Phe Glu Arg Lys Gly Ile
1 5 10 15

<210> SEQ ID NO 2038
<211> LENGTH: 15
<212> TYPE: PRT
<213> ORGANISM: Homo sapiens

<400> SEQUENCE: 2038

Trp Lys Asn Arg Ala Ala Ser Arg Phe Ser Gly Phe Phe Ser Ser
1 5 10 15

<210> SEQ ID NO 2039
<211> LENGTH: 15
<212> TYPE: PRT
<213> ORGANISM: Homo sapiens

<400> SEQUENCE: 2039

Lys Asn Met Ser Glu Phe Leu Gly Glu Ala Ser Ile Pro Gly Gln
1 5 10 15

<210> SEQ ID NO 2040
<211> LENGTH: 15
<212> TYPE: PRT
<213> ORGANISM: Homo sapiens

<400> SEQUENCE: 2040

Gly Ser Ser Gly Ser Thr Asn Thr Gly Asp Ser Trp Lys Asn Arg
1 5 10 15

<210> SEQ ID NO 2041
<211> LENGTH: 15
<212> TYPE: PRT
<213> ORGANISM: Homo sapiens

<400> SEQUENCE: 2041

Thr Phe Glu Ala Tyr Arg Phe Gly Gly His Tyr Leu Arg Val Lys
1 5 10 15

<210> SEQ ID NO 2042
<211> LENGTH: 15
<212> TYPE: PRT
<213> ORGANISM: Homo sapiens

<400> SEQUENCE: 2042

Thr His His Thr Leu Trp Met Gly Leu Ala Leu Leu Gly Val Leu
1 5 10 15

<210> SEQ ID NO 2043
<211> LENGTH: 15
<212> TYPE: PRT
<213> ORGANISM: Homo sapiens

<400> SEQUENCE: 2043

His Thr Leu Trp Met Gly Leu Ala Leu Leu Gly Val Leu Gly Asp
1 5 10 15

<210> SEQ ID NO 2044
<211> LENGTH: 15
<212> TYPE: PRT
<213> ORGANISM: Homo sapiens

<400> SEQUENCE: 2044

Ala Pro Glu Ala Gln Val Ser Val Gln Pro Asn Phe Gln Gln Asp
1 5 10 15

<210> SEQ ID NO 2045
<211> LENGTH: 12
<212> TYPE: PRT
<213> ORGANISM: Homo sapiens

<400> SEQUENCE: 2045

Met Ala Thr His His Thr Leu Trp Met Gly Leu Ala
1 5 10

<210> SEQ ID NO 2046
<211> LENGTH: 15
<212> TYPE: PRT
<213> ORGANISM: Homo sapiens

<400> SEQUENCE: 2046

Gly Pro Ser Lys Met Arg Asp Cys Tyr Cys Thr Val Asn Leu Asp
1 5 10 15

<210> SEQ ID NO 2047
<211> LENGTH: 15
<212> TYPE: PRT
<213> ORGANISM: Homo sapiens

<400> SEQUENCE: 2047

Glu Ile Pro Arg Ser Phe Arg His Leu Ser Phe Tyr Ile Phe Asp
1 5 10 15

<210> SEQ ID NO 2048
<211> LENGTH: 15
<212> TYPE: PRT
<213> ORGANISM: Homo sapiens

<400> SEQUENCE: 2048

Arg Tyr Thr Ala Val Ser Ser Phe Ile Phe Leu Arg Phe Phe Ala
1 5 10 15

<210> SEQ ID NO 2049

<211> LENGTH: 15
<212> TYPE: PRT
<213> ORGANISM: Homo sapiens

<400> SEQUENCE: 2049

Phe Lys Glu Ser Tyr Met Ala Thr Phe Tyr Glu Phe Phe Asn Glu
1 5 10 15

<210> SEQ ID NO 2050
<211> LENGTH: 15
<212> TYPE: PRT
<213> ORGANISM: Homo sapiens

<400> SEQUENCE: 2050

Leu Ser Phe Tyr Ile Phe Asp Arg Asp Val Phe Arg Arg Asp Ser
1 5 10 15

<210> SEQ ID NO 2051
<211> LENGTH: 15
<212> TYPE: PRT
<213> ORGANISM: Homo sapiens

<400> SEQUENCE: 2051

Lys Glu Ser Tyr Met Ala Thr Phe Tyr Glu Phe Phe Asn Glu Gln
1 5 10 15

<210> SEQ ID NO 2052
<211> LENGTH: 15
<212> TYPE: PRT
<213> ORGANISM: Homo sapiens

<400> SEQUENCE: 2052

Asp Ala Asp Ser Glu Val Gln Gly Lys Val His Leu Glu Leu Arg
1 5 10 15

<210> SEQ ID NO 2053
<211> LENGTH: 15
<212> TYPE: PRT
<213> ORGANISM: Homo sapiens

<400> SEQUENCE: 2053

Asp Val Arg Tyr Thr Ala Val Ser Ser Phe Ile Phe Leu Arg Phe
1 5 10 15

<210> SEQ ID NO 2054
<211> LENGTH: 15
<212> TYPE: PRT
<213> ORGANISM: Homo sapiens

<400> SEQUENCE: 2054

Asp His Val Phe Ser Ser Asp Tyr Tyr Ser Pro Leu Arg Asp Leu
1 5 10 15

<210> SEQ ID NO 2055
<211> LENGTH: 15
<212> TYPE: PRT
<213> ORGANISM: Homo sapiens

<400> SEQUENCE: 2055

Gly Glu Asp Phe Tyr Cys Glu Ile Pro Arg Ser Phe Arg His Leu
1 5 10 15

<210> SEQ ID NO 2056
<211> LENGTH: 15
<212> TYPE: PRT

<213> ORGANISM: Homo sapiens

<400> SEQUENCE: 2056

Ser Ser Asp Tyr Tyr Ser Pro Leu Arg Asp Leu Leu Leu Lys Ser
1 5 10 15

<210> SEQ ID NO 2057
<211> LENGTH: 15
<212> TYPE: PRT
<213> ORGANISM: Homo sapiens

<400> SEQUENCE: 2057

His Ser Lys Leu Gln Met His His Val Ala Gln Val Leu Arg Glu
1 5 10 15

<210> SEQ ID NO 2058
<211> LENGTH: 15
<212> TYPE: PRT
<213> ORGANISM: Homo sapiens

<400> SEQUENCE: 2058

Arg Leu Lys Ser Ile Phe Arg Arg Gly Leu Val Lys Val Ala Gln
1 5 10 15

<210> SEQ ID NO 2059
<211> LENGTH: 15
<212> TYPE: PRT
<213> ORGANISM: Homo sapiens

<400> SEQUENCE: 2059

His Pro Thr Met Thr Ala Ala Leu Ile Ser Asn Lys Pro Glu Phe
1 5 10 15

<210> SEQ ID NO 2060
<211> LENGTH: 15
<212> TYPE: PRT
<213> ORGANISM: Homo sapiens

<400> SEQUENCE: 2060

Leu Leu Gly Asp Phe Thr Gln Pro Leu Tyr Pro Arg Pro Arg His
1 5 10 15

<210> SEQ ID NO 2061
<211> LENGTH: 15
<212> TYPE: PRT
<213> ORGANISM: Homo sapiens

<400> SEQUENCE: 2061

Glu Cys Gly Leu Met Lys Lys Ala Ala Leu Tyr Phe Ser Asp Phe
1 5 10 15

<210> SEQ ID NO 2062
<211> LENGTH: 15
<212> TYPE: PRT
<213> ORGANISM: Homo sapiens

<400> SEQUENCE: 2062

Val Gln Leu Lys Glu Phe Val Thr Trp Asp Thr Leu Leu Tyr Leu
1 5 10 15

<210> SEQ ID NO 2063
<211> LENGTH: 15
<212> TYPE: PRT
<213> ORGANISM: Homo sapiens

<400> SEQUENCE: 2063

Met Lys Lys Ala Ala Leu Tyr Phe Ser Asp Phe Trp Asn Lys Leu
1 5 10 15

<210> SEQ ID NO 2064
<211> LENGTH: 15
<212> TYPE: PRT
<213> ORGANISM: Homo sapiens

<400> SEQUENCE: 2064

His Val Thr Phe Thr Met Asp Pro Ile Arg Asp Leu Leu Ile Trp
1 5 10 15

<210> SEQ ID NO 2065
<211> LENGTH: 15
<212> TYPE: PRT
<213> ORGANISM: Homo sapiens

<400> SEQUENCE: 2065

Ala Ala Leu Tyr Phe Ser Asp Phe Trp Asn Lys Leu Asp Val Gly
1 5 10 15

<210> SEQ ID NO 2066
<211> LENGTH: 15
<212> TYPE: PRT
<213> ORGANISM: Homo sapiens

<400> SEQUENCE: 2066

Ser Ala Ala Val Leu Asn Asp Tyr Ser Leu Thr Lys Ser His Glu
1 5 10 15

<210> SEQ ID NO 2067
<211> LENGTH: 15
<212> TYPE: PRT
<213> ORGANISM: Homo sapiens

<400> SEQUENCE: 2067

Leu Glu Arg His Val Val Ser Phe Asp Ser Ser Arg Pro Thr Ser
1 5 10 15

<210> SEQ ID NO 2068
<211> LENGTH: 15
<212> TYPE: PRT
<213> ORGANISM: Homo sapiens

<400> SEQUENCE: 2068

Leu Asn Asp Tyr Ser Leu Thr Lys Ser His Glu Met Glu Asn Val
1 5 10 15

EPIGENOMIC PROFILING REVEALS THE SOMATIC PROMOTER LANDSCAPE OF PRIMARY GASTRIC ADENOCARCINOMA

CROSS-REFERENCE TO RELATED APPLICATIONS

This patent application is a U.S. National Phase application under 35 U.S.C. § 371 of International Application No. PCT/SG2017/050072, filed on 16 Feb. 2017, entitled EPIGENOMIC PROFILING REVEALS THE SOMATIC PROMOTER LANDSCAPE OF PRIMARY GASTRIC ADENOCARCINOMA, which claims the benefit of priority of Singapore Application No. 10201601142V, filed 16 Feb. 2016, the contents of which were hereby incorporated by reference in their entirety.

INCORPORATION BY REFERENCE

This patent application incorporates by reference the written sequence listing identified as 9869SG4275-amended_seq_listing_8162794, which is a written print out of an ASCII text file in computer readable form (CRF) named 9869SG4275-amended_seq_listing_8162794.txt, created Jun. 9, 2021, having a file size of 549 kilobytes.

FIELD OF THE INVENTION

The invention relates to a method for determining the presence or absence of at least one promoter in a cancerous biological sample relative to a non-cancerous biological sample.

BACKGROUND OF THE INVENTION

Gastric cancer (GC) is the third leading cause of global cancer mortality with high prevalence in many East Asian countries. GC patients often present with late-stage disease, and clinical management remains challenging as exemplified by several recent negative Phase II and Phase III clinical trials. At the molecular level, studies have identified characteristic gene mutations, copy number alterations, gene fusions, and transcriptional patterns in GC. However, few of these have been clinically translated into targeted therapies, with the exception of HER2-positive GC and traztuzumab. There is thus a strong need for additional and more comprehensive explorations of GC, as these may highlight new biomarkers for disease detection, predicting patient prognosis or responses to therapy, as well as new therapeutic modalities.

Promoter elements are cis-regulatory elements which function to link gene transcription initiation to upstream regulatory stimuli, integrating inputs from diverse signaling pathways. Promoters represent an important reservoir of biological, functional, and regulatory diversity, as current estimates suggest that 30-50% of genes in the human genome are associated with multiple promoters, which can be selectively activated as a function of developmental lineage and cellular state. Differential usage of alternative promoters causes the generation of distinct 5' untranslated regions (5' UTRs) and first exons in transcripts, which in turn can influence mRNA expression levels, translational efficiencies, and generation of different protein isoforms through gain and loss of 5' coding domains. To date, promoter alterations in cancer have been largely studied on a gene-by-gene basis, and very little is known about the global extent of promoter-level diversity in GC and other solid malignancies.

Accordingly, there is a need for a method of profiling promoter elements in cancer.

SUMMARY

In one aspect there is provided a method for determining the presence or absence of at least one promoter in a cancerous biological sample relative to a non-cancerous biological sample, comprising: contacting the cancerous biological sample with at least one antibody specific for histone modifications H3K4me3 and H3K4me1; isolating nucleic acid from the cancerous biological sample having a signal ratio of H3K4me3 relative to H3K4me1 greater than 1, wherein the isolated nucleic acid comprises at least one region specific to said histone modifications; detecting a signal intensity of H3K4me3 in the isolated nucleic acid; and determining the presence or absence of at least one promoter in the cancerous biological sample based on the change in the signal intensity of H3K4me3 relative to the signal intensity of H3K4me3 in a non-cancerous biological sample.

In another aspect there is provided a method for determining the prognosis of cancer in a subject, comprising, contacting a cancerous biological sample obtained from the subject with at least one antibody specific for histone modification H3K4me3 and H3K4me1; isolating nucleic acid from the cancerous biological sample having a signal ratio of H3K4me3 relative to H3K4me1 greater than 1, wherein the isolated nucleic acid comprises at least one region specific to said histone modifications; detecting a signal intensity of H3K4me3 in the isolated nucleic acid; and determining the presence or absence of at least one cancer-associated promoter in the cancerous biological sample based on the change in the signal intensity of H3K4me3 relative to the signal intensity of H3K4me3 in a reference nucleic acid sequence, wherein the presence or absence of the at least one cancer-associated promoter in the cancerous biological sample is indicative of the prognosis of the cancer in the subject.

In another aspect there is provided a biomarker for detecting cancer in a subject, the biomarker comprising at least one promoter having a change in signal intensity of H3K4me3 in a cancerous biological sample relative to a non-cancerous biological sample.

In another aspect there is provided a method for modulating the activity of at least one cancer-associated promoter in a cell, comprising administering an inhibitor of EZH2 to the cell.

In another aspect there is provided a method for modulating the immune response of a subject to cancer, comprising administering to the subject an inhibitor of EZH2, wherein the EZH2 is associated with at least one cancer-associated promoter in the subject.

In another aspect there is provided a method for determining the presence or absence of at least one cancer-associated promoter in a cancerous biological sample relative to a non-cancerous biological sample, comprising: contacting the cancerous biological sample with at least one antibody specific for histone modifications H3K4me3 and H3K4me1; isolating nucleic acid from the cancerous biological sample having a signal ratio of H3K4me3 relative to H3K4me1 greater than 1, wherein the isolated nucleic acid comprises at least one region specific to said histone modifications; detecting a signal intensity of H3K4me3 in the isolated nucleic acid at a read depth of 20M; and determining the presence or absence of at least one cancer-associated promoter in the cancerous biological sample based on the change in the signal intensity of H3K4me3 relative to the signal intensity of H3K4me3 in a non-cancerous biological sample.

In one aspect, there is provided a biomarker comprising at least one promoter having a change in signal intensity of H3K4me3 in a cancerous biological sample relative to a non-cancerous biological sample for use in detecting cancer in a subject.

In one aspect, there is provided a use of a biomarker comprising at least one promoter having a change in signal intensity of H3K4me3 in a cancerous biological sample relative to a non-cancerous biological sample in the manufacture of a medicament for detecting cancer in a subject.

In one aspect, there is provided an inhibitor of EZH2 for use in modulating the activity of at least one cancer-associated promoter in a cell.

In one aspect, there is provided a use of an inhibitor of EZH2 in the manufacture of a medicament for modulating the activity of at least one cancer-associated promoter in a cell.

In one aspect, there is provided an inhibitor of EZH2 for use in modulating the immune response of a subject to cancer, wherein the EZH2 is associated with at least one cancer-associated promoter in the subject.

In one aspect, there is provided a use of an inhibitor of EZH2 in the manufacture of a medicament for modulating the immune response of a subject to cancer, wherein the EZH2 is associated with at least one cancer-associated promoter in the subject.

DEFINITIONS

The following are some definitions that may be helpful in understanding the description of the present invention. These are intended as general definitions and should in no way limit the scope of the present invention to those terms alone, but are put forth for a better understanding of the following description.

As used herein, the term "promoter" is intended to refer to a region of DNA that initiates transcription of a particular gene.

As used herein, the term "cancerous" relates to being affected by or showing abnormalities characteristic of cancer.

As used herein, the term "biological sample" refers to a sample of tissue or cells from a patient that has been obtained from, removed or isolated from the patient. The term "obtained or derived from" as used herein is meant to be used inclusively. That is, it is intended to encompass any nucleotide sequence directly isolated from a biological sample or any nucleotide sequence derived from the sample.

As used herein, the term "antibody" or "antibodies" as used herein refers to molecules with an immunoglobulin-like domain and includes antigen binding fragments, monoclonal, recombinant, polyclonal, chimeric, fully human, humanised, bispecific and heteroconjugate antibodies; a single variable domain, single chain Fv, a domain antibody, immunologically effective fragments and diabodies.

The term "specifically binds" as used throughout the present specification in relation to antigen binding proteins means that the antigen binding protein binds to a target epitope on an antigen with a greater affinity than that which results when bound to a non-target epitope. In certain embodiments, specific binding refers to binding to a target with an affinity that is at least 10, 50, 100, 250, 500, or 1000 times greater than the affinity for a non-target epitope. For example, binding affinity may be as measured by routine methods, e.g., by competition ELISA or by measurement of Kd with BIACORE™, KINEXA™ or PROTEON™.

As used herein, the term "isolated" relates to a biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

As used herein, the term "nucleic acid" refers to a deoxyribonucleotide or ribonucleotide polymer in either single or double stranded form, and unless otherwise limited, encompassing known analogues of natural nucleotides that hybridize to nucleic acids in a manner similar to naturally occurring nucleotides. "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

As used herein, the term "prognosis" or grammatical variants thereof, as used herein refers to a prediction of the probable course and outcome of a clinical condition or disease. A prognosis of a patient is usually made by evaluating factors or symptoms of a disease that are indicative of a favorable or unfavorable course or outcome of the disease. The term "prognosis" does not refer to the ability to predict the course or outcome of a condition with 100% accuracy. Instead, the term "prognosis" refers to an increased probability that a certain course or outcome will occur; that is, that a course or outcome is more likely to occur in a patient exhibiting a given condition, when compared to those individuals not exhibiting the condition.

As used herein, the term "modulating" is intended to refer to an adjustment of the immune response to a desired level.

As used herein, the term "annotated promoter" refers to a promoter mapping close (<500 bp) to a known Gencode transcription start site (TSS).

The term "unannotated promoter" refers to a promoter mapping to genomic regions devoid of known Gencode TSSs.

As used herein, the term "canonical" in the context of a promoter refers to a promoter region exhibiting unaltered H3K4me3 peaks.

As used herein, the term "detectable label" or "reporter" refers to a detectable marker or reporter molecules, which can be attached to nucleic acids. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

As used herein, the term "hypomethylated" refers to a decrease in the normal methylation level of DNA.

As used herein, the term "hypermethylated" refers to an increase in the normal methylation level of DNA.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

Unless the context requires otherwise or specifically stated to the contrary, integers, steps, or elements of the invention recited herein as singular integers, steps or elements clearly encompass both singular and plural forms of the recited integers, steps or elements.

The word "substantially" does not exclude "completely" e.g. a composition which is "substantially free" from Y may be completely free from Y. Where necessary, the word "substantially" may be omitted from the definition of the invention.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which.

A) Example of an unaltered GC promoter. The UCSC genome track of the RHOA TSS (shaded box) highlights similar H3K4me3 signals in GC and matched normal samples. Similar signals are seen in GC lines. The bottom two tracks display similar levels of RNA expression in the same GC and matched normal sample (RNAseq).

B) Example of a gained somatic promoter. The UCSC genome track of the CEACAM6 TSS (shaded box) highlights gain of H3K4me3 signals in GC samples and GC lines, compared to matched normal samples. In contrast, no changes are observed at the TSS of CEACAM5, an adjacent gene. Concordant tumor-specific gain of RNA expression is shown in the bottom 2 tracks displaying RNA-seq profiles of the same GC and matched normal samples.

C) Example of a lost somatic promoter. The UCSC genome track of the ATP4A TSS (shaded box) highlights loss of H3K4me3 signals in GC samples and GC lines compared to matched normal samples. Concordant tumor-specific loss of RNA expression is shown in the bottom 2 tracks displaying RNA-seq profiles of the same GC and gastric normal samples.

D) Heatmap of H3K4me3 read densities (row scaled) of somatic promoters (rows) in primary GCs and matched normal samples.

E) Correlation between H3K4me3 promoter signals and H3K27ac activity signals in primary gastric samples ($r=0.91$, $P<0.001$). Each data point corresponds to a single H3K4me3 hi/H3K4me1 lo region. Analysis was performed using data from 16 N/T pairs (Table 4).

F) Top 5 gene sets associated with canonical gained and lost somatic promoters. Genesets associated with genes up and downregulated in GC are rediscovered. Also note that gene sets related to H3K27me3 and SUZ12, a PRC2 component, are enriched.

Figure 2:
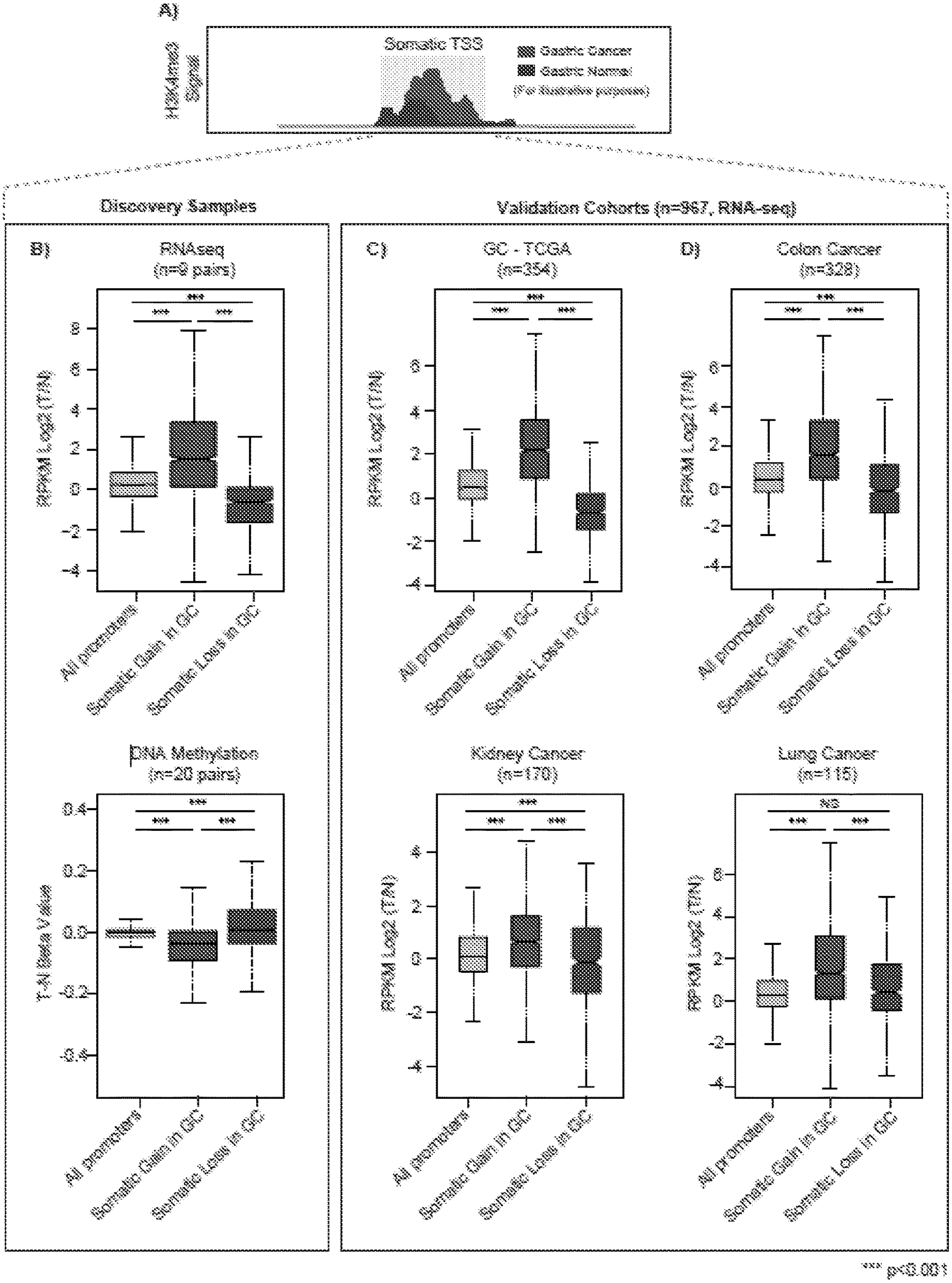

FIG. 2: Association of Somatic Promoter Alterations with Gene Expression in GC and Other Tumor Types A) Example of a GC somatic promoter. Example is for illustrative purposes only.

B) Changes in RNA-seq expression (top) and DNA methylation (bottom) in discovery samples between somatic promoters and all promoters. Top—Boxplot depicting changes in RNA-seq expression between 9 paired primary GC and gastric normal samples at genomic regions exhibiting somatic promoters (gained and lost) (*$P<0.001$, Wilcoxon Test). Bottom—Boxplot depicting changes in DNA methylation (β-values) at regions exhibiting somatic promoters between 20 paired GC and gastric normal samples, compared to all promoters. (*$P<0.001$, Wilcoxon test)

C) Independent Validation Cohorts. Boxplot depicting changes in RNA-seq expression at genomic regions exhibiting somatic promoters across 354 (321 GC, 33 normal) TCGA Stomach adenocarcinoma (STAD) samples, compared to all promoters (***P<0.001, Wilcoxon test)

D) Somatic Promoters in Other Cancer Types. Boxplot depicting changes in RNA-seq expression at genomic regions exhibiting GC somatic promoters compared against all promoters, across 326 TCGA Colon adenocarcinoma (COAD) samples (286 COAD, 40 normal; *P<0.001, Wilcoxon test), 170 TCGA kidney renal clear cell carcinoma (ccRCC) samples (98 ccRCC and 72 normal; *P<0.001, Wilcoxon test), and 115 TCGA lung adenocarcinoma (LUAD) samples (58 LUAD, 57 normal; ***P<0.001 somatic gain vs all promoters and somatic gain vs. somatic loss, Wilcoxon test).

Figure 3:
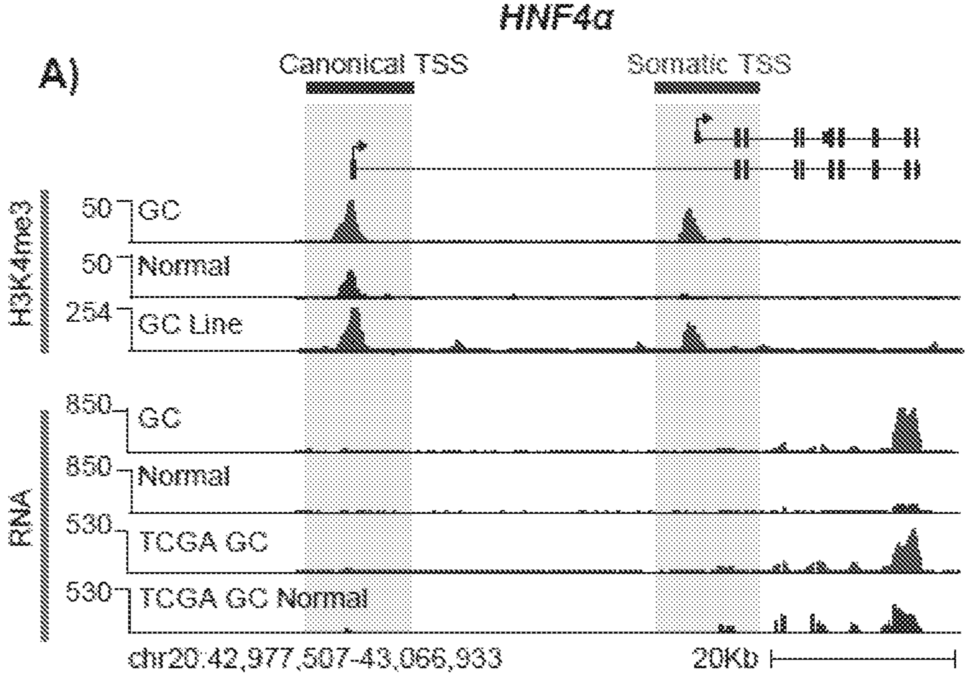
Figure 3:
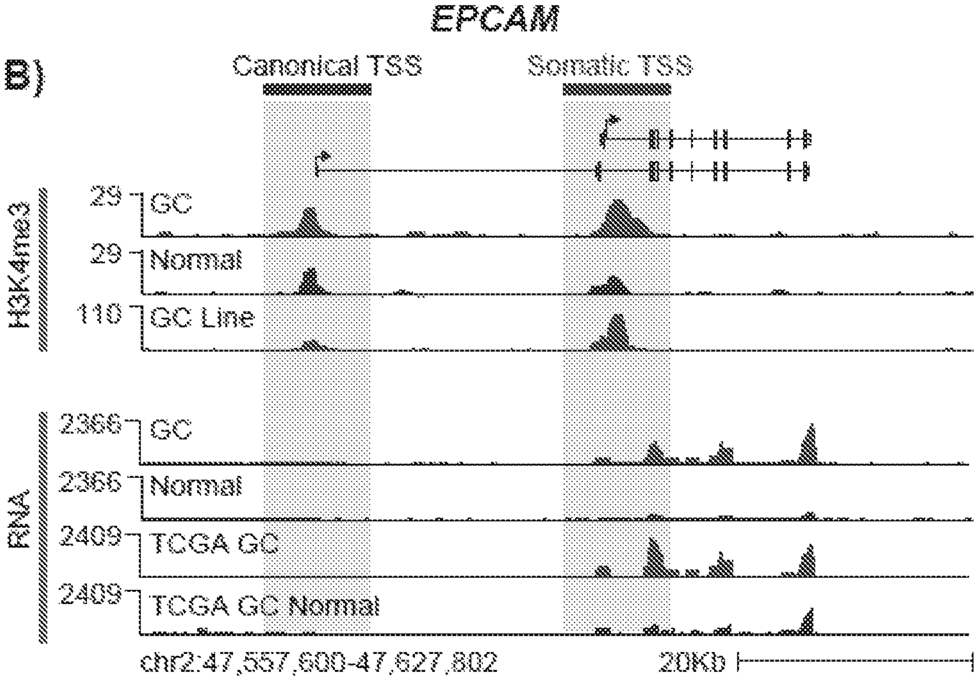
Figure 3:
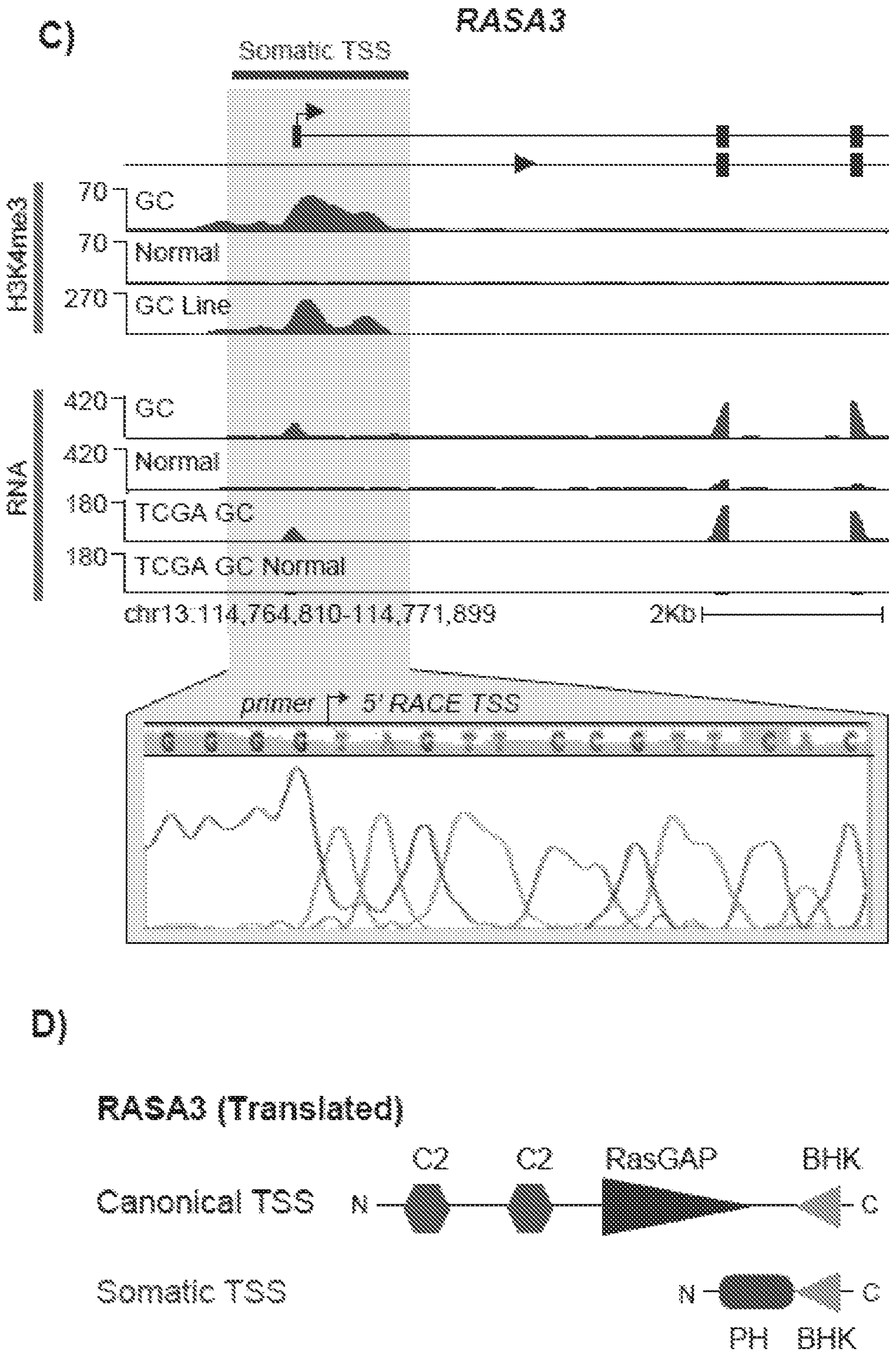
Figure 3:
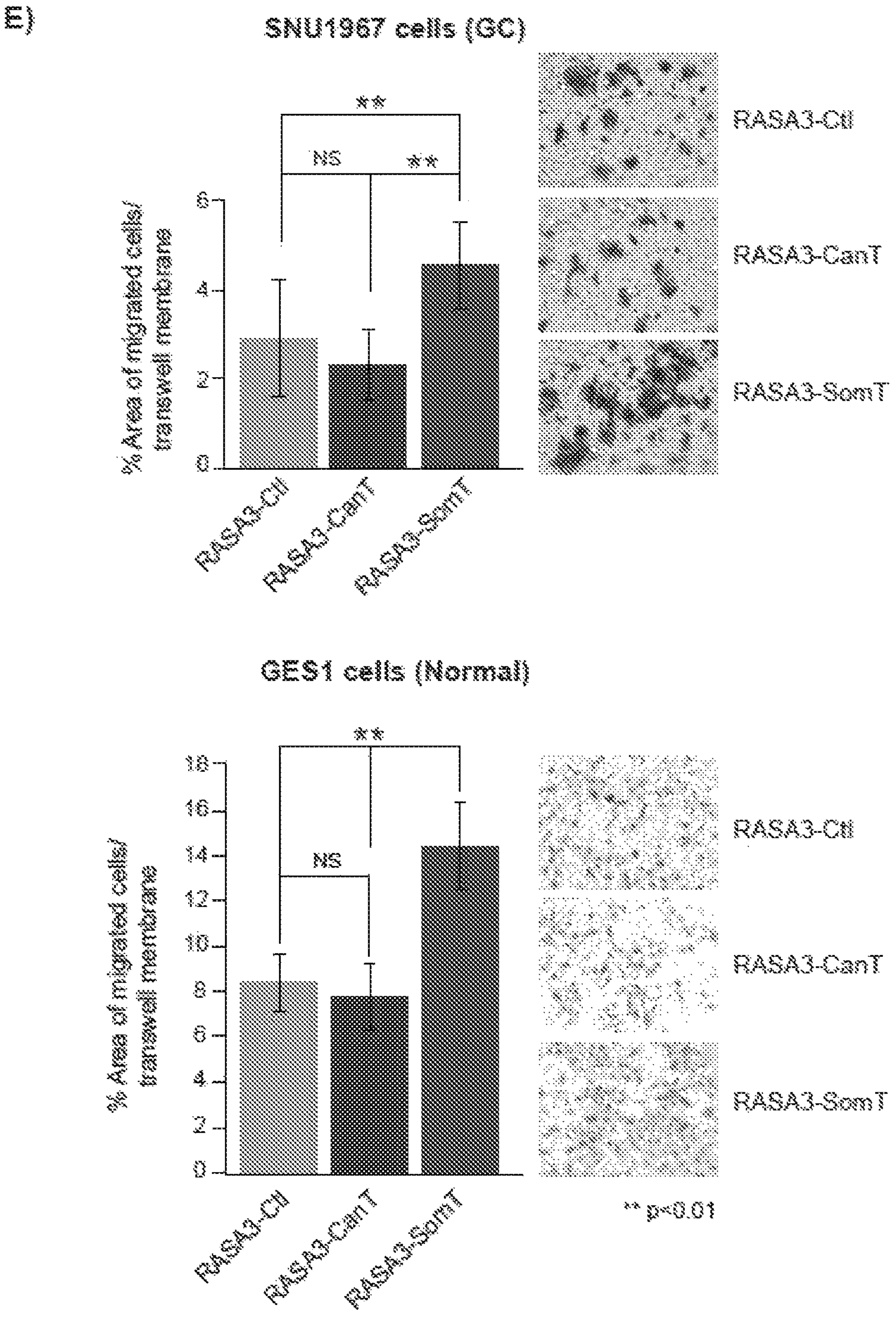

FIG. 3: Alternative Promoters in GC

A) UCSC browser track of the HNF4α gene. GC and matched gastric normal samples have equal H3K4me3 signals at the canonical HNF4α promoter. However, an alternative promoter, seen by H3K4me3 gain, can be observed at a downstream TSS in GCs compared to matched normals. At the RNA level, both in-house and TCGA STAD samples also show gain of gene expression at the alternate promoter TSS compared to normal samples.

B) UCSC browser track of the EPCAM gene. Another example of alternative promoter usage at a downstream TSS. Gain of H3K4me3 is observed at a TSS downstream of the canonical promoter, while the canonical promoter exhibits equal H3K4me3 signals in GC and gastric normal. Gain of RNA-seq expression can also be observed in GC at the alternative promoter driven transcript in both in-house and TCGA STAD samples.

C) UCSC browser track of the RASA3 gene, demonstrating H3K4me3 and RNA-seq signals highlighting gain of promoter activity at an un-annotated TSS (dark grey box) corresponding to a novel N-terminal truncated RASA3 transcript. Expression of this variant transcript was validated through 5'RACE in GC lines (bottom).

D) Functional domains of the translated RASA3 canonical and alternate isoform. The alternate transcript is predicted to encode a RASA3 protein missing the RASGAP domain.

E) Effect of overexpression of RASA3 canonical (CanT) and alternate (SomT) isoforms on the migration capability of SNU1967 (top) and GES1 (bottom) cells. Representative images of RASA3-Ctl (Empty vector), RASA3-CanT and RASA3-SomT in migration assays (n=3). Barplots show the % area of migrated cells vs the area of transwell membrane. Data is shown as mean±SD; n=3. (*P<0.05, P<0.01, *P<0.001, Student's one sided t-test)

Figure 4:
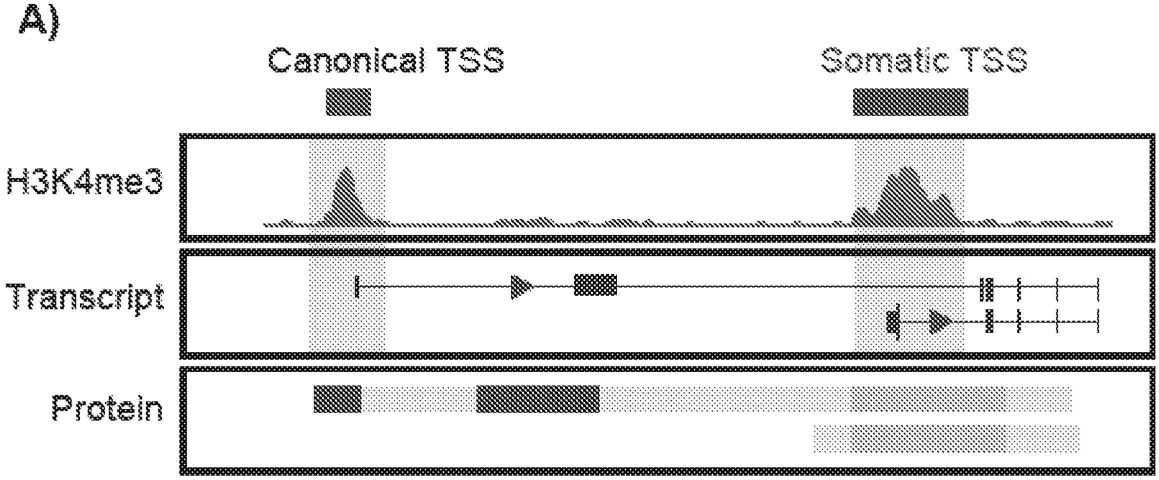
Figure 4:
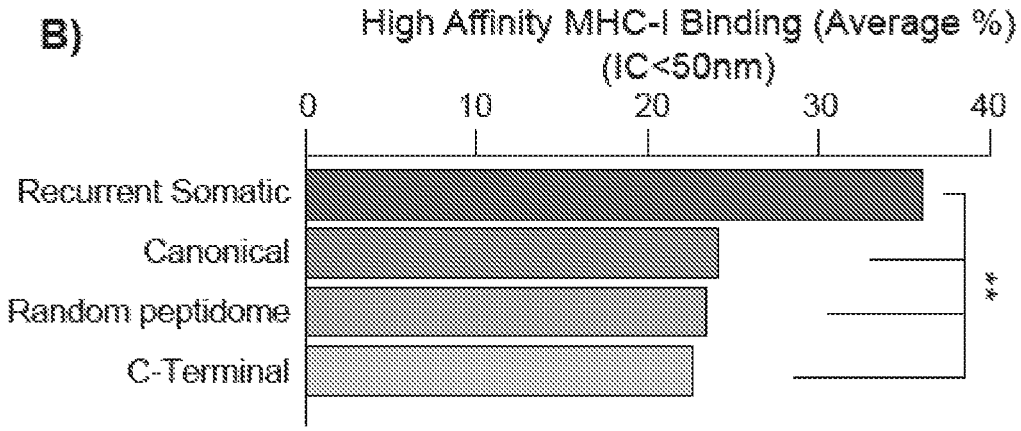
Figure 4:
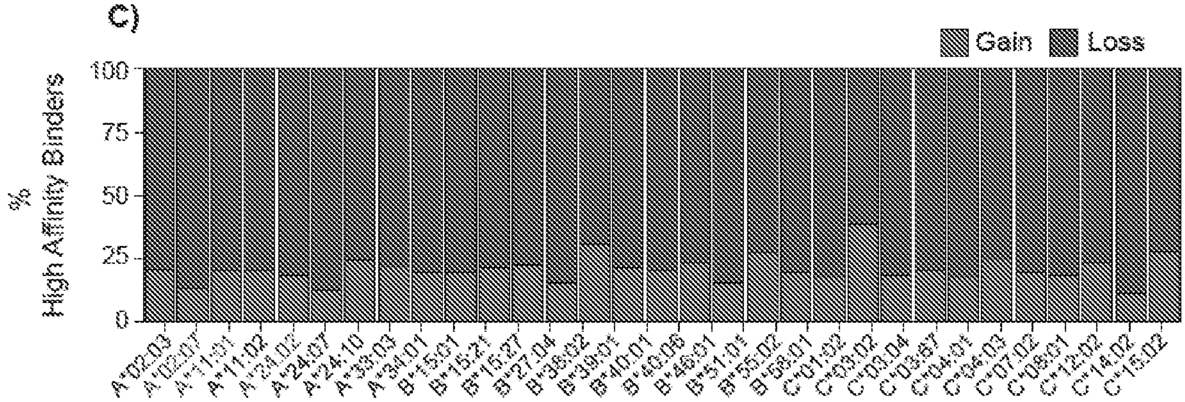
Figure 4:
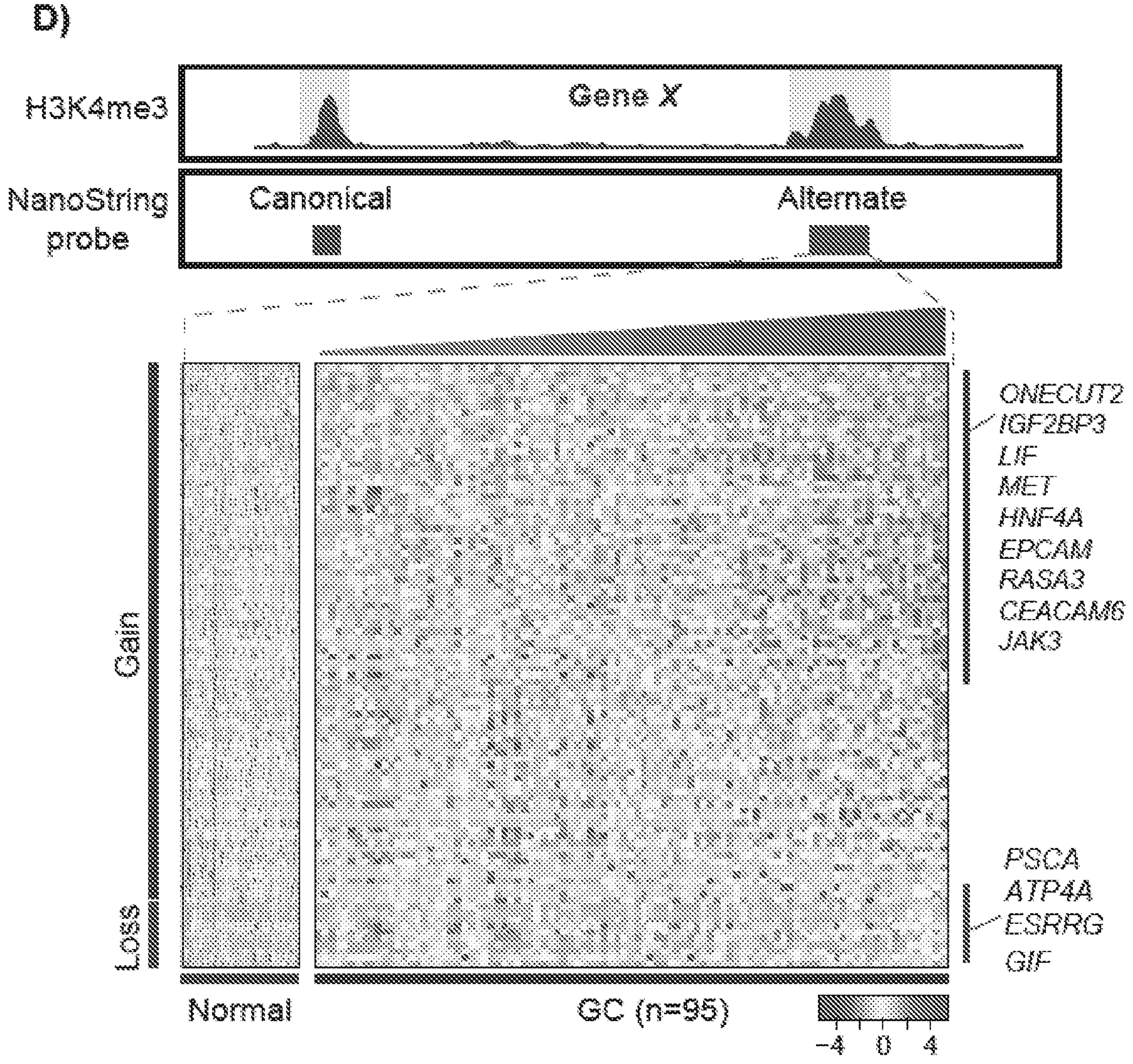
Figure 4:
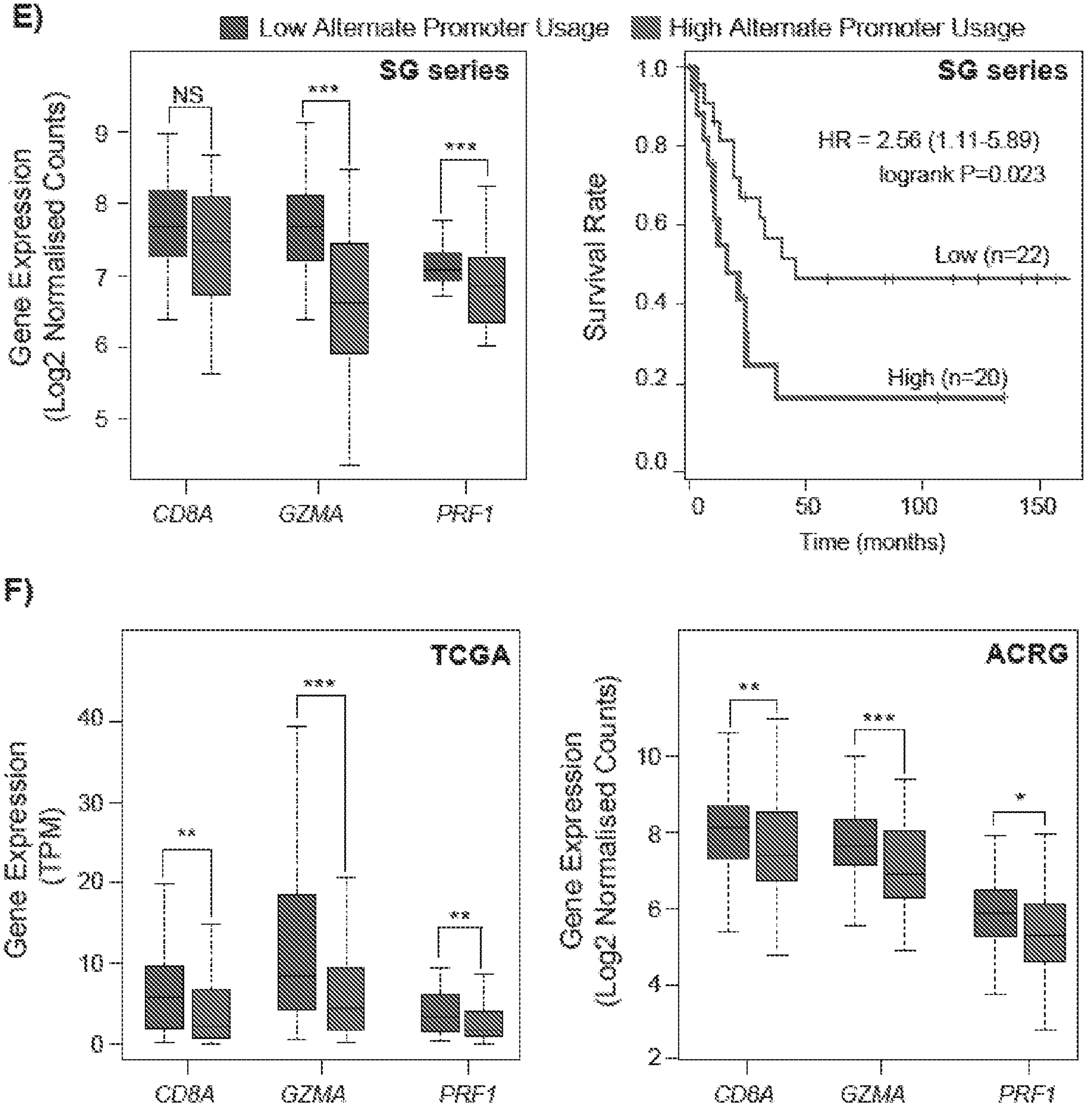
Figure 4:
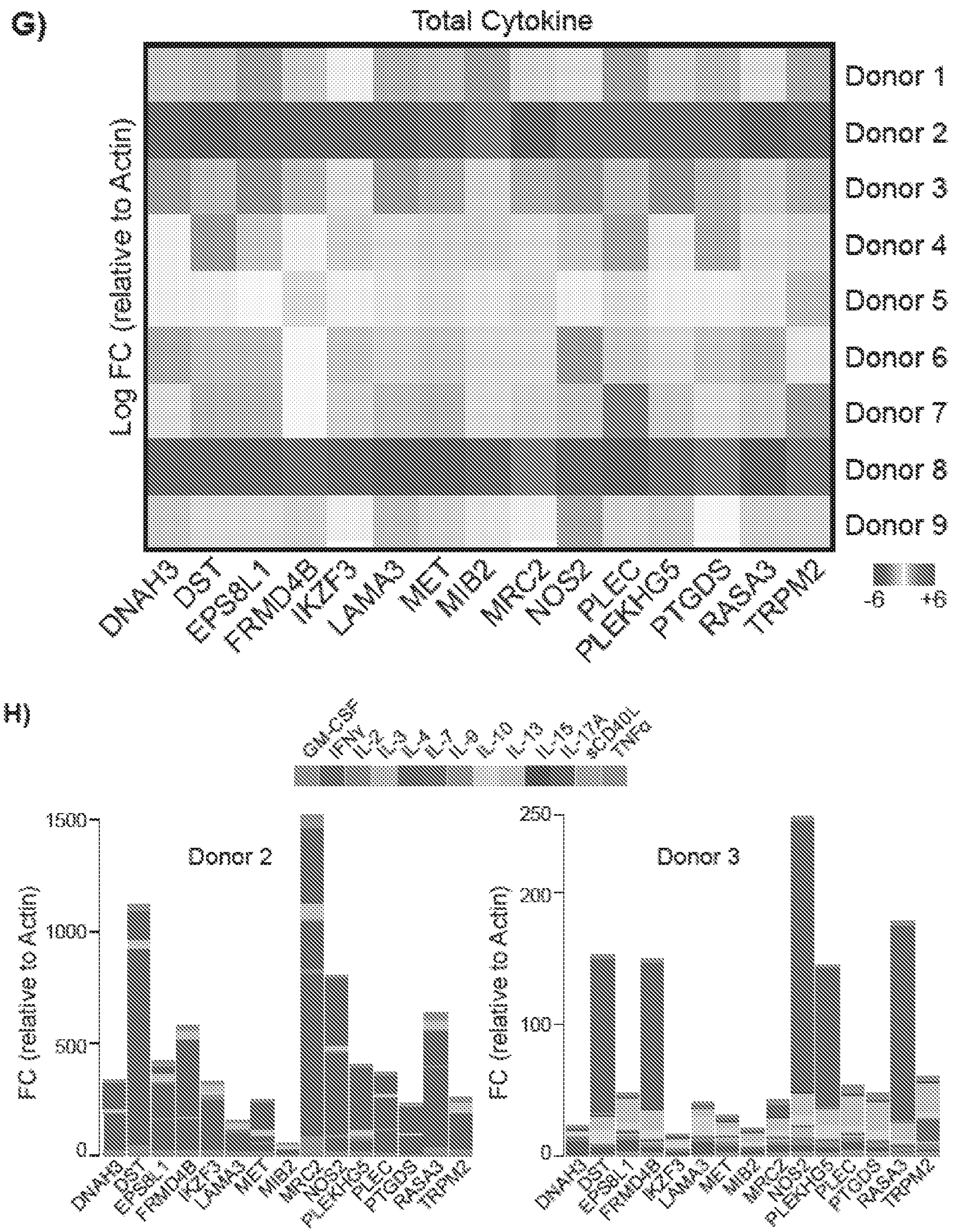

FIG. 4: Somatic Promoter Alterations Exhibit Immunoediting Signatures

A) Schematic outlining alternative promoter usage leading to alternative transcript usage (Transcript box) and N terminally truncated protein isoforms (protein box).

B) Barplot showing the average % of peptides with predicted high-affinity binding to MHC Class I (HLA-A, B, and C, IC<=50 nm). N-terminal peptides associated with recurrent somatic promoters (alternative promoters) show significantly enriched predicted MHC I binding compared to canonical GC peptides (P<0.01, Fisher's test), random peptides from the human proteome (P<0.001) and C-terminal peptides (P<0.01) derived from the same genes exhibiting the N-terminal alterations. Canonical peptides refer to peptides derived from protein coding genes overexpressed in GC through non-alternative promoters.

C) Percentage (%) of high affinity peptides predicted to bind different HLA-alleles categorized by somatic gain or loss. Most alleles have a greater number of N-terminal lost peptides predicted to have high binding affinity.

D) Quantification of somatic promoter expression using Nanostring profiling. Top—Distinct Nanostring probes were designed to measure expression of alternate and canonical promoter driven transcripts. 2 probes were designed for each gene—a canonical probe at the 5' transcript marked by unaltered H3K4me3, and an alternate probe at 5' transcript of the somatic promoter. Bottom—Heatmap of alternative promoter expression from 95 GCs and matched normal samples. GC samples have been ordered left to right by their levels of somatic promoter usage.

E) Association between Somatic Promoters and T-cell immune correlates (Singapore (SG) cohort). Top left-Expression of T-cell markers CD8A (P=0.1443) and the T-cell cytolytic markers GZMA (P=0.0001) and PRF1 (P=0.00806) in GC samples with either high or low somatic promoter usage (SG). Samples with high alternative promoter usage show lower expression of immune markers. All P values are from Wilcoxon one sided test. Right—Kaplan-Meier analysis comparing overall survival curves between validation samples with high somatic promoter usage (top 25%) and low somatic promoter usage (bottom 25%) (HR=2.56, P=0.02).

F) Association of Somatic Promoters with T-cell Correlates in TCGA and ACRG Cohorts. (Left) Expression of T-cell markers CD8A (P=0.02), GZMA (P=0.01) and PRF1 (P=0.03) in TCGA STAD with either high or low somatic promoter usage. T-cell markers were evaluated by RNA-seq (Transcripts per million, Right) Expression of T-cell markers CD8A (P=0.035), GZMA (P=0.001) and PRF1 (P=0.025) in ACRG GC samples with either high or low somatic promoter usage. All P values are from Wilcoxon one sided test.

G) EpiMAX Heatmap of total cytokine responses (Fold change relative to Actin) for 15 peptide pools against 9 donors.

H) Individual cytokine responses against 15 peptides for two individual donors (Donor 2 and Donor 3) showing complex cytokine responses (FC≥2).

Figure 5:
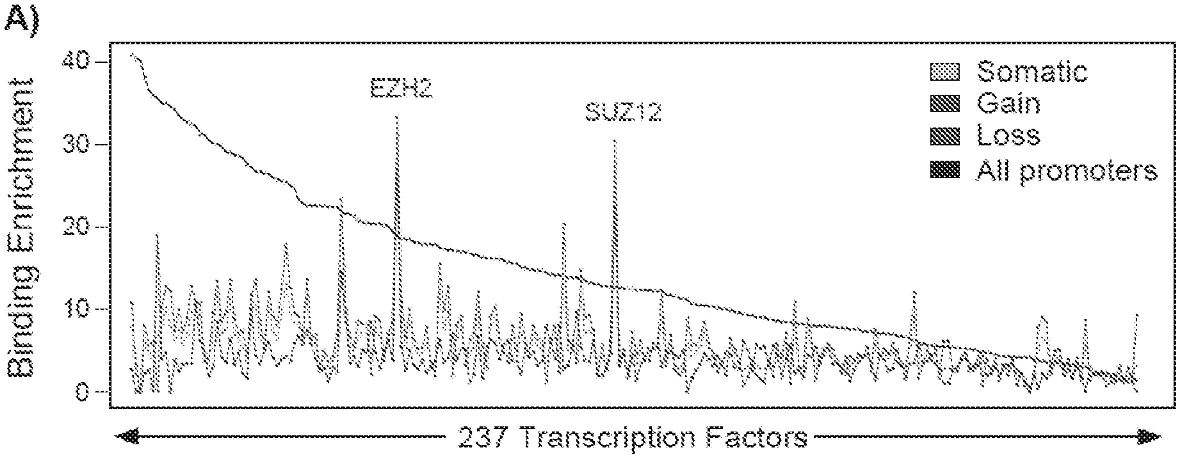
Figure 5:
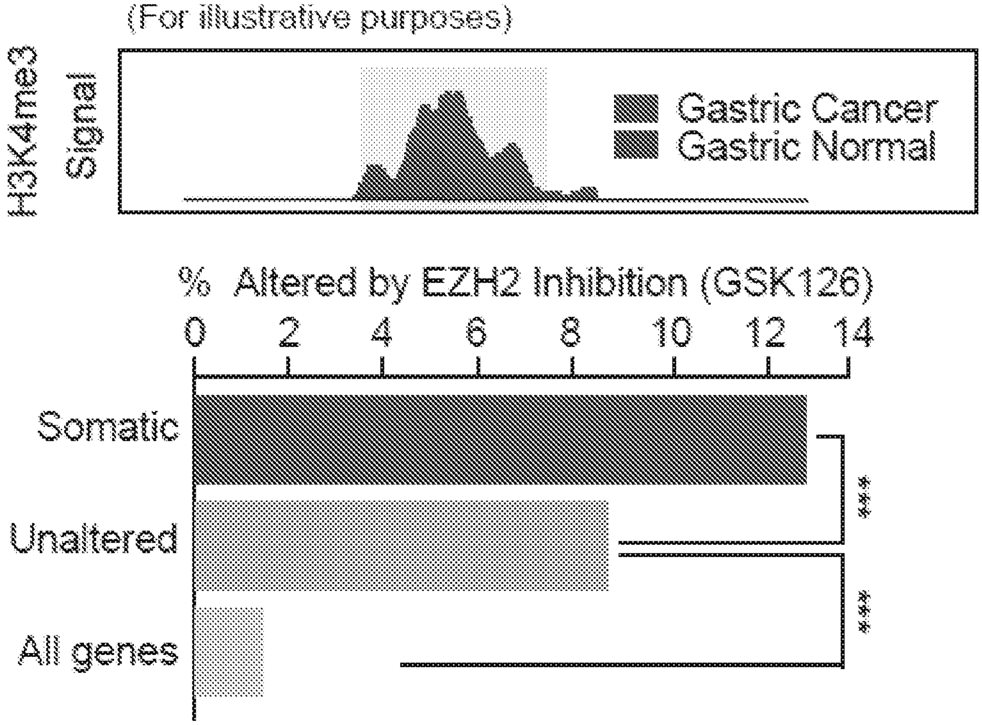
Figure 5:
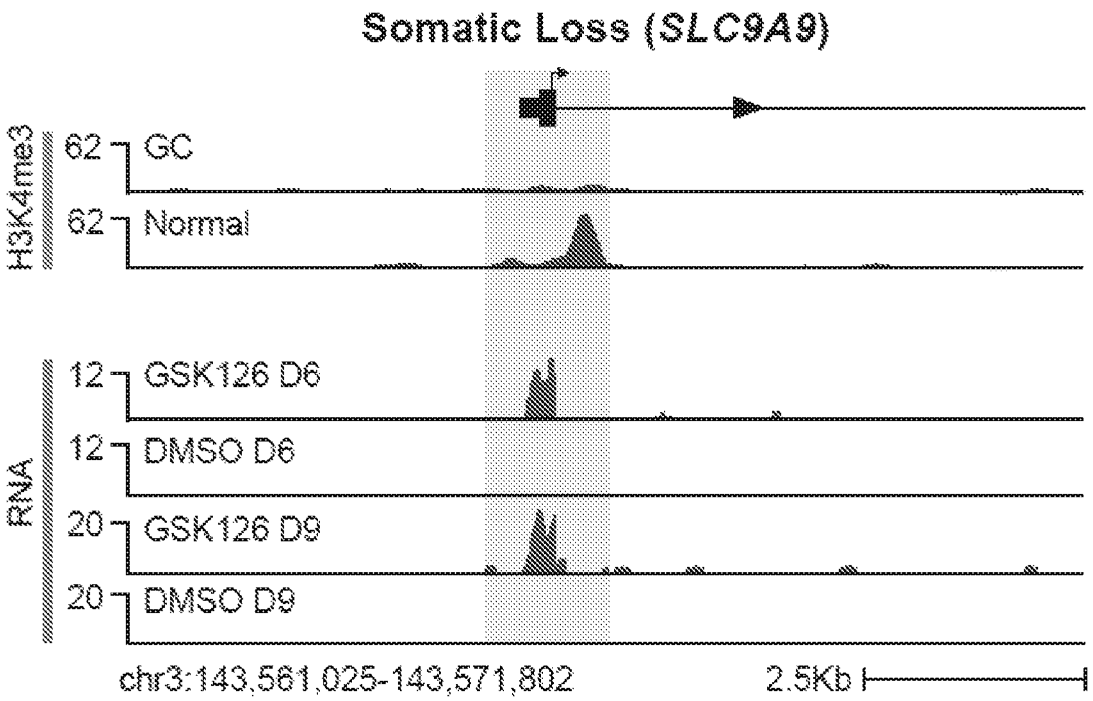
Figure 5:
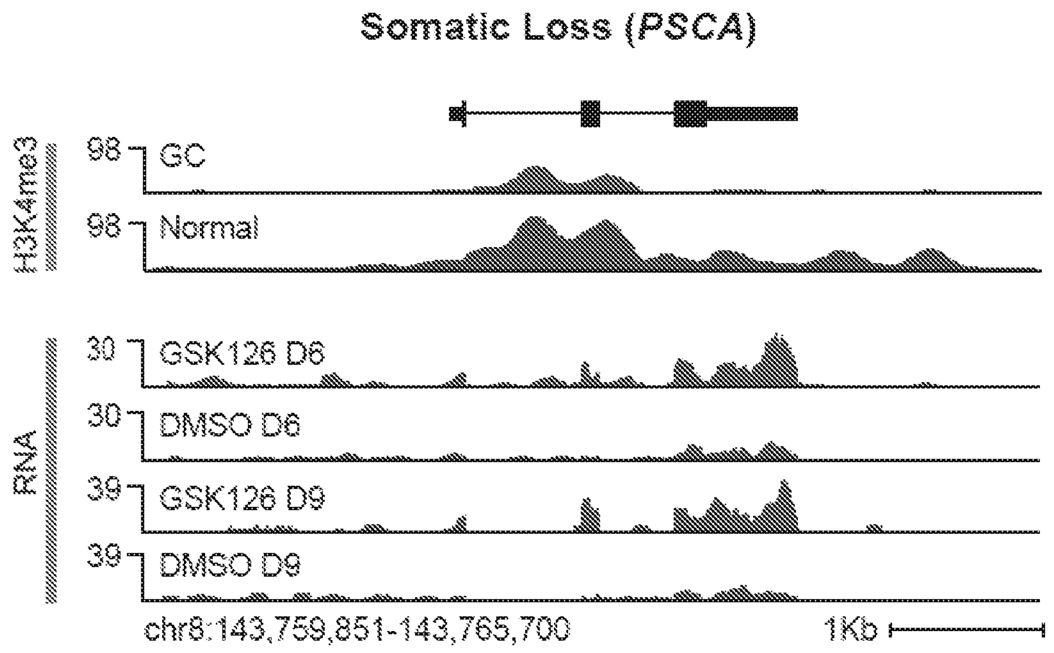

FIG. 5: Somatic Promoters are Associated with EZH2 Occupancy

A) Binding enrichment of ReMap-defined TFBSs at genomic regions exhibiting somatic promoters. TFs were sorted according to their binding frequency at all H3K4me3-defined promoter regions. EZH2 and SUZ12 binding sites significantly overlap regions exhibiting somatic promoters (gained and lost) (P<0.01, Empirical distribution test).

B) Proportion of RNA transcripts associated with somatic promoters changing upon GSK126 treatment in IM95 cells, compared to RNA transcripts associated with unaltered promoters. The top somatic promoter figure is for illustrative purposes only. Unaltered promoters were defined as all gene promoters except the somatic promoters. The proportion of genes changing upon treatment, as a proportion of all genes, is also shown. Somatic promoters are more likely to change expression after GSK126 treatment relative to unaltered promoters (OR 1.46, P<0.001) or all GSK126 regulated genes (OR 9.21, P<0.001, Fisher Test)

C) UCSC browser track of the SLC9A9 TSS, a gene with loss of promoter activity. Gain of expression is seen after inhibition of EZH2 using GSK126 in IM95 cells at both day 6 (D6) and Day 9 (D9) treatment.

D) UCSC browser track of the PSCA TSS, with loss of promoter activity. Gain of expression is seen after inhibition of EZH2 using GSK126 in IM95 cells at both day 6 (D6) and Day 9 (D9) treatment.

Figure 6:
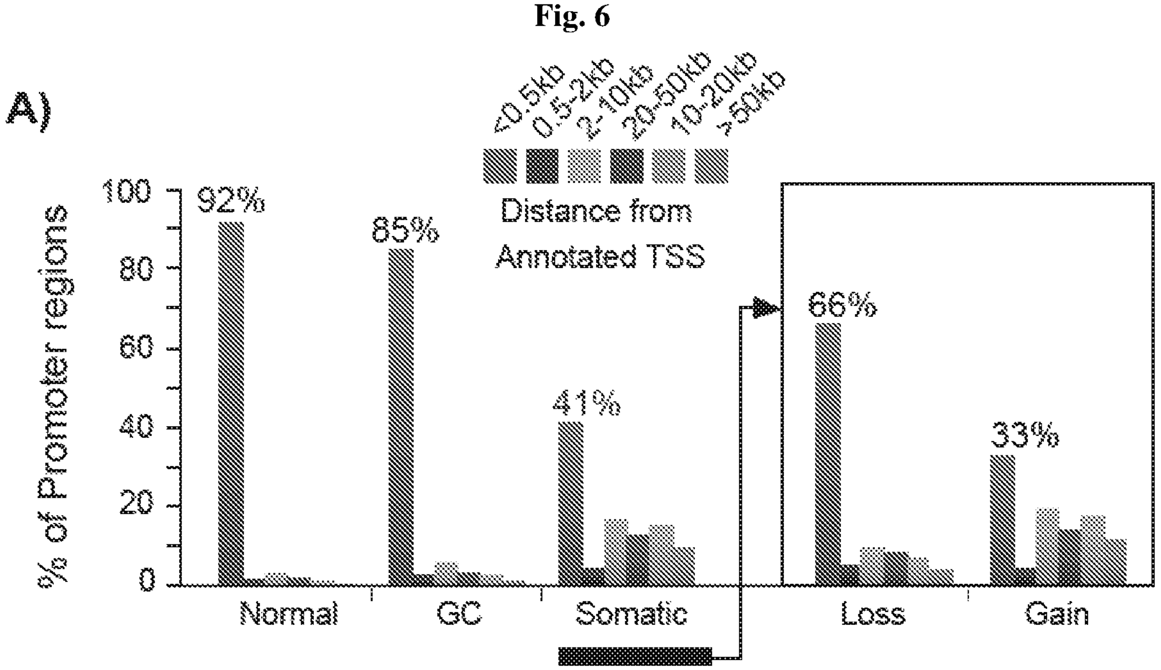
Figure 6:
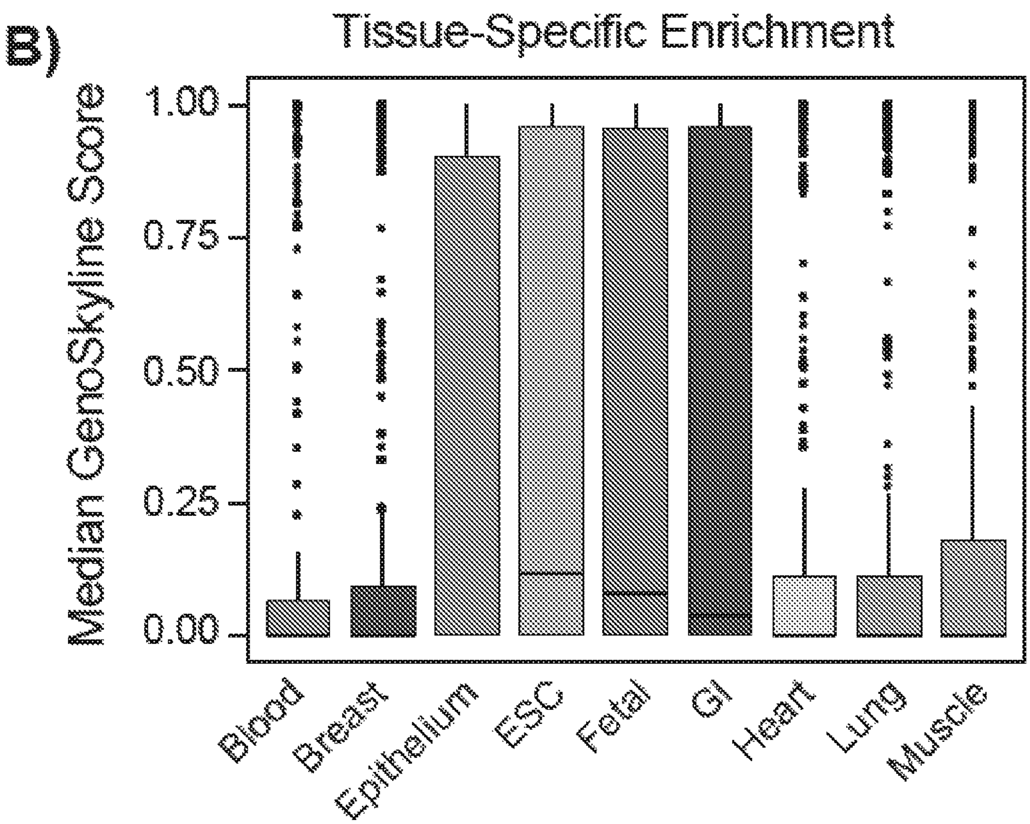
Figure 6:
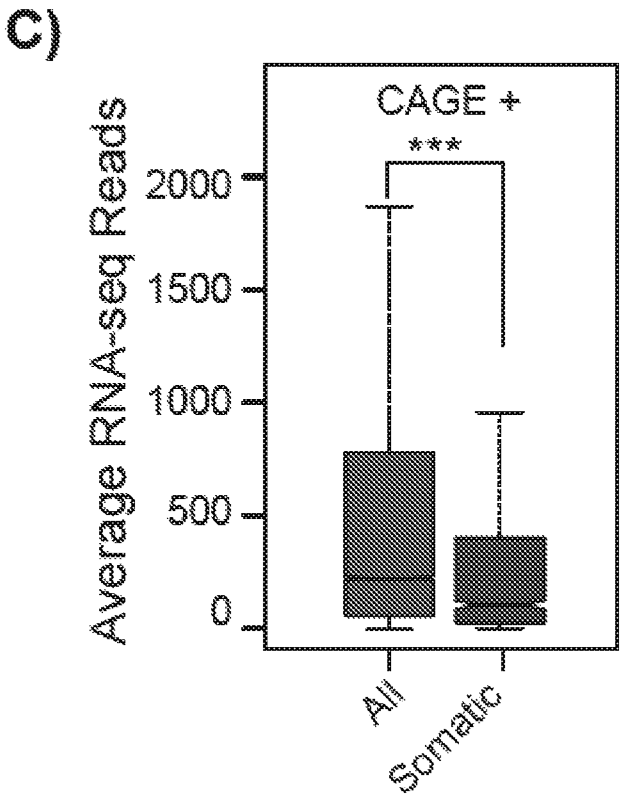
Figure 6:
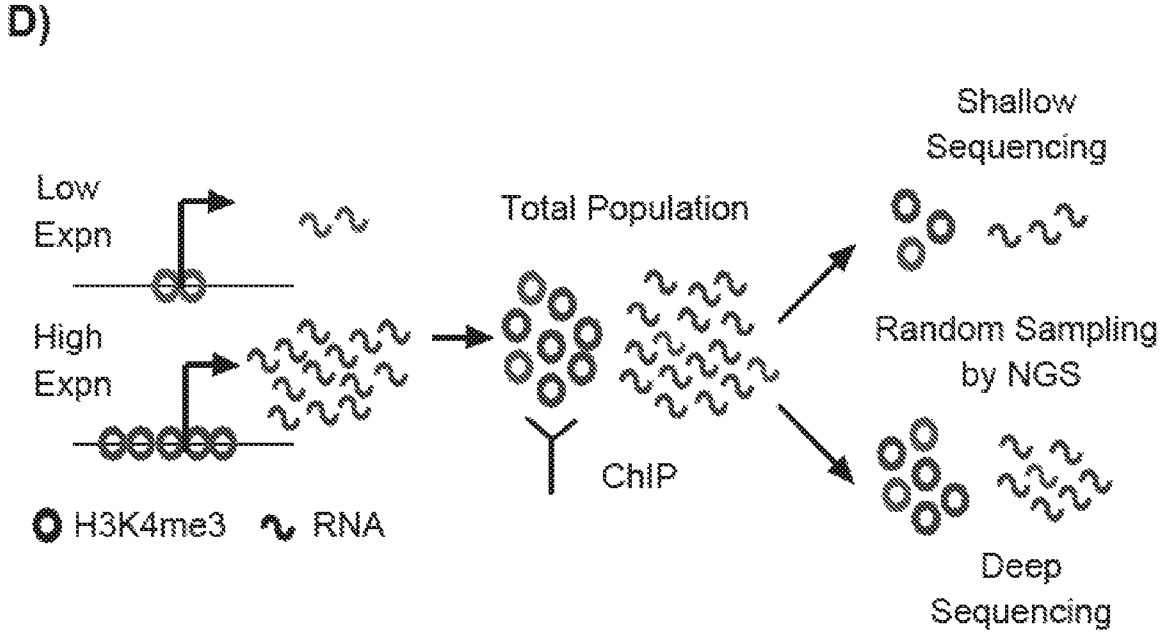
Figure 6:
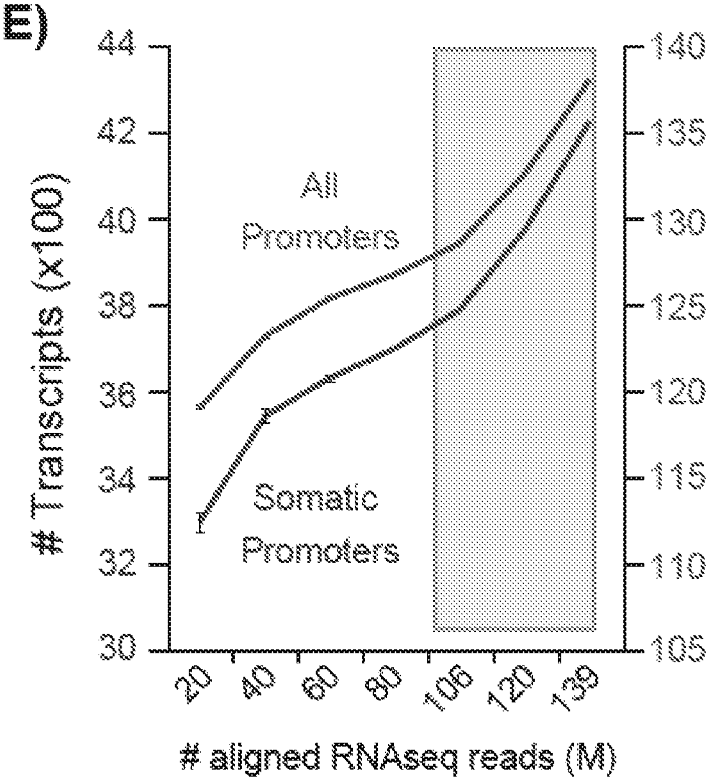
Figure 6:
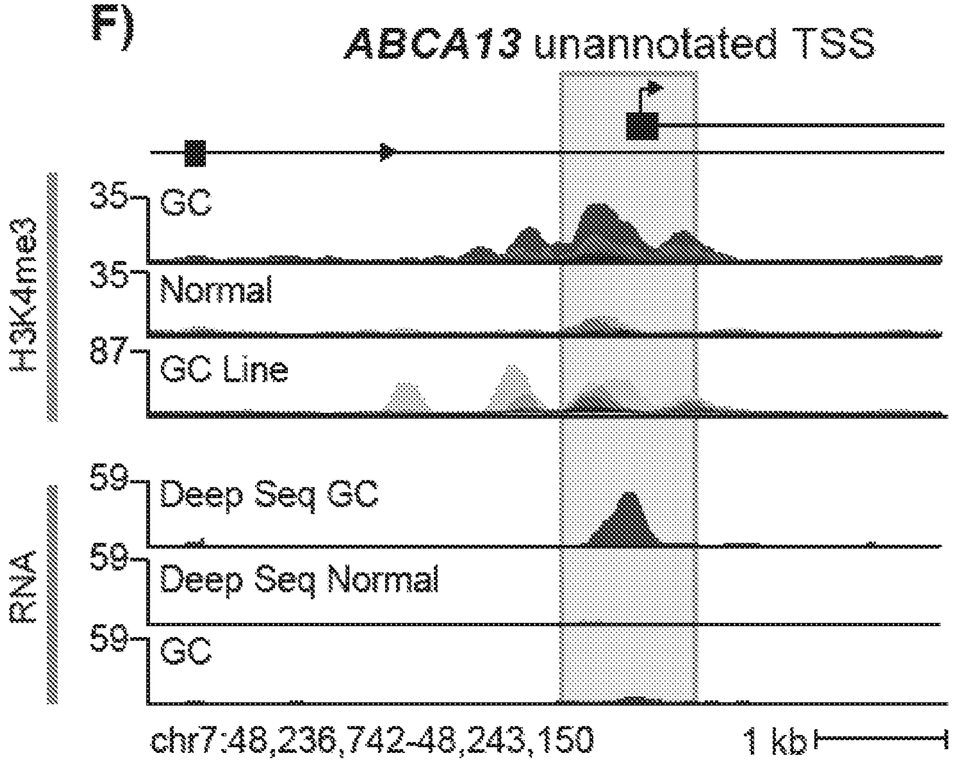

FIG. 6: Somatic promoters reveal novel cancer-associated transcripts

A) Distribution of distances for different promoter categories to the nearest annotated TSSs. (left) The first barplot shows distance distributions for promoters present in gastric normal tissues, the second for promoter present in GC samples, and the third for promoters exhibiting somatic alterations (i.e. different in tumor vs normal). (right) The barplots present distance distributions associated with either lost or gained somatic promoters. A substantial proportion of gained somatic promoters occupy locations distant from previously annotated TSSs B) Median functional scores of unannotated promoters as predicted by GenoSkyline across 7 different tissues. Unannotated promoters exhibited high functional scores for GI, fetal and ESC tissues.

C) Boxplot depicting average RNA-seq reads for CAGE-validated promoters, comparing either all promoters or somatic promoters and also supported by CAGE data. (**P<0.001, Wilcoxon one sided test). Somatic promoters are observed to have lower levels of RNA-seq expression.

D) Cartoon depicting proposed effects of dynamic range on NanoChIP-seq and RNA-seq sensitivity in detecting lowly expressed transcripts. Due to a more restricted dynamic range, epigenomic profiling may detect active promoters missed by RNA-sequencing, due to the random sampling of abundantly expressed genes by RNAseq.

E) Down and Up-sampling analysis. The y-axis depicts the number of transcripts detected that overlap either all promoters or somatic promoters at varying RNA-sequencing depths. Original primary sample RNA-seq data was sequenced at ~106M reads which was down-sampled to 20M, 40M and 60M reads. Deep RNA-seq data was additionally generated at ~139M read depth.

F) Cancer-associated transcripts detected at deep but not regular RNA-seq depth. The UCSC genome browser track for ABCA13 shows an example of a novel transcript detected by NanoChIP-seq at a read depth of 20M but only detected by RNA-sequencing at read depth of ~139M (Deep sequencing GC). This transcript is not detected by regular depth RNA-seq (GC).

Figure 7:
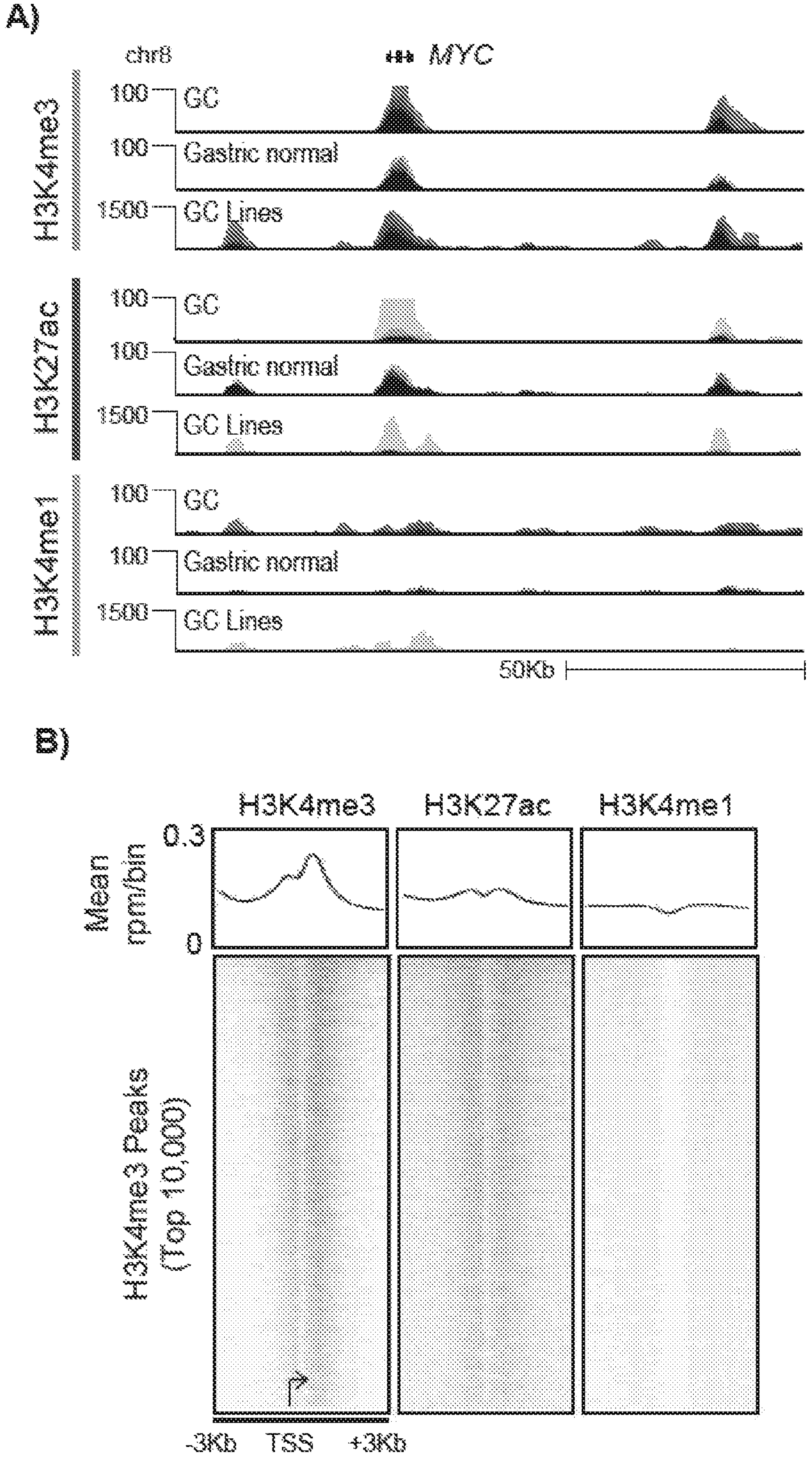
Figure 7:
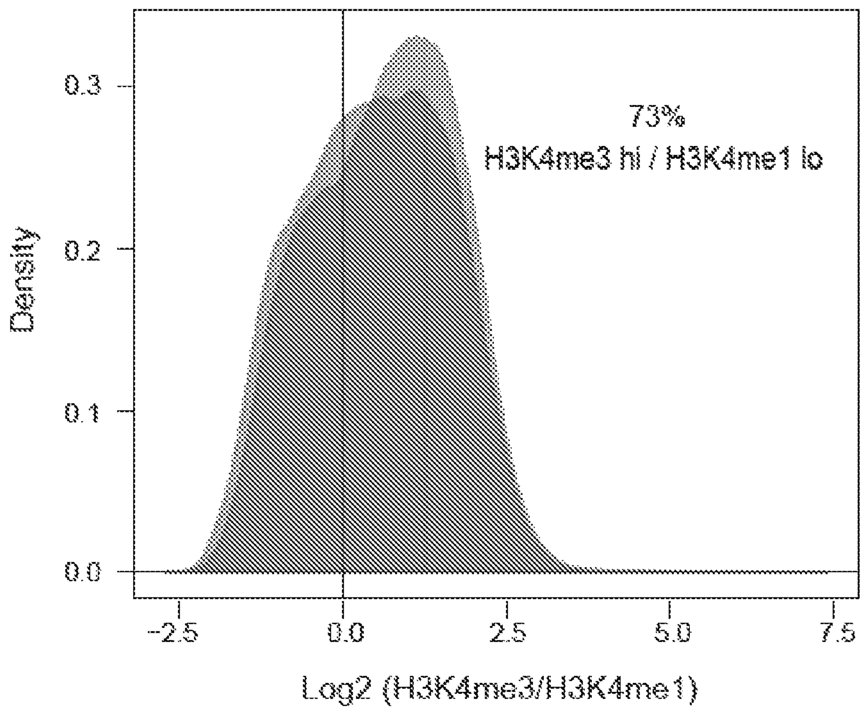
Figure 7:
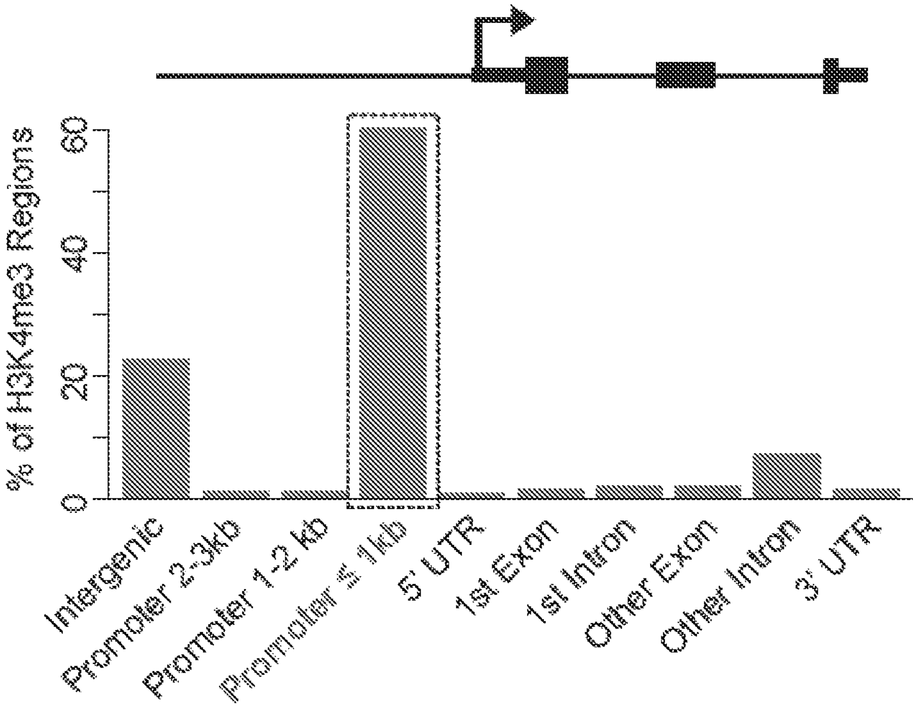
Figure 7:
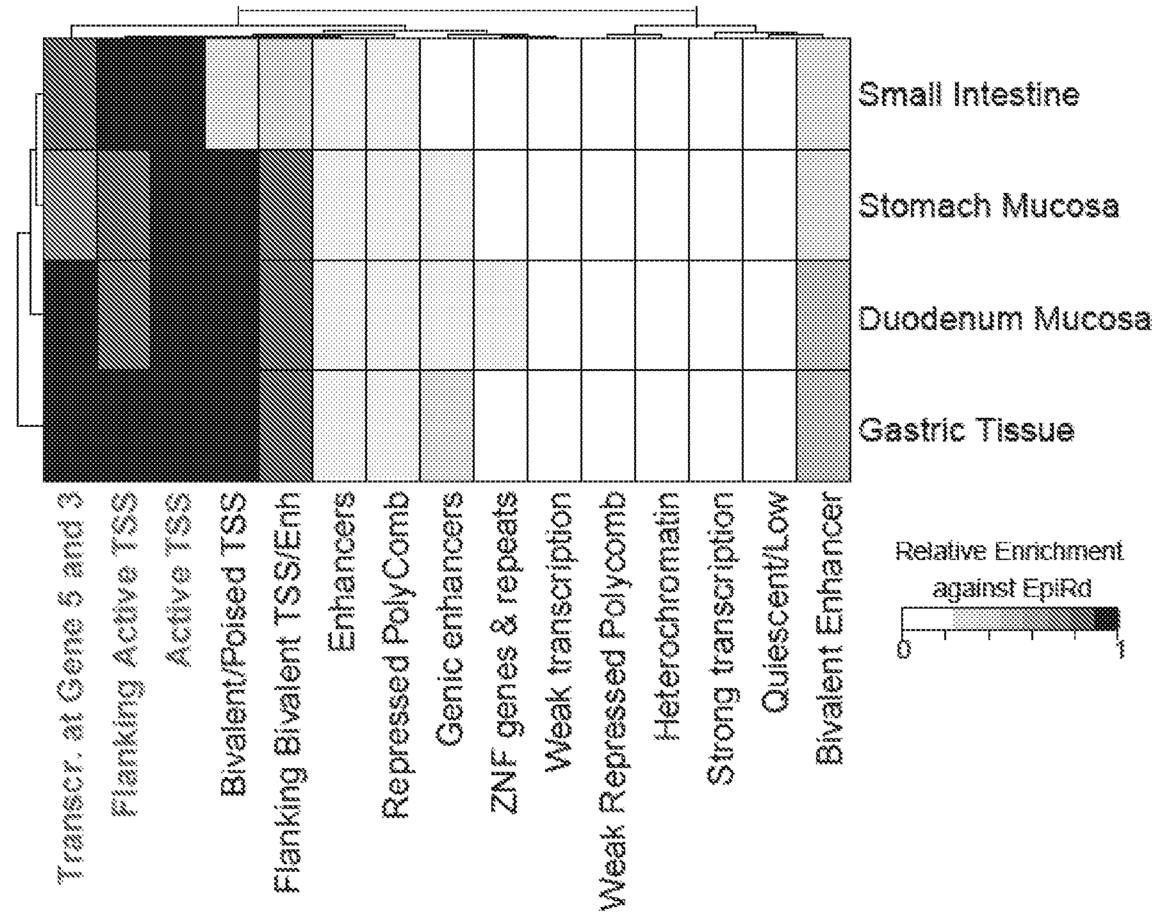
Figure 7:
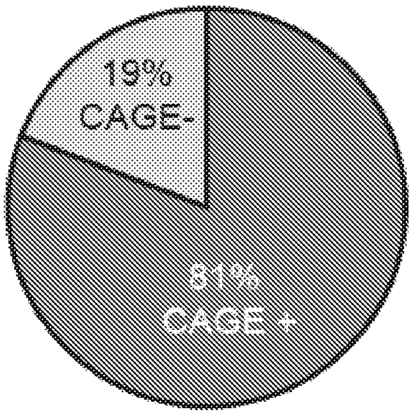

FIG. 7: Chromatin Profiles of Primary GC

A) Chromatin profiles of primary GCs, matched normal gastric mucosae, and GC cell lines for 3 marks (H3K4me3, H3K27ac and H3K4me1). Shown are UCSC genome browser tracks of the GC driver gene MYC highlighting strong H3K4me3 and H3K27ac signals and low H3K4me1 at promoter locations B) H3K4me3, H3K27ac and H3K4me1 signal distributions at transcription start sites (TSS). Line plots show the distribution of chromatin signals for H3K4me3 hi/H3K4me1 lo regions at TSS regions (+/−3 kb). Heatmaps were plotted using ngs.plot(6) for the top 10,000 H3K4me3 hi/H3K4me1 lo regions C) Density distributions of H3K4me3:H3K4me1 ratios at identified H3K4me3 regions. All regions with H3K4me3/H3K4me1 ratios >1 were selected for further analysis (73%)

D) Distribution of H3K4me3 hi/H3k4me1 lo regions against representative gene body features (top). The arrow represents the TSS.

E) Enrichment of H3K4me3 hi/H3K4me1 lo regions against 15 chromatin states (columns) defined in different gastrointestinal tissues from the Epigenome Roadmap database (rows). Each column is scaled from 0 to 1.

F) Overlap of H3K4me3 hi/H3K4me1 lo regions with FANTOM5 CAGE data

Figure 8:
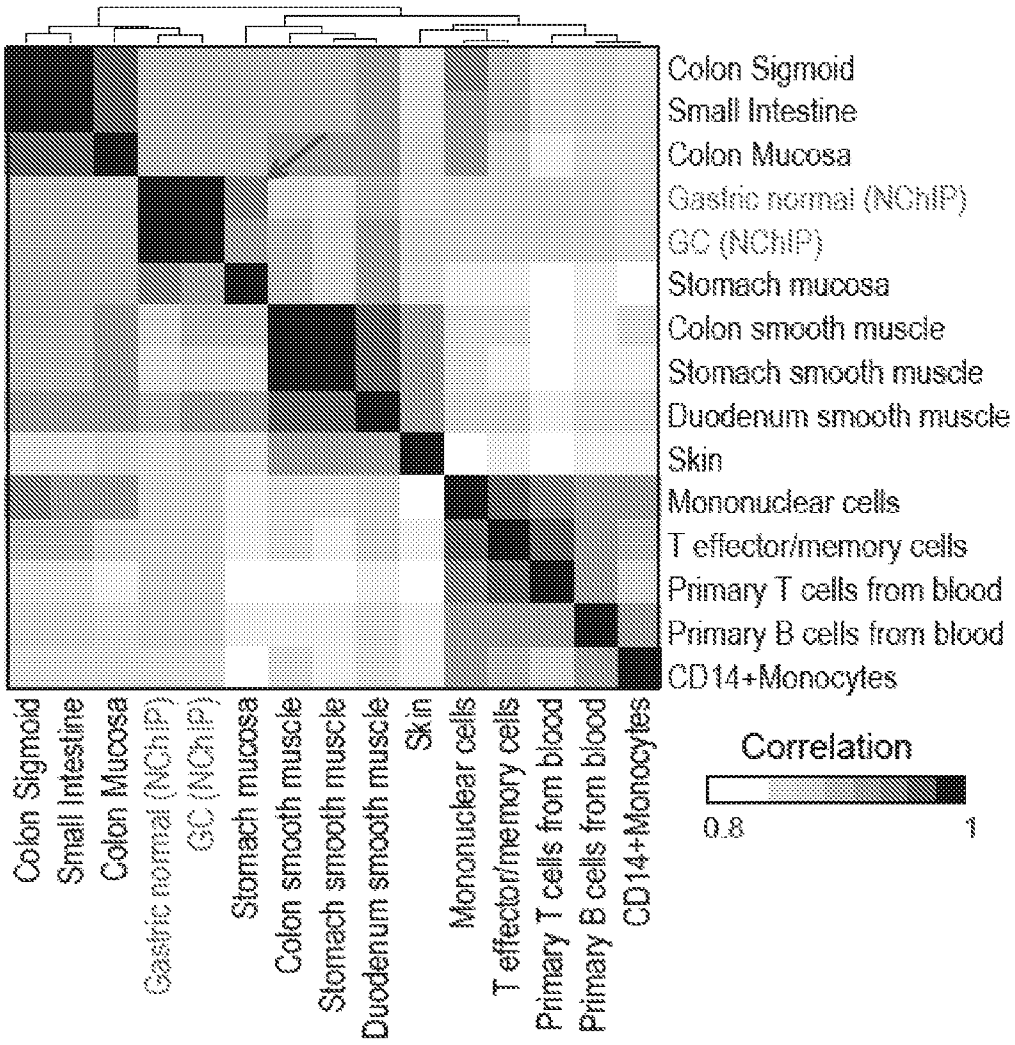
Figure 8:
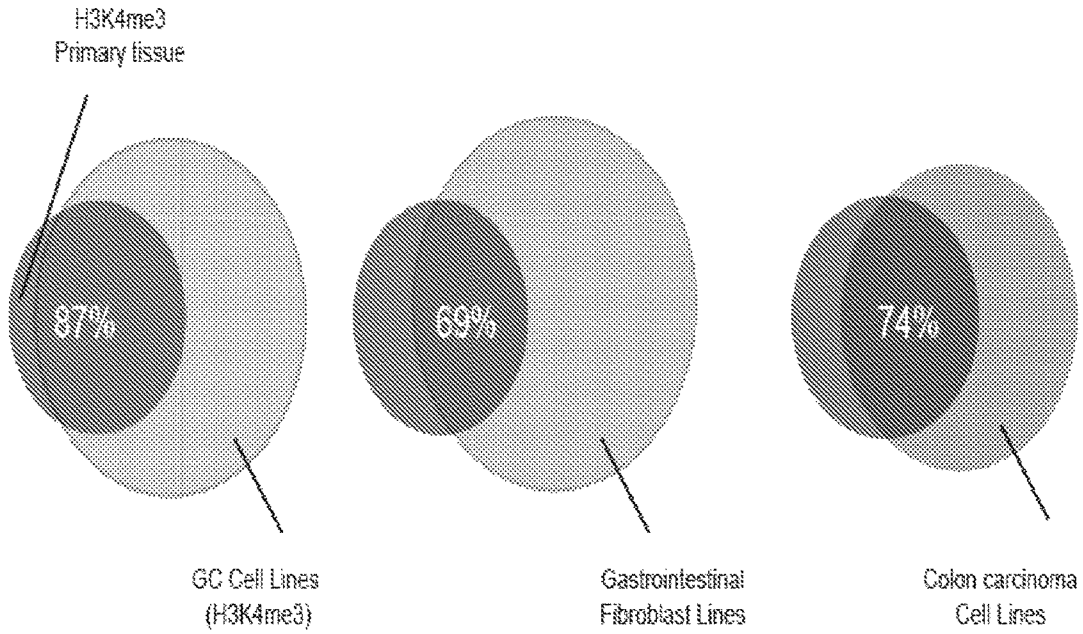

FIG. 8: Epithelial features of GC promoters

A) Spearman correlation heat-map between H3K4me3 signals of primary GC, gastric normal samples (red type, highlighted by red arrow) and various tissue types from the Epigenome Roadmap database across all H3K4me3 hi/H3K4me1 lo regions B) Overlap of H3K4me3 hi/H3K4me1 lo regions with H3K4me3 regions identified in GC cell lines (87%), gastrointestinal fibroblast cells (61%) and colon carcinoma lines (74%)

Figure 9:
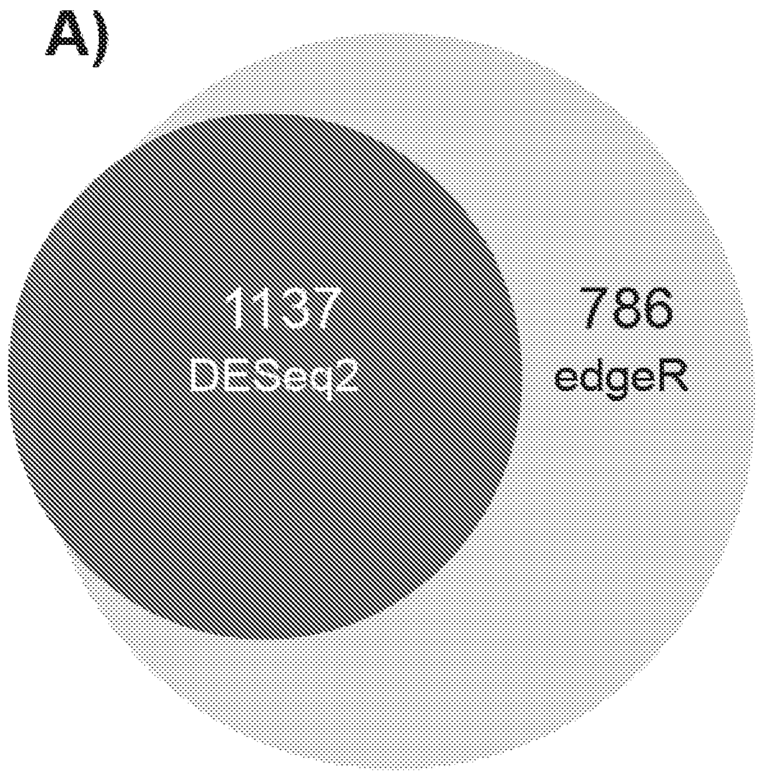
Figure 9:
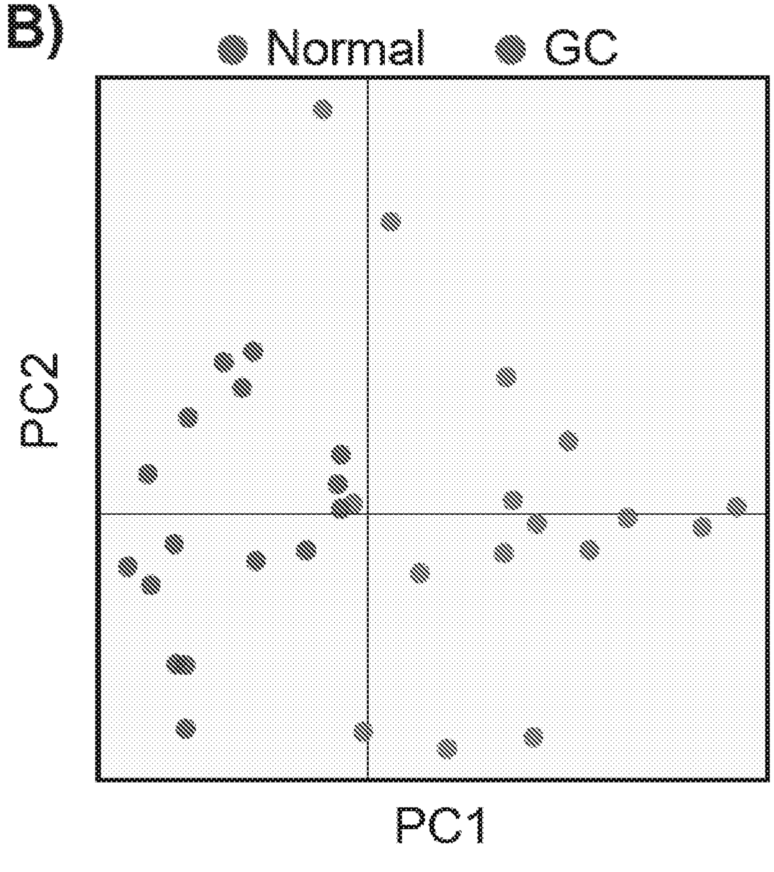
Figure 9:
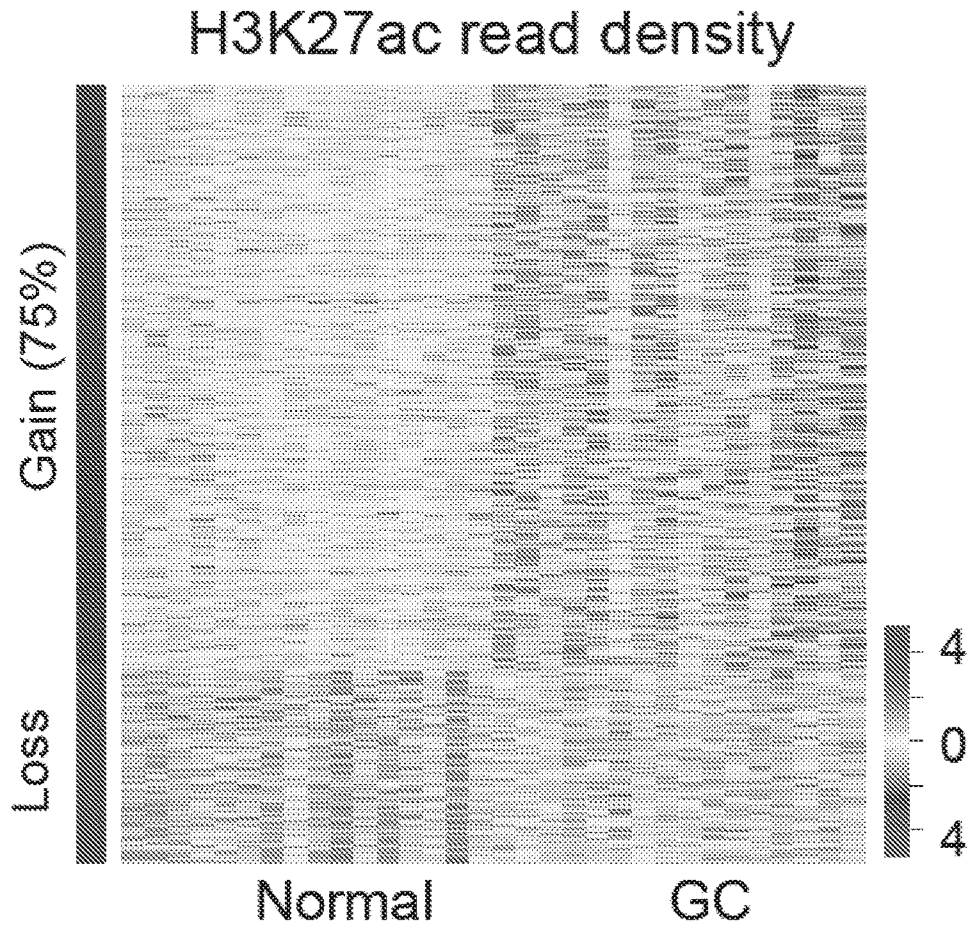
Figure 9:
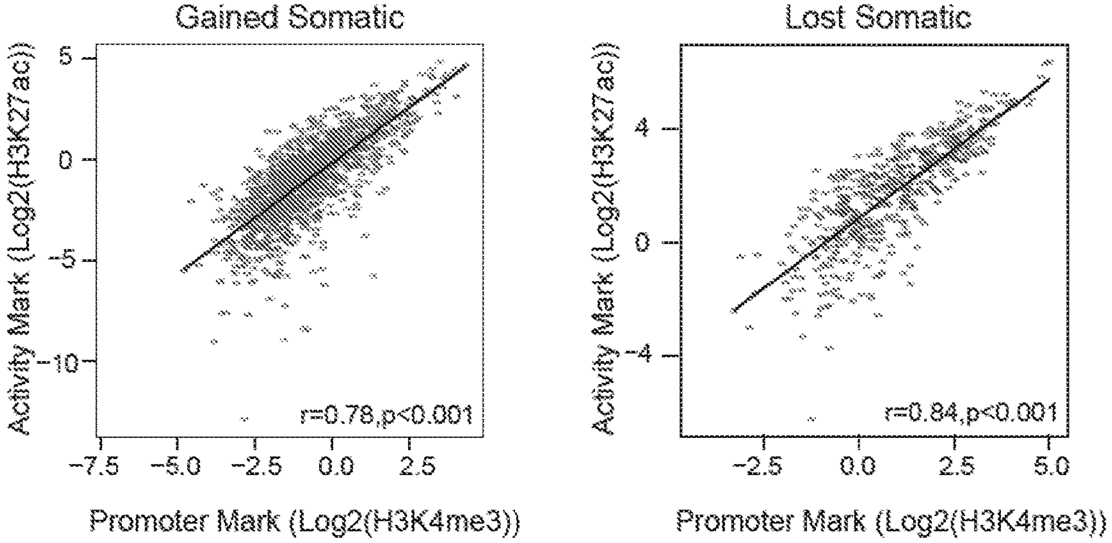
Figure 9:
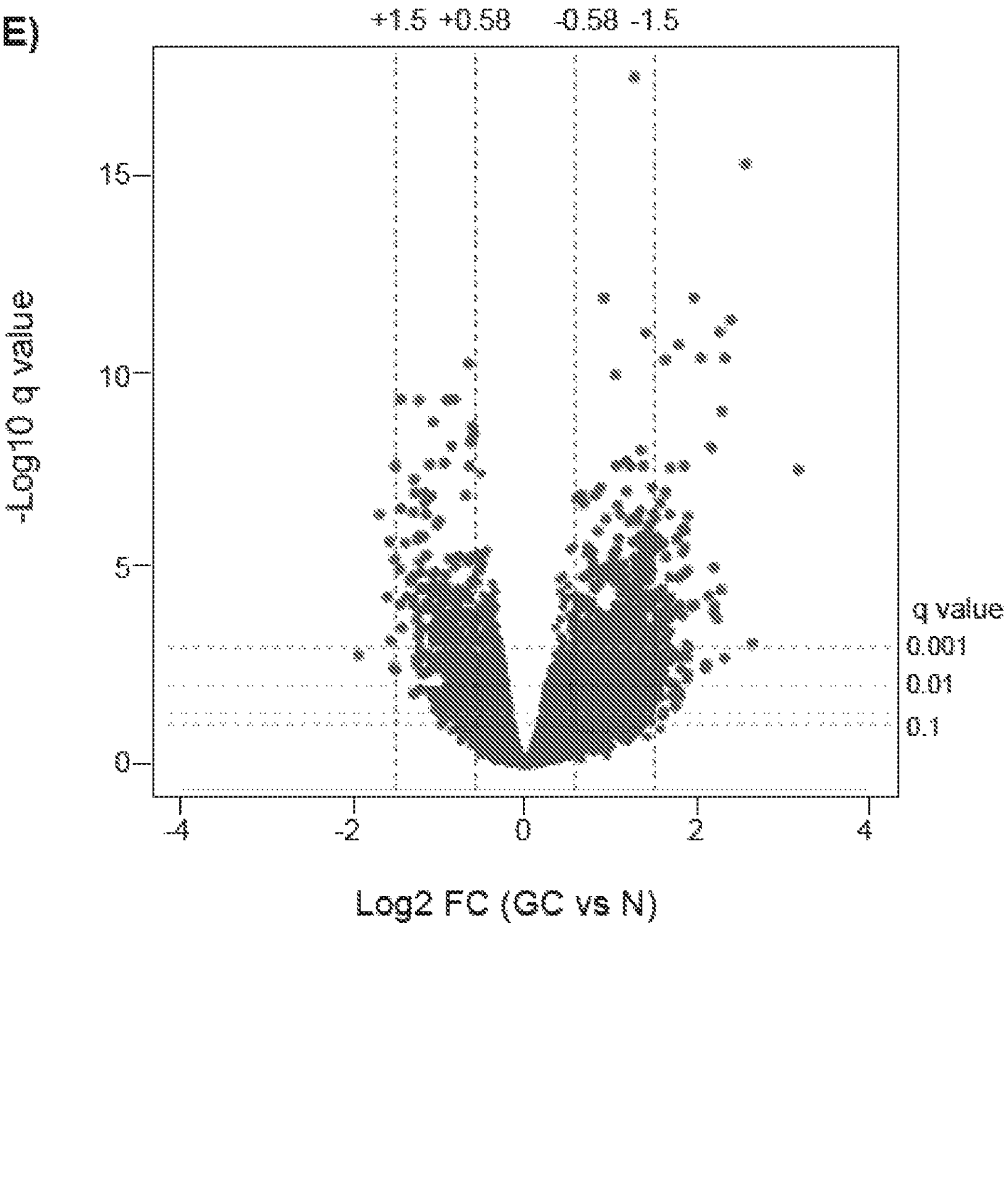
Figure 9:
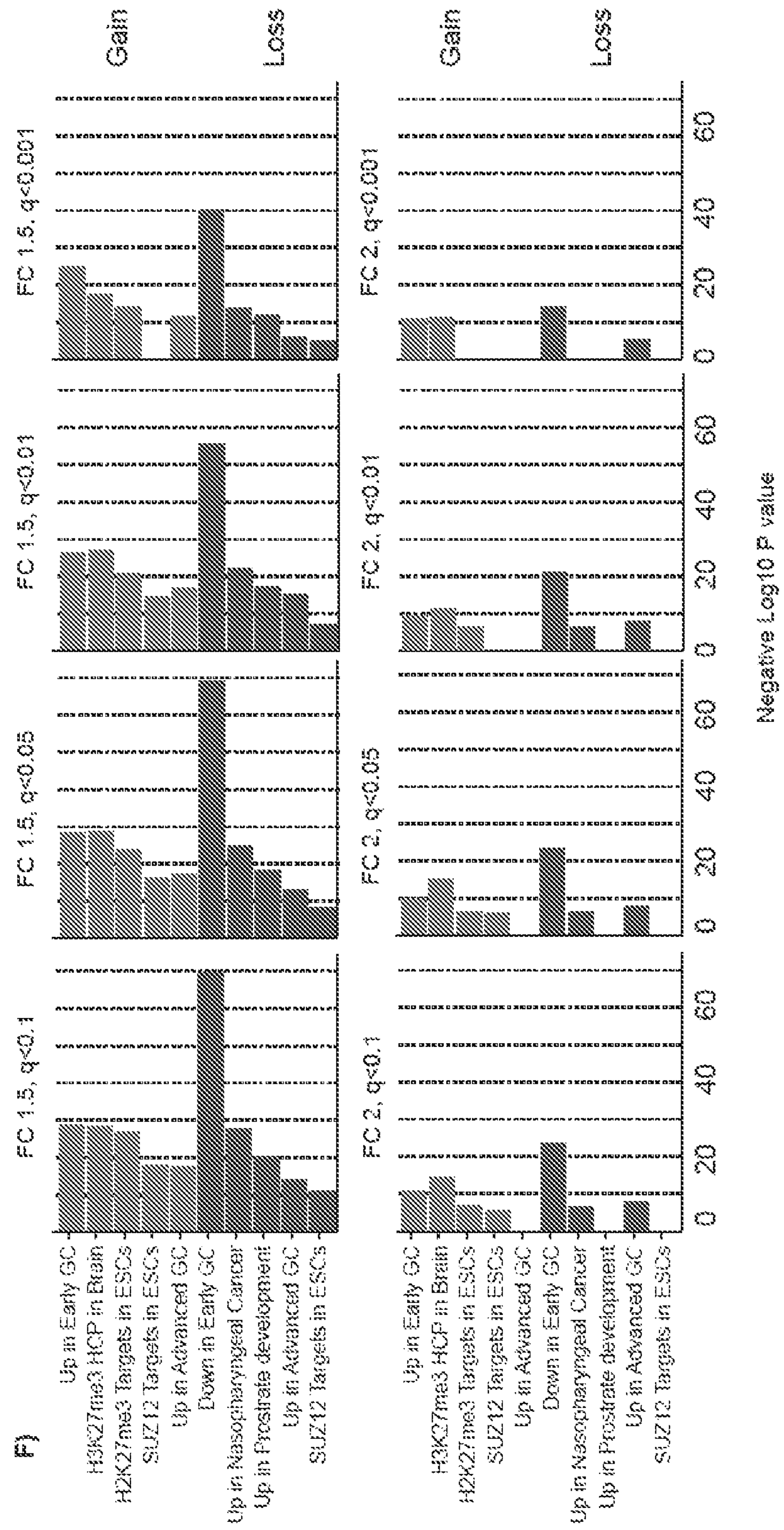

FIG. 9: GC Somatic Promoter Features

A) Differential (somatic) H3K4me3 regions identified from 2 independent algorithms DESeq2 and edgeR. 96% of regions identified from DESeq2 overlapped those identified using edgeR. Both sets were pooled for subsequent analysis.

B) Principal component analysis of 16 GC and gastric normal samples based on somatic promoters C) Heatmap of H3K27ac read densities across 16 GC and gastric normal samples across 1959 somatic promoters.

D) Correlation between H3K4me3 promoter signals and H3K27ac activity signals in primary gastric samples for gained somatic (Left, r=0.78, p<0.001) and lost somatic (Right, r=0.82, p<0.001) promoters. Each data point corresponds to a single H3K4me3 hi/H3K4me1 lo region. Analysis was performed using data from 16 N/T pairs (Table 4).

E) Volcano plot of somatic promoters (Top) highlighting the dynamic range of fold changes differences (x-axis) and the false discovery rate (FDR)-adjusted significance (−log 10 scale, y axis). The majority of the somatic promoters lie between FC 1 and 2.82, which likely reflects the dynamic range of Chip-seq. The Table (bottom) lists the number of somatic promoters identified at differing levels of stringency. Despite varying FDR thresholds, the majority of differential peaks are still preserved (e.g. 59% at q<0.01).

Figure 1:
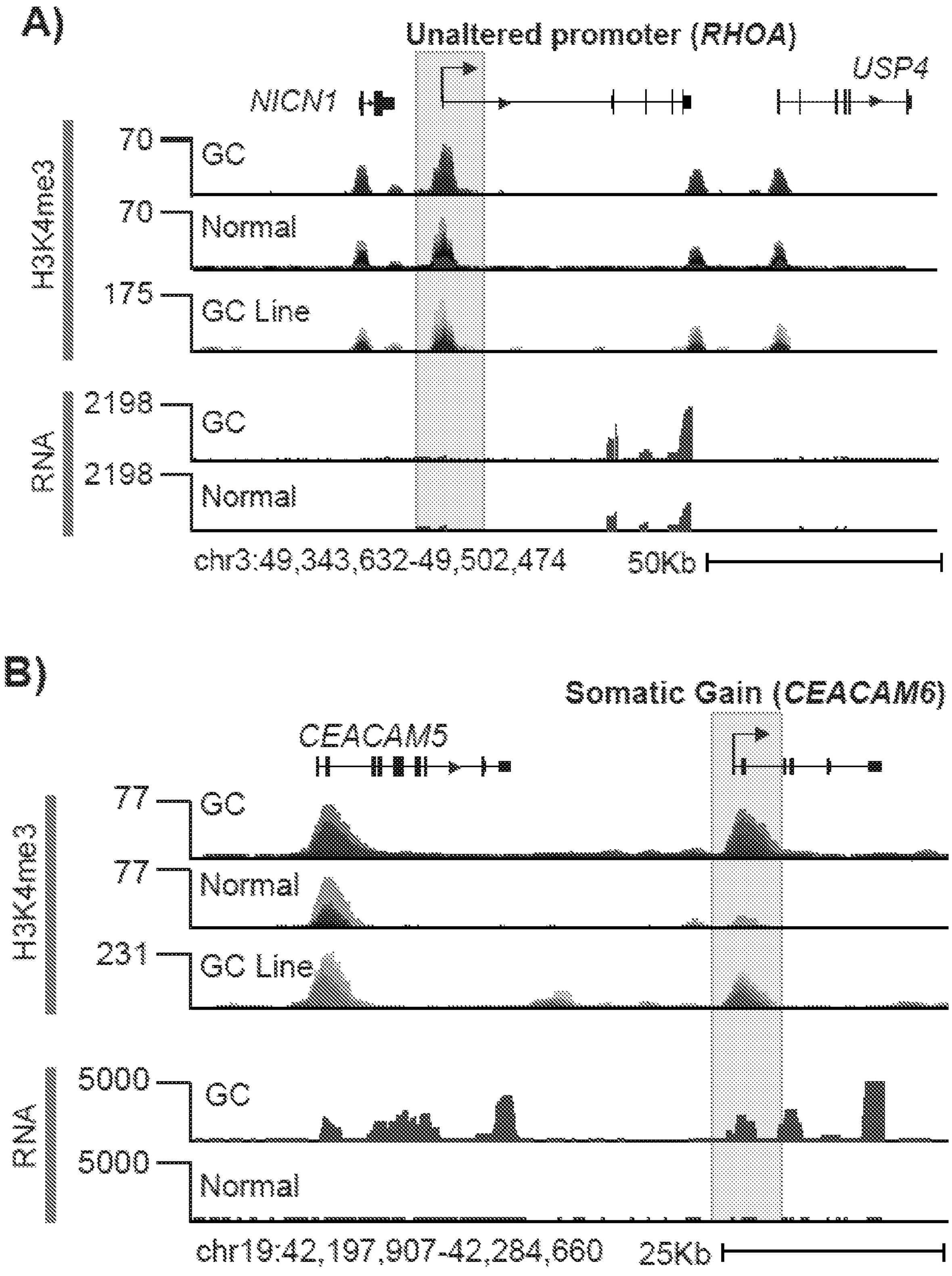
FIG. 1: Somatic Promoter Alterations in Primary Gastric Adenocarcinoma.
Figure 1:
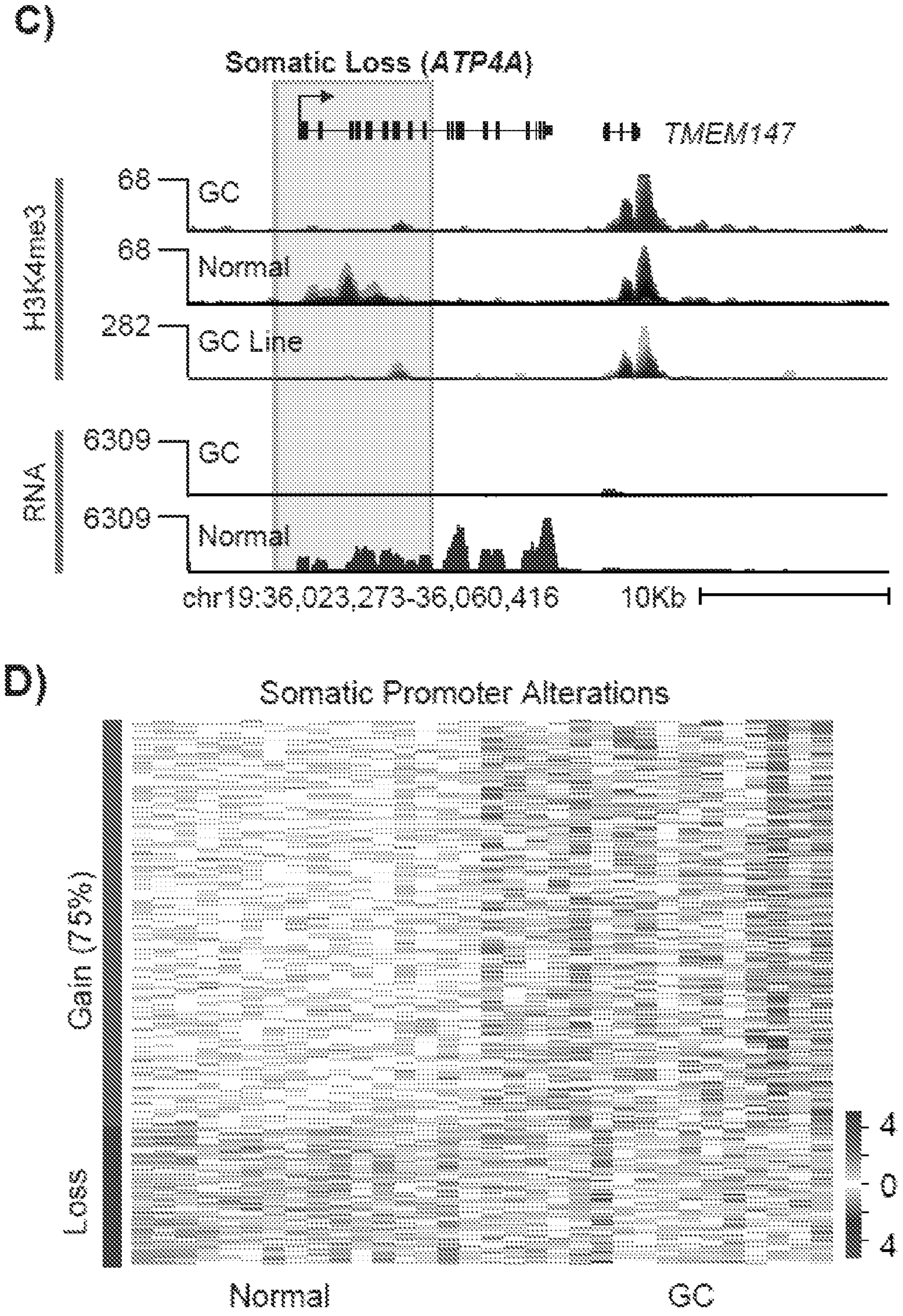
Figure 1:
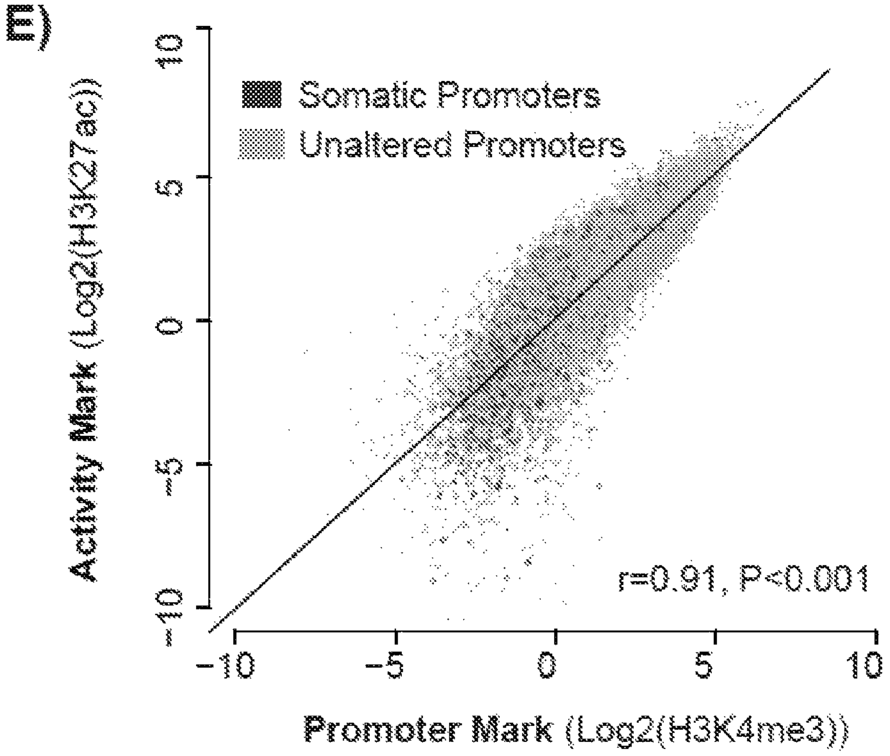
Figure 1:
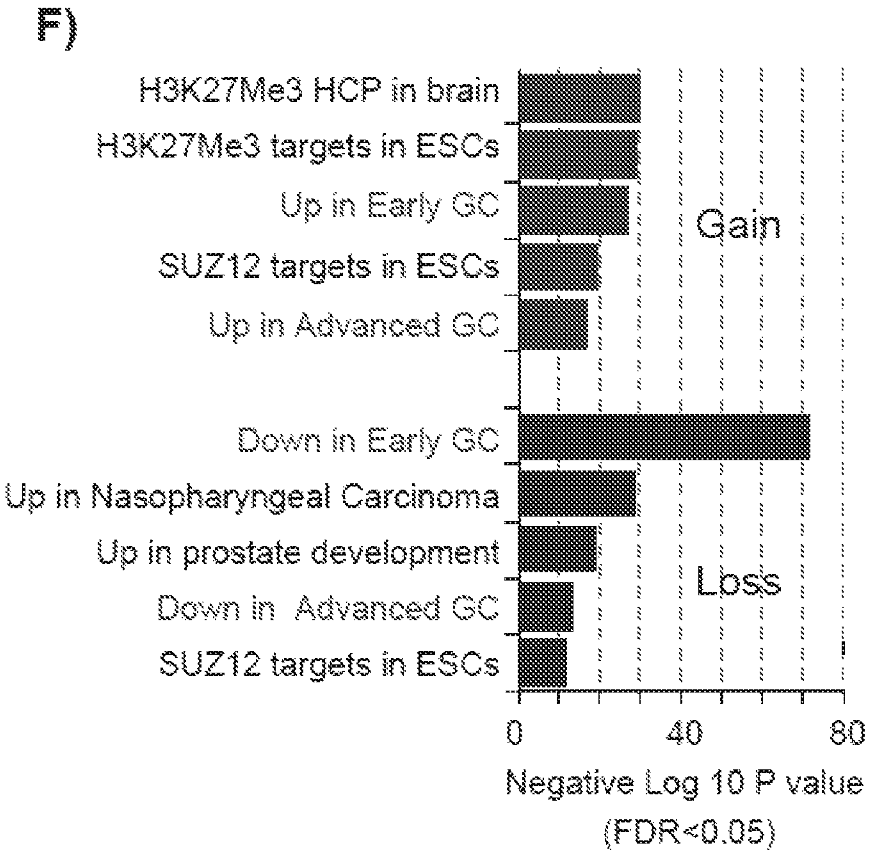

F) Enrichment analysis of somatic promoters at varying fold change and FDR (q value) for top 5 genesets (FIG. 1F) associated with gained (red) and lost somatic promoters (blue). X axis reflects the −log 10 p value for gene-sets found to be enriched in subsets of somatic promoters. Even at stricter fold change (FC 2) and q-value thresholds (0.05, 0.01 and 0.001), similar GC specific and PRC2 associated signatures are still observed.

Figure 10:
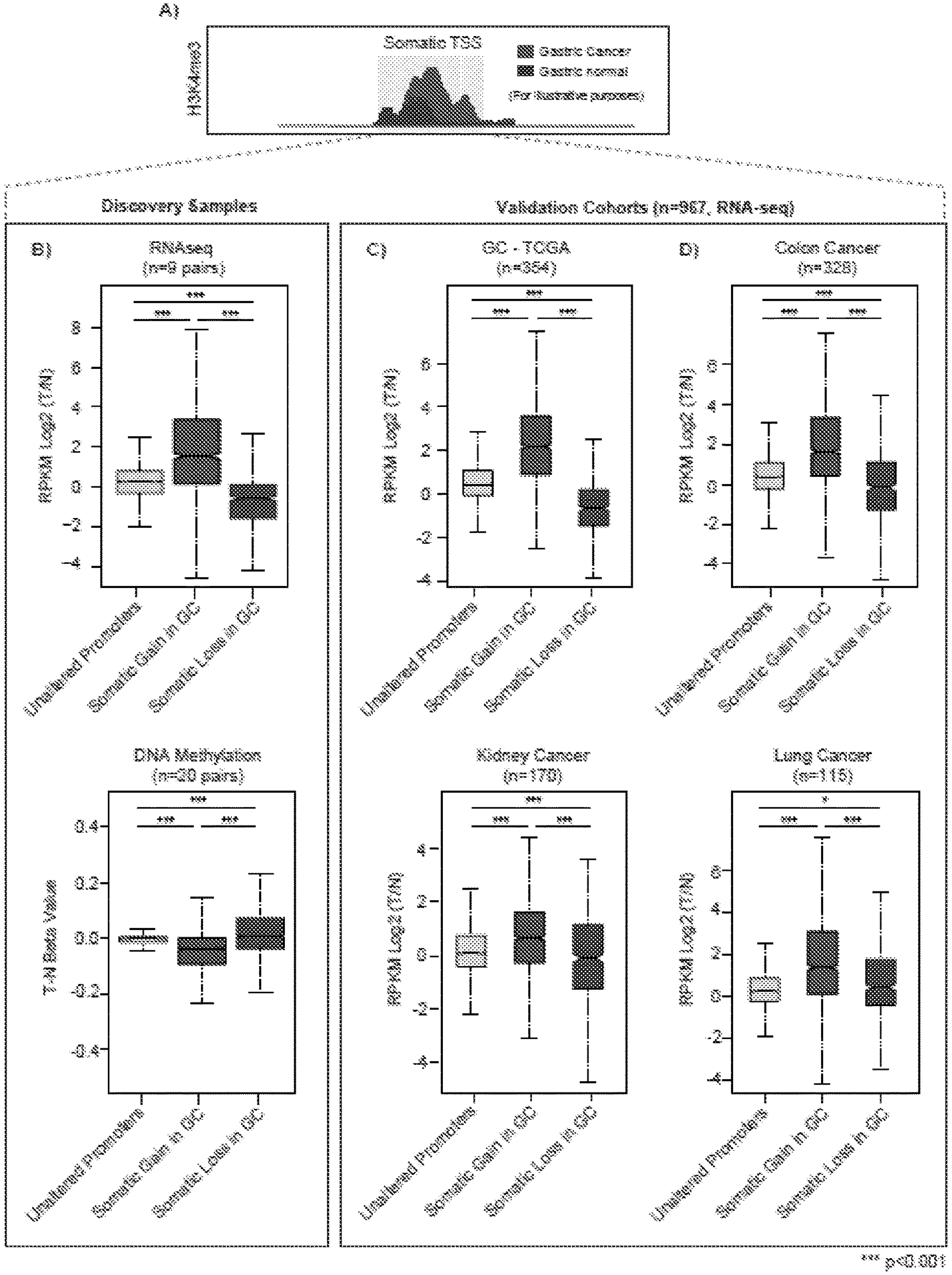

FIG. 10: Association of Somatic Promoters with Gene Expression in GC and Other Tumor Types A) Example of a GC somatic promoter. Example is for illustrative purposes only.

B) Changes in RNA-seq expression (top) and DNA methylation (bottom) discovery samples between somatic promoters and unaltered promoters. Top—Boxplot depicting changes in RNA-seq expression between 9 paired primary GC and gastric normal samples at genomic regions exhibiting somatic promoters (gained and lost) (*P<0.001, Wilcoxon Test). Bottom—Boxplot depicting changes in DNA methylation (β-values) at regions exhibiting somatic promoters between 20 paired GC and gastric normal samples, compared to unaltered promoters (*P<0.001, Wilcoxon test)

C) Independent Validation Cohorts. Boxplot depicting changes in RNA-seq expression at genomic regions exhibiting somatic promoters across 354 (321 GC, 33 normal) TCGA Stomach adenocarcinoma (STAD) samples, compared to unaltered promoters (***P<0.001, Wilcoxon test)

D) Somatic Promoters in Other Cancer Types. Boxplot depicting changes in RNA-seq expression at genomic regions exhibiting GC somatic promoters compared to unaltered promoters, across 328 TCGA Colon adenocarcinoma (COAD) samples (286 COAD, 40 normal; *P<0.001, Wilcoxon test), 170 TCGA kidney renal clear cell carcinoma (ccRCC) samples (98 ccRCC and 72 normal; *P<0.001, Wilcoxon test), and 115 TCGA lung adenocarcinoma (LUAD) samples (58 LUAD, 57 normal; ***P<0.001 Somatic gain vs unaltered and somatic gain vs somatic loss, *P<0.05 Somatic loss vs unaltered, Wilcoxon test).

Figure 11:
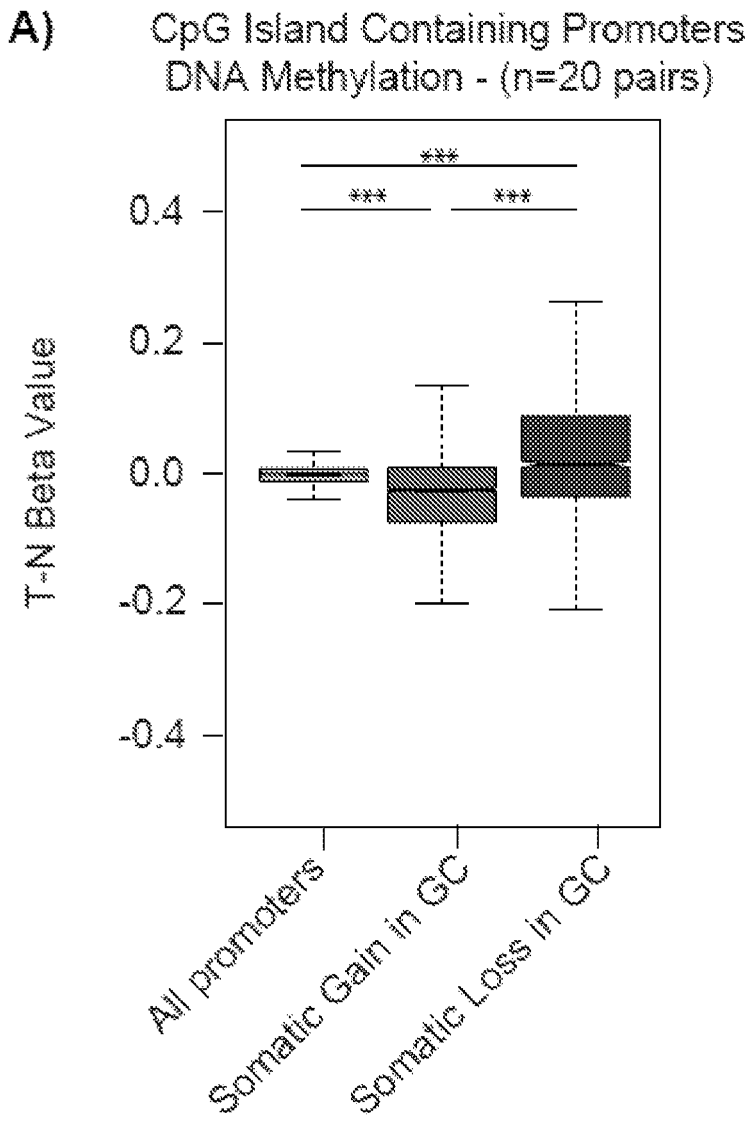

FIG. 11: Changes in DNA methylation at CpG island containing promoters

A) Boxplot depicting changes in DNA methylation (β-values) at CpG island bearing somatic promoters between 20 paired GC and gastric normal samples, compared to all promoters bearing CpG islands (**P<0.001, Wilcoxon test)

Figure 12:
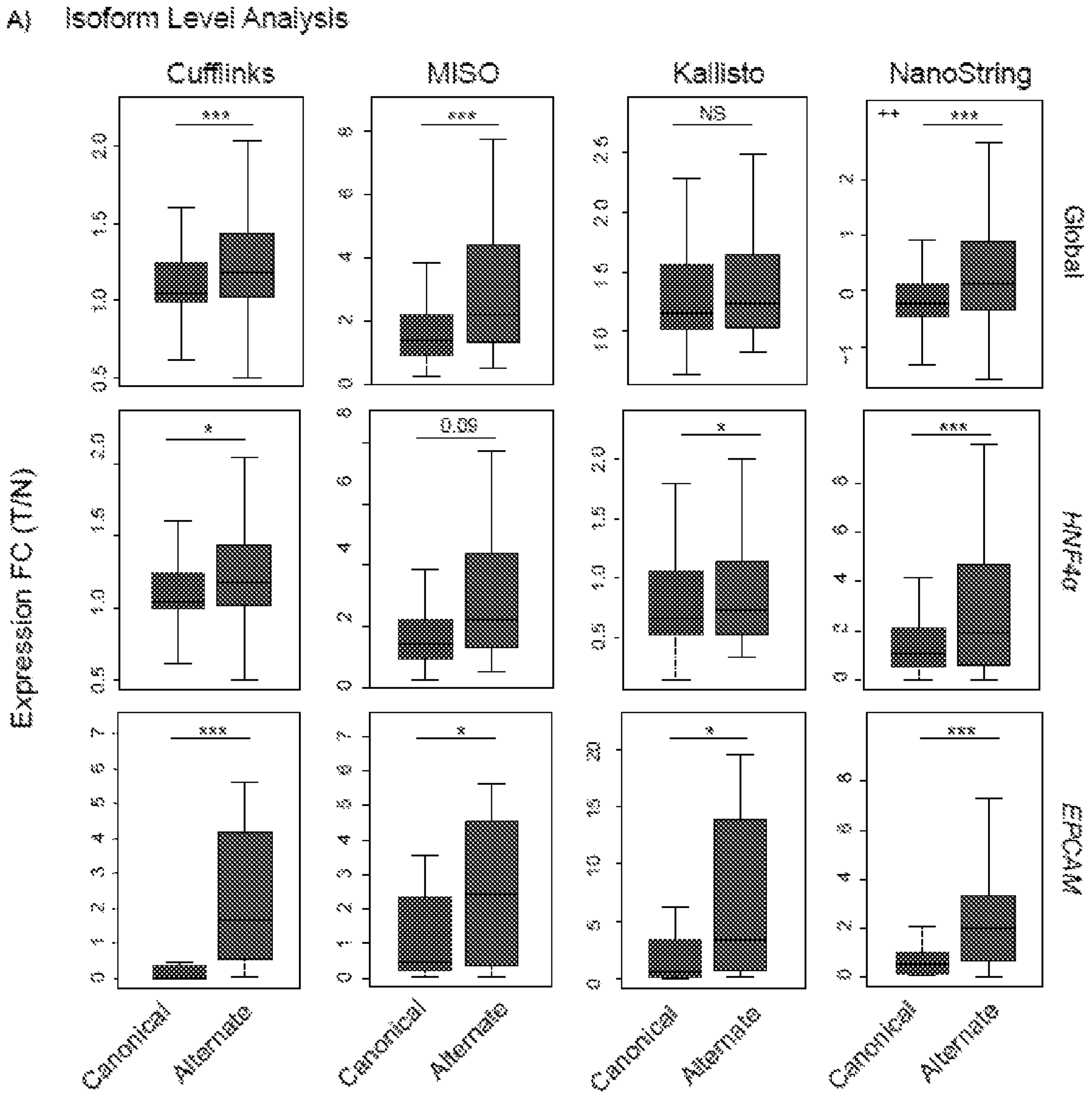
Figure 12:
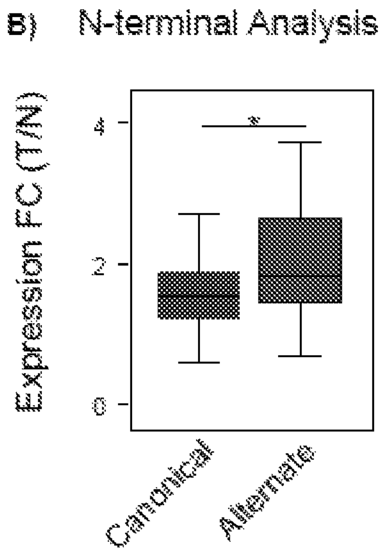

FIG. 12: Expression distribution of alternative and canonical isoforms

A) Barplot showing distribution of T/N ratios of canonical and alternative transcript isoforms for all alternative transcripts (Global—top), HNF4α (middle), and EPCAM (bottom) using four independent quantification techniques, Cufflinks, MISO, Kallisto and NanoString. The Nanostring platform is introduced in FIG. 4 of the Main Text. ++ Nanostring analysis is confined to queried probes. (*P<0.05, P<0.01, *P<0.001, Wilcoxon one sided test).

B) Boxplot showing the T/N ratio of N-terminal reads mapping to canonical promoters, compared to N-terminal reads mapping to alternative promoters. Alternative promoter driven transcripts exhibit significantly higher T/N ratios (p=0.04, Wilcoxon one sided test).

Figure 13:
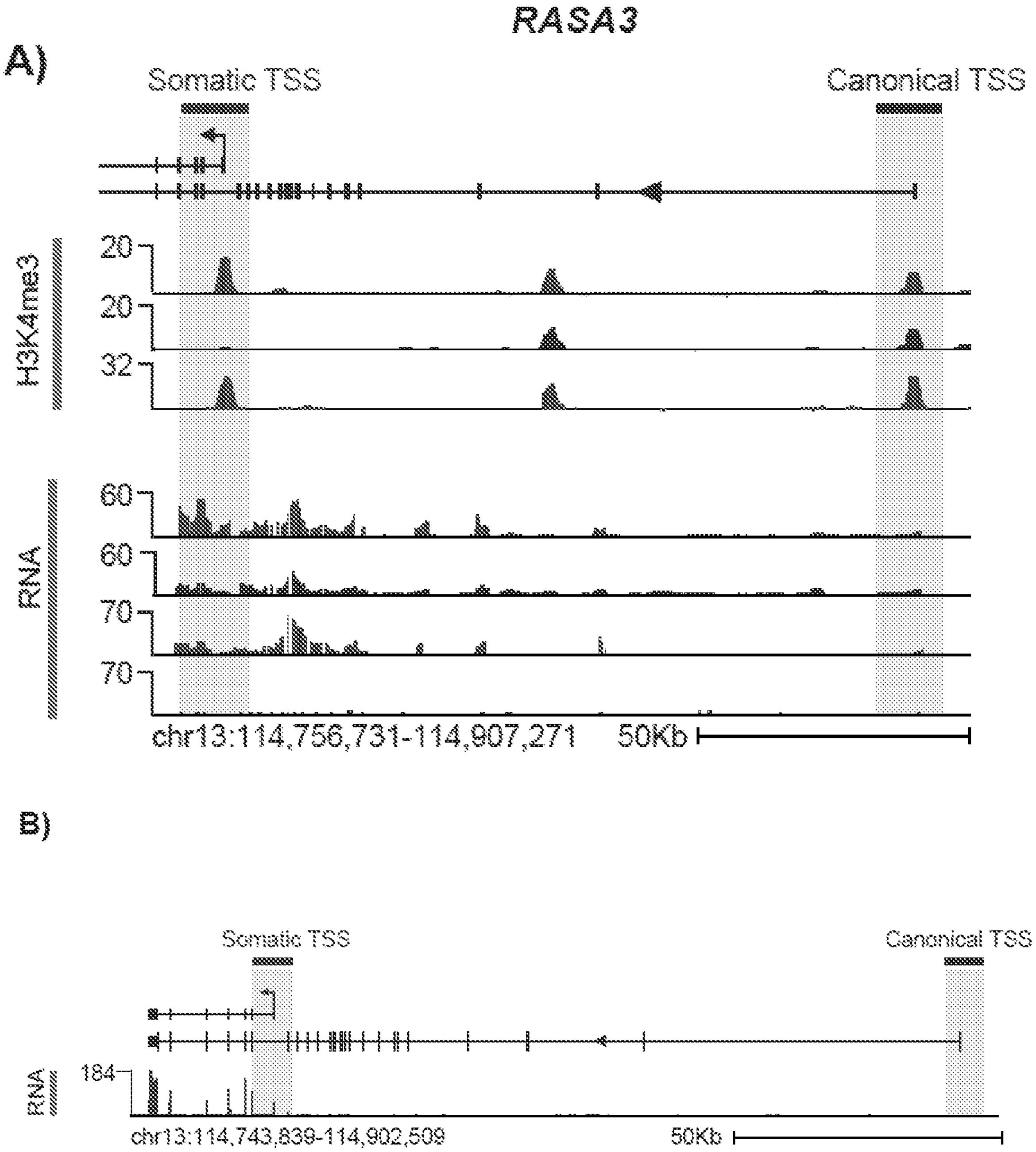
Figure 13:
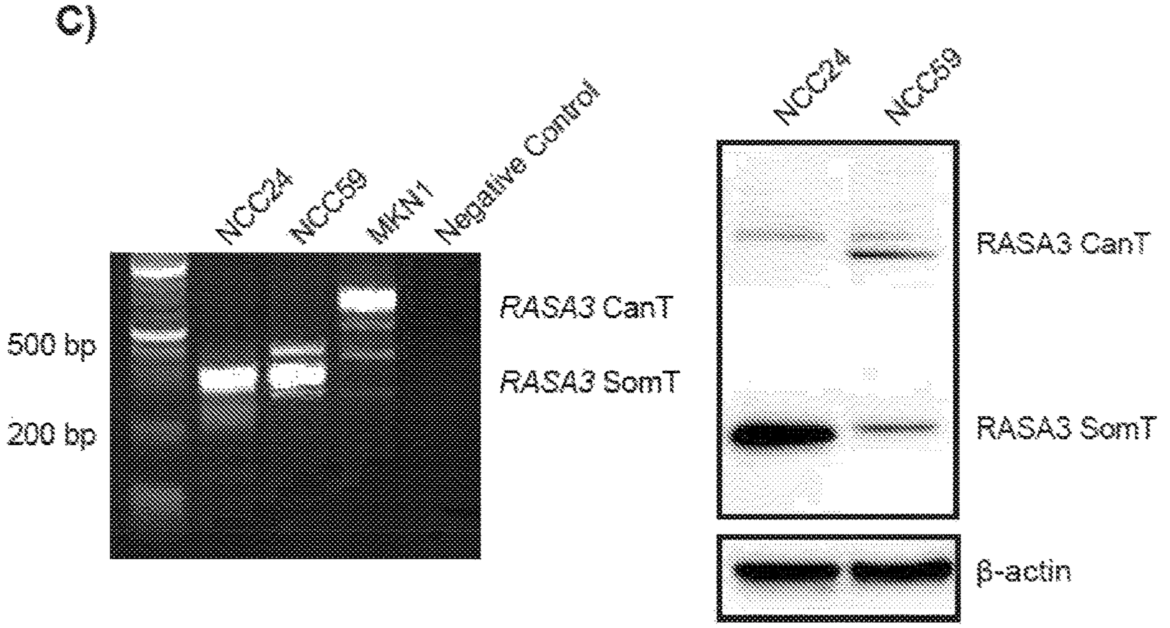
Figure 13:
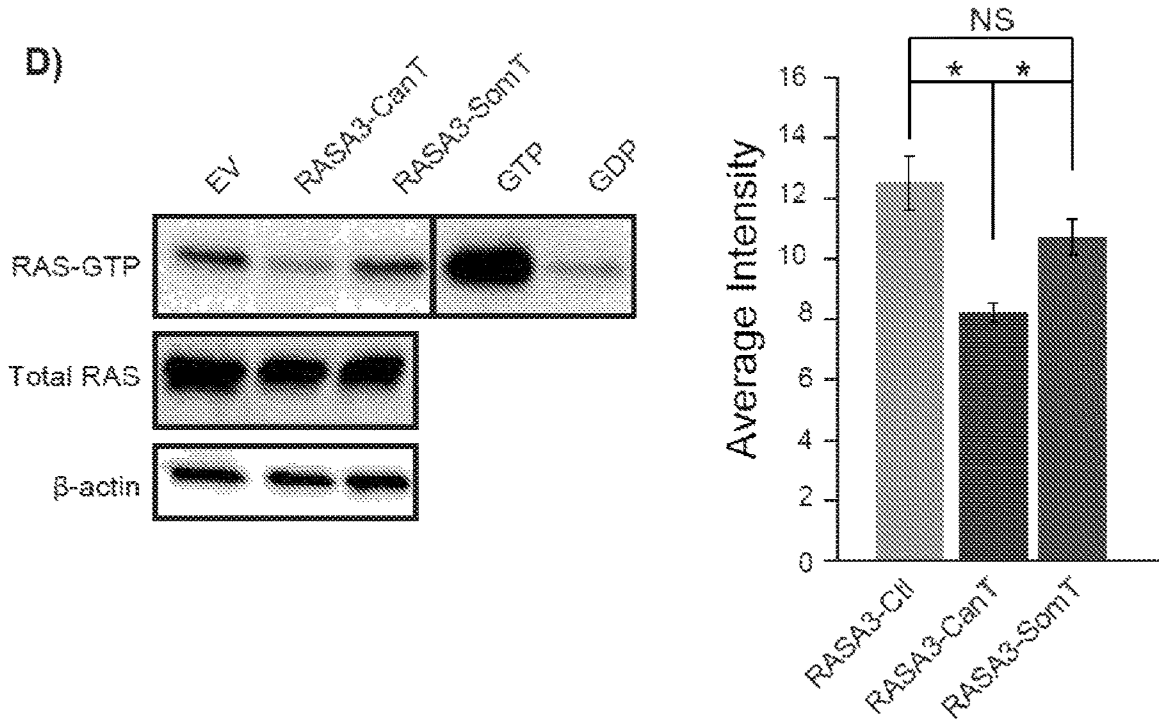
Figure 13:
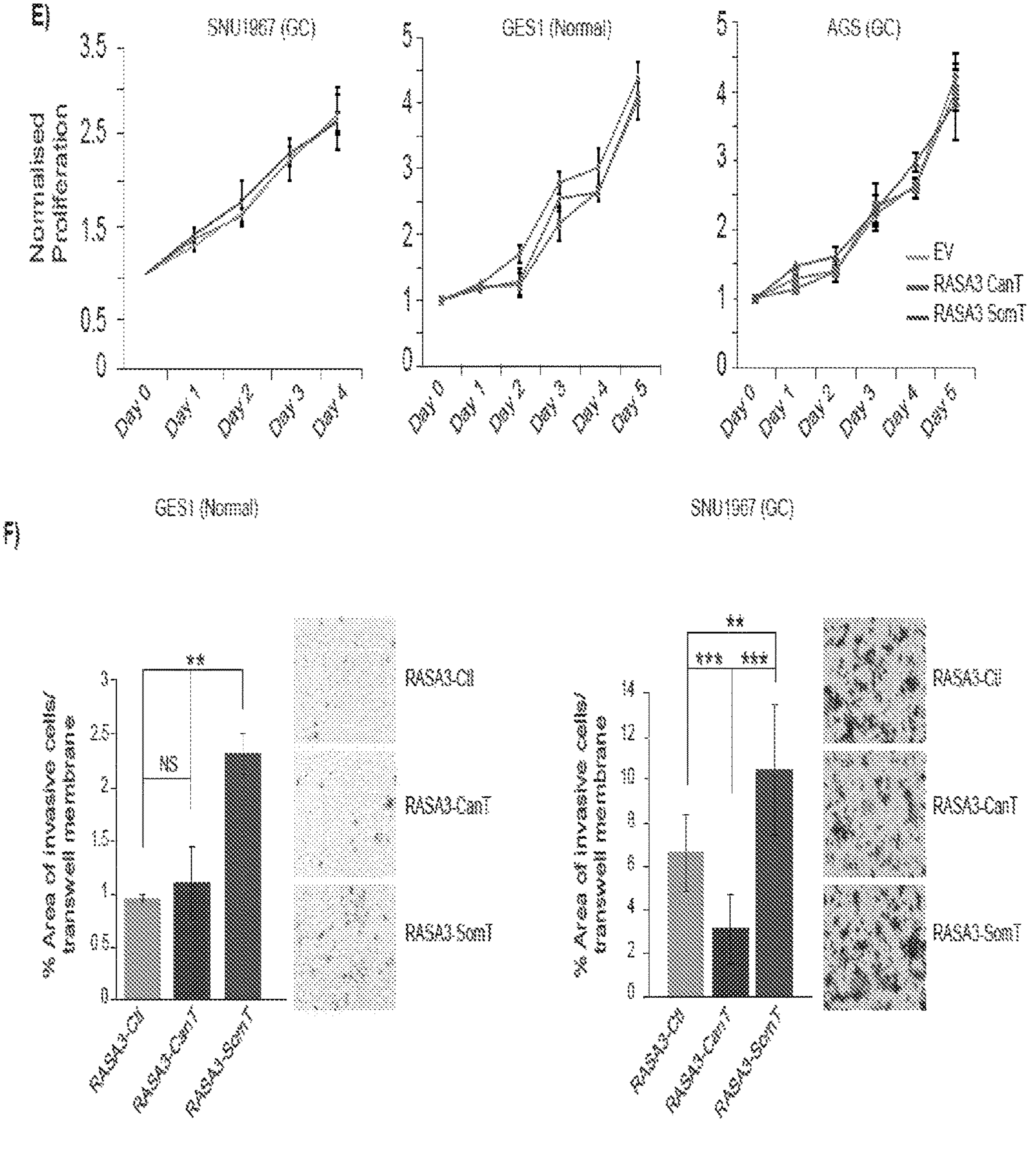
Figure 13:
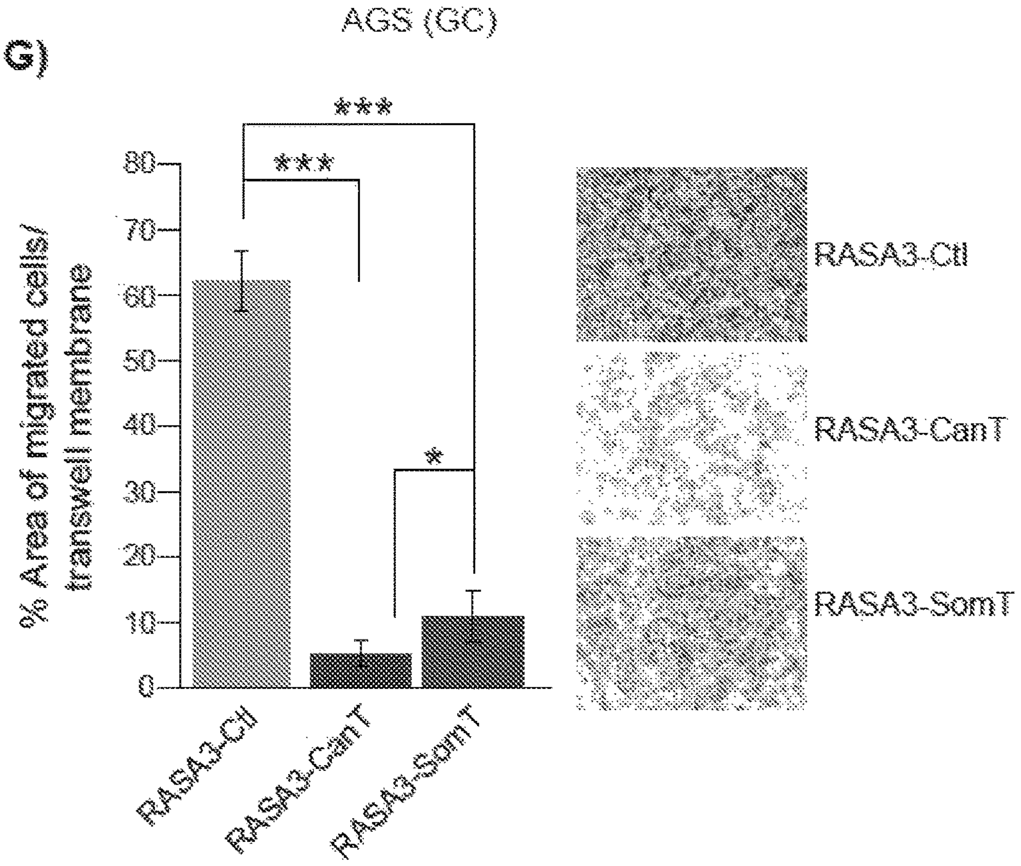
Figure 13:
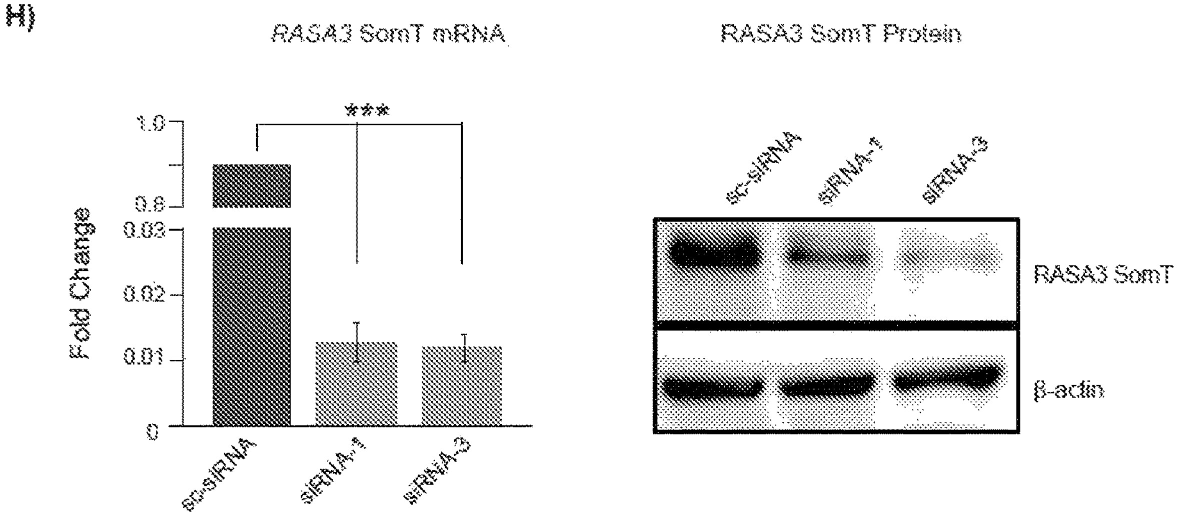
Figure 13:
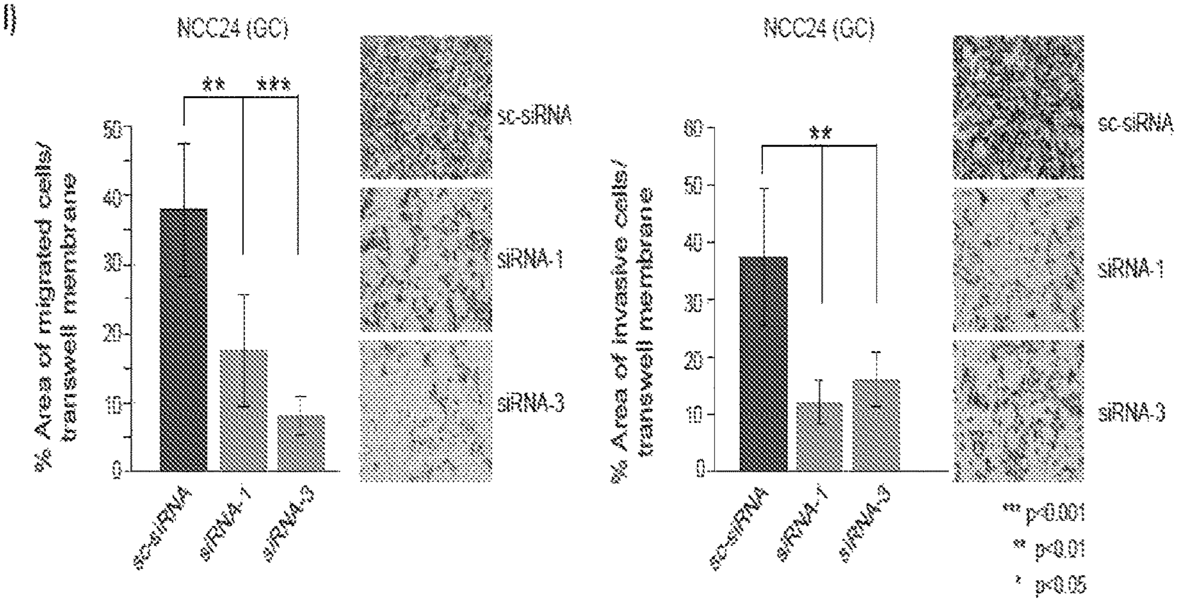

FIG. 13: Characterization of RASA3 Isoform

A) UCSC browser track of the RASA3 gene demonstrating H3K4me3 and RNA-seq signals at Somatic and Canonical TSSs. The Canonical TSS has equal signals while the Somatic TSS shows gain of promoter activity at an unannotated TSS corresponding to a novel N-terminal truncated RASA3 transcript.

B) UCSC browser track of the RASA3 gene demonstrating RNA-seq signals for the NCC24 GC cell line at Somatic and Canonical TSSs. NCC24 only expresses RASA3 SomT (also see C).

C) Left-Identification of RASA3 SomT and CanT transcripts in NCC24 and NCC59 GC cells by 5'RACE. A third line (MKN1), was negative for RASA3 SomT as shown in the gel picture. A no-RNA template was run as a negative control. Right-Western Blot highlighting expression of RASA3 SomT protein in NCC24 cells.

D) RAS GTP assays. (left) The Western blot shows levels of RAS in GES1 cells transfected with either empty vector (EV), RASA3 CanT or RASA3 SomT (n=3). GES1 cells were serum-starved overnight followed by serum stimulation for 30 minutes prior to harvest and a RAS-GTP pull down assay. Total RAS was measured in corresponding whole cell protein lysates. β-actin was used as a loading control. Positive (GTP) and negative (GDP) controls from the pull down assay are also shown. (right) The barplot quantifies active RAS intensity from three independent pull-down assays, performed in GES1 cells transfected with either empty vector (EV), RASA3 CanT or RASA3 SomT under FBS exposed conditions. Data is shown as mean±SD; n=3. (*P<0.05, Student's two sided t-test).

E) Cell proliferation assays of SNU1967, GES1 and AGS cells after transfection with RASA3 CanT and SomT normalized to Day 0. (Data is shown as mean±SD performed in triplicate, representative of 3 independent experiments).

F) Effect of overexpression of RASA3 CanT and SomT isoforms on the invasive capability of GES1 and SNU1967 cells. Representative images of EV, RASA3-WT and RASA3-Var in invasion assay (n=3). Barplot showing % area of invaded cells vs the area of transwell membrane. Data is shown as mean±SD; n=3. (*P<0.05, P<0.01, *P<0.001, Student's one sided t-test).

G) Effect of overexpression of RASA3 CanT and SomT protein isoforms on the migration capability of highly migratory KRAS mutated AGS cells. Barplot showing % area of migrated cells vs the area of transwell membrane. Data is shown as mean±SD; n=3. (*P<0.05, P<0.01, *P<0.001, Student's one sided t-test). RASA3 WT induces more potent migration suppression than RASA3 Var, suggesting that RASA3 WT is a migration inhibitor.

H) siRNA-mediated knockdown of RASA3 SomT in NCC24 cells. Cells were treated with sc-siRNA (control) and 2 RASA3 siRNAs (siRNA1—hs.Ri.RASA3.13 TriFECTa® Kit DsiRNA and siRNA-3—Silencer® Select Pre-Designed siRNA s355). (Left) Barplots showing fold change differences in mRNA expression of RASA3 SomT after treatment with siRNA-1 and siRNA-3. Data is shown as mean±SD; n=3. (Right) Western blotting results confirming RASA3 SomT protein reductions. Cells were harvested and lysed after 48 hrs of transfection. (***P<0.001, Student's one sided t-test).

I) Effect of siRNA knockdown of RASA3 SomT isoform on the migration (left) and invasive (right) capability of NCC24 cells from two independent siRNAs. Representative images of sc-siRNA (control), siRNA-1, and siRNA-3 in migration and invasion assays (n=3). Barplot showing % area of migrated/invaded cells vs the area of transwell membrane. Data is shown as mean±SD; n=3. (*P<0.05, P<0.01, *P<0.001, Student's one sided t-test).

Figure 14:
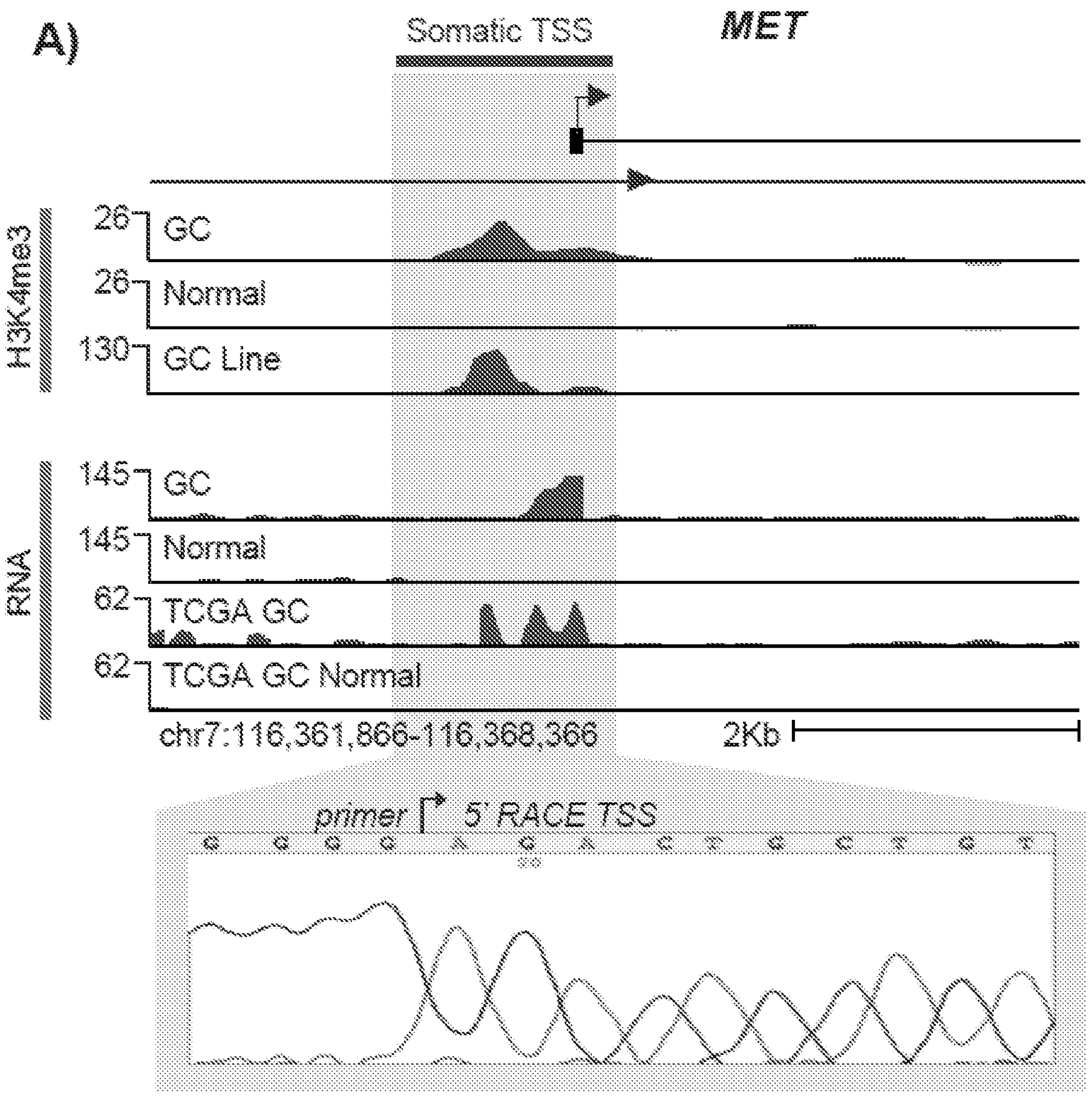
Figure 14:
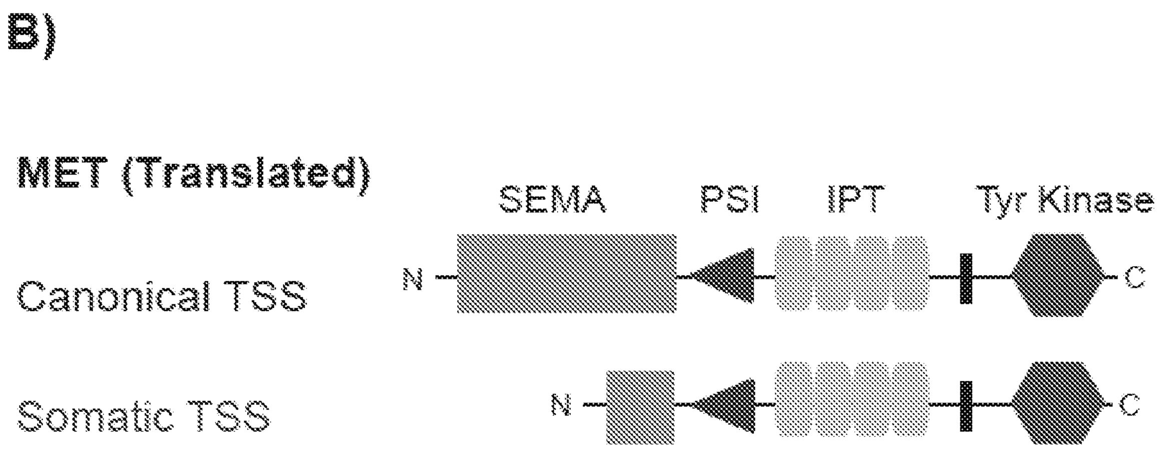
Figure 14:
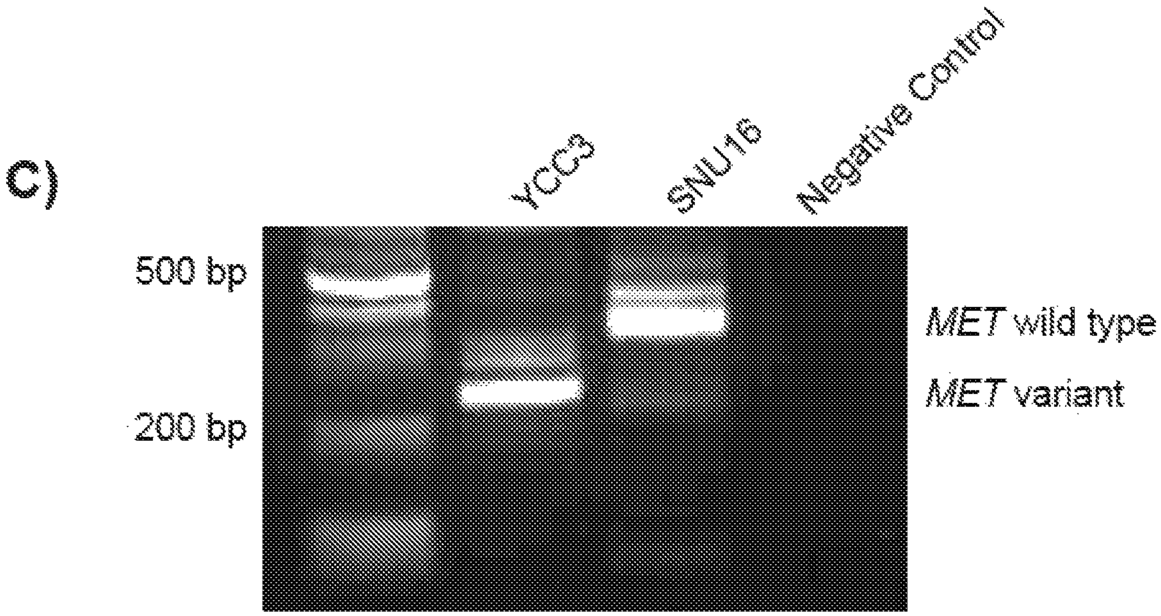
Figure 14:
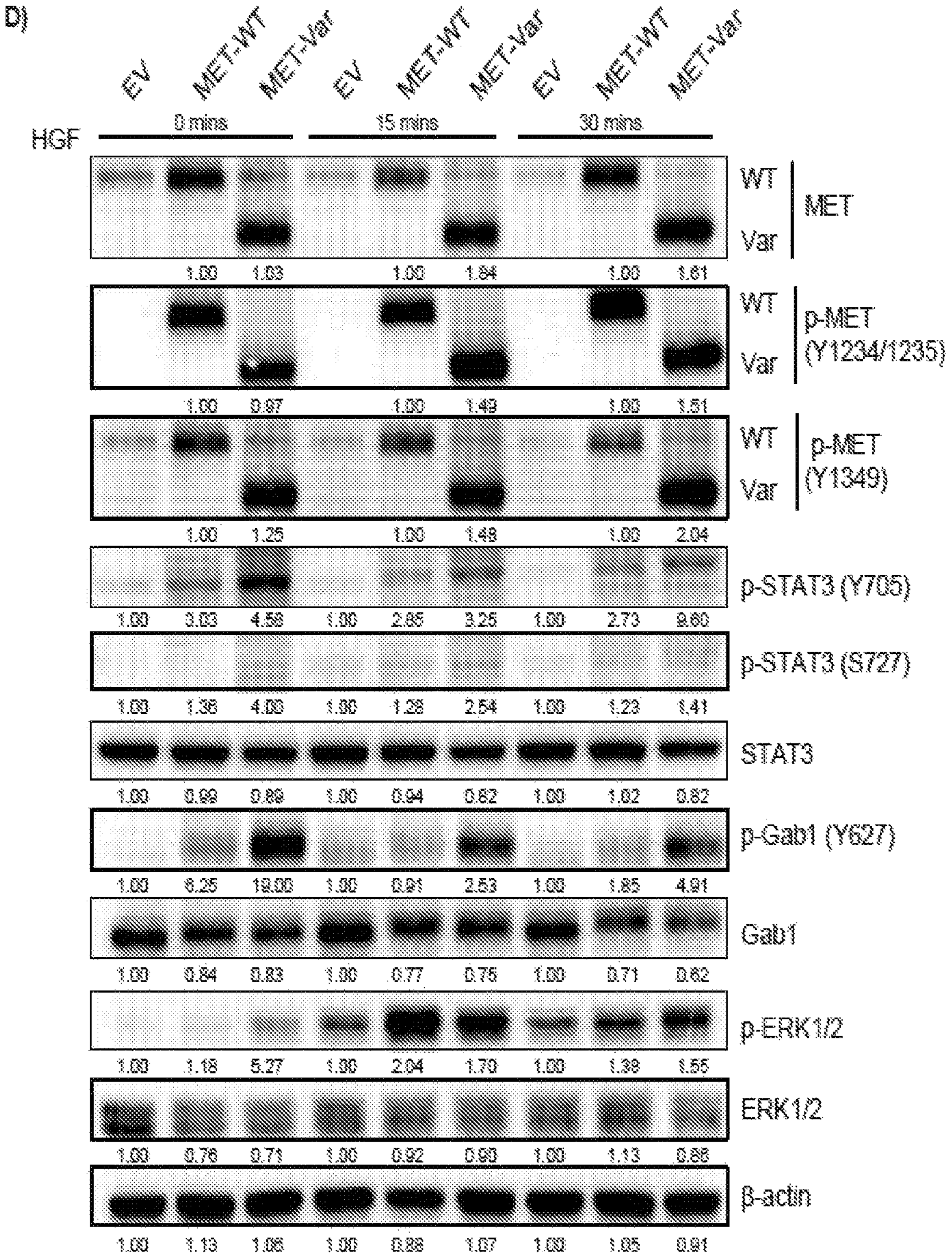
Figure 14:
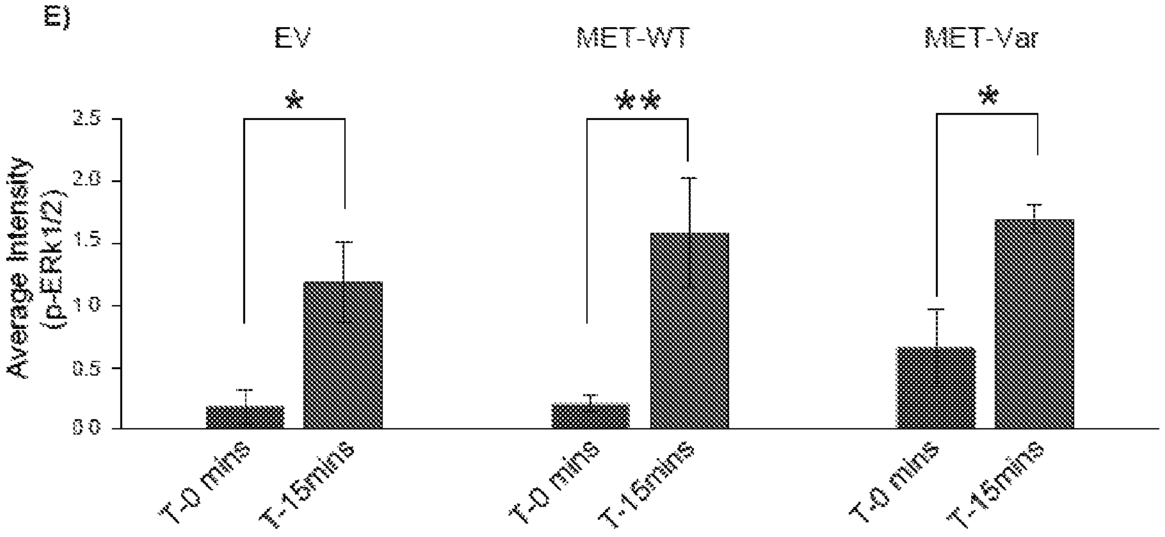
Figure 14:
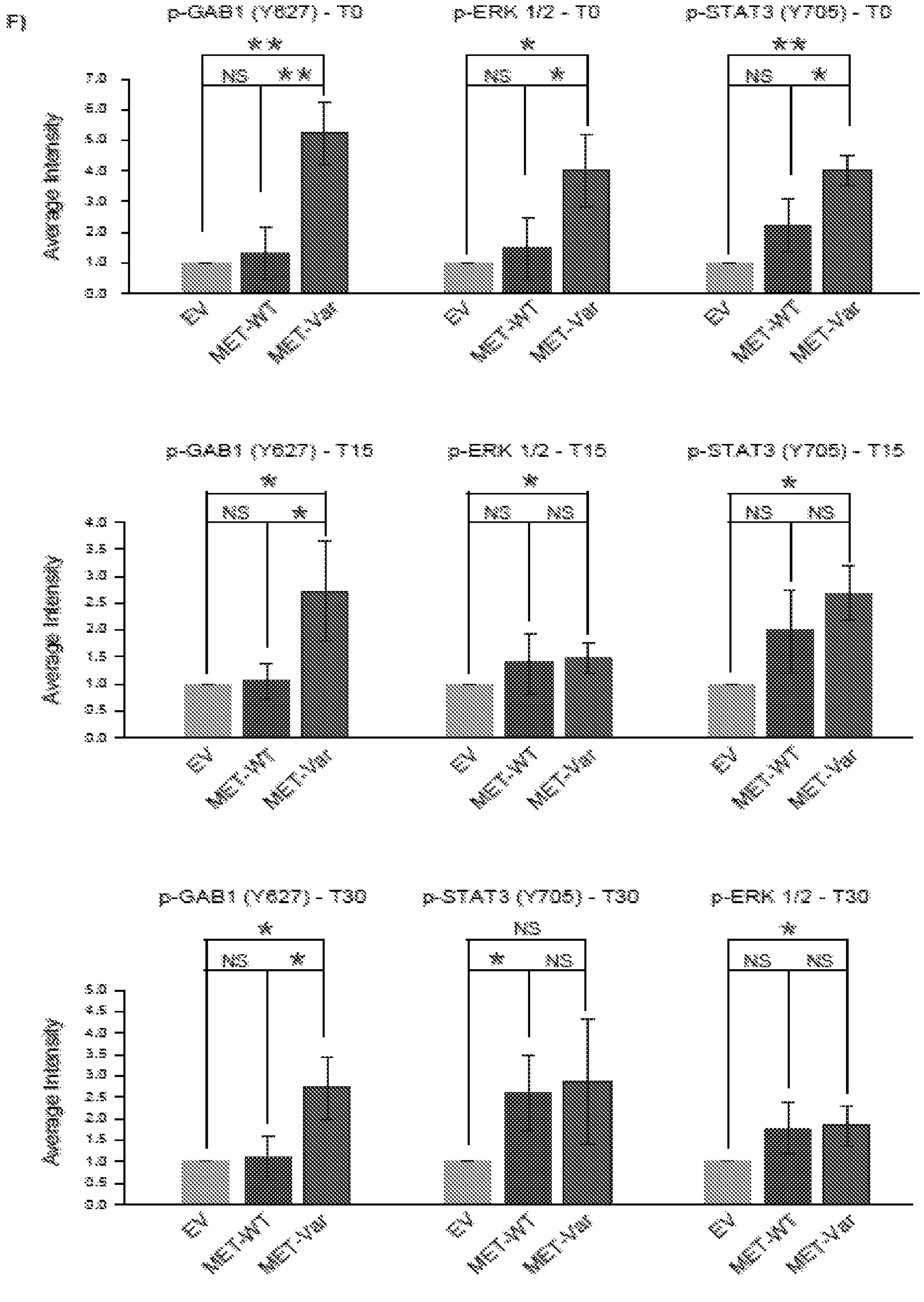

FIG. 14: Characterization of MET Isoforms

A) UCSC browser track of the MET gene, demonstrating H3K4me3 and RNA-seq signals highlighting gain of promoter activity at an alternative downstream locus (dark grey box).

B) Functional domains of the MET canonical (WT) and alternative (Var) isoform. The alternative isoform is predicted to encode a MET protein with an N terminally truncated SEMA domain.

C) Expression of MET (Var) transcripts in GC lines, as detected by 5'RACE.

D) Western blot of HEK293 cells transfected with empty vector (EV), MET canonical full length (MET-WT) and truncated Variant (MET-Var) at 0, 15 and 30 minutes of HGF treatment (100 ng/ml) (n=3). GAB1, STAT3 and ERK1/2 are known downstream effectors of MET signaling. Number below each band is the quantified intensity using Image Lab. In both untreated and HGF-treated conditions, MET-Var transfected cells exhibited higher levels of p-Gab1 (Y627), a key mediator of MET signaling (2.48-3.95 fold, p=0.003 (untreated), p<0.05 (T15 and T30). In untreated samples, cells transfected with MET-Var also exhibited higher pERK1/2 levels (2.74 fold) and also higher p-STAT3 (Y705) levels (1.80 fold) compared to MET-WT (p=0.023 and p=0.026 for pERK and p-STAT3 (Y705) respectively).

E) Bar graphs showing increase in pERK1/2 for EV, MET-WT and MET-Var at TO, T15 and T30, reflecting effects of HGF treatment. Data is shown as mean±SD; n=3. (*P<0.05, P<0.01, *P<0.001, Student's one sided t-test)

F) Bar graphs showing increase in p-GAB1 (Y627), p-STAT3 (Y705), and pERK1/2 in cells transfected with MET-Var compared to EV and MET-WT. Graphs for all 3 time points are shown. Data is shown as mean±SD; n=3. (*P<0.05, P<0.01, *P<0.001, Student's one sided t-test)

Figure 15:
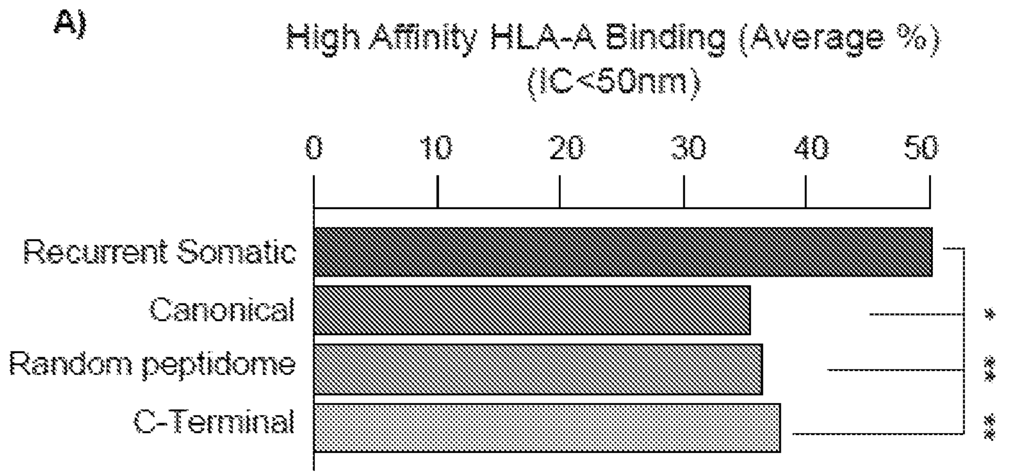
Figure 15:
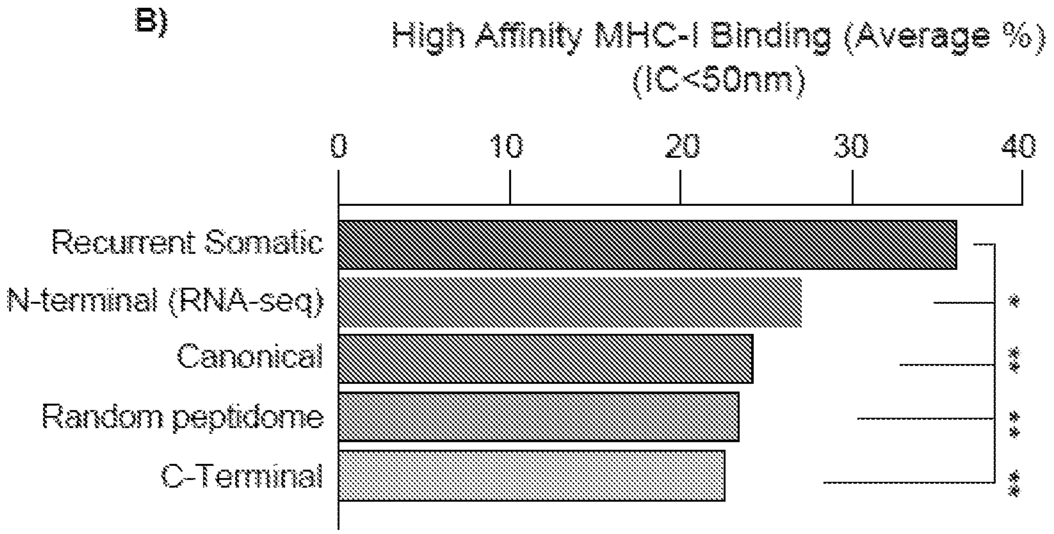

FIG. 15: Immunogenicity of N-terminal peptides

A) Barplot showing average % of N-terminal peptides with predicted high-affinity binding to MHC Class I HLA-A (IC<=50 nm). As comparison, the figure in the Main Text represents average % s based on all three HLA classes (HLA-A, HLA-B, HLA-C). N-terminal peptides associated with recurrent somatic alternative promoters show significantly enriched predicted MHC I binding compared to canonical GC peptides (p<0.01), random peptides from human proteome and C-terminal peptides (p<0.001, Fisher's Test) derived from the same genes exhibiting the N-terminal alterations.

B) MHC Binding Predictions using N-terminal peptides inferred by RNA-seq analysis alone. Annotated transcripts exhibiting different N-terminal exons in GC vs normals were identified using two different RNA-seq algorithms (DEXSeq (7) and Voom-diffsplice(8)) (FC>=2, FDR 0.05). This analysis identified 96 genes with potential alternative N-terminal transcripts, of which 46 (48%) were predicted to result in differing N terminal peptides (Purple bar).

Figure 16:
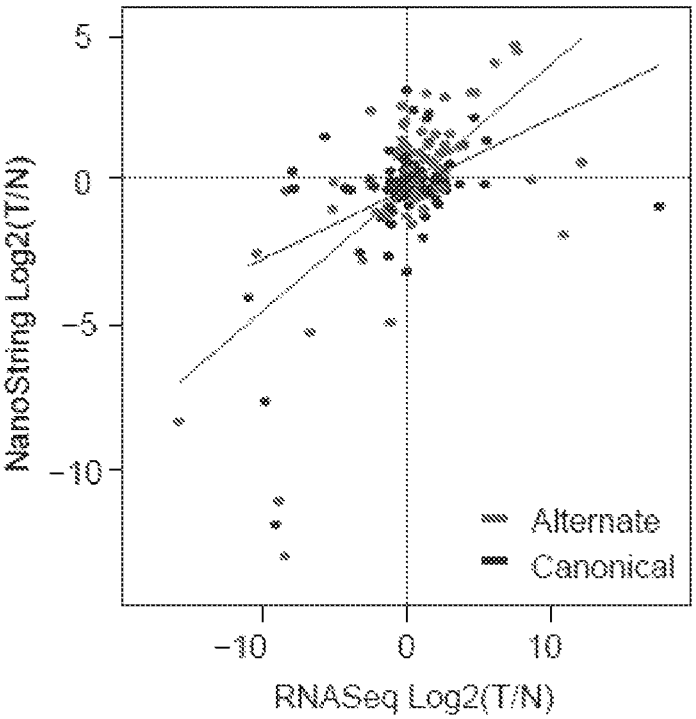
Figure 16:
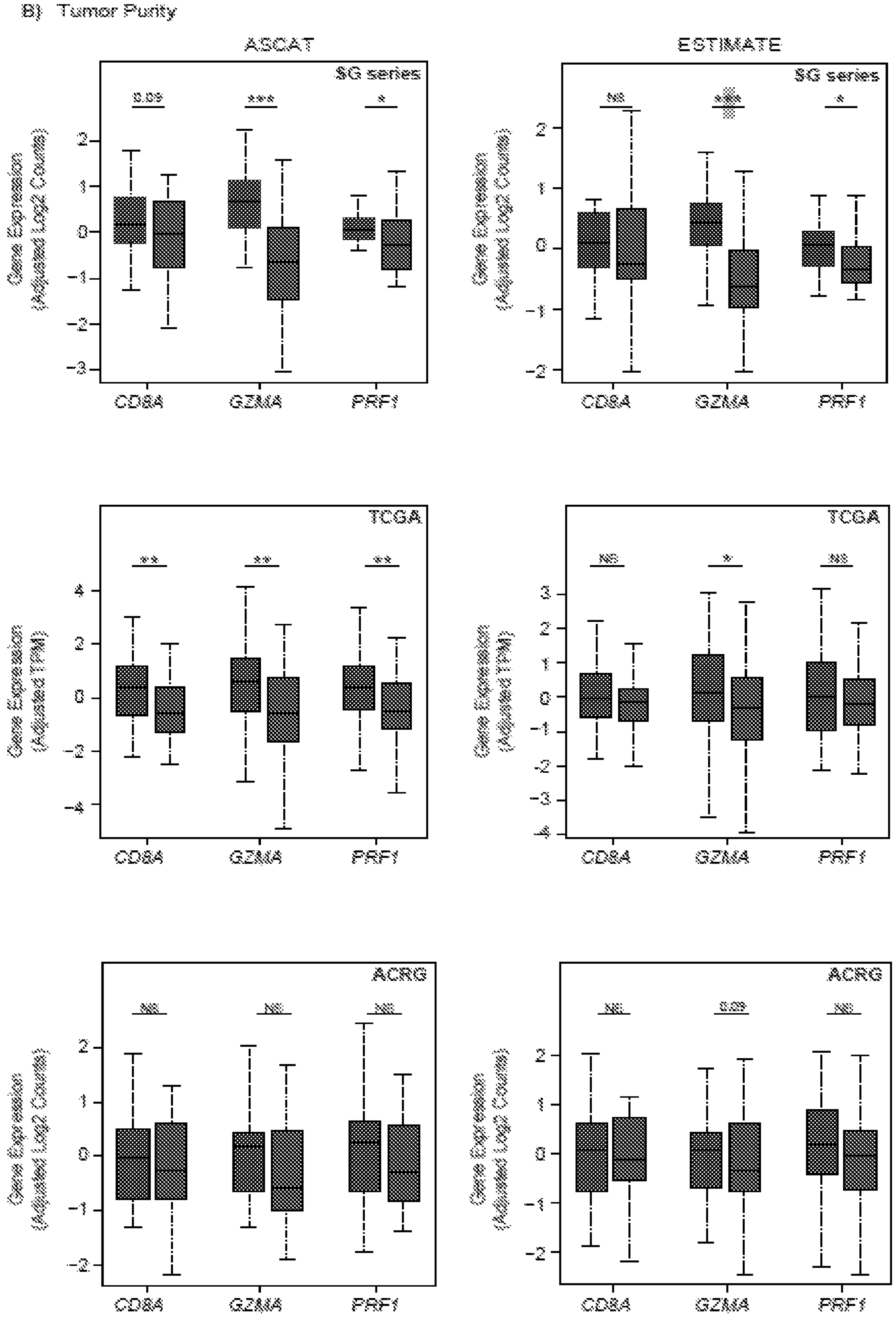
Figure 16:
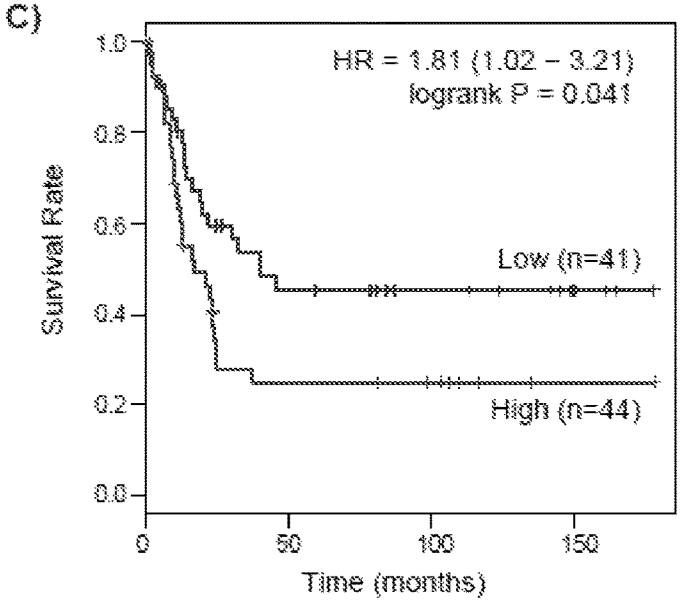
Figure 16:
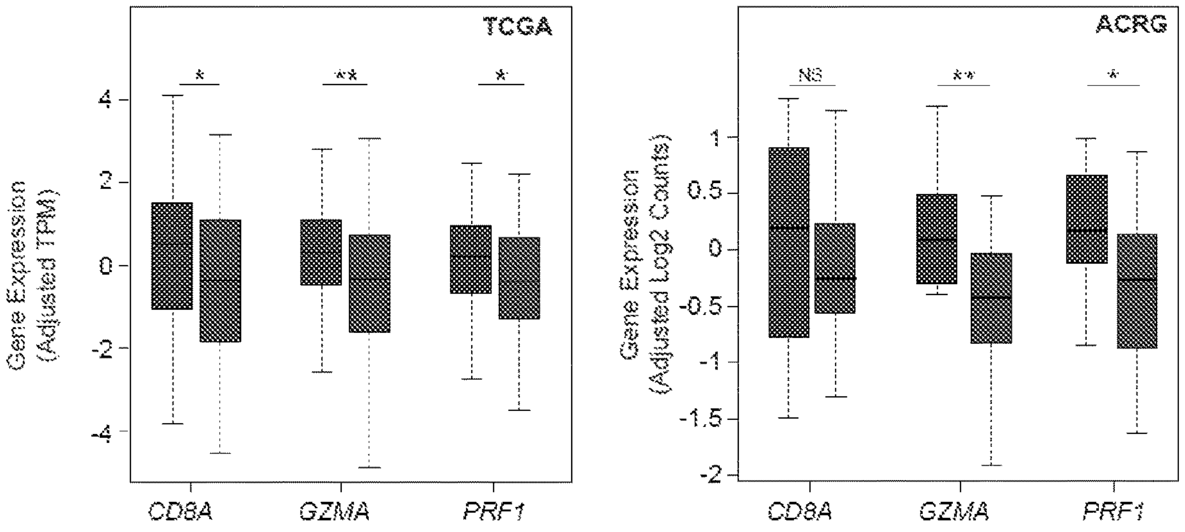
Figure 16:
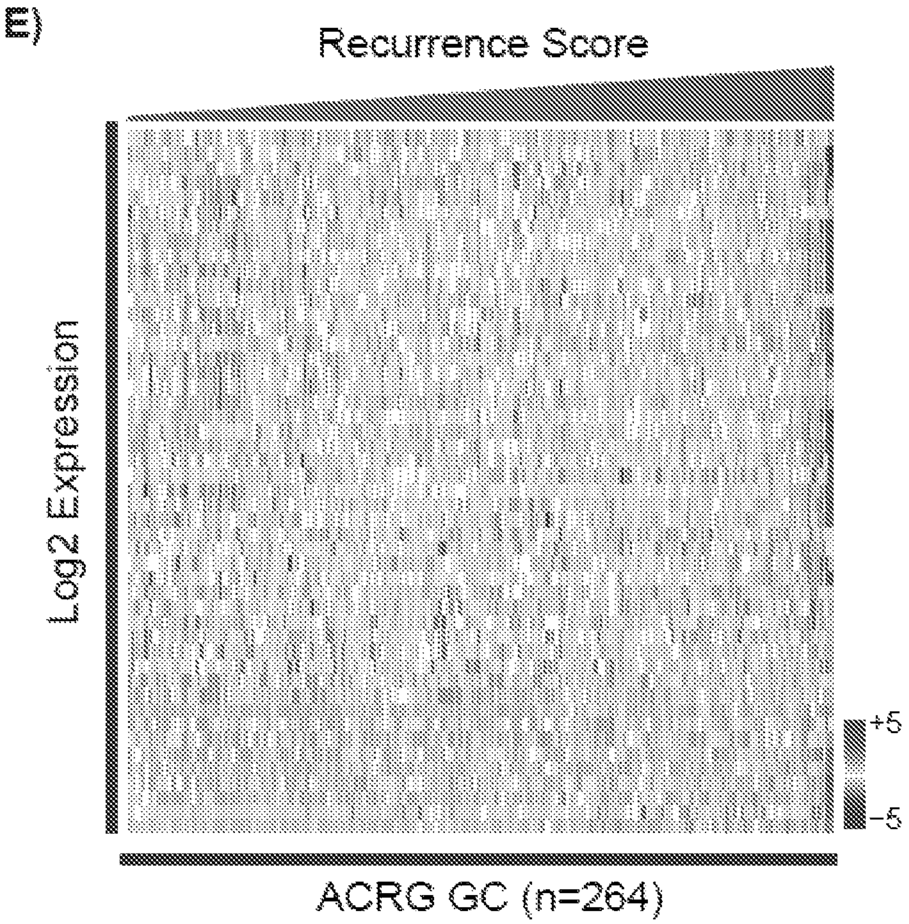

FIG. 16: Immunogenicity Assay and Nanostring Profiling

A) Scatter plot of fold change (T vs N) of expression of alternate and canonical probes from NanoString and RNA-seq data of the same samples. An improved correlation is observed using the alternate probes B) Left-Expression of T-cell markers CD8A, GZMA and PRF1 in SG series (top), TCGA STAD (middle) and ACRG cohort (bottom) with high or low somatic promoter usage after adjustment of tumor purities as estimated by ASCAT. P values (Wilcoxon one sided test) are: CD8A—p=0.09 (SG), 0.004 (TCGA), 0.3 (ACRG); GZMA—0.0001 (SG), 0.002 (TCGA), 0.166 (ACRG), PRF1—0.013 (SG), 0.006 (TCGA), 0.3 (ACRG). Right—Expression of T-cell markers CD8A, GZMA and PRF1 in SG series (top), TCGA STAD (middle) and ACRG cohort (bottom) with high or low somatic promoter usage after adjustment of tumor content as estimated by ESTIMATE. p values (Wilcoxon one sided test) are: CD8A—p=0.28 (SG), 0.17 (TCGA), 0.37 (ACRG), GZMA—0.0005 (SG), 0.03 (TCGA), 0.09 (ACRG), PRF1—0.02 (SG), 0.22 (TCGA), 0.17 (ACRG). Samples with high alternative promoter usage are in red, while those with low usage are in blue.

C) Kaplan-Meier analysis comparing overall survival curves between validation samples with high somatic promoter usage and low somatic promoter usage (split by median) (HR=1.81, P=0.04)

D) Left-Expression of T-cell markers CD8A, GZMA and PRF1 in TCGA STAD with high or low somatic promoter usage after adjustment of mutation burden. P values (Wilcoxon one sided test) are: P=0.02 (CD8A), 0.01 (GZMA) and 0.03 (PRF1). Right—Expression of T-cell markers CD8A, GZMA and PRF1 in ACRG cohort with high or low somatic promoter usage after adjustment of mutation burden. P values (Wilcoxon one sided test) are: P=0.167 (CD8A), 0.009 (GZMA) and 0.03 (PRF1).

E) Heatmap of alternative promoter expression from 264 ACRG GCs for all gained alternative promoters. GC samples have been ordered left to right by their levels of somatic promoter usage.

Figure 17:
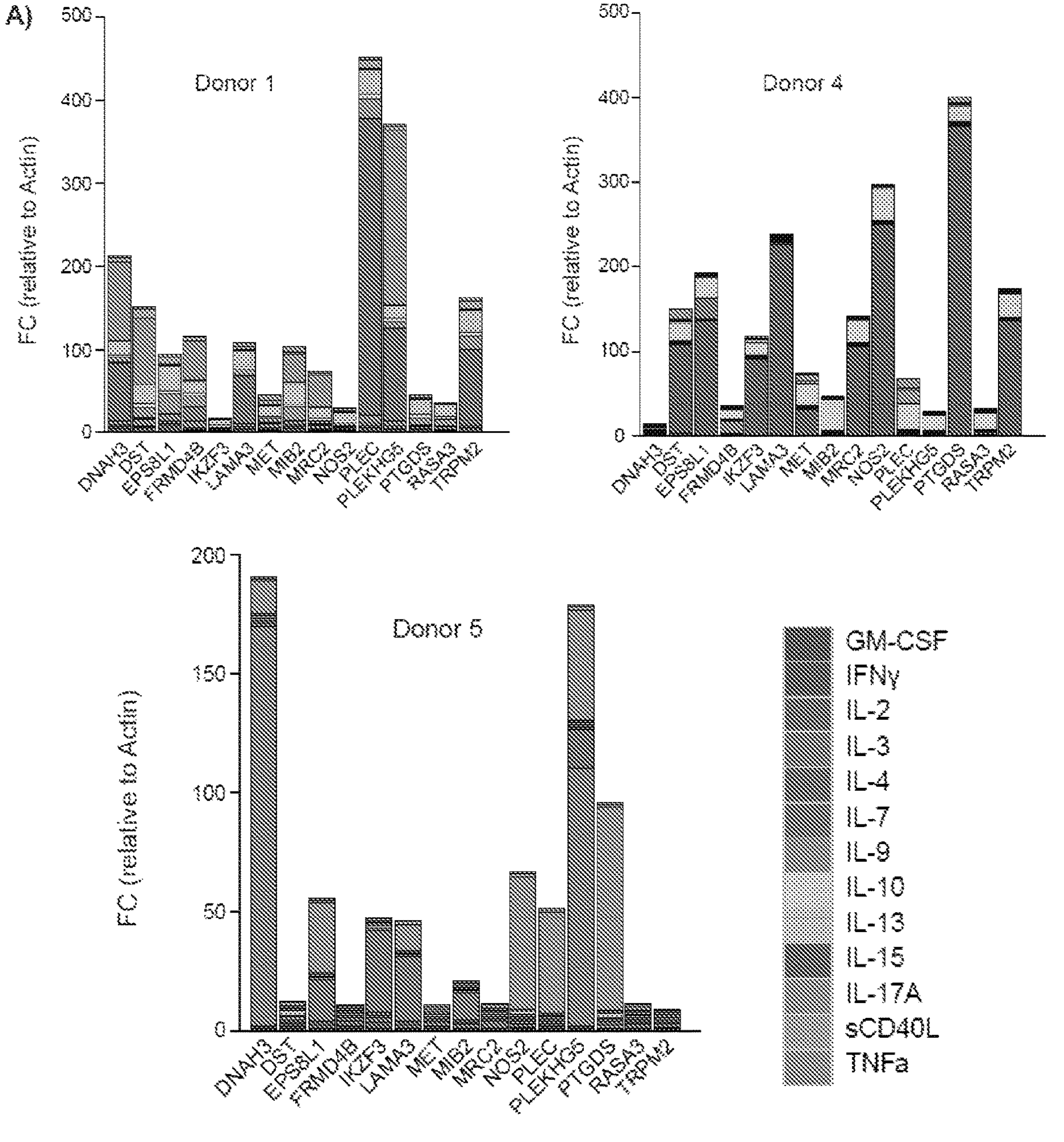
Figure 17:
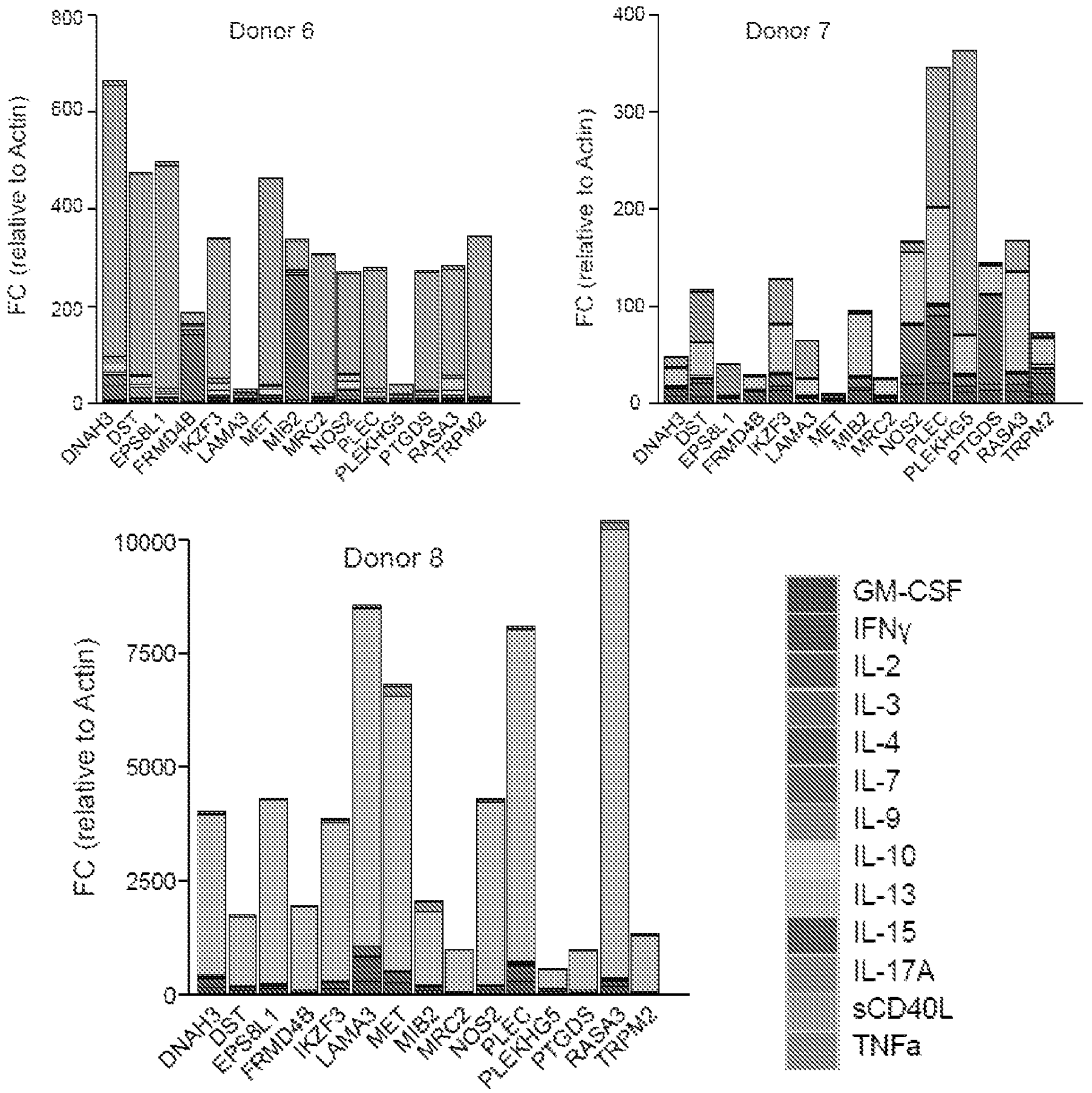
Figure 17:
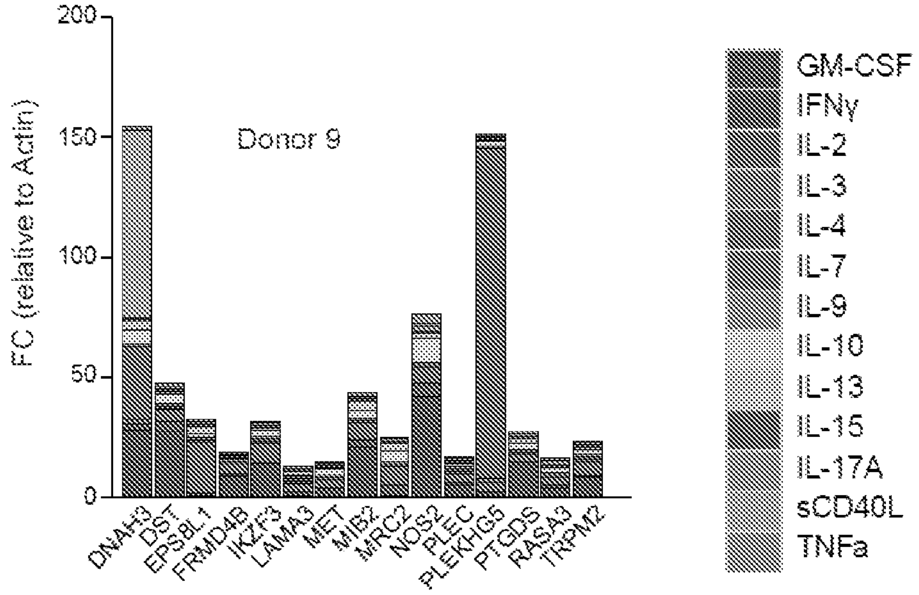
Figure 17:
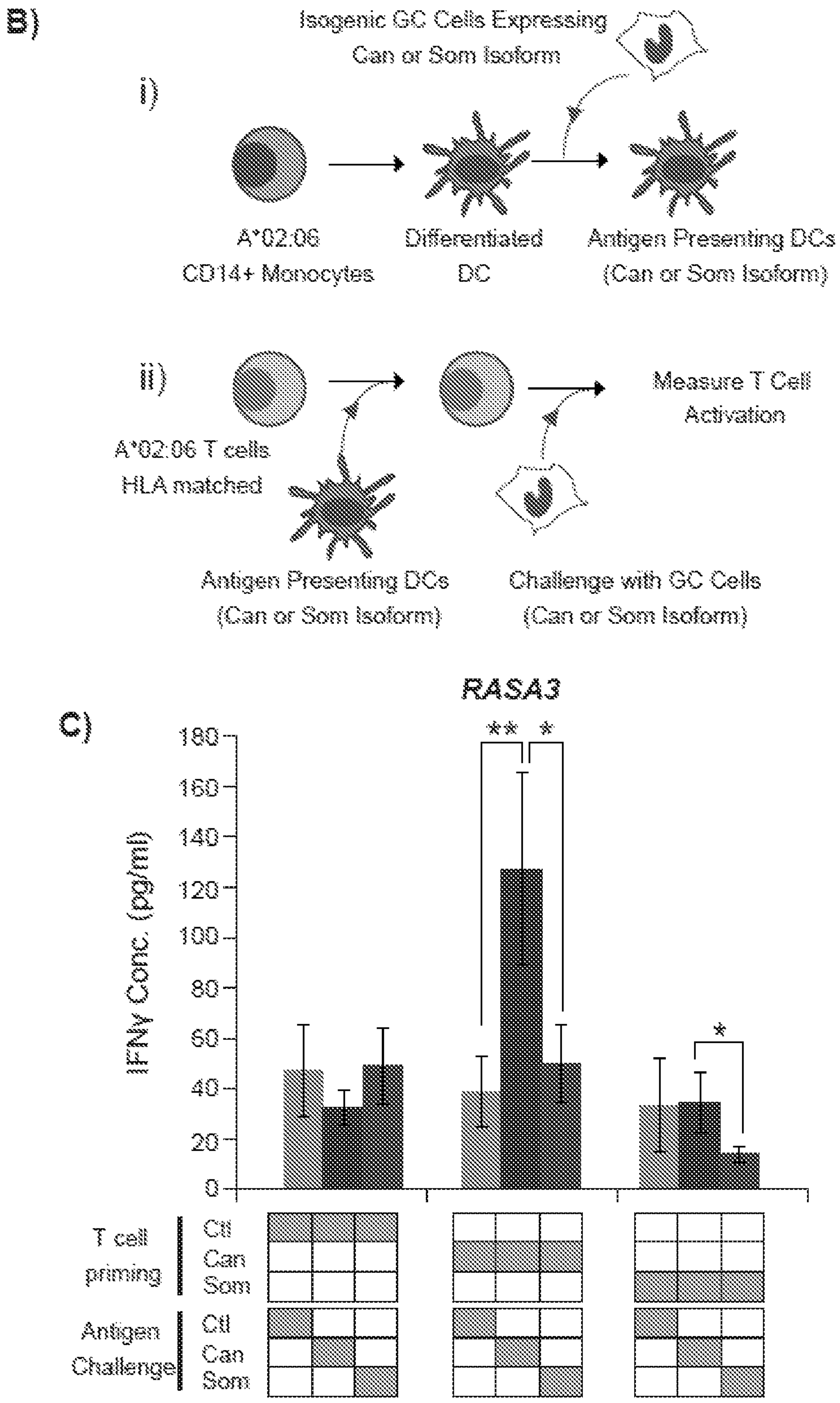

FIG. 17: Functional Assessment of Peptide Immunogenicity

A) Individual cytokine responses against 15 peptides for other normal donor PBMCs tested against different peptide pools.

B) Experimental Immunogenicity Assay. Experimental design of in-vitro assay—i) Immature dendritic cells (DCs) cultured from $CD14^+$ monocytes from HLA-A02:06 donors were differentiated in mature DCs (see Methods). Mature DCs were exposed to isogenic GC cell lysates (AGS cells) expressing Canonical (CanT) and Somatic (SomT) RASA3 isoforms. ii) Antigen presentation and T-cell activation: DCs presenting Can or Som RASA3 isoforms were co-cultured with HLA-matched T cells, resulting in T-cells primed against CanT or SomT RASA3. Primed T cells were then independently co-cultured with RASA3 CanT or RASA3 SomT expressing GC cells for two days, and markers of T-cell activation were assessed.

C) Concentration of interferon-gamma (IFN-γ) secretion by co-culture of T cells primed with RASA3 CanT or SomT Isoforms, after antigen challenge. RASA3 CanT primed T cells released significantly more IFN-γ when co-cultured with RASA3 CanT expressing cells, compared to T cells primed with RASA3 SomT and co-cultured with RASA3 SomT expressing cells (P=0.02, representative of n=3 experiments). IFN-γ levels were determined by ELISA.

Figure 18:
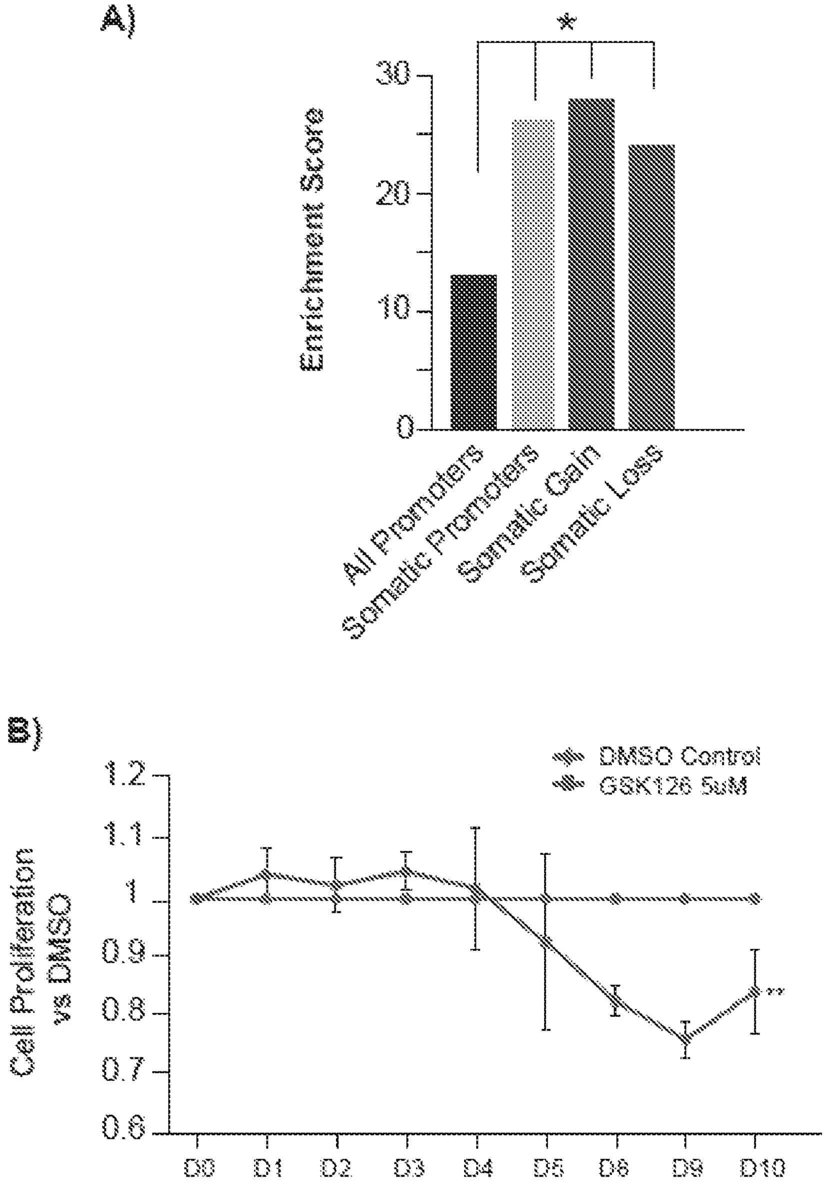
Figure 18:
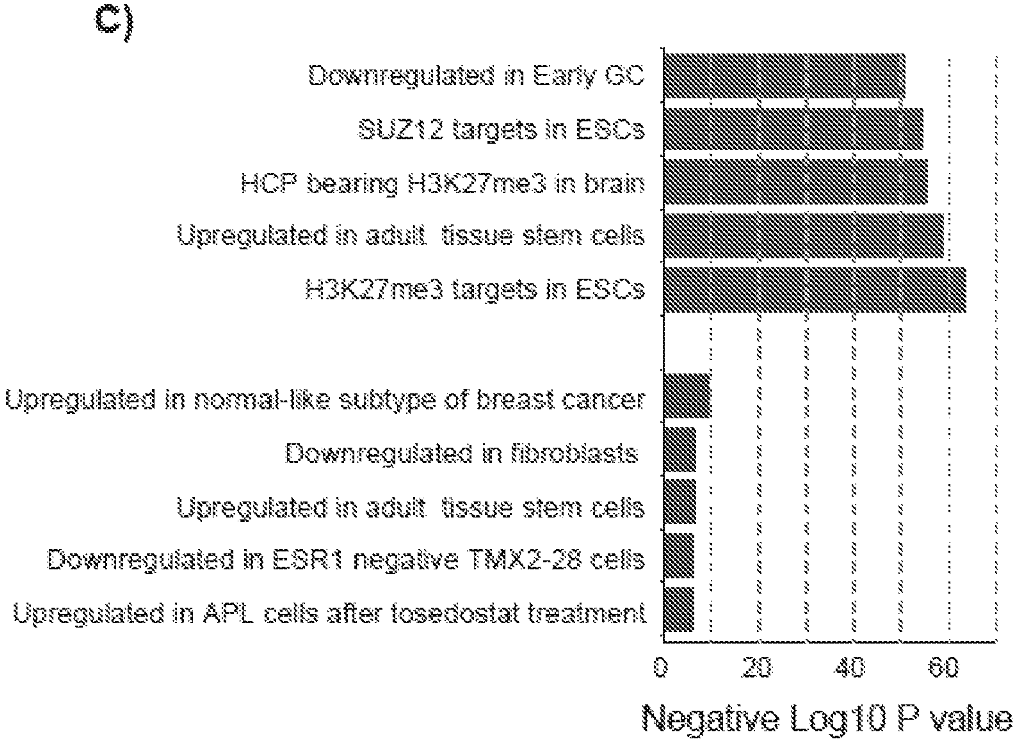
Figure 18:
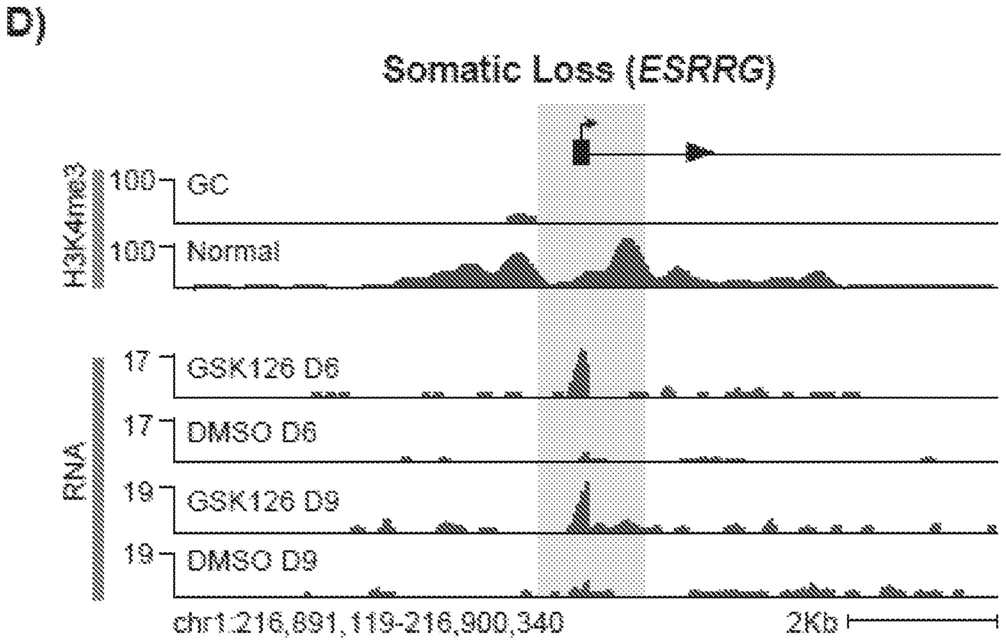

FIG. 18: EZH2 Inhibition

A) Barplot showing increased enrichment of EZH2 binding sites in HFE-145 cells at somatic promoters compared to all promoters (P<0.01).

B) Growth curves of IM95 GC cells after GSK126 administration. Cell proliferation was monitored from 24 to 216 hours and represented relative to DMSO control treated cells (means±s.e.m. represents data from three experiments, and each experiment was performed in duplicate)

C) Top 5 enriched curated gene sets (C2) for the set of genes identified from differential analysis of GSK126 treated vs DMSO control IM95 RNA-seq data at promoter loci.

D) UCSC browser track of alternative promoter ESRRG with loss of promoter activity (GC (red) and normal gastric tissue (blue) H3K4me3). Gain of expression is seen after inhibition of EZH2 using GSK126 in IM95 cells at both day 6 (D6) and Day 9 (D9) treatment.

Figure 19:
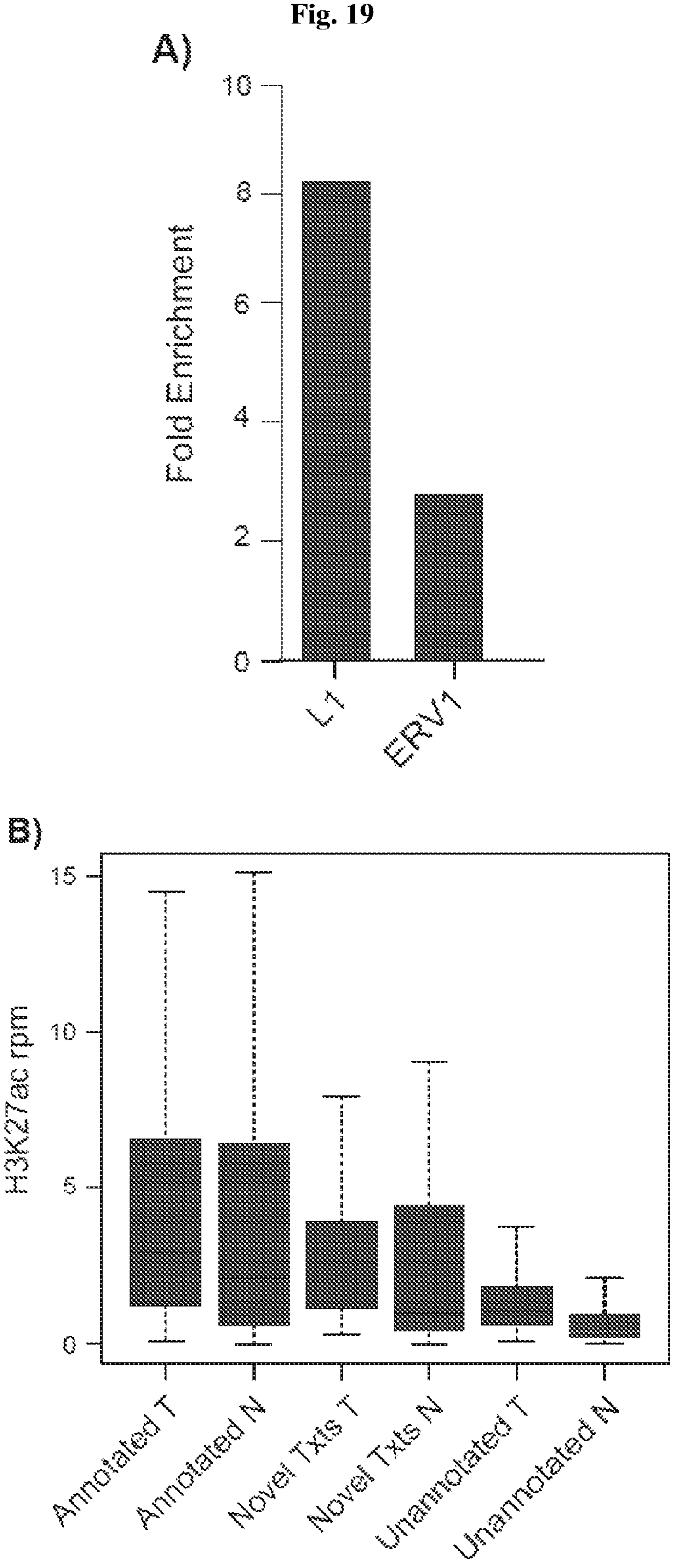

FIG. 19: Unannotated somatic promoters

A) Barplot showing fold enrichment of L1 (FC-8.02, P<0.001) and ERV1 (FC=2.78, P<0.001) repeat elements at unannotated promoter regions compared to all promoters B) Boxplot comparing H3K27ac signals (rpm) at unannotated somatic promoters with annotated somatic promoters. Unannotated somatic promoters have lower H3K27ac signals.

DETAILED DESCRIPTION OF THE PRESENT INVENTION

In a first aspect, the present invention refers to a method for determining the presence or absence of at least one promoter in a cancerous biological sample relative to a non-cancerous biological sample. The method comprises contacting the cancerous biological sample with at least one antibody or antibodies specific for histone modifications H3K4me3 and H3K4me1; isolating nucleic acid from the cancerous biological sample having a signal ratio of H3K4me3 relative to H3K4me1 greater than 1, wherein the isolated nucleic acid comprises at least one region or regions specific to said histone modifications; detecting a signal intensity of H3K4me3 in the isolated nucleic acid; and determining the presence or absence of at least one promoter in the cancerous biological sample based on the change in the signal intensity of H3K4me3 relative to the signal intensity of H3K4me3 in a non-cancerous biological sample.

In one embodiment, the cancerous and non-cancerous biological sample may comprise a single cell, multiple cells, fragments of cells, body fluid or tissue. In one embodiment the cancerous and non-cancerous biological sample may be obtained from the same subject.

In one embodiment, the cancerous and non-cancerous biological sample are each obtained from different subjects.

The contacting step in accordance with the method as described herein may comprise the immunoprecipitation of chromatin with the antibodies specific for the histone modifications. Examples of histone modification include but are not limited to H3K27ac, H3K4me3, H3K4me1. In a preferred embodiment, the histone modification is H3K4me3 and/or H3K4me1. In yet another embodiment, the histone modification is H3K27ac.

The method may further comprise mapping at least one promoter from the cancerous biological sample against at least one reference nucleic acid sequence to identify a gene transcript associated with the at least one promoter.

In some embodiments, the at least one reference nucleic acid sequence may comprise a nucleic acid sequence derived from: i) an annotated genome sequence; ii) a de novo transcriptome assembly; and/or iii) a non-cancerous nucleic acid sequence library or database.

In one embodiment, the change of signal intensity of H3K4me3 may be greater than a 0.5 fold, greater than a 1 fold, greater than a 1.5 fold, greater than a 2 fold, greater than a 2.5 fold or greater than a 3 fold increase or decrease relative to the signal intensity of H3K4me3 in the non-cancerous biological sample. In a preferred embodiment, the change of signal intensity of H3K4me3 may be greater than a 1.5 fold increase or decrease relative to the signal intensity of H3K4me3 in the non-cancerous biological sample. In another embodiment, the change of signal intensity of H3K4me3 greater than a 0.5 fold, greater than a 1 fold, greater than a 1.5 fold, greater than a 2 fold, greater than a 2.5 fold or greater than a 3 fold increase relative to the signal intensity of H3K4me3 in a non-cancerous biological sample, may correlate to the presence of at least one cancer-associated promoter in the cancerous biological sample.

In a preferred embodiment the change of signal intensity of H3K4me3 greater than a 1.5 fold increase relative to the signal intensity of H3K4me3 in a non-cancerous biological sample, may correlate to the presence of at least one cancer-associated promoter in the cancerous biological sample.

In one embodiment, the activity of the at least one cancer-associated promoter may correlate with an increase of SUZ12 or EZH2 binding sites relative to the total promoter population.

In one embodiment, an increase of SUZ12 or EZH2 binding sites correlates with an upregulation of activity of the at least one cancer-associated promoter. In another embodiment, the increase of SUZ12 or EZH2 binding sites correlates with a downregulation of activity of the at least one cancer-associated promoter.

In one embodiment, the at least one promoter may be a canonical promoter that is positioned within 100 bp, 200 bp, 300 bp, 400 bp, 500 bp, 600 bp, 700 bp, 800 bp, 900 bp or 1000 bp from a known gene transcript start site. In a preferred embodiment, the at least one promoter may be a canonical promoter that is positioned within 500 bp from a known gene transcript start site. The gene transcript start site may be associated with one or more of a cell-type specification gene, a cell adhesion gene, a cell mediated immunity gene, a gastric cancer-associated or deregulated gene, a PRC2 target gene or a transcription factor. In one embodiment, the gene transcript start site may be associated with an oncogene. The gene transcript start site may be associated with a gene selected from the group consisting of MYC, MET, CEACAM6, CLDN7, CLDN3, HOTAIR, PVT1, HNF4α, RASA3, GRIN2D, EpCAM and a combination thereof.

In one embodiment, the cancer is gastrointestinal cancer, gastric cancer or colon cancer.

In another embodiment, the at least one promoter may be an alternative promoter that may be associated with a canonical promoter, wherein the canonical promoter may be present in both the cancerous biological sample and the non-cancerous biological sample, and i) wherein the alternative promoter may be only present in the cancerous biological sample, or ii) wherein the alternative promoter may be only absent in the cancerous biological sample.

In some embodiments, the at least one promoter is an unannotated promoter that is positioned more than 100 bp, more than 200 bp, more than 300 bp, more than 400 bp, more than 500 bp away, more than 600 bp, more than 700 bp, more than 800 bp, more than 900 bp or more than 1000 bp from a gene transcript start site. In a preferred embodiment, the at least one promoter is an unannotated promoter that is positioned more than 500 bp away from a gene transcript start site.

In one embodiment, the method as described herein further comprises measuring the expression level of the at least one alternative promoter in the cancerous biological sample and non-cancerous biological sample, wherein the measuring comprises digital profiling of reporter probes; and determining the differential expression level of the at least one alternative promoter relative to the non-cancerous biological sample, based on the digital profiling of the reporter probes, to validate the presence or absence of at least one alternative promoter in the cancerous biological sample relative to a non-cancerous biological sample.

The step of measuring may be conducted using a NanoString™ platform.

In another aspect, the present invention provides a method for determining the prognosis of cancer in a subject. The method comprises contacting a cancerous biological sample obtained from the subject with at least one antibody or antibodies specific for histone modification H3K4me3 and H3K4me1; isolating nucleic acid from the cancerous biological sample having a signal ratio of H3K4me3 relative to H3K4me1 greater than 1, wherein the isolated nucleic acid comprises at least one region or regions specific to said histone modifications; detecting a signal intensity of H3K4me3 in the isolated nucleic acid; and determining the presence or absence of at least one cancer-associated promoter in the cancerous biological sample based on the change in the signal intensity of H3K4me3 relative to the signal intensity of H3K4me3 in a reference nucleic acid sequence, wherein the presence or absence of the at least one cancer-associated promoter in the cancerous biological sample is indicative of the prognosis of the cancer in the subject.

In one embodiment, the at least one cancer-associated promoter may be an alternative promoter that is associated with a canonical promoter, wherein the canonical promoter may be present in both the cancerous biological sample and the reference nucleic acid sequence, and i) wherein the alternative promoter may be only present in the cancerous biological sample, or ii) wherein the alternative promoter may be only absent in the cancerous biological sample.

The presence or absence of the at least one alternative promoter in the cancerous sample may indicative of a poor prognosis of cancer survival in the subject.

In one embodiment the method as described herein further comprises measuring the expression level of the at least one alternative promoter in the cancerous biological sample and the reference nucleic acid sequence, wherein the measuring comprises digital profiling of reporter probes; and determining the differential expression level of the at least one alternative promoter relative to the non-cancerous biological sample, based on the digital profiling of the reporter probes, to validate the presence or absence of at least one alternative promoter in the cancerous biological sample relative to the reference nucleic acid sequence.

The step of measuring may be conducted using a NanoString™ platform.

In another aspect the present invention provides a biomarker for detecting cancer in a subject, the biomarker comprising at least one promoter having a change in signal intensity of H3K4me3 in a cancerous biological sample relative to a non-cancerous biological sample.

In one embodiment, the at least one promoter comprises an increase of EZH2 binding sites relative to the total promoter population. In one embodiment, the at least one promoter may be hypomethylated. In another embodiment, the at least one promoter may be hypermethylated.

The at least one promoter may be a canonical promoter that is positioned less than 500 bp away from a gene transcript start site. In one embodiment, the gene transcript start site may be associated with one or more of a cell-type specification gene, a cell adhesion gene, a cell mediated immunity gene, a gastric cancer-associated or deregulated gene, a PRC2 target gene or a transcription factor. In one embodiment, the gene transcript start site may be associated with an oncogene.

In one embodiment, the gene transcript start site may be associated with a gene selected from the group consisting of MYC, MET, CEACAM6, CLDN7, CLDN3, HOTAIR, PVT1, HNF4α, RASA3, GRIN2D, EpCAM or a combination thereof.

In one embodiment, the at least one promoter may be an alternative promoter that may be associated with a canonical promoter, wherein the canonical promoter may be present in both a cancerous sample and a non-cancerous sample, and i) wherein the alternative promoter may be only present in a cancerous sample, or ii) wherein the alternative promoter may be only absent in a cancerous sample.

In one embodiment, the at least one promoter may be an unannotated promoter that may be positioned more than 100 bp, more than 200 bp, more than 300 bp, more than 400 bp, more than 500 bp, more than 600 bp, more than 700 bp, more than 800 bp, more than 900 bp or more than 1000 bp away from a gene transcript start site. In a preferred embodiment, the at least one promoter may be an unannotated promoter that may be positioned more than 500 bp away from a gene transcript start site.

In another aspect, there is provided a method for modulating the activity of at least one cancer-associated promoter in a cell, comprising administering an inhibitor of EZH2 to the cell. In another aspect there is provided a method for modulating the immune response of a subject to cancer, comprising administering to the subject an inhibitor of EZH2, wherein the EZH2 is associated with at least one cancer-associated promoter in the subject.

In one embodiment, the inhibitor of EZH2 may modulate the expression of immunogenic N-terminal peptides.

In one embodiment, the at least one cancer-associated promoter may be an alternative promoter that may be associated with a canonical promoter, wherein the canonical promoter may be present in both a cancerous sample and a non-cancerous sample, and i) wherein the alternative promoter may only be present in a cancerous sample, or ii) wherein the alternative promoter may only be absent in a cancerous sample.

In one embodiment, the alternative promoter is associated with a transcript variant, and wherein the transcript variant encodes a N-terminal protein variant.

In one embodiment, the N-terminal protein variant may be an N-terminal truncated protein or an N-terminal elongated protein. In one embodiment, the inhibitor of EZH2 may be a siRNA or a small molecule.

In one embodiment, the inhibitor of EZH2 may be GSK126.

In another aspect, there is provided use of an inhibitor of EZH2 in the manufacture of a medicament for modulating the activity of at least one cancer-associated promoter in a cell.

In another aspect there is provided use of an inhibitor of EZH2, wherein the EZH2 is associated with at least one cancer-associated promoter in the subject, in the manufacture of a medicament for modulating the immune response of a subject to cancer.

In another aspect, there is provided an inhibitor of EZH2 for use in modulating the activity of at least one cancer-associated promoter in a cell. In yet another aspect, there is provided an inhibitor of EZH2 for use in modulating the immune response of a subject to cancer, wherein the EZH2 is associated with at least one cancer-associated promoter in the subject.

In another aspect there is provided a method for determining the presence or absence of at least one cancer-associated promoter in a cancerous biological sample relative to a non-cancerous biological sample. The method comprises: contacting the cancerous biological sample with antibodies specific for histone modifications H3K4me3 and H3K4me1; isolating nucleic acid from the cancerous biological sample having a signal ratio of H3K4me3 relative to H3K4me1 greater than 1, wherein the isolated nucleic acid comprises regions specific to said histone modifications; detecting a signal intensity of H3K 4me3 in the isolated nucleic acid at a read depth of 20M; and determining the presence or absence of at least one cancer-associated promoter in the cancerous biological sample based on the change in the signal intensity of H3K4me3 relative to the signal intensity of H3K4me3 in a non-cancerous biological sample.

EXPERIMENTAL SECTION

Methods and Materials

Primary Tissue Samples and Cell Lines

Primary patient samples were obtained from the SingHealth tissue repository with approvals from institutional research ethics review committees and signed patient informed consent. 'Normal' (non-malignant) samples used in this study refers to samples harvested from the stomach, from sites distant from the tumour and exhibiting no visible evidence of tumour or intestinal metaplasia/dysplasia upon surgical assessment. Tumor samples were confirmed by cryosectioning to contain >60% tumor cells. FU97, IM95, MKN7, OCUM1 and RERF-GC-1B cell lines were obtained from the Japan Health Science Research Resource Bank. AGS, KATOIII and SNU16, Hs 1.Int and Hs 738.St/Int gastrointestinal fibroblast lines were obtained from the American Type Culture Collection. NCC-59, NCC-24 and SNU-1967 and SNU-1750 were obtained from the Korean Cell Line Bank. YCC3, YCC7, YCC21, YCC22 were gifts from Yonsei Cancer Centre, South Korea. HFE145 cells were a gift from Dr. Hassan Ashktorab, Howard University. GES-1 cells were a gift from Dr. Alfred Cheng, Chinese University of Hong Kong. Cell line identifies were confirmed by STR DNA profiling using ANSI/ATCC ASN-0002-2011 guidelines. For our study, MKN7 cells, listed as a commonly misidentified cell line by ICLAC (http://iclac.org/databases/cross-contaminations/), exhibited a perfect match (100%) with MKN7 reference profiles in the Japanese Collection of Research Bioresources Cell Bank. All cell lines were negative for *mycoplasma* contamination as assessed by the MycoAlert™ *Mycoplasma* Detection Kit (Lonza) and the MycoSensor qPCR Assay Kit (Agilent Technologies). PBMCs from healthy donors were collected under protocol CIRB Ref No. 2010/720/E.

Nano-ChIPseq

Nano-ChIP-Seq was performed as described below.

Primary Tissue and Cell Line Fixation

Fresh-frozen cancer and normal tissues were dissected using a razor blade in liquid nitrogen to obtain ~5 mg sized pieces for each ChIP. Tissue pieces were fixed in 1% formaldehyde/PBS buffer for 10 min at room temperature. Fixation was stopped by addition of glycine to a final concentration of 125 mM. Tissue pieces were washed 3 times with TBSE buffer. For cell lines, 1 million fresh harvested cells were fixed in 1% formaldehyde/medium buffer for 10 minutes (min) at room temperature. Fixation was stopped by addition of glycine to a final concentration of 125 mM. Fixed cells were washed 3 times with TBSE buffer, and centrifuged (5,000 r.p.m., 5 min).

ChIP

Pelleted cells and pulverized tissues were lysed in 100 μl 1% SDS lysis buffer and sonicated to 300-500 bp using a Bioruptor (Diagenode). ChIP was performed using the following antibodies: H3K4me3 (07-473, Millipore); H3K4me1 (ab8895, Abcam); H3K27ac (ab4729, Abcam).

WGA

After recovery of ChIP and input DNA, whole-genome-amplification was performed using the WGA4 kit (Sigma-Aldrich) and BpmI-WGA primers. Amplified DNAs were purified using PCR purification columns (QIAGEN) and digested with BpmI (New England Biolabs) to remove WGA adapters.

Library Preparation and Sequencing 30 ng of amplified DNA was used for each sequencing library preparation (New England Biolabs). 8 libraries were multiplexed (New England Biolabs) and sequenced on 2 lanes of a Hiseq2500 sequencer (Illumina) to an average depth of 20-30 million reads per library.

Sequencing reads were trimmed (10 bp from front and back) and mapped against human genome reference hg19 using the Burrows-Wheeler Aligner (BWA) (version 0.6.2) 'aln' algorithm. Reading statistics were generated using mapstat from samtools. We filtered reads based on their mapping quality (MAPQ >=10) and used uniquely mapped reads to perform peak calling using CCAT v3.0. We chose a MAPQ value of ≥10 because i) MAPQ>10 has been previously reported as a reliable value for confident read mapping, ii) MAPQ>10 has been recommended by the developers of the BWA-algorithm as a suitable threshold for confident mapping, and iii) independent studies comparing various read alignment algorithms have shown that mapping accuracies plateau at a 10-12 MAPQ threshold.

EZH2 ChIP-seq

Cells were cross-linked with 1% formaldehyde for 10 minutes at room temperature, and stopped by adding glycine to a final concentration of 0.2M. Chromatin was extracted and sonicated to ~500 bp fragments. EZH2 antibodies (Catalog #5246, Cell Signaling) were used for chromatin immunoprecipitation (ChIP). 30 ng of ChIPed DNA was used for each sequencing library preparation (New England Biolabs). The library was sequenced on a Hiseq2500 (Illumina). Input DNA from cells prior to immunoprecipitation was used to normalize ChIP-seq peak calling. Prior to sequencing, qPCR was used to verify that positive and negative control ChIP regions were amplified in the linear range. Sequencing reads were mapped against human genome reference hg19 using the Burrows-Wheeler Aligner (BWA) (version 0.7) 'aln' algorithm. Reading statistics were generated using mapstat from samtools. We filtered reads based on their mapping quality (MAPQ >=10) and used uniquely mapped reads to perform peak calling using MACS2.

Quality Control Assessments of Nano-ChIPseq Data

ChIP Enrichment Assessment

We assessed ChIP library qualities (H3K27ac, H3K4me3 and H3K4me1) using two different methods. First, we estimated ChIP qualities, particularly H3K27ac and H3K4me3, by interrogating their enrichment levels at annotated promoters of protein-coding genes. Specifically, we computed median read densities of input and input-corrected ChIP signals around the transcription start sites (TSSs, +/−500 bp) of highly expressed protein-coding genes. For each sample, we then compared read density ratios of ChIP over input as a surrogate of data quality, retaining only those samples where the ChIP/input ratio was greater than 2-fold. Using this criteria, all H3K4me3 and H3K27ac samples (GC lines and primary samples) exhibited greater than 2-fold enrichment, indicating successful enrichment. Second, we used CHANCE (ChIp-seq ANalytics and Confidence Estimation), a software for ChIP-seq quality control and protocol optimization that indicates whether a ChIP library shows successful or weak enrichment. CHANCE assessment confirmed that the large majority (81%) of samples in our study exhibited successful enrichment. Quality status of each library, as assessed by both methods, are reported in Table 1.

TABLE 1

Read Mapping statistics of Nano ChIP-seq libraries

| S.No | Patient No | Group | Sample ID | Library ID | Histone Modification | Total Reads | Total Mapped Reads | # of Peaks (FDR < 5%, CCAT) | CHANCE Enrichment | ChIP enrichment around TSS (>2 Fold) |
|---|---|---|---|---|---|---|---|---|---|---|
| 1 | 1 | N | 2000639 | CHG023 | H3K4Me1 | 116,179,997 | 56,009,114 | 11,438 | successful | yes |
| 2 | 1 | N | 2000639 | CHG079 | H3K4Me3 | 144,760,092 | 45,662,594 | 13,301 | successful | yes |
| 3 | 1 | N | 2000639 | CHG022 | H3K27Ac | 107,005,238 | 47,688,264 | 30,155 | successful | yes |
| 4 | 1 | N | 2000639 | CHG021 | Input | 108,432,681 | 53,434,667 | — | — | — |
| 5 | 1 | T | 2000639 | CHG019 | H3K4Me1 | 139,751,844 | 62,529,719 | 9,133 | successful | yes |

TABLE 1-continued

Read Mapping statistics of Nano ChIP-seq libraries

| S.No | Patient No | Group | Sample ID | Library ID | Histone Modification | Total Reads | Total Mapped Reads | # of Peaks (FDR < 5%, CCAT) | CHANCE Enrichment | ChIP enrichment around TSS (>2 Fold) |
|---|---|---|---|---|---|---|---|---|---|---|
| 6 | 1 | T | 2000639 | CHG078 | H3K4Me3 | 176,761,815 | 52,219,714 | 15,417 | successful | yes |
| 7 | 1 | T | 2000639 | CHG018 | H3K27Ac | 125,811,014 | 56,636,793 | 22,220 | successful | yes |
| 8 | 1 | T | 2000639 | CHG017 | Input | 133,549,980 | 62,465,142 | — | — | — |
| 9 | 2 | N | 2000721 | CHG081 | H3K4Me3 | 123,984,264 | 41,723,243 | 13,046 | successful | yes |
| 10 | 2 | N | 2000721 | CHG031 | H3K4Me1 | 142,898,092 | 61,716,210 | 17,896 | successful | yes |
| 11 | 2 | N | 2000721 | CHG030 | H3K27Ac | 142,881,448 | 56,328,103 | 24,624 | successful | yes |
| 12 | 2 | N | 2000721 | CHG029 | Input | 144,582,591 | 67,254,098 | — | — | — |
| 13 | 2 | T | 2000721 | CHG080 | H3K4Me3 | 128,094,707 | 52,416,345 | 12,751 | successful | yes |
| 14 | 2 | T | 2000721 | CHG026 | H3K27Ac | 132,143,844 | 52,416,345 | 45,274 | successful | yes |
| 15 | 2 | T | 2000721 | CHG027 | H3K4Me1 | 120,824,194 | 54,688,706 | 48,701 | successful | yes |
| 16 | 2 | T | 2000721 | CHG025 | Input | 150,621,523 | 65,242,401 | — | — | — |
| 17 | 3 | N | 2000986 | CHG083 | H3K4Me3 | 145,813,278 | 44,476,466 | 13,305 | successful | yes |
| 18 | 3 | N | 2000986 | CHG039 | H3K4Me1 | 112,190,461 | 52,061,916 | 14,977 | successful | yes |
| 19 | 3 | N | 2000986 | CHG038 | H3K27Ac | 136,195,033 | 47,671,991 | 26,993 | successful | yes |
| 20 | 3 | N | 2000986 | CHG037 | Input | 125,858,642 | 58,503,831 | — | — | — |
| 21 | 3 | T | 2000986 | CHG082 | H3K4Me3 | 199,735,230 | 48,070,517 | 13,296 | successful | yes |
| 22 | 3 | T | 2000986 | CHG035 | H3K4Me1 | 99,757,592 | 48,602,649 | 25,882 | successful | yes |
| 23 | 3 | T | 2000986 | CHG034 | H3K27Ac | 127,564,120 | 45,231,776 | 29,278 | successful | yes |
| 24 | 3 | T | 2000986 | CHG033 | Input | 127,392,001 | 57,846,771 | — | — | — |
| 25 | 4 | N | 980437 | CHG087 | H3K4Me3 | 252,269,976 | 16,106,111 | 6,925 | weak | yes |
| 26 | 4 | N | 980437 | CHG089 | H3K27Ac | 248,399,140 | 21,095,856 | 20,018 | weak | yes |
| 27 | 4 | N | 980437 | CHG086 | input | 223,083,607 | 13,951,728 | — | — | — |
| 28 | 4 | T | 980437 | CHG091 | H3K4Me3 | 254,777,628 | 12,340,257 | 7,007 | weak | yes |
| 29 | 4 | T | 980437 | CHG093 | H3K27Ac | 215,915,787 | 19,054,278 | 48,614 | weak | yes |
| 30 | 4 | T | 980437 | CHG090 | input | 214,007,053 | 18,743,433 | — | — | — |
| 31 | 5 | N | 980097 | CHG097 | H3K27Ac | 254,991,965 | 17,871,717 | 10,566 | weak | yes |
| 32 | 5 | N | 980097 | CHG094 | Input | 248,345,017 | 15,056,998 | — | — | — |
| 33 | 5 | T | 980097 | CHG101 | H3K27Ac | 254,857,885 | 16,050,861 | 81,607 | successful | yes |
| 34 | 5 | T | 980097 | CHG098 | Input | 235,148,448 | 16,412,565 | — | — | — |
| 35 | 6 | N | 990068 | CHG441 | H3K4Me3 | 25,942,766 | 18,661,944 | 9,040 | successful | yes |
| 36 | 6 | N | 990068 | CHG443 | H3K27Ac | 28,993,775 | 20,404,671 | 30,306 | successful | yes |
| 37 | 6 | N | 990068 | CHG444 | Input | 16,583,307 | 14,164,125 | — | — | — |
| 38 | 6 | T | 990068 | CHG437 | H3K4Me3 | 19,295,687 | 15,981,638 | 23,546 | successful | yes |
| 39 | 6 | T | 990068 | CHG439 | H3K27Ac | 30,394,067 | 26,279,884 | 84,958 | successful | yes |
| 40 | 6 | T | 990068 | CHG440 | Input | 54,957,058 | 46,535,339 | — | — | — |
| 41 | 7 | N | 2000085 | CHG449 | H3K4Me3 | 22,207,074 | 17,120,624 | 13,421 | weak | yes |
| 42 | 7 | N | 2000085 | CHG451 | H3K27Ac | 31,752,518 | 26,505,029 | 93,432 | successful | yes |
| 43 | 7 | N | 2000085 | CHG452 | Input | 23,861,825 | 20,188,881 | — | — | — |
| 44 | 7 | T | 2000085 | CHG445 | H3K4Me3 | 27,386,842 | 17,898,292 | 16,274 | successful | yes |
| 45 | 7 | T | 2000085 | CHG447 | H3K27Ac | 37,833,126 | 29,893,873 | 67,464 | successful | yes |
| 46 | 7 | T | 2000085 | CHG448 | Input | 25,476,868 | 21,590,215 | — | — | — |
| 47 | 8 | N | 980401 | GCC005 | H3K4Me3 | 47,143,397 | 32,011,124 | 9,739 | weak | yes |
| 48 | 8 | N | 980401 | GCC006 | H3K4Me1 | 49,813,057 | 38,517,830 | 29,304 | successful | yes |
| 49 | 8 | N | 980401 | GCC007 | H3K27Ac | 49,333,955 | 34,378,734 | 104,483 | successful | yes |
| 50 | 8 | N | 980401 | GCC008 | Input | 48,654,609 | 39,027,473 | — | — | — |
| 51 | 8 | T | 980401 | GCC002 | H3K4Me1 | 46,014,858 | 35,781,553 | 5,374 | weak | yes |
| 52 | 8 | T | 980401 | GCC001 | H3K4Me3 | 40,037,248 | 16,724,980 | 11,773 | successful | yes |
| 53 | 8 | T | 980401 | GCC003 | H3K27Ac | 70,844,500 | 51,841,868 | 108,169 | successful | yes |
| 54 | 8 | T | 980401 | GCC004 | Input | 55,650,648 | 46,769,330 | — | — | — |
| 55 | 9 | N | 980447 | GCC013 | H3K4Me3 | 49,510,760 | 43,302,748 | 10,442 | successful | yes |
| 56 | 9 | N | 980447 | GCC014 | H3K4Me1 | 51,911,778 | 46,524,450 | 18,916 | weak | yes |
| 57 | 9 | N | 980447 | GCC015 | H3K27Ac | 43,725,655 | 38,581,698 | 147,189 | successful | yes |
| 58 | 9 | N | 980447 | GCC016 | Input | 43,722,729 | 36,570,838 | — | — | — |
| 59 | 9 | T | 980447 | GCC010 | H3K4Me1 | 51,224,701 | 40,643,956 | 7,959 | successful | yes |
| 60 | 9 | T | 980447 | GCC009 | H3K4Me3 | 41,895,137 | 28,002,598 | 9,325 | weak | yes |
| 61 | 9 | T | 980447 | GCC011 | H3K27Ac | 75,243,898 | 63,172,397 | 98,169 | successful | yes |
| 62 | 9 | T | 980447 | GCC012 | Input | 40,502,678 | 33,280,117 | — | — | — |
| 63 | 10 | N | 2001206 | GCC021 | H3K4Me3 | 42,094,067 | 35,485,202 | 12,682 | successful | yes |
| 64 | 10 | N | 2001206 | GCC022 | H3K4Me1 | 44,213,793 | 38,760,554 | 50,615 | weak | yes |
| 65 | 10 | N | 2001206 | GCC023 | H3K27Ac | 47,356,714 | 34,355,781 | 112,565 | successful | yes |
| 66 | 10 | N | 2001206 | GCC024 | Input | 58,885,884 | 49,927,340 | — | — | — |
| 67 | 10 | T | 2001206 | GCC017 | H3K4Me3 | 48,193,228 | 36,729,294 | 13,835 | successful | yes |
| 68 | 10 | T | 2001206 | GCC018 | H3K4Me1 | 43,730,845 | 35,480,758 | 44,504 | weak | yes |
| 69 | 10 | T | 2001206 | GCC019 | H3K27Ac | 52,518,766 | 42,398,517 | 111,758 | successful | yes |
| 70 | 10 | T | 2001206 | GCC020 | Input | 81,949,870 | 70,380,385 | — | — | — |
| 71 | 11 | N | 980436 | GCC029 | H3K4Me3 | 27,612,232 | 20,121,957 | 12,398 | weak | yes |
| 72 | 11 | N | 980436 | GCC030 | H3K4Me1 | 22,983,565 | 20,452,059 | 53,077 | weak | yes |
| 73 | 11 | N | 980436 | GCC031 | H3K27Ac | 23,061,305 | 15,315,483 | 104,880 | successful | yes |
| 74 | 11 | N | 980436 | GCC032 | Input | 24,411,542 | 21,182,579 | — | — | — |
| 75 | 11 | T | 980436 | GCC025 | H3K4Me3 | 31,564,679 | 24,866,375 | 8,625 | weak | yes |
| 76 | 11 | T | 980436 | GCC026 | H3K4Me1 | 51,645,661 | 38,028,800 | 58,456 | successful | yes |
| 77 | 11 | T | 980436 | GCC027 | H3K27Ac | 51,093,256 | 35,496,776 | 102,351 | successful | yes |

TABLE 1-continued

Read Mapping statistics of Nano ChIP-seq libraries

| S.No | Patient No | Group | Sample ID | Library ID | Histone Modification | Total Reads | Total Mapped Reads | # of Peaks (FDR < 5%, CCAT) | CHANCE Enrichment | ChIP enrichment around TSS (>2 Fold) |
|---|---|---|---|---|---|---|---|---|---|---|
| 78 | 11 | T | 980436 | GCC028 | Input | 25,606,490 | 20,820,223 | — | — | — |
| 79 | 12 | N | 980417 | GCC037 | H3K4Me3 | 18,976,505 | 15,277,228 | 10,387 | successful | yes |
| 80 | 12 | N | 980417 | GCC039 | H3K27Ac | 30,443,642 | 25,447,390 | 70,910 | successful | yes |
| 81 | 12 | N | 980417 | GCC038 | H3K4Me1 | 22,127,416 | 18,537,610 | 109,119 | successful | yes |
| 82 | 12 | N | 980417 | GCC040 | Input | 33,758,416 | 28,242,473 | — | — | — |
| 83 | 12 | T | 980417 | GCC033 | H3K4Me3 | 42,615,610 | 27,972,601 | 10,260 | successful | yes |
| 84 | 12 | T | 980417 | GCC035 | H3K27Ac | 33,438,272 | 29,141,996 | 76,369 | successful | yes |
| 85 | 12 | T | 980417 | GCC034 | H3K4Me1 | 31,115,402 | 26,172,044 | 142,635 | weak | yes |
| 86 | 12 | T | 980417 | GCC036 | Input | 26,806,807 | 22,277,771 | — | — | — |
| 87 | 13 | N | 980319 | GCC075 | H3K4Me3 | 34,503,108 | 26,201,666 | 9,466 | successful | yes |
| 88 | 13 | N | 980319 | GCC076 | H3K4Me1 | 32,308,832 | 28,194,660 | 56,964 | weak | yes |
| 89 | 13 | N | 980319 | GCC077 | H3K27Ac | 28,534,828 | 24,595,902 | 73,073 | successful | yes |
| 90 | 13 | N | 980319 | GCC078 | Input | 31,533,287 | 26,147,884 | — | — | — |
| 91 | 13 | T | 980319 | GCC071 | H3K4Me3 | 31,707,599 | 22,793,555 | 14,049 | successful | yes |
| 92 | 13 | T | 980319 | GCC073 | H3K27Ac | 42,548,744 | 35,755,479 | 102,971 | successful | yes |
| 93 | 13 | T | 980319 | GCC072 | H3K4Me1 | 28,112,304 | 24,361,418 | 196,347 | weak | yes |
| 94 | 13 | T | 980319 | GCC074 | Input | 28,895,896 | 24,529,014 | — | — | — |
| 95 | 14 | N | 990275 | GCC088 | H3K4Me3 | 39,968,810 | 31,536,231 | 7,964 | successful | yes |
| 96 | 14 | N | 990275 | GCC089 | H3K27Ac | 52,738,627 | 22,089,449 | 70,246 | successful | yes |
| 97 | 14 | N | 990275 | GCC090 | Input | 33,342,252 | 21,049,309 | — | — | — |
| 98 | 14 | T | 990275 | GCC085 | H3K4Me3 | 26,399,904 | 14,795,436 | 25,423 | weak | yes |
| 99 | 14 | T | 990275 | GCC086 | H3K27Ac | 45,712,891 | 25,668,453 | 183,458 | successful | yes |
| 100 | 14 | T | 990275 | GCC087 | Input | 40,285,061 | 32,790,063 | — | — | — |
| 101 | 15 | N | 2000877 | GCC082 | H3K4Me3 | 52,151,546 | 22,229,998 | 11,368 | successful | yes |
| 102 | 15 | N | 2000877 | GCC083 | H3K27Ac | 45,775,899 | 41,027,897 | 61,175 | weak | yes |
| 103 | 15 | N | 2000877 | GCC084 | Input | 38,226,148 | 30,117,584 | — | — | — |
| 104 | 15 | T | 2000877 | GCC079 | H3K4Me3 | 49,368,282 | 24,022,463 | 9,837 | successful | yes |
| 105 | 15 | T | 2000877 | GCC080 | H3K27Ac | 38,621,705 | 33,990,267 | 41,048 | successful | yes |
| 106 | 15 | T | 2000877 | GCC081 | Input | 38,824,621 | 32,814,299 | — | — | — |
| 107 | 16 | N | 20020720 | GCC100 | H3K4Me3 | 58,679,413 | 34,278,884 | 9,901 | successful | yes |
| 108 | 16 | N | 20020720 | GCC101 | H3K27Ac | 43,532,496 | 37,750,917 | 65,167 | successful | yes |
| 109 | 16 | N | 20020720 | GCC102 | Input | 39,544,734 | 31,454,551 | — | — | — |
| 110 | 16 | T | 20020720 | GCC097 | H3K4Me3 | 57,599,648 | 16,022,427 | 12,922 | successful | yes |
| 111 | 16 | T | 20020720 | GCC098 | H3K27Ac | 35,400,105 | 29,507,542 | 74,115 | successful | yes |
| 112 | 16 | T | 20020720 | GCC099 | Input | 37,092,424 | 29,452,932 | — | — | — |
| 113 | 17 | N | 20021007 | GCC094 | H3K4Me3 | 56,788,147 | 18,217,449 | 16,073 | successful | yes |
| 114 | 17 | N | 20021007 | GCC095 | H3K27Ac | 40,488,514 | 33,372,754 | 122,851 | successful | yes |
| 115 | 17 | N | 20021007 | GCC096 | Input | 40,712,616 | 34,440,613 | — | — | — |
| 116 | 17 | T | 20021007 | GCC091 | H3K4Me3 | 33,903,211 | 27,230,052 | 7,843 | weak | yes |
| 117 | 17 | T | 20021007 | GCC092 | H3K27Ac | 50,268,912 | 19,156,361 | 98,104 | successful | yes |
| 118 | 17 | T | 20021007 | GCC093 | Input | 34,936,961 | 29,417,989 | — | — | — |
| 119 | CL1 | FU97 | FU97 | GCC043 | H3K27Ac | 30,087,131 | 22,566,178 | 21,867 | successful | yes |
| 120 | CL1 | FU97 | FU97 | GCC041 | H3K4Me3 | 26,986,288 | 23,243,556 | 26,562 | successful | yes |
| 121 | CL1 | FU97 | FU97 | GCC045 | Input | 33,566,067 | 23,430,741 | — | — | — |
| 122 | CL10 | RERF-GC-1B | RERF-GC-1B | CHG374 | H3K27Ac | 39,882,820 | 19,500,590 | 11,201 | successful | yes |
| 123 | CL10 | RERF-GC-1B | RERF-GC-1B | CHG371 | H3K4Me3 | 42,450,431 | 25,988,948 | 16,625 | successful | yes |
| 124 | CL10 | RERF-GC-1B | RERF-GC-1B | CHG376 | Input | 21,437,700 | 16,948,709 | — | — | — |
| 125 | CL11 | SNU16 | SNU16 | CHG236 | H3K27Ac | 21,726,635 | 16,967,938 | 13,619 | successful | yes |
| 126 | CL11 | SNU16 | SNU16 | CHG233 | H3K4Me3 | 20,136,058 | 18,151,002 | 19,445 | successful | yes |
| 127 | CL11 | SNU16 | SNU16 | CHG232 | Input | 19,522,181 | 14,558,761 | — | — | — |
| 128 | CL12 | SNU1750 | SNU1750 | CHG230 | H3K27Ac | 18,716,777 | 15,805,037 | 15,074 | successful | yes |
| 129 | CL12 | SNU1750 | SNU1750 | CHG227 | H3K4Me3 | 16,655,044 | 14,883,880 | 18,130 | successful | yes |
| 130 | CL12 | SNU1750 | SNU1750 | CHG226 | Input | 19,602,424 | 13,575,272 | — | — | — |
| 131 | CL13 | YCC21 | YCC21 | CHG429 | H3K27Ac | 22,884,268 | 13,861,557 | 21,415 | successful | yes |
| 132 | CL13 | YCC21 | YCC21 | CHG427 | H3K4Me3 | 22,788,225 | 15,669,142 | 20,120 | successful | yes |
| 133 | CL13 | YCC21 | YCC21 | CHG431 | Input | 40,378,916 | 34,747,778 | — | — | — |
| 134 | CL13 | YCC22 | YCC22 | GCC063 | H3K27Ac | 33,314,935 | 23,877,905 | 11,774 | successful | yes |
| 135 | CL13 | YCC22 | YCC22 | GCC061 | H3K4Me3 | 27,410,298 | 24,163,717 | 25,417 | successful | yes |
| 136 | CL13 | YCC22 | YCC22 | GCC065 | Input | 26,685,596 | 18,976,555 | — | — | — |
| 137 | CL14 | YCC3 | YCC3 | GCC053 | H3K27Ac | 27,581,400 | 21,579,098 | 14,118 | successful | yes |
| 138 | CL14 | YCC3 | YCC3 | GCC051 | H3K4Me3 | 22,106,259 | 18,914,296 | 17,276 | successful | yes |
| 139 | CL14 | YCC3 | YCC3 | GCC055 | Input | 27,745,993 | 18,854,658 | — | — | — |
| 140 | CL15 | YCC7 | YCC7 | CHG424 | H3K27Ac | 38,599,550 | 22,445,268 | 32,770 | successful | yes |
| 141 | CL15 | YCC7 | YCC7 | CHG422 | H3K4Me3 | 19,594,480 | 14,546,474 | 22,521 | successful | yes |
| 142 | CL15 | YCC7 | YCC7 | CHG426 | Input | 24,527,190 | 21,748,808 | — | — | — |

TABLE 1-continued

Read Mapping statistics of Nano ChIP-seq libraries

| S.No | Patient No | Group | Sample ID | Library ID | Histone Modification | Total Reads | Total Mapped Reads | # of Peaks (FDR < 5%, CCAT) | CHANCE Enrichment | ChIP enrichment around TSS (>2 Fold) |
|---|---|---|---|---|---|---|---|---|---|---|
| 143 | CL2 | HFE145 | HFE145 | CHG245 | H3K4Me3 | 24,122,708 | 19,760,850 | 18,492 | successful | yes |
| 144 | CL2 | HFE145 | HFE145 | CHG244 | Input | 22,447,791 | 17,960,470 | — | — | — |
| 145 | CL2 | HFE145 | HFE145 | HFE145-EZH2-MJ-5246 | H3K4Me3 | 50,701,700 | 45,821,209 | 17,299 | weak | — |
| 146 | CL2 | HFE145 | HFE145 | HFE145-input-MJ | Input | 36,885,332 | 36,157,452 | — | — | — |
| 147 | CL3 | Hs1.Int | Hs1.Int | HsInt-K4me3.merged | H3K4Me3 | 37,088,221 | 32,789,363 | 22,518 | successful | — |
| 148 | CL3 | Hs1.Int | Hs1.Int (replicate) | HsInt-G-K4me3.merged | H3K4Me3 | 30,617,105 | 27,713,302 | 20,298 | successful | — |
| 149 | CL3 | Hs1.Int | Hs1.Int | HsInt-input.merged | Input | 32,275,816 | 28,576,200 | — | — | — |
| 150 | CL4 | Hs738.St/Int | Hs738.St/Int | Hs738-K4me3.merged | H3K4Me3 | 37,945,394 | 33,334,651 | 150,552 | successful | — |
| 151 | CL4 | Hs738.St/Int | Hs738.St/Int | Hs738-K4me3.merged | Input | 32,275,816 | 24,581,922 | — | — | — |
| 152 | CL5 | IM95 | IM95 | CHG434 | H3K27Ac | 23,309,435 | 9,168,213 | 27,692 | successful | yes |
| 153 | CL5 | IM95 | IM95 | CHG432 | H3K4Me3 | 25,179,506 | 14,069,213 | 19,956 | successful | yes |
| 154 | CL5 | IM95 | IM95 | CHG436 | Input | 37,968,519 | 33,292,944 | — | — | — |
| 155 | CL6 | KATO3 | KATO3 | CHG242 | H3K27Ac | 24,559,532 | 17,356,721 | 28,730 | successful | yes |
| 156 | CL6 | KATO3 | KATO3 | CHG238 | Input | 20,527,352 | 14,593,025 | — | — | — |
| 157 | CL7 | MKN7 | MKN7 | CHG419 | H3K27Ac | 35,301,333 | 30,804,178 | 24,268 | successful | yes |
| 158 | CL7 | MKN7 | MKN7 | CHG417 | H3K4Me3 | 28,119,400 | 24,793,006 | 23,766 | successful | yes |
| 159 | CL7 | MKN7 | MKN7 | CHG421 | Input | 35,839,896 | 31,791,610 | — | — | — |
| 160 | CL8 | NCC59 | NCC59 | CHG218 | H3K27Ac | 22,973,156 | 19,828,610 | 14,937 | successful | yes |
| 161 | CL8 | NCC59 | NCC59 | CHG215 | H3K4Me3 | 15,642,441 | 13,907,147 | 12,410 | successful | yes |
| 162 | CL8 | NCC59 | NCC59 | CHG214 | Input | 17,926,188 | 13,139,789 | — | — | — |
| 163 | CL9 | OCUM1 | OCUM1 | CHG212 | H3K27Ac | 24,573,737 | 20,570,185 | 17,284 | successful | yes |
| 164 | CL9 | OCUM1 | OCUM1 | CHG209 | H3K4Me3 | 19,557,872 | 17,178,274 | 15,445 | successful | yes |
| 165 | CL9 | OCUM1 | OCUM1 | CHG208 | Input | 20,585,679 | 16,680,529 | — | — | — |

Promoter Analysis

Promoter (H3K4Me3 hi/H3K4Me1 lo) regions were identified by calculating the H3K4Me3:H3K4Me1 ratio for all H3K4Me3 regions merged across normal and GC samples. We estimated the required sample size to achieve 80% power and 10% type I error (http://powerandsamplesize.com/) based on the average signals of top 100 differential promoters between tumor and normal samples. This result yielded a recommended sample size of 11 (average), which is met in our study (16 N/T). Regions with H3K4Me3:H3K4Me1 ratios <1 in both normal and GC samples were excluded from further analysis. For all analyses performed in this study, promoter regions were defined as genomic locations exhibiting H3K4me3 hi/me1 low signals, and for all subsequent analyses, it was only within this pre-defined H3K4me3 hi/me1 low subset that H3K4me3 signals were compared. H3K27ac data was used for correlative analysis. H3K4me3 data (fastqs) for colon carcinoma lines was downloaded from public databases—Hct116 and Caco2 from ENCODE and V503 and V400 from GSE36204. To compare promoter signals between GC and normal samples, we used the DESeq2 and edgeR bioconductor packages using a read count matrix of chipseq signals, adjusting for replicate information. Regions with fold changes greater than 1.5 (FDR 0.1) were selected as significantly different. The criteria of FC 1.5 and q<0.1 was based on previous literature comparing ChIP-seq profiles using DESeq2 and edgeR also using similar thresholds. Significantly altered promoters identified by DESeq2 overlapped almost completely with altered promoters found by edgeR. A regularized log transformation of the DESeq2 read counts was used to plot PCAs and heatmaps.

Transcriptome Analysis

RNA-seq data was obtained from the European Genome-phenome Archive under Accession No: EGAS00001001128. Data was processed by first aligning to GENCODE v19 transcript annotations using TopHat v2.0.12. Cufflinks 2.2.0 was used to generate FPKM abundance measures. For identification of novel transcripts, Cufflinks was used without employing a reference transcript annotation. Transcripts were then merged across all GC and normal samples and compared against GENCODE annotations to identify novel transcripts using Cuffmerge 2.2.0. Deep-depth strand-specific RNA sequencing was also performed on 10 additional primary samples. Total RNA was extracted using the Qiagen RNeasy Mini kit, and RNA-seq libraries were constructed according to manufacturer's instructions using Illumina Stranded Total RNA Sample Prep Kit v2 (Illumina, San Diego, California, USA) Ribo-Zero Gold option (Epicentre, Madison, Wisconsin, USA), and 1 ug total RNA. Sequencing was performed using the paired-end 101 bp read option. TCGA datasets were downloaded from TCGA Data Portal (https://tcga-data.nci.nih.gov/tcga) in form of fastq files which were then aligned to GENCODE v19 transcript annotations using TopHat v2.0.12. To analyze promoter-associated RNA expression, RNA-seq reads from TCGA samples (tumors and normals) were mapped against the genomic locations of promoter regions originally defined by epigenomic profiling in the discovery samples, including all promoters, gained somatic promoters, and lost somatic promoters (see FIG. 1 in Main Text). RNA-seq reads mapping to these epigenome-defined promoter regions were then quantified, normalized by promoter length (kilobases) and by total library size, and fold changes in expression were computed between tumor and normal TCGA sample groups. Length of promoter loci was defined as the number of base pairs (bps) between the start and stop genomic coordinate of the H3K4me3 region as identified by the peak caller program CCAT v3.0. (190) Isoform level quantification for alternative promoter driven transcripts was performed using cufflinks (FPKM), Kallisto (TPM) and MISO (isoform centric analysis). Assigned counts for each isoform were normalized by DESeq2.

DNA Methylation Analysis

Genomic DNA of gastric tumors and matched normal gastric tissues was extracted (QIAGEN) and processed for DNA methylation profiling using Illumina HumanMethylation450 BeadChips (HM450). Methylation β-values were calculated and background corrected using the methylumi R BioConductor package. Normalization was performed using the BMIQ method (watermelon package in R). CpG island locations were downloaded from the UCSC genome browser. Overlaps of at least 1 bp between promoter loci and CpG islands were identified using BEDTools intersect. For each group (all promoters, gained somatic promoters and lost somatic promoters), we identified probes overlapping the predicted promoter regions and calculated average beta value differences. A two-sample Wilcoxon test was performed.

Survival Analysis

Kaplan-Meier survival analysis was used with overall survival as the outcome metric. Log-rank tests were used to assess the significance of the Kaplan-Meier analysis.

Gene Set Enrichment Analysis

Gene set enrichment analysis was performed using MsigDB by computing the overlap of genes associated with somatic promoters against the C2 set of curated genes.

Mass Spectrometry and Data Analysis

Peptide level mass spectrometry data for 90 colon and rectal cancer (CRC) samples and 60 normal colon epithelium samples were downloaded from the CPTAC portal generated by the Clinical Proteomic Tumor Analysis Consortium (NCI/NIH). (https://cptac-data-portal.georgetown.edu/cptac). Spectral counts were extracted using IDPicker's idQuery tool. Differentially expressed peptides were identified by fitting a linear model (limma R) on quantile normalized and log 2 transformed spectral counts. For GC cell line mass spectrometry, AGS, GES-1, SNU1750 and MKN1 cells were extracted with RIPA buffer supplemented with protease inhibitor. 150 μg protein extract of each biological quadruplicate (i.e. 4 replicates per cell line) were separated on a 12% NuPAGE Novel Bis-Tris precast gel (Thermo Scientific). For in-gel digestion, samples were separated into two fractions and reduced in 10 mM DTT for 1 h at 56° C. followed by alkylation with 55 mM iodoacetamide (Sigma) for 45 min in the dark. Tryptic digests were performed in 50 mM ammonium bicarbonate buffer with 2 μg trypsin (Promega) at 37° C. overnight. Peptides were desalted on StageTips and analysed by nanoflow liquid chromatography on an EASY-nLC 1200 system coupled to a Q Exactive HF mass spectrometer (Thermo Fisher Scientific). Peptides were separated on a C18-reversed phase column (25 cm long, 75 μm inner diameter) packed in-house with ReproSil-Pur C18-QAQ 1.9 μm resin (Dr Maisch). The column was mounted on an Easy Flex Nano Source and temperature controlled by a column oven (Sonation) at 40° C. A 225-min gradient from 2 to 40% acetonitrile in 0.5% formic acid at a flow of 225 nl/min was used. Spray voltage was set to 2.4 kV. The Q Exactive HF was operated with a TOP20 MS/MS spectra acquisition method per MS full scan. MS scans were conducted with 60,000 and MS/MS scans with 15,000 resolution. For data analysis, raw files were processed with MaxQuant version 1.5.2.8 against the UNIPROT annotated human protein database. Carbamidomethylation was set as a fixed modification while methionine oxidation and protein N-acetylation were considered as variable modifications. Search results were processed with MaxQuant filtered with a false discovery rate of 0.01. The match between run option and LFQ quantitation were activated. LFQ intensities were filtered for potential contaminants, reverse proteins and log 2 transformed. They were then imputed using open source software Perseus (0.5 width, 1.8 downshift) and fitted using linear models (limma R).

5'RACE and Gene Cloning

5' Rapid amplification of cDNA ends (5' RACE) was performed using 5' RACE System for Rapid Amplification of cDNA Ends, Version 2 (Invitrogen, 18374-058). Briefly, 2 μg of total RNA was used for each reverse transcription reaction with SuperScript™ II reverse transcriptase and gene-specific primer 1 for each gene. After cDNA synthesis, RNase mix (RNase H and RNase T1) was used to degrade the RNA. First strand cDNAs were then purified with S.N.A.P. columns, and tailed with dCTP and TdT. dC-tailed cDNAs were amplified using the abridged anchor primer and nested gene-specific primer 2 by Go Taq® Hot Start Polymerase (Promega, M5001). Subsequently, primary PCR products were reamplified with the abridged universal amplification primer (AUAP), and gene-specific primer 3. Gel electrophoresis was performed. PCR bands of interest were excised and purified for cloning with the TA Cloning Kit (Invitrogen, K2020). A minimum of 12 independent colonies were isolated, and purified plasmid DNA was sequenced bi-directionally on an ABI 3730 DNA analyzer (Applied Biosystems) (Table 2). Constructs for MET transcripts were generated by PCR amplification of full-length cDNAs encoding wild type and variant MET from KATOIII cells. Wild type and variant RASA3 full-length transcripts were PCR amplified from NCC59 cells. cDNA fragments were cloned into the pCI-Puro-HA vector (modified from Promega's pCI-Neo vector, a gift from Wanjin Hong, Institute of Molecular and Cell Biology, Singapore). Plasmids were transiently transfected into cell lines using Lipofectamine 3000 (Thermo Scientific).

TABLE 2

| RACE Primers | | | |
|---|---|---|---|
| Gene | Gene specific primer 1 | Gene specific primer 2 | Gene specific primer 3 |
| RASA3 | 5'GGAGTAGATACGC TCCGT3' (SEQ ID NO: 1837) | 5'CACAGCCAGTGGC CGCTCAGGTA3' (SEQ ID NO: 1838) | 5'CTTCTCCACTG CCAGGATGTT3' (SEQ ID NO: 1839) |

TABLE 2-continued

| RACE Primers | | | |
|---|---|---|---|
| Gene | Gene specific primer 1 | Gene specific primer 2 | Gene specific primer 3 |
| MET | 5'TAGGAGAATGTAC TGTAT 3' (SEQ ID NO: 1840) | 5'GGAGACACTGGAT GGGAGTC3' (SEQ ID NO: 1841) | 5'CGAGAAACCAC AACCTGCAT3' (SEQ ID NO: 1842) |

Western Blotting $3\times10^5$ HEK293 cells were seeded and transfected using Lipofectamine 3000 (Thermo Scientific). Cells were serum starved for 16 hours before addition of human HGF (R&D systems, 100 ng/ml) for 0, 15 and 30 minutes, and immediately harvested with cold Triton-X100 Lysis Buffer (50 mM Tris pH 8.0, 150 mM NaCl, 1% Triton X-100) with protease and phosphatase inhibitors (Roche) on ice. Protein concentration was measured by Pierce BCA protein assay (Thermo Scientific). Cell lysates were heated at 95° C. for 10 min in SDS sample buffer and 20 μg of each cell lysate was loaded per well. Proteins were transferred to nitrocellulose membranes. Western blotting was performed by incubating membranes 4 hrs at room temperature with the following antibodies: Met & β-actin (Santa Cruz), p-MET (Y1234/1235 & Y1349), pSTAT3 (S727 & Y705), STAT3, ERK, p-ERK, Gab1, pGab1 (Y627) (Cell Signaling). Membranes were incubated in secondary antibodies at 1:3,000 for 1 hr at room temperature and developed with SuperSignal West Femto Maximum Sensitivity substrate (Thermo Scientific) using ChemiDoc™ MP Imaging System (BIO-RAD). Western blot bands were quantified using Image Lab software (BIO-RAD). Experiments were repeated in triplicate.

Cell Proliferation Assays $3\times10^3$ GES1, SNU1967 and AGS cells were plated into 96-well plates in media with 10% fetal bovine serum and left overnight to attach. The next day (Day 0), cells were transiently transfected with wild-type and variant RASA3 constructs using Lipofectamine 3000 (Thermo Scientific). The amount of the constructs was 40 ng/well for AGS and 100 ng/well for GES1 and SNU1967 cells. Cell proliferation was measured by the WST-8 assay (Cell Counting Kit-8, Dojindo) from 24 to 120 hours post-transfection. 10 μL of WST-8 solution was added per well and the absorbance reading was measured at 450 nm after 2 hours of incubation in a humidified incubator.

Transfection with RASA3 siRNAs

Two RASA3 siRNAs were used to silence the RASA3 SomT transcript in NCC24 cells (hs.Ri.RASA3.13.1 TriFECTa® Kit DsiRNA Duplex (Integrated DNA Technologies), and Silencer® Select Pre-Designed siRNA s355 (Life Technologies)). NCC24 cells were transfected either with the above two siRNAs or a non-targeting control (ON-TARGETplus Non-targeting pool, Dharmacon) at a final concentration of 100 nM for 48 hours, subsequently followed by qPCR and western validation and migration/invasion assays.

Migration and Invasion Assays

To determine cell migratory capacities, RASA3 wild type and variant transfected AGS and GES1, SNU1967 and AGS, and siRNA treated NCC24 cells were tested using Corning Costar 6.5 mm Transwell with 8.0 μm Pore Polycarbonate Membrane Inserts (3422, Corning, NY, USA). $2.5\times10^4$ AGS cells and $2\times10^4$ GES1 cells, $3\times10^4$ SNU1967 cells and $5\times10^4$ NCC24 cells were suspended in 0.1 ml serum-free RPMI medium and added to the top of the Transwell insert. 0.6 ml RPMI containing 10% FBS was added into the bottom well as a chemoattractant. After incubation for 24 h at 37° C. in a 5% CO2 incubator, cells were fixed with 3.7% formaldehyde and permeabilized with 100% methanol. Non-migrated cells were scraped off with cotton swabs from the upper surface of the membrane. Migrated cells were stained with 0.5% crystal violet. The number of migrated cells were represented as the total area of migrated cells vs the area of transwell membrane calculated using ImageJ software. For cell invasion assays, the above Transwell inserts were coated with 0.1 ml (300 μg/mL) Corning Matrigel matrix (354234, Corning, NY, USA) for 2 to 4 h at 37° C. before use. All subsequent steps were identical to the migration assay protocol.

Measurement of RASA3 mRNA Levels

Total RNA was extracted from three independent experiments using the Qiagen RNAeasy mini kit according to manufacturer's instructions. RNA was reverse transcribed using Improm-II™ Reverse Transcriptase (Promega). Real time PCR was performed in triplicate using Quantifast SYBR Green PCR kit (Qiagen) on an Applied Biosystems HT7900 Real Time PCR System. Fold change was calculated using the Delta Ct method and normalised to β-actin. Primer sequences are as follows

```
β-actin:
                                    (SEQ ID NO: 1843)
F - 5' TCCCTGGAGAAGAGCTACG 3',

                                    (SEQ ID NO: 1844)
R - 5' GTAGTTTCGTGGATGCCACA 3';

RASA3 SomT:
                                    (SEQ ID NO: 1845)
F - 5' TTGTGAGTGGTTCAGCGGTA 3',

                                    (SEQ ID NO: 1846)
R - 5' TCAAGCGAAACCATCTCTTCT 3'.
```

RAS-GTP Assay

GES1 cells were transfected with either RASA3 CanT, RASA3 SomT or empty vector for 48 hours. Cells were harvested for protein in FBS containing media or subjected to over-night serum starvation followed by serum stimulation for 30 minutes prior to harvest. Proteins were extracted using ice-cold lysis buffer (Active RAS Pull-down and Detection Kit) containing protease inhibitor cocktail (Nacalai Tesque). Active RAS fraction was obtained using the Active RAS Pull-down and Detection Kit (Thermo Fisher Scientific) according to manufacturer's instructions. Total RAS was measured in corresponding whole cell protein lysates. β-actin was used as a loading control. Protein concentrations were determined using the Pierce BCA protein assay (Thermo Scientific). SDS sample buffer was added to the lysates and boiled at 100° C. for 5 minutes. Samples were loaded in each well of a 4-15% Mini-Protean TGX gel (Biorad) and transferred to a PVDF membrane using a semi-dry blotting system (Biorad). Membranes were probed with anti-RAS (1 in 200 dilution, supplied in Active RAS Pull-down and Detection Kit), or B-actin (1 in 5000 dilution, Sigma A5316) in 5% milk-PBST at 4° C. overnight. Secondary anti-mouse antibody (LNA931, Amersham) was used at a dilution of 1 in 2000 for 1 hour at room temperature. Membranes were developed using Amersham ECL Prime Western Blotting Detection Reagent and imaged using a Chemidoc Imaging system (Biorad).

Altered Peptide and Antigen Prediction

Altered peptides were defined as variant N-terminal protein sequences arising from somatic alterations in alternative promoter usage. The following filters were applied to select the pool of altered peptides—i) Fold change of at least 1.5 for alternate vs. canonical RNA-seq expression ii) Only one canonical and one alternate isoform per gene loci iii) Annotated transcripts are confirmed as protein coding by Gencode. Canonical promoters were defined as regions exhibiting unaltered H3K4me3 peaks. Random peptides from the human proteome were generated from amino acid sequences of Gencode coding transcripts. N-terminal peptide gains were identified as cases where the alternative transcript was associated with a different 5' region predicted to result in a different translated protein sequence compared to the canonical transcript. For each N terminal altered protein, we evaluated binding of 9-mer peptides using the NetMHCpan 2.8 using a strict threshold of IC<=50 nm to identify strong MHC binders. N-terminal gained peptides were mapped against protein assembly data of the same gene to evaluate protein expression. Antigen predictions were performed against HLA types of 13 GC samples predicted using OptiType. OptiType was run using default parameters except BWA mem was used as an aligner for pre-filtering reads aligning to the Optitype provided reference sequences. 3 samples with poor coverage and unpaired reads with mismatches were omitted from analysis. Eleven HLA-A, HLA-B, and HLA-C allelic variants of increased prevalence in the South East Asian population (HLA-A*02:07/HLA-A*11:01/HLA-A*24:02/HLA-A*33:03/HLA-A*24:07, HLA-B*13:01/HLA-B*40:01/HLA-B*46:01, HLA-C*03:04/HLA-C*07:02/HLA-C*08:01) were obtained from the Allele Frequency Net Database (http://www.allelefrequencies.net).

Association of Cytolytic Markers with Alternative Promoter Usage

Local immune cytolytic activity was evaluated using the expression of Granzyme A (GZMA) and Perforin (PRF1). Tumor content was estimated using two algorithms-ASCAT (79) (aberrant cell fraction) and ESTIMATE (tumor purity). Expression data for the SG series was downloaded (GSE15460) and normalized using the robust multi-array average algorithm in the 'affy' R package and log 2 transformed. Affymetrix SNP Array 6.0 data for the SG series was downloaded from GSE31168 and GSE85466. Mutation frequencies for TCGA STAD samples were downloaded from the TCGA STAD publication data (https://tcga-data.nci.nih.gov/docs/publications/stad_2014/) using level 2 curated MAF files (QCv5_blacklist_Pass.aggregated.capture.tcga.uuid.curated.somatic.maf) filtered for "Missense" variant classification. Expression data for TCGA STAD samples (TPM) was computed using the kallisto algorithm. Raw SNP Array 6.0.CEL files for TCGA gastric cancers (STAD) were downloaded from the GDC data portal (https://gdc-portal.nci.nih.gov/). Access to this dataset was obtained using dbGaP credentials and an ID issued by eRA commons. Precomputed ESTIMATE scores for TCGA STAD were downloaded from http://bioinformatics.mdanderson.org/estimate/and converted to tumor purity using the formula cos (0.6049872018+0.0001467884×ESTIMATE score). Preprocessed expression data for the ACRG series was downloaded from GSE62254, and pre-computed ASCAT scores obtained from collaborators (JL). Expression of cytolytic markers was adjusted for missense mutation and tumor purity frequencies using a spline regression model.

Peptides and Cells for Cytokine Assays

A set of peptides for 15 representative alternative promoters was purchased from GenScript (GenScript). Peptide sequences and composition of peptide pools for each alternative promoter are described in Table 3. Control peptide pools for human Actin were purchased from JPT (PM-ACTS, PepMix™ Human (Actin) JPT). Peripheral blood mononuclear cells (PBMCs) were obtained from 9 healthy volunteers of whom 8 PBMC samples were HLA-typed (Table 3).

TABLE 3

HLA types of healthy PBMC donors

| Sample | HLA-A | | HLA-B | | HLA-C | |
|---|---|---|---|---|---|---|
| Donor 1 | A*11:01 | A*24:02 | B*15:01 | B*51:01 | C*04:01 | C*14:02 |
| Donor 2 | A*11:01 | A*33:03 | B*40:01 | B*58:01 | C*03:02 | C*07:02 |
| Donor 3 | A*03:01 | A*33:03 | B*35:03 | B*38:01 | C*12:03 | C*12:03 |
| Donor 4 | A*02:07 | A*24:07 | B*15:02 | B*46:01 | C*01:02 | C*08:01 |
| Donor 5 | A*02:03 | A*11:01 | B*15:02 | B*51:01 | C*08:01 | C*14:02 |
| Donor 6 | A*02:01 | A*68:01 | B*15:13 | B*40:06 | C*08:01 | C*15:02 |
| Donor 7 | A*02:07 | A*33:03 | B*27:04 | B*58:01 | C*03:02 | C*12:02 |
| Donor 8 | A*02:03 | A*11:01 | B*38:02 | B*46:01 | C*01:02 | C*07:02 |
| Donor 9 | Not determined | | | | | |

EpiMAX Assay

PBMCs were labelled with 1 μM CFSE (Life Technologies, Thermo Fisher Scientific) and cultured at a density of 200,000 cells per well in complete culture medium (cRPMI comprising RPMI 1640 medium (Gibco, Thermo Fisher Scientific), 15 mM HEPES (Gibco), 1% non-essential amino acid (Gibco), 1 mM sodium pyruvate (Gibco), 1% penicillin/streptomycin (Gibco), 2 mM L-glutamine (Gibco), 50 μM β2-mercaptoethanol (Sigma, Merck), and 10% heat-inactivated FCS (Hyclone)) for 5 days. Individual peptide pools of each alternative promoter were added at the start of the culture at a concentration of 1 μg/ml for each peptide. At the end of day 5, cells were stained with LIVE/DEAD® fixable near-IR dead cell stain kit (Life Technologies), and labelled with CD4-BUV737 (BD), CD8-PacificBlue (BD), CD3-PE (BioLegend), CD19-PE/TexasRed (Beckman), and CD56-APC (BD). Analysis of T cell proliferation by CFSE dilution was performed by flow cytometry using a LSRII (BD). In addition, magnetic bead-based cytokine multiplex analysis (human cytokine panel 1, Millipore, Merck) was performed on cell culture supernatants to measure secreted cytokine levels.

IFN-γ Assay

To test the immunogenicity of the RASA3 WT and Variant protein sequences, CD14+ monocytes were isolated from a HLA-A*02:06 donor by positive selection using magnetic beads (Miltenyi, Germany). Dendritic cells were generated by GM-CSF (1000 IU/ml) and IL-4 (400 IU/ml), and further matured by TNF (10 ng/ml), IL-1b (10 ng/ml), IL-6 (10 ng/ml) (Miltenyi, Germany) and PGE2 (1 μg/ml) (Stemcell Technologies, Canada) for 24 hours. The DCs were then primed with AGS cell lysates expressing WT RASA3 or Variant RASA3 for 24 hours, before being co-cultured with T cells from the same donor at the ratio of 1:5. After 5 days of co-culture with DC, T cells were isolated by positive selection using CD3 magnetic beads (Miltenyi, Germany) and co-cultured with AGS cells expressing either WT or Variant RASA3 at the ratio of 20:1 for two days. Supernatants were harvested and IFN-γ release was measured by ELISA (R&D, USA).

NanoString Analysis

Nanostring nCounter Reporter CodeSets were designed for 95 genes (83 upregulated in GC and 11 downregulated) and 5 housekeeping genes (AGPAT1, CLIC, B2M, POL2RL and TBP covering a broad expression range) on the SG series samples. For each gene, we designed 3 probes, targeting a) 5' end of the alternate promoter location, b) 5' end of the canonical promoter (defined by promoter regions of equal enrichment in both GC and normal samples OR the longest protein coding transcript) and c) a common downstream probe. Vendor-provided nCounter software (nSolver) was used for data analysis. Raw counts were normalized using the geometric mean of the internal positive control probes included in each CodeSet.

A separate NanoString assay was designed for 88 genes on the ACRG cohort. For each gene, we designed 3 probes, targeting a) 5' end of the alternate promoter location, b) 5' end of the canonical promoter (defined by promoter regions of equal enrichment in both GC and normal samples OR the longest protein coding transcript).

Repeat Enrichment Analysis

Repetitive element families over-represented at regions exhibiting somatic promoter alterations were identified using RepeatMasker annotations from the UCSC Table Browser (GRCh37/hg19). "Unknown", "Simple_Repeat" and "Satellite" annotations were filtered from the repeat set. Repetitive elements were included only if they overlapped a promoter by a minimum of 50%. Enrichment of repetitive element families was assessed using a binomial test with Benjamini-Hochberg FDR correction and all promoter regions were used as the background.

Functional Prediction Analysis

Genome wide and tissue specific functional scores were downloaded from GenoCanyon (http://genocanyon.med.vale.edu/GenoCanyon Downloads. html, Version 1.0.3) and GenoSkyline (http://genocanyon med yale.edu/GenoSkyline) respectively. Overlaps were calculated using bedtools IntersectBed and functional scores over each unannotated somatic promoter were computed.

Transcription Factor Enrichment

Transcription factor binding sites for 237 TFs were obtained from the ReMap database, a public database of ENCODE and other public Chip-seq TFBS data sets. Overlaps were calculated and counted against the somatic promoter set. Relative enrichment scores were calculated as ratio of (#bases in state and overlap feature)/(#bases in genome) and [(#bases overlap feature)/(#bases in genome)×(#bases in state)/(#bases in genome)].

EZH2 Inhibition

IM95 were treated with GSK126 (Selleck, USA), a selective EZH2 inhibitor, at a concentration of 5 μM. Cell proliferation was monitored in 96-well plates post-treatment with GSK126 using the CellTiter-Glo® Luminescent Cell Viability Assay (Promega) for three independent experiments. For RNA-seq analysis, total RNA was extracted using the Qiagen RNAeasy mini kit according to manufacturer's instructions. Cells were treated with GSK126 (Selleck, USA; dissolved in DMSO) at a concentration of 5 μM. Control cells were treated with the same concentration of DMSO (0.1%). RNAseq differential analysis for promoter loci was carried out using edgeR on read counts mapping to H3K4me3 regions estimated using featureCounts. RNAseq gene level differential analysis was performed using cuffdiff2.2.1.

Additional Information

Accession codes: Genomic data for this study has been deposited in the National Center for Biotechnology GEO database, under accession numbers GSE51776 and GSE75898. (https://www.ncbi.nlm.nih.gov/geo/query/acc.cgi?token=kfoxgeamzfetpal&acc=GSE75898)

Results

Identifying Epigenomic Promoter Alterations in GC

Using NanoChIP-seq, we profiled three histone modification marks (H3K4me3, H3K27ac and H3K4me1) across 17 GCs, matched normal gastric mucosae (34 samples) and 13 GC cell lines, generating 110 epigenomic profiles (Tables 1 and 4 provide clinical and sequencing metrics) (FIG. 1*a*). Quality control of the Nano-ChIPseq data was performed using two independent methods: ChIP-enrichment at known promoters, and employing the ChIP-seq quality control and validation tool CHANCE (CHip-seq ANalytics and Confidence Estimation). Comparisons of Nano-ChIPseq read densities at 1,000 promoters associated with highly expressed protein-coding genes confirmed successful enrichment in all H3K27ac and H3K4me3 libraries. CHANCE analysis also revealed that the large majority (81%) of samples exhibited successful enrichment (Table 1). We have previously also shown that Nano-ChIP signals exhibit a good concordance with orthogonal ChIP-qPCR results.

TABLE 4

Clinicopathological Parameters of samples used

| Sample ID | Platform | Age | Gender | Site of Tumor | Stage (T) | Stage (N) | Stage (M) | Stage AJCC7 | Grade | Lauren's Classification | EBV status | TCGA Subtype |
|---|---|---|---|---|---|---|---|---|---|---|---|---|
| 20021007 | ChiPseq + Infinium450K | 53.8 | male | GE junction | T2b | N0 | m0 | 2A | poorly differentiated | intestinal type adenocarcinoma | unknown | GS |
| 20020720 | ChIPseq + Infinium450K | 75.2 | male | antrum | T2a | N1 | m0 | 2A | moderately differentiated | intestinal type adenocarcinoma | unknown | CIN |
| 2001206 | ChIPseq + Infinium450K | 64.8 | male | antrum | T4a | N3a | m1 | 4 | poorly differentiated | diffuse type adenocarcinoma | unknown | CIN |
| 2000877 | ChIPseq + Infinium450K | 44.6 | male | cardia | T2a | N1 | m0 | 2A | poorly differentiated | intestinal type adenocarcinoma | unknown | CIN |
| 2000085 | ChIPseq + Infinium450K | 52.6 | male | lesser curve | T2 | N0 | m0 | 1B | moderately differentiated | intestinal type adenocarcinoma | yes | GS |
| 990275 | ChIPseq + Infinium450K | 71.6 | male | lesser curve | T4a | N0 | m0 | 2B | moderately differentiated | intestinal type adenocarcinoma | no | CIN |

TABLE 4-continued

Clinicopathological Parameters of samples used

| Sample ID | Platform | Age | Gender | Site of Tumor | Stage (T) | Stage (N) | Stage (M) | Stage AJCC7 | Grade | Lauren's Classification | EBV status | TCGA Subtype |
|---|---|---|---|---|---|---|---|---|---|---|---|---|
| 990068 | ChIPseq + Infinium450K | 73.3 | male | body | T4a | N2 | m0 | 3B | poorly differentiated | diffuse type adenocarcinoma | no | GS |
| 980447 | ChIPseq + Infinium450K | 68.8 | male | lesser curve | T4a | T3b | m1 | 4 | poorly differentiated | intestinal type adenocarcinoma | unknown | CIN |
| 980436 | ChiPseq + Infinium450K | 65.0 | female | lesser curve | T4a | N1 | m0 | 3A | moderately differentiated | intestinal type adenocarcinoma | unknown | GS |
| 980401 | ChIPseq + Infinium450K | 82.9 | female | unknown | T4a | N1 | m0 | 3A | poorly differentiated | diffuse type adenocarcinoma | unknown | GS |
| 980319 | ChIPseq + Infinium450K | 67.8 | male | unknown | T4a | N1 | m0 | 3A | poorly differentiated | mixed/OTH ERS | yes | GS |
| 2000986 | ChIPseq + Infinium450K + RNA-seq | 39.0 | female | pylorus | T4a | T3b | m1 | 4 | poorly differentiated | diffuse type adenocarcinoma | unknown | GS |
| 2000721 | ChIPseq + Infinium450K + RNA-seq | 70.9 | male | lesser curve | T4a | T3b | m1 | 4 | poorly differentiated | diffuse type adenocarcinoma | yes | GS |
| 2000639 | ChIPseq + Infinium450K + RNA-seq | 69.5 | male | lesser curve | T4a | N3a | m1 | 4 | moderately differentiated | intestinal type adenocarcinoma | yes | GS |
| 980437 | ChIPseq + Infinium450K + RNA-seq | 67.8 | female | incisura | T4a | T3b | m0 | 3C | poorly differentiated | intestinal type adenocarcinoma | unknown | CIN |
| 980417 | ChIPseq + Infinium450K + RNA-seq | 67.0 | male | lesser curve | T4a | T3b | m0 | 3C | poorly differentiated | diffuse type adenocarcinoma | yes | GS |
| 980097 | ChiPseq + Infinium450K + RNAseq | 65.4 | male | unknown | T2 | N1 | m0 | 2A | undifferentiated | mixed/OTH ERS | unknown | EBV |
| 980418 | Infinium450K | 88.0 | male | greater curve | T4a | N2 | m0 | 3B | moderately differentiated | intestinal type adenocarcinoma | unknown | — |
| 57689477 | RNA-seq | 84.5 | female | greater curve | T1b | N0 | m0 | 1A | moderately differentiated | intestinal type adenocarcinoma | no | — |
| 43658255 | RNA-seq | 66.6 | male | antrum | T4a | N3a | m1 | 4 | moderately differentiated | intestinal type adenocarcinoma | unknown | — |
| 2000892 | RNA-seq | 71.3 | female | lesser curve | T2 | N1 | m0 | 2A | moderately differentiated | intestinal type adenocarcinoma | no | — |

To enable accurate promoter identification, we integrated data from multiple histone modifications, selecting H3K4me3 regions simultaneously co-depleted for H3K 4me1[42] ("H3K4me3 hi/H3K4me1 lo regions"; FIG. 7, Methods). Comparisons against data from external sources, including GENCODE reference transcripts, ENCODE chromatin-state models, and CAGE (CAP analysis gene expression) databases, validated the vast majority of H3K4me3 hi/H3K4me1 lo regions as true promoter elements (see section titled "Validation of H3K4me3 hi/H3K4me1 lo regions as true promoters" and FIG. 7). Because primary gastric tissues comprise several different tissue types, including epithelial cells, immune cells, and stroma, we further confirmed that our promoter profiles were reflective of bona-fide gastric epithelia by comparisons against Epigenome Roadmap data for gastric and non-gastric tissues. Gastric tumor and matched normal promoter profiles exhibited the highest correlations to Roadmap gastric mucosae, and were distinct from other gastrointestinal tissues (small intestine, colon mucosa, colon sigmoid), stomach-associated muscle, skin, and blood (CD14) (FIG. 8). Primary tissue promoter profiles also showed a significant overlap with promoter profiles of GC cell lines (87%), which are purely epithelial in origin, compared to gastrointestinal fibroblast lines (58-69%), and colon carcinoma lines (59-74%) (FIG. 8).

In total, we mapped ~23,000 promoter elements in the Nano-ChIPseq cohort. Visual exploration of these promoter elements identified three main promoter categories-unaltered promoters, promoters gained in tumors (gained somatic or tumor-specific promoters), and promoters present in normal gastric tissues but lost or decreased in GC (lost somatic or normal-specific promoters) (FIG. 1*a-c*). Representative examples of unaltered promoters included RhoA (FIG. 1*a*), while CEACAM6, an intracellular adhesion gene, exhibited somatic promoter gain at the CEACAM6 transcription start site (TSS) in tumor samples and cell lines (FIG. 1*b*). Conversely, ATP4A, a parietal cell-associated H+/K+ ATPase with decreased expression in GC[43], exhibited somatic promoter loss (FIG. 1*c*). Both CEACAM6 and ATP4A promoter alterations were correlated with increased and decreased CEACAM6 and ATP4A gene expression in the same samples respectively (FIGS. 1*b* and 1*c*).

Previous studies have established distinct molecular subtypes of GC. Due to limited sample sizes however, we elected in the current stay to identify promoter alterations ("somatic promoters") present in multiple GC tissues relative to control tissues irrespective of subtype. Focusing on recurrent alterations also has the benefit of reducing potential artefacts due to "private" epigenomic variation or individual sample-specific technical errors. Using two complementary read-count based algorithms commonly used for analysis of ChIP-seq data, we identified ~2000 highly recurrent somatic promoters, of which 75% were gained in GCs (FC 1.5, q<0.1). Two-dimensional heat-map clustering and principal components analysis (PCA) plots based on somatic promoters confirmed a separation of GCs from normal samples based on promoter alterations (FIG. 1*d* and FIG. 9). Somatic promoter H3K4me3 levels were also highly correlated with H3K27ac signals (r=0.91, P<0.001, FIG. 1*e*), commonly regarded as a marker of active regulatory activity. This correlation was observed across all somatic promoters (r=0.84, P<0.001, FIG. 1E), and also when gained somatic and lost somatic promoters were analyzed separately (r=0.78, P<0.001 for gained somatic; r=0.82, P<0.001 for lost somatic, FIG. 9). Pathway analysis revealed that both gained somatic and lost somatic promoters were significantly associated with expression genesets previously reported to be up and downregulated in GC respectively (FIG. 1*f*). These included upregulated oncogenes (MET, ABL2), cell adhesion genes (CEACAM6) and claudin family members (CLDN7, CLDN3). 15-18% of somatic promoters mapped to non-coding RNAs (ncRNAs), including HOTAIR and PVT1, previously associated with GC (Table 5). Additional analyses at increasing thresholds of stringency (FC from 1.5-2 and FDR from 0.1-0.001) yielded similar results, supporting the robustness of this analysis (FIG. 9). These results demonstrate that normal gastric epithelia and GCs can be distinguished on the basis of epigenomic promoter profiles.

TABLE 5

Non coding RNAs associated with Altered promoters

| Gene | H3K4Me3 (T/N) |
|---|---|
| AC004158.2 | Gain |
| AC004870.4 | Gain |
| AC005281.1 | Gain |
| AC005550.4 | Gain |
| AC007040.5 | Gain |
| AC007392.3 | Gain |
| AC009229.6 | Gain |
| AC012531.23 | Gain |
| AC016683.6 | Gain |
| AC016995.3 | Gain |
| AC019201.1 | Loss |
| AC068134.6 | Gain |
| AC069277.2 | Gain |
| AC073479.1 | Loss |
| AC079779.4 | Loss |
| AC090051.1 | Loss |
| AC092296.1 | Gain |
| AC092594.1 | Gain |
| AC092635.1 | Loss |
| AC096579.1 | Loss |
| AC096579.13 | Loss |
| AC096579.7 | Loss |
| AC116351.2 | Gain |
| AC128653.1 | Loss |
| AC131951.1 | Loss |
| AC133680.1 | Loss |
| AC140912.1 | Gain |
| AC144521.1 | Gain |
| AF127936.5 | Loss |
| AJ003147.8 | Gain |
| AL031721.1 | Gain |
| AL109618.1 | Gain |
| AL122015.1 | Gain |
| AL122127.1 | Loss |
| AL122127.2 | Loss |
| AL122127.3 | Loss |
| AL122127.4 | Loss |
| AL122127.5 | Loss |

TABLE 5-continued

Non coding RNAs associated with Altered promoters

| Gene | H3K4Me3 (T/N) |
|---|---|
| AL139319.1 | Gain |
| AP000525.9 | Gain |
| AP001065.15 | Gain |
| C11orf95 | Gain |
| C1orf132 | Loss |
| CASC9 | Gain |
| CCAT1 | Gain |
| CECR7 | Loss |
| CT49 | Gain |
| CTB-175P5.4 | Gain |
| CTC-228N24.1 | Gain |
| CTC-276P9.1 | Loss |
| CTC-480C2.1 | Gain |
| CTD-2008P7.9 | Loss |
| CTD-2147F2.1 | Gain |
| CTD-2201E18.5 | Gain |
| CTD-2314B22.1 | Gain |
| CTD-2314B22.3 | Gain |
| CTD-2532K18.1 | Gain |
| CTD-2591A6.2 | Gain |
| FENDRR | Loss |
| FZD10-AS1 | Gain |
| GS1-179L18.1 | Gain |
| GS1-259H13.2 | Gain |
| H19 | Gain |
| hsa-mir-4537 | Loss |
| hsa-mir-4538 | Loss |
| hsa-mir-4539 | Loss |
| JRK | Loss |
| LINC00237 | Gain |
| LINC00278 | Loss |
| LINC00355 | Gain |
| LINC00365 | Loss |
| LINC00393 | Gain |
| LINC00665 | Gain |
| LINC00668 | Gain |
| LINC00669 | Gain |
| LINC00675 | Loss |
| LINC00858 | Gain |
| LINC00898 | Gain |
| LINC00939 | Gain |
| LINC00960 | Gain |
| MIR1184-1 | Gain |
| MIR135B | Gain |
| MIR144 | Loss |
| MIR196B | Gain |
| MIR3147 | Gain |
| MIR3185 | Gain |
| MIR31HG | Loss |
| MIR4488 | Gain |
| MIR4634 | Gain |
| MIR663A | Gain |
| MIR663B | Loss |
| MIR935 | Gain |
| MLLT4-AS1 | Gain |
| PVT1 | Gain |
| RN7SKP258 | Gain |
| RN7SL773P | Gain |
| RNA5S17 | Gain |
| RNA5SP18 | Gain |
| RNA5SP19 | Gain |
| RNA5SP75 | Loss |
| RNU1-92P | Gain |
| RNVU1-10 | Gain |
| RP11-108K3.1 | Gain |
| RP11-138J23.1 | Gain |
| RP11-13A1.1 | Gain |
| RP11-161I10.1 | Gain |
| RP11-163N6.2 | Gain |
| RP11-168L22.2 | Gain |
| RP11-16E12.2 | Loss |
| RP11-177F15.1 | Gain |
| RP11-191L9.4 | Gain |
| RP11-211C9.1 | Gain |
| RP11-229C3.2 | Loss |
| RP11-246A10.1 | Gain |

TABLE 5-continued

Non coding RNAs associated with Altered promoters

| Gene | H3K4Me3 (T/N) |
|---|---|
| RP11-25H12.1 | Gain |
| RP11-276H19.2 | Gain |
| RP11-288G11.3 | Loss |
| RP11-299P2.1 | Loss |
| RP11-2E17.1 | Loss |
| RP11-308B16.2 | Gain |
| RP11-326A19.4 | Gain |
| RP11-346D19.1 | Gain |
| RP11-347D21.4 | Gain |
| RP11-348J24.2 | Gain |
| RP11-351J23.2 | Gain |
| RP11-356J5.12 | Gain |
| RP11-357H14.17 | Gain |
| RP11-37111.2 | Gain |
| RP1-137D17.1 | Gain |
| RP11-395B7.2 | Gain |
| RP11-3J1.1 | Gain |
| RP11-400N13.2 | Gain |
| RP11-403113.5 | Gain |
| RP11-408B11.2 | Gain |
| RP11-426L16.8 | Gain |
| RP11-431M3.1 | Loss |
| RP11-434D9.2 | Gain |
| RP11-43F13.4 | Gain |
| RP11-44H4.1 | Gain |
| RP11-44N12.5 | Gain |
| RP11-451B8.1 | Gain |
| RP11-453F18_B.1 | Gain |
| RP11-460N16.1 | Gain |
| RP11-469L4.1 | Loss |
| RP11-472N13.2 | Gain |
| RP11-48020.4 | Loss |
| RP11-499F3.2 | Gain |
| RP11-514D23.1 | Loss |
| RP11-54717.2 | Gain |
| RP11-575F12.1 | Gain |
| RP11-576D8.4 | Gain |
| RP11-599B13.3 | Loss |
| RP11-608021.1 | Gain |
| RP11-60A8.1 | Gain |
| RP11-61G19.1 | Gain |
| RP11-626G11.4 | Gain |
| RP11-626H12.1 | Gain |
| RP11-627G23.1 | Loss |
| RP11-632K5.3 | Gain |
| RP11-66B24.2 | Gain |
| RP11-66B24.7 | Gain |
| RP11-689K5.3 | Gain |
| RP1-170019.14 | Gain |
| RP1-170019.17 | Gain |
| RP11-776H12.1 | Gain |
| RP11-79P5.7 | Gain |
| RP11-809C18.5 | Gain |
| RP11-81H14.2 | Loss |
| RP11-831A10.2 | Loss |
| RP11-834C11.14 | Gain |
| RP11-834C11.6 | Loss |
| RP11-867G2.6 | Gain |
| RP11-89F3.2 | Gain |
| RP11-933H2.4 | Gain |
| RP11-963H4.3 | Loss |
| RP1-274L7.1 | Gain |
| RP13-137A17.4 | Loss |
| RP13-137A17.6 | Loss |
| RP13-379024.3 | Loss |
| RP1-63G5.5 | Gain |
| RP1-79C4.4 | Gain |
| RP3-522D1.1 | Gain |
| RP4-562J12.2 | Gain |
| RP4-594A5.1 | Gain |
| RP5-1077H22.2 | Loss |
| RP5-1121A15.3 | Gain |
| RP5-884M6.1 | Gain |
| RP5-916L7.2 | Gain |
| RP6-114E22.1 | Gain |
| SNORA31 | Gain |
| SNORA48 | Gain |
| SNORD56B | Loss |
| snoU13 | Gain |
| SOX21-AS1 | Loss |
| TPTEP1 | Loss |
| TTTY15 | Loss |
| U3 | Loss |
| U8 | Loss |

Validation of H3K4Me3 Hi/H3K4Me1 lo Regions as True Promoters

Four lines of evidence support the vast majority of H3K4me3 hi/H3K4me1 lo regions as true promoters. First, H3K4me3 hi/H3K4me1 lo regions were strongly enriched at genomic locations located 1 kb upstream of known GENCODE transcription start sites (TSSs) (FIG. 7). Second, at TSS regions, H3K4me3 signals exhibited a classical skewed bimodal intensity pattern, previously reported to be associated with promoters (FIG. 7). Third, when overlapped with regions defined by the Epigenomic Roadmap (EpiRd) 15 state model, we observed significant enrichments of H3K4me3 hi/H3K4me1 lo regions at proximal promoter states (TSSs/Regions flanking transcription sites) in gastrointestinal tissues relative to other tissues (FIG. 7). Fourth, CAGE (CAP analysis gene expression) is a specialized transcriptome sequencing method used to map gene promoters using 5' mRNA data. Integration with CAGE data from the FANTOM5 consortium revealed an 81% overlap of H3K4me3 hi/H3K4me1 lo regions with robust CAGE tag clusters. (FIG. 7).

Somatic Promoters in GC Exhibit Deregulation in Diverse Cancer Types

To explore relationships between epigenomic promoter alterations and gene expression, we analyzed RNA-seq data from the same discovery cohort (~106 million reads/sample), quantifying RNA-seq transcript reads mapping to the epigenome-guided promoter regions or directly downstream. Examining somatic promoter regions (FIG. 2A provides an illustrative example of a gained somatic promoter), we observed significantly increased expression at gained somatic promoters in GCs, and significantly decreased expression at lost somatic promoters, compared to either all promoters ($P<0.001$, FIG. 2B), or unaltered promoters ($P<0.001$, FIG. 10). Among other types of epigenetic modifications, previous studies have also reported a reciprocal relationship between active regulatory regions and DNA methylation. Using Infinium 450K DNA methylation arrays, we identified 7,505 CpG sites overlapping somatic promoter regions (5,213 sites for gained somatic promoters, 2,292 sites for lost somatic promoters). Promoters gained in GC were significantly hypomethylated compared to all promoters, ($P<0.001$, Wilcoxon test) while promoters lost in GC were hypermethylated ($P<0.001$, Wilcoxon test) (FIG. 2*b*, bottom). As DNA methylation typically occurs in CpG rich regions, (56) we then repeated the analysis focusing only on CpG island bearing promoters (Methods and Materials). Similar to the original results, CpG island bearing promoters gained in GC were significantly hypomethylated compared to all CpG island bearing promoters, ($P<0.001$, Wilcoxon test) while CpG island bearing promoters lost in GC were hypermethylated ($P<0.001$, Wilcoxon test) (FIG. 11).

To validate the somatic promoter alterations in a larger independent GC cohort and also to examine their behavior in other cancer types, we proceeded to query RNA-seq data of 354 GC samples from the TCGA consortium (n=321 GC, n=33 matched normals). To perform this analysis, RNA-seq reads from TCGA samples were mapped against the epigenome-guided somatic promoter regions defined by the discovery samples, and normalized to calculate fold change differences in expression in GC vs. normals (see Methods and Materials). Similar to the discovery series, we observed that TCGA GCs also exhibited significantly increased expression at gained somatic promoters, while lost somatic promoters exhibited decreased expression, relative to either all promoters (P<0.001, FIG. 2C) or unaltered promoters (P<0.001, FIG. 10). We further tested the tissue-specificity of the GC somatic promoters by querying RNA-seq data from other tumor types, including colon, kidney renal clear cell carcinoma (ccRCC), and lung adenocarcinoma (LUAD) (FIG. 2*d*). Almost two-thirds (n=1231, 63%, FC=1.5) of GC somatic promoters were also differentially regulated in TCGA colon cancer samples and similarly, a significant proportion of GC somatic promoters were also associated with differential RNA-seq expression in TCGA ccRCC (n=939, 48%, FC=1.5) and LUAD samples (n=1059, 54%, FC=1.5) (FIG. 2D). This result suggests that many GC somatic promoters are also likely associated with deregulated promoter activity in other solid epithelial malignancies.

Role of Alternative Promoters

By comparing the somatic promoters against the reference Gencode database (V19), we discovered extensive use of alternative promoters (18%) in GCs, defined as situations where a common unaltered promoter is present in both normal tissues and tumors (canonical promoter) but a secondary tumor-specific promoter is engaged in the latter (alternative promoter). The remaining 82% of somatic promoters corresponded to single major isoforms or unannotated transcripts (see later). 57% of the alternative promoters occurred downstream of the canonical promoter. Using multiple RNA-seq analysis methods, we confirmed that transcript isoforms driven by alternative promoters are overexpressed in GCs to a significantly greater degree than canonical promoters in the same gene (Methods and Materials, FIG. 12). For example, HNF4α, a transcription factor overexpressed in GC, is driven by two promoters (P1 and P2). At the HNF4α canonical promoter ("P2"), we observed equal promoter signals in GCs and normal tissues; however we also further observed gain of an additional promoter in GCs at a transcription start site 45 kb downstream ("P1'). Similar HNF4α P1 promoter gains were also observed in GC cell lines (FIG. 3*a*), with RNA-seq analysis supporting HNF4α P1 isoform expression in GCs. Alternative promoter usage was also observed at the EpCAM gene, frequently used to identify circulating tumor cells, causing expression of EpCAM transcript ENST00000263735.4 (FIG. 3*b*). Notably, both the HNF4α and EpCAM alternative isoforms exhibited significantly greater cancer overexpression compared to their canonical isoforms (FIG. 12). Other genes associated with tumor-specific alternative promoters, many reported for the first time, including NKX6-3 (FC 1.83, q<0.05) and GRIN2D (FC 1.9, q<0.001). A complete list of GC tumor-specific promoters is provided (Table 6).

TABLE 6

Alternative Promoters

| Loci | H3K4Me3 (T/N) | Type | Change in protein | Gene |
|---|---|---|---|---|
| chr2:69900550-69901900 | Loss | Alternate | 1 | AAK1 |
| chr2:44058400-44060450 | Gain | Alternate | 1 | ABCG5 |
| chr1:179108750-179113100 | Gain | Alternate | 1 | ABL2 |
| chr1:6451200-6453300 | Gain | Alternate | 1 | ACOT7 |
| chr7:991700-995250 | Gain | Alternate | 1 | ADAP1 |
| chr11:69811750-69814800 | Gain | Alternate | 1 | ANO1 |
| chr19:50308050-50309350 | Gain | Alternate | 1 | AP2A1 |
| chr17:36620950-36622550 | Gain | Alternate | 1 | ARHGAP23 |
| chr2:10902450-10904150 | Gain | Alternate | 1 | ATP6V1C2 |
| chr7:70060000-70066050 | Gain | Alternate | 1 | AUTS2 |
| chr18:60804550-60807050 | Loss | Alternate | 1 | BCL2 |
| chr11:1463100-1464700 | Gain | Alternate | 1 | BRSK2 |
| chr4:2038150-2039400 | Gain | Alternate | 1 | C4orf48 |
| chr21:44482600-44484300 | Gain | Alternate | 1 | CBS |
| chr3:46988600-46990000 | Gain | Alternate | 1 | CCDC12 |
| chr16:28946800-28948350 | Gain | Alternate | 1 | CD19 |
| chr6:4836100-4837550 | Gain | Alternate | 1 | CDYL |
| chr6:118985250-118986450 | Loss | Alternate | 1 | CEP85L |
| chr9:124497650-124504300 | Gain | Alternate | 1 | DAB2IP |
| chr19:6474700-6477300 | Gain | Alternate | 1 | DENND1C |
| chr4:955250-957700 | Gain | Alternate | 1 | DGKQ |
| chr16:21059250-21060650 | Gain | Alternate | 1 | DNAH3 |
| chr7:35074250-35076850 | Gain | Alternate | 1 | DPY19L1 |
| chr6:56553350-56559100 | Gain | Alternate | 1 | DST |
| chr2:47595450-47602500 | Gain | Alternate | 1 | EPCAM |
| chrX:137860100-137861300 | Gain | Alternate | 1 | FGF13 |
| chr3:69283500-69286950 | Gain | Alternate | 1 | FRMD4B |
| chr7:99774000-99776200 | Gain | Alternate | 1 | GPC2 |
| chr10:25754300-25755900 | Gain | Alternate | 1 | GPR158 |
| chr11:123458150-123465950 | Gain | Alternate | 1 | GRAMD1B |
| chr20:43029650-43032200 | Gain | Alternate | 1 | HNF4A |
| chr17:46639600-46642950 | Gain | Alternate | 1 | HOXB3 |
| chr7:23506000-23515500 | Gain | Alternate | 1 | IGF2BP3 |
| chr1:38410700-38414500 | Loss | Alternate | 1 | INPP5B |

TABLE 6-continued

| Alternative Promoters | | | | |
|---|---|---|---|---|
| Loci | H3K4Me3 (T/N) | Type | Change in protein | Gene |
| chr19:17952000-17953950 | Gain | Alternate | 1 | JAK3 |
| chr14:24891600-24897600 | Loss | Alternate | 1 | KHNYN |
| chr18:21452050-21455250 | Gain | Alternate | 1 | LAMA3 |
| chr5:154091500-154095100 | Loss | Alternate | 1 | LARP1 |
| chr5:38605950-38609550 | Loss | Alternate | 1 | LIFR |
| chr16:1013250-1015550 | Gain | Alternate | 1 | LMF1 |
| chr19:49003900-49005550 | Gain | Alternate | 1 | LMTK3 |
| chr1:156896950-156898350 | Gain | Alternate | 1 | LRRC71 |
| chr1:156893100-156894550 | Gain | Alternate | 1 | LRRC71 |
| chr1:236045300-236047550 | Loss | Alternate | 1 | LYST |
| chr20:33134200-33135900 | Gain | Alternate | 1 | MAP1LC3A |
| chr7:130125100-130127800 | Gain | Alternate | 1 | MEST |
| chr7:116363550-116365500 | Gain | Alternate | 1 | MET |
| chr3:158448250-158451400 | Gain | Alternate | 1 | MFSD1 |
| chr1:1562700-1565700 | Gain | Alternate | 1 | MIB2 |
| chr14:102700300-102702150 | Gain | Alternate | 1 | MOK |
| chr17:60756900-60758850 | Gain | Alternate | 1 | MRC2 |
| chr8:144652950-144655550 | Gain | Alternate | 1 | MROH6 |
| chr7:100607850-100613600 | Gain | Alternate | 1 | MUC12 |
| chr11:76902300-76903800 | Gain | Alternate | 1 | MYO7A |
| chr1:24434350-24435800 | Gain | Alternate | 1 | MYOM3 |
| chr6:126136250-126140700 | Loss | Alternate | 1 | NCOA7 |
| chr2:233755200-233756650 | Gain | Alternate | 1 | NGEF |
| chr2:233791350-233792700 | Gain | Alternate | 1 | NGEF |
| chr17:26119900-26121850 | Gain | Alternate | 1 | NOS2 |
| chr1:200007500-200010950 | Gain | Alternate | 1 | NR5A2 |
| chr18:55099800-55108900 | Gain | Alternate | 1 | ONECUT2 |
| chr8:107629450-107632850 | Loss | Alternate | 1 | OXR1 |
| chr4:169575100-169577200 | Loss | Alternate | 1 | PALLD |
| chr19:18364400-18366800 | Loss | Alternate | 1 | PDE4C |
| chr4:111557000-111559350 | Gain | Alternate | 1 | PITX2 |
| chr8:145009000-145018500 | Gain | Alternate | 1 | PLEC |
| chr19:49370000-49372300 | Gain | Alternate | 1 | PLEKHA4 |
| chr11:16944700-16947800 | Gain | Alternate | 1 | PLEKHA7 |
| chr1:6530450-6535000 | Gain | Alternate | 1 | PLEKHG5 |
| chr5:74990850-74992350 | Gain | Alternate | 1 | POC5 |
| chr6:35359200-35364100 | Loss | Alternate | 1 | PPARD |
| chr19:49631500-49632100 | Gain | Alternate | 1 | PPFIA3 |
| chr22:22900650-22902550 | Gain | Alternate | 1 | PRAME |
| chr9:132458700-132461300 | Gain | Alternate | 1 | PRRX2 |
| chr9:139873000-139874300 | Gain | Alternate | 1 | PTGDS |
| chr1:29562850-29565950 | Gain | Alternate | 1 | PTPRU |
| chr17:2878500-2880550 | Gain | Alternate | 1 | RAP1GAP2 |
| chr9:134548500-134553400 | Loss | Alternate | 1 | RAPGEF1 |
| chr3:24851300-24854350 | Loss | Alternate | 1 | RARB |
| chr13:114769100-114771100 | Gain | Alternate | 1 | RASA3 |
| chr20:399750-402500 | Gain | Alternate | 1 | RBCK1 |
| chr19:14088450-14090950 | Gain | Alternate | 1 | RFX1 |
| chr4:3310150-3312100 | Gain | Alternate | 1 | RGS12 |
| chr8:74035400-74036300 | Loss | Alternate | 1 | SBSPON |
| chr21:38063750-38066650 | Loss | Alternate | 1 | SIM2 |
| chr19:19215350-19217300 | Gain | Alternate | 1 | SLC25A42 |
| chr7:103021250-103022850 | Loss | Alternate | 1 | SLC26A5 |
| chr12:40425950-40427700 | Loss | Alternate | 1 | SLC2A13 |
| chr12:20975550-20976900 | Gain | Alternate | 1 | SLCO1B3 |
| chr16:68418000-68421750 | Loss | Alternate | 1 | SMPD3 |
| chr4:186729400-186734150 | Loss | Alternate | 1 | SORBS2 |
| chr2:231206350-231208750 | Gain | Alternate | 1 | SP140L |
| chr7:87854350-87856200 | Gain | Alternate | 1 | SRI |
| chr3:17734300-17735900 | Gain | Alternate | 1 | TBC1D5 |
| chr8:67866500-67867950 | Gain | Alternate | 1 | TCF24 |
| chr6:10409250-10419650 | Gain | Alternate | 1 | TFAP2A |
| chr3:129512300-129514550 | Gain | Alternate | 1 | TMCC1 |
| chr18:20910450-20912050 | Gain | Alternate | 1 | TMEM241 |
| chr2:218874000-218875450 | Gain | Alternate | 1 | TNS1 |
| chr8:141017700-141019200 | Gain | Alternate | 1 | TRAPPC9 |
| chr4:8435700-8439650 | Loss | Alternate | 1 | TRMT44 |
| chr21:45844650-45846700 | Gain | Alternate | 1 | TRPM2 |
| chrX:107016000-107021000 | Loss | Alternate | 1 | TSC22D3 |
| chr2:3371900-3374350 | Gain | Alternate | 1 | TSSC1 |
| chr17:40784750-40786950 | Loss | Alternate | 1 | TUBG2 |
| chr16:1428050-1430700 | Gain | Alternate | 1 | UNKL |
| chr12:109507100-109508350 | Gain | Alternate | 1 | USP30 |
| chr20:50719850-50723350 | Gain | Alternate | 1 | ZFP64 |

TABLE 6-continued

Alternative Promoters

| Loci | H3K4Me3 (T/N) | Type | Change in protein | Gene |
|---|---|---|---|---|
| chr4:8128400-8130450 | Gain | Alternate | 0 | ABLIM2 |
| chr16:72660100-72662050 | Gain | Alternate | 0 | AC004158.2 |
| chr2:66801200-66811950 | Gain | Alternate | 0 | AC007392.3 |
| chr2:114081700-114084050 | Gain | Alternate | 0 | AC016745.3 |
| chr19:52104750-52106000 | Loss | Alternate | 0 | AC018755.16 |
| chr2:19504600-19506400 | Gain | Alternate | 0 | AC092594.1 |
| chr2:118899750-118901550 | Gain | Alternate | 0 | AC093901.1 |
| chr17:263900-267650 | Loss | Alternate | 0 | AC108004.3 |
| chr3:18734950-18736300 | Gain | Alternate | 0 | AC144521.1 |
| chr12:109568950-109570000 | Loss | Alternate | 0 | ACACB |
| chrX:23783150-23786000 | Gain | Alternate | 0 | ACOT9 |
| chr7:5601050-5603800 | Gain | Alternate | 0 | ACTB |
| chr7:15600650-15602200 | Gain | Alternate | 0 | AGMO |
| chr21:45336050-45337600 | Loss | Alternate | 0 | AGPAT3 |
| chr15:86232000-86236800 | Loss | Alternate | 0 | AKAP13 |
| chr9:112909300-112915400 | Loss | Alternate | 0 | AKAP2 |
| chr2:241496150-241498200 | Gain | Alternate | 0 | ANKMY1 |
| chr2:242127000-242129850 | Loss | Alternate | 0 | ANO7 |
| chr5:139972550-139973900 | Gain | Alternate | 0 | APBB3 |
| chr18:24443050-24445900 | Loss | Alternate | 0 | AQP4-AS1 |
| chr4:86395150-86399900 | Loss | Alternate | 0 | ARHGAP24 |
| chr19:47362700-47367650 | Gain | Alternate | 0 | ARHGAP35 |
| chr9:35672750-35677150 | Loss | Alternate | 0 | ARHGEF39 |
| chrX:100739600-100741600 | Gain | Alternate | 0 | ARMCX4 |
| chr9:120175650-120177900 | Loss | Alternate | 0 | ASTN2 |
| chr3:193270000-193274550 | Loss | Alternate | 0 | ATP13A4 |
| chr18:77102950-77104300 | Loss | Alternate | 0 | ATP9B |
| chr1:179486050-179487950 | Loss | Alternate | 0 | AXDND1 |
| chr4:102332100-102333250 | Gain | Alternate | 0 | BANK1 |
| chr1:94046300-94051100 | Loss | Alternate | 0 | BCAR3 |
| chr11:27686500-27687900 | Gain | Alternate | 0 | BDNF-AS |
| chr20:11897750-11902000 | Loss | Alternate | 0 | BTBD3 |
| chr11:63531650-63533550 | Gain | Alternate | 0 | C11orf95 |
| chr19:30199050-30200500 | Gain | Alternate | 0 | C19orf12 |
| chr1:207991400-208001200 | Loss | Alternate | 0 | C1orf132 |
| chr6:109571700-109573350 | Gain | Alternate | 0 | C6orf183 |
| chr8:128305850-128307550 | Gain | Alternate | 0 | CASC8 |
| chr5:43409150-43412850 | Loss | Alternate | 0 | CCL28 |
| chr8:95245700-95247400 | Gain | Alternate | 0 | CDH17 |
| chr7:105603300-105604700 | Loss | Alternate | 0 | CDHR3 |
| chr7:90338500-90340500 | Loss | Alternate | 0 | CDK14 |
| chr7:29184550-29187650 | Gain | Alternate | 0 | CHN2 |
| chr15:79011600-79013200 | Gain | Alternate | 0 | CHRNB4 |
| chr7:139226300-139228850 | Gain | Alternate | 0 | CLEC2L |
| chr6:25164900-25167200 | Loss | Alternate | 0 | CMAHP |
| chr16:81684900-81687600 | Loss | Alternate | 0 | CMIP |
| chr6:37391200-37392800 | Gain | Alternate | 0 | CMTR1 |
| chr3:74662150-74664400 | Loss | Alternate | 0 | CNTN3 |
| chr11:111172600-111176650 | Loss | Alternate | 0 | COLCA1 |
| chr6:36722500-36725900 | Loss | Alternate | 0 | CPNE5 |
| chr11:85392850-85394650 | Loss | Alternate | 0 | CREBZF |
| chr16:21288600-21290700 | Gain | Alternate | 0 | CRYM |
| chr5:60597450-60601050 | Loss | Alternate | 0 | CTC-436P18.3 |
| chr15:45544050-45548600 | Loss | Alternate | 0 | CTD-2651B20.3 |
| chr20:110300-111350 | Gain | Alternate | 0 | DEFB126 |
| chr2:234326350-234331500 | Loss | Alternate | 0 | DGKD |
| chr1:223101350-223104800 | Loss | Alternate | 0 | DISP1 |
| chr11:111852050-111855050 | Loss | Alternate | 0 | DIXDC1 |
| chr13:50759600-50762100 | Gain | Alternate | 0 | DLEU1 |
| chr1:46954600-46956800 | Gain | Alternate | 0 | DMBX1 |
| chr16:30021900-30023950 | Gain | Alternate | 0 | DOC2A |
| chr6:56715250-56717500 | Gain | Alternate | 0 | DST |
| chr18:46894350-46895900 | Loss | Alternate | 0 | DYM |
| chr5:106838450-106842400 | Loss | Alternate | 0 | EFNA5 |
| chr4:111331750-111333350 | Gain | Alternate | 0 | ENPEP |
| chr14:74461400-74463450 | Loss | Alternate | 0 | ENTPD5 |
| chr19:55590850-55593800 | Gain | Alternate | 0 | EPS8L1 |
| chr5:172332450-172333000 | Loss | Alternate | 0 | ERGIC1 |
| chr1:17024500-17028900 | Gain | Alternate | 0 | ESPNP |
| chr1:216892850-216898200 | Loss | Alternate | 0 | ESRRG |
| chr1:217249050-217252200 | Loss | Alternate | 0 | ESRRG |
| chr6:36326200-36331550 | Gain | Alternate | 0 | ETV7 |
| chr12:124778800-124786100 | Loss | Alternate | 0 | FAM101A |
| chr17:47822200-47825200 | Loss | Alternate | 0 | FAM117A |

TABLE 6-continued

| Alternative Promoters | | | | |
|---|---|---|---|---|
| Loci | H3K4Me3 (T/N) | Type | Change in protein | Gene |
| chr4:187025100-187028650 | Loss | Alternate | 0 | FAM149A |
| chr1:178986050-178987900 | Loss | Alternate | 0 | FAM20B |
| chr7:102574000-102576900 | Loss | Alternate | 0 | FBXL13 |
| chr16:86529000-86534050 | Loss | Alternate | 0 | FENDRR |
| chr20:34192700-34196000 | Loss | Alternate | 0 | FER1L4 |
| chr8:124926550-124929550 | Gain | Alternate | 0 | FER1L6 |
| chr7:121942750-121947900 | Gain | Alternate | 0 | FEZF1 |
| chr12:32654200-32659150 | Loss | Alternate | 0 | FGD4 |
| chr16:86608950-86611800 | Gain | Alternate | 0 | FOXL1 |
| chr8:75230900-75235150 | Gain | Alternate | 0 | GDAP1 |
| chr7:100288750-100293000 | Gain | Alternate | 0 | GIGYF1 |
| chr11:58694450-58696550 | Loss | Alternate | 0 | GLYATL1 |
| chr5:89854500-89855350 | Loss | Alternate | 0 | GPR98 |
| chr2:165476750-165479250 | Gain | Alternate | 0 | GRB14 |
| chr9:140056700-140058300 | Gain | Alternate | 0 | GRIN1 |
| chr19:48900250-48904400 | Gain | Alternate | 0 | GRIN2D |
| chr9:104466750-104468450 | Gain | Alternate | 0 | GRIN3A |
| chr3:14642850-14644150 | Loss | Alternate | 0 | GRIP2 |
| chr11:2016000-2021350 | Gain | Alternate | 0 | H19 |
| chrX:152760450-152761150 | Gain | Alternate | 0 | HAUS7 |
| chr7:18534500-18539050 | Loss | Alternate | 0 | HDAC9 |
| chr15:83619150-83622750 | Loss | Alternate | 0 | HOMER2 |
| chr7:27159450-27164850 | Gain | Alternate | 0 | HOXA3 |
| chr7:27208400-27220700 | Gain | Alternate | 0 | HOXA9 |
| chr17:46678350-46683450 | Gain | Alternate | 0 | HOXB6 |
| chr17:46694850-46697150 | Gain | Alternate | 0 | HOXB8 |
| chr3:11178050-11179900 | Gain | Alternate | 0 | HRH1 |
| chr3:11195250-11198600 | Gain | Alternate | 0 | HRH1 |
| chr3:11265900-11269000 | Gain | Alternate | 0 | HRH1 |
| chr1:23543800-23544900 | Gain | Alternate | 0 | HTR1D |
| chrX:130711450-130713600 | Gain | Alternate | 0 | IGSF1 |
| chr17:38016450-38022250 | Loss | Alternate | 0 | IKZF3 |
| chr2:113619100-113622250 | Loss | Alternate | 0 | IL1B |
| chr4:143394250-143396200 | Gain | Alternate | 0 | INPP4B |
| chr19:2255550-2257400 | Loss | Alternate | 0 | JSRP1 |
| chr17:68071050-68073700 | Loss | Alternate | 0 | KCNJ16 |
| chr14:88788450-88791000 | Gain | Alternate | 0 | KCNK10 |
| chr4:56914350-56916700 | Gain | Alternate | 0 | KIAA1211 |
| chr10:24725650-24728200 | Loss | Alternate | 0 | KIAA1217 |
| chr11:33398050-33400750 | Gain | Alternate | 0 | KIAA1549L |
| chr15:31637200-31640250 | Loss | Alternate | 0 | KLF13 |
| chr19:55019200-55020400 | Gain | Alternate | 0 | LAIR2 |
| chr1:65991250-65992850 | Loss | Alternate | 0 | LEPR |
| chr5:78014050-78017100 | Loss | Alternate | 0 | LHFPL2 |
| chr12:113904650-113906650 | Gain | Alternate | 0 | LHX5 |
| chr22:30651400-30654850 | Gain | Alternate | 0 | LIF |
| chr20:21085550-21087550 | Gain | Alternate | 0 | LINC00237 |
| chr13:74234250-74236800 | Gain | Alternate | 0 | LINC00393 |
| chr3:8652200-8654000 | Gain | Alternate | 0 | LMCD1-AS1 |
| chr20:6031700-6033850 | Gain | Alternate | 0 | LRRN4 |
| chr3:116161150-116164900 | Gain | Alternate | 0 | LSAMP |
| chr11:1889150-1894600 | Loss | Alternate | 0 | LSP1 |
| chrX:149588950-149590100 | Gain | Alternate | 0 | MAMLD1 |
| chr1:27683050-27684600 | Loss | Alternate | 0 | MAP3K6 |
| chrX:20115700-20118300 | Loss | Alternate | 0 | MAP7D2 |
| chr3:150959500-150960300 | Gain | Alternate | 0 | MED12L |
| chr22:42148300-42150300 | Loss | Alternate | 0 | MEI1 |
| chr1:205537050-205540700 | Loss | Alternate | 0 | MFSD4 |
| chr1:22489600-22491100 | Gain | Alternate | 0 | MIR4418 |
| chr19:748150-750100 | Gain | Alternate | 0 | MISP |
| chr3:69914350-69917750 | Loss | Alternate | 0 | MITF |
| chr6:168215700-168217350 | Gain | Alternate | 0 | MLLT4-AS1 |
| chr19:1286150-1288700 | Gain | Alternate | 0 | MUM1 |
| chr19:50690700-50695700 | Gain | Alternate | 0 | MYH14 |
| chr17:73606350-73609450 | Gain | Alternate | 0 | MYO15B |
| chr17:31010250-31012000 | Gain | Alternate | 0 | MYO1D |
| chr18:55888350-55892150 | Loss | Alternate | 0 | NEDD4L |
| chr2:131965200-131968600 | Gain | Alternate | 0 | NF1P8 |
| chr14:27147750-27148900 | Gain | Alternate | 0 | NOVA1-AS1 |
| chr11:108040050-108041550 | Loss | Alternate | 0 | NPAT |
| chr7:98248450-98250250 | Gain | Alternate | 0 | NPTX2 |
| chr15:76302650-76305350 | Loss | Alternate | 0 | NRG4 |
| chr9:132370500-132373750 | Gain | Alternate | 0 | NTMT1 |
| chr3:32118200-32120100 | Gain | Alternate | 0 | OSBPL10 |

TABLE 6-continued

Alternative Promoters

| Loci | H3K4Me3 (T/N) | Type | Change in protein | Gene |
|---|---|---|---|---|
| chr19:14171500-14173250 | Loss | Alternate | 0 | PALM3 |
| chr7:32107350-32111900 | Loss | Alternate | 0 | PDE1C |
| chr3:111450850-111453300 | Loss | Alternate | 0 | PHLDB2 |
| chr12:18395250-18399450 | Loss | Alternate | 0 | PIK3C2G |
| chr8:110534900-110536100 | Loss | Alternate | 0 | PKHD1L1 |
| chr20:8094750-8096650 | Gain | Alternate | 0 | PLCB1 |
| chr1:6544500-6545600 | Gain | Alternate | 0 | PLEKHG5 |
| chr22:41990400-41991450 | Gain | Alternate | 0 | PMM1 |
| chr6:31150550-31154950 | Loss | Alternate | 0 | POU5F1 |
| chr11:7626600-7631400 | Loss | Alternate | 0 | PPFIBP2 |
| chr2:182895050-182896750 | Gain | Alternate | 0 | PPP1R1C |
| chr8:143759850-143765700 | Loss | Alternate | 0 | PSCA |
| chr8:27237450-27239750 | Loss | Alternate | 0 | PTK2B |
| chr8:142384050-142385550 | Gain | Alternate | 0 | PTP4A3 |
| chr9:96767600-96770450 | Loss | Alternate | 0 | PTPDC1 |
| chr12:120661250-120664850 | Loss | Alternate | 0 | PXN |
| chr18:52384600-52386250 | Loss | Alternate | 0 | RAB27B |
| chr11:82706750-82709350 | Loss | Alternate | 0 | RAB30 |
| chr8:95485350-95488300 | Gain | Alternate | 0 | RAD54B |
| chr4:82964050-82966400 | Gain | Alternate | 0 | RASGEF1B |
| chr4:40512300-40518850 | Loss | Alternate | 0 | RBM47 |
| chr9:116225550-116228700 | Gain | Alternate | 0 | RGS3 |
| chr10:62758000-62762450 | Loss | Alternate | 0 | RHOBTB1 |
| chr8:104510350-104514700 | Gain | Alternate | 0 | RIMS2 |
| chr21:38379100-38379750 | Gain | Alternate | 0 | RIPPLY3 |
| chr8:61324800-61327100 | Gain | Alternate | 0 | RP11-163N6.2 |
| chr20:6301750-6304300 | Gain | Alternate | 0 | RP11-199014.1 |
| chr3:187606800-187608950 | Gain | Alternate | 0 | RP11-30015.1 |
| chr1:39191950-39194400 | Loss | Alternate | 0 | RP11-334L9.1 |
| chr11:112140350-112142500 | Gain | Alternate | 0 | RP11-356J5.12 |
| chr6:82809950-82812100 | Gain | Alternate | 0 | RP11-379B8.1 |
| chr14:39702300-39706400 | Loss | Alternate | 0 | RP11-407N17.3 |
| chr1:203394800-203398950 | Gain | Alternate | 0 | RP11-435P24.3 |
| chr9:72091300-72092650 | Gain | Alternate | 0 | RP11-470P21.2 |
| chr15:82161650-82163400 | Gain | Alternate | 0 | RP11-499F3.2 |
| chr4:88631250-88631950 | Gain | Alternate | 0 | RP11-742B18.1 |
| chr11:94372300-94374550 | Gain | Alternate | 0 | RP11-867G2.5 |
| chr3:131049650-131051500 | Gain | Alternate | 0 | RP11-933H2.4 |
| chr17:10746250-10749200 | Loss | Alternate | 0 | RP11-963H4.3 |
| chr6:85334900-85337050 | Gain | Alternate | 0 | RP1-90L14.1 |
| chr7:156735150-156736500 | Gain | Alternate | 0 | RP5-1121A15.3 |
| chr2:55236200-55238400 | Loss | Alternate | 0 | RTN4 |
| chr16:51186150-51187850 | Loss | Alternate | 0 | SALL1 |
| chr2:200326950-200329550 | Gain | Alternate | 0 | SATB2 |
| chr3:53031650-53034600 | Gain | Alternate | 0 | SFMBT1 |
| chr14:71849000-71850350 | Loss | Alternate | 0 | SIPA1L1 |
| chr1:232760700-232767700 | Gain | Alternate | 0 | SIPA1L2 |
| chr7:100448750-100451750 | Gain | Alternate | 0 | SLC12A9 |
| chr12:105344050-105348050 | Loss | Alternate | 0 | SLC41A2 |
| chr6:31843950-31847850 | Loss | Alternate | 0 | SLC44A4 |
| chr1:75840850-75842350 | Gain | Alternate | 0 | SLC44A5 |
| chr1:205637750-205639250 | Gain | Alternate | 0 | SLC45A3 |
| chr11:26985950-26987450 | Gain | Alternate | 0 | SLC5A12 |
| chr14:23622000-23623950 | Loss | Alternate | 0 | SLC7A8 |
| chr22:31459200-31461650 | Gain | Alternate | 0 | SMTN |
| chr20:10197250-10201300 | Gain | Alternate | 0 | SNAP25-AS1 |
| chr16:1842850-1844950 | Loss | Alternate | 0 | SPSB3 |
| chr11:4010850-4011700 | Loss | Alternate | 0 | STIM1 |
| chr8:99951150-99961750 | Gain | Alternate | 0 | STK3 |
| chr7:23761400-23764000 | Gain | Alternate | 0 | STK31 |
| chr1:110573450-110574700 | Loss | Alternate | 0 | STRIP1 |
| chr7:73131100-73134700 | Gain | Alternate | 0 | STX1A |
| chr20:46411750-46414250 | Gain | Alternate | 0 | SULF2 |
| chr12:79438650-79440250 | Gain | Alternate | 0 | SYT1 |
| chr15:57509850-57515600 | Loss | Alternate | 0 | TCF12 |
| chr12:110411050-110419200 | Gain | Alternate | 0 | TCHP |
| chr21:32640100-32641350 | Loss | Alternate | 0 | TIAM1 |
| chr19:3707600-3711250 | Loss | Alternate | 0 | TJP3 |
| chr10:102830000-102833650 | Loss | Alternate | 0 | TLX1NB |
| chr2:228241600-228244450 | Gain | Alternate | 0 | TM4SF20 |
| chr16:19427700-19435900 | Gain | Alternate | 0 | TMC5 |
| chr7:47490900-47493500 | Loss | Alternate | 0 | TNS3 |
| chr8:144436800-144438000 | Gain | Alternate | 0 | TOP1MT |
| chr13:45955000-45957700 | Gain | Alternate | 0 | TPT1-AS1 |

TABLE 6-continued

| Alternative Promoters | | | | |
|---|---|---|---|---|
| Loci | H3K4Me3 (T/N) | Type | Change in protein | Gene |
| chr17:3459750-3462900 | Loss | Alternate | 0 | TRPV3 |
| chr3:12522200-12524700 | Gain | Alternate | 0 | TSEN2 |
| chr22:46683150-46685350 | Loss | Alternate | 0 | TTC38 |
| chr6:133003800-133008900 | Gain | Alternate | 0 | VNN1 |
| chr15:53831700-53833550 | Gain | Alternate | 0 | WDR72 |
| chr11:102617350-102619450 | Gain | Alternate | 0 | WTAPP1 |
| chr11:68436350-68438200 | Gain | Alternate | 0 | Novel Gene |
| chr12:125226400-125228400 | Loss | Alternate | 0 | Novel Gene |
| chr12:89240400-89241750 | Gain | Alternate | 0 | Novel Gene |
| chr14:99752650-99754000 | Loss | Alternate | 0 | Novel Gene |
| chr18:76805850-76809250 | Gain | Alternate | 0 | Novel Gene |
| chr19:53560600-53562700 | Gain | Alternate | 0 | Novel Gene |
| chr2:45227500-45229600 | Gain | Alternate | 0 | Novel Gene |
| chr2:134784950-134786450 | Gain | Alternate | 0 | Novel Gene |
| chr2:176458500-176460750 | Gain | Alternate | 0 | Novel Gene |
| chr20:46600150-46603250 | Gain | Alternate | 0 | Novel Gene |
| chr4:10830100-10832350 | Gain | Alternate | 0 | Novel Gene |
| chr5:35404300-35405800 | Gain | Alternate | 0 | Novel Gene |
| chr5:42999400-43001150 | Gain | Alternate | 0 | Novel Gene |
| chr5:72496650-72498300 | Gain | Alternate | 0 | Novel Gene |
| chr1:204682350-204684550 | Loss | Alternate | 0 | Novel Gene |
| chr6:868400-871100 | Loss | Alternate | 0 | Novel Gene |
| chr1:220635500-220637400 | Gain | Alternate | 0 | Novel Gene |
| chr6:47146850-47150550 | Loss | Alternate | 0 | Novel Gene |
| chr6:160720200-160722150 | Gain | Alternate | 0 | Novel Gene |
| chr6:170474550-170475800 | Gain | Alternate | 0 | Novel Gene |
| chr1:242107250-242109450 | Gain | Alternate | 0 | Novel Gene |
| chr7:27274550-27276500 | Gain | Alternate | 0 | Novel Gene |
| chr9:17905350-17908250 | Loss | Alternate | 0 | Novel Gene |
| chr9:31848250-31849950 | Gain | Alternate | 0 | Novel Gene |
| chrX:56133300-56134800 | Gain | Alternate | 0 | Novel Gene |
| chrX:3466450-3468750 | Gain | Alternate | 0 | Novel Gene |
| chrX:6849150-6851300 | Gain | Alternate | 0 | Novel Gene |
| chr11:60941900-60945700 | Loss | Alternate | 0 | Novel Gene |
| chr11:71350450-71351500 | Gain | Alternate | 0 | Novel Gene |
| chr11:119775600-119779600 | Loss | Alternate | 0 | Novel Gene |
| chr5:82391600-82392950 | Gain | Alternate | 0 | XRCC4 |
| chr3:141107100-141108400 | Loss | Alternate | 0 | ZBTB38 |
| chr18:45660800-45664950 | Loss | Alternate | 0 | ZBTB7C |
| chr13:100619800-100623100 | Gain | Alternate | 0 | ZIC5 |
| chr2:180425300-180426950 | Loss | Alternate | 0 | ZNF385B |
| chr19:53539900-53541600 | Gain | Alternate | 0 | ZNF702P |

To explore the influence of alternative promoters on protein diversity, we identified 714 tumor-specific promoter alterations predicted to change N-terminal protein composition and also supported by both H3K4me3 and RNA-seq data. The vast majority of these alterations (>95%) were in-frame to that of the canonical protein. Of these, 47% (n=338) were predicted to cause gains of new N-terminal peptides in tumors (see Methods). To confirm protein-level expression of these N-terminal peptides in gastrointestinal cancer, we queried publically available peptide spectral data of 90 TCGA colorectal cancer (CRC) and 60 normal colon samples. CRC data was used for this analysis as large-scale proteomic data of primary GCs are not currently available, and because many GC somatic promoters are also observed in CRC (FIG. 2*d*). Among N-terminal peptides predicted to be gained in tumors, we confirmed protein expression of 33% (112/338) in the CRC data (Table 7), of which 51.8% were overexpressed in CRC samples relative to normal colon samples (FDR 10%). In a separate experiment, we further investigated if these N-terminal peptides also exhibit tumor overexpression in proteomic data from 3 GC cell lines and 1 normal gastric epithelial line (GES1) (Methods and Materials). Similar to the CRC data, 48% of the N-terminal peptides were overexpressed in the GC lines relative to normal GES1 gastric cells. Taken collectively, these analyses suggest that alternative promoters may contribute significantly towards proteomic diversity in gastrointestinal cancer.

TABLE 7

| Spectral Counts from CRC samples of N terminal peptides predicted to be gained in GC | | | |
|---|---|---|---|
| SEQ_ID_NO | Peptide | Geneld | SpectralCount |
| SEQ ID NO: 1 | IDNSQVESGSLEDDWDFLPPKK | ENSG00000179218.9 | 2602 |
| SEQ ID NO: 2 | FYALSASFEPFSNK | ENSG00000179218.9 | 2047 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 3 | EQFLDGDGWTSR | ENSG00000179218.9 | 1370 |
| SEQ ID NO: 4 | IKDPDASKPEDWDER | ENSG00000179218.9 | 805 |
| SEQ ID NO: 5 | GDVTAQIALQPALK | ENSG00000112096.12 | 601 |
| SEQ ID NO: 6 | GISLNPEQWSQLK | ENSG00000113387.7 | 536 |
| SEQ ID NO: 7 | AYHSFLVEPISCHAWNK | ENSG00000130429.8 | 497 |
| SEQ ID NO: 8 | IAVQPGTVGPQGR | ENSG00000134871.13 | 468 |
| SEQ ID NO: 9 | VLAQNSGFDLQETLVK | ENSG00000146731.6 | 435 |
| SEQ ID NO: 10 | CKDDEFTHLYTLIVRPDNTYEVK | ENSG00000179218.9 | 424 |
| SEQ ID NO: 11 | AKIDDPTDSKPEDWDKPEHIPDP DAK | ENSG00000179218.9 | 414 |
| SEQ ID NO: 12 | VHVIFNYK | ENSG00000179218.9 | 396 |
| SEQ ID NO: 13 | HEQNIDCGGGYVK | ENSG00000179218.9 | 361 |
| SEQ ID NO: 14 | LIDFGLAR | ENSG00000065534.14 | 359 |
| SEQ ID NO: 15 | TWKPTLVILR | ENSG00000130429.8 | 358 |
| SEQ ID NO: 16 | AIWNVINWENVTER | ENSG00000112096.12 | 353 |
| SEQ ID NO: 17 | IDDPTDSKPEDWDKPEHIPDPDA K | ENSG00000179218.9 | 323 |
| SEQ ID NO: 18 | NVRPDYLK | ENSG00000112096.12 | 320 |
| SEQ ID NO: 19 | NSVSQISVLSGGK | ENSG00000130429.8 | 317 |
| SEQ ID NO: 20 | DGNVLLHEMQIQHPTASLIAK | ENSG00000146731.6 | 314 |
| SEQ ID NO: 21 | AGATHVER | ENSG00000145016.9 | 311 |
| SEQ ID NO: 22 | LVALLNTLDR | ENSG00000119383.15 | 298 |
| SEQ ID NO: 23 | HHAAYVNNLNVTEEK | ENSG00000112096.12 | 296 |
| SEQ ID NO: 24 | FYGDEEKDKGLQTSQDAR | ENSG00000179218.9 | 290 |
| SEQ ID NO: 25 | KVHVIFNYK | ENSG00000179218.9 | 283 |
| SEQ ID NO: 26 | GPLPAAPPVAPER | ENSG00000115310.13 | 282 |
| SEQ ID NO: 27 | VLLSALER | ENSG00000100714.11 | 277 |
| SEQ ID NO: 28 | SVSIGYLLVK | ENSG00000134871.13 | 276 |
| SEQ ID NO: 29 | IQQEIAVQNPLVSER | ENSG00000167770.7 | 271 |
| SEQ ID NO: 30 | GELLEAIKR | ENSG00000112096.12 | 268 |
| SEQ ID NO: 31 | AHNQDLGLAGSCLAR | ENSG00000134871.13 | 265 |
| SEQ ID NO: 32 | YVVVTGITPTPLGEGK | ENSG00000100714.11 | 256 |
| SEQ ID NO: 33 | MEDLDQSPLVSSSDSPPRPQPAF K | ENSG00000115310.13 | 254 |
| SEQ ID NO: 34 | AAQAPSSFOLLYDLK | ENSG00000100714.11 | 253 |
| SEQ ID NO: 35 | LQAQLNELQAQLSQK | ENSG00000137497.13 | 250 |
| SEQ ID NO: 36 | ALQFLEEVK | ENSG00000146731.6 | 244 |
| SEQ ID NO: 37 | LLTSGYLQR | ENSG00000167770.7 | 242 |
| SEQ ID NO: 38 | GDLNDCFIPCTPK | ENSG00000100714.11 | 241 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 39 | ASSEGGTAAGAGLDSLHK | ENSG00000130429.8 | 240 |
| SEQ ID NO: 40 | EAVTEILGIEPDREK | ENSG00000211460.7 | 236 |
| SEQ ID NO: 41 | EVEERPAPTPWGSK | ENSG00000130429.8 | 235 |
| SEQ ID NO: 42 | IITEGFEAAK | ENSG00000146731.6 | 235 |
| SEQ ID NO: 43 | YLNIFGESQPNPK | ENSG00000004864.9 | 234 |
| SEQ ID NO: 44 | LTAASVGVQGSGWGWLGFNK | ENSG00000112096.12 | 229 |
| SEQ ID NO: 45 | IAPLEEGTLPFNLAEAQR | ENSG00000004864.9 | 221 |
| SEQ ID NO: 46 | GQTLVVQFTVK | ENSG00000179218.9 | 220 |
| SEQ ID NO: 47 | AQLGVQAFADALLIIPK | ENSG00000146731.6 | 217 |
| SEQ ID NO: 48 | QVAPEKPVK | ENSG00000113387.7 | 217 |
| SEQ ID NO: 49 | VATAQDDITGDGTTSNVLIIGELL K | ENSG00000146731.6 | 215 |
| SEQ ID NO: 50 | GLLPQLLGVAPEK | ENSG00000004864.9 | 214 |
| SEQ ID NO: 51 | NAYVWTLK | ENSG00000130429.8 | 214 |
| SEQ ID NO: 52 | IYGADDIELLPEAQHK | ENSG00000100714.11 | 211 |
| SEQ ID NO: 53 | CHAIIDEQPLIFK | ENSG00000169756.12 | 210 |
| SEQ ID NO: 54 | KGISLNPEQWSQLK | ENSG00000113387.7 | 209 |
| SEQ ID NO: 55 | GIDPFSLDALSK | ENSG00000146731.6 | 207 |
| SEQ ID NO: 56 | LLQCYPPPEDAAVK | ENSG00000196961.8 | 207 |
| SEQ ID NO: 57 | GVPTGFILPIR | ENSG00000100714.11 | 204 |
| SEQ ID NO: 58 | IVTCGTDR | ENSG00000130429.8 | 204 |
| SEQ ID NO: 59 | TPVPSDIDISR | ENSG00000100714.11 | 203 |
| SEQ ID NO: 60 | YQEALAK | ENSG00000112096.12 | 198 |
| SEQ ID NO: 61 | VAWVSHDSTVCLADADKK | ENSG00000130429.8 | 197 |
| SEQ ID NO: 62 | LDIDPETITWQR | ENSG00000100714.11 | 194 |
| SEQ ID NO: 63 | IDNSQVESGSLEDDWDFLPPK | ENSG00000179218.9 | 192 |
| SEQ ID NO: 64 | LAILQVGNR | ENSG00000100714.11 | 192 |
| SEQ ID NO: 65 | AQAALAVNISAAR | ENSG00000146731.6 | 191 |
| SEQ ID NO: 66 | GALALAQAVQR | ENSG00000100714.11 | 189 |
| SEQ ID NO: 67 | TDPTTLTDEEINR | ENSG00000100714.11 | 189 |
| SEQ ID NO: 68 | LELSVLYK | ENSG00000167770.7 | 188 |
| SEQ ID NO: 69 | GLDGYQGPDGPR | ENSG00000134871.13 | 187 |
| SEQ ID NO: 70 | LSGLEQPQGALQTR | ENSG00000133316.11 | 184 |
| SEQ ID NO: 71 | SCQTALVEILDVIVR | ENSG00000067704.8 | 182 |
| SEQ ID NO: 72 | DDNMFQIGK | ENSG00000113387.7 | 181 |
| SEQ ID NO: 73 | EHNGQVTGIDWAPESNR | ENSG00000130429.8 | 179 |
| SEQ ID NO: 74 | KIKDPDASKPEDWDER | ENSG00000179218.9 | 178 |
| SEQ ID NO: 75 | MFGIPVVVAVNAFK | ENSG00000100714.11 | 178 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 76 | FFEHFIEGGR | ENSG00000167770.7 | 177 |
| SEQ ID NO: 77 | IFHELTQTDK | ENSG00000100714.11 | 174 |
| SEQ ID NO: 78 | FINLFPETK | ENSG00000196961.8 | 172 |
| SEQ ID NO: 79 | FYGDEEKDK | ENSG00000179218.9 | 172 |
| SEQ ID NO: 80 | FNGGGHINHSIFWTNLSPNGGG EPK | ENSG00000112096.12 | 169 |
| SEQ ID NO: 81 | DPDASKPEDWDER | ENSG00000179218.9 | 16 |
| SEQ ID NO: 82 | LGSPDYGNSALLSLPGYRPTTR | ENSG00000137497.13 | 168 |
| SEQ ID NO: 83 | ASGDSARPVLLQVAESAYR | ENSG00000004864.9 | 167 |
| SEQ ID NO: 84 | TDTESELDLISR | ENSG00000100714.11 | 166 |
| SEQ ID NO: 85 | LDFVCSFLOK | ENSG00000137497.13 | 165 |
| SEQ ID NO: 86 | WIDETPPVDQPSR | ENSG00000119383.15 | 165 |
| SEQ ID NO: 87 | GLLGALTSTPYSPTQHLER | ENSG00000153310.14 | 164 |
| SEQ ID NO: 88 | KPEDWDEEMDGEWEPPVIQNP EYK | ENSG00000179218.9 | 162 |
| SEQ ID NO: 89 | FSDIQIR | ENSG00000100714.11 | 160 |
| SEQ ID NO: 90 | STSFNVQDLLPDHEYK | ENSG00000065534.14 | 160 |
| SEQ ID NO: 91 | GEQGFMGNTGPTGAVGDR | ENSG00000134871.13 | 159 |
| SEQ ID NO: 92 | QPSQGPTFGIK | ENSG00000100714.11 | 157 |
| SEQ ID NO: 93 | THLSLSHNPEQK | ENSG00000100714.11 | 157 |
| SEQ ID NO: 94 | APVPSTCSSTFPEELSPPSHQAK | ENSG00000137497.13 | 155 |
| SEQ ID NO: 95 | GEGGTTNPHIFPEGSEPK | ENSG00000167770.7 | 155 |
| SEQ ID NO: 96 | TALAEAELEYNPEHVSR | ENSG00000067704.8 | 155 |
| SEQ ID NO: 97 | FPLLKPSPK | ENSG00000067704.8 | 154 |
| SEQ ID NO: 98 | DQAANLMANR | ENSG00000198947.10 | 153 |
| SEQ ID NO: 99 | HLTAQVR | ENSG00000137497.13 | 153 |
| SEQ ID NO: 100 | FVLSSGK | ENSG00000179218.9 | 149 |
| SEQ ID NO: 101 | SSLPPVLGTESDATVK | ENSG00000065534.14 | 148 |
| SEQ ID NO: 102 | AWGAVVPLVGK | ENSG00000153310.14 | 146 |
| SEQ ID NO: 103 | IEGYPDPEVVWFK | ENSG00000065534.14 | 145 |
| SEQ ID NO: 104 | GKNVLINK | ENSG00000179218.9 | 144 |
| SEQ ID NO: 105 | GLQTSQDAR | ENSG00000179218.9 | 144 |
| SEQ ID NO: 106 | HTLTQIK | ENSG00000146731.6 | 144 |
| SEQ ID NO: 107 | VHAELADVLTEAVVDSILAIK | ENSG00000146731.6 | 144 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 108 | YVIHTVGPIAYGEPSASQAAELR | ENSG00000133315.6 | 142 |
| SEQ ID NO: 109 | IQSSHNFQLESVNK | ENSG00000135052.12 | 14 |
| SEQ ID NO: 110 | QIDNPDYK | ENSG00000179218.9 | 140 |
| SEQ ID NO: 111 | DAEGILEDLQSYR | ENSG00000153310.14 | 139 |
| SEQ ID NO: 112 | YTAESSDTLCPR | ENSG00000067704.8 | 139 |
| SEQ ID NO: 113 | EESREPAPASPAPAGVEIR | ENSG00000113657.8 | 138 |
| SEQ ID NO: 114 | EMDRETLIDVAR | ENSG00000146731.6 | 138 |
| SEQ ID NO: 115 | NEVSFVIHNLPVLAK | ENSG00000086475.10 | 138 |
| SEQ ID NO: 116 | QVAPEKPVKK | ENSG00000113387.7 | 137 |
| SEQ ID NO: 117 | FLINLEGGDIR | ENSG00000067704.8 | 136 |
| SEQ ID NO: 118 | LSVNSVTAGDYSR | ENSG00000211460.7 | 135 |
| SEQ ID NO: 119 | QAQVNLTVVDKPDPPAGTPCAS DIR | ENSG00000065534.14 | 135 |
| SEQ ID NO: 120 | IFDDVSSGVSQLASK | ENSG00000101199.8 | 134 |
| SEQ ID NO: 121 | PDASKPEDWDER | ENSG00000179218.9 | 134 |
| SEQ ID NO: 122 | YGGAPQALTLK | ENSG00000196961.8 | 132 |
| SEQ ID NO: 123 | LVTPGETPSWTGSGFVR | ENSG00000172037.9 | 131 |
| SEQ ID NO: 124 | EQISDIDDAVR | ENSG00000113387.7 | 129 |
| SEQ ID NO: 125 | KPAAGLSAAPVPTAPAAGAPLM DFGNDFVPPAPR | ENSG00000115310.13 | 129 |
| SEQ ID NO: 126 | ATSSTQSLAR | ENSG00000137497.13 | 128 |
| SEQ ID NO: 127 | LLVPTQFVGAIIGK | ENSG00000136231.9 | 128 |
| SEQ ID NO: 128 | GELLEAIK | ENSG00000112096.12 | 126 |
| SEQ ID NO: 129 | FFQPTEMAAQDFFQR | ENSG00000196961.8 | 124 |
| SEQ ID NO: 130 | GSGSRPGIEGDTPR | ENSG00000113657.8 | 121 |
| SEQ ID NO: 131 | NAIDDGCVVPGAGAVEVAMAE ALIK | ENSG00000146731.6 | 121 |
| SEQ ID NO: 132 | AAAAAAVGPGAGGAGSAVPGG AGPCATVSVFPGAR | ENSG00000142453.7 | 120 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 133 | DFLTPPLLSVR | ENSG00000196961.8 | 120 |
| SEQ ID NO: 134 | LFVVPADEAQAR | ENSG00000105223.14 | 120 |
| SEQ ID NO: 135 | WMIQYNNLNLK | ENSG00000100714.11 | 120 |
| SEQ ID NO: 136 | SLPISLVFLVPVR | ENSG00000169896.12 | 119 |
| SEQ ID NO: 137 | ALQVGCLLR | ENSG00000196961.8 | 118 |
| SEQ ID NO: 138 | ESFNPESYELDK | ENSG00000086475.10 | 118 |
| SEQ ID NO: 139 | TGWISTSSIWK | ENSG00000067704.8 | 118 |
| SEQ ID NO: 140 | EYAEDDNIYQQK | ENSG00000167770.7 | 117 |
| SEQ ID NO: 141 | TQIAICPNNHEVHIYEK | ENSG00000130429.8 | 117 |
| SEQ ID NO: 142 | SLEAQVAHADQQLR | ENSG00000137497.13 | 116 |
| SEQ ID NO: 143 | SVTLLIK | ENSG00000146731.6 | 116 |
| SEQ ID NO: 144 | IHFVPGWDCHGLPIEIK | ENSG00000067704.8 | 115 |
| SEQ ID NO: 145 | QQPDTELEIQQK | ENSG00000067704.8 | 115 |
| SEQ ID NO: 146 | KGEPVSAEDLGVSGALTVLMK | ENSG00000100714.11 | 114 |
| SEQ ID NO: 147 | LGIGMDTCVIPLR | ENSG00000086475.10 | 113 |
| SEQ ID NO: 148 | QPSWDPSPVSSTVPAPSPLSAAAVSPSK | ENSG00000115310.13 | 113 |
| SEQ ID NO: 149 | QISEGVEYIHK | ENSG00000065534.14 | 109 |
| SEQ ID NO: 150 | SEGGTAAGAGLDSLHK | ENSG00000130429.8 | 108 |
| SEQ ID NO: 151 | PTGFILPIR | ENSG00000100714.11 | 107 |
| SEQ ID NO: 152 | SQAGVSSGAPPGR | ENSG00000137497.13 | 107 |
| SEQ ID NO: 153 | VCGDSDKGFVVINQK | ENSG00000146731.6 | 107 |
| SEQ ID NO: 154 | LGIVQGIVGAR | ENSG00000172037.9 | 104 |
| SEQ ID NO: 155 | FLSLPEVR | ENSG00000106066.9 | 103 |
| SEQ ID NO: 156 | GLVLDHGAR | ENSG00000146731.6 | 102 |
| SEQ ID NO: 157 | LKNQVTQLK | ENSG00000100714.11 | 102 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 158 | TSVQFQNFSPTVVHPGDLQTQLAVQTK | ENSG00000196961.8 | 102 |
| SEQ ID NO: 159 | EPPYGADVLR | ENSG00000067704.8 | 101 |
| SEQ ID NO: 160 | AAGPLLTDECR | ENSG00000133315.6 | 100 |
| SEQ ID NO: 161 | IIEVAPQVATQNVNPTPGATS | ENSG00000086475.10 | 100 |
| SEQ ID NO: 162 | LFSQGQDVSNK | ENSG00000130396.16 | 100 |
| SEQ ID NO: 163 | VSGPWEEADAEAVAR | ENSG00000090006.13 | 100 |
| SEQ ID NO: 164 | VTGTQPITCTWMK | ENSG00000065534.14 | 100 |
| SEQ ID NO: 165 | VLIDIR | ENSG00000113387.7 | 99 |
| SEQ ID NO: 166 | AVLEEGTDVVIK | ENSG00000067704.8 | 98 |
| SEQ ID NO: 167 | QFAEILHFTLR | ENSG00000153310.14 | 97 |
| SEQ ID NO: 168 | IVGAPMHDLLLWNNATVTTCHSK | ENSG00000100714.11 | 96 |
| SEQ ID NO: 169 | AYIQENLELVEK | ENSG00000100714.11 | 95 |
| SEQ ID NO: 170 | EIGLLSEEVELYGETK | ENSG00000100714.11 | 95 |
| SEQ ID NO: 171 | DSFLGSIPGK | ENSG00000067704.8 | 94 |
| SEQ ID NO: 172 | QLDALLEALK | ENSG00000172037.9 | 94 |
| SEQ ID NO: 173 | IIDEDFELTER | ENSG00000065534.14 | 93 |
| SEQ ID NO: 174 | DTINLLDQR | ENSG00000135052.12 | 92 |
| SEQ ID NO: 175 | VVQSLEQTAR | ENSG00000211460.7 | 92 |
| SEQ ID NO: 176 | DDSNLYINVK | ENSG00000100714.11 | 90 |
| SEQ ID NO: 177 | VSGQPQSVTASSDK | ENSG00000101199.8 | 90 |
| SEQ ID NO: 178 | EFCQQEVEPMCK | ENSG00000167770.7 | 89 |
| SEQ ID NO: 179 | AGNSLAASTAEETAGSAQGR | ENSG00000172037.9 | 88 |
| SEQ ID NO: 180 | EYWMDPEGEMKPGR | ENSG00000113387.7 | 88 |
| SEQ ID NO: 181 | LQSQLLSIEK | ENSG00000106976.14 | 88 |
| SEQ ID NO: 182 | AGESVELFGK | ENSG00000065534.14 | 86 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 183 | NGEFFMSPNDFVTR | ENSG00000004864.9 | 86 |
| SEQ ID NO: 184 | VVVGAPQEIVAANQR | ENSG00000169896.12 | 86 |
| SEQ ID NO: 185 | SQAPLESSLDSLGDVFLDSGRK | ENSG00000137497.13 | 85 |
| SEQ ID NO: 186 | GCLELIK | ENSG00000100714.11 | 84 |
| SEQ ID NO: 187 | HSQTDQEPMCPVGMNK | ENSG00000134871.13 | 84 |
| SEQ ID NO: 188 | NPQVCGPGR | ENSG00000090006.13 | 83 |
| SEQ ID NO: 189 | SRGPGAPCQDVDECAR | ENSG00000090006.13 | 83 |
| SEQ ID NO: 190 | TKDEYLINSQTTEHIVK | ENSG00000067704.8 | 83 |
| SEQ ID NO: 191 | IATTTASAATAAAIGATPR | ENSG00000137497.13 | 82 |
| SEQ ID NO: 192 | LGHELQQAGLK | ENSG00000137497.13 | 82 |
| SEQ ID NO: 193 | TEVPPLLLILDR | ENSG00000136631.8 | 82 |
| SEQ ID NO: 194 | YGDEEKDK | ENSG00000179218.9 | 82 |
| SEQ ID NO: 195 | SESQGTAPAFK | ENSG00000065534.14 | 81 |
| SEQ ID NO: 196 | LPQEPGREQVVEDRPVGGR | ENSG00000135052.12 | 80 |
| SEQ ID NO: 197 | LPYGGQCRPCPCPEGPGSQR | ENSG00000172037.9 | 79 |
| SEQ ID NO: 198 | VYLLYRPGHYDILYK | ENSG00000167770.7 | 79 |
| SEQ ID NO: 199 | FQVATDALK | ENSG00000137497.13 | 78 |
| SEQ ID NO: 200 | LQEGQTLEFLVASVPK | ENSG00000172037.9 | 78 |
| SEQ ID NO: 201 | LQGAVCGVSSGPPPPR | ENSG00000011028.9 | 78 |
| SEQ ID NO: 202 | IQNVVTSFAPQR | ENSG00000172037.9 | 77 |
| SEQ ID NO: 203 | VSTLQNQR | ENSG00000169896.12 | 77 |
| SEQ ID NO: 204 | LSQLEEHLSQLQDNPPQEK | ENSG00000137497.13 | 76 |
| SEQ ID NO: 205 | SQAPLESSLDSLGDVFLDSGR | ENSG00000137497.13 | 76 |
| SEQ ID NO: 206 | AGPDLASCLDVDECR | ENSG00000090006.13 | 75 |
| SEQ ID NO: 207 | GTCHYYANK | ENSG00000134871.13 | 74 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 208 | HKSETDTSLIR | ENSG00000146731.6 | 74 |
| SEQ ID NO: 209 | KQQNQELQEQLR | ENSG00000137497.13 | 74 |
| SEQ ID NO: 210 | SGDLYVLAADK | ENSG00000067704.8 | 74 |
| SEQ ID NO: 211 | AFGFSHLEALLDDSK | ENSG00000167770.7 | 73 |
| SEQ ID NO: 212 | EILTLLOGVHQGAGFQDIPK | ENSG00000211460.7 | 73 |
| SEQ ID NO: 213 | IQQCPGTETAEYQSLCPHGR | ENSG00000090006.13 | 73 |
| SEQ ID NO: 214 | KDPDASKPEDWDER | ENSG00000179218.9 | 73 |
| SEQ ID NO: 215 | SYWLSTTAPLPMMPVAEDEIKPYISR | ENSG00000134871.13 | 73 |
| SEQ ID NO: 216 | VPQDVLQK | ENSG00000086475.10 | 73 |
| SEQ ID NO: 217 | DFGSFDKFK | ENSG00000112096.12 | 72 |
| SEQ ID NO: 218 | FIILSQEGSLCSVSIEK | ENSG00000065534.14 | 72 |
| SEQ ID NO: 219 | LAVATFAGIENK | ENSG00000004864.9 | 72 |
| SEQ ID NO: 220 | RLENAGSLK | ENSG00000065534.14 | 72 |
| SEQ ID NO: 221 | AAMPPQIIQFPEDQK | ENSG00000065534.14 | 71 |
| SEQ ID NO: 222 | EAQNLSAMEIR | ENSG00000067704.8 | 71 |
| SEQ ID NO: 223 | ILVAGDSMDSVK | ENSG00000196961.8 | 71 |
| SEQ ID NO: 224 | LVHSYPYDWR | ENSG00000067704.8 | 71 |
| SEQ ID NO: 225 | AEAGDAALSVAEWLR | ENSG00000186635.10 | 70 |
| SEQ ID NO: 226 | ELSNFYFSIIK | ENSG00000067704.8 | 70 |
| SEQ ID NO: 227 | AEAAAPYTVLAQSAPR | ENSG00000090006.13 | 69 |
| SEQ ID NO: 228 | GPGAPCQDVDECAR | ENSG00000090006.13 | 69 |
| SEQ ID NO: 229 | VSDFYDIEER | ENSG00000065534.14 | 69 |
| SEQ ID NO: 230 | NNDFYVTGESYAGK | ENSG00000106066.9 | 68 |
| SEQ ID NO: 231 | QPVVDTFDIR | ENSG00000142453.7 | 68 |
| SEQ ID NO: 232 | QQLQALSEPQPR | ENSG00000135052.12 | 68 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 233 | APAEILNGKEISAQIR | ENSG00000100714.11 | 67 |
| SEQ ID NO: 234 | KLDVEEPDSANSSFYSTR | ENSG00000137497.13 | 67 |
| SEQ ID NO: 235 | QPPPDSSEEAPPATQNFIIPK | ENSG00000119383.15 | 67 |
| SEQ ID NO: 236 | SLADVDAILAR | ENSG00000172037.9 | 67 |
| SEQ ID NO: 237 | TGGSAQPETPYSGPGLLIDSLVLLPR | ENSG00000172037.9 | 67 |
| SEQ ID NO: 238 | CDLCQEVLADIGFVK | ENSG00000169756.12 | 66 |
| SEQ ID NO: 239 | FIAGTGCLVR | ENSG00000184207.8 | 66 |
| SEQ ID NO: 240 | HHAAYVNNLNVTEEKYQEALAK | ENSG00000112096.12 | 66 |
| SEQ ID NO: 241 | QGIVHLDLKPENIMCVNK | ENSG00000065534.14 | 66 |
| SEQ ID NO: 242 | TLGDQLSLLLGAR | ENSG00000011028.9 | 66 |
| SEQ ID NO: 243 | CTHWAEGGK | ENSG00000100714.11 | 65 |
| SEQ ID NO: 244 | FGLYLPLFKPSVSTSK | ENSG00000004864.9 | 65 |
| SEQ ID NO: 245 | GSCYPATGDLLVGR | ENSG00000172037.9 | 65 |
| SEQ ID NO: 246 | VMPLIIQGFK | ENSG00000086475.10 | 65 |
| SEQ ID NO: 247 | TPLWIGLAGEEGSR | ENSG00000011028.9 | 64 |
| SEQ ID NO: 248 | TQPDGTSVPGEPASPISQR | ENSG00000137497.13 | 64 |
| SEQ ID NO: 249 | VWGVPIPVFHHK | ENSG00000067704.8 | 64 |
| SEQ ID NO: 250 | ALLNVVDNAR | ENSG00000105223.14 | 63 |
| SEQ ID NO: 251 | GGTTNPHIFPEGSEPK | ENSG00000167770.7 | 63 |
| SEQ ID NO: 252 | YTVNFLEAK | ENSG00000142453.7 | 63 |
| SEQ ID NO: 253 | ATIQGVLR | ENSG00000196961.8 | 62 |
| SEQ ID NO: 254 | GPLGDQYQTVK | ENSG00000172037.9 | 62 |
| SEQ ID NO: 255 | VAAQVDGGAQVQQVLNIECLR | ENSG00000196961.8 | 62 |
| SEQ ID NO: 256 | FTPVVCGLR | ENSG00000090006.13 | 61 |
| SEQ ID NO: 257 | LFPNSLDQTDMHGDSEYNIMFGPDICGPGTK | ENSG00000179218.9 | 61 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 258 | TILLSTTDPADFAVAEALEK | ENSG00000130396.16 | 61 |
| SEQ ID NO: 259 | LTYLGCASVNAPR | ENSG00000011454.12 | 60 |
| SEQ ID NO: 260 | SCYLSSLDLLLEHR | ENSG00000133315.6 | 60 |
| SEQ ID NO: 261 | VVATTQMQAADAR | ENSG00000166825.9 | 60 |
| SEQ ID NO: 262 | GVGGSQPPDIDKTELVEPTEYLVVHLK | ENSG00000166825.9 | 59 |
| SEQ ID NO: 263 | KEIHTVPDMGK | ENSG00000119383.15 | 59 |
| SEQ ID NO: 264 | LFTALFPFEK | ENSG00000169896.12 | 59 |
| SEQ ID NO: 265 | SLESALK | ENSG00000130429.8 | 59 |
| SEQ ID NO: 266 | VDDQIAIVFK | ENSG00000119383.15 | 59 |
| SEQ ID NO: 267 | VLDPAIPIPDPYSSR | ENSG00000172037.9 | 59 |
| SEQ ID NO: 268 | ATPFIECNGGR | ENSG00000134871.13 | 58 |
| SEQ ID NO: 269 | CSVCEAPAIAIAVHSQDVSIPHCPAGWR | ENSG00000134871.13 | 58 |
| SEQ ID NO: 270 | EAQVAHADQQLR | ENSG00000137497.13 | 58 |
| SEQ ID NO: 271 | EIILDDDECPLQIFR | ENSG00000130396.16 | 58 |
| SEQ ID NO: 272 | TPAAIPATPVAVSQPIR | ENSG00000130396.16 | 58 |
| SEQ ID NO: 273 | DLGFFGIYK | ENSG00000004864.9 | 57 |
| SEQ ID NO: 274 | EERPAPTPWGSK | ENSG00000130429.8 | 57 |
| SEQ ID NO: 275 | YVGFGNTPPPQK | ENSG00000101199.8 | 57 |
| SEQ ID NO: 276 | CLFQSPLFAK | ENSG00000142453.7 | 56 |
| SEQ ID NO: 277 | SETDTSLIR | ENSG00000146731.6 | 56 |
| SEQ ID NO: 278 | ILETWGELLSK | ENSG00000011454.12 | 54 |
| SEQ ID NO: 279 | YSGLCPHVVVLVATVR | ENSG00000100714.11 | 54 |
| SEQ ID NO: 280 | ENSLLFDPLSSSSSNK | ENSG00000166825.9 | 53 |
| SEQ ID NO: 281 | IKNEAEPEFASR | ENSG00000198947.10 | 53 |
| SEQ ID NO: 282 | VSAPDGPCPTGFER | ENSG00000090006.13 | 53 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 283 | AQGIAQGAIR | ENSG00000172037.9 | 52 |
| SEQ ID NO: 284 | KVCGDSDKGFVVINQK | ENSG00000146731.6 | 52 |
| SEQ ID NO: 285 | LWSGYSLLYFEGQEK | ENSG00000134871.13 | 52 |
| SEQ ID NO: 286 | VPIWDQDIQFLPGSQK | ENSG00000133316.11 | 52 |
| SEQ ID NO: 287 | YLSYTLNPDLIR | ENSG00000166825.9 | 52 |
| SEQ ID NO: 288 | YVIGVGDAFR | ENSG00000169896.12 | 52 |
| SEQ ID NO: 289 | DLEVVEGSAAR | ENSG00000065534.14 | 51 |
| SEQ ID NO: 290 | FAVGSGSR | ENSG00000130429.8 | 50 |
| SEQ ID NO: 291 | GFGQSVVQLQGSR | ENSG00000169896.12 | 50 |
| SEQ ID NO: 292 | GLPGEVLGAQPGPR | ENSG00000134871.13 | 50 |
| SEQ ID NO: 293 | LAETLGR | ENSG00000169756.12 | 50 |
| SEQ ID NO: 294 | LPPKVESLESLYFTPIPAR | ENSG00000137497.13 | 50 |
| SEQ ID NO: 295 | PTDSKPEDWDKPEHIPDPDAK | ENSG00000179218.9 | 50 |
| SEQ ID NO: 296 | QLSLPQQEAQK | ENSG00000196961.8 | 50 |
| SEQ ID NO: 297 | DVTTFFSGK | ENSG00000101199.8 | 49 |
| SEQ ID NO: 298 | GQVEQANQELQELIQSVK | ENSG00000172037.9 | 49 |
| SEQ ID NO: 299 | IDDVLHTLTGAMSLLR | ENSG00000130396.16 | 49 |
| SEQ ID NO: 300 | LQLPNCIEDPVSPIVLR | ENSG00000169896.12 | 49 |
| SEQ ID NO: 301 | VESLESLYFTPIPAR | ENSG00000137497.13 | 49 |
| SEQ ID NO: 302 | FGDPLGYEDVIPEADREGVIR | ENSG00000169896.12 | 48 |
| SEQ ID NO: 303 | LEPNAQAQMYR | ENSG00000196961.8 | 48 |
| SEQ ID NO: 304 | DSLEDCVTIWGPEGR | ENSG00000011028.9 | 47 |
| SEQ ID NO: 305 | EAVTEILGIEPDR | ENSG00000211460.7 | 47 |
| SEQ ID NO: 306 | FQNLDKK | ENSG00000130429.8 | 47 |
| SEQ ID NO: 307 | GGECASPLPGLR | ENSG00000090006.13 | 47 |

TABLE 7-continued

Spectral Counts from CRC samples of N terminal peptides predicted to be gained in GC

| SEQ_ID_NO | Peptide | Geneld | SpectralCount |
|---|---|---|---|
| SEQ ID NO: 308 | IAVSKPSGPQPQADLQALLQSGAQVR | ENSG00000105223.14 | 47 |
| SEQ ID NO: 309 | VLELSIPASAEQIQHLAGAIAER | ENSG00000172037.9 | 47 |
| SEQ ID NO: 310 | AAPVPTAPAAGAPLMDFGNDFVPPAPR | ENSG00000115310.13 | 46 |
| SEQ ID NO: 311 | GGYTCVCPDGFLLDSSR | ENSG00000090006.13 | 46 |
| SEQ ID NO: 312 | VLLTRPGEGGTGLPGPPLITR | ENSG00000152894.10 | 46 |
| SEQ ID NO: 313 | ELQPQQQPR | ENSG00000130396.16 | 45 |
| SEQ ID NO: 314 | FCQLHSSGARPPAPAVPGLTR | ENSG00000090006.13 | 45 |
| SEQ ID NO: 315 | LAAGDQLLSVDGR | ENSG00000130396.16 | 45 |
| SEQ ID NO: 316 | SLTLDTWEPELLK | ENSG00000114331.8 | 45 |
| SEQ ID NO: 317 | EQVPGFTPR | ENSG00000100714.11 | 44 |
| SEQ ID NO: 318 | ETGVPIAGR | ENSG00000100714.11 | 44 |
| SEQ ID NO: 319 | KITIGQAPTEK | ENSG00000100714.11 | 44 |
| SEQ ID NO: 320 | FSTMPFLYCNPGDVCYYASR | ENSG00000134871.13 | 43 |
| SEQ ID NO: 321 | LLTIGDANGEIQR | ENSG00000142453.7 | 43 |
| SEQ ID NO: 322 | LQSQVISELDACK | ENSG00000132205.6 | 43 |
| SEQ ID NO: 323 | LTILAAR | ENSG00000065534.14 | 43 |
| SEQ ID NO: 324 | LVECLETVLNK | ENSG00000196961.8 | 43 |
| SEQ ID NO: 325 | SSPQFGVTLLTYELLQR | ENSG00000004864.9 | 43 |
| SEQ ID NO: 326 | YQCHEEGLVPSK | ENSG00000172037.9 | 43 |
| SEQ ID NO: 327 | GCQLCPPFGSEGFR | ENSG00000090006.13 | 42 |
| SEQ ID NO: 328 | KPGLEEAVESACAMR | ENSG00000067704.8 | 42 |
| SEQ ID NO: 329 | LVQCVDAFEEK | ENSG00000065534.14 | 42 |
| SEQ ID NO: 330 | QWFINITDIK | ENSG00000067704.8 | 42 |
| SEQ ID NO: 331 | SQLEAIFLR | ENSG00000105223.14 | 42 |
| SEQ ID NO: 332 | VLEGSELELAK | ENSG00000137497.13 | 42 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 333 | VVQDLAAR | ENSG00000172037.9 | 42 |
| SEQ ID NO: 334 | AIMEFNPR | ENSG00000169896.12 | 41 |
| SEQ ID NO: 335 | ALAEGGSILSR | ENSG00000172037.9 | 41 |
| SEQ ID NO: 336 | EICPAGPGYHYSASDLR | ENSG00000090006.13 | 41 |
| SEQ ID NO: 337 | EQVVEDRPVGGR | ENSG00000135052.12 | 41 |
| SEQ ID NO: 338 | LYCNPGDVCYYASR | ENSG00000134871.13 | 41 |
| SEQ ID NO: 339 | TODASGPELILPASIEFR | ENSG00000130396.16 | 41 |
| SEQ ID NO: 340 | YSEIEPSTEGEVIYR | ENSG00000172037.9 | 41 |
| SEQ ID NO: 341 | AWCVNCFACSTCNTK | ENSG00000169756.12 | 40 |
| SEQ ID NO: 342 | DDPTDSKPEDWDKPEHIPDPDAK | ENSG00000179218.9 | 40 |
| SEQ ID NO: 343 | IVQATTLLTMDK | ENSG00000130396.16 | 40 |
| SEQ ID NO: 344 | VDLSTSTDWK | ENSG00000133315.6 | 40 |
| SEQ ID NO: 345 | AQLLQQTR | ENSG00000213380.9 | 39 |
| SEQ ID NO: 346 | DVDECQLFR | ENSG00000090006.13 | 39 |
| SEQ ID NO: 347 | IEGYPDPEVVWFKDDQSIR | ENSG00000065534.14 | 39 |
| SEQ ID NO: 348 | LSSMAMISGLSGR | ENSG00000065534.14 | 39 |
| SEQ ID NO: 349 | NNGVLFENQLLQIGVK | ENSG00000196961.8 | 39 |
| SEQ ID NO: 350 | RADPAELR | ENSG00000004864.9 | 39 |
| SEQ ID NO: 351 | SAPASQASLR | ENSG00000137497.13 | 39 |
| SEQ ID NO: 352 | DWEQFEYK | ENSG00000137497.13 | 38 |
| SEQ ID NO: 353 | IQAELAVILK | ENSG00000137497.13 | 38 |
| SEQ ID NO: 354 | SNRDELELELAENRK | ENSG00000137497.13 | 38 |
| SEQ ID NO: 355 | TPVPEKVPPPKPATPDFR | ENSG00000065534.14 | 38 |
| SEQ ID NO: 356 | VSLEPHQGPGTPESK | ENSG00000137497.13 | 38 |
| SEQ ID NO: 357 | CTEPEDQLYYVK | ENSG00000106066.9 | 37 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 358 | ECYFDTAAPDACDNILAR | ENSG00000090006.13 | 37 |
| SEQ ID NO: 359 | FGLGSVAGAVGATAVYPIDLVK | ENSG00000004864.9 | 37 |
| SEQ ID NO: 360 | GQEDAILSYEPVTR | ENSG00000082458.7 | 37 |
| SEQ ID NO: 361 | IMELEGR | ENSG00000135052.12 | 37 |
| SEQ ID NO: 362 | TCVSLAVSR | ENSG00000196961.8 | 37 |
| SEQ ID NO: 363 | TILTLTGVSTLGDVK | ENSG00000184207.8 | 37 |
| SEQ ID NO: 364 | VLQIVTNRDDVQGYAAK | ENSG00000196961.8 | 37 |
| SEQ ID NO: 365 | AFGFSHLEALLDDSKELQR | ENSG00000167770.7 | 36 |
| SEQ ID NO: 366 | AGPDSAGIALYSHEDVCVFK | ENSG00000142453.7 | 36 |
| SEQ ID NO: 367 | AQGVLAAQAR | ENSG00000172037.9 | 36 |
| SEQ ID NO: 368 | LPSFQQSCR | ENSG00000213380.9 | 36 |
| SEQ ID NO: 369 | MLSSFLSEDVFK | ENSG00000166825.9 | 36 |
| SEQ ID NO: 370 | DTEQTLYQVQER | ENSG00000172037.9 | 35 |
| SEQ ID NO: 371 | DVEVTKEEFVLAAQK | ENSG00000004864.9 | 35 |
| SEQ ID NO: 372 | INQLSEENGDLSFK | ENSG00000137497.13 | 35 |
| SEQ ID NO: 373 | LNIPATNVFANR | ENSG00000146733.9 | 35 |
| SEQ ID NO: 374 | SLVKPITQLLGR | ENSG00000169896.12 | 35 |
| SEQ ID NO: 375 | YLCEGTESPYQTGQLHPAIR | ENSG00000152894.10 | 35 |
| SEQ ID NO: 376 | ASMQPIQIAEGTGITTR | ENSG00000137497.13 | 34 |
| SEQ ID NO: 377 | IAGALGGLLTPLFLR | ENSG00000064545.10 | 34 |
| SEQ ID NO: 378 | LGASALDSIQEFR | ENSG00000032444.11 | 34 |
| SEQ ID NO: 379 | SGTIFDNFLITNDEAYAEEFGNETWGVTK | ENSG00000179218.9 | 34 |
| SEQ ID NO: 380 | TVLDLQSSLAGVSENLK | ENSG00000132205.6 | 34 |
| SEQ ID NO: 381 | AGPDLASCLDVDECRER | ENSG00000090006.13 | 33 |
| SEQ ID NO: 382 | EGGTAAGAGLDSLHK | ENSG00000130429.8 | 33 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 383 | FYEFSQR | ENSG00000153310.14 | 33 |
| SEQ ID NO: 384 | GEWIKPGAIVIDCGINYVPDDK | ENSG00000100714.11 | 33 |
| SEQ ID NO: 385 | NDPYHPDHFNCANCGK | ENSG00000169756.12 | 33 |
| SEQ ID NO: 386 | SLEPHQGPGTPESK | ENSG00000137497.13 | 33 |
| SEQ ID NO: 387 | SLGEENFEVVK | ENSG00000132561.9 | 33 |
| SEQ ID NO: 388 | THIDTVINALK | ENSG00000196961.8 | 33 |
| SEQ ID NO: 389 | VHAELADVLTEAVVDSILAIKK | ENSG00000146731.6 | 33 |
| SEQ ID NO: 390 | VMQHQYQVSNLGQR | ENSG00000169896.12 | 33 |
| SEQ ID NO: 391 | ASFITPVPGGVGPMTVAMLMQ STVESAK | ENSG00000100714.11 | 32 |
| SEQ ID NO: 392 | FEHFIEGGR | ENSG00000167770.7 | 32 |
| SEQ ID NO: 393 | LQQAQLYPIAIFIKPK | ENSG00000082458.7 | 32 |
| SEQ ID NO: 394 | MTLADIER | ENSG00000004864.9 | 32 |
| SEQ ID NO: 395 | TVELLSGVVDQTK | ENSG00000004864.9 | 32 |
| SEQ ID NO: 396 | AMDYDLLLR | ENSG00000172037.9 | 31 |
| SEQ ID NO: 397 | DFGSFDK | ENSG00000112096.12 | 31 |
| SEQ ID NO: 398 | EPAVYFKEQFLDGDGWTSR | ENSG00000179218.9 | 31 |
| SEQ ID NO: 399 | FLINLEGGDIREESSYK | ENSG00000067704.8 | 31 |
| SEQ ID NO: 400 | GEWIKPGAIVIDCGINYVPDDKK PNGR | ENSG00000100714.11 | 31 |
| SEQ ID NO: 401 | HAVVVGR | ENSG00000100714.11 | 31 |
| SEQ ID NO: 402 | LEGDTFLLLIQSLK | ENSG00000104450.8 | 31 |
| SEQ ID NO: 403 | NTSVVDSEPVR | ENSG00000162614.14 | 31 |
| SEQ ID NO: 404 | PGTTDQVPR | ENSG00000113657.8 | 31 |
| SEQ ID NO: 405 | QLDQHLDLLK | ENSG00000172037.9 | 31 |
| SEQ ID NO: 406 | TVIVHGFTLGEK | ENSG00000067704.8 | 31 |
| SEQ ID NO: 407 | YAPDDIPNINSTCFK | ENSG00000130396.16 | 31 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 408 | AADLLYAMCDR | ENSG00000196961.8 | 30 |
| SEQ ID NO: 409 | EMGEAFAADIPR | ENSG00000196961.8 | 30 |
| SEQ ID NO: 410 | IQGTLQPHAR | ENSG00000172037.9 | 30 |
| SEQ ID NO: 411 | LPIAVNGSLIYGVCAGK | ENSG00000059691.7 | 30 |
| SEQ ID NO: 412 | VNDDLISEFPHK | ENSG00000082458.7 | 30 |
| SEQ ID NO: 413 | DGGCSLPILR | ENSG00000090006.13 | 29 |
| SEQ ID NO: 414 | ENVDYIIQELR | ENSG00000136631.8 | 29 |
| SEQ ID NO: 415 | GAAVDEYFR | ENSG00000142453.7 | 29 |
| SEQ ID NO: 416 | GETAVPGAPEALR | ENSG00000184207.8 | 29 |
| SEQ ID NO: 417 | ILYSFATAFR | ENSG00000011454.12 | 29 |
| SEQ ID NO: 418 | NVFECNDQVVK | ENSG00000169896.12 | 29 |
| SEQ ID NO: 419 | STGSFVGELMYK | ENSG00000004864.9 | 29 |
| SEQ ID NO: 420 | TIRDLEVVEGSAAR | ENSG00000065534.14 | 29 |
| SEQ ID NO: 421 | TVFEALQAPACHENMVK | ENSG00000196961.8 | 29 |
| SEQ ID NO: 422 | VGLLQYGSTVK | ENSG00000132561.9 | 29 |
| SEQ ID NO: 423 | YVLSNQYRPDISPTER | ENSG00000130396.16 | 29 |
| SEQ ID NO: 424 | AEAELEYNPEHVSR | ENSG00000067704.8 | 28 |
| SEQ ID NO: 425 | ASPDLVPMGEWTAR | ENSG00000196961.8 | 28 |
| SEQ ID NO: 426 | CEACAPGHFGDPSRPGGR | ENSG00000172037.9 | 28 |
| SEQ ID NO: 427 | EDGYSDASGFGYCFR | ENSG00000090006.13 | 28 |
| SEQ ID NO: 428 | GDLIGVVEALTR | ENSG00000032444.11 | 28 |
| SEQ ID NO: 429 | LAILQVGNRDDSNLYINVK | ENSG00000100714.11 | 28 |
| SEQ ID NO: 430 | NDAGQAECSCQVTVDDAPASE NTK | ENSG00000065534.14 | 28 |
| SEQ ID NO: 431 | QNWFEAFEILDK | ENSG00000106066.9 | 28 |
| SEQ ID NO: 432 | SSEGLLATATVPLDLFK | ENSG00000157617.12 | 28 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 433 | STTTIGLVQALGAHLYQNVFACVR | ENSG00000100714.11 | 28 |
| SEQ ID NO: 434 | VLVLEMFSGGDAAALER | ENSG00000172037.9 | 28 |
| SEQ ID NO: 435 | KQVAPEKPVK | ENSG00000113387.7 | 27 |
| SEQ ID NO: 436 | LQELEGTYEENER | ENSG00000172037.9 | 27 |
| SEQ ID NO: 437 | LVEQHGSDIWWTLPPEQLLPK | ENSG00000067704.8 | 27 |
| SEQ ID NO: 438 | NPTFMCLALHCIANVGSR | ENSG00000196961.8 | 27 |
| SEQ ID NO: 439 | SSDGRPDSGGTLR | ENSG00000130396.16 | 27 |
| SEQ ID NO: 440 | AAPQPLNLVSSVTLSK | ENSG00000114861.14 | 26 |
| SEQ ID NO: 441 | AVQAQGGESQQEAQR | ENSG00000137497.13 | 26 |
| SEQ ID NO: 442 | DFLNQEGADPDSIEMVATR | ENSG00000172037.9 | 26 |
| SEQ ID NO: 443 | GQVLDVVER | ENSG00000172037.9 | 26 |
| SEQ ID NO: 444 | LALIQPSR | ENSG00000146733.9 | 26 |
| SEQ ID NO: 445 | LQQDVLQFQK | ENSG00000135052.12 | 26 |
| SEQ ID NO: 446 | LTFEELER | ENSG00000162614.14 | 26 |
| SEQ ID NO: 447 | QVTPLFIHFR | ENSG00000166825.9 | 26 |
| SEQ ID NO: 448 | SFNVQDLLPDHEYK | ENSG00000065534.14 | 26 |
| SEQ ID NO: 449 | SSCISQHVISEAK | ENSG00000090006.13 | 26 |
| SEQ ID NO: 450 | VLQIVTNR | ENSG00000196961.8 | 26 |
| SEQ ID NO: 451 | VVGDVAYDEAK | ENSG00000100714.11 | 26 |
| SEQ ID NO: 452 | ALQSGPPQSR | ENSG00000136231.9 | 25 |
| SEQ ID NO: 453 | ITIGQAPTEK | ENSG00000100714.11 | 25 |
| SEQ ID NO: 454 | KAQGVLAAQAR | ENSG00000172037.9 | 25 |
| SEQ ID NO: 455 | LKENLYPYLGPSTLR | ENSG00000136631.8 | 25 |
| SEQ ID NO: 456 | LPVTINK | ENSG00000196961.8 | 25 |
| SEQ ID NO: 457 | SILTAIPNDDPYFHITK | ENSG00000213380.9 | 25 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 458 | SLGNVIHPDVVVNGGQDQSK | ENSG00000067704.8 | 25 |
| SEQ ID NO: 459 | AVQTSIATAYR | ENSG00000114331.8 | 24 |
| SEQ ID NO: 460 | DASKPEDWDER | ENSG00000179218.9 | 24 |
| SEQ ID NO: 461 | IPVSGPFLVK | ENSG00000136231.9 | 24 |
| SEQ ID NO: 462 | LLGPAGLTWER | ENSG00000138162.13 | 24 |
| SEQ ID NO: 463 | LPVEAFSAVFTK | ENSG00000032444.11 | 24 |
| SEQ ID NO: 464 | SEESTTVHSSPGATGTALFPTR | ENSG00000205277.5 | 24 |
| SEQ ID NO: 465 | SEESTTVHSSPGATGTALFPTR | ENSG00000205277.5 | 24 |
| SEQ ID NO: 466 | SEESTTVHSSPGATGTALFPTR | ENSG00000205277.5 | 24 |
| SEQ ID NO: 467 | TKVHAELADVLTEAVVDSILAIK | ENSG00000146731.6 | 24 |
| SEQ ID NO: 468 | YGEGHQAWIIGIVEK | ENSG00000086475.10 | 24 |
| SEQ ID NO: 469 | ADLYLEGK | ENSG00000067704.8 | 23 |
| SEQ ID NO: 470 | CLEEKNEILQGK | ENSG00000137497.13 | 23 |
| SEQ ID NO: 471 | FIFDCVSQEYGINPER | ENSG00000184207.8 | 23 |
| SEQ ID NO: 472 | IHGTEEGQQILK | ENSG00000137497.13 | 23 |
| SEQ ID NO: 473 | KIQTQLQR | ENSG00000166825.9 | 23 |
| SEQ ID NO: 474 | KVVGDVAYDEAK | ENSG00000100714.11 | 23 |
| SEQ ID NO: 475 | LDSISGNLQR | ENSG00000132205.6 | 23 |
| SEQ ID NO: 476 | LFEDLEFQQLER | ENSG00000019144.12 | 23 |
| SEQ ID NO: 477 | SLGNVIHPDVVVNGGQDQSKEP PYGADVLR | ENSG00000067704.8 | 23 |
| SEQ ID NO: 478 | TEVNSGFFYK | ENSG00000146731.6 | 23 |
| SEQ ID NO: 479 | TSAGTFPGSQPQAPASPVLPARP PPPPLPR | ENSG00000090006.13 | 23 |
| SEQ ID NO: 480 | VHSPQQVDFR | ENSG00000065534.14 | 23 |
| SEQ ID NO: 481 | VLTGNTIALVLGGGGAR | ENSG00000032444.11 | 23 |
| SEQ ID NO: 482 | VSALSVVR | ENSG00000004864.9 | 23 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 483 | ASLENGVLLCDLINK | ENSG00000136153.15 | 22 |
| SEQ ID NO: 484 | ETLIDVAR | ENSG00000146731.6 | 22 |
| SEQ ID NO: 485 | FESKPQSQEVK | ENSG00000065534.14 | 22 |
| SEQ ID NO: 486 | GHLQIAACPNQDPLQGTTGLIPL LGIDVWEHAYYLQYK | ENSG00000112096.12 | 22 |
| SEQ ID NO: 487 | GICEALEDSDGRQDSPAGELPK | ENSG00000132561.9 | 22 |
| SEQ ID NO: 488 | GYLAPSGDLSLR | ENSG00000090006.13 | 22 |
| SEQ ID NO: 489 | LQSQLLSIEKEVEEYK | ENSG00000106976.14 | 22 |
| SEQ ID NO: 490 | SGQGSDRGSGSRPGIEGDTPR | ENSG00000113657.8 | 22 |
| SEQ ID NO: 491 | VAISTFQK | ENSG00000213380.9 | 22 |
| SEQ ID NO: 492 | GQDIFIIQTIPR | ENSG00000161542.12 | 21 |
| SEQ ID NO: 493 | ITLDAQDVLAHLVQMAFK | ENSG00000130396.16 | 21 |
| SEQ ID NO: 494 | RTEVPPLLLILDR | ENSG00000136631.8 | 21 |
| SEQ ID NO: 495 | SSPPVQFSLLHSK | ENSG00000196961.8 | 21 |
| SEQ ID NO: 496 | SSTGSPTSPLNAEK | ENSG00000065534.14 | 21 |
| SEQ ID NO: 497 | TKFPAEQYYR | ENSG00000211460.7 | 21 |
| SEQ ID NO: 498 | ANFWYQPSFHGVDLSALR | ENSG00000142453.7 | 20 |
| SEQ ID NO: 499 | DAQIAMMQQR | ENSG00000137497.13 | 20 |
| SEQ ID NO: 500 | EHGAFDAVK | ENSG00000100714.11 | 20 |
| SEQ ID NO: 501 | GLAQADGTLITCVDSGILR | ENSG00000133316.11 | 20 |
| SEQ ID NO: 502 | GLNCEQCQDFYR | ENSG00000172037.9 | 20 |
| SEQ ID NO: 503 | KVVATTQMQAADAR | ENSG00000166825.9 | 20 |
| SEQ ID NO: 504 | MKLTHSLQEELEK | ENSG00000151914.13 | 20 |
| SEQ ID NO: 505 | NIDVFNVEDQKR | ENSG00000135052.12 | 20 |
| SEQ ID NO: 506 | QASDKDDRPFQGEDVENSR | ENSG00000130396.16 | 20 |
| SEQ ID NO: 507 | SLDQTDMHGDSEYNIMFGPDIC GPGTK | ENSG00000179218.9 | 20 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 508 | STIFHSSPDASGTTPSSAHSTTSGR | ENSG00000205277.5 | 20 |
| SEQ ID NO: 509 | STIFHSSPDASGTTPSSAHSTTSGR | ENSG00000205277.5 | 20 |
| SEQ ID NO: 510 | STIFHSSPDASGTTPSSAHSTTSGR | ENSG00000205277.5 | 20 |
| SEQ ID NO: 511 | STIFHSSPDASGTTPSSAHSTTSGR | ENSG00000205277.5 | 20 |
| SEQ ID NO: 512 | VCLHVQK | ENSG00000169896.12 | 20 |
| SEQ ID NO: 513 | VSQFLQVLETDLYR | ENSG00000213380.9 | 20 |
| SEQ ID NO: 514 | VSSTATTQDVIETLAEK | ENSG00000130396.16 | 20 |
| SEQ ID NO: 515 | YNTRPLGQEPPR | ENSG00000090006.13 | 20 |
| SEQ ID NO: 516 | ANHPMDAEVTK | ENSG00000196961.8 | 19 |
| SEQ ID NO: 517 | ASELGHSLNENVLKPAQEK | ENSG00000101199.8 | 19 |
| SEQ ID NO: 518 | AWVSHDSTVCLADADKK | ENSG00000130429.8 | 19 |
| SEQ ID NO: 519 | FSYDLSQCINQMK | ENSG00000135052.12 | 19 |
| SEQ ID NO: 520 | IYQFTAASPK | ENSG00000005020.8 | 19 |
| SEQ ID NO: 521 | KQDEPIDLFMIEIMEMK | ENSG00000146731.6 | 19 |
| SEQ ID NO: 522 | NIMAGLQQTNSEK | ENSG00000198947.10 | 19 |
| SEQ ID NO: 523 | RPDYLK | ENSG00000112096.12 | 19 |
| SEQ ID NO: 524 | SEESTTVHSSPVATATTPSPAR | ENSG00000205277.5 | 19 |
| SEQ ID NO: 525 | SEESTTVHSSPVATATTPSPAR | ENSG00000205277.5 | 19 |
| SEQ ID NO: 526 | SEESTTVHSSPVATATTPSPAR | ENSG00000205277.5 | 19 |
| SEQ ID NO: 527 | SEESTTVHSSPVATATTPSPAR | ENSG00000205277.5 | 19 |
| SEQ ID NO: 528 | THLTSLK | ENSG00000211460.7 | 19 |
| SEQ ID NO: 529 | AQEAEQLLR | ENSG00000172037.9 | 18 |
| SEQ ID NO: 530 | AQIINDAFNLASAHK | ENSG00000166825.9 | 18 |
| SEQ ID NO: 531 | DQLGGWFQSSLLTSVAAR | ENSG00000067704.8 | 18 |
| SEQ ID NO: 532 | GADDIELLPEAQHK | ENSG00000100714.11 | 18 |

TABLE 7-continued

Spectral Counts from CRC samples of N terminal peptides predicted to be gained in GC

| SEQ_ID_NO | Peptide | Geneld | SpectralCount |
|---|---|---|---|
| SEQ ID NO: 533 | GFSHLEALLDDSK | ENSG00000167770.7 | 18 |
| SEQ ID NO: 534 | GLLTDSPAATVLAEAR | ENSG00000019144.12 | 18 |
| SEQ ID NO: 535 | HSNFLGAYDSIR | ENSG00000172037.9 | 18 |
| SEQ ID NO: 536 | KNEFQGELEK | ENSG00000135052.12 | 18 |
| SEQ ID NO: 537 | SFLEEVLASGLHSR | ENSG00000136631.8 | 18 |
| SEQ ID NO: 538 | TEILGIEPDREK | ENSG00000211460.7 | 18 |
| SEQ ID NO: 539 | VILLDPSIIEAK | ENSG00000104450.8 | 18 |
| SEQ ID NO: 540 | AETVQAALEEAQR | ENSG00000172037.9 | 17 |
| SEQ ID NO: 541 | AFVENYPQFK | ENSG00000136631.8 | 17 |
| SEQ ID NO: 542 | DFISNLLK | ENSG00000065534.14 | 17 |
| SEQ ID NO: 543 | DGFFGLSISDR | ENSG00000172037.9 | 17 |
| SEQ ID NO: 544 | DHVFQVNNFEALK | ENSG00000169896.12 | 17 |
| SEQ ID NO: 545 | DPTDSKPEDWDKPEHIPDPDAK | ENSG00000179218.9 | 17 |
| SEQ ID NO: 546 | KIIELK | ENSG00000146731.6 | 17 |
| SEQ ID NO: 547 | LCCPVALAQDVTGALEDALAK | ENSG00000213380.9 | 17 |
| SEQ ID NO: 548 | PAIAHLIHSLNPVR | ENSG00000106066.9 | 17 |
| SEQ ID NO: 549 | PSSTPTTHFSASSTTLGR | ENSG00000205277.5 | 17 |
| SEQ ID NO: 550 | PSSTPTTHFSASSTTLGR | ENSG00000205277.5 | 17 |
| SEQ ID NO: 551 | PSSTPTTHFSASSTTLGR | ENSG00000205277.5 | 17 |
| SEQ ID NO: 552 | PSSTPTTHFSASSTTLGR | ENSG00000205277.5 | 17 |
| SEQ ID NO: 553 | PSSTPTTHFSASSTTLGR | ENSG00000205277.5 | 17 |
| SEQ ID NO: 554 | PSSTPTTHFSASSTTLGR | ENSG00000205277.5 | 17 |
| SEQ ID NO: 555 | PSSTPTTHFSASSTTLGR | ENSG00000205277.5 | 17 |
| SEQ ID NO: 556 | QFVTGIIDSLTISPK | ENSG00000132561.9 | 17 |
| SEQ ID NO: 557 | SEAVLQSPEFAIFR | ENSG00000198947.10 | 17 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 558 | TTQGLTALLLSLK | ENSG00000136631.8 | 17 |
| SEQ ID NO: 559 | VPLSVQLKPEVSPTQDIR | ENSG00000125826.15 | 17 |
| SEQ ID NO: 560 | VTAIDFR | ENSG00000004864.9 | 17 |
| SEQ ID NO: 561 | YLIFPNPVCLEPGISYK | ENSG00000172037.9 | 17 |
| SEQ ID NO: 562 | YRLPNTLKPDSYR | ENSG00000166825.9 | 17 |
| SEQ ID NO: 563 | AFLLSLAALR | ENSG00000105223.14 | 16 |
| SEQ ID NO: 564 | DLAQYSSNDAVVETSLTK | ENSG00000114331.8 | 16 |
| SEQ ID NO: 565 | DRLPQEPGREQVVEDRPVGGR | ENSG00000135052.12 | 16 |
| SEQ ID NO: 566 | EAIQHPADEKLQEK | ENSG00000153310.14 | 16 |
| SEQ ID NO: 567 | EFQNNPNPR | ENSG00000169896.12 | 16 |
| SEQ ID NO: 568 | ELSAALQDKK | ENSG00000137497.13 | 16 |
| SEQ ID NO: 569 | ELSGSGLER | ENSG00000213380.9 | 16 |
| SEQ ID NO: 570 | ELWILNR | ENSG00000166825.9 | 16 |
| SEQ ID NO: 571 | FSTEYELQQLEQFKK | ENSG00000166825.9 | 16 |
| SEQ ID NO: 572 | GPALCGSQR | ENSG00000090006.13 | 16 |
| SEQ ID NO: 573 | GPLEPGPPKPGVPQEPGR | ENSG00000125826.15 | 16 |
| SEQ ID NO: 574 | GSLYQCDYSTGSCEPIR | ENSG00000169896.12 | 16 |
| SEQ ID NO: 575 | IQTQLQR | ENSG00000166825.9 | 16 |
| SEQ ID NO: 576 | KNSSIIGDYKQICSQLSER | ENSG00000011454.12 | 16 |
| SEQ ID NO: 577 | LEINFEELLK | ENSG00000162614.14 | 16 |
| SEQ ID NO: 578 | LIVPEPDVDFDAK | ENSG00000132205.6 | 16 |
| SEQ ID NO: 579 | LVGPEGFVVTEAGFGADIGMEK | ENSG00000100714.11 | 16 |
| SEQ ID NO: 580 | QEHCGCYTLLVENK | ENSG00000065534.14 | 16 |
| SEQ ID NO: 581 | RSQAGVSSGAPPGR | ENSG00000137497.13 | 16 |
| SEQ ID NO: 582 | SPGSTPTTHFPASSTTSGHSEK | ENSG00000205277.5 | 16 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 583 | SPGSTPTTHFPASSTTSGHSEK | ENSG00000205277.5 | 16 |
| SEQ ID NO: 584 | SPGSTPTTHFPASSTTSGHSEK | ENSG00000205277.5 | 16 |
| SEQ ID NO: 585 | SPGSTPTTHFPASSTTSGHSEK | ENSG00000205277.5 | 16 |
| SEQ ID NO: 586 | VLSQIDVAQK | ENSG00000198947.10 | 16 |
| SEQ ID NO: 587 | YGGMFCNVEGAFESK | ENSG00000113657.8 | 16 |
| SEQ ID NO: 588 | ATVVVEATEPEPSGSIANPAASTSPSLSHR | ENSG00000131711.10 | 15 |
| SEQ ID NO: 589 | EMTADVIELK | ENSG00000067704.8 | 15 |
| SEQ ID NO: 590 | GEQGFMGNTGPTGAVGDRGPK | ENSG00000134871.13 | 15 |
| SEQ ID NO: 591 | LAEAELEYNPEHVSR | ENSG00000067704.8 | 15 |
| SEQ ID NO: 592 | LESEEDVSQAFLEAVAEEKPHVKPYFSK | ENSG00000065534.14 | 15 |
| SEQ ID NO: 593 | LMCELGNDVINR | ENSG00000114331.8 | 15 |
| SEQ ID NO: 594 | QQQDYWLIDVR | ENSG00000166825.9 | 15 |
| SEQ ID NO: 595 | SSEGGTAAGAGLDSLHK | ENSG00000130429.8 | 15 |
| SEQ ID NO: 596 | SYKPVFWSPSSR | ENSG00000067704.8 | 15 |
| SEQ ID NO: 597 | TAHLDEEVNKGDILVVATGQPEMVK | ENSG00000100714.11 | 15 |
| SEQ ID NO: 598 | TRPDGNCFYR | ENSG00000167770.7 | 15 |
| SEQ ID NO: 599 | TSGQCLCR | ENSG00000172037.9 | 15 |
| SEQ ID NO: 600 | AFCVANK | ENSG00000114331.8 | 14 |
| SEQ ID NO: 601 | AMISGLSGR | ENSG00000065534.14 | 14 |
| SEQ ID NO: 602 | AVESSKPLSNAQPSGPLKPVGN | ENSG00000065534.14 | 14 |
| SEQ ID NO: 603 | AYHSFLVEPISCHAWNKDR | ENSG00000130429.8 | 14 |
| SEQ ID NO: 604 | EGVVDIYNCVK | ENSG00000152894.10 | 14 |
| SEQ ID NO: 605 | GTWIHPEIDNPEYSPDPSIYAYDNFGVLGLDLWQVK | ENSG00000179218.9 | 14 |
| SEQ ID NO: 606 | HLTQAVCTVK | ENSG00000141447.12 | 14 |
| SEQ ID NO: 607 | ITISPLQELTLYNPER | ENSG00000136231.9 | 14 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 608 | LACESASSTEVSGALK | ENSG00000169896.12 | 14 |
| SEQ ID NO: 609 | LDCTQCLQHPWLMK | ENSG00000065534.14 | 14 |
| SEQ ID NO: 610 | LDEEAENLVATVVPTHLAAAVPE VAVYLK | ENSG00000119383.15 | 14 |
| SEQ ID NO: 611 | LPEDDEPPARPPPPPPASVSPQA EPVWTPPAPAPAAPPSTPAAPK | ENSG00000115310.13 | 14 |
| SEQ ID NO: 612 | LPNTLKPDSYR | ENSG00000166825.9 | 14 |
| SEQ ID NO: 613 | LSSTQQSLAEK | ENSG00000082805.15 | 14 |
| SEQ ID NO: 614 | LVALETGIQK | ENSG00000019144.12 | 14 |
| SEQ ID NO: 615 | MHGGGPTVTAGLPLPK | ENSG00000100714.11 | 14 |
| SEQ ID NO: 616 | QQALELVVQEVSSVLR | ENSG00000157617.12 | 14 |
| SEQ ID NO: 617 | QSMAFSILNTPK | ENSG00000137497.13 | 14 |
| SEQ ID NO: 618 | SSNLLDLK | ENSG00000142453.7 | 14 |
| SEQ ID NO: 619 | VLQDQLK | ENSG00000135052.12 | 14 |
| SEQ ID NO: 620 | WVSHDSTVCLADADKK | ENSG00000130429.8 | 14 |
| SEQ ID NO: 621 | AAQLDGLEAR | ENSG00000172037.9 | 13 |
| SEQ ID NO: 622 | ANALASATCER | ENSG00000169756.12 | 13 |
| SEQ ID NO: 623 | ATDNEPSQFSEPR | ENSG00000132205.6 | 13 |
| SEQ ID NO: 624 | CGFSELYSWQR | ENSG00000067704.8 | 13 |
| SEQ ID NO: 625 | DLLQAAQDK | ENSG00000172037.9 | 13 |
| SEQ ID NO: 626 | EPAPASPAPAGVEIR | ENSG00000113657.8 | 13 |
| SEQ ID NO: 627 | EYELFEFR | ENSG00000136631.8 | 13 |
| SEQ ID NO: 628 | HKPGIVQETTFDLGGDIHSGTAL PTSK | ENSG00000130396.16 | 13 |
| SEQ ID NO: 629 | IWDLQGSEEPVFR | ENSG00000133316.11 | 13 |
| SEQ ID NO: 630 | LFGDVEASLGR | ENSG00000213380.9 | 13 |
| SEQ ID NO: 631 | LHTLGDNLLDPR | ENSG00000172037.9 | 13 |
| SEQ ID NO: 632 | RFSDIQIR | ENSG00000100714.11 | 13 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 633 | SEVYGPMK | ENSG00000166825.9 | 13 |
| SEQ ID NO: 634 | SLSESAATR | ENSG00000159788.14 | 13 |
| SEQ ID NO: 635 | VTCVEMEPLAEYVVR | ENSG00000152894.10 | 13 |
| SEQ ID NO: 636 | YLFEEDNLLR | ENSG00000132561.9 | 13 |
| SEQ ID NO: 637 | AAECLDVDECHR | ENSG00000090006.13 | 12 |
| SEQ ID NO: 638 | AGMSSLKG | ENSG00000146731.6 | 12 |
| SEQ ID NO: 639 | ALASATCER | ENSG00000169756.12 | 12 |
| SEQ ID NO: 640 | CDSHDDPALGLVSGQCR | ENSG00000172037.9 | 12 |
| SEQ ID NO: 641 | DCSIALPYVCK | ENSG00000011028.9 | 12 |
| SEQ ID NO: 642 | DISLQGPGLAPEHCYIENLR | ENSG00000019144.12 | 12 |
| SEQ ID NO: 643 | FVLDHEDGLNLNEDLENFLOK | ENSG00000137497.13 | 12 |
| SEQ ID NO: 644 | GANQHATDEEGKDPLSIAVEAANADIVTLLR | ENSG00000114331.8 | 12 |
| SEQ ID NO: 645 | GFSHLEALLDDSKELQR | ENSG00000167770.7 | 12 |
| SEQ ID NO: 646 | GSGVSNFAQLIVR | ENSG00000152894.10 | 12 |
| SEQ ID NO: 647 | IINDAFNLASAHK | ENSG00000166825.9 | 12 |
| SEQ ID NO: 648 | KVVQSLEQTAR | ENSG00000211460.7 | 12 |
| SEQ ID NO: 649 | QPAVEEPAEVTATVLASR | ENSG00000076662.5 | 12 |
| SEQ ID NO: 650 | QTQVLGLTQTCETLK | ENSG00000169896.12 | 12 |
| SEQ ID NO: 651 | RVEDAYILTCNVSLEYEK | ENSG00000146731.6 | 12 |
| SEQ ID NO: 652 | TLDFDALSVGQR | ENSG00000113657.8 | 12 |
| SEQ ID NO: 653 | VVNAMGK | ENSG00000169756.12 | 12 |
| SEQ ID NO: 654 | AKIDDPTDSKPEDWDKPEHIPD | ENSG00000179218.9 | 11 |
| SEQ ID NO: 655 | ALEQLLTELDDFLK | ENSG00000169129.10 | 11 |
| SEQ ID NO: 656 | ASKPEDWDER | ENSG00000179218.9 | 11 |
| SEQ ID NO: 657 | DLNQLFQQDSSSR | ENSG00000082805.15 | 11 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 658 | ETPGRPPDPTGAPLPGPTGDPVKPTSLETPSAPLLSR | ENSG00000032444.11 | 11 |
| SEQ ID NO: 659 | GSACEEDVDECAQEPPPCGPGR | ENSG00000090006.13 | 11 |
| SEQ ID NO: 660 | KASSEGGTAAGAGLDSLHK | ENSG00000130429.8 | 11 |
| SEQ ID NO: 661 | LGFITNNSSK | ENSG00000184207.8 | 11 |
| SEQ ID NO: 662 | LPSHSDFLAELR | ENSG00000169896.12 | 11 |
| SEQ ID NO: 663 | LQDVHVAEGK | ENSG00000065534.14 | 11 |
| SEQ ID NO: 664 | LVTCTGYHQVR | ENSG00000133316.11 | 11 |
| SEQ ID NO: 665 | SIQLPTTVR | ENSG00000166825.9 | 11 |
| SEQ ID NO: 666 | VLSELGR | ENSG00000067704.8 | 11 |
| SEQ ID NO: 667 | WAPNENKFAVGSGSR | ENSG00000130429.8 | 11 |
| SEQ ID NO: 668 | AQELQQTGVLGAFESSFWHMQEK | ENSG00000172037.9 | 10 |
| SEQ ID NO: 669 | ASAAAAAGGGATGHPGGGQGAENPAGLK | ENSG00000104450.8 | 10 |
| SEQ ID NO: 670 | EAENFHEEDDVDVRPAR | ENSG00000162614.14 | 10 |
| SEQ ID NO: 671 | ERLPSHSDFLAELR | ENSG00000169896.12 | 10 |
| SEQ ID NO: 672 | EWSLESSPAQNWTPPQPR | ENSG00000101199.8 | 10 |
| SEQ ID NO: 673 | FYALSASFEPFSNKG | ENSG00000179218.9 | 10 |
| SEQ ID NO: 674 | GISLNPEQWSQLKEQISDIDDAVR | ENSG00000113387.7 | 10 |
| SEQ ID NO: 675 | HPLLVGHMPVMVAK | ENSG00000104728.11 | 10 |
| SEQ ID NO: 676 | IAHGNSSIIADR | ENSG00000100714.11 | 10 |
| SEQ ID NO: 677 | IYADSLKPNIPYK | ENSG00000130396.16 | 10 |
| SEQ ID NO: 678 | LAILDSQAGQIR | ENSG00000019144.12 | 10 |
| SEQ ID NO: 679 | NMVVDDDSPEMYK | ENSG00000162614.14 | 10 |
| SEQ ID NO: 680 | NRLDCTQCLQHPWLMK | ENSG00000065534.14 | 10 |
| SEQ ID NO: 681 | PVLLQVAESAYR | ENSG00000004864.9 | 10 |
| SEQ ID NO: 682 | QEPLGSDSEGVNCLAYDEAIMAQQDR | ENSG00000167770.7 | 10 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 683 | QEVEELWIGLNDLK | ENSG00000011028.9 | 10 |
| SEQ ID NO: 684 | SFVIHNLPVLAK | ENSG00000086475.10 | 10 |
| SEQ ID NO: 685 | STTFHSSPR | ENSG00000205277.5 | 10 |
| SEQ ID NO: 686 | STTFHSSPR | ENSG00000205277.5 | 10 |
| SEQ ID NO: 687 | STTFHSSPR | ENSG00000205277.5 | 10 |
| SEQ ID NO: 688 | TAAGLMHTFNAHAATDITGFGIL GHAQNLAK | ENSG00000086475.10 | 10 |
| SEQ ID NO: 689 | TGAFGLR | ENSG00000172037.9 | 10 |
| SEQ ID NO: 690 | TSLTVVLLR | ENSG00000076662.5 | 10 |
| SEQ ID NO: 691 | VPPLLIYGPFGTGK | ENSG00000130589.12 | 10 |
| SEQ ID NO: 692 | VPSFAAGR | ENSG00000136231.9 | 10 |
| SEQ ID NO: 693 | VPVGDQPPDIEFQIR | ENSG00000106976.14 | 10 |
| SEQ ID NO: 694 | VYDPASPQR | ENSG00000133316.11 | 10 |
| SEQ ID NO: 695 | WFYIDFGGVKPMGSEPVPK | ENSG00000004864.9 | 10 |
| SEQ ID NO: 696 | WTPPAPAPAAPPSTPAAPK | ENSG00000115310.13 | 10 |
| SEQ ID NO: 697 | YDNQWFHGCTSTGR | ENSG00000011028.9 | 10 |
| SEQ ID NO: 698 | YFSYDCGADFPGVPLAPPR | ENSG00000172037.9 | 10 |
| SEQ ID NO: 699 | YGDEEKDKGLQTSQDAR | ENSG00000179218.9 | 10 |
| SEQ ID NO: 700 | YLETADYAIR | ENSG00000196961.8 | 10 |
| SEQ ID NO: 701 | AKQPDLAPGLTTIGASPTQTVTL VTQPVVTK | ENSG00000198947.10 | 9 |
| SEQ ID NO: 702 | ASPLLPANHVTMAK | ENSG00000067704.8 | 9 |
| SEQ ID NO: 703 | AVLELLQRPGNAR | ENSG00000105963.9 | 9 |
| SEQ ID NO: 704 | CFQVQGQEPQSR | ENSG00000011028.9 | 9 |
| SEQ ID NO: 705 | DKGLQTSQDAR | ENSG00000179218.9 | 9 |
| SEQ ID NO: 706 | DLTALSNMLPK | ENSG00000166825.9 | 9 |
| SEQ ID NO: 707 | DPFSLDALSK | ENSG00000146731.6 | 9 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 708 | FGDPLGYEDVIPEADR | ENSG00000169896.12 | 9 |
| SEQ ID NO: 709 | FGLYLPLFK | ENSG00000004864.9 | 9 |
| SEQ ID NO: 710 | FSTEYELQQLEQFK | ENSG00000166825.9 | 9 |
| SEQ ID NO: 711 | GAVYLFHGTSGSGISPSHSQR | ENSG00000169896.12 | 9 |
| SEQ ID NO: 712 | HLCELLAQQF | ENSG00000196961.8 | 9 |
| SEQ ID NO: 713 | ILDQENLSSTALVK | ENSG00000169129.10 | 9 |
| SEQ ID NO: 714 | ISETTMLQSGMK | ENSG00000130396.16 | 9 |
| SEQ ID NO: 715 | ISYHGSCPQGLADSAWIPFR | ENSG00000011028.9 | 9 |
| SEQ ID NO: 716 | KQNWFEAFEILDK | ENSG00000106066.9 | 9 |
| SEQ ID NO: 717 | PISLVFLVPVR | ENSG00000169896.12 | 9 |
| SEQ ID NO: 718 | SKESSQVTSR | ENSG00000136631.8 | 9 |
| SEQ ID NO: 719 | SPPPCTYGR | ENSG00000090006.13 | 9 |
| SEQ ID NO: 720 | SQLNCLLLSGR | ENSG00000133316.11 | 9 |
| SEQ ID NO: 721 | TPLSAAAHTHPVYCVNVVGTQN AHNLITVSTDGK | ENSG00000158560.10 | 9 |
| SEQ ID NO: 722 | VNYDEENWR | ENSG00000166825.9 | 9 |
| SEQ ID NO: 723 | VSFVIHNLPVLAK | ENSG00000086475.10 | 9 |
| SEQ ID NO: 724 | VTLRPYLTPNDR | ENSG00000166825.9 | 9 |
| SEQ ID NO: 725 | WNVINWENVTER | ENSG00000112096.12 | 9 |
| SEQ ID NO: 726 | ADTDGGLIFR | ENSG00000163975.7 | 8 |
| SEQ ID NO: 727 | AGYTGLR | ENSG00000172037.9 | 8 |
| SEQ ID NO: 728 | AVESSKPLSNAQPSGPLKPVGNA K | ENSG00000065534.14 | 8 |
| SEQ ID NO: 729 | CSEGFVLAEDGRR | ENSG00000132561.9 | 8 |
| SEQ ID NO: 730 | DLMVLNDVYR | ENSG00000166825.9 | 8 |
| SEQ ID NO: 731 | FPAEQYYR | ENSG00000211460.7 | 8 |
| SEQ ID NO: 732 | FTGHCSCRPGVSGVR | ENSG00000172037.9 | 8 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 733 | GDPGDTGAPGPVGMK | ENSG00000134871.13 | 8 |
| SEQ ID NO: 734 | GGPSLSSVLNELPSAATLR | ENSG00000167608.7 | 8 |
| SEQ ID NO: 735 | IKDPDASKPEDWDERAK | ENSG00000179218.9 | 8 |
| SEQ ID NO: 736 | ILCIGAVPGLQPR | ENSG00000110237.3 | 8 |
| SEQ ID NO: 737 | IQSDLTSHEISLEEMKK | ENSG00000198947.10 | 8 |
| SEQ ID NO: 738 | ITGHFYACQVAQR | ENSG00000136231.9 | 8 |
| SEQ ID NO: 739 | KVVGDVAYDEAKER | ENSG00000100714.11 | 8 |
| SEQ ID NO: 740 | LDTDILLGATCGLK | ENSG00000184207.8 | 8 |
| SEQ ID NO: 741 | LVSAVVEYGGK | ENSG00000136631.8 | 8 |
| SEQ ID NO: 742 | MLGVAAGMTHSNMANALASATCER | ENSG00000169756.12 | 8 |
| SEQ ID NO: 743 | NIPNGLQEFLDPLCQR | ENSG00000130396.16 | 8 |
| SEQ ID NO: 744 | QADIIGKPSR | ENSG00000184207.8 | 8 |
| SEQ ID NO: 745 | QEISIMNCLHHPK | ENSG00000065534.14 | 8 |
| SEQ ID NO: 746 | QIVSEMLR | ENSG00000196961.8 | 8 |
| SEQ ID NO: 747 | RAEQLLQDAR | ENSG00000172037.9 | 8 |
| SEQ ID NO: 748 | RFENAPDSAK | ENSG00000082805.15 | 8 |
| SEQ ID NO: 749 | SGAPWFK | ENSG00000162614.14 | 8 |
| SEQ ID NO: 750 | SIVEHVASK | ENSG00000146733.9 | 8 |
| SEQ ID NO: 751 | SLVGLSQER | ENSG00000130396.16 | 8 |
| SEQ ID NO: 752 | TVNELQNLSSAEVVVPR | ENSG00000136231.9 | 8 |
| SEQ ID NO: 753 | VIAVVNK | ENSG00000130396.16 | 8 |
| SEQ ID NO: 754 | VSHSELR | ENSG00000146733.9 | 8 |
| SEQ ID NO: 755 | WSDGVGFSYHNFDR | ENSG00000011028.9 | 8 |
| SEQ ID NO: 756 | YGADDIELLPEAQHK | ENSG00000100714.11 | 8 |
| SEQ ID NO: 757 | AKPEASFQVWNK | ENSG00000073849.10 | 7 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 758 | ALQLSNSPGASSAFLK | ENSG00000170776.15 | 7 |
| SEQ ID NO: 759 | ASSEGGTAAGAGLDSLHKNSVSQISVLSGGK | ENSG00000130429.8 | 7 |
| SEQ ID NO: 760 | AVEMAAQR | ENSG00000184207.8 | 7 |
| SEQ ID NO: 761 | AVLELLQR | ENSG00000105963.9 | 7 |
| SEQ ID NO: 762 | AYAQQLADWAR | ENSG00000165912.11 | 7 |
| SEQ ID NO: 763 | DHSAIPVINR | ENSG00000166825.9 | 7 |
| SEQ ID NO: 764 | DLRDPAVCR | ENSG00000172037.9 | 7 |
| SEQ ID NO: 765 | FGSCVPHTTRPR | ENSG00000082458.7 | 7 |
| SEQ ID NO: 766 | GPQYGTLEK | ENSG00000165912.11 | 7 |
| SEQ ID NO: 767 | HWDDVVCESR | ENSG00000172037.9 | 7 |
| SEQ ID NO: 768 | IVLYQTDASLTPWTVR | ENSG00000032444.11 | 7 |
| SEQ ID NO: 769 | KVHSPQQVDFR | ENSG00000065534.14 | 7 |
| SEQ ID NO: 770 | LCTDHGSQLVTITNR | ENSG00000011028.9 | 7 |
| SEQ ID NO: 771 | LDFLPDMMVEGR | ENSG00000048740.13 | 7 |
| SEQ ID NO: 772 | LEAVAEEKPHVKPYFSK | ENSG00000065534.14 | 7 |
| SEQ ID NO: 773 | LEVDAIVNAANSSLLGGGGVDGCIHR | ENSG00000133315.6 | 7 |
| SEQ ID NO: 774 | LLHEMQIQHPTASLIAK | ENSG00000146731.6 | 7 |
| SEQ ID NO: 775 | LLVEELPLR | ENSG00000198947.10 | 7 |
| SEQ ID NO: 776 | LMNSQLVTTEK | ENSG00000073849.10 | 7 |
| SEQ ID NO: 777 | LSNPPSAGPIVVHCSAGAGR | ENSG00000152894.10 | 7 |
| SEQ ID NO: 778 | LSPSSTETTTLPGSPTTPSLSEK | ENSG00000205277.5 | 7 |
| SEQ ID NO: 779 | LSPSSTETTTLPGSPTTPSLSEK | ENSG00000205277.5 | 7 |
| SEQ ID NO: 780 | LSPSSTETTTLPGSPTTPSLSEK | ENSG00000205277.5 | 7 |
| SEQ ID NO: 781 | LSPSSTETTTLPGSPTTPSLSEK | ENSG00000205277.5 | 7 |
| SEQ ID NO: 782 | MYLFYGNK | ENSG00000196961.8 | 7 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 783 | PPLLLILDR | ENSG00000136631.8 | 7 |
| SEQ ID NO: 784 | PSLSLGTITDEEMK | ENSG00000137497.13 | 7 |
| SEQ ID NO: 785 | QCHECIEHIR | ENSG00000106066.9 | 7 |
| SEQ ID NO: 786 | QQNQELQEQLR | ENSG00000137497.13 | 7 |
| SEQ ID NO: 787 | SFAPILPHLAEEVFQHIPY | ENSG00000067704.8 | 7 |
| SEQ ID NO: 788 | SGLCPHVVVLVATVR | ENSG00000100714.11 | 7 |
| SEQ ID NO: 789 | SITILSTPEGTSAACK | ENSG00000136231.9 | 7 |
| SEQ ID NO: 790 | SLEGSDDAVLLQR | ENSG00000198947.10 | 7 |
| SEQ ID NO: 791 | SMDAETYVEGQR | ENSG00000130396.16 | 7 |
| SEQ ID NO: 792 | STTSGLVGESTPSR | ENSG00000205277.5 | 7 |
| SEQ ID NO: 793 | STTSGLVGESTPSR | ENSG00000205277.5 | 7 |
| SEQ ID NO: 794 | STTSGLVGESTPSR | ENSG00000205277.5 | 7 |
| SEQ ID NO: 795 | STTSGLVGESTPSR | ENSG00000205277.5 | 7 |
| SEQ ID NO: 796 | TQGSSTSWFGSNQSKPEFTVDLK | ENSG00000165322.13 | 7 |
| SEQ ID NO: 797 | VIMIVTDGRPQDSVAEVAAK | ENSG00000132561.9 | 7 |
| SEQ ID NO: 798 | VPPPKPATPDFR | ENSG00000065534.14 | 7 |
| SEQ ID NO: 799 | WGFCPIK | ENSG00000011028.9 | 7 |
| SEQ ID NO: 800 | YAVQVAEGMGYLESKR | ENSG00000061938.12 | 7 |
| SEQ ID NO: 801 | AAEEIGIKATHIKLPR | ENSG00000100714.11 | 6 |
| SEQ ID NO: 802 | AGDAVNVVVTGGK | ENSG00000132205.6 | 6 |
| SEQ ID NO: 803 | AGDTLSGTCLLIANK | ENSG00000142453.7 | 6 |
| SEQ ID NO: 804 | AGDTLSGTCLLIANKR | ENSG00000142453.7 | 6 |
| SEQ ID NO: 805 | AIDYEIQR | ENSG00000059691.7 | 6 |
| SEQ ID NO: 806 | ALEQALEK | ENSG00000166825.9 | 6 |
| SEQ ID NO: 807 | ALSSAGER | ENSG00000172037.9 | 6 |

TABLE 7-continued

Spectral Counts from CRC samples of N terminal peptides predicted to be gained in GC

| SEQ_ID_NO | Peptide | Geneld | SpectralCount |
|---|---|---|---|
| SEQ ID NO: 808 | CFLCDSR | ENSG00000172037.9 | 6 |
| SEQ ID NO: 809 | DAEEWVQQLK | ENSG00000005020.8 | 6 |
| SEQ ID NO: 810 | DDEFTHLYTLIVRPDNTYEVK | ENSG00000179218.9 | 6 |
| SEQ ID NO: 811 | DFGSFDKFKEK | ENSG00000112096.12 | 6 |
| SEQ ID NO: 812 | DGDVQAGANLSFNR | ENSG00000158560.10 | 6 |
| SEQ ID NO: 813 | EFASHLQQLQDALNELTEEHSK | ENSG00000137497.13 | 6 |
| SEQ ID NO: 814 | ETLPELPSVTR | ENSG00000059691.7 | 6 |
| SEQ ID NO: 815 | GAPMHDLLLWNNATVTTCHSK | ENSG00000100714.11 | 6 |
| SEQ ID NO: 816 | HKSDFGK | ENSG00000179218.9 | 6 |
| SEQ ID NO: 817 | IALETSLSK | ENSG00000076662.5 | 6 |
| SEQ ID NO: 818 | IGDFGLMR | ENSG00000061938.12 | 6 |
| SEQ ID NO: 819 | ILREEGPK | ENSG00000004864.9 | 6 |
| SEQ ID NO: 820 | KSEAPFTHK | ENSG00000162614.14 | 6 |
| SEQ ID NO: 821 | LCGDLVSCFQER | ENSG00000165912.11 | 6 |
| SEQ ID NO: 822 | LLDLLEGLTGQK | ENSG00000198947.10 | 6 |
| SEQ ID NO: 823 | LLEQSIQSAQETEK | ENSG00000198947.10 | 6 |
| SEQ ID NO: 824 | LQAEDCSIACLPR | ENSG00000152894.10 | 6 |
| SEQ ID NO: 825 | MNVVFAVK | ENSG00000136631.8 | 6 |
| SEQ ID NO: 826 | NPPAAYIQK | ENSG00000184922.9 | 6 |
| SEQ ID NO: 827 | NTSLNPQELQR | ENSG00000125826.15 | 6 |
| SEQ ID NO: 828 | NVLINKDIR | ENSG00000179218.9 | 6 |
| SEQ ID NO: 829 | PAETLKPMGN | ENSG00000065534.14 | 6 |
| SEQ ID NO: 830 | PAETLKPMGN | ENSG00000065534.14 | 6 |
| SEQ ID NO: 831 | PFSLDALSK | ENSG00000146731.6 | 6 |
| SEQ ID NO: 832 | PLLPANHVTMAK | ENSG00000067704.8 | 6 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 833 | PSGYTCACDSGFR | ENSG00000090006.13 | 6 |
| SEQ ID NO: 834 | PSVVLSAAHTVAAR | ENSG00000032444.11 | 6 |
| SEQ ID NO: 835 | QASNGVLIR | ENSG00000166825.9 | 6 |
| SEQ ID NO: 836 | QGLELAADCHLSR | ENSG00000130396.16 | 6 |
| SEQ ID NO: 837 | QVEELLMAMEK | ENSG00000082805.15 | 6 |
| SEQ ID NO: 838 | QVEKEETNEIQVVNEEPQR | ENSG00000135052.12 | 6 |
| SEQ ID NO: 839 | RLEAEFPPHHSQSTFR | ENSG00000061938.12 | 6 |
| SEQ ID NO: 840 | SWDTNLIECNLDQELK | ENSG00000131711.10 | 6 |
| SEQ ID NO: 841 | TGEPCVAELTEENFQR | ENSG00000082805.15 | 6 |
| SEQ ID NO: 842 | VECEPSWQPFQGHCYR | ENSG00000011028.9 | 6 |
| SEQ ID NO: 843 | VRFTPVVCGLR | ENSG00000090006.13 | 6 |
| SEQ ID NO: 844 | VSLSQPR | ENSG00000090006.13 | 6 |
| SEQ ID NO: 845 | AAEGYTQFYYVDVLDGK | ENSG00000205277.5 | 5 |
| SEQ ID NO: 846 | AALEEVEGDVAELELK | ENSG00000114331.8 | 5 |
| SEQ ID NO: 847 | AEEFGNETWGVTK | ENSG00000179218.9 | 5 |
| SEQ ID NO: 848 | AFEDWLNDDLGSYQGAQGNR | ENSG00000101199.8 | 5 |
| SEQ ID NO: 849 | ATQEWLEK | ENSG00000137497.13 | 5 |
| SEQ ID NO: 850 | CSQFCTTGMDGGMSIWDVK | ENSG00000130429.8 | 5 |
| SEQ ID NO: 851 | DQLVIPDGQEEEQEAAGEGR | ENSG00000135052.12 | 5 |
| SEQ ID NO: 852 | EAQEAEAFALYHK | ENSG00000099991.12 | 5 |
| SEQ ID NO: 853 | EGNCSGCIQDCNR | ENSG00000104450.8 | 5 |
| SEQ ID NO: 854 | EGQIQSVVTYDLALDSGRPHSR | ENSG00000169896.12 | 5 |
| SEQ ID NO: 855 | EIDAALQKK | ENSG00000162614.14 | 5 |
| SEQ ID NO: 856 | ERFQNLDKK | ENSG00000130429.8 | 5 |
| SEQ ID NO: 857 | ETQPPDLPTTALGGCPSDWIQFLNK | ENSG00000011028.9 | 5 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 858 | FREFLESQEDYDPCWSLQEK | ENSG00000101199.8 | 5 |
| SEQ ID NO: 859 | GGTAAGAGLDSLHK | ENSG00000130429.8 | 5 |
| SEQ ID NO: 860 | GLNPGTLNILVR | ENSG00000152894.10 | 5 |
| SEQ ID NO: 861 | GQLAPVFQR | ENSG00000213380.9 | 5 |
| SEQ ID NO: 862 | GSAASTCILTIESK | ENSG00000162614.14 | 5 |
| SEQ ID NO: 863 | ICGVEDAVSEMTR | ENSG00000146733.9 | 5 |
| SEQ ID NO: 864 | IITEGFEAAKEK | ENSG00000146731.6 | 5 |
| SEQ ID NO: 865 | ILKDIANR | ENSG00000067704.8 | 5 |
| SEQ ID NO: 866 | IQDLEHHLGLALNEVQAAK | ENSG00000011454.12 | 5 |
| SEQ ID NO: 867 | IVDAVIEQVK | ENSG00000170776.15 | 5 |
| SEQ ID NO: 868 | KVNVLQK | ENSG00000082805.15 | 5 |
| SEQ ID NO: 869 | LLLQCQVSSDPPATIIWTLNGK | ENSG00000065534.14 | 5 |
| SEQ ID NO: 870 | LSFEEMER | ENSG00000162614.14 | 5 |
| SEQ ID NO: 871 | LSPIPAVPASVPLQAWHPAK | ENSG00000104450.8 | 5 |
| SEQ ID NO: 872 | NODNEDEWPLAEILSVK | ENSG00000172977.8 | 5 |
| SEQ ID NO: 873 | PTTLTDEEINR | ENSG00000100714.11 | 5 |
| SEQ ID NO: 874 | QIIEDQSGHYIWVPSPEKL | ENSG00000082458.7 | 5 |
| SEQ ID NO: 875 | QIQESEHMK | ENSG00000065534.14 | 5 |
| SEQ ID NO: 876 | RDFGSFDK | ENSG00000112096.12 | 5 |
| SEQ ID NO: 877 | RPQLEELITAAQNLK | ENSG00000198947.10 | 5 |
| SEQ ID NO: 878 | RPYWCISR | ENSG00000067704.8 | 5 |
| SEQ ID NO: 879 | SEESTASHSSQDATGTIVLPAR | ENSG00000205277.5 | 5 |
| SEQ ID NO: 880 | SEESTASHSSQDATGTIVLPAR | ENSG00000205277.5 | 5 |
| SEQ ID NO: 881 | SEESTASHSSQDATGTIVLPAR | ENSG00000205277.5 | 5 |
| SEQ ID NO: 882 | SEESTASHSSQDATGTIVLPAR | ENSG00000205277.5 | 5 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 883 | SGTIFDNFLITNDEAY | ENSG00000179218.9 | 5 |
| SEQ ID NO: 884 | SQDADSPGSSGAPENLTFK | ENSG00000130396.16 | 5 |
| SEQ ID NO: 885 | TCYPLESRPSLSLGTITDEEMK | ENSG00000137497.13 | 5 |
| SEQ ID NO: 886 | TGLFTPDMAFETIVK | ENSG00000106976.14 | 5 |
| SEQ ID NO: 887 | VATEAEFSPEDSPSVR | ENSG00000155629.10 | 5 |
| SEQ ID NO: 888 | VPPPCDLGR | ENSG00000090006.13 | 5 |
| SEQ ID NO: 889 | VVSNFILQALQGEPLTVYGSGSQTR | ENSG00000115652.10 | 5 |
| SEQ ID NO: 890 | AAIVFTDGR | ENSG00000132561.9 | 4 |
| SEQ ID NO: 891 | AGKGEVTFEDVK | ENSG00000004864.9 | 4 |
| SEQ ID NO: 892 | AIDLEIK | ENSG00000162614.14 | 4 |
| SEQ ID NO: 893 | AIEEELQEIASEPTNK | ENSG00000132561.9 | 4 |
| SEQ ID NO: 894 | ASFITPVPGGVGPMTVAMLMQSTVESAKR | ENSG00000100714.11 | 4 |
| SEQ ID NO: 895 | CAVVSSAGSLK | ENSG00000073849.10 | 4 |
| SEQ ID NO: 896 | CHYYANK | ENSG00000134871.13 | 4 |
| SEQ ID NO: 897 | CLTALPYICK | ENSG00000011028.9 | 4 |
| SEQ ID NO: 898 | DEELPTLLHFAAK | ENSG00000155629.10 | 4 |
| SEQ ID NO: 899 | DKVMPLIIQGFK | ENSG00000086475.10 | 4 |
| SEQ ID NO: 900 | DKVVALAEGR | ENSG00000101199.8 | 4 |
| SEQ ID NO: 901 | DQVFGSNLANLCQR | ENSG00000165322.13 | 4 |
| SEQ ID NO: 902 | DVFNVEDQKR | ENSG00000135052.12 | 4 |
| SEQ ID NO: 903 | EAELEYNPEHVSR | ENSG00000067704.8 | 4 |
| SEQ ID NO: 904 | EATDVIIIHSK | ENSG00000166825.9 | 4 |
| SEQ ID NO: 905 | EQYDVPQEWR | ENSG00000205277.5 | 4 |
| SEQ ID NO: 906 | ESPQDSAITR | ENSG00000011454.12 | 4 |
| SEQ ID NO: 907 | EVVLQWFTENSK | ENSG00000166825.9 | 4 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 908 | EYFTFPASK | ENSG00000130396.16 | 4 |
| SEQ ID NO: 909 | FFDSACTMGAYHPLLYEK | ENSG00000073849.10 | 4 |
| SEQ ID NO: 910 | FGSFDKFK | ENSG00000112096.12 | 4 |
| SEQ ID NO: 911 | FIEAGQFNDNLYGTSIQSVR | ENSG00000082458.7 | 4 |
| SEQ ID NO: 912 | FIPGSALNGMVEMMDR | ENSG00000067704.8 | 4 |
| SEQ ID NO: 913 | GHLQIAACPNQD | ENSG00000112096.12 | 4 |
| SEQ ID NO: 914 | GSWQPVGDLLIDSLQDHLEK | ENSG00000198947.10 | 4 |
| SEQ ID NO: 915 | HVVPGVER | ENSG00000130589.12 | 4 |
| SEQ ID NO: 916 | IDYGTGHEAAFAAFLCCLCK | ENSG00000119383.15 | 4 |
| SEQ ID NO: 917 | IVGNGSEQQLQK | ENSG00000011454.12 | 4 |
| SEQ ID NO: 918 | KESEETIIQTDEDVPGPVPVK | ENSG00000152894.10 | 4 |
| SEQ ID NO: 919 | LEPAGPACPEGGR | ENSG00000213380.9 | 4 |
| SEQ ID NO: 920 | LETLTNQFSDSK | ENSG00000082805.15 | 4 |
| SEQ ID NO: 921 | LFSGSQVR | ENSG00000059691.7 | 4 |
| SEQ ID NO: 922 | LLEILK | ENSG00000082805.15 | 4 |
| SEQ ID NO: 923 | LLQQFPLDLEK | ENSG00000198947.10 | 4 |
| SEQ ID NO: 924 | LLTESVNSVIAQAPPVAQEALKK | ENSG00000198947.10 | 4 |
| SEQ ID NO: 925 | LPVEDKIR | ENSG00000100714.11 | 4 |
| SEQ ID NO: 926 | LPYGGQCR | ENSG00000172037.9 | 4 |
| SEQ ID NO: 927 | LSTAITLLPLEEGR | ENSG00000019144.12 | 4 |
| SEQ ID NO: 928 | LTASSTCGLNGPQPYCIVSHLQDEKK | ENSG00000172037.9 | 4 |
| SEQ ID NO: 929 | LVTPHGESEQIGVIPSK | ENSG00000082458.7 | 4 |
| SEQ ID NO: 930 | NAEVRPPFTYASLIR | ENSG00000114861.14 | 4 |
| SEQ ID NO: 931 | PAETLKPMGNAKPDENLK | ENSG00000065534.14 | 4 |
| SEQ ID NO: 932 | PGGAGPCATVSVFPGAR | ENSG00000142453.7 | 4 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 933 | QELNTIASKPPR | ENSG00000169896.12 | 4 |
| SEQ ID NO: 934 | RFSTEYELQQLEQFKK | ENSG00000166825.9 | 4 |
| SEQ ID NO: 935 | RVPPPCAPGR | ENSG00000090006.13 | 4 |
| SEQ ID NO: 936 | SCHAGFGSPAGWDVPVGALIQR | ENSG00000163975.7 | 4 |
| SEQ ID NO: 937 | SFGHFPGPEFLDVEK | ENSG00000165322.13 | 4 |
| SEQ ID NO: 938 | SITEVGEALK | ENSG00000198947.10 | 4 |
| SEQ ID NO: 939 | SLQADTTNTDTALTTLEEALAEKE R | ENSG00000082805.15 | 4 |
| SEQ ID NO: 940 | SSNLLDLKNPFFR | ENSG00000142453.7 | 4 |
| SEQ ID NO: 941 | TGYAFVDCPDESWALK | ENSG00000136231.9 | 4 |
| SEQ ID NO: 942 | TQVTFFFPLDLSYR | ENSG00000169896.12 | 4 |
| SEQ ID NO: 943 | TSKDDLLLTDFEGALK | ENSG00000011454.12 | 4 |
| SEQ ID NO: 944 | TVTINTEQK | ENSG00000065534.14 | 4 |
| SEQ ID NO: 945 | VADLLQHINLMK | ENSG00000152894.10 | 4 |
| SEQ ID NO: 946 | VDANISVHHPGEPLGVR | ENSG00000059691.7 | 4 |
| SEQ ID NO: 947 | VMVGDLEDINEMIIK | ENSG00000198947.10 | 4 |
| SEQ ID NO: 948 | VVGDVAYDEAKER | ENSG00000100714.11 | 4 |
| SEQ ID NO: 949 | VYLLYR | ENSG00000167770.7 | 4 |
| SEQ ID NO: 950 | WANGLSEEKPLSVPR | ENSG00000064545.10 | 4 |
| SEQ ID NO: 951 | WAPNENK | ENSG00000130429.8 | 4 |
| SEQ ID NO: 952 | WCVLSTPEIQK | ENSG00000163975.7 | 4 |
| SEQ ID NO: 953 | WMDPEGEMKPGR | ENSG00000113387.7 | 4 |
| SEQ ID NO: 954 | WVLLQDILLK | ENSG00000198947.10 | 4 |
| SEQ ID NO: 955 | YEEQRPSLK | ENSG00000162614.14 | 4 |
| SEQ ID NO: 956 | YGLLNVTK | ENSG00000165322.13 | 4 |
| SEQ ID NO: 957 | YQHIGLVAMFR | ENSG00000169896.12 | 4 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 958 | YVPAIAHLIHSLNPVR | ENSG00000106066.9 | 4 |
| SEQ ID NO: 959 | AAILQTEVDALR | ENSG00000082805.15 | 3 |
| SEQ ID NO: 960 | ADGGPEAGELPSIGEATAALALAGR | ENSG00000019144.12 | 3 |
| SEQ ID NO: 961 | AENYWWR | ENSG00000061938.12 | 3 |
| SEQ ID NO: 962 | AEQPPHLTPGIR | ENSG00000146733.9 | 3 |
| SEQ ID NO: 963 | AIEALSGK | ENSG00000136231.9 | 3 |
| SEQ ID NO: 964 | AIGNIELGIR | ENSG00000131711.10 | 3 |
| SEQ ID NO: 965 | AMNNSWHPECFR | ENSG00000169756.12 | 3 |
| SEQ ID NO: 966 | APNLSSGNVSLK | ENSG00000155629.10 | 3 |
| SEQ ID NO: 967 | AQVAHADQQLR | ENSG00000137497.13 | 3 |
| SEQ ID NO: 968 | AREHFGTVK | ENSG00000211460.7 | 3 |
| SEQ ID NO: 969 | ARFEQMAKAREE | ENSG00000162614.14 | 3 |
| SEQ ID NO: 970 | ASFANEDGQVSPGSLLLAGAIAGMPAASLVTPADVIK | ENSG00000004864.9 | 3 |
| SEQ ID NO: 971 | AVVVGFDPHFSYMK | ENSG00000184207.8 | 3 |
| SEQ ID NO: 972 | DDLLLTDFEGALK | ENSG00000011454.12 | 3 |
| SEQ ID NO: 973 | DNEETGFGSGTR | ENSG00000166825.9 | 3 |
| SEQ ID NO: 974 | DVDGLTSINAGK | ENSG00000100714.11 | 3 |
| SEQ ID NO: 975 | EAGIQPSLLCVR | ENSG00000163975.7 | 3 |
| SEQ ID NO: 976 | EDFNSKHMANQRALGK | ENSG00000172037.9 | 3 |
| SEQ ID NO: 977 | EEGDLGPVYGFQWR | ENSG00000176890.11 | 3 |
| SEQ ID NO: 978 | EELSSGDSLSPDPWK | ENSG00000130396.16 | 3 |
| SEQ ID NO: 979 | ELQKAVEEMK | ENSG00000198947.10 | 3 |
| SEQ ID NO: 980 | ENSMLREEMHRRFENAPDSAKTK | ENSG00000082805.15 | 3 |
| SEQ ID NO: 981 | EQISDIDDAVRK | ENSG00000113387.7 | 3 |
| SEQ ID NO: 982 | EVVDAGLVGLER | ENSG00000138162.13 | 3 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 983 | FEALQAPACHENMVK | ENSG00000196961.8 | 3 |
| SEQ ID NO: 984 | FHLCSVATR | ENSG00000196961.8 | 3 |
| SEQ ID NO: 985 | FNLDTENAMTFQENAR | ENSG00000169896.12 | 3 |
| SEQ ID NO: 986 | FTEEIPLK | ENSG00000136231.9 | 3 |
| SEQ ID NO: 987 | GALTSTPYSPTQHLER | ENSG00000153310.14 | 3 |
| SEQ ID NO: 988 | GDEGPIGHQGPIGQEGAPGR | ENSG00000134871.13 | 3 |
| SEQ ID NO: 989 | GDSGQPLFLTPYIEAGK | ENSG00000106066.9 | 3 |
| SEQ ID NO: 990 | GEPVSAEDLGVSGALTVLMK | ENSG00000100714.11 | 3 |
| SEQ ID NO: 991 | GFSGIFPACHPCHACFGDWDR | ENSG00000172037.9 | 3 |
| SEQ ID NO: 992 | GIDTPQCHR | ENSG00000172037.9 | 3 |
| SEQ ID NO: 993 | GWDSSHEDDLPVYLAR | ENSG00000113657.8 | 3 |
| SEQ ID NO: 994 | HEQNIDCGGGYV | ENSG00000179218.9 | 3 |
| SEQ ID NO: 995 | HLNQGTDEDIYLLGK | ENSG00000073849.10 | 3 |
| SEQ ID NO: 996 | IAELQQR | ENSG00000137497.13 | 3 |
| SEQ ID NO: 997 | ILVVITDGEK | ENSG00000169896.12 | 3 |
| SEQ ID NO: 998 | INDAFNLASAHK | ENSG00000166825.9 | 3 |
| SEQ ID NO: 999 | INLPAPNPDHVGGYK | ENSG00000004864.9 | 3 |
| SEQ ID NO: 1000 | IQEILTQVK | ENSG00000136231.9 | 3 |
| SEQ ID NO: 1001 | IQPTTPSEPTAIK | ENSG00000198947.10 | 3 |
| SEQ ID NO: 1002 | ISPGSTEITTLPGSTTTPGLSEAST TFYSSPR | ENSG00000205277.5 | 3 |
| SEQ ID NO: 1003 | ISPGSTEITTLPGSTTTPGLSEAST TFYSSPR | ENSG00000205277.5 | 3 |
| SEQ ID NO: 1004 | ISPGSTEITTLPGSTTTPGLSEAST TFYSSPR | ENSG00000205277.5 | 3 |
| SEQ ID NO: 1005 | ISPGSTEITTLPGSTTTPGLSEAST TFYSSPR | ENSG00000205277.5 | 3 |
| SEQ ID NO: 1006 | ISSMERGLR | ENSG00000082805.15 | 3 |
| SEQ ID NO: 1007 | IVLDVGCGSGILSFFAAQAGAR | ENSG00000142453.7 | 3 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1008 | IYGADDIELLPEAQHKAEVYTK | ENSG00000100714.11 | 3 |
| SEQ ID NO: 1009 | KDVKLDK | ENSG00000170776.15 | 3 |
| SEQ ID NO: 1010 | KFQETEQTIQK | ENSG00000132205.6 | 3 |
| SEQ ID NO: 1011 | KFSYDLSQCINQMK | ENSG00000135052.12 | 3 |
| SEQ ID NO: 1012 | KLPAENGSSSAETLNAK | ENSG00000065534.14 | 3 |
| SEQ ID NO: 1013 | KLTELENELNTK | ENSG00000130396.16 | 3 |
| SEQ ID NO: 1014 | KQTENPK | ENSG00000198947.10 | 3 |
| SEQ ID NO: 1015 | KQVTPLFIHFR | ENSG00000166825.9 | 3 |
| SEQ ID NO: 1016 | KRVEDAYILTCNVSLEYEK | ENSG00000146731.6 | 3 |
| SEQ ID NO: 1017 | KVPFAWCAPESLK | ENSG00000061938.12 | 3 |
| SEQ ID NO: 1018 | LAGAPAPK | ENSG00000184207.8 | 3 |
| SEQ ID NO: 1019 | LHELYEKVFSRRADR | ENSG00000032444.11 | 3 |
| SEQ ID NO: 1020 | LLDPEDVDTTYPDKK | ENSG00000198947.10 | 3 |
| SEQ ID NO: 1021 | LLESLQENHFQEDEQFLGAVMPR | ENSG00000086475.10 | 3 |
| SEQ ID NO: 1022 | LLQVAVEDR | ENSG00000198947.10 | 3 |
| SEQ ID NO: 1023 | LLVSDIQTIQPSLNSVNEGGQK | ENSG00000198947.10 | 3 |
| SEQ ID NO: 1024 | LNLHSADWQR | ENSG00000198947.10 | 3 |
| SEQ ID NO: 1025 | LPAENGSSSAETLNAK | ENSG00000065534.14 | 3 |
| SEQ ID NO: 1026 | LPLEDADIIK | ENSG00000110237.3 | 3 |
| SEQ ID NO: 1027 | LPLQMALTELETLAEK | ENSG00000104728.11 | 3 |
| SEQ ID NO: 1028 | LPTEWNVLGTDQSLHDAGPR | ENSG00000170776.15 | 3 |
| SEQ ID NO: 1029 | LQEALSQLDFQWEK | ENSG00000198947.10 | 3 |
| SEQ ID NO: 1030 | LQEPSAQANCCDSEKNGDIGQQIK | ENSG00000132205.6 | 3 |
| SEQ ID NO: 1031 | LQSQVISELDACKECTQGVQR | ENSG00000132205.6 | 3 |
| SEQ ID NO: 1032 | LYIGNLSENAAPSDLESIFK | ENSG00000136231.9 | 3 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1033 | MLESYLHAK | ENSG00000142453.7 | 3 |
| SEQ ID NO: 1034 | NLLLATR | ENSG00000061938.12 | 3 |
| SEQ ID NO: 1035 | NVLLHEMQIQHPTASLIAK | ENSG00000146731.6 | 3 |
| SEQ ID NO: 1036 | QKPCDLPLR | ENSG00000136231.9 | 3 |
| SEQ ID NO: 1037 | QPAAFIVTQYPLPNTVK | ENSG00000152894.10 | 3 |
| SEQ ID NO: 1038 | QQLGHIEAWAEK | ENSG00000130396.16 | 3 |
| SEQ ID NO: 1039 | QREEHYFCK | ENSG00000133315.6 | 3 |
| SEQ ID NO: 1040 | QVFHALEDELQK | ENSG00000151914.13 | 3 |
| SEQ ID NO: 1041 | QWMENPNNNPIHPNLR | ENSG00000166825.9 | 3 |
| SEQ ID NO: 1042 | SAQALVEQMVNEGVNADSIK | ENSG00000198947.10 | 3 |
| SEQ ID NO: 1043 | SATSVLVGEPTTSPISSGSTETTALPGSTTTAGLSEK | ENSG00000205277.5 | 3 |
| SEQ ID NO: 1044 | SATSVLVGEPTTSPISSGSTETTALPGSTTTAGLSEK | ENSG00000205277.5 | 3 |
| SEQ ID NO: 1045 | SATSVLVGEPTTSPISSGSTETTALPGSTTTAGLSEK | ENSG00000205277.5 | 3 |
| SEQ ID NO: 1046 | SAVEGMPSNLDSEVAWGK | ENSG00000198947.10 | 3 |
| SEQ ID NO: 1047 | SEDSTIYDLLKDPVSLR | ENSG00000104728.11 | 3 |
| SEQ ID NO: 1048 | SLESALKDLK | ENSG00000130429.8 | 3 |
| SEQ ID NO: 1049 | SPNPALTFCVK | ENSG00000019144.12 | 3 |
| SEQ ID NO: 1050 | STTFYTSPR | ENSG00000205277.5 | 3 |
| SEQ ID NO: 1051 | STTFYTSPR | ENSG00000205277.5 | 3 |
| SEQ ID NO: 1052 | STTFYTSPR | ENSG00000205277.5 | 3 |
| SEQ ID NO: 1053 | STTFYTSPR | ENSG00000205277.5 | 3 |
| SEQ ID NO: 1054 | TCHYYANK | ENSG00000134871.13 | 3 |
| SEQ ID NO: 1055 | TCSECQELHWGDPGLQCHACDCDSR | ENSG00000172037.9 | 3 |
| SEQ ID NO: 1056 | TCYPLESR | ENSG00000137497.13 | 3 |
| SEQ ID NO: 1057 | TEFQLELPVK | ENSG00000169896.12 | 3 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1058 | TKEPVIMSTLETVR | ENSG00000198947.10 | 3 |
| SEQ ID NO: 1059 | TPLWIGLAGEEGSRR | ENSG00000011028.9 | 3 |
| SEQ ID NO: 1060 | TQSLNPAPFSPLTAQQMKPEKPSTLQRPQETVIR | ENSG00000130396.16 | 3 |
| SEQ ID NO: 1061 | TVGWNVPVGYLVESGR | ENSG00000163975.7 | 3 |
| SEQ ID NO: 1062 | VASSSSGNNFLSGSPASPMGDILQTPQFQMR | ENSG00000137497.13 | 3 |
| SEQ ID NO: 1063 | VAWVSHDSTVCLADADK | ENSG00000130429.8 | 3 |
| SEQ ID NO: 1064 | VEQQPDYR | ENSG00000130396.16 | 3 |
| SEQ ID NO: 1065 | VIQEVSGLPSEGASEGNQYTPDAQR | ENSG00000169129.10 | 3 |
| SEQ ID NO: 1066 | VLDLLDPASGDLVIR | ENSG00000079616.8 | 3 |
| SEQ ID NO: 1067 | VLLHEMQIQHPTASLIAK | ENSG00000146731.6 | 3 |
| SEQ ID NO: 1068 | VMDKVTSDETR | ENSG00000138162.13 | 3 |
| SEQ ID NO: 1069 | VPRYELLLK | ENSG00000127084.13 | 3 |
| SEQ ID NO: 1070 | VQFGASHVFK | ENSG00000130396.16 | 3 |
| SEQ ID NO: 1071 | VSCIVSAAK | ENSG00000169129.10 | 3 |
| SEQ ID NO: 1072 | VTEILGIEPDREK | ENSG00000211460.7 | 3 |
| SEQ ID NO: 1073 | VVDALNQGLPR | ENSG00000079616.8 | 3 |
| SEQ ID NO: 1074 | WKTPAAIPATPVAVSQPIR | ENSG00000130396.16 | 3 |
| SEQ ID NO: 1075 | YLETADYAIREEIVLK | ENSG00000196961.8 | 3 |
| SEQ ID NO: 1076 | YLNWESDQPDNPSEENCGVIR | ENSG00000011028.9 | 3 |
| SEQ ID NO: 1077 | YVGFGNTPPPQKK | ENSG00000101199.8 | 3 |
| SEQ ID NO: 1078 | AAGNFATK | ENSG00000130396.16 | 2 |
| SEQ ID NO: 1079 | AEGERQPPPDSSEEAPPATQNFIIPK | ENSG00000119383.15 | 2 |
| SEQ ID NO: 1080 | AGLVVEDALFETLPSDVR | ENSG00000171488.10 | 2 |
| SEQ ID NO: 1081 | AHCGDPVSLAAAGDGSPDIGPTGELSGSLK | ENSG00000127084.13 | 2 |
| SEQ ID NO: 1082 | AILQNHTDFKDK | ENSG00000142453.7 | 2 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1083 | AINVYGTSEPSQESELTTVGEKPEEPK | ENSG00000065534.14 | 2 |
| SEQ ID NO: 1084 | ALGEDQVAETSAMSDVLKDILK | ENSG00000157617.12 | 2 |
| SEQ ID NO: 1085 | ANIVMVLEIVSGGELFER | ENSG00000065534.14 | 2 |
| SEQ ID NO: 1086 | APEEQGLLPNGEPSQHSSAPQK | ENSG00000169129.10 | 2 |
| SEQ ID NO: 1087 | APGLGVLSPSGEER | ENSG00000065534.14 | 2 |
| SEQ ID NO: 1088 | AQDDVSEWASK | ENSG00000132561.9 | 2 |
| SEQ ID NO: 1089 | ASSISEEVAVGSIAATLK | ENSG00000170776.15 | 2 |
| SEQ ID NO: 1090 | ATLALDSVLTEEGK | ENSG00000170776.15 | 2 |
| SEQ ID NO: 1091 | AVGGDRQEAIQPGCIGGPKGLPGLPGPPGPTGAKGLRGIPGFAGADGGP | ENSG00000134871.13 | 2 |
| SEQ ID NO: 1092 | AVGLVSTWTQR | ENSG00000127084.13 | 2 |
| SEQ ID NO: 1093 | AVSSADPR | ENSG00000138162.13 | 2 |
| SEQ ID NO: 1094 | AWHAFFTAAER | ENSG00000165912.11 | 2 |
| SEQ ID NO: 1095 | DCTQCLQHPWLMK | ENSG00000065534.14 | 2 |
| SEQ ID NO: 1096 | DEISDDAKDFISNLLK | ENSG00000065534.14 | 2 |
| SEQ ID NO: 1097 | DFGPASQHFLSTSVQGPWER | ENSG00000198947.10 | 2 |
| SEQ ID NO: 1098 | DFLDSLGFSTR | ENSG00000176890.11 | 2 |
| SEQ ID NO: 1099 | DGEWEPPVIQNPEYK | ENSG00000179218.9 | 2 |
| SEQ ID NO: 1100 | DTSPAPSGTTSAFVK | ENSG00000205277.5 | 2 |
| SEQ ID NO: 1101 | EAEDRARQEEERR | ENSG00000130396.16 | 2 |
| SEQ ID NO: 1102 | EAPYGAPR | ENSG00000090006.13 | 2 |
| SEQ ID NO: 1103 | ECAIYTNR | ENSG00000104450.8 | 2 |
| SEQ ID NO: 1104 | EGIVALRR | ENSG00000146731.6 | 2 |
| SEQ ID NO: 1105 | EGPYTVDAIQK | ENSG00000198947.10 | 2 |
| SEQ ID NO: 1106 | EKELQTIFDTLPPMR | ENSG00000198947.10 | 2 |
| SEQ ID NO: 1107 | ELEQQLQESAR | ENSG00000019144.12 | 2 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1108 | EQLDKIQSSHNFQLESVNK | ENSG00000135052.12 | 2 |
| SEQ ID NO: 1109 | EVTKEEFVLAAQK | ENSG00000004864.9 | 2 |
| SEQ ID NO: 1110 | EVVPGDSVNSLLSILDVITGHQHPQR | ENSG00000032444.11 | 2 |
| SEQ ID NO: 1111 | EYWMDPEGEMKPGRK | ENSG00000113387.7 | 2 |
| SEQ ID NO: 1112 | FGFSHLEALLDDSK | ENSG00000167770.7 | 2 |
| SEQ ID NO: 1113 | FGSQASQK | ENSG00000101199.8 | 2 |
| SEQ ID NO: 1114 | FHELTQTDK | ENSG00000100714.11 | 2 |
| SEQ ID NO: 1115 | FLDLGISIAENR | ENSG00000125826.15 | 2 |
| SEQ ID NO: 1116 | FLLDCGIR | ENSG00000065534.14 | 2 |
| SEQ ID NO: 1117 | FVDPSQDHALAK | ENSG00000130396.16 | 2 |
| SEQ ID NO: 1118 | FYGDEEK | ENSG00000179218.9 | 2 |
| SEQ ID NO: 1119 | GAWLGMNFNPK | ENSG00000011028.9 | 2 |
| SEQ ID NO: 1120 | GILVFQLK | ENSG00000130396.16 | 2 |
| SEQ ID NO: 1121 | GISLNPEQWSQL | ENSG00000113387.7 | 2 |
| SEQ ID NO: 1122 | GLYLPLFKPSVSTSK | ENSG00000004864.9 | 2 |
| SEQ ID NO: 1123 | GMEDLIPLVNR | ENSG00000106976.14 | 2 |
| SEQ ID NO: 1124 | GPIGHQGPIGQEGAPGR | ENSG00000134871.13 | 2 |
| SEQ ID NO: 1125 | GPNKHTLTQIK | ENSG00000146731.6 | 2 |
| SEQ ID NO: 1126 | GPTCNEFTGQCHCR | ENSG00000172037.9 | 2 |
| SEQ ID NO: 1127 | GSEGEPGIR | ENSG00000134871.13 | 2 |
| SEQ ID NO: 1128 | GTDVREPDDSPQGR | ENSG00000011028.9 | 2 |
| SEQ ID NO: 1129 | GWAGDSGPQGR | ENSG00000134871.13 | 2 |
| SEQ ID NO: 1130 | HAQEELPPPPPQKK | ENSG00000198947.10 | 2 |
| SEQ ID NO: 1131 | HSTVLENTDGK | ENSG00000163975.7 | 2 |
| SEQ ID NO: 1132 | IEELEEALR | ENSG00000082805.15 | 2 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1133 | IEGSGDQIDTYELSGGAR | ENSG00000106976.14 | 2 |
| SEQ ID NO: 1134 | IELHGKPIEVEHSVPK | ENSG00000136231.9 | 2 |
| SEQ ID NO: 1135 | IIDEDFELTERECIK | ENSG00000065534.14 | 2 |
| SEQ ID NO: 1136 | IKLIDFGLAR | ENSG00000065534.14 | 2 |
| SEQ ID NO: 1137 | ILDLLNEGSAR | ENSG00000079616.8 | 2 |
| SEQ ID NO: 1138 | ILMELDGPNWR | ENSG00000104450.8 | 2 |
| SEQ ID NO: 1139 | IPQAVVDVSSHLQK | ENSG00000171488.10 | 2 |
| SEQ ID NO: 1140 | IQAEQVDAVTLSGEDIYTAGK | ENSG00000163975.7 | 2 |
| SEQ ID NO: 1141 | IVIYVQQTTNK | ENSG00000011454.12 | 2 |
| SEQ ID NO: 1142 | IVSEFDYVEK | ENSG00000166825.9 | 2 |
| SEQ ID NO: 1143 | KADTLPR | ENSG00000049323.11 | 2 |
| SEQ ID NO: 1144 | KINQLSEENGDLSFK | ENSG00000137497.13 | 2 |
| SEQ ID NO: 1145 | KIQEILTQVK | ENSG00000136231.9 | 2 |
| SEQ ID NO: 1146 | KKLPAENGSSSAETLNAK | ENSG00000065534.14 | 2 |
| SEQ ID NO: 1147 | KLLLQCQVSSDPPATIIWTLNGK | ENSG00000065534.14 | 2 |
| SEQ ID NO: 1148 | KPAAGLSAAPVPTAPAAGAPL | ENSG00000115310.13 | 2 |
| SEQ ID NO: 1149 | KSPSSDSWTCADTSTER | ENSG00000101199.8 | 2 |
| SEQ ID NO: 1150 | KSSTGSPTSPLNAEK | ENSG00000065534.14 | 2 |
| SEQ ID NO: 1151 | LALLNEK | ENSG00000137497.13 | 2 |
| SEQ ID NO: 1152 | LDIDEK | ENSG00000130396.16 | 2 |
| SEQ ID NO: 1153 | LIAPLEGYTR | ENSG00000167608.7 | 2 |
| SEQ ID NO: 1154 | LKEEEEDKK | ENSG00000179218.9 | 2 |
| SEQ ID NO: 1155 | LKNQVTQLKEQVPGFTPR | ENSG00000100714.11 | 2 |
| SEQ ID NO: 1156 | LLDPQTNTEIANYPIYK | ENSG00000011454.12 | 2 |
| SEQ ID NO: 1157 | LLDRLPSFQQSCR | ENSG00000213380.9 | 2 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1158 | LLEAIKR | ENSG00000112096.12 | 2 |
| SEQ ID NO: 1159 | LLGFGSALLDNVDPNPENFVGA GIIQTK | ENSG00000196961.8 | 2 |
| SEQ ID NO: 1160 | LQAQLNELQAQLSQKEQAAEHY K | ENSG00000137497.13 | 2 |
| SEQ ID NO: 1161 | LQDVHVAEGKK | ENSG00000065534.14 | 2 |
| SEQ ID NO: 1162 | LQGEVLALEEER | ENSG00000019144.12 | 2 |
| SEQ ID NO: 1163 | LSALHLEVR | ENSG00000165912.11 | 2 |
| SEQ ID NO: 1164 | LSSQLVEHCQK | ENSG00000198947.10 | 2 |
| SEQ ID NO: 1165 | LSVMGCDVLK | ENSG00000163975.7 | 2 |
| SEQ ID NO: 1166 | LTAASVGVQGSGWGWLGFNKE R | ENSG00000112096.12 | 2 |
| SEQ ID NO: 1167 | LTDVAIGAPGEEDNR | ENSG00000169896.12 | 2 |
| SEQ ID NO: 1168 | LTHGVLHTK | ENSG00000105223.14 | 2 |
| SEQ ID NO: 1169 | LVTDPDSGLCSHYWGAIIR | ENSG00000130396.16 | 2 |
| SEQ ID NO: 1170 | MDPEGEMKPGR | ENSG00000113387.7 | 2 |
| SEQ ID NO: 1171 | MELLVK | ENSG00000145362.12 | 2 |
| SEQ ID NO: 1172 | MVSMMEGVIQK | ENSG00000130396.16 | 2 |
| SEQ ID NO: 1173 | MVVASSK | ENSG00000100714.11 | 2 |
| SEQ ID NO: 1174 | NDAGQAECSCQVTVDDAPASE NTKAPEMK | ENSG00000065534.14 | 2 |
| SEQ ID NO: 1175 | NILSEFQR | ENSG00000198947.10 | 2 |
| SEQ ID NO: 1176 | NLLEVSEVEQELACONDHSSALQ NIK | ENSG00000136631.8 | 2 |
| SEQ ID NO: 1177 | NLVDSYMAIVNK | ENSG00000106976.14 | 2 |
| SEQ ID NO: 1178 | NVNVFFPHFK | ENSG00000151116.12 | 2 |
| SEQ ID NO: 1179 | PASAEQIQHLAGAIAER | ENSG00000172037.9 | 2 |
| SEQ ID NO: 1180 | PAVPASVPLQAWHPAK | ENSG00000104450.8 | 2 |
| SEQ ID NO: 1181 | PFSAIYFPCYAHVK | ENSG00000004864.9 | 2 |
| SEQ ID NO: 1182 | PGPVPAHSLCGHLVPK | ENSG00000172037.9 | 2 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1183 | PLQGTTGLIPLLGIDVWEHAYYLQYK | ENSG00000112096.12 | 2 |
| SEQ ID NO: 1184 | PNENKFAVGSGSR | ENSG00000130429.8 | 2 |
| SEQ ID NO: 1185 | PPVQFSLLHSK | ENSG00000196961.8 | 2 |
| SEQ ID NO: 1186 | QAPIGGDFPAVQK | ENSG00000198947.10 | 2 |
| SEQ ID NO: 1187 | QKLQDVHVAEGK | ENSG00000065534.14 | 2 |
| SEQ ID NO: 1188 | QLAAYIADKVDAAQMPQEAQK | ENSG00000198947.10 | 2 |
| SEQ ID NO: 1189 | QLSESSKLK | ENSG00000157617.12 | 2 |
| SEQ ID NO: 1190 | QQTANKVEIEK | ENSG00000011454.12 | 2 |
| SEQ ID NO: 1191 | QSSSSRDDNMFQIGK | ENSG00000113387.7 | 2 |
| SEQ ID NO: 1192 | QYTYGLVSCGLDR | ENSG00000004139.9 | 2 |
| SEQ ID NO: 1193 | RAGNSLAASTAEETAGSAQGR | ENSG00000172037.9 | 2 |
| SEQ ID NO: 1194 | REAPYGAPR | ENSG00000090006.13 | 2 |
| SEQ ID NO: 1195 | REPAPNAPGDIAAAFPAER | ENSG00000138162.13 | 2 |
| SEQ ID NO: 1196 | RGWDSSHEDDLPVYLAR | ENSG00000113657.8 | 2 |
| SEQ ID NO: 1197 | RLEEESAQLK | ENSG00000011454.12 | 2 |
| SEQ ID NO: 1198 | RQVEKEETNEIQVVNEEPQR | ENSG00000135052.12 | 2 |
| SEQ ID NO: 1199 | RSESQGTAPAFK | ENSG00000065534.14 | 2 |
| SEQ ID NO: 1200 | SCTEETHGFICQK | ENSG00000011028.9 | 2 |
| SEQ ID NO: 1201 | SDFGKFVLSSGK | ENSG00000179218.9 | 2 |
| SEQ ID NO: 1202 | SEYMEGNVR | ENSG00000166825.9 | 2 |
| SEQ ID NO: 1203 | SFAPILPHLAEEVFQHIPYIK | ENSG00000067704.8 | 2 |
| SEQ ID NO: 1204 | SKVPQETQSGGGSR | ENSG00000049323.11 | 2 |
| SEQ ID NO: 1205 | SPATTLSPASTTSSGVSEESTTSHSR | ENSG00000205277.5 | 2 |
| SEQ ID NO: 1206 | SPATTLSPASTTSSGVSEESTTSHSR | ENSG00000205277.5 | 2 |
| SEQ ID NO: 1207 | SPATTLSPASTTSSGVSEESTTSHSRPGSTHTTAFPDSTTTPGLSR | ENSG00000205277.5 | 2 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1208 | SPATTLSPASTTSSGVSEESTTSHSRPGSTHTTAFPDSTTTPGLSR | ENSG00000205277.5 | 2 |
| SEQ ID NO: 1209 | SQDLQVIDLLTVGESR | ENSG00000169231.9 | 2 |
| SEQ ID NO: 1210 | SREPQAKPQLDLSIDSLDLSCEEGTPLSITSK | ENSG00000137497.13 | 2 |
| SEQ ID NO: 1211 | SRQELASGLPSPAATQELPVER | ENSG00000138162.13 | 2 |
| SEQ ID NO: 1212 | SSAAAGAPSR | ENSG00000049323.11 | 2 |
| SEQ ID NO: 1213 | SSPNVANQPPSPGGK | ENSG00000130396.16 | 2 |
| SEQ ID NO: 1214 | SSSEVLVLAETLDGVR | ENSG00000130589.12 | 2 |
| SEQ ID NO: 1215 | SVQEIAEQLLLENHPAR | ENSG00000151914.13 | 2 |
| SEQ ID NO: 1216 | TCTGYHQVR | ENSG00000133316.11 | 2 |
| SEQ ID NO: 1217 | TGETSR | ENSG00000113387.7 | 2 |
| SEQ ID NO: 1218 | TIQNQLR | ENSG00000169896.12 | 2 |
| SEQ ID NO: 1219 | TLFSLMQYSEEFR | ENSG00000169896.12 | 2 |
| SEQ ID NO: 1220 | TPAPDGPR | ENSG00000032444.11 | 2 |
| SEQ ID NO: 1221 | TPGQIVSEK | ENSG00000059691.7 | 2 |
| SEQ ID NO: 1222 | TPVPEK | ENSG00000065534.14 | 2 |
| SEQ ID NO: 1223 | TTLLDPDSCR | ENSG00000205277.5 | 2 |
| SEQ ID NO: 1224 | TTTESEVMK | ENSG00000100714.11 | 2 |
| SEQ ID NO: 1225 | TVLQIDCGLQLANDSVNR | ENSG00000104450.8 | 2 |
| SEQ ID NO: 1226 | VAQQPLSLVGCEVVPDPSPDHLYSFR | ENSG00000169129.10 | 2 |
| SEQ ID NO: 1227 | VHALNNVNK | ENSG00000198947.10 | 2 |
| SEQ ID NO: 1228 | VIVMPTTK | ENSG00000067704.8 | 2 |
| SEQ ID NO: 1229 | VLQEDLEQEQVR | ENSG00000198947.10 | 2 |
| SEQ ID NO: 1230 | VPAHAVVVR | ENSG00000163975.7 | 2 |
| SEQ ID NO: 1231 | WLNEVEFK | ENSG00000198947.10 | 2 |
| SEQ ID NO: 1232 | WTDGSIINFISWAPGK | ENSG00000011028.9 | 2 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1233 | WTDGSIINFISWAPGKPR | ENSG00000011028.9 | 2 |
| SEQ ID NO: 1234 | WVNAQFSK | ENSG00000198947.10 | 2 |
| SEQ ID NO: 1235 | YDNFGVLGLDLWQVK | ENSG00000179218.9 | 2 |
| SEQ ID NO: 1236 | YLLYRPGHYDILYK | ENSG00000167770.7 | 2 |
| SEQ ID NO: 1237 | YLSSLDLLLEHR | ENSG00000133315.6 | 2 |
| SEQ ID NO: 1238 | YLVHCLQSELNNYMPAFLDDPEE NSLQRPK | ENSG00000130396.16 | 2 |
| SEQ ID NO: 1239 | YRDPGVLPWGALEEEEEDGGR | ENSG00000167608.7 | 2 |
| SEQ ID NO: 1240 | AAAAAVGPGAGGAGSAVPGGA GPCATVSVFPGAR | ENSG00000142453.7 | 1 |
| SEQ ID NO: 1241 | AAAKVALTKRADPAELR | ENSG00000004864.9 | 1 |
| SEQ ID NO: 1242 | AAATEEPEVIPDPAK | ENSG00000152894.10 | 1 |
| SEQ ID NO: 1243 | AAEEPQQQK | ENSG00000167770.7 | 1 |
| SEQ ID NO: 1244 | AAGDGSPDIGPTGELSGSLKIPNR | ENSG00000127084.13 | 1 |
| SEQ ID NO: 1245 | AAGLQAEIGQVK | ENSG00000082805.15 | 1 |
| SEQ ID NO: 1246 | AASGVPR | ENSG00000155629.10 | 1 |
| SEQ ID NO: 1247 | ACGNMFGLMHGTCPETSGGLLI CLPR | ENSG00000086475.10 | 1 |
| SEQ ID NO: 1248 | ADSAVSQEQLR | ENSG00000165912.11 | 1 |
| SEQ ID NO: 1249 | AEEKPHVKPYFSK | ENSG00000065534.14 | 1 |
| SEQ ID NO: 1250 | AELEYNPEHVSR | ENSG00000067704.8 | 1 |
| SEQ ID NO: 1251 | AEQLLQDAR | ENSG00000172037.9 | 1 |
| SEQ ID NO: 1252 | AEYMRIQAQQQATKPSKEMS | ENSG00000017373.11 | 1 |
| SEQ ID NO: 1253 | AFCGLGTTGMWR | ENSG00000110237.3 | 1 |
| SEQ ID NO: 1254 | AFLEAVAEEKPHVKPYFSK | ENSG00000065534.14 | 1 |
| SEQ ID NO: 1255 | AHKQCALKLLR | ENSG00000141447.12 | 1 |
| SEQ ID NO: 1256 | ALMDLLQLTR | ENSG00000079616.8 | 1 |
| SEQ ID NO: 1257 | ALQDFEEPDK | ENSG00000061938.12 | 1 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1258 | ALQFLEEVKVSR | ENSG00000146731.6 | 1 |
| SEQ ID NO: 1259 | ALQHMAAMSSAQIVSATAIHNK LGLPGIPRPT | ENSG00000187079.10 | 1 |
| SEQ ID NO: 1260 | AMAYETLEQYGK | ENSG00000104450.8 | 1 |
| SEQ ID NO: 1261 | AMLAAVLEQELPALAENLHQEQ K | ENSG00000142733.10 | 1 |
| SEQ ID NO: 1262 | AMLAAVLEQELPALAENLHQEQ K | ENSG00000142733.10 | 1 |
| SEQ ID NO: 1263 | ANGITMYAVGVGKAIEEELQEIA SEPTNK | ENSG00000132561.9 | 1 |
| SEQ ID NO: 1264 | APAPDVPGCSR | ENSG00000172037.9 | 1 |
| SEQ ID NO: 1265 | APILPHLAEEVFQHIPYIK | ENSG00000067704.8 | 1 |
| SEQ ID NO: 1266 | AQALLADVDTLLFDCDGVLWR | ENSG00000184207.8 | 1 |
| SEQ ID NO: 1267 | AQNSGFDLQETLVK | ENSG00000146731.6 | 1 |
| SEQ ID NO: 1268 | ARFEQMAK | ENSG00000162614.14 | 1 |
| SEQ ID NO: 1269 | ARPEAYQVPASYQPDEEER | ENSG00000125826.15 | 1 |
| SEQ ID NO: 1270 | ARTSAGVGAWGAAAVGRTAGV R | ENSG00000133315.6 | 1 |
| SEQ ID NO: 1271 | ASIPLKELEQFNSDIQK | ENSG00000198947.10 | 1 |
| SEQ ID NO: 1272 | ATSCFPRPMTPRDR | ENSG00000137497.13 | 1 |
| SEQ ID NO: 1273 | AVTSVSGPGEHLR | ENSG00000169231.9 | 1 |
| SEQ ID NO: 1274 | CAEVVSGK | ENSG00000067704.8 | 1 |
| SEQ ID NO: 1275 | CFGLLLSPGK | ENSG00000011454.12 | 1 |
| SEQ ID NO: 1276 | CGDSDKGFVVINQK | ENSG00000146731.6 | 1 |
| SEQ ID NO: 1277 | CGGLSCNGAAATADLALGR | ENSG00000172037.9 | 1 |
| SEQ ID NO: 1278 | CLCPPDFAGK | ENSG00000090006.13 | 1 |
| SEQ ID NO: 1279 | CLQHPWLMK | ENSG00000065534.14 | 1 |
| SEQ ID NO: 1280 | CLVENAGDVAFVR | ENSG00000163975.7 | 1 |
| SEQ ID NO: 1281 | CSGNIDPMDPDACDPHTGQCLR | ENSG00000172037.9 | 1 |
| SEQ ID NO: 1282 | CTEGPIDLVFVIDGSK | ENSG00000132561.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1283 | CTQCLQHPWLMK | ENSG00000065534.14 | 1 |
| SEQ ID NO: 1284 | CVRWAPNENK | ENSG00000130429.8 | 1 |
| SEQ ID NO: 1285 | DALLEALK | ENSG00000172037.9 | 1 |
| SEQ ID NO: 1286 | DCCFEISAPDKR | ENSG00000005020.8 | 1 |
| SEQ ID NO: 1287 | DDRTGTGTLSVFGMQARYSLR | ENSG00000176890.11 | 1 |
| SEQ ID NO: 1288 | DEDFELTERECIK | ENSG00000065534.14 | 1 |
| SEQ ID NO: 1289 | DISLQGPGLAPE | ENSG00000019144.12 | 1 |
| SEQ ID NO: 1290 | DITAALAAER | ENSG00000106976.14 | 1 |
| SEQ ID NO: 1291 | DLNVISSLLK | ENSG00000225485.3 | 1 |
| SEQ ID NO: 1292 | DQREPLPPAPAENEMK | ENSG00000104728.11 | 1 |
| SEQ ID NO: 1293 | DQSPLVSSSDSPPRPQPAFK | ENSG00000115310.13 | 1 |
| SEQ ID NO: 1294 | DRRGSGKPR | ENSG00000130396.16 | 1 |
| SEQ ID NO: 1295 | DSSHAFTLDELR | ENSG00000163975.7 | 1 |
| SEQ ID NO: 1296 | DWDSPYSHDLDTSADSVGNACR | ENSG00000105223.14 | 1 |
| SEQ ID NO: 1297 | EAEQLLRGPLGDQYQTVK | ENSG00000172037.9 | 1 |
| SEQ ID NO: 1298 | EAEVQTWLQQIGFSK | ENSG00000004139.9 | 1 |
| SEQ ID NO: 1299 | EDTVQSVK | ENSG00000106066.9 | 1 |
| SEQ ID NO: 1300 | EEAEQVLGQAR | ENSG00000198947.10 | 1 |
| SEQ ID NO: 1301 | EGIVALR | ENSG00000146731.6 | 1 |
| SEQ ID NO: 1302 | EGTEAEPLPLR | ENSG00000142733.10 | 1 |
| SEQ ID NO: 1303 | EGTEAEPLPLR | ENSG00000142733.10 | 1 |
| SEQ ID NO: 1304 | EGTPGIFQK | ENSG00000205277.5 | 1 |
| SEQ ID NO: 1305 | EGVIQNFK | ENSG00000130396.16 | 1 |
| SEQ ID NO: 1306 | EIDAALQK | ENSG00000162614.14 | 1 |
| SEQ ID NO: 1307 | EIHTVPDMGKWKR | ENSG00000119383.15 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1308 | EKLTAASVGVQGSGWGWLGFNK | ENSG00000112096.12 | 1 |
| SEQ ID NO: 1309 | ELEAKMLAQKAEEKENHCPTMLR | ENSG00000079616.8 | 1 |
| SEQ ID NO: 1310 | ELEEKDGDVQAGANLSFNR | ENSG00000158560.10 | 1 |
| SEQ ID NO: 1311 | ELETLTTNYQWLCTR | ENSG00000198947.10 | 1 |
| SEQ ID NO: 1312 | ELLLSGPPEVAAPDTPYLHVDSAAQR | ENSG00000138162.13 | 1 |
| SEQ ID NO: 1313 | ELQDGIGQR | ENSG00000198947.10 | 1 |
| SEQ ID NO: 1314 | EMSKKAPSEISRK | ENSG00000198947.10 | 1 |
| SEQ ID NO: 1315 | ENIRQEISIMNCLHHPK | ENSG00000065534.14 | 1 |
| SEQ ID NO: 1316 | EPMKAPLCGEGDQPGGFESQEK | ENSG00000138162.13 | 1 |
| SEQ ID NO: 1317 | EPYAREMLAISFISAVNR | ENSG00000225485.3 | 1 |
| SEQ ID NO: 1318 | ERARKFSGSGLAMGLGSASASAWRR | ENSG00000082458.7 | 1 |
| SEQ ID NO: 1319 | ERARKFSGSGLAMGLGSASASAWRR | ENSG00000082458.7 | 1 |
| SEQ ID NO: 1320 | ERVLSLSQALATEASQWHR | ENSG00000105559.7 | 1 |
| SEQ ID NO: 1321 | ESGRGSSTPPGPIAALGMPDTGPGSSSLGK | ENSG00000127084.13 | 1 |
| SEQ ID NO: 1322 | ESGSLEDDWDFLPPKK | ENSG00000179218.9 | 1 |
| SEQ ID NO: 1323 | EVARNVFECNDQVVK | ENSG00000169896.12 | 1 |
| SEQ ID NO: 1324 | EVPEEGPGAPAR | ENSG00000186635.10 | 1 |
| SEQ ID NO: 1325 | EYQEDLALR | ENSG00000125826.15 | 1 |
| SEQ ID NO: 1326 | FAGDSLK | ENSG00000151914.13 | 1 |
| SEQ ID NO: 1327 | FGPGDQVR | ENSG00000114331.8 | 1 |
| SEQ ID NO: 1328 | FGVLGLDLWQVK | ENSG00000179218.9 | 1 |
| SEQ ID NO: 1329 | FKDNPTVVVEDLR | ENSG00000114331.8 | 1 |
| SEQ ID NO: 1330 | FNGAPTANFQQDVGTK | ENSG00000073849.10 | 1 |
| SEQ ID NO: 1331 | FNHPAEAKWMK | ENSG00000019144.12 | 1 |
| SEQ ID NO: 1332 | FNRALNCMNLPPDK | ENSG00000184922.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1333 | FRLAEDGKR | ENSG00000132561.9 | 1 |
| SEQ ID NO: 1334 | FSAEALR | ENSG00000073849.10 | 1 |
| SEQ ID NO: 1335 | FSPEVPGQK | ENSG00000131711.10 | 1 |
| SEQ ID NO: 1336 | FTDFEEVR | ENSG00000106976.14 | 1 |
| SEQ ID NO: 1337 | FVPIIGIAMPLSSR | ENSG00000151835.9 | 1 |
| SEQ ID NO: 1338 | FWPAIDDGLRR | ENSG00000105223.14 | 1 |
| SEQ ID NO: 1339 | FWVVDQTHFYLGSANMDWR | ENSG00000105223.14 | 1 |
| SEQ ID NO: 1340 | GAAVDEYFRQPVVDTFDIR | ENSG00000142453.7 | 1 |
| SEQ ID NO: 1341 | GAFHRPVLGGFR | ENSG00000165912.11 | 1 |
| SEQ ID NO: 1342 | GAGLAWGVHDCQLCSER | ENSG00000090006.13 | 1 |
| SEQ ID NO: 1343 | GAPISAYQIVVEELHPHRT | ENSG00000152894.10 | 1 |
| SEQ ID NO: 1344 | GATGHPGGGQGAENPAGLKSQ GNELFR | ENSG00000104450.8 | 1 |
| SEQ ID NO: 1345 | GCLELIKETGVPIAGR | ENSG00000100714.11 | 1 |
| SEQ ID NO: 1346 | GCPQEDSDIAFLIDGSGSIIPHDF R | ENSG00000169896.12 | 1 |
| SEQ ID NO: 1347 | GDEGPIGHQGPIGQEGAPGRPG SPGLPGMPGR | ENSG00000134871.13 | 1 |
| SEQ ID NO: 1348 | GDKGERGAPGVTGPK | ENSG00000134871.13 | 1 |
| SEQ ID NO: 1349 | GDNVLINTFSGLLK | ENSG00000142733.10 | 1 |
| SEQ ID NO: 1350 | GDNVLINTFSGLLK | ENSG00000142733.10 | 1 |
| SEQ ID NO: 1351 | GDTGNPGAPGTPGTKGWAGDS GPQGRP | ENSG00000134871.13 | 1 |
| SEQ ID NO: 1352 | GEFAIDGYSVR | ENSG00000005020.8 | 1 |
| SEQ ID NO: 1353 | GEGLYADPYGLLHEGR | ENSG00000017373.11 | 1 |
| SEQ ID NO: 1354 | GEIAPLKENVSHVNDLAR | ENSG00000198947.10 | 1 |
| SEQ ID NO: 1355 | GEWKPRQIDNPDYK | ENSG00000179218.9 | 1 |
| SEQ ID NO: 1356 | GGCVALATGSAMGLWEVK | ENSG00000011028.9 | 1 |
| SEQ ID NO: 1357 | GGHDIILAAFDNFK | ENSG00000184922.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1358 | GGSQPPDIDKTELVEPTEYLVVHLK | ENSG00000166825.9 | 1 |
| SEQ ID NO: 1359 | GGVSAVPGFR | ENSG00000134871.13 | 1 |
| SEQ ID NO: 1360 | GHLQIAACPNQDPLOGTTGLIPLLGIDVWEHAY | ENSG00000112096.12 | 1 |
| SEQ ID NO: 1361 | GHPDRLPLQMALTELETLAEK | ENSG00000104728.11 | 1 |
| SEQ ID NO: 1362 | GKEAGEVR | ENSG00000169896.12 | 1 |
| SEQ ID NO: 1363 | GKNVLINKDIR | ENSG00000179218.9 | 1 |
| SEQ ID NO: 1364 | GLCFLFGSNLR | ENSG00000169896.12 | 1 |
| SEQ ID NO: 1365 | GLEEAVESACAMR | ENSG00000067704.8 | 1 |
| SEQ ID NO: 1366 | GLGKYICQKCHAIIDEQPL | ENSG00000169756.12 | 1 |
| SEQ ID NO: 1367 | GNCFCYGHASECAPAPGAPAHAEGMVHGACICK | ENSG00000172037.9 | 1 |
| SEQ ID NO: 1368 | GPAPARPKMLVISGGDGYEDFRLSSGGGSSS | ENSG00000110237.3 | 1 |
| SEQ ID NO: 1369 | GPGAGSALDDGRR | ENSG00000196961.8 | 1 |
| SEQ ID NO: 1370 | GPPSSVPK | ENSG00000184922.9 | 1 |
| SEQ ID NO: 1371 | GQLQDELEKGER | ENSG00000082805.15 | 1 |
| SEQ ID NO: 1372 | GQTPEAGADKRSPRRASAAAAAGGGATGHPGG | ENSG00000104450.8 | 1 |
| SEQ ID NO: 1373 | GREPASCEDLCGGGVGADGGGSDR | ENSG00000065534.14 | 1 |
| SEQ ID NO: 1374 | GRISVSLQEEASGGSLAAPAR | ENSG00000032444.11 | 1 |
| SEQ ID NO: 1375 | GSDGMDAVRSAPTLIR | ENSG00000150672.12 | 1 |
| SEQ ID NO: 1376 | GSRPGIEGDTPR | ENSG00000113657.8 | 1 |
| SEQ ID NO: 1377 | GTISFFEIDGR | ENSG00000172977.8 | 1 |
| SEQ ID NO: 1378 | GTWIHPEIDNPEYSPD | ENSG00000179218.9 | 1 |
| SEQ ID NO: 1379 | GVTDTLAQIR | ENSG00000017373.11 | 1 |
| SEQ ID NO: 1380 | GWDCHGLPIEIK | ENSG00000067704.8 | 1 |
| SEQ ID NO: 1381 | HCELCRPFFYR | ENSG00000172037.9 | 1 |
| SEQ ID NO: 1382 | HFQIDYDEDGNCSLIISDVCGDDDAK | ENSG00000065534.14 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1383 | HGGLSLVQTTDYIYPIVDDPYM MGR | ENSG00000086475.10 | 1 |
| SEQ ID NO: 1384 | HLDTLHNFVSR | ENSG00000151914.13 | 1 |
| SEQ ID NO: 1385 | HLNPGLQLYR | ENSG00000114331.8 | 1 |
| SEQ ID NO: 1386 | HTEILEILEIPQLMDTCVR | ENSG00000213380.9 | 1 |
| SEQ ID NO: 1387 | HTLTQIKDAVR | ENSG00000146731.6 | 1 |
| SEQ ID NO: 1388 | IAALNASSTIEDDHEGSFK | ENSG00000099991.12 | 1 |
| SEQ ID NO: 1389 | IAEIQAR | ENSG00000152894.10 | 1 |
| SEQ ID NO: 1390 | IDALREELMEGMDR | ENSG00000132205.6 | 1 |
| SEQ ID NO: 1391 | IFEEQPCLRK | ENSG00000099991.12 | 1 |
| SEQ ID NO: 1392 | IFLTEQPLEGLEK | ENSG00000198947.10 | 1 |
| SEQ ID NO: 1393 | IFSAYIK | ENSG00000130429.8 | 1 |
| SEQ ID NO: 1394 | IIDRIHGTEEGQQILK | ENSG00000137497.13 | 1 |
| SEQ ID NO: 1395 | ILHKGEELAK | ENSG00000169129.10 | 1 |
| SEQ ID NO: 1396 | INELENGGEILNETRSFHHK | ENSG00000059691.7 | 1 |
| SEQ ID NO: 1397 | IPASAEQIQHLAGAIAER | ENSG00000172037.9 | 1 |
| SEQ ID NO: 1398 | IQGTLQPH | ENSG00000172037.9 | 1 |
| SEQ ID NO: 1399 | IQNQWDEVQEHLQNR | ENSG00000198947.10 | 1 |
| SEQ ID NO: 1400 | IQNVVTSFAPQRRAAWWQSEN GIPA | ENSG00000172037.9 | 1 |
| SEQ ID NO: 1401 | IRQKVDDCERCR | ENSG00000011454.12 | 1 |
| SEQ ID NO: 1402 | ITEQEKLK | ENSG00000151914.13 | 1 |
| SEQ ID NO: 1403 | ITSVSTGNLCTEEQTPPPRPEAYPI PTQTYTR | ENSG00000130396.16 | 1 |
| SEQ ID NO: 1404 | IVLGGTTVHNTK | ENSG00000136631.8 | 1 |
| SEQ ID NO: 1405 | IVTTHIR | ENSG00000106976.14 | 1 |
| SEQ ID NO: 1406 | KDAEGILEDLQSYR | ENSG00000153310.14 | 1 |
| SEQ ID NO: 1407 | KDVEVTKEEFVLAAQK | ENSG00000004864.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1408 | KEADMQQK | ENSG00000158560.10 | 1 |
| SEQ ID NO: 1409 | KHPSSPECLVSAQK | ENSG00000137497.13 | 1 |
| SEQ ID NO: 1410 | KIQNHIQTLK | ENSG00000198947.10 | 1 |
| SEQ ID NO: 1411 | KISEESGETAKRR | ENSG00000099991.12 | 1 |
| SEQ ID NO: 1412 | KIYAVEASTMAQHAEVLVK | ENSG00000142453.7 | 1 |
| SEQ ID NO: 1413 | KKEELNAVR | ENSG00000198947.10 | 1 |
| SEQ ID NO: 1414 | KKGPGAGSALDDGR | ENSG00000196961.8 | 1 |
| SEQ ID NO: 1415 | KLMQIR | ENSG00000151914.13 | 1 |
| SEQ ID NO: 1416 | KLSSQLVEHCQK | ENSG00000198947.10 | 1 |
| SEQ ID NO: 1417 | KLTFEYR | ENSG00000119383.15 | 1 |
| SEQ ID NO: 1418 | KMEEEPLGPDLEDLKR | ENSG00000198947.10 | 1 |
| SEQ ID NO: 1419 | KMSGTVSK | ENSG00000136631.8 | 1 |
| SEQ ID NO: 1420 | KQVAPEKPVKK | ENSG00000113387.7 | 1 |
| SEQ ID NO: 1421 | KSSTGSPTSPLNAEKLESEEDVSQAF | ENSG00000065534.14 | 1 |
| SEQ ID NO: 1422 | KTRPDGNCFYR | ENSG00000167770.7 | 1 |
| SEQ ID NO: 1423 | KVSTLQNQR | ENSG00000169896.12 | 1 |
| SEQ ID NO: 1424 | LAGEEEALR | ENSG00000125826.15 | 1 |
| SEQ ID NO: 1425 | LCDNIVSESESTTAR | ENSG00000170776.15 | 1 |
| SEQ ID NO: 1426 | LCIEHVEEHGLDIDGIYR | ENSG00000165322.13 | 1 |
| SEQ ID NO: 1427 | LCQFEEAKQDCDQALQLADGNVK | ENSG00000104450.8 | 1 |
| SEQ ID NO: 1428 | LDAWEEAQVEFMASHGNDAAR | ENSG00000105963.9 | 1 |
| SEQ ID NO: 1429 | LDEDLTTLGQMSK | ENSG00000110237.3 | 1 |
| SEQ ID NO: 1430 | LDLFEISQPTEDLEFHGVMR | ENSG00000130396.16 | 1 |
| SEQ ID NO: 1431 | LEAIKR | ENSG00000112096.12 | 1 |
| SEQ ID NO: 1432 | LEMLQQIANR | ENSG00000151914.13 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1433 | LESEEDVSQAFLEAVAEEKPHVK | ENSG00000065534.14 | 1 |
| SEQ ID NO: 1434 | LESEEDVSQAFLEAVAEEKPHVKPY | ENSG00000065534.14 | 1 |
| SEQ ID NO: 1435 | LETMARNEVIADINCK | ENSG00000141447.12 | 1 |
| SEQ ID NO: 1436 | LEYNVDAANGIVMEGYLFK | ENSG00000114331.8 | 1 |
| SEQ ID NO: 1437 | LFPNSLDQTDMHGDSEYNIMFGPDICGPGTKK | ENSG00000179218.9 | 1 |
| SEQ ID NO: 1438 | LGCTMSMR | ENSG00000059691.7 | 1 |
| SEQ ID NO: 1439 | LGIEKTDPTTLTDEEINR | ENSG00000100714.11 | 1 |
| SEQ ID NO: 1440 | LGIVNVDEAVLHFK | ENSG00000155629.10 | 1 |
| SEQ ID NO: 1441 | LGYTPLIVACHYGNVK | ENSG00000145362.12 | 1 |
| SEQ ID NO: 1442 | LHEMQIQHPTASLIAK | ENSG00000146731.6 | 1 |
| SEQ ID NO: 1443 | LHYNELGAK | ENSG00000198947.10 | 1 |
| SEQ ID NO: 1444 | LKAVQAQGGESQQEAQR | ENSG00000137497.13 | 1 |
| SEQ ID NO: 1445 | LKEDMKKIVAVPLNEQK | ENSG00000138640.10 | 1 |
| SEQ ID NO: 1446 | LKEEEEDKKR | ENSG00000179218.9 | 1 |
| SEQ ID NO: 1447 | LKELNDWLTK | ENSG00000198947.10 | 1 |
| SEQ ID NO: 1448 | LKLSFEEMER | ENSG00000162614.14 | 1 |
| SEQ ID NO: 1449 | LKLTFEELER | ENSG00000162614.14 | 1 |
| SEQ ID NO: 1450 | LKPEIQCVSAK | ENSG00000163975.7 | 1 |
| SEQ ID NO: 1451 | LLEATPTDSCGYFR | ENSG00000142733.10 | 1 |
| SEQ ID NO: 1452 | LLEATPTDSCGYFR | ENSG00000142733.10 | 1 |
| SEQ ID NO: 1453 | LLKGESALQR | ENSG00000114331.8 | 1 |
| SEQ ID NO: 1454 | LLNEGQR | ENSG00000163975.7 | 1 |
| SEQ ID NO: 1455 | LNGFQLENFTLK | ENSG00000136231.9 | 1 |
| SEQ ID NO: 1456 | LNKILK | ENSG00000067704.8 | 1 |
| SEQ ID NO: 1457 | LNREVAESPRPR | ENSG00000019144.12 | 1 |

TABLE 7-continued

Spectral Counts from CRC samples of N terminal peptides predicted to be gained in GC

| SEQ_ID_NO | Peptide | Geneld | SpectralCount |
|---|---|---|---|
| SEQ ID NO: 1458 | LPPSSPQKLADVAAPPGGPPPPH SPYSGPPSR | ENSG00000017373.11 | 1 |
| SEQ ID NO: 1459 | LQDAFSAIGONADLDLPQIAVVG GQSAGK | ENSG00000106976.14 | 1 |
| SEQ ID NO: 1460 | LQELEGTYEENERALESK | ENSG00000172037.9 | 1 |
| SEQ ID NO: 1461 | LQQQCDDYGSSYLGVIELIGEK | ENSG00000132205.6 | 1 |
| SEQ ID NO: 1462 | LSAHTHTLSLTDINELVCGAPGD APCATSPCGGAGCR | ENSG00000172037.9 | 1 |
| SEQ ID NO: 1463 | LSFEEMERQRR | ENSG00000162614.14 | 1 |
| SEQ ID NO: 1464 | LSGWLAQQEDAHR | ENSG00000032444.11 | 1 |
| SEQ ID NO: 1465 | LSHFEYVKNEDLEK | ENSG00000061938.12 | 1 |
| SEQ ID NO: 1466 | LSIPQLSVTDYEIM | ENSG00000198947.10 | 1 |
| SEQ ID NO: 1467 | LSIPQLSVTDYEIMEQR | ENSG00000198947.10 | 1 |
| SEQ ID NO: 1468 | LSPAYSLGSLTGASPCQSPCVQR | ENSG00000019144.12 | 1 |
| SEQ ID NO: 1469 | LSSGGGSSSETVGR | ENSG00000110237.3 | 1 |
| SEQ ID NO: 1470 | LTEEQCLFSAWLSEKEDAVNK | ENSG00000198947.10 | 1 |
| SEQ ID NO: 1471 | LVAAGGLDAVLYWCR | ENSG00000004139.9 | 1 |
| SEQ ID NO: 1472 | LVEFSAFLEQQR | ENSG00000187079.10 | 1 |
| SEQ ID NO: 1473 | LVPSVNGVR | ENSG00000100714.11 | 1 |
| SEQ ID NO: 1474 | LVTPHGESEQIGVIPSKK | ENSG00000082458.7 | 1 |
| SEQ ID NO: 1475 | LVVTQEDVELAYQEAMMNMAR LNRTAAGLMH | ENSG00000086475.10 | 1 |
| SEQ ID NO: 1476 | MAAAEAGGDDAR | ENSG00000184207.8 | 1 |
| SEQ ID NO: 1477 | MAVWEAEQLGGLQR | ENSG00000130589.12 | 1 |
| SEQ ID NO: 1478 | MEALENR | ENSG00000132561.9 | 1 |
| SEQ ID NO: 1479 | MEFDEKELRR | ENSG00000106976.14 | 1 |
| SEQ ID NO: 1480 | MESGRGSSTPPGPIAALGMPDT GPG | ENSG00000127084.13 | 1 |
| SEQ ID NO: 1481 | MESGRGSSTPPGPIAALGMPDT GPGSSSLGK | ENSG00000127084.13 | 1 |
| SEQ ID NO: 1482 | MESQLK | ENSG00000082805.15 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1483 | MGMSFGLESGK | ENSG00000114126.13 | 1 |
| SEQ ID NO: 1484 | MGNAAGSAEQPAGPAAPPPK | ENSG00000184922.9 | 1 |
| SEQ ID NO: 1485 | MIISTPQRLTSSGSVLIGSPYTPAPAMVTQTHIA | ENSG00000114126.13 | 1 |
| SEQ ID NO: 1486 | MILTNPEGR | ENSG00000152894.10 | 1 |
| SEQ ID NO: 1487 | MKAAKSGTKDGLEK | ENSG00000074964.12 | 1 |
| SEQ ID NO: 1488 | MLEDLGFKDLTLQPR | ENSG00000125826.15 | 1 |
| SEQ ID NO: 1489 | MNSLTLNR | ENSG00000213380.9 | 1 |
| SEQ ID NO: 1490 | MSDKSDLKAELER | ENSG00000158560.10 | 1 |
| SEQ ID NO: 1491 | MSGSSGGAAAPAASSGPAAAASAAGSGCGGGA | ENSG00000038382.13 | 1 |
| SEQ ID NO: 1492 | MSKSLGNVIHP | ENSG00000067704.8 | 1 |
| SEQ ID NO: 1493 | MVSTSATDEPR | ENSG00000032444.11 | 1 |
| SEQ ID NO: 1494 | NANSSPVASTTPSASATTNPASATTLDQSKA | ENSG00000166825.9 | 1 |
| SEQ ID NO: 1495 | NATLVNEADKLR | ENSG00000166825.9 | 1 |
| SEQ ID NO: 1496 | NAVLEHMEELQEQVALLTER | ENSG00000184922.9 | 1 |
| SEQ ID NO: 1497 | NDKSYWLSTTAPLPMMPVAEDEIKPYISR | ENSG00000134871.13 | 1 |
| SEQ ID NO: 1498 | NFVKEAEEISSNRR | ENSG00000213380.9 | 1 |
| SEQ ID NO: 1499 | NILVSDMEMNEQQE | ENSG00000011028.9 | 1 |
| SEQ ID NO: 1500 | NLAATLQDIETK | ENSG00000019144.12 | 1 |
| SEQ ID NO: 1501 | NLEELYLVGSLSHDISR | ENSG00000171488.10 | 1 |
| SEQ ID NO: 1502 | NLLEVSEVEQELACONDHSSALQNIKR | ENSG00000136631.8 | 1 |
| SEQ ID NO: 1503 | NLVGSGSEIQFLSEAQDDPQKR | ENSG00000115652.10 | 1 |
| SEQ ID NO: 1504 | NRTEAEVKR | ENSG00000169129.10 | 1 |
| SEQ ID NO: 1505 | NSLSVLSPK | ENSG00000171488.10 | 1 |
| SEQ ID NO: 1506 | NTSAASTAQLVEATEELRR | ENSG00000172037.9 | 1 |
| SEQ ID NO: 1507 | NVQVFLISGGFR | ENSG00000146733.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1508 | NYPSSLCALCVGDEQGR | ENSG00000163975.7 | 1 |
| SEQ ID NO: 1509 | PCPCPEGPGSQR | ENSG00000172037.9 | 1 |
| SEQ ID NO: 1510 | PCQDVDECAR | ENSG00000090006.13 | 1 |
| SEQ ID NO: 1511 | PDENLKSASKEELKK | ENSG00000065534.14 | 1 |
| SEQ ID NO: 1512 | PEAYQVPASYQPDEEERAR | ENSG00000125826.15 | 1 |
| SEQ ID NO: 1513 | PEGEMKPGR | ENSG00000113387.7 | 1 |
| SEQ ID NO: 1514 | PETPYSGPGLLIDSLVLLPR | ENSG00000172037.9 | 1 |
| SEQ ID NO: 1515 | PEVVWFK | ENSG00000065534.14 | 1 |
| SEQ ID NO: 1516 | PGAGAVEVAMAEALIK | ENSG00000146731.6 | 1 |
| SEQ ID NO: 1517 | PGEMGPQGPPGEPGFRGAPGK | ENSG00000134871.13 | 1 |
| SEQ ID NO: 1518 | PGETPSWTGSGFVR | ENSG00000172037.9 | 1 |
| SEQ ID NO: 1519 | PGFHGQAAR | ENSG00000172037.9 | 1 |
| SEQ ID NO: 1520 | PGHVGQMGPVGAPGRPGPPGP PGPK | ENSG00000134871.13 | 1 |
| SEQ ID NO: 1521 | PILPHLAEEVFQHIPYIK | ENSG00000067704.8 | 1 |
| SEQ ID NO: 1522 | PKIDDVLHTLTGAMSLLRR | ENSG00000130396.16 | 1 |
| SEQ ID NO: 1523 | PKMLVISGGDGYEDFR | ENSG00000110237.3 | 1 |
| SEQ ID NO: 1524 | PPDIDKTELVEPTEYLVVHLK | ENSG00000166825.9 | 1 |
| SEQ ID NO: 1525 | PPKPATPDFR | ENSG00000065534.14 | 1 |
| SEQ ID NO: 1526 | PPVIQNPEYK | ENSG00000179218.9 | 1 |
| SEQ ID NO: 1527 | PPVLGTESDATVK | ENSG00000065534.14 | 1 |
| SEQ ID NO: 1528 | PQLLGVAPEK | ENSG00000004864.9 | 1 |
| SEQ ID NO: 1529 | PRMSAQEQLERMR | ENSG00000105559.7 | 1 |
| SEQ ID NO: 1530 | PSGPATAEDPGRRPVLPQR | ENSG00000132205.6 | 1 |
| SEQ ID NO: 1531 | PTPRPVPMKRHIFR | ENSG00000186635.10 | 1 |
| SEQ ID NO: 1532 | PVAGSELPR | ENSG00000176890.11 | 1 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1533 | PYWCISR | ENSG00000067704.8 | 1 |
| SEQ ID NO: 1534 | QAASPLEPK | ENSG00000137497.13 | 1 |
| SEQ ID NO: 1535 | QAEEVNTEWEK | ENSG00000198947.10 | 1 |
| SEQ ID NO: 1536 | QAEGLSEDGAAMAVEPTQIQLSK | ENSG00000198947.10 | 1 |
| SEQ ID NO: 1537 | QAPSSFQLLYDLK | ENSG00000100714.11 | 1 |
| SEQ ID NO: 1538 | QAQLEKELSAALQDKK | ENSG00000137497.13 | 1 |
| SEQ ID NO: 1539 | QAQVNLTVVDKPD | ENSG00000065534.14 | 1 |
| SEQ ID NO: 1540 | QDCDQALQLADGNVK | ENSG00000104450.8 | 1 |
| SEQ ID NO: 1541 | QEMVIEVKAIGGKK | ENSG00000110237.3 | 1 |
| SEQ ID NO: 1542 | QETPPPRSPPVANSGSTGFSRRGSGRGGGPTP | ENSG00000105559.7 | 1 |
| SEQ ID NO: 1543 | QGPMTQAINR | ENSG00000170776.15 | 1 |
| SEQ ID NO: 1544 | QHEVEEATNILTATR | ENSG00000114331.8 | 1 |
| SEQ ID NO: 1545 | QIASLTGLVQSALLR | ENSG00000017373.11 | 1 |
| SEQ ID NO: 1546 | QICSQLSER | ENSG00000011454.12 | 1 |
| SEQ ID NO: 1547 | QKASGDSAR | ENSG00000004864.9 | 1 |
| SEQ ID NO: 1548 | QKMEEEKRRTEEER | ENSG00000162614.14 | 1 |
| SEQ ID NO: 1549 | QLELACETQEEVDSWK | ENSG00000106976.14 | 1 |
| SEQ ID NO: 1550 | QLNETGGPVLVSAPISPEEQDKLENK | ENSG00000198947.10 | 1 |
| SEQ ID NO: 1551 | QLPKPNQDTMQILFR | ENSG00000165322.13 | 1 |
| SEQ ID NO: 1552 | QLQTLAPK | ENSG00000105223.14 | 1 |
| SEQ ID NO: 1553 | QNGDSAYLYLLSAR | ENSG00000125826.15 | 1 |
| SEQ ID NO: 1554 | QPDVEEILSK | ENSG00000198947.10 | 1 |
| SEQ ID NO: 1555 | QQNLAVSESPVTPSALAELLDLLDSR | ENSG00000059691.7 | 1 |
| SEQ ID NO: 1556 | QQQMHIVDMLSK | ENSG00000130396.16 | 1 |
| SEQ ID NO: 1557 | QSSHNFQLESVNK | ENSG00000135052.12 | 1 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1558 | QTLLAESEALTSYSHR | ENSG00000167608.7 | 1 |
| SEQ ID NO: 1559 | QTSVADLLASFNDQSTSDYLVVYLR | ENSG00000167770.7 | 1 |
| SEQ ID NO: 1560 | QVFGQTTIHQHIPFNWDSEFVQLHFGK | ENSG00000004864.9 | 1 |
| SEQ ID NO: 1561 | QVVQDLLK | ENSG00000141447.12 | 1 |
| SEQ ID NO: 1562 | RASAAAAAGGGATGHPGGGQGAENPAGLK | ENSG00000104450.8 | 1 |
| SEQ ID NO: 1563 | RCDLCAPGYYGFGPTGCOACQCSHEGALSSLCEK | ENSG00000172037.9 | 1 |
| SEQ ID NO: 1564 | RCEQVQPGYFR | ENSG00000172037.9 | 1 |
| SEQ ID NO: 1565 | RDNEVDGQDYHFVVSR | ENSG00000082458.7 | 1 |
| SEQ ID NO: 1566 | RDPSSNDINGGMEPTPSTVSTPSPSADLLGLR | ENSG00000196961.8 | 1 |
| SEQ ID NO: 1567 | REMAAASAAAISGAGR | ENSG00000079616.8 | 1 |
| SEQ ID NO: 1568 | RETLFTLDDQALGPELTAPAPEPPAEEPR | ENSG00000213380.9 | 1 |
| SEQ ID NO: 1569 | RFSTEYELQQLEQFK | ENSG00000166825.9 | 1 |
| SEQ ID NO: 1570 | RGSDELTVPRYR | ENSG00000017373.11 | 1 |
| SEQ ID NO: 1571 | RIEGSGDQIDTYELSGGAR | ENSG00000106976.14 | 1 |
| SEQ ID NO: 1572 | RKEEEEAEDK | ENSG00000179218.9 | 1 |
| SEQ ID NO: 1573 | RLDIDEKPLVVQLNWNKDDR | ENSG00000130396.16 | 1 |
| SEQ ID NO: 1574 | RPPEPEKAPPAAPTRPSALELK | ENSG00000184922.9 | 1 |
| SEQ ID NO: 1575 | RPRPQGRSVSEPR | ENSG00000125744.7 | 1 |
| SEQ ID NO: 1576 | RQAEGLSEDGAAMAVEPTQIQLSK | ENSG00000198947.10 | 1 |
| SEQ ID NO: 1577 | RRKVPPSGSGGSELSNGEAGEAYR | ENSG00000110237.3 | 1 |
| SEQ ID NO: 1578 | RSLELQTRTEEEKK | ENSG00000127084.13 | 1 |
| SEQ ID NO: 1579 | RSSYLLAITTERSK | ENSG00000225485.3 | 1 |
| SEQ ID NO: 1580 | RVAAQVDGGAQVQQVLNIECLR | ENSG00000196961.8 | 1 |
| SEQ ID NO: 1581 | SAEESDRLR | ENSG00000130396.16 | 1 |
| SEQ ID NO: 1582 | SCDCDPMGSQDGGR | ENSG00000172037.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1583 | SDVLETVVLINPSDEAVSTEVR | ENSG00000131711.10 | 1 |
| SEQ ID NO: 1584 | SEDYELLCPNGAR | ENSG00000163975.7 | 1 |
| SEQ ID NO: 1585 | SFGSSLMESEVNLDR | ENSG00000198947.10 | 1 |
| SEQ ID NO: 1586 | SGHDQVVELLLERGAPLLAR | ENSG00000145362.12 | 1 |
| SEQ ID NO: 1587 | SGLTSLHLAAQEDKVNVADILTK | ENSG00000145362.12 | 1 |
| SEQ ID NO: 1588 | SGRPSCLYSAARPSGSYR | ENSG00000124831.14 | 1 |
| SEQ ID NO: 1589 | SGTIFDNFLITNDEA | ENSG00000179218.9 | 1 |
| SEQ ID NO: 1590 | SGTLALVEPLVASLDPGR | ENSG00000004139.9 | 1 |
| SEQ ID NO: 1591 | SKIVGAPMHDLLLWNNATVTTCHSK | ENSG00000100714.11 | 1 |
| SEQ ID NO: 1592 | SKPEDWDER | ENSG00000179218.9 | 1 |
| SEQ ID NO: 1593 | SLEGSDDAVLLQRRLDNMNFKWSELR | ENSG00000198947.10 | 1 |
| SEQ ID NO: 1594 | SLNPEQWSQLK | ENSG00000113387.7 | 1 |
| SEQ ID NO: 1595 | SLSDPSRRGELAGPGFEGPGGEPIREV | ENSG00000110237.3 | 1 |
| SEQ ID NO: 1596 | SNRDELELELAENR | ENSG00000137497.13 | 1 |
| SEQ ID NO: 1597 | SPARPQPGEGPGGPGGPPEVSR | ENSG00000105559.7 | 1 |
| SEQ ID NO: 1598 | SPARPQPGEGPGGPGGPPEVSR | ENSG00000105559.7 | 1 |
| SEQ ID NO: 1599 | SPDTTLSPASTTSSGVSEESTTSHSR | ENSG00000205277.5 | 1 |
| SEQ ID NO: 1600 | SPDTTLSPASTTSSGVSEESTTSHSR | ENSG00000205277.5 | 1 |
| SEQ ID NO: 1601 | SPDTTLSPASTTSSGVSEESTTSHSR | ENSG00000205277.5 | 1 |
| SEQ ID NO: 1602 | SPFPSQHLEAPEDK | ENSG00000198947.10 | 1 |
| SEQ ID NO: 1603 | SPGPPQVDGTPTMSLERPPR | ENSG00000155629.10 | 1 |
| SEQ ID NO: 1604 | SPTTTLSPASMTSLGVGEESTTSR | ENSG00000205277.5 | 1 |
| SEQ ID NO: 1605 | SPTTTLSPASMTSLGVGEESTTSR | ENSG00000205277.5 | 1 |
| SEQ ID NO: 1606 | SPTTTLSPASMTSLGVGEESTTSR | ENSG00000205277.5 | 1 |
| SEQ ID NO: 1607 | SPTTTLSPASMTSLGVGEESTTSR | ENSG00000205277.5 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1608 | SQAYADYIGFILTLNEGVK | ENSG00000119383.15 | 1 |
| SEQ ID NO: 1609 | SQMNCNLGTCQLQR | ENSG00000205277.5 | 1 |
| SEQ ID NO: 1610 | SRQELNTIASKPPR | ENSG00000169896.12 | 1 |
| SEQ ID NO: 1611 | SSHVTIDTLK | ENSG00000163975.7 | 1 |
| SEQ ID NO: 1612 | SSQNDSPGDASEGPEYLAIGNLDPRGR | ENSG00000145016.9 | 1 |
| SEQ ID NO: 1613 | STEYELQQLEQFKK | ENSG00000166825.9 | 1 |
| SEQ ID NO: 1614 | STSFNVQDLLPDHEYKFR | ENSG00000065534.14 | 1 |
| SEQ ID NO: 1615 | SVEQEVVQSQLNHCVNLYK | ENSG00000198947.10 | 1 |
| SEQ ID NO: 1616 | SVYTMPLANHR | ENSG00000090006.13 | 1 |
| SEQ ID NO: 1617 | SWAEDEKQKAETVQAALEEAQR | ENSG00000172037.9 | 1 |
| SEQ ID NO: 1618 | SWCSGHLHLRCPR | ENSG00000032444.11 | 1 |
| SEQ ID NO: 1619 | SYVDTGGVSR | ENSG00000184922.9 | 1 |
| SEQ ID NO: 1620 | SYVITGSWNPK | ENSG00000011454.12 | 1 |
| SEQ ID NO: 1621 | TAIWEDQNLR | ENSG00000205277.5 | 1 |
| SEQ ID NO: 1622 | TALLTAGDIYLLSTFR | ENSG00000169231.9 | 1 |
| SEQ ID NO: 1623 | TEALMDAQKEDFNSK | ENSG00000172037.9 | 1 |
| SEQ ID NO: 1624 | TEFCLHDGPPYANGDPHVGHALNK | ENSG00000067704.8 | 1 |
| SEQ ID NO: 1625 | TESSGGWQNR | ENSG00000011028.9 | 1 |
| SEQ ID NO: 1626 | THIESSGHGVDTCLHVVLSSKVCR | ENSG00000019144.12 | 1 |
| SEQ ID NO: 1627 | TKVHAELADVLTEAVVDSILAIKK | ENSG00000146731.6 | 1 |
| SEQ ID NO: 1628 | TLEIALEQKKEECLK | ENSG00000082805.15 | 1 |
| SEQ ID NO: 1629 | TLNATGEEIIQQSSK | ENSG00000198947.10 | 1 |
| SEQ ID NO: 1630 | TLPSMVHR | ENSG00000101199.8 | 1 |
| SEQ ID NO: 1631 | TMNGDMR | ENSG00000120549.11 | 1 |
| SEQ ID NO: 1632 | TNHIGWVQEFLNEENR | ENSG00000184922.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1633 | TNIQLPACLR | ENSG00000213380.9 | 1 |
| SEQ ID NO: 1634 | TPDELQK | ENSG00000198947.10 | 1 |
| SEQ ID NO: 1635 | TPLERDDLHESVFR | ENSG00000151914.13 | 1 |
| SEQ ID NO: 1636 | TSGNQDEILVIR | ENSG00000106976.14 | 1 |
| SEQ ID NO: 1637 | TTLSPASSTSPGLQGESTAFQTHPASTHTTPSPPSTATAPVEESTTYHR | ENSG00000205277.5 | 1 |
| SEQ ID NO: 1638 | TTLSPASSTSPGLQGESTAFQTHPASTHTTPSPPSTATAPVEESTTYHR | ENSG00000205277.5 | 1 |
| SEQ ID NO: 1639 | TTLSPASSTSPGLQGESTAFQTHPASTHTTPSPPSTATAPVEESTTYHR | ENSG00000205277.5 | 1 |
| SEQ ID NO: 1640 | TTQGLTALLLSLKK | ENSG00000136631.8 | 1 |
| SEQ ID NO: 1641 | TTQIINITMTK | ENSG00000137497.13 | 1 |
| SEQ ID NO: 1642 | TWVQQSETK | ENSG00000198947.10 | 1 |
| SEQ ID NO: 1643 | VAIGPSVLNAAR | ENSG00000067704.8 | 1 |
| SEQ ID NO: 1644 | VAYIPDEMAAQQNPLQQPR | ENSG00000136231.9 | 1 |
| SEQ ID NO: 1645 | VDSDMNDAYLGYAAAIILR | ENSG00000169896.12 | 1 |
| SEQ ID NO: 1646 | VEDAYILTCNVSLEYEK | ENSG00000146731.6 | 1 |
| SEQ ID NO: 1647 | VGAPMHDLLLWNNATVTTCHSK | ENSG00000100714.11 | 1 |
| SEQ ID NO: 1648 | VHLFDIITQYR | ENSG00000213380.9 | 1 |
| SEQ ID NO: 1649 | VIECFNVESR | ENSG00000104728.11 | 1 |
| SEQ ID NO: 1650 | VLGHFEKPLFLELCR | ENSG00000032444.11 | 1 |
| SEQ ID NO: 1651 | VLMDLQNQK | ENSG00000198947.10 | 1 |
| SEQ ID NO: 1652 | VLTTSPSR | ENSG00000019144.12 | 1 |
| SEQ ID NO: 1653 | VMLPPGAQHSDEK | ENSG00000130396.16 | 1 |
| SEQ ID NO: 1654 | VNFRPRYVTRYKTVTQLEWRCCPGFRGGDCQEGPK | ENSG00000132205.6 | 1 |
| SEQ ID NO: 1655 | VPDMAEIQSR | ENSG00000032444.11 | 1 |
| SEQ ID NO: 1656 | VOLLSQYDNEK | ENSG00000184922.9 | 1 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1657 | VSRASSPEGRHLPSPQLGTK | ENSG00000105559.7 | 1 |
| SEQ ID NO: 1658 | VTCTGYHQVR | ENSG00000133316.11 | 1 |
| SEQ ID NO: 1659 | VTEFDAAR | ENSG00000136631.8 | 1 |
| SEQ ID NO: 1660 | VVQEENQHMQMTIQALQDELR | ENSG00000082805.15 | 1 |
| SEQ ID NO: 1661 | VYLDLTPVK | ENSG00000169129.10 | 1 |
| SEQ ID NO: 1662 | WCATSDPEQHK | ENSG00000163975.7 | 1 |
| SEQ ID NO: 1663 | WFSIQNNQLVYQK | ENSG00000114331.8 | 1 |
| SEQ ID NO: 1664 | WIEFCQLLSER | ENSG00000198947.10 | 1 |
| SEQ ID NO: 1665 | WYQNPDYNFFNNYK | ENSG00000073849.10 | 1 |
| SEQ ID NO: 1666 | YADSLKPNIPYK | ENSG00000130396.16 | 1 |
| SEQ ID NO: 1667 | YENHSATAESSR | ENSG00000152894.10 | 1 |
| SEQ ID NO: 1668 | YLITATLTPER | ENSG00000132205.6 | 1 |
| SEQ ID NO: 1669 | YLQQPGCLLVGTNMDNR | ENSG00000184207.8 | 1 |
| SEQ ID NO: 1670 | YLRELSGSGLER | ENSG00000213380.9 | 1 |
| SEQ ID NO: 1671 | YLSASEYGSSVDGHPEVPETK | ENSG00000169129.10 | 1 |
| SEQ ID NO: 1672 | YNASSQQQR | ENSG00000165322.13 | 1 |
| SEQ ID NO: 1673 | YQETMSAIR | ENSG00000198947.10 | 1 |
| SEQ ID NO: 1674 | YSFWLTTIPEQSFQGSPSADTLK | ENSG00000134871.13 | 1 |
| SEQ ID NO: 1675 | YTKQGFGNLPICMAK | ENSG00000100714.11 | 1 |
| SEQ ID NO: 1676 | YVPAIAHLIHSLN | ENSG00000106066.9 | 1 |
| SEQ ID NO: 1677 | AAECLDVDECHRVPPPCDLGR | ENSG00000090006.13 | 0 |
| SEQ ID NO: 1678 | AEGGKRPAR | ENSG00000104450.8 | 0 |
| SEQ ID NO: 1679 | AEPVWTPPAPAPAAPPSTPAAPK | ENSG00000115310.13 | 0 |
| SEQ ID NO: 1680 | AFLCPLICHNGGVCVKPDR | ENSG00000090006.13 | 0 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1681 | AHLIHSLNPVR | ENSG00000106066.9 | 0 |
| SEQ ID NO: 1682 | AIAHLIHSLNPVR | ENSG00000106066.9 | 0 |
| SEQ ID NO: 1683 | AIWNVINW | ENSG00000112096.12 | 0 |
| SEQ ID NO: 1684 | AIWNVINWENV | ENSG00000112096.12 | 0 |
| SEQ ID NO: 1685 | ANGITMYAVGVGK | ENSG00000132561.9 | 0 |
| SEQ ID NO: 1686 | AQPVPFVPQVLGVMIGAGVAW VTAVLILLVVRR | ENSG00000032444.11 | 0 |
| SEQ ID NO: 1687 | ARILTAAR | ENSG00000004139.9 | 0 |
| SEQ ID NO: 1688 | AVGPGAGGAGSAVPGGAGPCA TVSVFPGAR | ENSG00000142453.7 | 0 |
| SEQ ID NO: 1689 | AYDNFGVLGLDLWQVK | ENSG00000179218.9 | 0 |
| SEQ ID NO: 1690 | CVCPAGFR | ENSG00000090006.13 | 0 |
| SEQ ID NO: 1691 | CVHGPTGSR | ENSG00000090006.13 | 0 |
| SEQ ID NO: 1692 | CVPPRTSAGTFPGSQPQAPASPV LPAR | ENSG00000090006.13 | 0 |
| SEQ ID NO: 1693 | DHPSSHSAQPPR | ENSG00000138162.13 | 0 |
| SEQ ID NO: 1694 | DKERLQAMMTHLHVKSTEPK | ENSG00000114861.14 | 0 |
| SEQ ID NO: 1695 | DLDNAEEKADALNK | ENSG00000011454.12 | 0 |
| SEQ ID NO: 1696 | DLYSALIQFFQIFPEYK | ENSG00000106066.9 | 0 |
| SEQ ID NO: 1697 | DPASDKLLGPAGLTWERNLPGA GVGKEMAGVPPTLR | ENSG00000138162.13 | 0 |
| SEQ ID NO: 1698 | DSAVMDDSVVIPSHQVSTLAK | ENSG00000145362.12 | 0 |
| SEQ ID NO: 1699 | DSSTPYQEIAAVPSAGR | ENSG00000138162.13 | 0 |
| SEQ ID NO: 1700 | DWDSPYSHDLDT | ENSG00000105223.14 | 0 |
| SEQ ID NO: 1701 | DWDSPYSHDLDTS | ENSG00000105223.14 | 0 |
| SEQ ID NO: 1702 | EDLDQSPLVSSSDSPPRPQPAFK | ENSG00000115310.13 | 0 |
| SEQ ID NO: 1703 | EESREPAPASPAPA | ENSG00000113657.8 | 0 |
| SEQ ID NO: 1704 | ELSSKGVK | ENSG00000176890.11 | 0 |
| SEQ ID NO: 1705 | EMELRRQALEEERR | ENSG00000019144.12 | 0 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1706 | ENGTVPK | ENSG00000165322.13 | 0 |
| SEQ ID NO: 1707 | ENKEVVLQWFTENSK | ENSG00000166825.9 | 0 |
| SEQ ID NO: 1708 | EVAESPRPR | ENSG00000019144.12 | 0 |
| SEQ ID NO: 1709 | FILDNLK | ENSG00000151835.9 | 0 |
| SEQ ID NO: 1710 | FLEAVAEEKPHVKPYFSK | ENSG00000065534.14 | 0 |
| SEQ ID NO: 1711 | FPIEGGQKDPK | ENSG00000107957.12 | 0 |
| SEQ ID NO: 1712 | FSTEYELQQLEQFKKDNEETGFGSGTR | ENSG00000166825.9 | 0 |
| SEQ ID NO: 1713 | FWPAIDDGLR | ENSG00000105223.14 | 0 |
| SEQ ID NO: 1714 | FYIDFGGVKPMGSEPVPKSR | ENSG00000004864.9 | 0 |
| SEQ ID NO: 1715 | GADLIEEAASRIVDAVIEQVKAAGALLTEGE | ENSG00000170776.15 | 0 |
| SEQ ID NO: 1716 | GADYAEPTWNLK | ENSG00000166825.9 | 0 |
| SEQ ID NO: 1717 | GDEEKDKGLQTSQDAR | ENSG00000179218.9 | 0 |
| SEQ ID NO: 1718 | GDILQTPQFQMR | ENSG00000137497.13 | 0 |
| SEQ ID NO: 1719 | GDNLPQYR | ENSG00000205277.5 | 0 |
| SEQ ID NO: 1720 | GNEAVASR | ENSG00000135052.12 | 0 |
| SEQ ID NO: 1721 | GPNKHTLTQIKDAVR | ENSG00000146731.6 | 0 |
| SEQ ID NO: 1722 | GQGPMFLDADFVAFTNHFK | ENSG00000198947.10 | 0 |
| SEQ ID NO: 1723 | GTATPELHTATDYR | ENSG00000170776.15 | 0 |
| SEQ ID NO: 1724 | GWAGDSGPQGRPGVFGLPGEK | ENSG00000134871.13 | 0 |
| SEQ ID NO: 1725 | GYLAPSGDLSLRR | ENSG00000090006.13 | 0 |
| SEQ ID NO: 1726 | HAEQQALR | ENSG00000142453.7 | 0 |
| SEQ ID NO: 1727 | IEDPSLLNSR | ENSG00000032444.11 | 0 |
| SEQ ID NO: 1728 | IFMEEVPGGSLSSLLRS | ENSG00000142733.10 | 0 |
| SEQ ID NO: 1729 | IFMEEVPGGSLSSLLRS | ENSG00000142733.10 | 0 |
| SEQ ID NO: 1730 | IIEVAPQVATQNVNPTPGAT | ENSG00000086475.10 | 0 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1731 | ILNSDQTTCR | ENSG00000132561.9 | 0 |
| SEQ ID NO: 1732 | ISCWGHSEPSMR | ENSG00000105223.14 | 0 |
| SEQ ID NO: 1733 | IVVHSVENMNFR | ENSG00000184922.9 | 0 |
| SEQ ID NO: 1734 | KAVAHMK | ENSG00000132561.9 | 0 |
| SEQ ID NO: 1735 | KDITAALAAER | ENSG00000106976.14 | 0 |
| SEQ ID NO: 1736 | KDNEETGFGSGTR | ENSG00000166825.9 | 0 |
| SEQ ID NO: 1737 | KHQGHFLLGTLSR | ENSG00000061938.12 | 0 |
| SEQ ID NO: 1738 | KIAEIQARR | ENSG00000152894.10 | 0 |
| SEQ ID NO: 1739 | KKEADMQQK | ENSG00000158560.10 | 0 |
| SEQ ID NO: 1740 | KLFGGPGSRR | ENSG00000110237.3 | 0 |
| SEQ ID NO: 1741 | KPAAGLSAAPVPTAPAAGAP | ENSG00000115310.13 | 0 |
| SEQ ID NO: 1742 | KSSTGSPTSPLNAEKLESEEDVSQA | ENSG00000065534.14 | 0 |
| SEQ ID NO: 1743 | KVVATTQMQAADARK | ENSG00000166825.9 | 0 |
| SEQ ID NO: 1744 | LADSDQASKVQQQK | ENSG00000137497.13 | 0 |
| SEQ ID NO: 1745 | LAYVSCVR | ENSG00000032444.11 | 0 |
| SEQ ID NO: 1746 | LGIVQGIVGARNTSAASTAQLVEATEELRREIG | ENSG00000172037.9 | 0 |
| SEQ ID NO: 1747 | LHYNELGAKVTERKQQ | ENSG00000198947.10 | 0 |
| SEQ ID NO: 1748 | LIEVGPSGAQFLGK | ENSG00000145362.12 | 0 |
| SEQ ID NO: 1749 | LKQTNLQWIK | ENSG00000198947.10 | 0 |
| SEQ ID NO: 1750 | LKTVFYR | ENSG00000104728.11 | 0 |
| SEQ ID NO: 1751 | LLISCWGHSEPSMR | ENSG00000105223.14 | 0 |
| SEQ ID NO: 1752 | LMFDRSEVYGPMK | ENSG00000166825.9 | 0 |
| SEQ ID NO: 1753 | LMLEWQFQK | ENSG00000130396.16 | 0 |
| SEQ ID NO: 1754 | LPAAPPVAPER | ENSG00000115310.13 | 0 |
| SEQ ID NO: 1755 | LPPVLGTESDATVK | ENSG00000065534.14 | 0 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1756 | LPQEPGR | ENSG00000135052.12 | 0 |
| SEQ ID NO: 1757 | LQGQDSERVRAWQR | ENSG00000165912.11 | 0 |
| SEQ ID NO: 1758 | LSRKGGHER | ENSG00000019144.12 | 0 |
| SEQ ID NO: 1759 | LTELENELNTK | ENSG00000130396.16 | 0 |
| SEQ ID NO: 1760 | LTGKAEGGK | ENSG00000104450.8 | 0 |
| SEQ ID NO: 1761 | LWEAVKRR | ENSG00000061938.12 | 0 |
| SEQ ID NO: 1762 | LWHLDPDTEYEIR | ENSG00000152894.10 | 0 |
| SEQ ID NO: 1763 | LYGVVLTPPMK | ENSG00000061938.12 | 0 |
| SEQ ID NO: 1764 | MELEEVTRLLNLKDK | ENSG00000104450.8 | 0 |
| SEQ ID NO: 1765 | MIEDSGPGMKVLL | ENSG00000136631.8 | 0 |
| SEQ ID NO: 1766 | MPVAGSELPR | ENSG00000176890.11 | 0 |
| SEQ ID NO: 1767 | NFVLVLSPGALDK | ENSG00000004139.9 | 0 |
| SEQ ID NO: 1768 | NIMFGPDICGPGTK | ENSG00000179218.9 | 0 |
| SEQ ID NO: 1769 | NITIIVEDPIAESCNDKAKLRGPL | ENSG00000145016.9 | 0 |
| SEQ ID NO: 1770 | NPKAEVARAQAALAVNISAARG LQDVLRTNLGPK | ENSG00000146731.6 | 0 |
| SEQ ID NO: 1771 | NQVTQLK | ENSG00000100714.11 | 0 |
| SEQ ID NO: 1772 | NVINWENVTER | ENSG00000112096.12 | 0 |
| SEQ ID NO: 1773 | PGHYDILYK | ENSG00000167770.7 | 0 |
| SEQ ID NO: 1774 | PGSPGLPGMPGR | ENSG00000134871.13 | 0 |
| SEQ ID NO: 1775 | PLEEGLNKAIHYFR | ENSG00000115652.10 | 0 |
| SEQ ID NO: 1776 | PLSTRVPR | ENSG00000132561.9 | 0 |
| SEQ ID NO: 1777 | PSAGFLPTHR | ENSG00000090006.13 | 0 |
| SEQ ID NO: 1778 | PSGPQPQADLQALLQSGAQVR | ENSG00000105223.14 | 0 |
| SEQ ID NO: 1779 | PSSSGSTGTKLSPARSTTSGLVGE STPSR | ENSG00000205277.5 | 0 |
| SEQ ID NO: 1780 | PSSSGSTGTKLSPARSTTSGLVGE STPSR | ENSG00000205277.5 | 0 |

TABLE 7-continued

Spectral Counts from CRC samples of N terminal peptides predicted to be gained in GC

| SEQ_ID_NO | Peptide | GeneId | SpectralCount |
|---|---|---|---|
| SEQ ID NO: 1781 | QGYILNSDQTTCR | ENSG00000132561.9 | 0 |
| SEQ ID NO: 1782 | QVFEELWK | ENSG00000059691.7 | 0 |
| SEQ ID NO: 1783 | QVKPKTVSEEERKV | ENSG00000065534.14 | 0 |
| SEQ ID NO: 1784 | QYISKMIEDSGPGMK | ENSG00000136631.8 | 0 |
| SEQ ID NO: 1785 | QYMPWEAALSSLSYFK | ENSG00000166825.9 | 0 |
| SEQ ID NO: 1786 | RADVLAFPSSGFTDLAEIVSR | ENSG00000032444.11 | 0 |
| SEQ ID NO: 1787 | RAVAAQPGRKR | ENSG00000172977.8 | 0 |
| SEQ ID NO: 1788 | RDEGSQDQTGSLSRARPSSR | ENSG00000110237.3 | 0 |
| SEQ ID NO: 1789 | RDPEVGKDELSKPSSDAESR | ENSG00000138162.13 | 0 |
| SEQ ID NO: 1790 | RMQSSADLIIQEFMDLRTR | ENSG00000151914.13 | 0 |
| SEQ ID NO: 1791 | SASFEPFSNK | ENSG00000179218.9 | 0 |
| SEQ ID NO: 1792 | SDQIGLPDFNAGAMENWGLVTYR | ENSG00000166825.9 | 0 |
| SEQ ID NO: 1793 | SFACQCPEGHVLR | ENSG00000132561.9 | 0 |
| SEQ ID NO: 1794 | SFLKLILQVEKWQEECEEGEGRTIIHCLNGGGR | ENSG00000152894.10 | 0 |
| SEQ ID NO: 1795 | SFPAAQIPIAVEEPGSSSRESVSKAGMPVSADAAK | ENSG00000138162.13 | 0 |
| SEQ ID NO: 1796 | SFTQGEGAR | ENSG00000132561.9 | 0 |
| SEQ ID NO: 1797 | SFTQGEGARPLSTR | ENSG00000132561.9 | 0 |
| SEQ ID NO: 1798 | SHTLSHASYLR | ENSG00000145362.12 | 0 |
| SEQ ID NO: 1799 | SLEQLQK | ENSG00000137497.13 | 0 |
| SEQ ID NO: 1800 | SPHTTLSPAGSTTR | ENSG00000205277.5 | 0 |
| SEQ ID NO: 1801 | SPHTTLSPAGSTTR | ENSG00000205277.5 | 0 |
| SEQ ID NO: 1802 | SPHTTLSPAGSTTR | ENSG00000205277.5 | 0 |
| SEQ ID NO: 1803 | SPHTTLSPAGSTTR | ENSG00000205277.5 | 0 |
| SEQ ID NO: 1804 | SQTLIDLNR | ENSG00000059691.7 | 0 |
| SEQ ID NO: 1805 | SSHNFQLESVNK | ENSG00000135052.12 | 0 |

TABLE 7-continued

| Spectral Counts from CRC samples of N terminal peptides predicted to be gained in GC | | | |
|---|---|---|---|
| SEQ_ID_NO | Peptide | GeneId | SpectralCount |
| SEQ ID NO: 1806 | STCAPSPQR | ENSG00000138162.13 | 0 |
| SEQ ID NO: 1807 | STTFYSSPR | ENSG00000205277.5 | 0 |
| SEQ ID NO: 1808 | STTFYSSPR | ENSG00000205277.5 | 0 |
| SEQ ID NO: 1809 | STTFYSSPR | ENSG00000205277.5 | 0 |
| SEQ ID NO: 1810 | STTFYSSPR | ENSG00000205277.5 | 0 |
| SEQ ID NO: 1811 | STTFYSSPR | ENSG00000205277.5 | 0 |
| SEQ ID NO: 1812 | STTFYSSPR | ENSG00000205277.5 | 0 |
| SEQ ID NO: 1813 | STTFYSSPR | ENSG00000205277.5 | 0 |
| SEQ ID NO: 1814 | STTFYSSPR | ENSG00000205277.5 | 0 |
| SEQ ID NO: 1815 | STTFYSSPR | ENSG00000205277.5 | 0 |
| SEQ ID NO: 1816 | TATAGAISELTESRLR | ENSG00000128487.12 | 0 |
| SEQ ID NO: 1817 | TEVAIGPSVLNAAR | ENSG00000067704.8 | 0 |
| SEQ ID NO: 1818 | TGDPQETLRR | ENSG00000137497.13 | 0 |
| SEQ ID NO: 1819 | THLSLSHNPEQKGVPTGFILPIRDIR | ENSG00000100714.11 | 0 |
| SEQ ID NO: 1820 | THTATGIR | ENSG00000169896.12 | 0 |
| SEQ ID NO: 1821 | TLATQLNQQK | ENSG00000151914.13 | 0 |
| SEQ ID NO: 1822 | TPVPEKVPPPKPATPDF | ENSG00000065534.14 | 0 |
| SEQ ID NO: 1823 | TVQQPTVQHR | ENSG00000132561.9 | 0 |
| SEQ ID NO: 1824 | TYQGFWNPPLAPR | ENSG00000152894.10 | 0 |
| SEQ ID NO: 1825 | VLCGDAGLLRGLADGLVQAGVGTEALLTPLVGRLARL | ENSG00000142733.10 | 0 |
| SEQ ID NO: 1826 | VLCGDAGLLRGLADGLVQAGVGTEALLTPLVGRLARL | ENSG00000142733.10 | 0 |
| SEQ ID NO: 1827 | VNYDEENWRK | ENSG00000166825.9 | 0 |
| SEQ ID NO: 1828 | VPEGFTCR | ENSG00000090006.13 | 0 |
| SEQ ID NO: 1829 | WSELRKKSLNIR | ENSG00000198947.10 | 0 |
| SEQ ID NO: 1830 | WSSRGSGGWGVYRSPSFGAGEGLLR | ENSG00000110237.3 | 0 |

TABLE 7-continued

| Spectral Counts from CRC samples of N terminal peptides predicted to be gained in GC | | | |
|---|---|---|---|
| SEQ_ID_NO | Peptide | Geneld | SpectralCount |
| SEQ ID NO: 1831 | WYQPSFHGVDLSALR | ENSG00000142453.7 | 0 |
| SEQ ID NO: 1832 | YCNPGDVCYYASR | ENSG00000134871.13 | 0 |
| SEQ ID NO: 1833 | YGNLGHVNIGAIQEPLAFILPK | ENSG00000213380.9 | 0 |
| SEQ ID NO: 1834 | YITISGNR | ENSG00000151914.13 | 0 |
| SEQ ID NO: 1835 | YLSYTLNPDLIRK | ENSG00000166825.9 | 0 |
| SEQ ID NO: 1836 | YMVTER | ENSG00000105223.14 | 0 |

To examine possible functions of somatic promoters on cancer development, we focused on RASA3, a RAS GTPase-activating protein required for $G_{\alpha i}$-induced inhibition of mitogen-activated protein kinases. In both GCs (50%) and GC lines, we observed gain of promoter activity at an intronic region 127 kb downstream apart from the canonical RASA3 TSS (FIG. 3*c*, top, FIG. 10). RNA-seq and 5' RACE analysis confirmed expression of this shorter RASA3 isoform (FIG. 3*c*, bottom), and expression of this shorter RASA3 isoform was also observed in TCGA RNA-seq data (FIG. 3*c*). Compared to the canonical full-length RASA3 protein (CanT), the shorter 31 kDa RASA3 somatic isoform (SomT) is predicted to lack the N-terminal RasGAP domain (FIG. 3*d*). Consistent with these predictions, transection of RASA3 CanT into GES1 normal gastric epithelial cells induced lower levels of active GTP-bound RAS compared to either empty vector or RASA3 SomT transfected cells, indicating that RASA3 CanT has higher RASGAP activity (FIG. 13).

To address functions of RASA3 SomT, we transfected the RASA3 CanT and SomT isoforms into SNU1967 GC cells. Compared to untransfected cells, transfection of RASA3 SomT into SNU1967 cells significantly stimulated migration (P<0.01) and invasion (P<0.01) while RASA3 CanT significantly suppressed invasion (P<0.001) (FIG. 3E, FIG. 13). Similarly, transfection of RASA3 SomT into GES1 cells significantly stimulated migration (p<0.01, FIG. 3*e*) and invasion (P<0.01, FIG. 13) while RASA3 CanT did not. When tested on KRAS mutated AGS GC cells that are innately highly migratory, expression of RASA3 CanT potently suppressed migration while RASA3 SomT exhibited significantly less attenuation (P<0.01, FIG. 13). These results suggest that tumor-specific use of RASA3 SomT is likely to increase GC cell migration and invasion. Notably, RASA3 CanT and SomT transfections did not alter SNU1967, GES1 or AGS cellular proliferation rates (FIG. 13). To confirm that these observations are not due to non-physiological in vitro expression levels, we then examined NCC24 GC cells, which normally express high endogenous levels of RASA3 SomT and minimal RASA3 CanT (FIG. 13). Silencing of endogenous RASA3 SomT using two independent siRNA constructs significantly inhibited NCC24 migration and invasion (P<0.01-0.001) (FIG. 13), consistent with RASA3 SomT playing a role in promoting cancer migration and invasion.

In an earlier study, we reported a transcript isoform of the MET receptor tyrosine kinase, driven by an internal alternative promoter, which has been independently confirmed in other cancer types. However, functional implications of this MET variant remain unclear. RNA-seq and 5' RACE analysis confirmed transcript expression of this shorter isoform, predicted to harbor a truncated SEMA domain (FIG. 14). To assess functional differences between wild type (WT) and variant (Var) MET, we performed transient transfections of MET (WT) and MET (Var) into HEK293 cells. In both untreated and HGF-treated conditions, MET-Var transfected cells exhibited significantly higher levels of p-Gab1 (Y627), a key mediator of MET signaling (e.g. 2.48-3.95 fold comparing MET-Var vs MET-WT, P=0.003 (untreated), P<0.05 (T15 and T30). (66) In addition, in HGF-untreated samples, cells transfected with MET-Var also exhibited higher p-ERK1/2 levels (2.74 fold) and also higher p-STAT3 (Y705) (67-70) levels (1.80 fold) compared to MET-WT (P=0.023 and P=0.026 for p-ERK and p-STAT3 (Y705) respectively). These results suggest that expression of the MET Var isoform may promote MET-downstream signaling kinetics in a manner important for GC tumorigenesis.

Somatic Promoters Correlate with Tumor Immunity

Cancer immunoediting is a process where developing tumors sculpt their immunogenic and antigenic profile to evade host immune surveillance. Mechanisms of cancer immunoediting are diverse, including upregulation of immune checkpoint inhibitors such as PD-L1. To explore potential contributions of somatic promoters to tumor immunity, we identified somatic promoter-associated N-terminal peptides with high predicted affinity binding to GC specific MHC Class I HLA alleles (Table 8 and 9), which are required for antigen presentation to CD8+ cytotoxic T cells (IC50≤50 nM, FIG. 4*a*). Analysis of recurrent somatic promoter-associated peptides using the NetMHCpan-2.8 algorithm revealed a significant enrichment in high-affinity MHC I binding compared to multiple control peptide populations, including canonical GC peptides (average 36% vs 24%; P<0.01), randomly selected peptides (P<0.001), and C-terminal peptides (P<0.01) (FIG. 4B shows HLA-A, B, and C combined, FIG. 15A depicts data for HLA-A only). The majority of high affinity somatic promoter-associated peptides corresponded to situations where the somatic transcript lacking the N-terminal peptide is overexpressed in tumors relative to normal tissues (78% lost; 76/97 high-affinity peptides, FIG. 4C). Notably, because transcripts driven by the N-terminal lacking somatic TSSs are also overexpressed in tumors to a significantly greater degree than transcripts driven by the canonical TSS ($P<0.05$, Wilcoxon one sided test) (FIG. 12), such a scenario would be predicted to result in relative depletion of these N-terminal immunogenic peptides in tumors. Interestingly, an analogous N-terminal analysis using RNA-seq data alone (in the absence of epigenomic data) revealed that epigenome-guided N-terminal peptides exhibited significantly higher predicted immunogenicity scores compared to RNA-seq-only identified peptides (36.10% vs 27% for MHC presentation, P=0.02, Fisher Test), suggesting that epigenome-guided promoter identification can provide complementary value to RNA-seq-only guided analyses (FIG. 15).

TABLE 8

HLA prediction of GC samples

| Sample | A1 | A2 | B1 | B2 | C1 | C2 |
|---|---|---|---|---|---|---|
| 2000639 | A*33:03 | A*24:02 | B*58:01 | B*40:01 | C*03:02 | C*03:67 |
| 2000721 | A*11:01 | A*11:01 | B*46:01 | B*15:01 | C*01:02 | C*04:01 |
| 2000986 | A*24:02 | A*11:01 | B*40:01 | B*38:02 | C*07:02 | C*15:02 |
| 980437 | A*33:03 | A*02:07 | B*40:01 | B*39:01 | C*07:02 | C*04:01 |
| 990068 | A*02:03 | A*11:01 | B*51:01 | B*55:02 | C*08:01 | C*14:02 |
| 2000085 | A*24:07 | A*34:01 | B*15:21 | B*15:21 | C*04:03 | C*04:03 |
| 980401 | A*33:03 | A*11:01 | B*58:01 | B*40:01 | C*03:02 | C*07:02 |
| 980447 | A*11:01 | A*11:01 | B*38:02 | B*27:04 | C*12:02 | C*07:02 |
| 2001206 | A*02:07 | A*24:02 | B*46:01 | B*40:06 | C*01:02 | C*08:01 |
| 980436 | A*02:03 | A*02:07 | B*46:01 | B*46:01 | C*01:02 | C*01:02 |
| 980417 | A*33:03 | A*11:01 | B*58:01 | B*46:01 | C*03:02 | C*01:02 |
| 980319 | A*33:03 | A*11:02 | B*58:01 | B*27:04 | C*03:02 | C*12:02 |
| 20021007 | A*24:10 | A*24:02 | B*15:27 | B*40:01 | C*03:04 | C*04:01 |

TABLE 9

Recurrent N terminal sequences with high affinity to MHC Class I

| SEQ ID NO. | Gene | N terminal sequence | High Affinity HLA |
|---|---|---|---|
| SEQ ID NO: 1847 | ENSG00000007171.12 | MACPWKFLFKTKFHQYA<br>MNGEKDINNNVEKAPCAT<br>SSPVTQDDLQYHNLSKQQ<br>NESPQPLVETGKKSPESLVK<br>LDATPLSSPRHVRIKNWGS<br>GMTFQDTLHHKAKGILTQR<br>SKSCLGSIMTPKSLTRGPRD<br>KPTPPDELLPQAIEFVNQYY<br>GSFKEAKIEEHLARVEAVTK<br>EIETTGTYQLTGDELIFATK<br>QAWRNAPRCIGRIQWSNL<br>QVFDARSCSTARE | A*02:03, A*02:07, A*11:01, A*11:02, A*24:10, A*34:01, B*15:01, B*15:21, B*15:27, B*27:04, B*39:01, B*40:01, B*46:01, B*58:01, C*03:02, C*12:02 |
| SEQ ID NO: 1848 | ENSG00000011028.9 | MGPGRPAPAPWPRHLLRC<br>VLLLGCLHLGRPGAPGDAA<br>LPEPNVFLIFSHGLQGCLEA<br>QGGQVRVTPACNTSLPAQ<br>RWKWVSRNRLFNLGTMQ<br>CLGTGWPGTNTTASLGMY<br>ECDREALNLRWHCRTLGD<br>QLSLLLGARTSNISKPGTLE<br>RGDQTRSGQWRIYGSEED<br>LCALPYHEVYTIQGNSHGK<br>PCTIPFKYDNQWFHGCTST<br>GREDGHLWCATTQDYGK<br>DERWGFCPIKSNDCETFW<br>DKDQLTDSCYQFNFQSTLS<br>WREAWASCEQQGADLLSI<br>TEIHEQTYINGLLTGYSSTL<br>WIGLNDLDTSGGWQWSD<br>NSPLKYLNWESDQPDNPS<br>EENCGVIRTESSGGWQNR<br>DCSIALPYVCKKKPNATAEP<br>TPPDRWANVKVECEPSW<br>QPFQGHCYRLQAEKRSW<br>QESKKACLRGGGDLVSIHS<br>MAELEFITKQIKQEVEELWI<br>GLNDLKLQMNFEWSDGSL<br>VSFTHWHPFEPNNFRDSLE<br>DCVTIWGPEGRWNDSPC<br>NQSLPSICKKAGQLSQGAA<br>EEDHGCRKGWTWHSPSC<br>YWLGEDQVTYSEARRLCT<br>DHGSQLVTITNRFEQAFVS<br>SLIYNWEGEYFWTALQDL<br>NSTGSFFWLSGDEVMYTH<br>WNRDQPGYSRGGCVALA<br>TGSAMGLWEVKNCTSFRA<br>RYICRQSLGTPVTPELPGPD<br>PTPSLTGSCPQGWASDTKL<br>RYCYKVFSSERLQDKKSWV<br>QAQGACQELGAQLLSLASY<br>EEEHFVANMLNKIFGESEP | A*02:03, A*11:01, A*11:02, A*24:02, A*24:07, A*24:10, A*33:03, B*15:01, B*15:27, B*38:02, B*39:01, B*40:01, B*40:06, B*51:01, B*58:01, C*03:02, C*03:04, C*12:02, C*14:02 |

TABLE 9-continued

Recurrent N terminal sequences with high affinity to MHC Class I

| SEQ ID NO. | Gene | N terminal sequence | High Affinity HLA |
|---|---|---|---|
| | | EIHEQHWFWIGLNRRDPR GGQSWRWSDGVGFSYHN FDRSRHDDDDIRGCAVLDL ASLQWVAMQCDTQLDWI CKIPRGTDVREPDDSPQGR REWLRFQEAEYKFFEHHST WAQAQRICTWFQAELTSV HSQAELDFLSHNLQKFSRA QEQHWWIGLHTSESDGRF RWTDGSIINFISWAPGKPR PVGKDKKCVYMTASRED WGDQRCLTALPYICKRSNV TKETQPPDLPTTALGGCPS DWIQFLNKCFQVQGQEPQ SRVKWSEAQFSCEQQEAQ LVTITNPLEQAFITASLPNV TFDLWIGLHASQRDFQWV EQEPLMYANWAPGEPSG PSPAPSGNKPTSCAVVLHS PSAHFTGRWDDRSCTEET HGFICQKGTDPSLSPSPAAL PPAPGTELSYLNGTFRLLQK PLRWHDALLLCESRNASLA YVPDPYTQAFLTQAARGLR TPLWIGLAGEEGSRRYSW VSEEPLNYVGWQDGEPQ QPGGCTYVDVDGAWRTT SCDTKLQGAVCGVSSGPPP PRRISYHGSCPQGLADSA WIPFREHCYSFHMELLLGH KEARQRCQRAGGAVLSILD EMENVFVWEHLQSYEGQS RGAWLGMNFNPKGGTLV WQDNTAVNYSNWGPPGL GPSMLSHNSCYWIQSNSG LWRPGACTNITMGVVCKL PRAEQSSFSPSALPENPAAL VVVLMAVLLLLALLTAALIL YRRRQSIERGAFEGARYSR SSSSPTEATEKNILVSDME MNEQQE | |
| SEQ ID NO: 1849 | ENSG00000020256.15 | MNASSEGESFAGSVQIPG GTTVLVELTPDIHICGICKQ QFNNLDAFVAHKQSGCQL TGTSAAAPSTVQFVSEETV PATQTQTTTRTITSETQTIT VSAPEFVFEHGYQTY | A*02:03, B*15:01, C*03:02, C*03:04 |
| SEQ ID NO: 1850 | ENSG00000032389.8 | MEDDAPVIYGLEFQARALT PQTAETDAIRFLVGTQSLKY DNQIHIIDFDDENNIINKNV LLHQAGEIWHISASPADRG VLTTCYNRRDIIESFGILPVA QSPTIVFVNTLHQVFFRGQ VAASDSKVLTCAAVWR | A*02:03, A*24:07, A*24:10, A*33:03, B*15:01, B*15:21, B*15:27, B*38:02, B*39:01, B*40:01, B*40:06, B*46:01, B*51:01, B*55:02, B*58:01, C*01:02, C*03:02, C*03:04, C*03:67, C*04:01, C*08:01, C*12:02, C*14:02, C*15:02 |
| SEQ ID NO: 1851 | ENSG00000037042.8 | MLEAILGGGGLPVEGRGST EFEAFRLILFGSEDSVLPSPL LYKMAHMGSDGGVLPVH YATILFSL | A*02:03, A*11:01, A*11:02, A*24:02, A*24:07, A*24:10, B*40:01, B*40:06, B*51:01, C*01:02, C*04:03, C*08:01, C*14:02 |
| SEQ ID NO: 1852 | ENSG00000053747.11 | MAAAARPRGRALGPVLPP TPLLLLVLRVLPACGATARD PGAAAGLSLHPTYFNLAEA ARIWATATCGERGPGEGR PQPELYCKLVGGPTAPGSG HTIQGQFCDYCNSEDPRKA HPVTNAIDGSERWWQSPP LSSGTQYNRVNLTLDLGQL FHVAYILIKFANSPRPDLWV LERSVDFGSTYSPWQYFAH SKVDCLKEFGREANMAVT | A*02:03, A*11:01, A*11:02, A*24:02, A*24:07, A*24:10, A*33:03, B*15:01, B*39:01, B*40:01, B*55:02, B*58:01, C*03:02, C*03:04, C*03:67, C*07:02, C*12:02, C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| | | RDDDVLCVTEYSRIVPLEN | |
| | | GEVVVSLINGRPGAKNFTF | |
| | | SHTLREFTKATNIRLRFLRT | |
| | | NTLLGHLISKAQRDPTVTR | |
| | | RYYYSIKDISIGGQCVCNGH | |
| | | AEVCNINNPEKLFRCECQH | |
| | | HTCGETCDRCCTGYNQRR | |
| | | WRPAAWEQSHECEACNC | |
| | | HGHASNCYYDPDVERQQA | |
| | | SLNTQGIYAGGGVCINCQH | |
| | | NTAGVNCEQCAKGYYRPY | |
| | | GVPVDAPDGCIPCSCDPEH | |
| | | ADGCEQGSGRCHCKPNFH | |
| | | GDNCEKCAIGYYNFPFCLRI | |
| | | PIFPVSTPSSEDPVAGDIKG | |
| | | CDCNLEGVLPEICDAHGRC | |
| | | LCRPGVEGPRCDTCRSGFY | |
| | | SFPICQACWCSALGSYQM | |
| | | PCSSVTGQCECRPGVTGQ | |
| | | RCDRCLSGAYDFPHCQGSS | |
| | | SACDPAGTINSNLGYCQCK | |
| | | LHVEGPTCSRCKLLYWNLD | |
| | | KENPSGCSECKCHKAGTVS | |
| | | GTGECRQGDGDCHCKSHV | |
| | | GGDSCDTCEDGYFALEKSN | |
| | | YFGCQGCQCDIGGALSSM | |
| | | CSGPSGVCQCREHVVGKV | |
| | | CQRPENNYYFPDLHHMKY | |
| | | EIEDGSTPNGRDLRFGFDP | |
| | | LAFPEFSWRGYAQMTSVQ | |
| | | NDVRITLNVGKSSGSLFRVI | |
| | | LRYVNPGTEAVSGHITIYPS | |
| | | WGAAQSKEIIFLPSKEPAFV | |
| | | TVPGNGFADPFSITPGIWV | |
| | | ACIKAEGVLLDYLVLLPRDY | |
| | | YEASVLQLPVTEPCAYAGP | |
| | | PQENCLLYQHLPVTRFPCT | |
| | | LACEARHFLLDGEPRPVAV | |
| | | RQPTPAHPVMVDLSGREV | |
| | | ELHLRLRIPQVGHYVVVVE | |
| | | YSTEAAQLFVVDVNVKSSG | |
| | | SVLAGQVNIYSCNYSVLCR | |
| | | SAVIDHMSRIAMYELLADA | |
| | | DIQLKGHMARFLLHQVCII | |
| | | PIEEFSAEYVRPQVHCIASY | |
| | | GRFVNQSATCVSLAHETPP | |
| | | TALILDVLSGRPFPHLPQQS | |
| | | SPSVDVLPGVTLKAPQNQ | |
| | | VTLRGRVPHLGRYVFVIHF | |
| | | YQAAHPTFPAQVSVDGG | |
| | | WPRAGSFHASFCPHVLGC | |
| | | RDQVIAEGQIEFDISEPEVA | |
| | | ATVKVPEGKSLVLVRVLVV | |
| | | PAENYDYQILHKKSMDKSL | |
| | | EFITNCGKNSFYLDPQTASR | |
| | | FCKNSARSLVAFYHKGALP | |
| | | CECHPTGATGPHCSPEGG | |
| | | QCPCQPNVIGRQCTRCAT | |
| | | GHYGFPRCKPCSCGRRLCE | |
| | | EMTGQCRCPPRTVRPQCE | |
| | | VCETHSFSFHPMAGCEGC | |
| | | NCSRRGTIEAAMPECDRDS | |
| | | GQCRCKPRITGRQCDRCAS | |
| | | GFYRFPECVPCNCNRDGTE | |
| | | PGVCDPGTGACLCKENVE | |
| | | GTECNVCREGSFHLDPANL | |
| | | KGCTSCFCFGVNNQCHSS | |
| | | HKRRTKFVDMLGWHLETA | |
| | | DRVDIPVSFNPGSNSMVA | |
| | | DLQELPATIHSASWVAPTS | |
| | | YLGDKVSSYGGYLTYQAKS | |
| | | FGLPGDMVLLEKKPDVQLT | |
| | | GQHMSIIYEETNTPRPDRL | |
| | | HHGRVHVVEGNFRHASSR | |
| | | APVSREELMTVLSRLADVRI | |
| | | QGLYFTETQRLTLSEVGLEE | |

TABLE 9-continued

Recurrent N terminal sequences with high affinity to MHC Class I

| SEQ ID NO. | Gene | N terminal sequence | High Affinity HLA |
|---|---|---|---|
| | | ASDTGSGRIALAVEICACPP AYAGDSC | |
| SEQ ID NO: 1853 | ENSG00000059145.14 | MPSVSKAAAAALSGSPPQ TEKPTHYRYLKEFRTEQCPL FSQHKCAQHRPFTCFHWH FLNQRRRRPLRRRDGTFNY SPDVYCSKYNEATGVCPDG DECPYLHRTTGDTERKYHL RYYKTGTCIHETDARGHCV KNGLHCAFAHGPLDLRPPV CDVRELQAQEALQNGQLG GGEGVPDLQPGVLASQA MIEKILSEDPRWQDANFVL GSYKTEQCPKPPRLCRQGY ACPHYHNSRDRRRNPRRF QYRSTPCPSVKHGDEWGE PSRCDGGDGCQYCHSRTE QQFHPESTKCNDMRQTGY CPRGPFCAFAHVEKSLGM VNEWGCHDLHLTSPSSTG SGQPGNAKRRDSPAEGGP RGSEQDSKQNHLAVFAAV HPPAPSVSSSVASSLASSAG SGSSSPTALPAPPARALPLG PASSTVEAVLGSALDLHLS NVNIASLEKDLEEQDGHDL GAAGPRSLAGSAPVAIPGS LPRAPSLHSPSSASTSPLGS LSQPLPGPVGSSA | A*02:03, A*24:10, A*33:03, B*15:01, B*39:01, B*40:01, B*58:01, C*03:02, C*03:04, C*15:02 |
| SEQ ID NO: 1854 | ENSG00000060656.15 | MARAQALVLALTFQLCAPE TETPAAGCTFEEASDPAVP CEYSQAQYDDFQWEQVRI HPGTRAPADLPHGSYLMV NTSQHAPGQRAHVIFQSLS ENDTHCVQFSYFLYSRDGH SPGTLGVYVRVNGGPLGS AVWNMTGSHGRQWHQA ELAVSTFWPNEYQVLFEALI SPDRRGYMGLDDILLLSYP CAKAPHFSRLGDVEVNAG QNASFQCMAAGRAAEAE RFLLQRQSGALVPAAGVR HISHRRFLATFPLAAVSRAE QDLYRCVSQAPRGAGVSN FAELIVKEPPTPIAPPQLLRA GPTYLIIQLNTNSIIGDGPIV RKEIEYRMARGPWAEVHA VSLQTYKLWHLDPDTEYEI SVLLTRPGDGGTGRPGPPL ISRTKCAEPMRAPKGLAFA EIQARQLTLQWEPLGYNVT RCHTYTVSLCYHYTLGSSH NQTIRECVKTEQGVSRYTIK NLLPYRNVHVRLVLTNPEG RKEGKEVTFQTDEDVPSGI AAESLTFTPLEDMIFLKWEE PQEPNGLITQYEISYQSIESS DPAVNVPGPRRTISKLRNE TYHVFSNLHPGTTYLFSVR ARTGKGFGQAALTEITTNIS APSFDYADMPSPLGESENT ITVLLRPAQGRGAPISVYQV IVEEERARRLRREPGGQDC FPVPLTFEAALARGLVHYF GAELAASSLPEAMPFTVGD NQTYRGFWNPPLEPRKAY LIYFQAASHLKGETRLNCIRI ARKAACKESKRPLEVSQRS EEMGLILGICAGGLAVLILLL GAIIVIIRKGKPVNMTKATV NYRQEKTHMMSAVDRSFT DQSTLQEDERLGLSFMDT HGYSTRGDQRSGGVTEAS SLLGGSPRRPCGRKGSPYH | A*02:03, A*11:01, A*11:02, A*24:02, A*24:10, A*33:03, A*34:01, B*15:01, B*15:27, B*38:02, B*39:01, B*40:01, B*55:02, B*58:01, C*03:02, C*03:04, C*07:02, C*12:02, C*14:02, C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | TGQLHPAVRVADLLQHIN<br>QMKTAEGYGFKQEYESFFE<br>GWDATKKKDKVKGSRQEP<br>MPAYDRHRVKLHPMLGD<br>PNADYINANYIDGYHRSNH<br>FIATQGPKPEMVYDFWR<br>MVWQEHCSSIVMITKLVE<br>VGRVKCSRYWPEDSDTYG<br>DIKIMLVKTETLAEYVVRTF<br>ALERRGYSARHEVRQFHFT<br>AWPEHGVPYHATGLLAFIR<br>RVKASTPPDAGPIVIHCSA<br>GTGRTGCYIVLDVMLDMA<br>ECEGVVDIYNCVKTLCSRR<br>VNMIQTEEQYIFIHDAILEA<br>CLCGETTIPVSEFKATYKEM<br>IRIDPQSNSSQLREEFQTLN<br>SVTPPLDVEECSIALLPRNR<br>DKNRSMDVLPPDRCLPFLI<br>STDGDSNNYINAALTDSYT<br>RSAAFIVTLHPLQSTTPDF<br>WRLVYDYGCTSIVMLNQL<br>NQSNSAWPCLQYWPEPG<br>RQQYGLMEVEFMSGTAD<br>EDLVARVFRVQNISRLQEG<br>HLLVRHFQFLRWSAYRDTP<br>DSKKAFLHLLAEVDKWQA<br>ESGDGRTIVHCLNGGGRS<br>GTFCACATVLEMIRCHNLV<br>DVFFAAKTLRNYKPNMVE<br>TMDQYHFCYDVALEYLEGL<br>ESR | |
| SEQ ID NO: 1855 | ENSG00000066248.10 | METRESEDLEKTRRKSASD<br>QWNTDNEPAKVKPELLPE<br>KEETSQADQDIQDKEPHC<br>HIPIKRNSIFNRSIRRKSKAK<br>ARDNPERNASCLADSQDN<br>GKSVNEPLTLNIPWSRMPP<br>CRT | A*02:03, A*11:01, A*11:01,<br>A*11:02, A*11:02, A*24:02,<br>A*24:10, A*33:03, A*33:03,<br>A*34:01, B*15:01, B*15:21,<br>B*15:27, B*39:01,<br>B*40:01, B*46:01, B*58:01,<br>C*03:02, C*03:04, C*03:67,<br>C*12:02, C*14:02 |
| SEQ ID NO: 1856 | ENSG00000077092.14 | MTTSGHACPVPAVNGHM<br>THYPATPYPLLFPPVIGGLS<br>LPPLHGLHGHPPPSGCSTP<br>SPATIETQS | A*24:02, A*24:07, A*24:10,<br>A*34:01, B*15:01, B*15:21,<br>B*15:27, B*46:01, B*51:01,<br>B*55:02, C*01:02,<br>C*03:02, C*04:01, C*07:02,<br>C*12:02, C*14:02 |
| SEQ ID NO: 1857 | ENSG00000079308.12 | MTRLSWCFSCVIRWGKYL<br>FSCLLPLRFCLRSQPEDLEA<br>PKTHRFKVKTFKKVKPCGIC<br>RQVITQEGCTCKVCSFSCH<br>RKCQAKVAAPCVPPSNHE<br>LVPITTENAPKNVVDKGEG<br>ASRGGNTRKSLEDNGSTRV<br>TPSVQPHLQPIRN | A*02:03, A*02:07, B*27:04,<br>B*39:01, B*46:01, C*01:02,<br>C*03:02, C*03:04, C*03:67,<br>C*08:01, C*14:02 |
| SEQ ID NO: 1858 | ENSG00000080823.17 | MKNYKAIGKIGEGTFSEVM<br>KMQSLRDGNYYACKQMK<br>QRFESIEQVNNLREIQALRR<br>LNPHPNILMLHEVVFDRKS<br>GSLALICELMDMNIYELIRG<br>RRYPLSEKKIMHYMYQLCK<br>SLDHIHRNGIFHRDVKPENI<br>LIKQDVLKLGD | A*02:03, A*33:03, B*40:01,<br>C*03:02, C*14:02 |
| SEQ ID NO: 1859 | ENSG00000097021.15 | MARPGLIHSAPGLPDTCAL<br>LQPPAASAAAAPS | A*02:03 |
| SEQ ID NO: 1860 | ENSG00000100441.5 | MPTWGARPASPDRFAVSA<br>EAENKVREQQPHVERIFSV<br>GVSVLPKDCPDNPHIWLQ<br>LEGPKENASRAKEYLKGLCS<br>PELQDEIHYPPKLHCIFLGA<br>QGFFLDCLAWSTSAHLVPR | A*02:03, A*02:07, A*11:01,<br>A*11:02, A*24:02, A*24:07,<br>A*24:10, A*33:03, B*15:01,<br>B*15:21, B*15:27,<br>B*40:01, B*40:06, B*55:02,<br>B*58:01, C*03:02, C*03:04, |

TABLE 9-continued

| Recurrent N terminal sequences with high affinity to MHC Class I | | | |
|---|---|---|---|
| SEQ ID NO. | Gene | N terminal sequence | High Affinity HLA |
| | | APGSLMISGLTEAFVMAQS<br>RVEELAERLSWDFTPGPSS<br>GASQCTGVLRDFSALLQSP<br>GDAHREALLQLPLAVQEEL<br>LSLVQEASSGQGPGALAS<br>WEGRSSALLGAQCQGVRA<br>PPSDGRESLDTGSMGPGD<br>CRGARGDTYAVEKEGGKQ<br>GGPREMDWGWKELPGEE<br>AWEREVALRPQSVGGGAR<br>ESAPLKGKALGKEEIALGG<br>GGFCVHREPPGAHGSCHR<br>AAQSRGASLLQRLHNGNA<br>SPPRVPSPPPAPEPPWHC<br>GDRGDCGDRGDVGDRGD<br>KQQGMARGRGPQWKRG<br>ARGGNLVTGTQRFKEALQ<br>DPFTLCLANVPGQPDLRHI<br>VIDGSNVAMVHGLQHYFS<br>SRGIAIAVQYFWDRGHRDI<br>TVFVPQWRFSKDAKVRES<br>HFLQKLYSLSLLSLTPSRVM<br>DGKRISSYDDRFMVKLAEE<br>TDGIIVSNDQFRDLAEESEK<br>W | C*03:67, C*04:01, C*04:03,<br>C*07:02, C*08:01, C*14:02,<br>C*15:02 |
| SEQ ID NO: 1861 | ENSG00000103056.7 | MVLYTTPFPNSCLSALHCV<br>SWALIFPCYWLVDRLAASF<br>IPTTYEKRQRADDPCCLQLL<br>CTALFTPIYLALLVASLPFAF<br>LGFLFWSPLQSARRPYIYSR<br>LEDKGLAGGAALLSEWKG<br>TGPGKSFCFATANVCLLPD<br>SLARVNNLFNTQARAKEIG<br>QRIRNGAARPQIKIYIDSPT<br>NTSISAASFSSLVSPQGGD<br>GVARAVPGSIKRTASVEYK<br>GDGGRHPGDEAANGPAS<br>GDPVDSSSPEDACIVRIGG<br>EEGGRPPEADDPVPGGQA<br>RNGAGGGPRGQTPNHNQ<br>QDGDSGSLGSPSASRESLV<br>KGRAGPDTSASGEPGANS<br>KLLYKASVVKKAAARRRRH<br>PDEAFDHEVSAFFPANLDF<br>LCLQEVFDKRAATKLKEQL<br>HGYFEYILYDVGVYGCQGC<br>CSFKCLNSGLLFASRYPI | A*02:03, A*02:07, A*11:01,<br>A*11:02, A*24:02, A*24:07,<br>A*24:10, B*15:01, B*15:21,<br>B*15:27, B*27:04,<br>B*38:02, B*39:01, B*40:01,<br>B*40:06, B*46:01, B*51:01,<br>B*55:02, B*58:01, C*01:02,<br>C*03:02, C*03:04, C*03:67,<br>C*04:01, C*04:03, C*07:02,<br>C*08:01, C*12:02, C*15:02 |
| SEQ ID NO: 1862 | ENSG00000103227.14 | MLGAGLIKIRGDRCWRDL<br>TCMDFHYETQPMPNPVA<br>YYLHHSPWWFHRFETLSN<br>HFIELLVPFFLFLGRRACIIH<br>GVLQILFQAVLIVSGNLSFL<br>NWLTMVPSLACFDDATLG<br>FLFPSGPGSLKDRVLQMQ<br>RDIRGARPEPRFGSVVRRA<br>ANVSLGVLLAWLSVPVVLN<br>LLSSRQVMNTHFNSLHIVN<br>TYGAFGSITKERAEVILQGT<br>ASSNASAPDAMWEDYEFK<br>CKPGDPSRRPCLISPYHYRL<br>DWLMWFAAFQTYEHND<br>WIIHLAGKLLASDAEALSLL<br>AHNPFAGRPPPRWVRGE<br>HYRYKFSRPGGRHAAEGK<br>WWVRKRIGAYFPPLS | A*02:03, A*11:01, A*11:02,<br>A*24:02, A*24:07, A*24:10,<br>A*33:03, B*15:01, B*38:02,<br>B*40:01, B*58:01, C*03:02,<br>C*03:04, C*07:02,<br>C*14:02, C*15:02 |
| SEQ ID NO: 1863 | ENSG00000105559.7 | MEGSRPRSSLSLASSASTIS<br>SLSSLSPKKPTRAVNKIHAF<br>GKRGNALRRDPNLPVHIR<br>GWLHKQDSSGLRLWKRR<br>WFVLSGHCLFYYKDSREES<br>VLGSVLLPSYNIRPDGPGA<br>PRGRRFTFTAEHPGMRTY<br>VLAADTLEDLRGWLRALG | A*02:03, A*11:01, A*11:02,<br>A*24:10, A*33:03, B*39:01,<br>B*40:01, B*58:01, C*03:02,<br>C*03:04, C*14:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | RASRAEGDDYGQPRSPAR | |
| | | PQPGEGPGGPGGPPEVSR | |
| | | GEEGRISESPEVTRLSRGRG | |
| | | RPRLLTPSPTTDLHSGLQM | |
| | | RRARSPDLFTPLSRPPSPLS | |
| | | LPRPRSAPARRPPAPSGDT | |
| | | APPARPHTPLSRIDVRPPLD | |
| | | WGPQRQTLSRPPTPRRGP | |
| | | PSEAGGGKPPRSPQHWSQ | |
| | | EPRTQAHSGSPTYLQLPPR | |
| | | PPGTRASMVLLPGPPLEST | |
| | | FHQSLETDTLLTKLCGQDR | |
| | | LLRRLQEEIDQKQEEKEQLE | |
| | | AALELTRQQLGQATREAG | |
| | | APGRAWGRQRLLQDRLVS | |
| | | VRATLCHLTQERERVWDT | |
| | | YSGLEQELGTLRETLEYLLH | |
| | | LGSPQDRVSAQQQLWMV | |
| | | EDTLAGLGGPQKPPPHTEP | |
| | | DSPSPVLQGEESSERESLPE | |
| | | SLELSSPRSPETDWGRPPG | |
| | | GDKDLASPHLGLGSPRVSR | |
| | | ASSPEGRHLPSPQLGTKAP | |
| | | VARPRMSAQEQLERMRR | |
| | | NQECGRPFPRPTSPRLLTL | |
| | | GRTLSPARRQPDVEQRPV | |
| | | VGHSGAQKWLRSSGSWSS | |
| | | PRNTTPYLPTSEGHRERVLS | |
| | | LSQALATEASQWHRMMT | |
| | | GGNLDSQGDPLPGVPLPP | |
| | | SDPTRQETPPPRSPPVANS | |
| | | GSTGFSRRGSGRGGGPTP | |
| | | WGPAWDAGIAPPVLPQD | |
| | | EGAWPLRVTLLQSSF | |
| SEQ ID NO: 1864 | ENSG00000105639.14 | MAPPSEETPLIPQRSCSLLS | A*02:03, A*11:01, A*11:02, |
| | | TEAGALHVLLPARGPGPPQ | A*24:02, A*24:07, A*24:10, |
| | | RLSFSFGDHLAEDLCVQAA | A*33:03, B*15:01, B*39:01, |
| | | KASGILPVYHSLFALATEDL | B*40:01, B*55:02, B*58:01, |
| | | SCWFPPSHIFSVEDASTQV | C*03:02, C*03:04, |
| | | LLYRIRFYFPNWFGLEKCHR | C*07:02, C*14:02 |
| | | FGLRKDLASAILDLPVLEHL | |
| | | FAQHRSDLVSGRLPVGLSL | |
| | | KEQGECLSLAVLDLARMAR | |
| | | EQAQRPGELLKTVSYKACL | |
| | | PPSLRDLIQGLSFVTRRRIR | |
| | | RTVRRALRRVAACQADRH | |
| | | SLMAKYIMDLERLDPAGA | |
| | | AETFHVGLPGALGGHDGL | |
| | | GLLRVAGDGGIAWTQGEQ | |
| | | EVLQPFCDFPEIVDISIKQA | |
| | | PRVGPAGEHRLVTVTRTD | |
| | | NQILEAEFPGLPEALSFVAL | |
| | | VDGYFRLTTDSQHFFCKEV | |
| | | APPRLLEEVAEQCHGPITLD | |
| | | FAINKLKTGGSRPGSYVLRR | |
| | | SPQDFDSFLLTVCVQNPLG | |
| | | PDYKGCLIRRSPTGTFLLVG | |
| | | LSRPHSSLRELLATCWDGG | |
| | | LHVDGVAVTLTSCCIPRPKE | |
| | | KSNLIVVQRGHSPPTSSLV | |
| | | QPQSQYQLSQMTFHKIPA | |
| | | DSLEWHENLGHGSFTKIYR | |
| | | GCRHEVVDGEARKTEVLLK | |
| | | VMDAKHKNCMESFLEAAS | |
| | | LMSQVSYRHLVLLHGVCM | |
| | | AGDSTMVQEFVHLGAIDM | |
| | | YLRKRGHLVPASWKLQVV | |
| | | KQLAYALNYLEDKGLPHGN | |
| | | VSARKVLLAREGADGSPPFI | |
| | | KLSDPGVSPAVLSLEMLTD | |
| | | RIPWVAPECLREAQTLSLE | |
| | | ADKWGFGATVWEVFSGV | |
| | | TMPISALDPAKKLQFYEDR | |
| | | QQLPAPKWTELALLIQQC | |
| | | MAYEPVQRPSFRAVIRDLN | |

TABLE 9-continued

| Recurrent N terminal sequences with high affinity to MHC Class I | | | |
|---|---|---|---|
| SEQ ID NO. | Gene | N terminal sequence | High Affinity HLA |
| | | SLISSDYELLSDPTPGALAPR DGLWNGAQLYACQDPTIF EERHLKYISQLGKGNFGSV ELCRYDPLGDNTGALVAVK QLQHSGPDQQRDFQREIQ ILKALHSDFIVKYRGVSYGP GRQSLRLVMEYLPSGCLRD FLQRHRARLDASRLLLYSSQ ICKGMEYLGSRRCVHRDLA ARNILVESEAHVKIADFGLA KLLPLDKDYYVVREPGQSPI FWYAPESLSDNIFSRQSDV WSFGVVLYELFTYCDKSCS PSAEFLRMMGCERDVPAL CRLLELLEEGQRLPAPPACP AEVHELMKLCWAPSPQDR PSFSALGPQLDMLWSGSR GCETHAFTAHPEGKHHSLS FS | |
| SEQ ID NO: 1865 | ENSG00000105650.17 | MQAPVPHSQRRESFLYRS DSDYELSPKAMSRNSSVAS DLHGEDMIVTPFAQVLASL RTVRSNVAALARQQCLGA AKQGPVGN | A*02:03, B*15:01, B*39:01, B*40:01, C*03:02, C*03:04, C*15:02 |
| SEQ ID NO: 1866 | ENSG00000105963.9 | MAKERRRAVLELLQRPGN ARCADCGAPDPDWASYTL GVFICLSCSGIHRNIPQVSK VKSVRLDAWEEAQVEFMA SHGNDAARARFESKVPSFY YRPTP | A*02:03, A*24:10, B*15:01, C*03:02, C*03:04 |
| SEQ ID NO: 1867 | ENSG00000105976.10 | MKAPAVLAPGILVLLFTLV QRSNGECKEALAKSEMNV NMKYQLPNFTAETPIQNVI LHEHHIFLGATNYIYVLNEE DLQKVAEYKTGPVLEHPDC FPCQDCSSKANLSGGVWK DNINMALVVDTYYDDQLIS CGSVNRGTCQRHVFPHNH TADIQSEVHCIFSPQIEEPS QCPDCVVSALGAKVLSSVK DRFINFFVGNTINSSYFPDH PLHSISVRRLKETKDGFMFL TDQSYIDVLPEFRDSYPIKY VHAFESNNFIYFLTVQRETL DAQTFHTRIIRFCSINSGLH SYMEMPLECILTEKRKKRST KKEVFNILQAAYVSKPGAQ LARQIGASLNDDILFGVFA QSKPDSAEPMDRSAMCAF PIKYVNDFFNKIVNKNNVR CLQHFYGPNHEHCFNRTLL RNSSGCEARRDEYRTEFTT ALQRVDLFMGQFSEVLLTS ISTFIKGDLTIANLGTSEGRF MQVVVSRSGPSTPHVNFL LDSHPVSPEVIVEHTLNQN GYTLVITGKKITKIPLNGLGC RHFQSCSQCLSAPPFVQCG WCHDKCVRSEECLSGTWT QQICLPAIYKVFPNSAPLEG GTRLTICGWDFGFRRNNK FDLKKTRVLLGNESCTLTLS ESTMNTLKCTVGPAMNKH FNMSIIISNGHGTTQYSTFS YVDPVITSISPKYGPMAGG TLLTLTGNYLNSGNSRHISI GGKTCTLKSVSNSILECYTP AQTISTEFAVKLKIDLANRE TSIFSYREDPIVYEIHPTKSFI SGGSTITGVGKNLNSVSVP RMVINVHEAGRNFTVACQ HRSNSEIICCTTPSLQQLNL QLPLKTKAFFMLDGILSKYF | A*02:03, A*11:01, A*11:02, A*24:02, A*24:07, A*24:10, A*33:03, A*34:01, B*15:01, B*15:27, B*39:01, B*40:01, B*58:01, C*03:02, C*03:04, C*03:67, C*07:02, C*12:02, C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| | | DLIYVHNPVFKPFEKPVMIS MGNENVLEIKGNDIDPEA VKGEVLKVGNKSCENIHLH SEAVLCTVPNDLLKLNSELN IEWKQAISSTVLGKVIVQP DQNFTGLIAGVVSISTALLL LLGFFLWLKKRKQIKDLGSE LVRYDARVHTPHLDRLVSA RSVSPTTEMVSNESVDYRA TFPEDQFPNSSQNGSCRQ VQYPLTDMSPILTSGDSDIS SPLLQNTVHIDLSALNPELV QAVQHVVIGPSSLIVHFNE VIGRGHFGCVYHGTLLDN DGKKIHCAVKSLNRITDIGE VSQFLTEGIIMKDFSHPNVL SLLGICLRSEGSPLVVLPYM KHGDLRNFIRNETHNPTVK DLIGFGLQVAKGMKYLASK KFVHRDLAARNCMLDEKF TVKVADFGLARDMYDKEY YSVHNKTGAKLPVKWMAL ESLQTQKFTTKSDVWSFGV LLWELMTRGAPPYPDVNT FDITVYLLQGRRLLQPEYCP DPLYEVMLKCWHPKAEM RPSFSELVSRISAIFSTFIGEH YVHVNATYVNVKCVAPYP SLLSSEDNADDEVDTRPAS FWETS | |
| SEQ ID NO: 1868 | ENSG00000107317.7 | MATHHTLWMGLALLGVL GDLQAAPEAQVSVQPNFQ QD | A*02:03, B*15:01, C*03:02, C*03:04, C*12:02 |
| SEQ ID NO: 1869 | ENSG00000111700.8 | MDQHQHLNKTAESASSEK KKTRRCNGFK | A*11:01, A*11:02 |
| SEQ ID NO: 1870 | ENSG00000111860.9 | MWGRFLAPEASGRDSPG GARSFPAGPDYSSAWLPA NESLWQATTVPSNHRNN HIRRHSIASDSGDTGIGTSC SDSVEDHSTSSGTLSFKPSQ SLITLPTAHVMPSNSSASIS KLRESLTPDGSKWSTSLMQ TLGNHSRGEQDSSLDMKD FRPLRKWSSLSKLTAPDNC GQGGTVCREESRNGLEKIG KAKALTSQLRTIGPSCLHDS MEMLRLEDKEINKKRSSTL DCKYKFESCSKEDFRASSST LRRQPVDMTYSALPESKPI MTSSEAFEPPKYLMLGQQ AVGGVPIQPSVRTQMWLT EQLRTNPLEGRNTEDSYSL APWQQQQIEDFRQGSETP MQVLTGSSRQSYSPGYQD FSKWESMLKIKEGLLRQKEI VIDRQKQQITHLHERIRDN ELRAQHAMLGHYVNCEDS YVASLQPQYENTSLQTPFS EESVSHSQQGEFEQKLAST EKEVLQLNEFLKQRLSLFSE EKKKLEEKLKTRDRYISSLKK KCQKESEQNKEKQRRIETL EKYLADLPTLDDVQSQSLQ LQILEEKNKNLQEALIDTEK KLEEIKKQCQDKETQLICQK KKEKELVTTVQSLQQKVER CLEDGIRLPMLDAKQLQNE NDNLRQQNETASKIIDSQQ DEIDRMILEIQSMQGKLSK EKLTTQKMMEELEKKERN VQRLTKALLENQRQTDETC SLLDQGQEPDQSRQQTVL SKRPLFDLTVIDQLFKEMSC | A*02:03, A*11:01, A*11:02, A*24:02, A*24:07, A*24:10, A*33:03, B*15:01, B*15:27, B*39:01, B*40:01, C*03:02, C*03:04, C*14:02 |

TABLE 9-continued

Recurrent N terminal sequences with high affinity to MHC Class I

| SEQ ID NO. | Gene | N terminal sequence | High Affinity HLA |
|---|---|---|---|
| | | CLFDLKALCSILNQRAQGK<br>EPNLSLLLGIRSMNCSAEET<br>ENDHSTETLTKKLSDVCQL<br>RRDIDELRTTISDRYAQDM<br>GDNCITQ | |
| SEQ ID NO: 1871 | ENSG00000111912.14 | XEKTCSSLEREPHFSLLTMR<br>GQRLPLDIQIFYCARPDEEP<br>FVKIITVEEAKRRKSTCSYYE<br>DEDEEVLPVLRPHSALLEN<br>MHIEQLARRLPARVQGYP<br>WRLAYSTLEHGTSLKTLYRK<br>SASLDSPVLLVIKDMDNQIF<br>GAYATHPFKFSDHYYGTGE<br>TFLYTFSPHFKVFKWSGEN<br>SYFINGDISSLELGGGGGRF<br>GLWLDADLYHGRSNSCST<br>FNNDILSKKEDFIVQDLEV<br>WAFD | A*02:03, A*11:01, A*11:02,<br>A*24:02, A*24:07, A*24:10,<br>A*33:03, B*15:01, B*15:27,<br>B*40:01, B*55:02, C*03:02,<br>C*03:04, C*03:67,<br>C*12:02, C*14:02, C*15:02 |
| SEQ ID NO: 1872 | ENSG00000112033.9 | MEQPQEEAPEVREEEEKEE<br>VAEAEGAPELNGGPQHAL<br>PSSSYTDLSRSSSPPSLLDQL<br>QMGCDGASCGSLNMECR<br>VCGDKASGFHYGVHACEG<br>CKGFFRRTIRMKLEYEKCER<br>SCKIQKKNRNKCQYCRFQK<br>CLALGMSHNAIRFGRMPE<br>AEKRKLVAGLTANEGSQYN<br>PQVADLKAFSKHIYNAYLK<br>NFNMTKKKARSILTGKASH<br>TAPFVIHDIETLWQAEKGL<br>VWKQLVNGLPPYKEISVHV<br>FYRCQCTTVETVRELTEFAK<br>SIPSFSSLFLNDQVTLLKYG<br>VHEAIFAMLASIVNKDGLL<br>VANGSGFVTREFLRSLRKP<br>FSDIIEPKFEFAVKFNALELD<br>DSDLALFIAAIILCGDRPGL<br>MNVPRVEAIQDTILRALEF<br>HLQANHPDAQYLFP | A*02:03, A*02:07, A*11:01,<br>A*11:02, A*24:02, A*24:07,<br>A*24:10, A*33:03, A*34:01,<br>B*15:01, B*15:21,<br>B*15:27, B*27:04, B*38:02,<br>B*39:01, B*40:01, B*40:06,<br>B*46:01, B*51:01, B*55:02,<br>B*58:01, C*01:02, C*03:02,<br>C*03:04, C*04:01, C*04:03,<br>C*07:02, C*08:01,<br>C*12:02, C*15:02 |
| SEQ ID NO: 1873 | ENSG00000113594.5 | MMDIYVCLKRPSWMVDN<br>KRMRTASNFQWLLSTFILL<br>YLMNQVNSQKKGAPHDLK<br>CVTNNLQVWNCSWKAPS<br>GTGRGTDYEVCIENRSRSC<br>YQLEKTSIKIPALSHGDYEITI<br>NSLHDFGSSTSKFTLNEQN<br>VSLIPDTPEILNLSADFSTST<br>LYLKWNDRGSVFPHRSNVI<br>WEIKVLRKESMELVKLVTH<br>NTTLNGKDTLHHWSWAS<br>DMPLECAIHFVEIRCYIDNL<br>HFSGLEEWSDWSPVKNIS<br>WIPDSQTKVFPQDKVILVG<br>SDITFCCVSQEKVLSALIGH<br>TNCPLIHLDGENVAIKIRNIS<br>VSASSGTNVVFTTEDNIFG<br>TVIFAGYPPDTPQQLNCET<br>HDLKEIICSWNPGRVTALV<br>GPRATSYTLVESFSGKYVRL<br>KRAEAPTNESYQLLFQMLP<br>NQEIYNFTLNAHNPLGRSQ<br>STILVNITEKVYPHTPTSFKV<br>KDINSTAVKLSWHLPGNFA<br>KINFLCEIEIKKSNSVQEQR<br>NVTIKGVENSSYLVALDKL<br>NPYTLYTFRIRCSTETFWK<br>WSKWSNKKQHLTTEASPS<br>KGPDTWREWSSDGKNLIIY<br>WKPLPINEANGKILSYNVS<br>CSSDEETQSLSEIPDPQHKA<br>EIRLDKNDYIISVVAKNSVG<br>SSPPSKIASMEIPNDDLKIE<br>QVVGMGKGILLTWHYDP | A*02:03, A*11:01, A*11:02,<br>A*24:02, A*24:07, A*24:10,<br>A*33:03, A*34:01, B*15:01,<br>B*39:01, B*40:01,<br>B*58:01, C*03:02, C*03:04,<br>C*03:67, C*12:02, C*14:02,<br>C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | NMTCDYVIKWCNSSRSEP<br>CLMDWRKVPSNSTETVIES<br>DEFRPGIRYNFFLYGCRNQ<br>GYQLLRSMIGYIEELAPIVA<br>PNFTVEDTSADSILVKWED<br>IPVEELRGFLRGYLFYFGKG<br>ERDTSKMRVLESGRSDIKV<br>KNITDISQKTLRIADLQGKT<br>SYHLVLRAYTDGGVGPEKS<br>MYVVTKENSVGLIIAILIPVA<br>VAVIVGVVTSILCYRKREWI<br>KETFYPDIPNPENCKALQF<br>QKSVCEGSSALKTLEMNPC<br>TPNNVEVLETRSAFPKIEDT<br>EIISPVAERPEDRSDAEPEN<br>HVVVSYCPPIIEEEIPNPAA<br>DEAGGTAQVIYIDVQSMY<br>QPQAKPEEEQENDPVGGA<br>GYKPQMHLPINSTVEDIAA<br>EEDLDKTAGYRPQANVNT<br>WNLVSPDSPRSIDSNSEIVS<br>FGSPCSINSRQFLIPPKDED<br>SPKSNGGGWSFTNFFQNK<br>PND | |
| SEQ ID NO: 1874 | ENSG00000114541.10 | MASVFMCGVEDLLFSGSR<br>FVWNLTVSTLRRWYTERLR<br>ACHQVLRTWCGLQDVYQ<br>MTEGRHCQVHLLDDRRLE<br>LLVQPKLLARELLDLVASHF<br>NLKEKEYFGITFIDDTGQQ<br>NWLQLDHRVLDHDLPKKP<br>GPTILHFAVRFYIESISFLKD<br>KTTVELFFLNAKACVHKGQ<br>IEVESETIFKLAAFILQEAKG<br>DYTSDENARKDLKTLPAFP<br>TKTLQEHPSLAYCEDRVIEH<br>YLKIKGLTRGQAVVQY | A*02:03, A*11:01, A*11:02, A*24:10, A*33:03, A*34:01, B*40:01, B*58:01, C*07:02, C*12:02, C*14:02 |
| SEQ ID NO: 1875 | ENSG00000115977.14 | MKKFFDSRREQGGSGLGS<br>GSSGGGGSTSGLGSGYIGR<br>VFGIGRQQVTVDEVLAEG<br>GFAIVFLVRTSNGMKCALK<br>RMFVNNEHDLQVCKREIQI<br>MRDLSGHKNIVGYIDSSIN<br>NVSSGDVWEVLILMDFCR<br>GGQVVNLMNQRLQTGFT<br>ENEVLQIFCDTCEAVARLH<br>QCKTPIIHRDLKVENILLHD<br>RGHYVLCDFGSATNKFQN<br>PQTEGVNAVEDEIKKYTTL<br>SYRAPEMVNLYSGKIITTKA<br>DIWALGCLLYKLCYFTLPFG<br>ESQVAICDGNFTIPDNSRYS<br>QDMHCLIRYMLEPDPDKR<br>PDIYQVSYFSFKLLKKECPIP<br>NVQNSPIPAKLPEPVKASE<br>AAAKKTQPKARLTDPIPTTE<br>TSIAPRQRPKAGQTQPNP<br>GILPIQPALTPRKRATVQPP<br>PQAAGSSNQPGLLASVPQ<br>PKPQAPPSQPLPQTQAKQ<br>PQAPPTPQQTPSTQAQGL<br>PAQAQATPQHQQQLFLK<br>QQQQQQQPPPAQQQPA<br>GTFYQQQQAQTQQFQAV<br>HPATQKPAIAQFPVVSQG<br>GSQQQLMQNFYQQQQQ<br>QQQQQQQQLATALHQ<br>QQLMTQQAALQQKPTMA<br>AGQQPQPQPAAAPQPAP<br>AQEPAIQAPVRQQPKVQT<br>TPPPAVQGQKVGSLTPPSS<br>PKTQRAGHRRILSDVTHSA<br>VFGVPASKSTQLLQAAAAE<br>AELLDPGRQTLQ | A*02:03, A*11:01, A*11:02, A*24:02, A*24:07, A*24:10, B*15:01, B*39:01, B*40:01, C*03:02, C*12:02, C*14:02 |

TABLE 9-continued

Recurrent N terminal sequences with high affinity to MHC Class I

| SEQ ID NO. | Gene | N terminal sequence | High Affinity HLA |
|---|---|---|---|
| SEQ ID NO: 1876 | ENSG00000116833.9 | MSSNSDTGDLQESLKHGLT PIGAGLPDRHGSPIPARGR LV | A*02:03 |
| SEQ ID NO: 1877 | ENSG00000118855.14 | MDAGKLARHPTDTGSERA VPALAEIRPWWAPPLRPQ | C*03:02, C*03:04, C*14:02 |
| SEQ ID NO: 1878 | ENSG00000119547.5 | MKAAYTAYRCLTKDLEGCA MNPELTMESLGTLHGPAG GGSGGGGGGGGGGGG GPGHEQELLASPSPHHAG RGAAGSLRGPPPPPTAHQ ELGTAAAAAAAASRSAMV TSMASILDGGDYRPELSIPL HHAMSMSCDSSPPGMG MSNTYTTLTPLQPLPPISTV SDKFHHPHPHHHPHHHH HHHHQRLSGNVSGSFTLM RDERGLPAMNNLYSPYKE MPGMSQSLSPLAATPLGN GLGGLHNAQQSLPNYGPP GHDKMLSPNFDAHHTAM LTRGEQHLSRGLGTPPAA MMSHLNGLHHPGHTQSH GPVLAPSRERPPSSSSGSQ VATSGQLEEINTKEVAQRIT AELKRYSIPQAIFAQRVLCR SQGTLSDLLRNPKPWSKLK SGRETFRRMWKWLQEPEF QRMSALRLAA | A*02:03, A*11:01, A*11:02, A*24:10, A*33:03, B*15:01, B*15:27, B*39:01, B*58:01, C*03:02, C*03:04, C*07:02, C*14:02 |
| SEQ ID NO: 1879 | ENSG00000125826.15 | MDEKTKKAEEMALSLTRA VAGGDEQVAMKCAIWLA EQRVPLSVQLKPEVSPTQD IRLWVSVEDAQMHTVTIW LTVRPDMTVASLKDMVFL DYGFPPVLQQWVIGQRLA RDQETLHSHGVRQNGDSA YLYLLSARNTSLNPQELQRE RQLRMLEDLGFKDLTLQPR GPLEPGPPKPGVPQEPGR GQPDAVPEPPPVGWQCP GCTFINKPTRPGCEMCCRA RPEAYQVPASYQPDEEERA RLAGEEEALRQYQQRKQQ QQEGNYLQHVQLDQRSLV LNTEPAECPVCYSVLAPGE AVVLRECLHTFCRECLQGTI RNSQEAEVSCPFIDNTYSCS GKLLEREIKALLTPEDYQRF LDLGISIAENRSAFSYHCKT PDCKGWCFFEDDVNEFTC PVCFHVNCLLCKAIHEQM NCKEYQEDLALRAQNDVA ARQTTEMLKVMLQQGEA MRCPQCQIVVQKKDGCD WIRCTVCHTEICWVTKGPR WGPGGPGDTSGGCRCRV NGIPCHPSCQNCH | A*02:03, A*02:07, A*11:01, A*11:02, A*24:10, A*33:03, B*40:01, C*03:02, C*03:04 |
| SEQ ID NO: 1880 | ENSG00000129116.13 | MSALASRSAPAMQSSGSF NYARPKQFIAAQNLGPAS GHGTPASSPSSSSLPSPMS PTPRQFGRAPVPPFAQPF GAEPEAPWGSSSPSPPPPP PPVFSPTAAFPVPDVFPLPP PPPPLPSPGQASHCSSPAT RFGHSQTPAAFLSALLPSQ PPPAAVNALGLPKGVTPA GFPKKASRTARIASDEEIQG TKDAVIQDLERKLRFKEDLL NNGQPRLTYEERMARRLL GADSATVFNIQEPEEETAN QEYKVSSCEQRLISEIEYRLE RSPVDESGDEVQYGDVPV | A*02:03, A*11:01, A*11:02, A*24:02, A*24:10, A*33:03, B*15:01, B*39:01, B*40:01, B*58:01, C*03:02, C*03:04 |

TABLE 9-continued

Recurrent N terminal sequences with high affinity to MHC Class I

| SEQ ID NO. | Gene | N terminal sequence | High Affinity HLA |
|---|---|---|---|
| | | ENGMAPFFEMKLKHYKIFE GMPVTFTCRVAGNPKPKIY WFKDGKQISPKSDHYTIQR DLDGTCSLHTTASTLDDDG NYTIMAANPQGRISCTGRL MVQAVNQRGRSPRSPSG HPHVRRPRSRSRDSGDEN EPIQERFFRPHFLQAPGDLT VQEGKLCRMDCKVSGLPT PDLSWQLDGKPVRPDSAH KMLVRENGVHSLIIEPVTSR DAGIYTCIATNRAGQNSFS LELVVAAKE | |
| SEQ ID NO: 1881 | ENSG00000129682.9 | MSGKVTKPKEEKDASKVLD DAPPGTQEYIMLRQDSIQS AELKKKESPFRAKCHEIFCC PLKQVHHKENTEPEEPQLK GIVTKLYSRQGYHLQLQAD GTIDGTKDEDSTYTLFNLIP VGLRVVAIQGVQTKLYLA | A*02:03, A*02:07, A*24:10, A*34:01, B*27:04, B*38:02, B*39:01, B*46:01, B*55:02, C*03:02, C*07:02, C*08:01, C*15:02 |
| SEQ ID NO: 1882 | ENSG00000131374.10 | MYHSLSETRHPLQPEEQEV GIDPLSSYSNKSGGDSNKN GRRTSSTLDSEGTFNSYRKE WEELFVNNNYLATIRQKGI NGQLRSSRFRSICWKLFLC VLPQDKSQWISRIEELRAW YSNIKEIHITNPRKVVGQQ DL | A*02:03, A*24:02, A*24:07, A*24:10, A*33:03, B*27:04, B*51:01, C*07:02, C*15:02 |
| SEQ ID NO: 1883 | ENSG00000131620.13 | MWEASGMEERALEELAM EETALDPLLAEAAGAVDGE GAPPGGPSAQAATMRVN EKYSTLPAEDRSVHIINICAI EDIGYLPSEGTLLNSLSVDP DAECKYGLYFRDGRRKVDY ILVYHHKRPSGNRTLVRRV QHSDTPSGARSVKQDHPL PGKGASLDAGSGEPP | A*02:03, A*24:10, A*33:03, B*38:02, B*40:01, C*01:02 |
| SEQ ID NO: 1884 | ENSG00000132005.4 | MATQAYTELQAAPPPSQP PQAPPQAQPQPPPPPPPA APQPPQPPTAAATPQPQY VTELQSPQPQAQPPGGQK QYVTELPAVPAPSQPTGAP TPSPAPQQYIVVTVSEGAM RASETVSEASPGSTASQTG VPTQVVQQVQGTQQRLL VQTSVQAKPGHVSPLQLT NIQVPQQALPTQRLVVQS AAPGSKGGQVSLTVHGTQ QVHSPPEQSPVQANSSSSK TAGAPTGTVPQQLQVHGV QQSVPVTQERSVVQATPQ APKPGPVQPLTVQGLQPV HVAQEVQQLQQVPVPHV YSSQVQYVEGGDASYTASA IRSSTYSYPETPLYTQTASTS YYEAAGTATQVSTPATSQA VASSGS | B*15:01, B*58:01, C*03:02, C*03:04, C*03:67, C*12:02, C*14:02 |
| SEQ ID NO: 1885 | ENSG00000132359.9 | MFGRKRSVSFGGFGWIDK TMLASLKVKKQELANSSDA TLPDRPLSPPLTAPPTMKSS EFFEMLEKMQGIKLEEQKP GPQKNKDDYIPYPSIDEVV EKGGPYPQVILPQFGGYWI EDPENVGTPTSLGSSICEEE EEDNLSPNTFGYKLECKGE ARAYRRHFLGKDHLNFYCT GSSLGNLILSVKCEEAEGIEY LRVILRSKLKTVHERIPLAGL SKLPSVPQIAKAFCDDAVG LRFNPVLYPKASQ | A*02:03, A*11:01, A*11:02, A*34:01, B*40:01, C*03:02, C*03:04, C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| SEQ ID NO: 1886 | ENSG00000134490.9 | MCVRRSLVGLTFCTCYLAS YLTNKYVLSVLKFTYPTLFQ GWQTLIGGLLLHVSWKLG WVEINSSSRSHVLVWLPAS VLFVGIIYAGSRALSRLAIPV FLTLHNVAEVIICGYQKCFQ KEKTSPAKICSALLLLAAAG CLPFNDSQFNPDGYFWAII HLLCVGAYKILQKSQKPSAL SDIDQQYLNYIFSVVLLAFA SHPTGDLFSVLDFPFLYFYR FHGSCCASGFLGFFLMFST VKLKNLLAPGQCAAWIFFA KIITAGLSILLFDAILTSATTG CLLLGALGEALLVFSERKSS | A*02:03, A*11:01, A*11:02, A*24:02, A*24:07, A*24:10, A*33:03, B*15:01, B*15:27, B*58:01, C*03:02, C*03:04, C*12:02 |
| SEQ ID NO: 1887 | ENSG00000135093.8 | MLSSRAEAAMTAADRAIQ RFLRTGAAVRYKVMKNW GVIGGIAAALAAGIYVIWG PITERKKRRKGLVPGLVNL GNTCFMNSLLQGLSACPA FIRWLEEFTSQYSRDQKEP PSHQYLSLTLLHLLKALSCQ EVTDDEVLDASCLLDVLRM YRWQISSFEEQDAHELFHV ITSSLEDERDRQPRVTHLFD VHSLEQQSEITPKQITCRTR GSPHPTSNHWKSQHPFHG RLTSN | A*02:03, A*02:07, A*11:01, A*11:02, A*24:02, A*24:07, A*24:10, B*15:21, B*27:04, B*38:02, B*39:01, B*40:01, B*51:01, B*58:01, C*03:02, C*07:02, C*14:02, C*15:02 |
| SEQ ID NO: 1888 | ENSG00000136231.9 | MNKLYIGNLSENAAPSDLE SIFKDAKIPVSGPFLVKTGY AFVDCPDESWALKAIEALS GKIELHGKPIEVEHSVPKRQ RIRKLQIRNIPPHLQWEVLD SLLVQYGVVESCEQVNTDS ETAVVNVTYSSKDQARQA LDKLNGFQLENFTLKVAYIP DEMAAQQNPLQQPRGRR GLGQRGSSRQGSPGSVSK QKPCDLPLRLLVPTQFVGAI IGKEGATIRNITKQTQSKID VHRKENAGAAEKSITILSTP EGTSAACKSILEIMHKEAQ DIKFTEEIPLKILAHNNFVG RLIGKEGRNLKKIEQDTDTK ITISPLQELTLYNPERTITVK GNVETCAKAEEEIMKKIRE SYENDIASMNLQAHLIPGL NLNALGLFPPTSGMPPPTS GPPSAMTPPYPQFEQSETE TVHLFIPALSVGAIIGKQGQ HIKQLSRFAGASIKIAPAEA PDAKVRMVIITGPPEAQFK AQGRIYGKIKEENFVSPKEE VKLEAHIRVPSFAAGRVIGK GGKTVNELQNLSSAEVVVP RDQTPDENDQVVVKITGH FYACQVAQRKIQEILTQVK QHQQQKALQSGPPQSRRK | A*02:03, A*11:01, A*11:02, A*24:10, A*33:03, A*34:01, B*15:01, B*15:27, C*03:02, C*03:04, C*14:02 |
| SEQ ID NO: 1889 | ENSG00000136848.12 | MEPDSLLDQDDSYESPQE RPGSRRSLPGSLSEKSPSM EPSAATPFRVTGFLSRRLKG SIKRTKSQPKLDRNHSFRHI | A*02:03 |
| SEQ ID NO: 1890 | ENSG00000137203.6 | MLWKLTDNIKYEDCEDRH DGTSNGTARLPQLGTVGQ SPYTSAPPLSHTPNADFQP PYFPPPYQPIYPQSQDPYS HVNDPYSLNPLHAQPQPQ HPGWPGQRQSQESGLLHT HRGLPHQLSGLDPRRDYRR HEDLLHGPHALSSGLGDLSI HSLPHAIEEVPHVEDPGINI PDQTVIKKGPVSLSKSNSN | A*02:03, A*11:01, A*11:02, A*24:02, A*24:10, A*33:03, B*39:01, C*14:02 |

TABLE 9-continued

Recurrent N terminal sequences with high affinity to MHC Class I

| SEQ ID NO. | Gene | N terminal sequence | High Affinity HLA |
|---|---|---|---|
| | | AVSAIPINKDNLFGGVVNP<br>NEVFCSVPGRLSLLSSTSK | |
| SEQ ID NO: 1891 | ENSG00000137474.15 | MVILQQGDHVWMDLRLG<br>QEFDVPIGAVVKLCDSGQV<br>QVVDDEDNEHWISPQNA<br>THIKPMHPTSVHGVEDMI<br>RLGDLNEAGILRNLLIRYRD<br>HLIYTYTGSILVAVNPYQLLS<br>IYSPEHIRQYTNKKIGEMPP<br>HIFAIADNCYFNMKRNSRD<br>QCCIISGESGAGKTESTKLIL<br>QFLAAISGQHSWIEQQVLE<br>ATPILEAFGNAKTIRNDNSS<br>RFGKYIDIHFNKRGAIEGAK<br>IEQYLLEKSRVCRQALDERN<br>YHVFYCMLEGMSEDQKKK<br>LGLGQASDYNYLAMGNCI<br>TCEGRVDSQEYANIRSAM<br>KVLMFTDTENWEISKLLAA<br>ILHLGNLQYEARTFENLDA<br>CEVLFSPSLATAASLLEVNP<br>PDLMSCLTSRTLITRGETVS<br>TPLSREQALDVRDAFVKGI<br>YGRLFVWIVDKINAAIYKPP<br>SQDVKNSRRSIGLLDIFGFE<br>NFAVNSFEQLCINFANEHL<br>QQFFVRHVFKLEQEEYDLE<br>SIDWLHIEFTDNQDALDMI<br>ANKPMNIISLIDEESKFPKG<br>TDTTMLHKLNSQHKLNAN<br>YIPPKNNHETQFGINHFAG<br>IVYYETQGFLEKNRDTLHG<br>DIIQLVHSSRNKFIKQIFQA<br>DVAMGAETRKRSPTLSSQF<br>KRSLELLMRTLGACQPFFV<br>RCIKPNEFKKPMLFDRHLC<br>VRQLRYSGMMETIRIRRAG<br>YPIRYSFVEFVERYRVLLPG<br>VKPAYKQGDLRGTCQRMA<br>EAVLGTHDDWQIGKTKIFL<br>KDHHDMLLEVERDKAITD<br>RVILLQKVIRGFKDRSNFLK<br>LKNAATLIQRHWRGHNCR<br>KNYGLMRLGFLRLQALHRS<br>RKLHQQYRLARQRIIQFQA<br>RCRAYLVRKAFRHRLWAVL<br>TVQAYARGMIARRLHQRL<br>RAEYLWRLEAEKMRLAEEE<br>KLRKEMSAKKAKEEAERKH<br>QERLAQLAREDAERELKEK<br>EAARRKKELLEQMERARH<br>EPVNHSDMVDKMFGFLG<br>TSGGLPGQEGQAPSGFED<br>LERGRREMVEEDLDAALPL<br>PDEDEEDLSEYKFAKFAATY<br>FQGTTTHSYTRRPLKQPLLY<br>HDDEGDQLAALAVWITILR<br>FMGDLPEPKYHTAMSDGS<br>EKIPVMTKIYETLGKKTYKR<br>ELQALQGEGEAQLPEGQK<br>KSSVRHKLVHLTLKKKSKLT<br>EEVTKRLHDGESTVQGNS<br>MLEDRPTSNLEKLHFIIGNG<br>ILRPALRDEIYCQISKQLTH<br>NPSKSSYARGWILVSLCVG<br>CFAPSEKFVKYLRNFIHGGP<br>PGYAPYCEERLRRTFVNGT<br>RTQPPSWLELQATKSKKPI<br>MLPVTFMDGTTKTLLTDSA<br>TTAKELCNALADKISLKDRF<br>GFSLYIALFD | A*02:03, A*11:01, A*11:02,<br>A*24:02, A*24:07, A*24:10,<br>A*33:03, B*15:01, B*39:01,<br>B*40:01, B*55:02, B*58:01,<br>C*03:02, C*03:04,<br>C*03:67, C*07:02, C*12:02,<br>C*14:02, C*15:02 |
| SEQ ID NO: 1892 | ENSG00000138075.7 | MGDLSSLTPGGSMGLQV<br>NRGSQSSLEGAPATAPEPH<br>SLGILHASYSVSHRVRPW | A*02:03, A*02:07, A*11:01,<br>A*11:02, A*24:02, A*24:07,<br>A*24:10, A*33:03, A*34:01, |

TABLE 9-continued

Recurrent N terminal sequences with high affinity to MHC Class I

| SEQ ID NO. | Gene | N terminal sequence | High Affinity HLA |
|---|---|---|---|
| | | WDITSCRQQWTRQILKDV<br>SLYVESGQIMCILGSSGSGK<br>TTLLDAMSGRLGRAGTFLG<br>EVYVNGRALRREQFQDCFS<br>YVLQSDTLLSSLTVRETLHY<br>TALLAIRRGNPGSFQKKVE<br>AVMAELSLSHVADRLIGNY<br>SLGGISTGERRRVSIAAQLL<br>QDPKVMLFDEPTTGLDCM<br>TANQIVVLLVELARRNRIVV<br>LTIHQPRSELFQLFDKIAILS<br>FGELIFCGTPAEMLDFFND<br>CGYPCPEHSNPFDFY | B*15:01, B*15:21,<br>B*15:27, B*27:04, B*38:02,<br>B*39:01, B*40:01, B*40:06,<br>B*46:01, B*55:02, B*58:01,<br>C*03:02, C*03:04, C*03:67,<br>C*04:01, C*04:03, C*07:02,<br>C*08:01, C*12:02,<br>C*14:02, C*15:02 |
| SEQ ID NO: 1893 | ENSG00000142185.12 | MEPSALRKAGSEQEEGFE<br>GLPRRVTDLGMVSNLRRS<br>NSSLFKSWRLQCPFGNND<br>KQESLSSWIPENIKKKECVY<br>FVESSKLSDAGKVVCQCGY<br>THEQHLEEATKPHTFQGT<br>QWDPKKHVQEMPTDAFG<br>DIVFTGLSQKVKKYVRVSQ<br>DTPSSVIYHLMTQHWGLD<br>VPNLLISVTGGAKNFNMKP<br>RLKSIFRRGLVKVAQTTGA<br>WIITGGSHTGVMKQVGEA<br>VRDFSLSSSYKEGELITIGVA<br>TWGTVHRREGLIHPTGSFP<br>AEYILDEDGQGNLTCLDSN<br>HSHFILVDDGTHGQYGVEI<br>PLRTRLEKFISEQTKERGGV<br>AIKIPIVCVVLEGGPGTLHTI<br>DNATTNGTPCVVVEGSGR<br>VADVIAQVANLPVSDITISLI<br>QQKLSVFFQEMFETFTESRI<br>VEWTKKIQDIVRRRQLLTV<br>FREGKDGQQDVDVAILQA<br>LLKASRSQDHFGHENWDH<br>QLKLAVAWNRVDIARSEIF<br>MDEWQWKPSDLHPTMT<br>AALISNKPEFVKLFLENGVQ<br>LKEFVTWDTLLYLYENLDPS<br>CLFHSKLQMHHVAQVLRE<br>LLGDFTQPLYPRPRHNDRL<br>RLLLPVPHVKLNVQGVSLR<br>SLYKRSSGHVTFTMDPIRD<br>LLIWAIVQNRRELAGIIWA<br>QSQDCIAAALACSKILKELS<br>KEEEDTDSSEEMLALAEEY<br>EHRAIGVFTECYRKDEERA<br>QKLLTRVSEAWGKTTCLQL<br>ALEAKDMKFVSHGGIQAFL<br>TKVWWGQLSVDNGLWR<br>VTLCMLAFPLLLTGLISFREK<br>RLQDVGTPAARARAFFTAP<br>VVVFHLNILSYFAFLCLFAY<br>VLMVDFQPVPSWCECAIY<br>LWLFSLVCEEMRQLFYDPD<br>ECGLMKKAALYFSDFWNK<br>LDVGAILLFVAGLTCRLIPA<br>TLYPGRVILSLDFILFCLRLM<br>HIFTISKTLGPKIIIVKRMMK<br>DVFFFLFLLAVWVVSFGVA<br>KQAILIHNERRVDWLFRGA<br>VYHSYLTIFGQIPGYIDGVN<br>FNPEHCSPNGTDPYKPKCP<br>ESDATQQRPAFPEWLTVLL<br>LCLYLLFTNILLLNLLIAMEN<br>YTFQQVQEHTDQIWKFQR<br>HDLIEEYHGRPAAPPPFILL<br>SHLQLFIKRVVLKTPAKRHK<br>QLKNKLEKNEEAALLSWEI<br>YLKENYLQNRQFQQKQRP<br>EQKIEDISNKVDAMVDLLD<br>LDPLKRSGSMEQRLASLEE<br>QVAQTAQALHWIVRTLRA | A*02:03, A*11:01, A*11:02,<br>A*24:02, A*24:07, A*24:10,<br>A*33:03, A*34:01, B*15:01,<br>B*15:27, B*39:01,<br>B*40:01, B*58:01, C*03:02,<br>C*03:04, C*12:02, C*14:02,<br>C*15:02 |

TABLE 9-continued

Recurrent N terminal sequences with high affinity to MHC Class I

| SEQ ID NO. | Gene | N terminal sequence | High Affinity HLA |
|---|---|---|---|
| | | SGFSSEADVPTLASQKAAE<br>EPDAEPGGRKKTEEPGDSY<br>HVNARHLLYPNCPVTRFPV<br>PNEKVPWETEFLIYDPPFYT<br>AERKDAAAMDPMGENP<br>MGRTGLRGRGSLSCFGPN<br>HTLYPMVTRWRRNEDGAI<br>CRKSIKKMLEVLVVKLPLSE<br>HWALPGGSREPGEMLPRK<br>LKRILRQEHWPSFENLLKC<br>GMEVYKGYMDDPRNTDN<br>AWIETVAVSVHFQDQNDV<br>ELNRLNSNLHACDSGASIR<br>WQVVDRRIPLYANHKTLL<br>QKAAAEFGAHY | |
| SEQ ID NO: 1894 | ENSG00000142235.4 | MRQVLWLCNVCVTARETR<br>HHLHLPAILDKMPAPGALI<br>LLAAVSASGCLASPAHPDG<br>FALGRAPLAPPYAVVLISCS<br>GLLAFIFLLLTCLCCKRGDV<br>GFKEFENPEGEDCSGEYTP<br>PAEETSSSQSLPDVYILPLAE<br>VSLPMPAPQPSHSDMTTP<br>LGLSRQHLSYLQEIGSGWF<br>GKVILGEIFSDYTPAQVVVK<br>ELRASAGPLEQRKFISEAQP<br>YRSLQHPNVLQCLGLCVET<br>LPFLLIMEFCQLGDLKRYLR<br>AQRPPEGLSPELPPRDLRTL<br>QRMGLEIARGLAHLHSHN<br>YV | A*02:03, A*33:03, B*15:01, B*39:01, B*40:01, C*03:02, C*03:04 |
| SEQ ID NO: 1895 | ENSG00000142661.14 | MTLPHSLGGAGDPRPPQA<br>MEVHRLEHRQEEEQKEER<br>QHSLRMGSSVRRRTFRSSE<br>EEHEFSAADYALAAALALT<br>ASSELSWEAQLRRQTSAVE<br>LEERGQKRVGFGNDWERT<br>EIAFLQTHRLLRQRRDWKT<br>LRRRTEEKVQEAKELRELCY<br>GRGPWFWIPLRSHAVWE<br>HTTVLLTCTVQASPPPQVT<br>WYKNDTRIDPRLFRAGKYR<br>ITNNYGLLSLEIRRCAIEDSA<br>TYTVRVKNAHGQASSFAK<br>VLVRTYLGKDAGFDSEIFKR<br>STFGPSVEFTSVLKPVFARE<br>KEPFSLSCLFSEDVLDAESIQ<br>WFRDGSLLRSSRRRKILYTD<br>RQASLKVSCTYKEDEGLYM<br>VRVPSPFGPREQSTYVLVR<br>DAEAENPGAPGSPLNVRCL<br>DVNRDCLILTWAPPSDTRG<br>NPITAYTIERCQGESGEWIA<br>CHEAPGGTCRCPIQGLVEG<br>QSYRFRVRAISRVGSSVPSK<br>ASELVVMGDHDAARRKTE<br>IPFDLGNKITISTDAFEDTVT<br>IPSPPTNVHASEIREAYVVL<br>AWEEPSPRDRAPLTYSLEK<br>SVIGSGTWEAISSESPVRSP<br>RFAVLDLEKKKSYVFRVRA<br>MNQYGLSDPSEPSEPIALR<br>GPPATLPPPAQVQAFRDT<br>QTSVSLTWDPVKDPELLGY<br>YIYSRKVGTSEWQTVNNKP<br>IQGTRFTVPGLRTGKEYEFC<br>VRSVSEAGVGESSAATEPIR<br>VKQALATPSAPYGFALLNC<br>GKNEMVIGWKPPKRRGG<br>GKILGYFLDQHDSEELDWH<br>AVNQQPIPTRVCKVSDLHE<br>GHFYEFRARAANWAGVG<br>ELSAPSSLFECKEWTMPQP<br>GPPYDVRASEVRATSLVLQ | A*02:03, A*11:01, A*11:02, A*24:02, A*24:07, A*24:10, A*33:03, B*15:01, B*15:27, B*39:01, B*40:01, B*58:01, C*03:02, C*03:04, C*03:67, C*07:02, C*08:01, C*12:02, C*14:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | WEPPLYMGAGPVTGYHVS<br>FQEEGSEQWKPVTPGPISG<br>THLRVSDLQPGKSYVFQVQ<br>AMNSAGLGQPSMPTDPV<br>LLEDKPGAHEIEVGVDEEG<br>FIYLAFEAPEAPDSSEFQWS<br>KDYKGPLDPQRVKIEDKVN<br>KSKVILKEPGLEDLGTYSVIV<br>TDADEDISASHTLTEEELEK<br>LKKLSHEIRNPVIKLISGWNI<br>DILERGEVRLWLEVEKLSPA<br>AELHLIFNNKEIFSSPNRKIN<br>FDREKGLVEVIIQNLSEEDK<br>GSYTAQLQDGKAKNQITLT<br>LVDDDFDKLLRKADAKRRD<br>WKRKQGPYFERPLQWKVT<br>EDCQVQLTCKVTNTKKETR<br>FQWFFQRAEMPDGQYDP<br>ETGTGLLCIEELSKKDKGIYR<br>AMVSDDRGEDDTILDLTG<br>DALDAIFTELGRIGALSATP<br>LKIQGTEEGIRIFSKVKYYNV<br>EYMKTTWFHKDKRLESGD<br>RIRTGTTLDEIWLHILDPKD<br>SDKGKYTLEIAAGKEVRQLS<br>TDLSGQAFEDAMAEHQRL<br>KTLAIIEKNRAKVVRGLPDV<br>ATIMEDKTLCLTCIVSGDPT<br>PEISWLKNDQPVTFLDRYR<br>MEVRGTEVTITIEKVNSEDS<br>GRYGVFVKNKYGSETGQV<br>TISVFKHGDEPKELKSM | |
| SEQ ID NO: 1896 | ENSG00000143669.9 | MSTDSNSLAREFLTDVNRL<br>CNAVVQRVEAREEEEETH<br>MATLGQYLVHGRGFLLLTK<br>LNSIIDQALTCREELLTLLLSL<br>LPLVWKIPVQEEKATDFNL<br>PLSADIILTKEKNSSSQRST<br>QEKLHLEGSALSSQVSAKV<br>NVFRKSRRQRKITHRYSVR<br>DARKTQLSTSDSEANSDEK<br>GIAMNKHRRPHLLHHFLTS<br>FPKQDHPKAKLDRLATKEQ<br>TPPDAMALENSREIIPRQG<br>SNTDILSEPAALSVISNMN<br>NSPFDLCHVLLSLLEKVCKF<br>DVTLNHNSPLAASVVPTLT<br>EFLAGFGDCCSLSDNLESR<br>VVSAGWTEEPVALIQRML<br>FRTVLHLLSVDVSTAEMM<br>PENLRKNLTELLRAALKIRIC<br>LEKQPDPFAPRQKKTLQEV<br>QEDFVFSKYRHRALLLPELL<br>EGVLQILICCLQSAASNPFY<br>FSQAMDLVQEFIQHHGFN<br>LFETAVLQMEWLVLRDGV<br>PPEASEHLKALINSVMKIM<br>STVKKVKSEQLHHSMCTRK<br>RHRRCEYSHFMHHHRDLS<br>GLLVSAFKNQVSKNPFEET<br>ADGDVYYPERCCCIAVCAH<br>QCLRLLQQASLSSTCVQILS<br>GVHNIGICCCMDPKSVIIPL<br>LHAFKLPALKNFQQHILNIL<br>NKLILDQLGGAEISPKIKKA<br>ACNICTVDSDQLAQLEETL<br>QGNLCDAELSSSLSSPSYRF<br>QGILPSSGSEDLLWKWDAL<br>KAYQNFVFEEDRLHSIQIA<br>NHICNLIQKGNIVVQWKLY<br>NYIFNPVLQRGVELAHHCQ<br>HLSVTSAQSHVCSHHNQC<br>LPQDVLQIYVKTLPILLKSRV<br>IRDLFLSCNGVSQIIELNCLN<br>GIRSHSLKAFETLIISLGEQQ | A*02:03, A*11:01, A*11:02,<br>A*24:02, A*24:07, A*24:10,<br>A*33:03, A*34:01, B*15:01,<br>B*15:27, B*39:01, B*40:01,<br>B*55:02, B*58:01,<br>C*03:02, C*03:04, C*03:67,<br>C*07:02, C*12:02, C*14:02,<br>C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | KDASVPDIDGIDIEQKELSS | |
| | | VHVGTSFHHQQAYSDSPQ | |
| | | SLSKFYAGLKEAYPKRRKTV | |
| | | NQDVHINTINLFLCVAFLCV | |
| | | SKEAESDRESANDSEDTSG | |
| | | YDSTASEPLSHMLPCISLES | |
| | | LVLPSPEHMHQAADIWS | |
| | | MCRWIYMLSSVFQKQFYR | |
| | | LGGFRVCHKLIFMIIQKLFR | |
| | | SHKEEQGKKEGDTSVNEN | |
| | | QDLNRISQPKRTMKEDLLS | |
| | | LAIKSDPIPSELGSLKKSADS | |
| | | LGKLELQHISSINVEEVSAT | |
| | | EAAPEEAKLFTSQESETSLQ | |
| | | SIRLLEALLAICLHGARTSQ | |
| | | QKMELELPNQNLSVESILFE | |
| | | MRDHLSQSKVIETQLAKPL | |
| | | FDALLRVALGNYSADFEHN | |
| | | DAMTEKSHQSAEELSSQP | |
| | | GDFSEEAEDSQCCSFKLLVE | |
| | | EEGYEADSESNPEDGETQD | |
| | | DGVDLKSETEGFSASSSPN | |
| | | DLLENLTQGEIIYPEICMLEL | |
| | | NLLSASKAKLDVLAHVFESF | |
| | | LKIIRQKEKNVFLLMQQGT | |
| | | VKNLLGGFLSILTQDDSDF | |
| | | QACQRVLVDLLVSLMSSRT | |
| | | CSEELTLLLRIFLEKSPCTKIL | |
| | | LLGILKIIESDTTMSPSQYLT | |
| | | FPLLHAPNLSNGVSSQKYP | |
| | | GILNSKAMGLLRRARVSRS | |
| | | KKEADRESFPHRLLSSWHI | |
| | | APVHLPLLGQNCWPHLSE | |
| | | GFSVSLWFNVECIHEAEST | |
| | | TEKGKKIKKRNKSLILPDSSF | |
| | | DGTESDRPEGAEYINPGER | |
| | | LIEEGCIHIISLGSKALMIQV | |
| | | WADPHNATLIFRVCMDSN | |
| | | DDMKAVLLAQVESQENIFL | |
| | | PSKWQHLVLTYLQQPQGK | |
| | | RRIHGKISIWVSGQRKPDV | |
| | | TLDFMLPRKTSLSSDSNKTF | |
| | | CMIGHCLSSQEEFLQLAGK | |
| | | WDLGNLLLFNGAKVGSQE | |
| | | AFYLYACGPNHTSVMPCK | |
| | | YGKPVNDYSKYINKEILRCE | |
| | | QIRELFMTKKDVDIGLLIESL | |
| | | SVVYTTYCPAQYTIYEPVIRL | |
| | | KGQMKTQLSQRPFSSKEV | |
| | | QSILLEPHHLKNLQPTEYKT | |
| | | IQGILHEIGGTGIFVFLFARV | |
| | | VELSSCEETQALALRVILSLI | |
| | | KYNQQRVHELENCNGLSM | |
| | | IHQVLIKQKCIVGFYILKTLL | |
| | | EGCCGEDIIYMNENGEFKL | |
| | | DVDSNAIIQDVKLLEELLLD | |
| | | WKIWSKAEQGVWETLLAA | |
| | | LEVLIRADHHQQMFNIKQL | |
| | | LKAQVVHHFLLTCQVLQEY | |
| | | KEGQLTPMPREVCRSFVKII | |
| | | AEVLGSPPDLELLTIIFNFLL | |
| | | AVHPPTNTYVCHNPTNFYF | |
| | | SLHIDGKIFQEKVRSIMYLR | |
| | | HSSSGGRSLMSPGFMVISP | |
| | | SGFTASPYEGENSSNIIPQQ | |
| | | MAAHMLRSRSLPAFPTSSL | |
| | | LTQSQKLTGSLGCSIDRLQ | |
| | | NIADTYVATQSKKQNSLGS | |
| | | SDTLKKGKEDAFISSCESAK | |
| | | TVCEMEAVLSAQVSVSDV | |
| | | PKGVLGFPVVKADHKQLG | |
| | | AEPRSEDDSPGDESCPRRP | |
| | | DYLKGLASFQRSHSTIASLG | |
| | | LAFPSQNGSAAVGRWPSL | |
| | | VDRNTDDWENFAYSLGYE | |
| | | PNYNRTASAHSVTEDCLVP | |

TABLE 9-continued

Recurrent N terminal sequences with high affinity to MHC Class I

| SEQ ID NO. | Gene | N terminal sequence | High Affinity HLA |
|---|---|---|---|
| | | ICCGLYELLSGVLLILPDVLL | |
| | | EDVMDKLIQADTLLVLVNH | |
| | | PSPAIQQGVIKLLDAYFARA | |
| | | SKEQKDKFLKNRGFSLLAN | |
| | | QLYLHRGTQELLECFIEMFF | |
| | | GRHIGLDEEFDLEDVRNM | |
| | | GLFQKWSVIPILGLIETSLYD | |
| | | NILLHNALLLLLQILNSCSKV | |
| | | ADMLLDNGLLYVLCNTVA | |
| | | ALNGLEKNIPMSEYKLLAC | |
| | | DIQQLFIAVTIHACSSSGSQ | |
| | | YFRVIEDLIVMLGYLQNSK | |
| | | NKRTQNMAVALQLRVLQ | |
| | | AAMEFIRTTANHDSENLTD | |
| | | SLQSPSAPHHAVVQKRKSI | |
| | | AGPRKFPLAQTESLLMKM | |
| | | RSVANDELHVMMQRRMS | |
| | | QENPSQATETELAQRLQRL | |
| | | TVLAVNRIIYQEFNSDIIDIL | |
| | | RTPENVTQSKTSVFQTEISE | |
| | | ENIHHEQSSVFNPFQKEIFT | |
| | | YLVEGFKVSIGSSKASGSKQ | |
| | | QWTKILWSCKETFRMQLG | |
| | | RLLVHILSPAHAAQERKQIF | |
| | | EIVHEPNHQEILRDCLSPSL | |
| | | QHGAKLVLYLSELIHNHQG | |
| | | ELTEEELGTAELLMNALKLC | |
| | | GHKCIPPSASTKADLIKMIK | |
| | | EEQKKYETEEGVNKAAWQ | |
| | | KTVNNNQQSLFQRLDSKS | |
| | | KDISKIAADITQAVSLSQGN | |
| | | ERKKVIQHIRGMYKVDLSA | |
| | | SRHWQELIQQLTHDRAV | |
| | | WYDPIYYPTSWQLDPTEG | |
| | | PNRERRRLQRCYLTIPNKYL | |
| | | LRDRQKSEDVVKPPLSYLFE | |
| | | DKTHSSFSSTVKDKAASESI | |
| | | RVNRRCISVAPSRETAGELL | |
| | | LGKCGMYFVEDNASDTVE | |
| | | SSSLQGELEPASFSWTYEEI | |
| | | KEVHKRWWQLRDNAVEIF | |
| | | LTNGRTLLLAFDNTKVRDD | |
| | | VYHNILTNNLPNLLEYGNIT | |
| | | ALTNLWYTGQITNFEYLTH | |
| | | LNKHAGRSFNDLMQYPVF | |
| | | PFILADYVSETLDLNDLLIYR | |
| | | NLSKPIAVQYKEKEDRYVD | |
| | | TYKYLEEEYRKGAREDDPM | |
| | | PPVQPYHYGSHYSNSGTVL | |
| | | HFLVRMPPFTKMFLAYQD | |
| | | QSFDIPDRTFHSTNTTWRL | |
| | | SSFESMTDVKELIPEFFYLPE | |
| | | FLVNREGFDFGVRQNGER | |
| | | VNHVNLPPWARNDPRLFI | |
| | | LIHRQALESDYVSQNICQW | |
| | | IDLVFGYKQKGKASVQAIN | |
| | | VFHPATYFGMDVSAVEDP | |
| | | VQRRALETMIKTYGQTPR | |
| | | QLFHMAHVSRPGAKLNIE | |
| | | GELPAAVGLLVQFAFRETR | |
| | | EQVKEITYPSPLSWIKGLK | |
| | | WGEYVGSPSAPVPVVCFS | |
| | | QPHGERFGSLQALPTRAIC | |
| | | GLSRNFCLLMTYSKEQGVR | |
| | | SMNSTDIQWSAILSWGYA | |
| | | DNILRLKSKQSEPPVNFIQS | |
| | | SQQYQVTSCAWVPDSCQL | |
| | | FTGSKCGVITAYTNRFTSST | |
| | | PSEIEMETQIHLYGHTEEIT | |
| | | SLFVCKPYSILISVSRDGTCII | |
| | | WDLNRLCYVQSLAGHKSP | |
| | | VTAVSASETSGDIATVCDS | |
| | | AGGGSDLRLWTVNGDLV | |
| | | GHVHCREIICSVAFSNQPE | |
| | | GVSINVIAGGLENGIVRLW | |
| | | STWDLKPVREITFPKSNKPI | |

TABLE 9-continued

| Recurrent N terminal sequences with high affinity to MHC Class I | | | |
|---|---|---|---|
| SEQ ID NO. | Gene | N terminal sequence | High Affinity HLA |
| | | ISLTFSCDGHHLYTANSDGT VIAWCRKDQQRLKQPMFY SFLSSYAAG | |
| SEQ ID NO: 1897 | ENSG00000143882.5 | MSEFWLISAPGDKENLQAL ERMNTVTSKSNLSYNTKFA IPDFKVGTLDSLVGLSDELG KLDTFAESLIRRMAQSVVE VMEDSKGKVQEHLLANGV DLTSFVTHFEWD | A*02:03, A*11:01, A*11:02, A*33:03, B*58:01, C*03:02, C*03:04 |
| SEQ ID NO: 1898 | ENSG00000145214.9 | MAAAAEPGARAWLGGGS PRPGSPACSPVLGSGGRAR PGPGPGPGPERAGVRAPG PAAAPGHSFRKVTLTKPTF CHLCSDFIWGLAGFLCDVC NFMSHEKCLKHVRIPCTSV APSLVRVPVAHCFGPRGLH KRKFCAVCRKVLEAPALHC EVCELHLHPDCVPFACSDC RQCHQDGHQDHDTHHH HWREGNLPSGARCEVCRK TCGSSDVLAGVRCEWCGV QAHSLCSAALAPECGFGRL RSLVLPPACVRLLPGGFSKT QSFRIVEAAEPGEGGDGA DGSAAVGPGRETQATPES GKQTLKIFDGDDAVRRSQF RLVTVSRLAGAEEVLEAALR AHHIPEDPGHLELCRLPPSS QACDAWAGGKAGSAVISE EGRSPGSGEATPEAWVIRA LPRAQEVLKIYPGWLKVGV AYVSVRVTPKSTARSVVLE VLPLLGRQAESPESFQLVEV AMGCRHVQRTMLMDEQ PLLDRLQDIRQMSVRQVS QTRFYVAESRDVAPHVSLF VGGLPPGLSPEEYSSLLHEA GATKATVVSVSHIYSSQGA VVLDVACFAEAERLYMLLK DMAVRGRLLTALVLPDLLH AKLPPDSCPLLVFVNPKSG GLKGRDLLCSFRKLLNPHQ VFDLTNGGPLPGLHLFSQV PCFRVLVCGGDGTVGWVL GALEETRYRLACPEPSVAIL PLGTGNDLGRVLRWGAGY SGEDPFSVLLSVDEADAVL MDRWTILLDAHEAGSAEN DTADAEP | A*02:03, A*11:01, A*11:02, A*33:03, B*15:01, B*39:01, B*40:01, C*03:02, C*03:04 |
| SEQ ID NO: 1899 | ENSG00000151025.9 | MGAMAYPLLLCLLLAQLGL GAVGASRDPQGRPDSPRE RTPKGKPHAQQPGRASAS DSSAPWSRSTDGTILAQKL AEEVPMDVASYLYTGDSH QLKRANCSGRYELAGLPGK WPALASAHPSLHRALDTLT HATNFLNVMLQSNKSREQ NLQDDLDWYQALVWSLLE GEPSISRAAITFSTDSLSAPA PQVFLQATREESRILLQDLS SSAPHLANATLETEWFHGL RRKWRPHLHRRGPNQGP RGLGHSWRRKDGLGGDKS HFKWSPPYLECENGSYKPG WLVTLSSAIYGLQPNLVPEF RGVMKVDINLQKVDIDQC SSDGWFSGTHKCHLNNSE CMPIKGLGFVLGAYECICK AGFYHPGVLPVNNFRRRG PDQHISGSTKDVSEEAYVC LPCREGCPFCADDSPCFVQ EDKYLRLAIISFQALCMLLD FVSMLVVYHFRKAKSIRAS | A*02:03, A*02:07, A*11:01, A*11:02, A*24:02, A*24:07, A*24:10, A*33:03, B*15:01, B*39:01, B*40:01, B*55:02, B*58:01, C*03:02, C*03:04, C*03:67, C*07:02, C*12:02, C*14:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | GLILLETILFGSLLLYFPVVILY FEPSTFRCILLRWARLLGFA TVYGTVTLKLHRVLKVFLSR TAQRIPYMTGGRVMRML AVILLVVFWFLIGWTSSVC QNLEKQISLIGQGKTSDHLI FNMCLIDRWDYMTAVAEF LFLLWGVYLCYAVRTVPSA FHEPRYMAVAVHNELIISAI FHTIRFVLASRLQSDWML MLYFAHTHLTVTVTIGLLLI PKFSHSSNNPRDDIATEAY EDELDMGRSGSYLNSSINS AWSEHSLDPEDIRDELKKL YAQLEIYKRKKMITNNPHL QKKRCSKKGLGRSIMRRIT EIPETVSRQCSKEDKEGAD HGTAKGTALIRKNPPESSG NTGKSKEETLKNRVFSLKKS HSTYDHVRDQTEESSSLPT ESQEEETTENSTLESLSGKK LTQKLKEDSEAESTESVPLV CKSASAHNLSSEKKTGHPR TSMLQKSLSVIASAKEKTLG LAGKTQTAGVEERTKSQKP LPKDKETNRNHSNSDNTET KDPAPQNSNPAEEPRKPQ KSGIMKQQRVNPTTANSD LNPGTTQMKDNFDIGEVC PWEVYDLTPGPVPSESKV QKHVSIVASEMEKNPTFSL KEKSHHKPKAAEVCQQSN QKRIDKAEVCLWESQGQSI LEDEKLLISKTPVLPERAKEE NGGQPRAANVCAGQSEEL PPKAVASKTENENLNQIGH QEKKTSSSEENVRGSYNSS NNFQQPLTSRAEVCPWEF ETPAQPNAGRSVALPASSA LSANKIAGPRKEEIWDSFK V | |
| SEQ ID NO: 1900 | ENSG00000151229.8 | MSRKASENVEYTLRSLSSL MGERRRKQPEPDAASAAG ECSLLAAAESSTSLQSAGA GGGGVGDLERAARRQFQ QDETPAFVYVVAVFSALGG FLFGYDTGVVSGAMLLLKR QLSLDALWQELLVSSTVGA AAVSALAGGALNGVFGRR AAILLASALFTAGSAVLAAA NNKETLLAGRLVVGLGIGIA SMTVPVYIAEVSPPNLRGR LVTINTLFITGGQFFASVVD GAFSYLQKDGW | A*02:03, A*02:07, A*11:01, A*11:02, A*24:10, A*34:01, B*15:01, B*15:21, B*15:27, B*27:04, B*40:01, B*40:06, B*46:01, B*55:02, B*58:01, C*01:02, C*03:02, C*03:04, C*03:67, C*04:01, C*04:03, C*08:01, C*12:02, C*15:02 |
| SEQ ID NO: 1901 | ENSG00000151914.13 | MAGYLSPAAYLYVEEQEYL QAYEDVLERYKDERDKVQ KKTFTKWINQHLMKVRKH VNDLYEDLRDGHNLISLLEV LSGDTLPREKGRMRFHRL QNVQIALDYLKRRQVKLVN IRNDDITDGNPKLTLGLIWT IILHFQISDIHVTGESEDMS AKERLLLWTQQATEGYAGI RCENFTTCWRDGKLFNAII HKYRPDLIDMNTVAVQSN LANLEHAFYVAEKIGVIRLL DPEDVDVSSPDEKSVITYVS SLYDAFPKVPEGGEGIGAN DVEVKWIEYQNMVNYLIQ WIRHHVTTMSERTFPNNP VELKALYNQYLQFKETEIPP KETEKSKIKRLYKLLEIWIEF GRIKLLQGYHPNDIEKEWG KLIIAMLEREKALRPEVERL | A*02:03, A*11:01, A*11:02, A*24:02, A*24:07, A*24:10, A*33:03, A*34:01, B*15:01, B*15:27, B*39:01, B*40:01, B*55:02, B*58:01, C*03:02, C*03:04, C*07:02, C*12:02, C*14:02, C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | EMLQQIANRVQRDSVICE | |
| | | DKLILAGNALQSDSKRLESG | |
| | | VQFQNEAEIAGYILECENLL | |
| | | RQHVIDVQILIDGKYYQAD | |
| | | QLVQRVAKLRDEIMALRN | |
| | | ECSSVYSKGRILTTEQTKLM | |
| | | ISGITQSLNSGFAQTLHPSL | |
| | | TSGLTQSLTPSLTSSSMTSG | |
| | | LSSGMTSRLTPSVTPAYTP | |
| | | GFPSGLVPNFSSGVEPNSL | |
| | | QTLKLMQIRKPLLKSSLLDQ | |
| | | NLTEEEINMKFVQDLLNW | |
| | | VDEMQVQLDRTEWGSDL | |
| | | PSVESHLENHKNVHRAIEE | |
| | | FESSLKEAKISEIQMTAPLKL | |
| | | TYAEKLHRLESQYAKLLNTS | |
| | | RNQERHLDTLHNFVSRAT | |
| | | NELIWLNEKEEEEVAYDWS | |
| | | ERNTNIARKKDYHAELMRE | |
| | | LDQKEENIKSVQEIAEQLLL | |
| | | ENHPARLTIEAYRAAMQT | |
| | | QWSWILQLCQCVEQHIKE | |
| | | NTAYFEFFNDAKEATDYLR | |
| | | NLKDAIQRKYSCDRSSSIHK | |
| | | LEDLVQESMEEKEELLQYK | |
| | | STIANLMGKAKTIIQLKPRN | |
| | | SDCPLKTSIPIKAICDYRQIEI | |
| | | TIYKDDECVLANNSHRAK | |
| | | WKVISPTGNEAMVPSVCF | |
| | | TVPPPNKEAVDLANRIEQQ | |
| | | YQNVLTLWHESHINMKSV | |
| | | VSWHYLINEIDRIRASNVAS | |
| | | IKTMLPGEHQQVLSNLQSR | |
| | | FEDFLEDSQESQVFSGSDIT | |
| | | QLEKEVNVCKQYYQELLKS | |
| | | AEREEQEESVYNLYISEVRN | |
| | | IRLRLENCEDRLIRQIRTPLE | |
| | | RDDLHESVFRITEQEKLKKE | |
| | | LERLKDDLGTITNKCEEFFS | |
| | | QAAASSSVPTLRSELNVVL | |
| | | QNMNQVYSMSSTYIDKLK | |
| | | TVNLVLKNTQAAEALVKLY | |
| | | ETKLCEEEAVIADKNNIENLI | |
| | | STLKQWRSEVDEKRQVFH | |
| | | ALEDELQKAKAISDEMFKT | |
| | | YKERDLDFDWHKEKADQL | |
| | | VERWQNVHVQIDNRLRDL | |
| | | EGIGKSLKYYRDTYHPLDD | |
| | | WIQQVETTQRKIQENQPE | |
| | | NSKTLATQLNQQKMLVSEI | |
| | | EMKQSKMDECQKYAEQYS | |
| | | ATVKDYELQTMTYRAMVD | |
| | | SQQKSPVKRRRMQSSADLI | |
| | | IQEFMDLRTRYTALVTLMT | |
| | | QYIKFAGDSLKRLEEEEKSL | |
| | | EEEKKEHVEKAKELQKWVS | |
| | | NISKTLKDAEKAGKPPFSK | |
| | | QKISSEEISTKKEQLSEALQT | |
| | | IQLFLAKHGDKMTDEERNE | |
| | | LEKQVKTLQESYNLLFSESL | |
| | | KQLQESQTSGDVKVEEKLD | |
| | | KVIAGTIDQTTGEVLSVFQ | |
| | | AVLRGLIDYDTGIRLLETQL | |
| | | MISGLISPELRKCFDLKDAK | |
| | | SHGLIDEQILCQLKELSKAK | |
| | | EIISAASPTTIPVLDALAQS | |
| | | MITESMAIKVLEILLSTGSLV | |
| | | IPATGEQLTLQKAFQQNLV | |
| | | SSALFSKVLERQNMCKDLI | |
| | | DPCTSEKVSLIDMVQRSTL | |
| | | QENTGMWLLPVRPQEGG | |
| | | RITLKCGRNISILRAAHEGLI | |
| | | DRETMFRLLSAQLLSGGLI | |
| | | NSNSGQRMTVEEAVREGV | |
| | | IDRDTASSILTYQVQTGGII | |
| | | QSNPAKRLTVDEAVQCDLI | |

TABLE 9-continued

| Recurrent N terminal sequences with high affinity to MHC Class I | | | |
|---|---|---|---|
| SEQ ID NO. | Gene | N terminal sequence | High Affinity HLA |
| | | TSSSALLVLEAQRGYVGLI | |
| | | WPHSGEIFPTSSSLQQELIT | |
| | | NELAYKILNGRQKIAALYIP | |
| | | ESSQVIGLDAAKQLGIIDNN | |
| | | TASILKNITLPDKMPDLGDL | |
| | | EACKNARRWLSFCKFQPST | |
| | | VHDYRQEEDVFDGEEPVT | |
| | | TQTSEETKKLFLSYLMINSY | |
| | | MDANTGQRLLLYDGDLDE | |
| | | AVGMLLEGCHAEFDGNTA | |
| | | IKECLDVLSSSGVFLNNASG | |
| | | REKDECTATPSSFNKCHCG | |
| | | EPEHEETPENRKCAIDEEFN | |
| | | EMRNTVINSEFSQSGKLAS | |
| | | TISIDPKVNSSPSVCVPSLIS | |
| | | YLTQTELADISMLRSDSENI | |
| | | LTNYENQSRVETNERANEC | |
| | | SHSKNIQNFPSDLIENPIMK | |
| | | SKMSKFCGVNETENEDNT | |
| | | NRDSPIFDYSPRLSALLSHD | |
| | | KLMHSQGSFNDTHTPESN | |
| | | GNKCEAPALSFSDKTMLSG | |
| | | QRIGEKFQDQFLGIAAINIS | |
| | | LPGEQYGQKSLNMISSNP | |
| | | QVQYHNDKYISNTSGEDEK | |
| | | THPGFQQMPEDKEDESEIE | |
| | | EYSCAVTPGGDTDNAIVSL | |
| | | TCATPLLDETISASDYETSLL | |
| | | NDQQNNTGTDTDSDDDF | |
| | | YDTPLFEDDDHDSLLLDGD | |
| | | DRDCLHPEDYDTLQEEND | |
| | | ETASPADVFYDVSKENENS | |
| | | MVPQGAPVGSLSVKNKAH | |
| | | CLQDFLMDVEKDELDSGE | |
| | | KIHLNPVGSDKVNGQSLET | |
| | | GSERECTNILEGDESDSLTD | |
| | | YDIVGGKESFTASLKFDDSG | |
| | | SWRGRKEEYVTGQEFHSD | |
| | | TDHLDSMQSEESYGDYIYD | |
| | | SNDQDDDDDGIDEEGG | |
| | | GIRDENGKPRCQNVAEDM | |
| | | DIQLCASILNENSDENENIN | |
| | | TMILLDKMHSCSSLEKQQR | |
| | | VNVVQLASPSENNLVTEKS | |
| | | NLPEYTTEIAGKSKENLLNH | |
| | | EMVLKDVLPPIIKDTESEKT | |
| | | FGPASISHDNNNISSTSELG | |
| | | TDLANTKVKLIQGSELPELT | |
| | | DSVKGKDEYFKNMTPKVD | |
| | | SSLDHIICTEPDLIGKPAEES | |
| | | HLSLIASVTDKDPQGNGSD | |
| | | LIKGRDGKSDILIEDETSIQK | |
| | | MYLGEGEVLVEGLVEEENR | |
| | | HLKLLPGKNTRDSFKLINSQ | |
| | | FPFPQITNNEELNQKGSLK | |
| | | KATVTLKDEPNNLQIIVSKS | |
| | | PVQFENLEEIFDTSVSKEIS | |
| | | DDITSDITSWEGNTHFEESF | |
| | | TDGPEKELDLFTYLKHCAK | |
| | | NIKAKDVAKPNEDVPSHVL | |
| | | ITAPPMKEHLQLGVNNTKE | |
| | | KSTSTQKDSPLNDMIQSN | |
| | | DLCSKESISGGGTEISQFTP | |
| | | ESIEATLSILSRKHVEDVGK | |
| | | NDFLQSERCANGLGNDNS | |
| | | SNTLNTDYSFLEINNKKERI | |
| | | EQQLPKEQALSPRSQEKEV | |
| | | QIPELSQVFVEDVKDILKSR | |
| | | LKEGHMNPQEVEEPSACA | |
| | | DTKILIQNLIKRITTSQLVNE | |
| | | ASTVPSDSQMSDSSGVSP | |
| | | MTNSSELKPESRDDPFCIG | |
| | | NLKSELLLNILKQDQHSQKI | |
| | | TGVFELMRELTHMEYDLEK | |
| | | RGITSKVLPLQLENIFYKLLA | |
| | | DGYSEKIEHVGDFNQKACS | |

TABLE 9-continued

| Recurrent N terminal sequences with high affinity to MHC Class I | | | |
|---|---|---|---|
| SEQ ID NO. | Gene | N terminal sequence | High Affinity HLA |
| | | TSEMMEEKPHILGDIKSKE GNYYSPNLETVKEIGLESST VWASTLPRDEKLKDLCNDF PSHLECTSGSKEMASGDSS TEQFSSELQQCLQHTEKM HEYLTLLQDMKPPLDNQES LDNNLEALKNQLRQLETFE LGLAPIAVILRKDMKLAEEF LKSLPSDFPRGHVEELSISH QSLKTAFSSLSNVSSERTKQ IMLAIDSEMSKLAVSHEEFL HKLKSFSDWVSEKSKSVKD IEIVNVQDSEYVKKRLEFLK NVLKDLGHTKMQLETTAF DVQFFISEYAQDLSPNQSK QLLRLLNTTQKCFLDVQES VTTQVERLETQLHLEQDLD DQKIVAERQQEYKEKLQGI CDLLTQTENRLIGHQEAFM IGDGTVELKKYQSKQEELQ KDMQGSAQALAEVVKNTE NFLKENGEKLSQEDKALIE QKLNEAKIKCEQLNLKAEQ SKKELDKVVTTAIKEETEKV AAVKQLEESKTKIENLLDW LSNVDKDSERAGTKHKQVI EQNGTHFQEGDGKSAIGE EDEVNGNLLETDVDGQVG TTQENLNQQYQKVKAQHE KIISQHQAVIIATQSAQVLL EKQGQYLSPEEKEKLQKN MKELKVHYETALAESEKKM KLTHSLQEELEKFDADYTEF EHWLQQSEQELENLEAGA DDINGLMTKLKRQKSFSED VISHKGDLRYITISGNRVLE AAKSCSKRDGGKVDTSAT HREVQRKLDHATDRFRSLY SKCNVLGNNLKDLVDKYQ HYEDASCGLLAGLQACEAT ASKHLSEPIAVDPKNLQRQ LEETKALQGQISSQQVAVE KLKKTAEVLLDARGSLLPAK NDIQKTLDDIVGRYEDLSKS VNERNEKLQITLTRSLSVQD GLDEMLDWMGNVESSLK EQDVGTGYCRSSEQYKCH E | |
| SEQ ID NO: 1902 | ENSG00000152359.10 | MSSDEEKYSLPVVQNDSSR GSSVSSNLQEEYEELLHYAI VTPNIEPCASQSSHPKGEL VPDVRISTIHDILHSQGNNS EVRETAIEVGKGCDFHISSH SKTDESSPVLSPRKPSHPV MDFFSSHLLADSSSPATNS SHTDAHEILVSDFLVSDENL QKMENVLDLWSSGLKTNII SELSKWRLNFIDWHRME MRKEKEKHAAHLKQLCNQ INELKELQKTFEISIGRKDEV ISSLSHAIGKQKEKIELMRTF FHWRIGHVRARQDVYEGK LADQYYQRTLLKKVWKVW RSVVQKQWKDVVERACQ ARAEEVCIQISNDYEAKVA MLSGALENAKAEIQRMQH EKEHFEDSMKKAFMRGVC ALNLEAMTIFQNRNDAGI DSTNNKKEEYGPGVQGKE HSAHLDPSAPPMPLPVTSP LLPSPPAAVGGASATAVPS AASMTSTRAASASSVHVP VSALGAGSAATAASEEMY VPRVVTSAQQKAGRTITAR ITGRCDFASKNRISSSLAIM | A*02:03, A*11:01, A*11:0 2, A*24:02, A*24:10, A*33: 03, A*34:01, B*39:01, B*4 0:01, B*55:02, C*03:02, C* 03:04, C*12:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | GVSPPMSSVVVEKHHPVT VQTIPQATAAKYPRTIHPES STSASRSLGTRSAHTQSLTS VHSIKVVD | |
| SEQ ID NO: 1903 | ENSG00000153046.13 | MASEELYEVERIVDKRKNK KGKTEYLVRWKGYDSEDD TWEPEQHLVNCEEYIHDF NRRHTEKQKESTLTRTNRT SPNNARKQISRSTNSNFSK TSPKALVIGKDHESKNSQLF AASQKFRKNTAPSLSSRKN | A*02:03, A*11:01, A*11:02, A*33:03, B*15:01, C*03:02, C*07:02, C*15:02 |
| SEQ ID NO: 1904 | ENSG00000154556.13 | MSYYQRPFSPSAYSLPASL NSSIVMQHGTSLDSTDTYP QHAQSLDGTTSSSIPLYRSS EEEKRVTVIKAPHYPGIGPV DESGIPTAIRTTVDRPKDW YKTMFKQIHMVHKPDDDT DMYNTPYTYNAGLYNPPY SAQSHPAAKTQTYRPLSKS HSDNSPNAFKDASSPVPPP HVPPPVPPLRPRDRSSTEK HDWDPPDRKVDTRKFRSE PRSIFEYEPGKSSILQHERPA SLYQSSIDRSLERPMSSAS MASDFRKRRKSEPAVGPP RGLGDQSASRTSPGRVDLP GSSTTLTKSFTSSSPSSPSRA KGGDDSKICPSLCSYSGLN GNPSSELDYCSTYRQHLDV PRDSPRAISFKNGWQMAR QNAEIWSSTEETVSPKIKSR SCDDLLNDDCDSFPDPKVK SESMGSLLCEEDSKESCPM AWGSPYVPEVRSNGRSRIR HRSARNAPGFLKMYKKM HRINRKDLMNSEVICSVKS RILQYESEQQHKDLLRAWS QCSTEEVPRDMVPTRISEF EKLIQKSKSMPNLGDDMLS PVTLEPPQNGLCPKRRFSIE YLLEEENQSGPPARGRRGC QSNALVPIHIEVTSDEQPR AHVEFSDSDQDGVVSDHS DYIHLEGSSFCSESDFDHFS FTSSESFYGSSHHHHHHH HHHRHLISSCKGRCPASYT RFTTMLKHERARHENTEEP RRQEMDPGLSKLAFLVSPV PFRRKKNSAPKKQTEKAKC KASVFEALDSALKDICDQIK AEKKRGSLPDNSILHRLISEL LPDVPERNSSLRALRRSPLH QPLHPLPPDGAIHCPPYQN DCGRMPRSASFQDVDTAN SSCHHQDRGGAL | A*02:03, A*11:01, A*11:02, A*24:10, A*33:03, B*15:01, B*15:27, B*39:01, B*58:01, C*03:02, C*03:04, C*07:02, C*12:02, C*14:02, C*15:02 |
| SEQ ID NO: 1905 | ENSG00000155275.14 | MAEVGRTGISYPGALLPQG FWAAVEVWLERPQVANK RLCGARLEARWSAALPCAE ARGPGTSAGSEQKERGPG PGQGSPGGGPGPRSLSGP EQGTACCELEEAQGQCQQ EEAQREAASVPLRDSGHP GHAEGREGDFPAADLDSL WEDFSQSLARGNSELLAFL TSSGAGSQPEAQRELDVVL RTVIPKTSPHCPLTTPRREIV VQDVLNGTITFLPLEEDDE GNLKVKMSNVYQIQLSHS KEEWFISVLIFCPERWHSD GIVYPKPTWLGEELLAKLAK WSVENKKSDFKSTLSLISIM KYSKAYQELKEKYKEMVKV WPEVTDPEKFVYEDVAIAA | A*02:03, A*11:01, A*11:02, A*24:02, A*24:10, A*33:03, B*15:01, B*15:27, B*39:01, B*40:01, B*55:02, B*58:01, C*03:02, C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| | | YLLILWEEERAERRLTARQS<br>FVDLGCGNGLLVHILSSEG<br>HPGRGIDVRRRKIWDMYG<br>PQTQLEEDAITPNDKTLFP<br>DVDWLIGNHSDELTPWIP<br>VIAARSSYNCRFFVLPCCFF<br>DFIGRYSRRQSKKTQYREYL<br>DFIKEVGFTCGFHVDEDCL<br>RIPSTKRVCLVGKSRTYPSS<br>REASVDEKRTQYIKSRRGC<br>PVSPPGWELSPSPRWVAA<br>GSAGHCDGQQALDARVG<br>CVTRAWAAEHGAGPQAE<br>GPWLPGFHPREKAERVRN<br>CAALPRDFIDQVVLQVANL<br>LLGGKQLNTRSSRNGSLKT<br>WNGGESLSLAEVANELDT<br>ETLRRLKRECGGLQTLLRNS<br>HQVFQVVNGRVHIRDWR<br>EETLWKTKQPEAKQRLLSE<br>ACKTRLCWFFMHHPDGC<br>ALSTDCCPFAHGPAELRPP<br>RTTPRKKIS | |
| SEQ ID NO: 1906 | ENSG00000155506.12 | MATQVEPLLPGGATLLQA<br>EEHGGLVRKKPPPAPEGKG<br>EPGPNDVRGGEPDGSARR<br>PRPPCAKPHKEGTGQQER<br>ESPRPLQLPGAEGPAISDG<br>EEGGGEPGAGGGAAGAA<br>GAGRRDFVEAPPPKVNPW<br>TKNALPPVLTTVNGQ | A*02:03 |
| SEQ ID NO: 1907 | ENSG00000157514.12 | MNTEMYQTPMEVAVYQL<br>HNFSISFFSSLLGGDVVSVK<br>LD | A*02:03, A*24:02, A*24:07,<br>A*24:10, B*15:01, C*03:02,<br>C*03:04, C*03:67,<br>C*12:02, C*15:02 |
| SEQ ID NO: 1908 | ENSG00000158321.11 | MDGPTRGHGLRKKRRSRS<br>QRDRERRSRGGLGAGAAG<br>GGGAGRTRALSLASSSGSD<br>KEDNGKPPSSAPSRPRPPR<br>RKRRESTSAEEDIIDGFAMT<br>SFVTFEALEKDVALKPQER<br>VEKRQTPLTKKKREALTNG<br>LSFHSKKSRLSHPHHYSSDR<br>ENDRNLCQHLGKRKKMPK<br>ALRQLKPGQNSCRDSDSES<br>ASGESKGFHRSSSRERLSDS<br>SAPSSLGTGYFCDSDSDQE<br>EKASDASSEKLENTVIVNKD<br>PELGVGTLPEHDSQDAGPI<br>VPKISGLERSQEKSQDCCKE<br>PIFEPVVLKDPCPQVAQPIP<br>QPQTEPQLRAPSPDPDLV<br>QRTEAPPQPPPLSTQPPQ<br>GPPEAQLQPAPQPQVQRP<br>PRPQSPTQLLHQNLPPVQ<br>AHPSAQSLSQPLSAYNSSSL<br>SLNSLSSSRSSTPAKTQPAP<br>PHISHHPSASPFPLSLPNHS<br>PLHSFTPTLQPPAHSHHPN<br>MFAPPTALPPPPPLT | A*02:03, A*24:10, B*15:01,<br>B*15:27, B*39:01, B*58:01,<br>C*03:02, C*03:04, C*03:67,<br>C*12:02, C*14:02,<br>C*15:02 |
| SEQ ID NO: 1909 | ENSG00000158486.9 | MGATGRLELTLAAPPHPG<br>PAFQRSKARETQGEEEGSE<br>MQIAKSDSIHHMSHSQGQ<br>PELPPLPASANEEPSGLYQT<br>VMSHSFYPPLMQRTSWTL<br>AAPFKEQHHHRGPSDSIA<br>NNYSLMAQDLKLKDLLKVY<br>QPATISVPRDRTGQGLPSS<br>GNRSSSEPMRKKTKFSSRN<br>KEDSTRIKLAFKTSIFSPMK<br>KEVKTSLTFPGSRPMSPEQ<br>QLDVMLQQEMEMESKEK | A*02:03, A*02:07, A*11:01,<br>A*11:02, A*24:02, A*24:07,<br>A*24:10, A*33:03, A*34:01,<br>B*15:01, B*15:21,<br>B*15:27, B*27:04, B*38:02,<br>B*39:01, B*40:01, B*40:06,<br>B*46:01, B*51:01, B*55:02,<br>B*58:01, C*01:02, C*03:02,<br>C*03:04, C*03:67, C*04:01,<br>C*04:03, C*07:02, C*08:01,<br>C*12:02, C*14:02,<br>C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | KPSESDLERYYYYLTNGIRK<br>DMIAPEEGEVMVRISKLIS<br>NTLLTSPFLEPLMVVLVQE<br>KENDYYCSLMKSIVDYILM<br>DPMERKRLFIESIPRLFPQR<br>VIRAPVPWHSVYRSAKKW<br>NEEHLHTVNPMMLRLKEL<br>WFAEFRDLRFVRTAEILAG<br>KLPLQPQEFWDVIQKHCLE<br>AHQTLLNKWIPTCAQLFTS<br>RKEHWIHFAPKSNYDSSRN<br>IEEYFASVASFMSLQLRELV<br>IKSLEDLVSLFMIHKDGNDF<br>KEPYQEMKFFIPQLIMIKLE<br>VSEPIIVFNPSFDGCWELIR<br>DSFLEIIKNSNGIPKLKYIPLK<br>FSFTAAAADRQCVKAAEP<br>GEPSMHAAATAMAELKGY<br>NLLLGTVNAEEKLVSDFLIQ<br>TFKVFQKNQVGPCKYLNV<br>YKKYVDLLDNTAEQNIAAF<br>LKENHDIDDFVTKINAIKKR<br>RNEIASMNITVPLAMFCLD<br>ATALNHDLCERAQNLKDH<br>LIQFQVDVNRDTNTSICNQ<br>YSHIADKVSEVPANTKELVS<br>LIEFLKKSSAVTVFKLRRQLR<br>DASERLEFLMDYADLPYQI<br>EDIFDNSRNLLLHKRDQAE<br>MDLIKRCSEFELRLEGYHRE<br>LESFRKREVMTTEEMKHN<br>VEKLNELSKNLNRAFAEFEL<br>INKEEELLEKEKSTYPLLQA<br>MLKNKVPYEQLWSTAYEF<br>SIKSEEWMNGPLFLLNAEQ<br>IAEEIGNMWRTTYKLIKTLS<br>DVPAPRRLAENVKIKIDKFK<br>QYIPILSISCNPGMKDRHW<br>QQISEIVGYEIKPTETTCLSN<br>MLEFGFGKFVEKLEPIGAA<br>ASKEYSLEKNLDRMKLDW<br>VNVTFSFVKYRDTDTNILC<br>AIDDIQMLLDDHVIKTQTM<br>CGSPFIKPIEAECRKWEEKLI<br>RIQDNLDAWLKCQATWLY<br>LEPIFSSEDIIAQMPEEGRK<br>FGIVDSYWKSLMSQAVKD<br>NRILVAADQPRMAEKLQE<br>ANFLLEDIQKGLNDYLEKKR<br>LFFPRFFFLSNDELLEILSETK<br>DPLRVQPHLKKCFEGIAKLE<br>FTDNLEIVGMISSEKETVPFI<br>QKIYPANAKGMVEKWLQ<br>QVEQMMLASMREVIGLGI<br>EAYVKVPRNHWVLQWPG<br>QVVICVSSIFWTQEVSQAL<br>AENTLLDFLKKSNDQIAQIV<br>QLVRGKLSSGARLTLGALT<br>VIDVHARDVVAKLSEDRVS<br>DLNDFQWISQLRYYWVAK<br>DVQVQIITTEALYGYEYLGN<br>SPRLVITPLTDRCYRTLMGA<br>LKLNLGGAPEGPAGTGKTE<br>TTKDLAKALAKQCVVFNCS<br>DGLDYKAMGKFFKGLAQA<br>GAWACFDEFNRIEVEVLSV<br>VAQQILSIQQAIIRKLKTFIF<br>EGTELSLNPTCAVFIT | |
| SEQ ID NO: 1910 | ENSG00000159263.11 | MKEKSKNAAKTRREKENG<br>EFYELAKLLPLPSAITSQLDK<br>ASIIRLTTSYLKMRAVFPEG<br>LGDA | A*02:03, A*24:02, A*24:07,<br>A*24:10, A*34:01, B*15:01,<br>B*15:21, B*15:27, B*38:02,<br>B*39:01, B*40:01, B*40:06,<br>B*51:01, B*55:02,<br>C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| SEQ ID NO: 1911 | ENSG00000159788.14 | MFRAGEASKRPLPGPSPPR VRSVEVARGRAGYGFTLSG QAPCVLSCVMRGSPADFV GLRAGDQILAVNEINVKKA SHEDVVKLIGKCSGVLHMV IAEGVGRFESCSSDEEGGLY EGKGWLKPKLDSKALGINR AERVVEEMQSGGIFNMIF ENPSLCASNSEPLKLKQRSL SESAATRFDVGHESINNPN PNMLSKEEISKVIHDDSVFS IGLESHDDFALDASILNVA MIVGYLGSIELPSTSSNLES DSLQAIRGCMRRLRAEQKI HSLVTMKIMHDCVQLSTD KAGVVAEYPAEKLAFSAVC PDDRRFFGLVTMQTNDD GSLAQEEEGALRTSCHVF MVDPDLFNHKIHQGIARR FGFECTADPDTNGCLEFPA SSLPVLQFISVLYRDMGELI EGMRARAFLDGDADAHQ NNSTSSNSDSGIGNFHQEE KSNRVLVVD | A*02:03, A*11:01, A*11:02, A*24:10, A*33:03, A*34:01, B*15:01, B*40:01, B*55:02, C*15:02 |
| SEQ ID NO: 1912 | ENSG00000160200.13 | MPSETPQAEVGPTGCPHR SGPHSAKGSLEKGSPEDKE AKEPLWIRPDAPSRCTWQ LGRPASESPHHHTAPAKSP KILPDILKKIGDTPMVRINKI GKKFGLKCELLAKCEFFNA GGSVKDRISLRMIEDAERD GTLKPGDTIIEPTSGNTGIG LALAAAVRGYRCIIVMPEK MSSEKVDVLRALGAEIVRT PTNARFDSPESHVGVAWR LKNEIPNSHILDQYRNASN PLAHYDTTADEILQQCDGK LDMLVASVGTGGTITGIAR KLKEKCPGCRIIGVDPEGSIL AEPEELNQTEQTTYEVEGI GYDFIPTVLDRTWDKWFK SNDEEAFTFARMLIAQEGL LCGGSAGSTVAVAVKAAQ ELQEGQRCVVILPDSVRNY MTKFLSDRWMLQKGFLKE EDLTEKKPWWWHLRVQE LGLSAPLTVLPTITCGHTIEIL REKGFDQAPVVDEAGVILG MVTLGNMLSSLLAGKVQP SDQVGKVIYKQFKQIRLTD TLGRLSHILEMDHFALVVH EQIQYHSTGKSSQRQMVF GVVTAIDLLNFVAAQERDQ K | A*02:03, A*11:01, A*11:02, A*24:10, A*33:03, B*15:01, B*38:02, B*39:01, B*40:01, B*58:01, C*03:02, C*03:04, C*07:02, C*14:02 |
| SEQ ID NO: 1913 | ENSG00000160799.7 | MQDGRKGGAYAGKMEAT TAGVGRLEEEALRRKERLK ALREKTG | A*02:03 |
| SEQ ID NO: 1914 | ENSG00000160838.9 | MSSEQSAPGASPRAPRPG TQKSSGAVTKKGERAAKEK PATVLPPVGEEEPKSPEEY QCSGVLETDFAELCTRWG YTDFPKVVNRPRPHPPFVP SASLSEKATLDDPRLSGSCS LNSLESKYVFFRPTIQVELE QEDSKSVKEIYIRGWKVEE RILGVFSKCLPPLTQLQAIN LWKVGLTDKTLTTFIELLPL CSSTLRKVSLEGNPLPEQSY HKL | A*02:03, A*11:01, A*11:02, A*24:02, A*24:07, A*24:10, B*40:01, B*55:02, C*01:02, C*03:02, C*04:01, C*04:03, C*07:02, C*15:02 |
| SEQ ID NO: 1915 | ENSG00000164093.11 | METNCRKLVSACVQLGVQ PAAVECLFSKDSEIKKVEFT DSPESRKEAASSKFFPRQH | A*11:01, A*11:02, A*33:03 |

TABLE 9-continued

Recurrent N terminal sequences with high affinity to MHC Class I

| SEQ ID NO. | Gene | N terminal sequence | High Affinity HLA |
|---|---|---|---|
| SEQ ID NO: 1916 | ENSG00000164764.10 | MRTLWMALCALSRLWPG<br>AQAGCAEAGRCCPGRDPA<br>CFARGWRLDRVYGTCFCD<br>QACRFTGDCCFDYDRACP<br>ARPCFVGEWSPWSGCAD<br>QCKPTTRVRRRSVQQEPQ<br>NGGAPCPPLEERAGCLEYS<br>TPQGQDCGHTYVPAFITTS<br>AFNKERTRQATSPHWSTH<br>TEDAGYCMEFKTESLTPHC<br>ALENWPLTRWMQYLREG<br>YTVCVDCQPPAMNSVSLR<br>CSGDGLDSDGNQTLHWQ<br>AIGNPRCQGTWKKVRRVD<br>QCSCPAVHSFIFI | A*11:01, A*11:02, A*24:10, A*33:03, B*55:02, C*03:02, C*03:04 |
| SEQ ID NO: 1917 | ENSG00000164830.13 | MDYLTTFTEKSGRLLRGTA<br>NRLLGFGGGGEARQVRFE<br>DYLREPAQGDLGCGSPPH<br>RPPAPSSPEGP | A*33:03 |
| SEQ ID NO: 1918 | ENSG00000166689.10 | MAAATVGRDTLPEHWSY<br>GVCRDGRVFFINDQLRCTT<br>WLHPRTGEPVNSGHMIRS<br>DLPRGWEE | A*33:03 |
| SEQ ID NO: 1919 | ENSG00000167157.9 | MDSAAAAFALDKPALGPG<br>PPPPPPALGPGDCAQARK<br>NFSVSHLLDLEEVAAAGRL<br>AARPGARAEAREGAAREP<br>SGGSSGSEAAPQ | A*11:01, A*11:02, C*03:02, C*03:04, C*03:67 |
| SEQ ID NO: 1920 | ENSG00000167632.10 | MSVPDYMQCAEDHQTLL<br>VVVQPVGIVSEENFFRIYKR<br>ICSVSQISVRDSQRVLYIRYR<br>HHYPPENNEWGDFQTHR<br>KVVGLITITDCFSAKDWPQ<br>TFEKFHVQKEIYGSTLYDSR<br>LFVFGLQGEIVEQPRTDVA<br>FYPNYEDCQTVEKRIEDFIE<br>SLFIVLESKRLDRATDKSGD<br>KIPLLCVPFEKKDFVGLDTD<br>SRHYKKRCQGRMRKHVG<br>DLCLQAGMLQDSLVHYH<br>MSVELLRSVNDFLWLGAA<br>LEGLCSASVIYHYPGGTGG<br>KSGARRFQGSTLPAEAANR<br>HRPGALTTNGINPDTSTEI<br>GRAKNCLSPEDIIDKYKEAIS<br>YYSKYKNAGVIELEACIKAV<br>RVLAIQKRSMEASEFLQNA<br>VYINLRQLSEEEKIQRYSILS<br>ELYELIGFHRKSAFFKRVAA<br>MQCVAPSIAEPGWRACYK<br>LLLETLPGYSLSLDPKDFSR<br>GTHRGWAAVQMRLLHEL<br>VYASRRMGNPALSVRHLSF<br>LLQTMLDFLSDQEKKDVA<br>QSLENYTSKCPGTMEPIAL<br>PGGLTLPPVPFTKLPIVRHV<br>KLLNLPASLRPHKMKSLLG<br>QNVSTKSPFIYSPIIAHNRG<br>EERNKKIDFQWVQGDVCE<br>VQLMVYNPMPFELRVEN<br>MGLLTSGVEFESLPAALSLP<br>AESGLYPVTLVGVPQTTGTI<br>TVNGYHTTVFGVFSDCLLD<br>NLPGIKTSGSTVEVIPALPR<br>LQISTSLPRSAHSLQPSSGD<br>EISTNVSVQLYNGESQQLII<br>KLENIGMEPLEKLEVTSKVL<br>TTKEKLYGDFLSWKLEETLA<br>QFPLQPGKVATFTINIKVKL<br>DFSCQENLLQDLSDDGISV<br>SGFPLSSPFRQVVRPRVEG | A*02:03, A*02:07, A*11:01, A*11:02, A*24:02, A*24:07, A*24:10, A*33:03, B*15:01, B*15:27, B*39:01, B*40:01, B*55:02, B*58:01, C*03:02, C*03:04, C*03:67, C*07:02, C*12:02, C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| | | KPVNPPESNKAGDYSHVKT | |
| | | LEAVLNFKYSGGPGHTEGY | |
| | | YRNLSLGLHVEVEPSVFFTR | |
| | | VSTLPATSTRQCHLLLDVF | |
| | | NSTEHELTVSTRSSEALILH | |
| | | AGECQRMAIQVDKENFES | |
| | | FPESPGEKGQFANPKQLEE | |
| | | ERREARGLEIHSKLGICWRI | |
| | | PSLKRSGEASVEGLLNQLVL | |
| | | EHLQLAPLQWDVLVDGQP | |
| | | CDREAVAACQVGDPVRLE | |
| | | VRLTNRSPRSVGPFALTVV | |
| | | PFQDHQNGVHNYDLHDT | |
| | | VSFVGSSTFYLDAVQPSGQ | |
| | | SACLGALLFLYTGDFFLHIRF | |
| | | HEDSTSKELPPSWFCLPSV | |
| | | HVCALEAQA | |
| SEQ ID NO: 1921 | ENSG00000170615.10 | MDHAEENEILAATQRYYVE | A*02:03, A*02:07, A*11:01, |
| | | RPIFSHPVLQERLHTKDKVP | A*11:02, A*24:02, A*24:07, |
| | | DSIADKLKQAFTCTPKKIRN | A*24:10, A*33:03, A*34:01, |
| | | IIYMFLPITKWLPAYKFKEY | B*15:01, B*15:21, B*15:27, |
| | | VLGDLVSGISTGVLQLPQG | B*27:04, B*38:02, |
| | | LAFAMLAAVPPIFGLYSSFY | B*39:01, B*40:01, B*40:06, |
| | | PVIMYCFLGTSRHISIGPFA | B*46:01, B*51:01, B*55:02, |
| | | VISLMIGGVAVRLVPDDIVI | B*58:01, C*01:02, C*03:02, |
| | | PGGVNATNGTEARDALRV | C*03:04, C*03:67, C*04:01, |
| | | KVAMSVTLLSGIIQFCLGVC | C*04:03, C*08:01, C*12:02, |
| | | RFGFVAIYLTEPLVRGFTTA | C*14:02, C*15:02 |
| | | AAVHVFTSMLKYLFGVKTK | |
| | | RYSGIFSVVYSTVAVLQNV | |
| | | KNLNVCSLGVGLMVFGLLL | |
| | | GGKEFNERFKEKLPAPIPLE | |
| | | FFAVVMGTGISAGFNLKES | |
| | | YNVDVVGTLPLGLLPPANP | |
| | | DTSLFHLVYVDAIAIAIVGFS | |
| | | VTISMAKTLANKHGYQVD | |
| | | GNQELIALGLCNSIGSLFQT | |
| | | FSISCSLSRSLVQEGTGGKT | |
| | | QLAGCLASLMILLVILATGF | |
| | | LFESLPQAVLSAIVIVNLKG | |
| | | MFMQFSDLPFFWRTSKIEL | |
| | | TIWLTTFVSSLFLGLDYGLIT | |
| | | AVIIALLTVIYRTQS | |
| SEQ ID NO: 1922 | ENSG00000171680.16 | MHYDGHVRFDLPPQGSVL | A*02:03, A*02:07, A*11:01, |
| | | ARNVSTRSCPPRTSPAVDL | A*11:02, A*24:10, A*33:03, |
| | | EEEEEESSVDGKGDRKSTG | B*15:01, B*39:01, B*40:01, |
| | | LKLSKKKARRRHTDDPSKE | B*58:01, C*03:02, C*03:04, |
| | | CFTLKFDLNVDIETEIVPAM | C*07:02, C*12:02, |
| | | KKKSLGEVLLPVFERKGIAL | C*14:02, C*15:02 |
| | | GKVDIYLDQSNTPLSLTFEA | |
| | | YRFGGHYLRVKAPAKPGDE | |
| | | GKVEQGMKDSKSLSLPILR | |
| | | PAGTGPPALERVDAQSRRE | |
| | | SLDILAPGRRRKNMSEFLG | |
| | | EASIPGQEPPTPSSCSLPSG | |
| | | SSGSTNTGDSWKNRAASR | |
| | | FSGFFSSGPSTSAFGREVDK | |
| | | MEQLEGKLHTYSLFGLPRL | |
| | | PRGLRFDHDSWEEEYDED | |
| | | EDEDNACLRLEDSWRELID | |
| | | GHEKLTRRQCHQQEAVW | |
| | | ELLHTEASYIRKLRVIINLFLC | |
| | | CLLNLQESGLLCEVEAERLF | |
| | | SNIPEIAQLHRRLWASVMA | |
| | | PVLEKARRTRALLQPGDFL | |
| | | KGFKMFGSLFKPYIRYCME | |
| | | EEGCMEYMRGLLRDNDLF | |
| | | RAYITWAEKHPQCQRLKLS | |
| | | DMLAKPHQRLTKYPLLLKS | |
| | | VLRKTEEPRAKEAVVAMIG | |
| | | SVERFIHHVNACMRQRQE | |
| | | RQRLAAVVSRIDAYEWES | |
| | | SSDEVDKLLKEFLHLDLTAPI | |
| | | PGASPEETRQLLLEGSLRM | |

TABLE 9-continued

| Recurrent N terminal sequences with high affinity to MHC Class I | | | |
|---|---|---|---|
| SEQ ID NO. | Gene | N terminal sequence | High Affinity HLA |
| | | KEGKDSKMDVYCFLFTDLL<br>LVTKAVKKAERTRVIRPPLL<br>VDKIVCRELRDPGSFLLIYLN<br>EFHSAVGAYTFQASGQALC<br>RGWVDTIYNAQNQLQQL<br>RAQEPPGSQQPLQSLEEEE<br>DEQEEEEEEEEEEEGEDS<br>GTSAASSPTIMRKSSGSPD<br>SQHCASDGSTETLAMVVV<br>EPGDTLSSPEFDSGPFSSQS<br>DETSLSTTASSATPTSELLPL<br>GPVDGRSCSMDSAYGTLS<br>PTSLQDFVAPGPMAELVP<br>RAPESPRVPSPPPSPRLRRR<br>TPVQLLSCPPHLLKSKSEAS<br>LLQLLAGAGTHGTPSAPSR<br>SLSELCLAVPAPGIRTQGSP<br>QEAGPSWDCRGAPSPGSG<br>PGLVGCLAGEPAGSHRKRC<br>GDLPSGASPRVQPEPPPGV<br>SAQHRKLTLAQLYRIRTTLL<br>LNSTLTASEV | |
| SEQ ID NO: 1923 | ENSG00000171791.10 | MAHAGRTGYDNREIVMK<br>YIHYKLSQRGYEWDAGDV<br>GAAPPGAAPAPGIFSSQPG<br>HTPHPAASRDPVARTSPLQ<br>TPAAPGAAAGPALSPVPPV<br>VHLTLRQAGDDFSRRYRRD<br>FAEMSSQLHLTPFTARGRF<br>ATVVEELFRDGVNWGRIV<br>AFFEFGGVMCVESVNREM<br>SPLVDNIALWMTEYLNRHL<br>HTWIQDNGGWDAFVELY<br>GPS | A*02:03, A*11:01, A*11:02,<br>A*24:02, A*24:07, A*24:10,<br>A*33:03, A*34:01, B*15:21,<br>B*27:04, B*40:01, B*40:06,<br>B*46:01, B*55:02,<br>B*58:01, C*01:02, C*03:02,<br>C*04:01, C*04:03, C*14:02 |
| SEQ ID NO: 1924 | ENSG00000172765.12 | MKRGTSLHSRRGKPEAPK<br>GSPQINRKSGQEMTAVM<br>QSGRPRSSSTTDAPTSSAM<br>MEIACAAAAAAAACLPGE<br>EGTAE | A*02:03, A*33:03, C*03:02,<br>C*03:04 |
| SEQ ID NO: 1925 | ENSG00000174672.11 | MTSTGKDGGAQHAQYVG<br>PYRLEKTLGKGQTGLVKLG<br>VHCVTCQKVAIKIVNREKLS<br>ESVLMKVEREIAILKLIEHPH<br>VLKLHDVYENKKYLYLVLEH<br>VSGGELFDYLVKKGRLTPK<br>EARKFFRQIISALDFCHSHSI<br>CHRDLKPENLLLDEKNNIRI<br>ADFGMASLQVGDSLLETSC<br>GSPHYACPEVIRGEKYDGR<br>KADVWSCGVILFALLVGAL<br>PFDDDNLRQLLEKVKRGVF<br>HMPHFIPPDCQSLLRGMIE<br>VDAARRLTLEHIQKHIWYI<br>GGKNEPEPEQPIPRKVQIR<br>SLPSLEDIDPDVLDSMHSL<br>GCFRDRNKLLQDLLSEEEN<br>QEKMIYFLLLDRKERYPSQE<br>DEDLPPRNEIDPPRKRVDS<br>PMLNRHGKRRPERKSMEV<br>LSVTDGGSPVPARRAIEMA<br>QHGQSKAMFSKSLDIAEA<br>HPQFSKEDRSRSISGASSGL<br>STSPLSSPRVTPHPSPRGSP<br>LPTPKGTPVHTPKESPAGT<br>PNPTPPSSPSVGGVPWRA<br>RLNSIKNSFLGSPRFHRRKL<br>QVPTPEEMSNLTPESSPEL<br>AKKSWFGNFISLEKEEQIFV<br>VIKDKPLSSIKADIVHAFLSI<br>PSLSHSVISQTSFRAEYKAT<br>GGPAVFQKPVKFQVDITYT<br>EGGEAQKENGIYSVTFTLLS<br>GPSRRFKRVVETIQAQLLST | A*02:03, A*11:01, A*11:02,<br>A*24:02, A*24:10, A*33:03,<br>B*40:01, C*03:02, C*03:04,<br>C*14:02 |

TABLE 9-continued

Recurrent N terminal sequences with high affinity to MHC Class I

| SEQ ID NO. | Gene | N terminal sequence | High Affinity HLA |
|---|---|---|---|
| | | HDPPAAQHLSEPPPPAPGL<br>SWGAGLKGQKVATSYESSL | |
| SEQ ID NO: 1926 | ENSG00000177380.9 | MMCEVMPTISEDGRRGSA<br>LGPDEAGGELERLMVTML<br>TERERLLETLREAQDGLAT<br>AQLRLRELGHEKDSLQRQL<br>SIALPQEFAALTKELNLCRE<br>QLLEREEEIAELKAERNNTR<br>LLLEHLECLVSRHERSLRMT<br>VVKRQAQSPGGVSSEVEV<br>LKALKSLFEHHKALDEKVRE<br>RLRMALERVAVLEEELELS<br>NQETLNLREQLSRRRSGLE<br>EPGKDGDGQTLANGLGPG<br>GDSNRRTAELEEALERQRA<br>EVCQLRERLAVLCRQMSQ<br>LEEELGTAHRELGKAEEAN<br>SKLQRDLKEALAQREDME<br>ERITTLEKRYLSAQREATSL<br>HDANDKLENELASKESLYR<br>QSEEKSRQLAEWLDDAKQ<br>KLQQTLQKAETLPEIEAQLA<br>QRVAALNKAEERHGNFEE<br>RLRQLEAQLEEKNQELQRA<br>RQREKMNDDHNKRLSETV<br>DKLLSESNERLQLHLKERM<br>GALEEKNSLSEEIANMKKL<br>QDELLLNKEQLLAEMERM<br>QMEIDQLRGRPPSSYSRSL<br>PGSALELRYSQAPTLPSGA<br>HLDPYVAGSGRAGKRGR<br>WSGVKEEPSKDWERSAPA<br>GSIPPPFPGELDGSDEEEAE<br>GMFGAELLSPSGQADVQT<br>LAIMLQEQLEAINKEIKLIQE<br>EKETTEQRAEELESRVSSSG<br>LDSLGRYRSSCSLPPSLTTST<br>LASPSPPSSGHSTPRLAPPS<br>PAREGTDKANHVPKEEAG<br>APRGEGPAIPGDTPPPTPR<br>SARLERMTQALALQAGSLE<br>DGGPPRGSEGTPDSLHKA<br>PKKKSIKSSIGRLFGKKEKG<br>RMGPPGRDSSSLAGTPSD<br>ETLATDPLGLAKLTGPGDK<br>DRRNKRKHELLEEACRQGL<br>PFAAWDGPTVVSWLELW<br>VGMPAWYVAACRANVKS<br>GAIMANLSDTEIQREIGISN<br>PLHRLKLRLAIQEMVSLTSP<br>SAPASSRTSTGNVWMTHE<br>EMESLTATTKPILAYGDMN<br>HEWVGNDWLPSLGLPQY<br>RSYFMESLVDARMLDHLN<br>KKELRGQLKMVDSFHRVSL<br>HYGIMCLKRLNYDRKDLER<br>RREESQTQIRDVMVWSNE<br>RVMGWVSGLGLKEFATNL<br>TESGVHGALLALDETFDYS<br>DLALLLQIPTQNAQARQLL<br>EKEFSNLISLGTDRRLDEDS<br>AKSFSRSPSWRKMFREKDL<br>RGVTPDSAEMLPPNFRSA<br>AAGALGSPGLPLRKLQPEG<br>QTSGSSRADGVSVRTYSC | A*02:03, A*11:01, A*11:02,<br>A*24:10, A*33:03, B*15:01,<br>B*39:01, B*40:01, B*58:01,<br>C*03:02, C*03:04, C*03:67,<br>C*12:02 |
| SEQ ID NO: 1927 | ENSG00000177455.7 | MPPPRLLFFLLFLTPMEVR<br>PEEPLVVKVEEGDNAVLQC<br>LKGTSDGPTQQLTWSRES<br>PLKPFLKLSLGLPGLGIHMR<br>PLAIWLFIFNVSQQMGGFY<br>LCQPGPPSEKAWQPGWT<br>VNVEGSGELFRWNVSDLG<br>GLGCGLKNRSSEGPSSPSG<br>KLMSPKLYVWAKDRPEIW | A*02:03, A*11:01, A*11:02,<br>A*24:10, B*39:01, B*40:01,<br>B*58:01, C*03:02, C*03:04,<br>C*12:02, C*14:02, C*15:02 |

TABLE 9-continued

Recurrent N terminal sequences with high affinity to MHC Class I

| SEQ ID NO. | Gene | N terminal sequence | High Affinity HLA |
|---|---|---|---|
| | | EGEPPCLPPRDSLNQSLSQ<br>DLTMAPGSTLWLSCGVPP<br>DSVSRGPLSWTHVHPKGP<br>KSLLSLELKDDRPARDMW<br>VMETGLLLPRATAQDAGK<br>YYCHRGNLTMSFHLEITAR<br>PVLWHWLLRTGGWKVSA<br>VTLAYLIFCLCSLVGILHLQR<br>ALVLRRKRKRMTDPTRRFF<br>KVTPPPGSGPQNQYGNVL<br>SLPTPTSGLGRAQRWAAG<br>LGGTAPSYGNPSSDVQAD<br>GALGSRSPPGVGPEEEEGE<br>GYEEPDSEEDSEFYENDSN<br>LGQDQLSQDGSGYENPED<br>EPLGPEDEDSFSNAESYEN<br>EDEELTQPVARTMDFLSPH<br>GSAWDPSREATSLGSQSYE<br>DMRGILYAAPQLRSIRGQP<br>GPNHEEDADSYENMDNP<br>DGPDPAWGGGGRMGTW<br>STR | |
| SEQ ID NO: 1928 | ENSG00000178209.10 | MVAGMLMPRDQLRAIYE<br>VLFREGVMVAKKDRRPRSL<br>HPHVPGVTNLQVMRAMA<br>SLRARGLVRETFAWCHFY<br>WYLTNEGIAHLRQYLHLPP<br>EIVPASLQRVRRPVAMVM<br>PARRTPHVQAVQGPLGSP<br>PKRGPLPTEEQRVYRRKEL<br>EEVSPETPVVPATTQRTLA<br>RPGPEPAPAT | A*02:03, A*11:01, A*11:02,<br>A*24:02, A*24:10, A*33:03,<br>A*34:01, B*55:02, C*03:02,<br>C*03:04 |
| SEQ ID NO: 1929 | ENSG00000181035.9 | MGNGVKEGPVRLHEDAE<br>AVLSSSVSSKRDHRQVLSSL<br>LSGALAGALAKTAVAPLDR<br>TKIIFQVSSKRFSAKEAFRVL<br>YYTYLNEGFLSLWRGNSAT<br>MVRVVPYAAIQFSAHEEYK<br>RILGSYYGFRGEALPPWPR<br>LFAGALAGTTAASLTYPLDL<br>VRARMAVTPKEMYSNIFH<br>VFIRISREEGLKTLYHGFMP<br>TVLGVIPYAGLSFFTYETLKS<br>LHREYSGRRQPYPFERMIF<br>GACAGLIGQSASYPLDVVR<br>RRMQTAGVTGYPRASIAR<br>TLRTIVREEGAVRGLYKGLS<br>MNWVKGPIAVGISFTTFDL<br>MQILLRHLQS | A*02:03, A*11:01, A*11:02,<br>A*24:02, A*24:07, A*24:10,<br>A*33:03, B*15:01, B*39:01,<br>B*40:01, C*03:02,<br>C*03:04, C*03:67, C*12:02,<br>C*14:02 |
| SEQ ID NO: 1930 | ENSG00000185404.12 | MAGGGSDLSTRGLNGGVS<br>QVANEMNHLPAHSQSLQ<br>RLFTEDQDVDEGLVYDTVF<br>KHFKRHKLEISNAIKKTFPFL<br>EGLRDRELITNK | A*02:03, A*24:10, A*33:03,<br>C*03:02 |
| SEQ ID NO: 1931 | ENSG00000185686.13 | MERRRLWGSIQSRYISMS<br>VWTSPRRLVELAGQSLLKD<br>EALAIAALELLPRELFPPLF<br>MAAFDGRHSQTLKAMVQ<br>AWPFTCLPLGVLMKGQHL<br>HLETFKAVLDGLDVLLAQE<br>VRPRRWKLQVLDLRKNSH<br>QDFWTVWSGNRASLYSFP<br>EPEAAQPMTKKRKVDGLS<br>TEAEQPFIPVEVLVDLFLKE<br>GACDELFSYLIEKVKRKKNV<br>LRLCCKKLKIFAMPMQDIK<br>MILKMVQLDSIEDLEVTCT<br>WKLPTLAKFSPYLGQMINL<br>RRLLLSHIHASSYISPEKEEQ<br>YIAQFTSQFLSLQCLQALYV<br>DSLFFLRGRLDQLLRHVMN<br>PLETLSITNCRLSEGDVMHL | A*02:03, A*11:01, A*11:02,<br>A*24:10, A*33:03, B*15:01,<br>B*39:01, B*40:01, B*58:01,<br>C*03:02, C*03:04,<br>C*14:02 |

TABLE 9-continued

Recurrent N terminal sequences with high affinity to MHC Class I

| SEQ ID NO. | Gene | N terminal sequence | High Affinity HLA |
|---|---|---|---|
| | | SQSPSVSQLSVLSLSGVML<br>TDVSPEPLQALLERASATL<br>QDLVFDECGITDDQLLALL<br>PSLSHCSQLTTLSFYGNSISI<br>SALQSLLQHLIGLSNLTHVL<br>YPVPLESYEDIHGTLHLERL<br>AYLHARLRELLCELGRPSM<br>VWLSANPCPHCGDRTFYD<br>PEPILCPCFMPN | |
| SEQ ID NO: 1932 | ENSG00000185989.9 | MAVEDEGLRVFQSVKIKIG<br>EAKNLPSYPGPSKMRDCYC<br>TVNLDQEEVFRTKIVEKSLC<br>PFYGEDFYCEIPRSFRHLSF<br>YIFDRDVFRRDSIIGKVAIQ<br>KEDLQKYHNRDTWFQLQH<br>VDADSEVQGKVHLELRLSE<br>VITDTGVVCHKLATRIVEC<br>QGLPIVNGQCDPYATVTLA<br>GPFRSEAKKTKVKRKTNNP<br>QFDEVFYFEVTRPCSYSKKS<br>HFDFEEEDVDKLEIRVDLW<br>NASNLKFGDEFLGELRIPLK<br>VLRQSSSYEAWYFLQPRD<br>NGSKSLKPDDLGSLRLNVV<br>YTEDHVFSSDYYSPLRDLLL<br>KSADVEPVSASAAHILGEV<br>CREKQEAAVPLVRLFLHYG<br>RVVPFISAIASAEVKRTQDP<br>NTIFRGNSLASKCIDETMKL<br>AGMHYLHVTLKPAIEEICQ<br>SHKPCEIDPVKLKDGENLE<br>NNMENLRQYVDRVFHAIT<br>ESGVSCPTVMCDIFFSLREA<br>AAKRFQDDPDVRYTAVSSF<br>IFLRFFAPAILSPNLFQLTPH<br>HTDPQTSRTLTLISKTVQTL<br>GSLSKSKSASFKESYMATFY<br>EFFNEQKYADAVKNFLDLIS<br>SSGRRDPKSVEQPIVLKEG | A*02:03, A*11:01, A*11:02,<br>A*24:02, A*24:07, A*24:10,<br>A*33:03, B*15:01, B*15:27,<br>B*39:01, B*40:01, B*58:01,<br>C*03:02, C*03:04,<br>C*07:02, C*12:02, C*14:02 |
| SEQ ID NO: 1933 | ENSG00000196961.8 | MPAVSKGDGMRGLAVFIS<br>DIRNCKSKEAEIKRINKELA<br>NIRSKFKGDKALDGYSKKK<br>YVCKLLFIFLLGHDIDFGHM<br>EAVNLLSSNKYTEKQIGYLFI<br>SVLVNSNSELIRLINNAIKN<br>DLASRNPTFMCLALHCIAN<br>VGSREMGEAFAADIPRILV<br>AGDSMDSVKQSAALCLLRL<br>YKASPDLVPMGEWTARVV<br>HLLNDQHMGVVTAAVSLI<br>TCLCKKNPDDFKTCVSLAV<br>SRLSRIVSSASTDLQDYTYY<br>FVPAPWLSVKLLRLLQCYP<br>PPEDAAVKGRLVECLETVL<br>NKAQEPPKSKKVQHSNAK<br>NAILFETISLIIHYDSEPNLLV<br>RACNQLGQFLQHRETNLR<br>YLALESMCTLASSEFSHEAV<br>KTHIDTVINALKTERDVSVR<br>QRAADLLYAMCDRSNAKQ<br>IVSEMLRYLETADYAIREEIV<br>LKVAILAEKYAVDYSWYVD<br>TILNLIRIAGDYVSEEVWYR<br>VLQIVTNRDDVQGYAAKT<br>VFEALQAPACHENMVKVG<br>GYILGEFGNLIAGDPRSSPP<br>VQFSLLHSKFHLCSVATRAL<br>LLSTYIKFINLFPETKATIQG<br>VLRAGSQLRNADVELQQR<br>AVEYLTLSSVASTDVLATVL<br>EEMPPFPERESSILAKLKRK<br>KGPGAGSALDDGRRDPSS<br>NDINGGMEPTPSTVSTPSP<br>SADLLGLRAAPPPAAPPAS | A*02:03, A*11:01, A*11:02,<br>A*24:02, A*24:07, A*24:10,<br>A*33:03, A*34:01, B*15:01,<br>B*15:27, B*39:01, B*40:01,<br>B*40:06, B*58:01,<br>C*03:02, C*03:04, C*03:67,<br>C*08:01, C*12:02, C*14:02,<br>C*15:02 |

TABLE 9-continued

Recurrent N terminal sequences with high affinity to MHC Class I

| SEQ ID NO. | Gene | N terminal sequence | High Affinity HLA |
|---|---|---|---|
| | | AGAGNLLVDVFDGPAAQP SLGPTPEEAFLSPGPEDIGP PIPEADELLNKFVCKNNGV LFENQLLQIGVKSEFRQNL GRMYLFYGNKTSVQFQNF SPTVVHPGDLQTQLAVQT KRVAAQVDGGAQVQQVL NIECLRDFLTPPLLSVRFRY GGAPQALTLKLPVTINKFF QPTEMAAQDFFQRWKQL SLPQQEAQKIFKANHPMD AEVTKAKLLGFGSALLDNV DPNPENFVGAGIIQTKALQ VGCLLRLEPNAQAQMYRL TLRTSKEPVSRHLCELLAQQ F | |
| SEQ ID NO: 1934 | ENSG00000197530.8 | MAGALRRGRALGSRPSGP TVSSRRSPQCPVAQEGLGA RSRPRVAPRSLARCGPSSRL MGWKPSEARGQSQSFQA SGLQPRSLKAARRATGRPD RSRAAPPNMDPDPQAGV QVGMRVVRGVDWKWGQ QDGGEGGVGTVVELGRH GSPSTPDRTVVVQWDQG TRTNYRAGYQGAHDLLLYD NAQIGVRHPNIICDCCKKH GLRGMRWKCRVCLDYDLC TQCYMHNKHELAHAFDRY ETAHSRPVTLSPRQGLPRIP LRGIFQGAKVVRGPDWE WGSQDGGEGKPGRVVDI RGWDVETGRSVASVTWA DGTTNVYRVGHKGKVDLK CVGEAAGGFYYKDHLPRLG KPAELQRRVSADSQPFQH GDKVKCLLDTDVLREMQE GHGGWNPRMAEFIGQTG TVHRITDRGDVRVQFNHE TRWTFHPGALTKHHSFWV GDVVRVIGDLDTVKRLQA GHGEWTDDMAPALGRVG KVVKVFGDGNLRVAVAGQ RWTFSPSCLVAYRPEEDAN LDVAERARENKSSLSVALD KLRAQKSDPEHPGRLVVEV ALGNAARALDLLRRRPEQV DTKNQGRTALQVAAYLGQ VELIRLLLQARAGVDLPDDE GNTALHYAALGNQPEATR VLLSAGCRADAINSTQSTA LHVAVQRGFLEVVRALCER GCDVNLPDAHSDTPLHSAI SAGTGASGIVEVLTEVPNID VTATNSQGFTLLHHASLKG HALAVRKILARARQLVDAK KEDGFTALHLAALNNHREV AQILIREGRCDVNVRNRKL QSPLHLAVQQAHVGLVPLL VDAGCSVNAEDEEGDTAL HVALQRHQLLPLVADGAG GDPGPLQLLSRLQASGLPG SAELTVGAAVACFLALEGA DVSYTNHRGRSPLDLAAEG RVLKALQGCAQRFRERQA GGGAAPGPRQTLGTPNTV TNLHVGAAPGPEAAECLV CSELALLVLFSPCQHRTVCE ECARRMKKCIRCQVVVSKK LRPDGSEVASAAPAPGPPR QLVEELQSRYRQMEERITC PICIDSHIRLVFQCGHGACA PCGSALSACPICRQPIRDRI QIFV | A*02:03, A*11:01, A*11:02, A*24:02, A*24:07, A*24:10, A*33:03, B*15:01, B*39:01, B*40:01, B*58:01, C*03:02, C*03:04, C*07:02, C*12:02, C*14:02 |

TABLE 9-continued

Recurrent N terminal sequences with high affinity to MHC Class I

| SEQ ID NO. | Gene | N terminal sequence | High Affinity HLA |
|---|---|---|---|
| SEQ ID NO: 1935 | ENSG00000204839.4 | MAGGVWGRSRAREAPVG ALTLTALTEGIRARQGQPQ GPPSAGPQPKSWEVKPEA EPQTQALTAPSEAEPGRGA TVPEAGSEPCSLNSALEPAP EGPHQVPQSSWEEGVLAD LALYTAACLEEAGFAGTQA TVLTLSSALEARGERLEDQV HALVRGLLAQVPSLAEGRP WRAALRVLSALALEHARD VVCALLPRSLPADRVAAEL WRSLSRNQRVNGQVLVQL LWALKGASGPEPQALAAT RALGEMLAVSGCVGATRG FYPHLLLALVTQLHKLARSP CSPDMPKIWVLSHRGPPH SHASCAVEALKALLTGDGG RMVVTCMEQAGGWRRLV GAHTHLEGVLLLASAMVA HADHHLRGLFADLLPRLRS ADDPQRLTAMAFFTGLLQ SRPTARLLREEVILERLLTW QGDPEPTVRWLGLLGLGH LALNRRKVRHVSTLLPALLG ALGEGDARLVGAALGALR RLLLRPRAPVRLLSAELGPR LPPLLDDTRDSIRASAVGLL GTLVRRGRGGLRLGLRGPL RKLVLQSLVPLLLRLHDPSR DAAESSEWTLARCDHAFC WGLLEELVTVAHYDSPEAL SHLCCRLVQRYPGHVPNFL SQTQGYLRSPQDPLRRAA AVLIGFLVHHASPGCVNQD LLDSLFQDLGRLQSDPKPA VAAAAHVSAQQVA | A*02:03, A*11:01, A*11:02, A*24:02, A*24:07, A*24:10, A*33:03, B*39:01, B*40:01, B*58:01, C*03:02, C*03:04, C*14:02 |
| SEQ ID NO: 1936 | ENSG00000205277.5 | MLVIWILTLALRLCASVTTV TPGSTVNTSIGGNTTSASTP SSSDPFTTFSDYGVSVTFIT GSTATKHFLDSSTNSGHSE ESTVSHSGPGATGTTLFPS HSATSVFVGEPKTSPITSAS METTALPGSTTTAGLSEKS TTFYSSPRSPDRTLSPARTT SSGVSEKSTTSHSRPGPTHT IAFPDSTTMPGVSQESTAS HSIPGSTDTTLSPGTTTPSSL GPESTTFHSSPGYTKTTRLP DNTTTSGLLEASTPVHSST GSPHTTLSPSSSTTHEGEPT TFQSWPSSKDTSPAPSGTT SAFVKLSTTYHSSPSSTPTT HFSASSTTLGHSEESTPVHS SPVATATTPPPARSATSGH VEESTAYHRSPGSTQTMHF PESSTTSGHSEESATFHGST THTKSSTPSTTAALAHTSYH SSLGSTETTHFRDSSTISGRS EESKASHSSPDAMATTVLP AGSTPSVLVGDSTPSPISSG SMETTALPGSTTKPGLSEKS TTFYSSPRSPDTTHLPASM TSSGVSEESTTSHSRPGSTH TTAFPGSTTMPGLSQESTA SHSSPGPTDTTLSPGSTTAS SLGPEYTTFHSRPGSTETTL LPDNTTASGLLEASMPVHS STRSPHTTLSPAGSTTRQG ESTTFHSWPSSKDTRPAPP TTTSAFVEPSTTSHGSPSSIP TTHISARSTTSGLVEESTTY HSSPGSTQTMHFPESDTTS GRGEESTTSHSSTTHTISSA PSTTSALVEEPTSYHSSPGS TATTHFPDSSTTSGRSEEST | A*02:03, A*11:01, A*11:02, A*24:02, A*24:10, A*33:03, B*15:01, B*39:01, B*40:01, B*55:02, B*58:01, C*03:02, C*03:04, C*03:67, C*07:02, C*12:02, C*14:02, C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | ASHSSQDATGTIVLPARSTT | |
| | | SVLLGESTTSPISSGSMETT | |
| | | ALPGSTTTPGLSERSTTFHS | |
| | | SPRSPATTLSPASTTSSGVS | |
| | | EESTTSRSRPGSTHTTAFPD | |
| | | STTTPGLSRHSTTSHSSPGS | |
| | | TDTTLLPASTTTSGPSQEST | |
| | | TSHSSSGSTDTALSPGSTTA | |
| | | LSFGQESTTFHSNPGSTHT | |
| | | TLFPDSTTSSGIVEASTRVH | |
| | | SSTGSPRTTLSPASSTSPGL | |
| | | QGESTAFQTHPASTHTTPS | |
| | | PPSTATAPVEESTTYHRSP | |
| | | GSTPTTHFPASSTTSGHSEK | |
| | | STIFHSSPDASGTTPSSAHS | |
| | | TTSGRGESTTSRISPGSTEIT | |
| | | TLPGSTTTPGLSEASTTFYSS | |
| | | PRSPTTTLSPASMTSLGVG | |
| | | EESTTSRSQPGSTHSTVSPA | |
| | | STTTPGLSEESTTVYSSSRG | |
| | | STETTVFPHSTTTSVHGEEP | |
| | | TTFHSRPASTHTTLFTEDST | |
| | | TSGLTEESTAFPGSPASTQT | |
| | | GLPATLTTADLGEESTTFPS | |
| | | SSGSTGTKLSPARSTTSGLV | |
| | | GESTPSRLSPSSTETTTLPGS | |
| | | PTTPSLSEKSTTFYTSPRSPD | |
| | | ATLSPATTTSSGVSEESSTS | |
| | | HSQPGSTHTTAFPDSTTTS | |
| | | DLSQEPTTSHSSQGSTEATL | |
| | | SPGSTTASSLGQQSTTFHSS | |
| | | PGDTETTLLPDDTITSGLVE | |
| | | ASTPTHSSTGSLHTTLTPAS | |
| | | STSAGLQEESTTFQSWPSS | |
| | | SDTTPSPPGTTAAPVEVST | |
| | | TYHSRPSSTPTTHFSASSTT | |
| | | LGRSEESTTVHSSPGATGT | |
| | | ALFPTRSATSVLVGEPTTSP | |
| | | ISSGSTETTALPGSTTTAGLS | |
| | | EKSTTFYSSPRSPDTTLSPAS | |
| | | TTSSGVSEESTTSHSRPGST | |
| | | HTTAFPGSTTMPGVSQEST | |
| | | ASHSSPGSTDTTLSPGSTTA | |
| | | SSLGPESTTFHSSPGSTETT | |
| | | LLPDNTTASGLLEASTPVHS | |
| | | STGSPHTTLSPAGSTTRQG | |
| | | ESTTFQSWPSSKDTMPAP | |
| | | PTTTSAFVELSTTSHGSPSS | |
| | | TPTTHFSASSTTLGRSEEST | |
| | | TVHSSPVATATTPSPARSTT | |
| | | SGLVEESTAYHSSPGSTQT | |
| | | MHFPESSTASGRSEESRTS | |
| | | HSSTTHTISSPPSTTSALVEE | |
| | | PTSYHSSPGSTATTHFPDSS | |
| | | TTSGRSEESTASHSSQDAT | |
| | | GTIVLPARSTTSVLLGESTTS | |
| | | PISSGSMETTALPGSTTTPG | |
| | | LSEKSTTFHSSPRSPATTLSP | |
| | | ASTTSSGVSEESTTSHSRPG | |
| | | STHTTAFPDSTTTPGLSRHS | |
| | | TTSHSSPGSTDTTLLPASTT | |
| | | TSGPSQESTTSHSSPGSTDT | |
| | | ALSPGSTTALSFGQESTTFH | |
| | | SSPGSTHTTLFPDSTTSSGI | |
| | | VEASTRVHSSTGSPRTTLSP | |
| | | ASSTSPGLQGESTAFQTHP | |
| | | ASTHTTPSPPSTATAPVEES | |
| | | TTYHRSPGSTPTTHFPASST | |
| | | TSGHSEKSTIFHSSPDASGT | |
| | | TPSSAHSTTSGRGESTTSRI | |
| | | SPGSTEITTLPGSTTTPGLSE | |
| | | ASTTFYSSPRSPTTTLSPAS | |
| | | MTSLGVGEESTTSRSQPGS | |
| | | THSTVSPASTTTPGLSEEST | |
| | | TVYSSSPGSTETTVFPRTPT | |
| | | TSVRGEEPTTFHSRPASTH | |

TABLE 9-continued

Recurrent N terminal sequences with high affinity to MHC Class I

| SEQ ID NO. | Gene | N terminal sequence | High Affinity HLA |
|---|---|---|---|
| | | TTLFTEDSTTSGLTEESTAFP | |
| | | GSPASTQTGLPATLTTADL | |
| | | GEESTTFPSSSGSTGTTLSP | |
| | | ARSTTSGLVGESTPSRLSPS | |
| | | STETTTLPGSPTTPSLSEKST | |
| | | TFYTSPRSPDATLSPATTTS | |
| | | SGVSEESSTSHSQPGSTHT | |
| | | TAFPDSTTTPGLSRHSTTSH | |
| | | SSPGSTDTTLLPASTTTSGP | |
| | | SQESTTSHSSPGSTDTALSP | |
| | | GSTTALSFGQESTTFHSSPG | |
| | | STHTTLFPDSTTSSGIVEAST | |
| | | RVHSSTGSPRTTLSPASSTS | |
| | | PGLQGESTTFQTHPASTHT | |
| | | TPSPPSTATAPVEESTTYHR | |
| | | SPGSTPTTHFPASSTTSGHS | |
| | | EKSTIFHSSPDASGTTPSSA | |
| | | HSTTSGRGESTTSRISPGST | |
| | | EITTLPGSTTTPGLSEASTTF | |
| | | YSSPRSPTTTLSPASMTSLG | |
| | | VGEESTTSRSQPGSTHSTV | |
| | | SPASTTTPGLSEESTTVYSSS | |
| | | PGSTETTVFPRSTTTSVRGE | |
| | | EPTTFHSRPASTHTTLFTED | |
| | | STTSGLTEESTAFPGSPAST | |
| | | QTGLPATLTTADLGEESTTF | |
| | | PSSSGSTGTTLSPARSTTSG | |
| | | LVGESTPSRLSPSSTETTTLP | |
| | | GSPTTPSLSEKSTTFYTSPRS | |
| | | PDATLSPATTTSSGVSEESS | |
| | | TSHSQPGSTHTTAFPDSTT | |
| | | TSGLSQEPTASHSSQGSTE | |
| | | ATLSPGSTTASSLGQQSTTF | |
| | | HSSPGDTETTLLPDDTITSG | |
| | | LVEASTPTHSSTGSLHTTLT | |
| | | PASSTSAGLQEESTTFQSW | |
| | | PSSSDTTPSPPGTTAAPVE | |
| | | VSTTYHSRPSSTPTTHFSAS | |
| | | STTLGRSEESTTVHSSPGAT | |
| | | GTALFPTRSATSVLVGEPTT | |
| | | SPISSGSTETTALPGSTTTA | |
| | | GLSEKSTTFYSSPRSPDTTLS | |
| | | PASTTSSGVSEESTTSHSRP | |
| | | GSTHTTAFPGSTTMPGVS | |
| | | QESTASHSSPGSTDTTLSP | |
| | | GSTTASSLGPESTTFHSGPG | |
| | | STETTLLPDNTTASGLLEAS | |
| | | TPVHSSTGSPHTTLSPAGST | |
| | | TRQGESTTFQSWPNSKDT | |
| | | TPAPPTTTSAFVELSTTSHG | |
| | | SPSSTPTTHFSASSTTLGRS | |
| | | EESTTVHSSPVATATTPSPA | |
| | | RSTTSGLVEESTTYHSSPGS | |
| | | TQTMHFPESDTTSGRGEES | |
| | | TTSHSSTTHTISSAPSTTSAL | |
| | | VEEPTSYHSSPGSTATTHFP | |
| | | DSSTTSGRSEESTASHSSQ | |
| | | DATGTIVLPARSTTSVLLGE | |
| | | STTSPISSGSMETTALPGST | |
| | | TTPGLSEKSTTFHSSPRSPA | |
| | | TTLSPASTTSSGVSEESTTS | |
| | | HSRPGSTHTTAFPDSTTTP | |
| | | GLSRHSTTSHSSPGSTDTTL | |
| | | LPASTTTSGSSQESTTSHSS | |
| | | SGSTDTALSPGSTTALSFG | |
| | | QESTTFHSSPGSTHTTLFPD | |
| | | STTSSGIVEASTRVHSSTGS | |
| | | PRTTLSPASSTSPGLQGEST | |
| | | AFQTHPASTHTTPSPPSTA | |
| | | TAPVEESTTYHRSPGSTPTT | |
| | | HFPASSTTSGHSEKSTIFHS | |
| | | SPDASGTTPSSAHSTTSGR | |
| | | GESTTSRISPGSTEITTLPGS | |
| | | TTTPGLSEASTTFYSSPRSP | |
| | | TTTLSPASMTSLGVGEESTT | |
| | | SRSQPGSTHSTVSPASTTTP | |

TABLE 9-continued

Recurrent N terminal sequences with high affinity to MHC Class I

| SEQ ID NO. | Gene | N terminal sequence | High Affinity HLA |
|---|---|---|---|
| | | GLSEESTTVYSSSPGSTETT | |
| | | VFPRSTTTSVRREEPTTFHS | |
| | | RPASTHTTLFTEDSTTSGLT | |
| | | EESTAFPGSPASTQTGLPA | |
| | | TLTTADLGEESTTFPSSSGS | |
| | | TGTKLSPARSTTSGLVGEST | |
| | | PSRLSPSSTETTTLPGSPTTP | |
| | | SLSEKSTTFYTSPRSPDATLS | |
| | | PATTTSSGVSEESSTSHSQP | |
| | | GSTHTTAFPDSTTTSGLSQ | |
| | | EPTTSHSSQGSTEATLSPGS | |
| | | TTASSLGQQSTTFHSSPGD | |
| | | TETTLLPDDTITSGLVEASTP | |
| | | THSSTGSLHTTLTPASSTST | |
| | | GLQEESTTFQSWPSSSDTT | |
| | | PSPPSTTAVPVEVSTTYHSR | |
| | | PSSTPTTHFSASSTTLGRSE | |
| | | ESTTVHSSPGATGTALFPTR | |
| | | SATSVLVGEPTTSPISSGSTE | |
| | | TTALPGSTTTAGLSEKSTTF | |
| | | YSSPRSPDTTLSPASTTSSG | |
| | | VSEESTTSHSRPGSMHTTA | |
| | | FPSSTTMPGVSQESTASHS | |
| | | SPGSTDTTLSPGSTTASSLG | |
| | | PESTTFHSSPGSTETTLLPD | |
| | | NTTASGLLEASTPVHSSTGS | |
| | | PHTTLSPAGSTTRQGESTT | |
| | | FQSWPNSKDTTPAPPTTTS | |
| | | AFVELSTTSHGSPSSTPTTH | |
| | | FSASSTTLGRSEESTTVHSS | |
| | | PVATATTPSPARSTTSGLVE | |
| | | ESTTYHSSPGSTQTMHFPE | |
| | | SNTTSGRGEESTTSHSSTTH | |
| | | TISSAPSTTSALVEEPTSYHS | |
| | | SPGSTATTHFPDSSTTSGRS | |
| | | EESTASHSSQDATGTIVLPA | |
| | | RSTTSVLLGESTTSPISSGS | |
| | | METTALPGSTTTPGLSEKST | |
| | | TFHSSPSSTPTTHFSASSTTL | |
| | | GRSEESTTVHSSPVATATTP | |
| | | SPARSTTSGLVEESTAYHSS | |
| | | PGSTQTMHFPESSTASGRS | |
| | | EESRTSHSSTTHTISSPPSTT | |
| | | SALVEEPTSYHSSPGSIATT | |
| | | HFPESSTTSGRSEESTASHS | |
| | | SPDTNGITPLPAHFTTSGRI | |
| | | AESTTFYISPGSMETTLAST | |
| | | ATTPGLSAKSTILYSSSRSPD | |
| | | QTLSPASMTSSSISGEPTSL | |
| | | YSQAESTHTTAFPASTTTSG | |
| | | LSQESTTFHSKPGSTETTLS | |
| | | PGSITTSSFAQEFTTPHSQP | |
| | | GSALSTVSPASTTVPGLSEE | |
| | | STTFYSSPGSTETTAFSHSN | |
| | | TMSIHSQQSTPFPDSPGFT | |
| | | HTVLPATLTTTDIGQESTAF | |
| | | HSSSDATGTTPLPARSTAS | |
| | | DLVGEPTTFYISPSPTYTTLF | |
| | | PASSSTSGLTEESTTFHTSPS | |
| | | FTSTIVSTESLETLAPGLCQE | |
| | | GQIWNGKQCVCPQGYVG | |
| | | YQCLSPLESFPVETPEKLNA | |
| | | TLGMTVKVTYRNFTEKMN | |
| | | DASSQEYQNFSTLFKNRM | |
| | | DVVLKGDNLPQYRGVNIR | |
| | | RLLNGSIVVKNDVILEADYT | |
| | | LEYEELFENLAEIVKAKIMN | |
| | | ETRTTLLDPDSCRKAILCYSE | |
| | | EDTFVDSSVTPGFDFQEQC | |
| | | TQKAAEGYTQFYYVDVLD | |
| | | GKLACVNKCTKGTKSQMN | |
| | | CNLGTCQLQRSGPRCLCPN | |
| | | TNTHWYWGETCEFNIAKS | |
| | | LVYGIVGAVMAVLLLALIILI | |
| | | ILFSLSQRKRHREQYDVPQ | |
| | | EWRKEGTPGIFQKTAIWE | |

TABLE 9-continued

Recurrent N terminal sequences with high affinity to MHC Class I

| SEQ ID NO. | Gene | N terminal sequence | High Affinity HLA |
|---|---|---|---|
| | | DQNLRESRFGLENAYNNF<br>RPTLETVDSGTELHIQRPE<br>MVASTV | |
| SEQ ID NO: 1937 | ENSG00000205744.5 | MESRAEGGSPAVFDWFFE<br>AACPASLQEDPPILRQFPP<br>DFRDQEAMQMVPKFCFP<br>FDVEREPPSPAVQHFTFAL<br>TDLAGNRRFGFCRLRAGT<br>QSCLCILSHLPWFEVFYKLL<br>NTVGDLLAQDQVTEAEELL<br>QNLFQQSLSGPQASVGLEL<br>GSGVTVSSGQGIPPPTRGN<br>SKPLSCFVAPDSGRLPSIPE<br>NRNLTELVVAVTDENIVGL<br>FAALLAERRVLLTASKLSTLT<br>SCVHASCALLYPMRWEHV<br>LIPTLPPHLLDYCCAPMPYL<br>IGVHASLAERVREKALEDV<br>VVLNVDANTLETTFNDVQ<br>ALPPDVVSLLRLRLRKVALA<br>PGEGVSRLFLKAQALLFGG<br>YRDALVCSPGQPVTFSEEV<br>FLAQKPGAPLQAFHRRAV<br>HLQLFKQFIEARLEKLNKGE<br>GFSDQFEQEITGCGASSGA<br>LRSYQLWADNLKKGGGAL<br>LHSVKAKTQPAVKNMYRS<br>AKSGLKGVQSLLMYKDGD<br>SVLQRGGSLRAPALPSRSD<br>RLQQRLPITQHFGKNRPLR<br>PSRRRQLEEGTSEPPGAGT<br>PPLSPEDEGCPWAEEALDS<br>SFLGSGEELDLLSEILDSLSM<br>GAKSAGSLRPSQSLDCCHR<br>GDLDSCFSLPNIPRWQPD<br>DKKLPEPEPQPLSLPSLQN<br>ASSLDATSSSKDSRSQLIPS<br>ESDQEVTSPSQSSTASADP<br>SIWGDPKPSPLTEPLILHLT<br>PSHKAAEDSTAQENPTPW<br>LSTAPTEPSPPESPQILAPTK<br>PNFDIAWTSQPLDPSSDPS<br>SLEDPRARPPKALLAERAHL<br>QPREEPGALNSPATPTSNC<br>QKSQPSSRPRVADLKKCFE<br>G | A*02:03, A*11:01, A*11:02,<br>A*24:10, A*33:03, B*15:01,<br>B*39:01, B*40:01, B*55:02,<br>B*58:01, C*03:02,<br>C*03:04, C*14:02 |
| SEQ ID NO: 1938 | ENSG00000213420.3 | MSALRPLLLLLLPLCPGPGP<br>GPGSEAKVTRSCAETRQVL<br>GARGYSLNLIPPALISGEHL<br>RVCPQEYTCCSSETEQRLIR<br>ETEATFRGLVEDSGSFLVHT<br>LAARHRKFDEFFLEMLSVA<br>QHSLTQLFSHSYGRLYAQH<br>ALIFNGLFSRLRDFYGESGE<br>GLDDTLADFWAQLLERVF<br>PLLHPQYSFPPDYLLCLSRL<br>ASSTDGSLQPFGDSPRRLR<br>LQITRTLVAARAFVQGLET<br>GRNVVSEALKVPVSEGCSQ<br>ALMRLIGCPLCRGVPSLMP<br>CQGFCLNVVRGCLSSRGLE<br>PDWGNYLDGLLILADKLQ<br>GPFSFELTAESIGVKISEGL<br>MYLQENSAKVSAQVFQEC<br>GPPDPVPARNRRAPPPRE<br>EAGRLWSMVTEEERPTTA<br>AGTNLHRLVWELRERLAR<br>MRGFWARLSLTVCGDSR<br>MAADASLEAAPCWTGAG<br>RGRYLPPVVGGSPAEQVN<br>NPELKVDASGPDVPTRRRR<br>LQLRAATARMKTAALGHD<br>LDGQDADEDASGSGGGQ<br>QYADDWMAGAVAPPARP | A*02:03, A*11:01, A*11:02,<br>A*24:02, A*24:10, A*33:03,<br>B*15:01, B*15:27, B*38:02,<br>B*39:01, B*40:01, B*58:01,<br>C*03:02, C*03:04, C*12:02,<br>C*14:02, C*15:02 |

TABLE 9-continued

| Recurrent N terminal sequences with high affinity to MHC Class I | | | |
|---|---|---|---|
| SEQ ID NO. | Gene | N terminal sequence | High Affinity HLA |
| | | PRPPYPPRRDGSGGKGGG<br>GSARYNQGRSRSGGASIGF<br>HTQTILILSLSALALLGPR | |
| SEQ ID NO: 1939 | ENSG00000225485.3 | MNGVAFCLVGIPPRPEPRP<br>PQLPLGPRDGCSPRRPFP<br>WQGPRTLLLYKSPQDGFG<br>FTLRHFIVYPPESAVHCSLK<br>EEENGGRGGGPSPRYRLEP<br>MDTIFVKNVKEDGPAHRA<br>GLRTGDRLVKVNGESVIGK<br>TYSQVIALIQNSDDTLELSI<br>MPKDEDILQLAYSQDAYLK<br>GNEPYSGEARSIPEPPPICY<br>PRKTYAPPARASTRATMVP<br>EPTSALPSDPRSPAAWSDP<br>GLRVPPAARAHLDNSSLG<br>MSQPRPSPGAFPHLSSEPR<br>TPRAFPEPGSRVPPSRLEC<br>QQALSHWLSNQVPRRAG<br>ERRCPAMAPRARSASQDR<br>LEEVAAPRPWPCSTSQDAL<br>SQLGQEGWHRARSDDYLS<br>RATRSAEALGPGALVSPRF<br>ERCGWASQRSSARTPACP<br>TRDLPGPQAPPPSGLQGL<br>DDLGYIGYRSYSPSFQRRT<br>GLLHALSFRDSPFGGLPTF<br>NLAQSPASFPPEASEPPRV<br>VRPEPSTRALEPPAEDRGD<br>EVVLRQKPPTGRKVQLTPA<br>RQMNLGFGDESPEPEASG<br>RGERLGRKVAPLATTEDSL<br>ASIPFIDEPTSPSIDLQAKHV<br>PASAVVSSAMNSAPVLGT<br>SPSSPTFTFTLGRHYSQDCS<br>SIKAGRRSSYLLAITTERSKS<br>CDDGLNTFRDEGRVLRRLP<br>NRIPSLRMLRSFFTDGSLDS<br>WGTSEDADAPSKRHSTSD<br>LSDATFSDIRREGWLYYKQI<br>LTKKGKKAGSGLRQWKRV<br>YAALRARSLSLSKERREPGP<br>AAAGAAAAGAGEDEAAPV<br>CIG | A*02:03, A*11:01, A*11:02,<br>A*24:02, A*24:07, A*24:10,<br>B*15:01, B*39:01, B*40:01,<br>B*55:02, B*58:01, C*03:02,<br>C*03:04, C*03:67, C*12:02,<br>C*14:02, C*15:02 |
| SEQ ID NO: 1940 | ENSG00000243449.2 | MFRAALEDSVEKKSSLKET<br>ETTSKGTSKYDRERETEMK<br>TVMGMKMHFWVRTPAS<br>GRGRGGSDHARSRAAPLP<br>LLA | A*02:03, A*24:10, A*33:03,<br>B*27:04, B*38:02, B*39:01,<br>B*40:01, C*01:02, C*03:02,<br>C*03:04, C*03:67, C*04:01,<br>C*07:02, C*14:02, C*15:02 |
| SEQ ID NO: 1941 | ENSG00000261787.1 | MDRGRPAGSPLSASAEPA<br>PLAAAIRDSRPGRTGPGPA<br>GPGGGSRSGSGRPAAANA<br>ARERSRVQTLRHAFLELQR<br>TLPSVPPDTKLSKLDVLLLA<br>TTYIAHLTRSLQDDAEAPA<br>DAGLGALRGDGYLHPVKK<br>WPMRSRLYIGATGQFLKH<br>SVSGEKTNHDNTPTDSQP | A*02:03, A*24:02, A*24:10,<br>A*33:03, B*40:01, C*03:02,<br>C*03:04, C*12:02, C*14:02 |

TABLE 10

| Peptide pools for alternative promoters | | | | |
|---|---|---|---|---|
| SEQ ID NO. | Peptide Pool | Alternative Promoter | Peptide Sequence | Corresponding HLA variant |
| SEQ ID NO: 1942 | 1 | DNAH3 | MAEKLQEANFLLEDI | A*02:01 |
| SEQ ID NO: 1943 | | | QYSHIADKVSEVPAN | A*02:03 |

TABLE 10-continued

Peptide pools for alternative promoters

| SEQ ID NO. | Peptide Pool | Alternative Promoter | Peptide Sequence | Corresponding HLA variant |
|---|---|---|---|---|
| SEQ ID NO: 1944 | | | FLKKSSAVTVFKLRR | A*03:01 |
| SEQ ID NO: 1945 | | | PKLKYIPLKFSFTAA | A*24:02 |
| SEQ ID NO: 1946 | | | EHLHTVNPMMLRLKE | A*33:03 |
| SEQ ID NO: 1947 | | | VSDFLIQTFKVFQKN | B*15:01 |
| SEQ ID NO: 1948 | | | DNTAEQNIAAFLKEN | B*40:01 |
| SEQ ID NO: 1949 | | | VNPMMLRLKELWFAE | B*58:01 |
| SEQ ID NO: 1950 | | | KTSLTFPGSRPMSPE | C*03:02 |
| SEQ ID NO: 1951 | | | IEEYFASVASFMSLQ | C*14:02 |
| SEQ ID NO: 1952 | | | NEIASMNITVPLAMF | C*15:02 |
| SEQ ID NO: 1953 | 2 | DST | NPKLTLGLIWTIILH | A*02:01 |
| SEQ ID NO: 1954 | | | FTKWINQHLMKVRKH | A*02:03 |
| SEQ ID NO: 1955 | | | ERDKVQKKTFTKWIN | A*03:01 |
| SEQ ID NO: 1956 | | | ISLLEVLSGDTLPRE | B*40:01 |
| SEQ ID NO: 1957 | | | MAGYLSPAAYLYVEE | C*03:02 |
| SEQ ID NO: 1958 | | | MAGYLSPAAYLYVE | C*14:02 |
| SEQ ID NO: 1959 | 3 | EPS8L1 | ADVSQYPVNHLVTFC | A*02:01 |
| SEQ ID NO: 1960 | | | EVDILNHVFDDVESF | A*02:03 |
| SEQ ID NO: 1961 | | | MSTATGPEAAPKPSA | A*11:01 |
| SEQ ID NO: 1962 | | | AQPDVHFFQGLRLGA | A*33:03 |
| SEQ ID NO: 1963 | | | ILNHVFDDVESFVSR | B*15:02 |
| SEQ ID NO: 1964 | | | VSQYPVNHLVTFCLG | B*35:03 |
| SEQ ID NO: 1965 | | | PASKEELESYPLGAI | B*40:01 |
| SEQ ID NO: 1966 | | | EPERAQPDVHFFQGL | B*58:01 |
| SEQ ID NO: 1967 | 4 | FRMD4B | VEDLLFSGSRFVWNL | A*02:01 |
| SEQ ID NO: 1968 | | | LLDLVASHFNLKEKE | A*11:01 |
| SEQ ID NO: 1969 | | | TVSTLRRWYTERLRA | A*33:03 |
| SEQ ID NO: 1970 | | | QIEVESETIFKLAAF | B*40:01 |
| SEQ ID NO: 1971 | | | VWNLTVSTLRRWYTE | B*58:01 |
| SEQ ID NO: 1972 | | | AVRFYIESISFLKDK | C*07:02 |
| SEQ ID NO: 1973 | 5 | LAMA3 | AEGVLLDYLVLLPRD | A*02:01 |
| SEQ ID NO: 1974 | | | SRIAMYELLADADIQ | A*02:03 |
| SEQ ID NO: 1975 | | | RTNTLLGHLISKAQR | A*03:01 |
| SEQ ID NO: 1976 | | | VIHFYQAAHPTFPAQ | A*24:02 |
| SEQ ID NO: 1977 | | | TKATNIRLRFLRTNT | A*33:03 |
| SEQ ID NO: 1978 | | | YAQMTSVQNDVRITL | A*68:01 |

TABLE 10-continued

Peptide pools for alternative promoters

| SEQ ID NO. | Peptide Pool | Alternative Promoter | Peptide Sequence | Corresponding HLA variant |
|---|---|---|---|---|
| SEQ ID NO: 1979 | | | CLLYQHLPVTRFPCT | B*15:01 |
| SEQ ID NO: 1980 | | | DKVSSYGGYLTYQAK | B*15:02 |
| SEQ ID NO: 1981 | | | LSGREVELHLRLRIP | B*40:01 |
| SEQ ID NO: 1982 | | | LHKKSMDKSLEFITN | B*58:01 |
| SEQ ID NO: 1983 | | | DGYFALEKSNYFGCQ | C*03:02 |
| SEQ ID NO: 1984 | | | ENNYYFPDLHHMKYE | C*07:02 |
| SEQ ID NO: 1985 | | | ILRYVNPGTEAVSGH | C*12:02 |
| SEQ ID NO: 1986 | | | ADPFSITPGIWVACI | C*15:02 |
| SEQ ID NO: 1987 | 6 | MET | QNVILHEHHIFLGAT | A*02:01 |
| SEQ ID NO: 1988 | | | CKEALAKSEMNVNMK | A*02:03 |
| SEQ ID NO: 1989 | | | MDRSAMCAFPIKYVN | A*11:01 |
| SEQ ID NO: 1990 | | | TDQSYIDVLPEFRDS | A*24:02 |
| SEQ ID NO: 1991 | | | LDAQTFHTRIIRFCS | A*33:03 |
| SEQ ID NO: 1992 | | | SNNFIYFLTVQRETL | A*68:01 |
| SEQ ID NO: 1993 | | | KDGFMFLTDQSYIDV | B*15:01 |
| SEQ ID NO: 1994 | | | RDSYPIKYVHAFESN | B*35:03 |
| SEQ ID NO: 1995 | | | QKVAEYKTGPVLEHP | B*40:01 |
| SEQ ID NO: 1996 | | | CSSKANLSGGVWKDN | B*58:01 |
| SEQ ID NO: 1997 | | | RDEYRTEFTTALQRV | C*07:02 |
| SEQ ID NO: 1998 | | | TINSSYFPDHPLHSI | C*12:03 |
| SEQ ID NO: 1999 | | | PMDRSAMCAFPIKYV | C*15:02 |
| SEQ ID NO: 2000 | 7 | MIB2 | GASGIVEVLTEVPNI | A*02:01 |
| SEQ ID NO: 2001 | | | QGFTLLHHASLKGHA | A*03:01 |
| SEQ ID NO: 2002 | | | ENKSSLSVALDKLRA | A*11:01 |
| SEQ ID NO: 2003 | | | QVAAYLGQVELIRLL | A*24:02 |
| SEQ ID NO: 2004 | | | TALHLAALNNHREVA | A*33:03 |
| SEQ ID NO: 2005 | | | CVGEAAGGFYYKDHL | A*68:01 |
| SEQ ID NO: 2006 | | | LQRRVSADSQPFQHG | B*15:01 |
| SEQ ID NO: 2007 | | | GNLRVAVAGQRWTFS | B*58:01 |
| SEQ ID NO: 2008 | | | EDGFTALHLAALNNH | C*03:02 |
| SEQ ID NO: 2009 | | | GGFYYKDHLPRLGKP | C*07:02 |
| SEQ ID NO: 2010 | 8 | MRC2 | DSCYQFNFQSTLSWR | A*02:01 |
| SEQ ID NO: 2011 | | | TDGSIINFISWAPGK | A*02:03 |
| SEQ ID NO: 2012 | | | RDCSIALPYVCKKKP | A*11:01 |
| SEQ ID NO: 2013 | | | EWLRFQEAEYKFFEH | A*24:02 |
| SEQ ID NO: 2014 | | | SGDEVMYTHWNRDQP | A*33:03 |

TABLE 10-continued

| Peptide pools for alternative promoters | | | | |
|---|---|---|---|---|
| SEQ ID NO. | Peptide Pool | Alternative Promoter | Peptide Sequence | Corresponding HLA variant |
| SEQ ID NO: 2015 | | | RFEQAFVSSLIYNWE | B*15:02 |
| SEQ ID NO: 2016 | | | GWTWHSPSCYWLGED | B*38:02 |
| SEQ ID NO: 2017 | | | TNRFEQAFVSSLIYN | B*40:01 |
| SEQ ID NO: 2018 | | | QGRREWLRFQEAEYK | B*40:06 |
| SEQ ID NO: 2019 | | | LCALPYHEVYTIQGN | B*51:01 |
| SEQ ID NO: 2020 | | | CPIKSNDCETFWDKD | B*58:01 |
| SEQ ID NO: 2021 | | | GGCVALATGSAMGLW | C*03:02 |
| SEQ ID NO: 2022 | | | EGEYFWTALQDLNST | C*14:02 |
| SEQ ID NO: 2023 | 9 | NOS2 | PDELLPQAIEFVNQY | A*02:01 |
| SEQ ID NO: 2024 | | | SKSCLGSIMTPKSLT | A*11:01 |
| SEQ ID NO: 2025 | | | VKLDATPLSSPRHVR | A*68:01 |
| SEQ ID NO: 2026 | | | IGRIQWSNLQVFDAR | B*15:01 |
| SEQ ID NO: 2027 | | | AIEFVNQYYGSFKEA | B*15:02 |
| SEQ ID NO: 2028 | | | TKEIETTGTYQLTGD | B*40:01 |
| SEQ ID NO: 2029 | | | MACPWKFLFKTK | B*58:01 |
| SEQ ID NO: 2030 | 10 | PLEC | RPRSLHPHVPGVTNL | A*02:01 |
| SEQ ID NO: 2031 | | | MVAGMLMPRDQL | A*11:01 |
| SEQ ID NO: 2032 | | | HLRQYLHLPPEIVPA | A*24:02 |
| SEQ ID NO: 2033 | | | RETFAWCHFYWYLTN | C*03:02 |
| SEQ ID NO: 2034 | 11 | PLEKHG5 | KKKSLGEVLLPVFER | A*02:01 |
| SEQ ID NO: 2035 | | | LWASVMAPVLEKARR | A*03:01 |
| SEQ ID NO: 2036 | | | LHTEASYIRKLRVII | A*33:03 |
| SEQ ID NO: 2037 | | | SLGEVLLPVFERKGI | A*68:01 |
| SEQ ID NO: 2038 | | | WKNRAASRFSGFFSS | B*15:01 |
| SEQ ID NO: 2039 | | | KNMSEFLGEASIPGQ | B*40:01 |
| SEQ ID NO: 2040 | | | GSSGSTNTGDSWKNR | B*58:01 |
| SEQ ID NO: 2041 | | | TFEAYRFGGHYLRVK | C*14:02 |
| SEQ ID NO: 2042 | 12 | PTGDS | THHTLWMGLALLGVL | A*02:01 |
| SEQ ID NO: 2043 | | | HTLWMGLALLGVLGD | A*02:03 |
| SEQ ID NO: 2044 | | | APEAQVSVQPNFQQD | B*15:01 |
| SEQ ID NO: 2045 | | | MATHHTLWMGLA | C*03:02 |
| SEQ ID NO: 2046 | 13 | RASA3 | GPSKMRDCYCTVNLD | A*02:03 |
| SEQ ID NO: 2047 | | | EIPRSFRHLSFYIFD | A*03:01 |
| SEQ ID NO: 2048 | | | RYTAVSSFIFLRFFA | A*11:01 |
| SEQ ID NO: 2049 | | | FKESYMATFYEFFNE | A*24:02 |

TABLE 10-continued

Peptide pools for alternative promoters

| SEQ ID NO. | Peptide Pool | Alternative Promoter | Peptide Sequence | Corresponding HLA variant |
|---|---|---|---|---|
| SEQ ID NO: 2050 | | | LSFYIFDRDVFRRDS | A*33:03 |
| SEQ ID NO: 2051 | | | KESYMATFYEFFNEQ | B*15:01 |
| SEQ ID NO: 2052 | | | DADSEVQGKVHLELR | B*40:01 |
| SEQ ID NO: 2053 | | | DVRYTAVSSFIFLRF | B*58:01 |
| SEQ ID NO: 2054 | | | DHVFSSDYYSPLRDL | C*03:02 |
| SEQ ID NO: 2055 | | | GEDFYCEIPRSFRHL | C*07:02 |
| SEQ ID NO: 2056 | | | SSDYYSPLRDLLLKS | C*14:02 |
| SEQ ID NO: 2057 | 14 | TRPM2 | HSKLQMHHVAQVLRE | A*02:03 |
| SEQ ID NO: 2058 | | | RLKSIFRRGLVKVAQ | A*03:01 |
| SEQ ID NO: 2059 | | | HPTMTAALISNKPEF | A*11:01 |
| SEQ ID NO: 2060 | | | LLGDFTQPLYPRPRH | A*33:03 |
| SEQ ID NO: 2061 | | | ECGLMKKAALYFSDF | B*15:01 |
| SEQ ID NO: 2062 | | | VQLKEFVTWDTLLYL | B*40:01 |
| SEQ ID NO: 2063 | | | MKKAALYFSDFWNKL | B*58:01 |
| SEQ ID NO: 2064 | | | HVTFTMDPIRDLLIW | C*12:02 |
| SEQ ID NO: 2065 | | | AALYFSDFWNKLDVG | C*14:02 |
| SEQ ID NO: 2066 | 15 | IKZF3 | SAAVLNDYSLTKSHE | A*03:01 |
| SEQ ID NO: 2067 | | | LERHVVSFDSSRPTS | A*33:03 |
| SEQ ID NO: 2068 | | | LNDYSLTKSHEMENV | C*03:02 |

To explore if somatic promoters might contribute to reducing tumor antigen burden and immunoreactivity in vivo, we proceeded to examine correlations between promoter alterations and intra-tumor T-cell activity in various primary GC cohorts. First, to detect promoter alterations in a cohort of 95 GC-normal pairs (SG cohort), we generated a customized Nanostring panel targeting the top 95 recurrent GC somatic promoters, measuring transcripts associated with either the canonical promoter or the alternative promoter. There was a significant correlation between the Nanostring data and RNA-seq (FIG. 16, r=0.65, P<0.001), with ~35% of transcripts driven by alternate promoters upregulated in more than half of the GCs (FIG. 4D). Second, to examine markers of T-cell activity in these same GC samples, we analyzed previously published microarray data to measure CD8A (a measure of CD8+ tumor infiltrating lymphocytes), and granzyme A (GZMA) and perforin (PRF1), which are both T-cell effectors and validated markers of T-cell cytolytic activity. We confirmed that these three genes (CD8A, GZMA, and PRF1) were not themselves associated with somatic promoters. Comparing the top and bottom quartiles, GCs with high somatic promoter usage exhibited significantly lower GZMA and PRF1 levels (P<0.001 and P=0.01, Wilcoxon Test) indicating lower T-cell cytolytic activity (FIG. 4E, top left), and also a trend towards lower CD8A levels (P=0.14, Wilcoxon one sided test). Using two different algorithms (ASCAT and ESTIMATE), we further confirmed that the decreased GZMA and PRF1 levels are independent of tumor purity differences between GCs (FIG. 16). Similar results were obtained upon splitting the GC samples based on median promoter usage score (GZMA, P<0.001 and PRF1, P=0.03). Patients with GCs exhibiting high somatic promoter usage (top 25%) also showed poor survival compared to patients with GCs with low somatic promoter usage (bottom 25%) (FIG. 4*e* top right, HR 2.55, P=0.02). Again, dividing patients by their median somatic promoter usage score also showed similar survival differences (FIG. 11, HR=1.81, P=0.04).

To validate these findings, we then analyzed two other prominent GC cohorts-one from TCGA, and another from the Asian Cancer Research Group (ACRG). In the TCGA cohort, availability of RNA-seq data allowed us to infer somatic promoter usage directly from next-generation sequencing (NGS) data (FIG. 2*c*). Similar to the Singapore cohort, TCGA GCs with high somatic promoter usage (top 25%) exhibited decreased CD8A (P=0.002, Wilcoxon one sided test), GZMA (P=0.001, Wilcoxon one sided test) and PRF1 levels (P=0.005, Wilcoxon one sided test, FIG. 4*e* bottom left) compared to GCs with low somatic promoter usage (bottom 25%) in a manner independent of tumor purity (FIG. 16). Notably, as previous studies have suggested that somatic mutation burden may also correlate with intra-tumor T-cell cytolytic response, we further repeated the analysis after adjusting for the total number of missense mutations in each sample using a regression based approach. Even after correcting for somatic mutation burden, we still observed decreased CD8A (P=0.02, Wilcoxon one sided test), GZMA (P=0.01, Wilcoxon one sided test) and PRF1 expression (P=0.03, Wilcoxon one sided test) in samples with high somatic promoter usage (top 25% against bottom 25%) (FIG. 11).

We leveraged a third independent cohort of GC samples from ACRG. Using NanoString to target 89 canonical and alternative promoters along with various immune markers, we profiled 264 primary GC samples from the ACRG cohort. 40% of alternative promoter transcripts showed tumor specific expression in more than half of the samples (FIG. 11). Once again, samples with high somatic promoter usage (top 25%) showed significantly lower expression of T-cell cytolytic activity markers including CD8A (P=0.035, Wilcoxon one sided test), CD4A (P=0.005, Wilcoxon one sided test), GZMA (P=0.001, Wilcoxon one sided test) and PRF1 (P=0.025, Wilcoxon one sided test) (FIG. 4*e*, bottom right) (FIG. 16). Similar results were obtained upon splitting the GC samples based on median promoter usage score (Table 11) Also, after adjusting for mutational burden (for cases where information is available), samples with high somatic promoter usage still showed decreased CD8A (P=0.167, Wilcoxon one sided test), GZMA (P=0.009, Wilcoxon one sided test), and PRF1 (P=0.03, Wilcoxon one sided test) expression (FIG. 11). Taken collectively, these results, observed across multiple GC cohorts and assessed using diverse technologies (microarray, RNA-seq, Nanostring) all support a significant association between somatic promoter usage and reduced tumor immunity levels. Importantly, the decreased levels of T-cell cytolytic activity associated with somatic promoter usage are likely independent of tumor purity and mutational load.

TABLE 11

P values of Wilcoxon test between ACRG samples with high and low somatic promoter usage.

| Immune Marker | Top and Bottom 25 pctl | Divided by median (50 pctl) |
|---|---|---|
| CD4A | 0.01151 | 0.06053 |
| CD8A | 0.07829 | 0.02482 |
| CTLA4 | 0.2048 | 0.2952 |
| FOXP3 | 0.1054 | 0.1673 |
| GZMA | 0.002593 | 0.005957 |
| IFNg | 0.2376 | 0.8045 |
| IL-10 | 0.8391 | 0.9311 |
| LAG3 | 0.1672 | 0.2627 |
| PD1 | 0.1192 | 0.1506 |
| PDL1 | 0.5668 | 0.5869 |
| PRF1 | 0.01272 | 0.05873 |
| TIM3 | 0.578 | 0.9424 |
| TNFA | 0.1394 | 0.7184 |

* All P values are from Wilcoxon two sided test

Somatic Promoter Associated Peptides are Immunogenic In Vitro

To functionally test the ability of N-terminal peptides depleted in GC to elicit immune responses, we conducted in-vitro assays using the high-throughput EPIMAX (EPItope MAXimum) platform, which allows multi-epitope testing for both T cell proliferation and cytokine production. First, we identified N terminal peptides predicted to exhibit high HLA-binding affinities across a pool of healthy PBMC (peripheral blood mononuclear cell) donors. Second, selecting 15 alternative promoter-associated peptides for testing, we generated peptide pools for each peptide (Tables 9 and 10, Methods), which were then used to stimulate PBMCs from 9 healthy donors. T cell proliferation and cytokine production levels were measured and benchmarked against control peptides (Table 12). Across all 135 exposures (15 peptides across 9 donors), we observed strong cytokine responses for 79 peptide pools (58%; FC≥2 relative to Actin peptides) (FIG. 4*g*) inducing complex Th1, Th2 and Th17 polarizations in a donor dependent fashion (FIG. 17).

TABLE 12

Cytokine Responses of N terminal Peptides

| | | Analyte concentration (pg/ml) | | | | | | | | | | | | | Total analytes | Fold change of total cytokine response (normalized against |
|---|---|---|---|---|---|---|---|---|---|---|---|---|---|---|---|---|
| Sample | Treatment | GM-CSF | IFNg | IL-2 | IL-3 | IL-4 | IL-7 | IL-9 | IL-10 | IL-13 | IL-15 | IL-17A | sCD40L | TNFa | (pg/ml) | Actin control) |
| Donor 1 | DNAH3 | 99.39 | 228.45 | 89 | 6.35 | 2.12 | 0.085 | 7.32 | 24.91 | 228.24 | 0.925 | 1.88 | 4.47 | 264.89 | 958.03 | 2.89 |
| Donor 1 | DST | 114.18 | 149.87 | 58.02 | 11.41 | 0.03 | 0.085 | 14.11 | 57.29 | 311.22 | 0.925 | 1.58 | 8.97 | 251.98 | 979.67 | 2.96 |
| Donor 1 | EPS8L1 | 153.07 | 351.34 | 100.97 | 11.8 | 0.03 | 0.085 | 28.88 | 33.71 | 431.94 | 0.925 | 0.02 | 6.17 | 434.22 | 1553.16 | 4.69 |
| Donor 1 | FRMD4B | 55.53 | 121.17 | 76.42 | 10.54 | 0.03 | 1.43 | 16.77 | 36.13 | 198.37 | 0.925 | 0.93 | 3.76 | 186.12 | 708.13 | 2.14 |
| Donor 1 | LAMA3 | 67.29 | 152.66 | 99.6 | 4.83 | 1.72 | 0.085 | 9.11 | 25.85 | 264.85 | 0.925 | 0.02 | 2.8 | 506.25 | 1135.99 | 3.43 |
| Donor 1 | MET | 54.4 | 93.08 | 96.36 | 6.27 | 0.03 | 0.085 | 5.52 | 25.85 | 179.02 | 0.925 | 0.02 | 3.76 | 606.67 | 1071.99 | 3.23 |
| Donor 1 | MIB2 | 97.14 | 201.48 | 94.37 | 5.92 | 0.03 | 0.085 | 18.62 | 27 | 381.6 | 0.925 | 0.67 | 1.81 | 684.34 | 1513.99 | 4.57 |
| Donor 1 | MRC2 | 52.57 | 63.61 | 53.15 | 5.58 | 0.03 | 0.085 | 3.32 | 37.5 | 184.11 | 0.925 | 0.76 | 1.81 | 290.69 | 694.14 | 2.09 |
| Donor 1 | NOS2 | 31.72 | 130.64 | 26.25 | 3.51 | 0.03 | 0.085 | 5.04 | 28.47 | 133.76 | 0.925 | 0.02 | 1.62 | 154.92 | 516.99 | 1.56 |
| Donor 1 | PLEC | 107.71 | 393.6 | 96.29 | 14.5 | 10.68 | 0.085 | 27.93 | 59.1 | 413.41 | 0.925 | 0.02 | 7.78 | 337.55 | 1469.58 | 4.43 |
| Donor 1 | PLEKHG5 | 74.89 | 128.23 | 96.23 | 9.37 | 3.33 | 0.085 | 9.16 | 40.97 | 207.45 | 0.925 | 4.22 | 3.64 | 236.32 | 814.82 | 2.46 |
| Donor 1 | PTGDS | 29.12 | 223.36 | 63.06 | 2.73 | 0.03 | 0.085 | 10.02 | 48.05 | 254.29 | 0.925 | 0.02 | 0.01 | 395.74 | 1027.44 | 3.10 |
| Donor 1 | RASA3 | 33.95 | 50.06 | 58.28 | 3.84 | 0.03 | 0.085 | 8.6 | 39.39 | 196.78 | 0.925 | 0.02 | 0.01 | 157.88 | 549.85 | 1.66 |
| Donor 1 | TRPM2 | 121.32 | 323.62 | 90.23 | 6.24 | 2.53 | 0.085 | 18.26 | 51.65 | 368.92 | 0.925 | 0.02 | 7.61 | 428.91 | 1420.32 | 4.29 |
| Donor 1 | IKZF3 | 9.53 | 59.94 | 23.36 | 0.94 | 0.03 | 0.085 | 1.22 | 42.98 | 76.06 | 0.925 | 0.02 | 0.01 | 48.83 | 263.93 | 0.80 |
| Donor 1 | Actin | 19.57 | 147.18 | 34.21 | 1.46 | 0.03 | 0.085 | 1.22 | 10.1 | 14.2 | 0.925 | 0.02 | 0.78 | 101.44 | 331.40 | 1.00 |
| Donor 2 | DNAH3 | 279.27 | 1324.9 | 24 | 0.5 | 0.03 | 0.085 | 1.22 | 18.44 | 156.05 | 0.925 | 2.26 | 4.59 | 130.71 | 1942.98 | 28.04 |
| Donor 2 | DST | 773.57 | 6732.16 | 46.6 | 2 | 0.03 | 0.085 | 1.22 | 23.76 | 370.78 | 0.925 | 2.56 | 3.88 | 257.33 | 8214.90 | 118.57 |
| Donor 2 | EPS8L1 | 427.99 | 1030.19 | 85.97 | 3.33 | 4.33 | 0.085 | 18.4 | 21.15 | 386.22 | 0.925 | 0.76 | 4.3 | 167.42 | 2151.07 | 31.05 |
| Donor 2 | FRMD4B | 390.31 | 1070.19 | 94.99 | 3.93 | 10.28 | 1.27 | 1.22 | 19.9 | 415.04 | 0.925 | 0.02 | 5.24 | 159.4 | 2172.72 | 31.36 |
| Donor 2 | LAMA3 | 358.14 | 643.22 | 67.18 | 2.34 | 0.03 | 0.085 | 1.22 | 11.66 | 362.67 | 0.925 | 0.02 | 0.17 | 109.58 | 1557.24 | 22.48 |
| Donor 2 | MET | 302.2 | 256.37 | 64.56 | 1.53 | 0.91 | 0.085 | 1.22 | 14.16 | 312.32 | 0.925 | 2.39 | 4.24 | 84.79 | 1045.70 | 15.09 |
| Donor 2 | MIB2 | 173.84 | 141.37 | 17.97 | 0.73 | 0.03 | 0.085 | 1.22 | 13.23 | 153.31 | 0.925 | 0.02 | 0.65 | 61.99 | 565.37 | 8.16 |
| Donor 2 | MRC2 | 1401.1 | 5545.58 | 205.47 | 5.98 | 6.32 | 0.085 | 13.83 | 14.06 | 889.87 | 0.925 | 6.68 | 4.59 | 531.62 | 8626.11 | 124.50 |
| Donor 2 | NOS2 | 342.89 | 462.07 | 83.01 | 2.88 | 10.88 | 2.29 | 15.36 | 21.57 | 288.7 | 0.925 | 5.91 | 3.82 | 89.68 | 1329.99 | 19.20 |
| Donor 2 | PLEC | 280.02 | 357.65 | 74.41 | 2.44 | 0.03 | 0.085 | 19.79 | 24.07 | 343.1 | 0.925 | 5.46 | 2.49 | 83.91 | 1194.38 | 17.24 |
| Donor 2 | PLEKHG5 | 236.12 | 757.03 | 103.14 | 2.69 | 4.13 | 0.085 | 1.22 | 24.39 | 155.22 | 0.925 | 1.54 | 6.63 | 89.39 | 1382.51 | 19.95 |
| Donor 2 | PTGDS | 142.7 | 621.5 | 33.17 | 1.39 | 0.03 | 0.17 | 1.22 | 13.75 | 63.73 | 0.925 | 2.39 | 4.83 | 57.06 | 942.87 | 13.61 |
| Donor 2 | RASA3 | 630.2 | 2755.29 | 67.63 | 0.98 | 4.53 | 0.085 | 15.24 | 36.44 | 363.46 | 0.925 | 0.02 | 3.28 | 281.27 | 4159.35 | 60.03 |
| Donor 2 | TRPM2 | 495.45 | 1211.48 | 60.61 | 2.96 | 0.03 | 0.085 | 2.44 | 5.29 | 542.44 | 0.925 | 0.02 | 3.28 | 143.48 | 2468.49 | 35.63 |
| Donor 2 | IKZF3 | 427.38 | 1705.57 | 71.33 | 1.36 | 0.03 | 0.085 | 21.04 | 43.4 | 419.93 | 0.925 | 0.02 | 4.77 | 116.74 | 2812.58 | 40.59 |
| Donor 2 | Actin | 15.58 | 7.71 | 11.28 | 0.76 | 0.03 | 1.73 | 1.22 | 5.29 | 13.75 | 0.925 | 0.02 | 1.81 | 9.18 | 69.29 | 1.00 |
| Donor 3 | DNAH3 | 42.21 | 664.34 | 19.01 | 0.005 | 0.03 | 0.085 | 1.22 | 5.08 | 15.32 | 0.925 | 0.02 | 0.01 | 29.25 | 777.51 | 4.56 |
| Donor 3 | DST | 100.36 | 273.74 | 14.76 | 0.005 | 0.03 | 0.085 | 1.22 | 27 | 58.89 | 0.925 | 7.41 | 1.17 | 63.68 | 549.28 | 3.22 |
| Donor 3 | EPS8L1 | 208.07 | 530.49 | 41.94 | 1.07 | 3.73 | 0.085 | 1.22 | 13.12 | 107.94 | 0.925 | 0.85 | 0.01 | 50.21 | 959.66 | 5.63 |
| Donor 3 | FRMD4B | 143.55 | 211.78 | 47.51 | 0.73 | 0.03 | 0.085 | 1.22 | 17.71 | 91.8 | 0.925 | 0.02 | 1.11 | 53.79 | 570.26 | 3.35 |
| Donor 3 | LAMA3 | 100.19 | 509.46 | 23.21 | 1.08 | 0.03 | 0.085 | 1.22 | 36.97 | 34.67 | 0.925 | 1.19 | 0.01 | 50.95 | 759.99 | 4.46 |
| Donor 3 | MET | 143.98 | 322.33 | 34.04 | 1.99 | 0.03 | 0.085 | 1.22 | 12.39 | 29.84 | 0.925 | 2.64 | 0.01 | 54.62 | 604.10 | 3.55 |
| Donor 3 | MIB2 | 113.31 | 127.71 | 16.28 | 0.05 | 0.03 | 0.085 | 1.22 | 9.27 | 39.67 | 0.925 | 0.02 | 0.01 | 39.41 | 347.99 | 2.04 |
| Donor 3 | MRC2 | 150.52 | 323.25 | 48.19 | 0.96 | 0.03 | 0.085 | 1.22 | 11.66 | 54.63 | 0.925 | 0.58 | 0.09 | 74.36 | 666.50 | 3.91 |
| Donor 3 | NOS2 | 186.72 | 328.5 | 75.34 | 4.54 | 0.03 | 0.085 | 1.22 | 18.02 | 95.19 | 0.925 | 1.96 | 2.06 | 69.18 | 783.77 | 4.60 |

TABLE 12-continued

Cytokine Responses of N terminal Peptides

| Sample | Treatment | Analyte concentration (pg/ml) GM-CSF | IFNg | IL-2 | IL-3 | IL-4 | IL-7 | IL-9 | IL-10 | IL-13 | IL-15 | IL-17A | sCD40L | TNFa | Total analytes (pg/ml) | Fold change of total cytokine response (normalized against Actin control) |
|---|---|---|---|---|---|---|---|---|---|---|---|---|---|---|---|---|
| Donor 3 | PLEC | 132.57 | 235.34 | 52.69 | 0.76 | 0.03 | 0.085 | 1.22 | 27.21 | 69.82 | 0.925 | 2.93 | 1.05 | 43.28 | 567.91 | 3.33 |
| Donor 3 | PLEKHG5 | 275.71 | 343.92 | 56.78 | 0.69 | 0.03 | 0.085 | 1.22 | 14.06 | 132.99 | 0.925 | 0.49 | 0.01 | 118.75 | 945.66 | 5.55 |
| Donor 3 | PTGDS | 185.73 | 186.82 | 57.3 | 0.005 | 0.28 | 0.085 | 1.22 | 18.44 | 127.35 | 0.925 | 0.02 | 0.01 | 90.73 | 668.92 | 3.93 |
| Donor 3 | RASA3 | 133.59 | 93.84 | 40.44 | 0.01 | 0.06 | 0.085 | 1.22 | 9.68 | 73.67 | 0.925 | 2.3 | 1.49 | 53.69 | 411.00 | 2.41 |
| Donor 3 | TRPM2 | 176.42 | 154.05 | 46.74 | 1.05 | 0.03 | 1.43 | 1.22 | 10.93 | 133.4 | 0.925 | 0.02 | 0.01 | 72 | 598.23 | 3.51 |
| Donor 3 | IKZF3 | 32.69 | 169.24 | 18.82 | 0.005 | 0.03 | 0.085 | 1.22 | 10.52 | 16.55 | 0.925 | 0.02 | 0.01 | 21.41 | 271.53 | 1.59 |
| Donor 3 | Actin | 56.66 | 60.86 | 13.4 | 0.56 | 4.53 | 0.085 | 1.22 | 2.56 | 5.96 | 0.925 | 2.89 | 0.01 | 20.69 | 170.35 | 1.00 |
| Donor 4 | DNAH3 | 0.66 | 0.005 | 2.21 | 0.005 | 0.03 | 0.085 | 1.22 | 0.41 | 0.58 | 0.925 | 0.02 | 0.01 | 2.38 | 8.54 | 1.24 |
| Donor 4 | DST | 1.83 | 1.05 | 1.06 | 0.005 | 0.03 | 0.085 | 1.22 | 3.61 | 2.32 | 0.925 | 0.02 | 0.01 | 19.23 | 31.40 | 4.55 |
| Donor 4 | EPS8L1 | 0.66 | 1.35 | 0.98 | 0.005 | 0.03 | 2.01 | 1.22 | 4.24 | 1.95 | 0.925 | 0.02 | 0.01 | 1.86 | 15.26 | 2.21 |
| Donor 4 | FRMD4B | 0.66 | 0.005 | 2.01 | 0.07 | 0.03 | 0.085 | 1.22 | 2.02 | 1.19 | 0.925 | 0.02 | 0.01 | 0.6 | 8.85 | 1.28 |
| Donor 4 | LAMA3 | 0.66 | 2.26 | 1.99 | 0.005 | 0.03 | 0.085 | 1.22 | 0.09 | 1.25 | 0.925 | 0.02 | 0.01 | 2.34 | 10.89 | 1.58 |
| Donor 4 | MET | 0.66 | 0.3 | 1.19 | 0.005 | 0.03 | 0.085 | 1.22 | 4.77 | 2.69 | 0.925 | 0.13 | 0.01 | 1.61 | 13.63 | 1.98 |
| Donor 4 | MIB2 | 0.66 | 0.005 | 1.6 | 0.005 | 0.03 | 0.085 | 1.22 | 6.55 | 0.03 | 0.925 | 0.02 | 0.01 | 2.12 | 13.26 | 1.92 |
| Donor 4 | MRC2 | 0.66 | 1.05 | 0.98 | 0.005 | 0.03 | 0.085 | 1.22 | 4.77 | 0.3 | 0.925 | 0.02 | 0.01 | 2.08 | 12.14 | 1.76 |
| Donor 4 | NOS2 | 0.66 | 2.49 | 1.02 | 0.005 | 0.03 | 0.085 | 1.22 | 6.55 | 2.14 | 0.925 | 0.02 | 0.01 | 1.47 | 16.63 | 2.41 |
| Donor 4 | PLEC | 1.42 | 0.005 | 1.66 | 0.005 | 0.03 | 0.085 | 1.22 | 5.29 | 0.79 | 0.925 | 0.31 | 0.02 | 16.87 | 28.63 | 4.15 |
| Donor 4 | PLEKHG5 | 0.66 | 0.005 | 1.15 | 0.005 | 0.03 | 0.085 | 1.22 | 3.19 | 1.19 | 0.925 | 0.02 | 0.01 | 0.8 | 9.29 | 1.35 |
| Donor 4 | PTGDS | 0.66 | 3.65 | 2.26 | 0.005 | 0.03 | 0.085 | 1.22 | 3.19 | 2.08 | 0.925 | 0.02 | 0.01 | 10.06 | 24.20 | 3.51 |
| Donor 4 | RASA3 | 0.66 | 0.01 | 2.55 | 0.005 | 0.03 | 0.085 | 1.22 | 3.3 | 1.44 | 0.925 | 0.02 | 0.01 | 1.81 | 12.07 | 1.75 |
| Donor 4 | TRPM2 | 0.66 | 1.35 | 1.32 | 0.005 | 0.03 | 0.085 | 1.22 | 4.98 | 1.05 | 0.925 | 0.02 | 0.01 | 1.7 | 13.36 | 1.94 |
| Donor 4 | IKZF3 | 0.66 | 0.9 | 1.21 | 0.005 | 0.03 | 0.085 | 1.22 | 2.56 | 3.12 | 0.925 | 0.02 | 0.01 | 3.25 | 14.00 | 2.03 |
| Donor 4 | Actin | 0.66 | 0.01 | 1.27 | 0.005 | 0.03 | 0.085 | 1.22 | 0.18 | 0.99 | 0.925 | 0.02 | 0.01 | 1.49 | 6.90 | 1.00 |
| Donor 5 | DNAH3 | 0.66 | 0.005 | 1.66 | 0.84 | 0.03 | 0.085 | 1.22 | 2.87 | 1.05 | 0.925 | 0.27 | 0.01 | 2.82 | 12.45 | 0.78 |
| Donor 5 | DST | 0.66 | 0.6 | 0.79 | 0.005 | 0.03 | 0.085 | 1.22 | 3.61 | 3.18 | 0.925 | 0.02 | 0.01 | 2.06 | 13.20 | 0.82 |
| Donor 5 | EPS8L1 | 0.66 | 0.16 | 1.93 | 0.005 | 0.03 | 1.43 | 1.22 | 3.4 | 1.19 | 0.925 | 0.58 | 0.01 | 3.54 | 15.08 | 0.94 |
| Donor 5 | FRMD4B | 0.66 | 2.03 | 1.71 | 0.005 | 0.03 | 0.085 | 1.22 | 0.09 | 0.3 | 0.925 | 0.02 | 0.01 | 1.86 | 8.95 | 0.56 |
| Donor 5 | LAMA3 | 0.66 | 0.01 | 1.93 | 0.005 | 0.03 | 2.29 | 1.22 | 0.41 | 0.3 | 0.925 | 0.22 | 0.01 | 1.86 | 9.87 | 0.62 |
| Donor 5 | MET | 0.66 | 0.005 | 1.69 | 0.005 | 0.03 | 0.085 | 1.22 | 0.09 | 1.44 | 0.925 | 0.02 | 0.01 | 2.54 | 8.72 | 0.54 |
| Donor 5 | MIB2 | 0.66 | 0.005 | 2.44 | 0.005 | 0.03 | 0.95 | 1.22 | 1.71 | 0.06 | 0.925 | 0.02 | 0.01 | 2.71 | 10.75 | 0.67 |
| Donor 5 | MRC2 | 0.66 | 0.005 | 3.06 | 0.005 | 0.03 | 0.085 | 1.22 | 0.09 | 0.92 | 0.925 | 0.02 | 0.01 | 1.38 | 8.41 | 0.52 |
| Donor 5 | NOS2 | 0.66 | 1.2 | 1.9 | 0.005 | 0.03 | 0.085 | 1.22 | 0.09 | 1.89 | 0.925 | 1.11 | 0.01 | 3.63 | 12.76 | 0.80 |
| Donor 5 | PLEC | 0.66 | 0.01 | 1.56 | 0.005 | 0.03 | 0.085 | 1.22 | 1.28 | 0.03 | 0.925 | 0.85 | 0.01 | 2.06 | 8.73 | 0.54 |
| Donor 5 | PLEKHG5 | 0.66 | 0.005 | 1.77 | 0.54 | 0.49 | 0.085 | 1.22 | 0.09 | 1.19 | 0.925 | 0.93 | 0.01 | 3.21 | 11.13 | 0.69 |
| Donor 5 | PTGDS | 0.66 | 0.005 | 0.48 | 0.005 | 0.03 | 0.085 | 1.22 | 2.66 | 2.57 | 0.925 | 1.71 | 0.01 | 2.08 | 12.44 | 0.78 |
| Donor 5 | RASA3 | 0.66 | 0.3 | 2.21 | 0.005 | 0.03 | 0.085 | 1.22 | 1.49 | 1.44 | 0.925 | 0.02 | 0.01 | 1.9 | 10.30 | 0.64 |
| Donor 5 | TRPM2 | 0.66 | 0.005 | 1.1 | 0.005 | 0.03 | 0.085 | 1.22 | 0.09 | 0.03 | 0.925 | 0.02 | 0.01 | 0.92 | 5.10 | 0.32 |
| Donor 5 | IKZF3 | 0.66 | 4.81 | 2.52 | 0.005 | 0.03 | 2.94 | 1.22 | 4.66 | 0.03 | 0.925 | 0.02 | 0.01 | 1.52 | 19.35 | 1.21 |
| Donor 5 | Actin | 0.66 | 1.65 | 1.4 | 0.005 | 0.03 | 0.085 | 1.22 | 5.5 | 1.44 | 0.925 | 0.02 | 0.01 | 3.08 | 16.03 | 1.00 |
| Donor 6 | DNAH3 | 59.45 | 150.57 | 19.71 | 0.58 | 0.91 | 1.73 | 1.22 | 26.38 | 150.33 | 0.925 | 28.58 | 5.59 | 367.48 | 813.46 | 3.66 |
| Donor 6 | DST | 44.3 | 186.38 | 22.05 | 1.56 | 0.03 | 0.085 | 28.27 | 21.57 | 149.86 | 0.925 | 6.68 | 4.12 | 170.36 | 636.19 | 2.86 |
| Donor 6 | EPS8L1 | 47.7 | 132.54 | 24.08 | 2.42 | 0.03 | 0.085 | 1.22 | 23.24 | 53.62 | 0.925 | 10.24 | 4.59 | 322.88 | 623.57 | 2.81 |
| Donor 6 | FRMD4B | 12.51 | 94.1 | 18.98 | 0.5 | 4.13 | 0.78 | 1.22 | 27 | 33.89 | 0.925 | 0.8 | 0.24 | 24.26 | 219.34 | 0.99 |

TABLE 12-continued

Cytokine Responses of N terminal Peptides

| Sample | Treatment | Analyte concentration (pg/ml) GM-CSF | IFNg | IL-2 | IL-3 | IL-4 | IL-7 | IL-9 | IL-10 | IL-13 | IL-15 | IL-17A | sCD40L | TNFa | Total analytes (pg/ml) | Fold change of total cytokine response (normalized against Actin control) |
|---|---|---|---|---|---|---|---|---|---|---|---|---|---|---|---|---|
| Donor 6 | LAMA3 | 47.4 | 31 | 11.77 | 0.54 | 0.03 | 0.085 | 1.22 | 15 | 48.92 | 0.925 | 8.14 | 0.01 | 254.81 | 419.85 | 1.89 |
| Donor 6 | MET | 36.59 | 255.47 | 19.03 | 1.92 | 0.03 | 0.4 | 1.22 | 59.85 | 64.07 | 0.925 | 3.14 | 4.24 | 56.57 | 503.46 | 2.27 |
| Donor 6 | MIB2 | 28.73 | 46.26 | 15.32 | 1.69 | 7.7 | 0.085 | 1.22 | 16.35 | 44.57 | 0.925 | 1.58 | 0.58 | 202.54 | 367.55 | 1.65 |
| Donor 6 | MRC2 | 30.56 | 173.28 | 11.42 | 0.3 | 0.03 | 0.085 | 1.22 | 15.31 | 25.45 | 0.925 | 13.84 | 2.86 | 70.54 | 345.82 | 1.56 |
| Donor 6 | NOS2 | 70.25 | 513.42 | 21.89 | 2.25 | 0.03 | 1.11 | 1.22 | 72.8 | 117.93 | 1.85 | 2.77 | 2.06 | 197.11 | 1004.69 | 4.52 |
| Donor 6 | PLEC | 52.82 | 69.38 | 21.92 | 1.42 | 0.03 | 0.085 | 1.22 | 20.11 | 58.11 | 0.925 | 16.23 | 2.43 | 262.58 | 507.26 | 2.28 |
| Donor 6 | PLEKHG5 | 23.2 | 140.24 | 15.8 | 0.19 | 0.03 | 0.085 | 1.22 | 20.73 | 55.53 | 0.925 | 1.96 | 0.17 | 136.4 | 396.48 | 1.78 |
| Donor 6 | PTGDS | 44.5 | 194.94 | 14.38 | 1.12 | 0.03 | 0.085 | 1.22 | 30.35 | 54.69 | 0.925 | 6.64 | 2.43 | 125.84 | 477.15 | 2.15 |
| Donor 6 | RASA3 | 67.6 | 91.21 | 19.34 | 1.53 | 0.03 | 0.085 | 7.62 | 43.82 | 212.13 | 0.925 | 14.56 | 2.18 | 273.27 | 734.30 | 3.31 |
| Donor 6 | TRPM2 | 24.72 | 145.01 | 12.57 | 0.005 | 0.03 | 0.085 | 1.22 | 22.4 | 16.66 | 0.925 | 1.5 | 3.28 | 67.52 | 295.93 | 1.33 |
| Donor 6 | IKZF3 | 63.92 | 108.75 | 23.63 | 1.97 | 0.03 | 0.085 | 5.1 | 46.57 | 131.23 | 0.925 | 22.4 | 2.86 | 116.65 | 524.12 | 2.36 |
| Donor 6 | Actin | 18.18 | 135.48 | 11.03 | 0.5 | 0.03 | 0.085 | 1.22 | 4.66 | 8.77 | 0.925 | 2.22 | 0.01 | 38.39 | 222.13 | 1.00 |
| Donor 7 | DNAH3 | 25.1 | 28.72 | 2.1 | 0.005 | 0.03 | 0.085 | 1.22 | 7.49 | 2.45 | 0.925 | 0.02 | 0.09 | 48.76 | 117.00 | 1.64 |
| Donor 7 | DST | 20.84 | 93.16 | 3.11 | 0.005 | 0.03 | 0.085 | 1.22 | 10.1 | 4.73 | 0.925 | 1.02 | 0.01 | 80.77 | 216.01 | 3.03 |
| Donor 7 | EPS8L1 | 1.32 | 0.9 | 2.84 | 0.005 | 0.03 | 0.085 | 1.22 | 3.4 | 0.03 | 0.925 | 0.63 | 0.01 | 7.74 | 19.14 | 0.27 |
| Donor 7 | FRMD4B | 12.7 | 21.99 | 3.25 | 0.005 | 0.03 | 0.085 | 1.22 | 2.66 | 1.7 | 0.925 | 0.02 | 0.01 | 27.73 | 72.33 | 1.01 |
| Donor 7 | LAMA3 | 2.88 | 3.49 | 3.13 | 0.005 | 0.03 | 0.085 | 1.22 | 1.06 | 2.32 | 0.925 | 0.02 | 0.38 | 7.3 | 22.85 | 0.32 |
| Donor 7 | MET | 0.66 | 1.05 | 1.82 | 0.005 | 0.03 | 0.085 | 1.22 | 3.09 | 0.22 | 0.925 | 0.02 | 0.01 | 8.53 | 17.67 | 0.25 |
| Donor 7 | MIB2 | 44.9 | 19.98 | 7.32 | 0.005 | 0.03 | 0.085 | 1.22 | 0.63 | 8.89 | 0.925 | 0.02 | 0.01 | 30.68 | 114.70 | 1.61 |
| Donor 7 | MRC2 | 4.99 | 6.61 | 2.17 | 0.005 | 0.03 | 0.085 | 1.22 | 0.09 | 2.2 | 0.925 | 0.02 | 0.01 | 15.08 | 33.44 | 0.47 |
| Donor 7 | NOS2 | 64.4 | 61.11 | 9.55 | 0.38 | 0.03 | 2.29 | 1.22 | 3.93 | 10.2 | 0.925 | 0.18 | 0.01 | 29.13 | 183.36 | 2.57 |
| Donor 7 | PLEC | 68.55 | 449.86 | 8.19 | 0.005 | 0.03 | 0.085 | 1.22 | 6.34 | 13.64 | 0.925 | 0.02 | 1.43 | 36.75 | 587.05 | 8.23 |
| Donor 7 | PLEKHG5 | 39.34 | 37.86 | 7.75 | 0.005 | 0.03 | 0.085 | 1.22 | 7.6 | 5.31 | 0.925 | 0.02 | 2.92 | 55.5 | 158.57 | 2.22 |
| Donor 7 | PTGDS | 32.88 | 24.01 | 4.51 | 0.005 | 2.73 | 0.085 | 1.22 | 7.6 | 3.9 | 0.925 | 0.02 | 0.01 | 45.13 | 123.03 | 1.73 |
| Donor 7 | RASA3 | 42.8 | 44.03 | 7.54 | 0.005 | 0.03 | 0.085 | 1.22 | 7.8 | 14.2 | 0.925 | 0.02 | 0.31 | 36.75 | 155.72 | 2.18 |
| Donor 7 | TRPM2 | 29.69 | 140.85 | 2.97 | 0.005 | 0.03 | 0.085 | 1.22 | 25.75 | 3.72 | 0.925 | 0.02 | 0.01 | 124.46 | 329.74 | 4.62 |
| Donor 7 | IKZF3 | 43.4 | 29.69 | 8.26 | 0.005 | 0.03 | 0.085 | 1.22 | 5.71 | 6.88 | 0.925 | 0.02 | 0.45 | 37.8 | 134.48 | 1.89 |
| Donor 7 | Actin | 3.31 | 6.53 | 0.77 | 0.01 | 0.03 | 2.29 | 1.22 | 7.7 | 0.14 | 0.925 | 0.02 | 0.01 | 48.35 | 71.31 | 1.00 |
| Donor 8 | DNAH3 | 110.13 | 191.67 | 72.91 | 1.32 | 0.03 | 4.85 | 3.47 | 9.27 | 105.51 | 0.925 | 0.4 | 0.78 | 121.93 | 623.20 | 47.79 |
| Donor 8 | DST | 58.57 | 75.26 | 15.34 | 0.38 | 0.49 | 0.085 | 1.22 | 12.81 | 45.35 | 0.925 | 0.02 | 2.43 | 79.79 | 292.67 | 22.44 |
| Donor 8 | EPS8L1 | 88.89 | 63.7 | 41.38 | 1.19 | 0.03 | 0.085 | 6.26 | 101 | 121.32 | 0.925 | 0.02 | 4.24 | 92.38 | 430.52 | 33.02 |
| Donor 8 | FRMD4B | 29.4 | 65.37 | 9.26 | 0.42 | 0.03 | 0.085 | 6.48 | 8.43 | 53.96 | 0.925 | 0.22 | 1.68 | 53.45 | 229.71 | 17.62 |
| Donor 8 | LAMA3 | 197.84 | 534.58 | 80.04 | 6.66 | 5.92 | 0.085 | 11.96 | 16.25 | 222.4 | 0.925 | 0.49 | 0.01 | 173.02 | 1250.18 | 95.87 |
| Donor 8 | MET | 166.16 | 260.07 | 34.37 | 1.29 | 0.03 | 0.95 | 6.15 | 19.79 | 180.96 | 0.925 | 3.81 | 0.01 | 150.63 | 825.15 | 63.28 |
| Donor 8 | MIB2 | 55.58 | 97.75 | 8.09 | 3.34 | 0.03 | 0.4 | 10.38 | 14.37 | 48.48 | 0.925 | 4.22 | 0.01 | 70.89 | 314.47 | 24.12 |
| Donor 8 | MRC2 | 18.72 | 20.86 | 7.27 | 0.005 | 0.03 | 0.085 | 1.22 | 5.92 | 27.67 | 0.925 | 0.02 | 0.01 | 27.96 | 110.70 | 8.49 |
| Donor 8 | NOS2 | 79.04 | 62.03 | 23.6 | 1.36 | 0.03 | 0.085 | 8.21 | 11.98 | 120.62 | 0.925 | 1.28 | 0.01 | 53.5 | 362.67 | 27.81 |
| Donor 8 | PLEC | 190.8 | 360.99 | 57.12 | 8.89 | 0.03 | 0.085 | 33.62 | 22.19 | 218.93 | 0.925 | 0.67 | 0.58 | 135.11 | 1029.94 | 78.98 |
| Donor 8 | PLEKHG5 | 30.37 | 80.65 | 6.89 | 0.005 | 0.03 | 0.085 | 1.22 | 12.39 | 12.62 | 0.925 | 0.08 | 0.01 | 34.21 | 179.49 | 13.76 |
| Donor 8 | PTGDS | 17.08 | 7.78 | 5.28 | 0.005 | 1.92 | 0.085 | 1.22 | 13.44 | 25.12 | 0.925 | 0.67 | 2.31 | 25.09 | 100.93 | 7.74 |
| Donor 8 | RASA3 | 125.64 | 123.92 | 31.79 | 2.26 | 0.03 | 0.085 | 51.42 | 14.69 | 295.64 | 0.925 | 3.02 | 1.3 | 122.48 | 773.20 | 59.29 |
| Donor 8 | TRPM2 | 24.34 | 6.76 | 9.28 | 0.54 | 0.03 | 0.085 | 1.22 | 10.62 | 36.72 | 0.925 | 0.76 | 0.38 | 38.24 | 129.90 | 9.96 |
| Donor 8 | IKZF3 | 91.55 | 147.61 | 33.66 | 1.15 | 0.03 | 0.085 | 3.39 | 9.16 | 104.46 | 0.925 | 1.02 | 2.8 | 80.67 | 476.51 | 36.54 |

TABLE 12-continued

Cytokine Responses of N terminal Peptides

| Sample | Treatment | Analyte concentration (pg/ml) GM-CSF | IFNg | IL-2 | IL-3 | IL-4 | IL-7 | IL-9 | IL-10 | IL-13 | IL-15 | IL-17A | sCD40L | TNFa | Total analytes (pg/ml) | Fold change of total cytokine response (normalized against Actin control) |
|---|---|---|---|---|---|---|---|---|---|---|---|---|---|---|---|---|
| Donor 8 | Actin | 0.66 | 1.12 | 1.9 | 0.22 | 0.03 | 0.085 | 1.22 | 3.61 | 0.03 | 0.925 | 0.02 | 0.58 | 2.64 | 13.04 | 1.00 |
| Donor 9 | DNAH3 | 18.58 | 8.02 | 1.45 | 0.005 | 0.91 | 0.085 | 1.22 | 12.71 | 4.02 | 0.925 | 0.18 | 0.78 | 106.41 | 155.30 | 2.24 |
| Donor 9 | DST | 18.20 | 15.32 | 3.89 | 0.17 | 0.03 | 0.085 | 1.22 | 8.22 | 1.19 | 0.925 | 0.02 | 0.01 | 64.97 | 114.07 | 1.64 |
| Donor 9 | EPS8L1 | 0.66 | 3.49 | 16.23 | 0.005 | 0.03 | 0.085 | 1.22 | 2.77 | 3.18 | 0.925 | 0.58 | 0.01 | 7.16 | 36.35 | 0.52 |
| Donor 9 | FRMD4B | 5.93 | 3.18 | 2.93 | 0.005 | 0.03 | 0.085 | 1.22 | 0.09 | 0.92 | 0.925 | 0.04 | 0.01 | 12.73 | 28.10 | 0.40 |
| Donor 9 | LAMA3 | 0.66 | 4.03 | 2.75 | 0.005 | 0.03 | 2.01 | 1.22 | 1.28 | 1.51 | 0.925 | 0.02 | 0.01 | 6.68 | 21.13 | 0.30 |
| Donor 9 | MET | 2.43 | 0.005 | 2.88 | 0.005 | 0.03 | 0.085 | 1.22 | 4.66 | 0.92 | 0.925 | 0.02 | 0.01 | 15.76 | 28.95 | 0.42 |
| Donor 9 | MIB2 | 13.91 | 10.55 | 5.42 | 0.005 | 0.03 | 0.085 | 1.22 | 6.55 | 4.25 | 0.925 | 0.02 | 0.01 | 63.45 | 106.43 | 1.53 |
| Donor 9 | MRC2 | 0.66 | 15.32 | 5.84 | 0.005 | 0.03 | 0.085 | 1.22 | 9.06 | 3.42 | 0.925 | 0.02 | 0.01 | 11.63 | 48.23 | 0.69 |
| Donor 9 | NOS2 | 27.96 | 18.69 | 4.86 | 0.005 | 0.03 | 0.085 | 1.22 | 22.19 | 2.01 | 0.925 | 1.19 | 0.01 | 220.43 | 299.61 | 4.32 |
| Donor 9 | PLEC | 3.36 | 4.73 | 2.7 | 0.005 | 0.03 | 2.01 | 1.22 | 1.92 | 0.65 | 0.925 | 0.02 | 0.01 | 15.95 | 33.53 | 0.48 |
| Donor 9 | PLEKHG5 | 1.42 | 1.35 | 2.97 | 0.56 | 4.13 | 0.085 | 1.22 | 4.03 | 0.51 | 0.925 | 0.22 | 0.01 | 8.07 | 25.50 | 0.37 |
| Donor 9 | PTGDS | 9.72 | 1.5 | 2.15 | 0.005 | 0.03 | 0.085 | 1.22 | 5.71 | 1.95 | 0.925 | 0.02 | 0.01 | 47.71 | 71.04 | 1.02 |
| Donor 9 | RASA3 | 2.48 | 6.14 | 2.12 | 0.005 | 0.03 | 0.085 | 1.22 | 4.03 | 0.03 | 0.925 | 1.19 | 0.01 | 14.78 | 33.05 | 0.48 |
| Donor 9 | TRPM2 | 5.56 | 0.9 | 4.77 | 0.38 | 0.03 | 0.085 | 1.22 | 4.03 | 1.32 | 0.925 | 0.02 | 0.01 | 10.04 | 29.29 | 0.42 |
| Donor 9 | IKZF3 | 9.67 | 0.005 | 6.18 | 0.005 | 0.03 | 1.43 | 1.22 | 5.08 | 1.32 | 0.925 | 0.08 | 0.01 | 31.98 | 57.94 | 0.83 |
| Donor 9 | Actin | 0.66 | 3.49 | 0.77 | 0.36 | 0.03 | 2.01 | 1.22 | 2.13 | 1.05 | 0.925 | 0.58 | 0.01 | 56.18 | 69.42 | 1.00 |

To test the immunogenic capacity of specific N-terminal peptides in a more cellular setting, we then assessed responses of T cells previously primed to recognize either altered or wild-type peptides, when co-cultured with HLA-matched isogenic GC cells expressing either altered or wild-type peptides respectively (FIG. 12). By MHC-I affinity screening, a VMCDIFFSL nonamer in the WT RASA3 N-terminus was predicted to exhibit high MHC-I affinity binding for both the HLA-A02:01 (IC50-6.93 nm) and HLA-A02:06 (IC50-9.74 nm) alleles. Using HLA-A*02:06 T cells that are cross-reactive to HLA-A*02:01-positive AGS cells, we tested release of interferon gamma (IFNγ) from primed T cells after exposure to AGS lysates expressing either RASA3 CanT or SomT isoforms. ELISA assays demonstrated that T cells primed to recognize RASA3 CanT released significantly more IFNγ when co-cultured with RASA3 CanT-expressing AGS cells than when co-cultured with RASA3 SomT-expressing AGS cells. In contrast, T-cells primed with RASA3 SomT did not exhibit appreciable IFNγ release when co-cultured with RASA3 SomT expressing AGS cells, indicating that RASA3 SomT is less immunogenic (FIG. 12). Taken collectively, these in vitro results demonstrate that peptides predicted to be depleted in GCs through somatic promoter alterations can produce immunogenic responses, with the magnitude of immune responses depending on both peptide sequence and host immune background.

Somatic Promoters are Associated with EZH2 Occupancy

To identify potential oncogenic mechanisms driving somatic promoter alterations, we intersected the genomic locations of the somatic promoters with transcription factor binding sites (TFBS) of 237 transcription factors from 83 different tissues. Regions exhibiting somatic promoters were significantly enriched in regions associated with EZH2 (P<0.01) and SUZ12 (P<0.01) binding (FIG. 6*a*, Table 13), confirming earlier findings on a smaller cohort. Both EZH2 and SUZ12 are components of the PRC2 epigenetic regulator complex, which is upregulated in many cancer types including GC. To validate these findings, we then performed EZH2 Chip-sequencing on HFE-145 normal gastric epithelial cells (Methods and Materials). Concordant with the previous findings, we observed significant enrichment of EZH2 binding sites at somatic promoters compared to all promoters (Enrichment score 27 vs. 13 for all promoters, P<0.01), and this EZH2 enrichment remained significant when the gained somatic (Enrichment Score 28, P<0.01) and lost somatic promoters (Enrichment Score 24, P<0.01) were analyzed separately (FIG. 18).

TABLE 13

Somatic Promoters Overlapping EZH2/SUZ12 Binding Sites

| Loci | Annotation Status | Associated Gene |
|---|---|---|
| chrX:136647100-136648150 | Known | ZIC3 |
| chr13:100634350-100638150 | Known | ZIC2 |
| chr13:100630200-100634000 | Known | ZIC2 |
| chr20:50719850-50723350 | Known | ZFP64 |
| chr18:45660800-45664950 | Known | ZBTB7C |
| chr1:185226150-185227950 | Known | Y_RNA |
| chr3:13920600-13921250 | Known | WNT7A |
| chr2:71126100-71129800 | Known | VAX2 |
| chr5:6448050-6451150 | Known | UBE2QL1 |
| chr8:72986650-72987850 | Known | TRPA1 |
| chr22:17082250-17084550 | Known | TPTEP1 |
| chr19:55657350-55658650 | Known | TNNT1 |
| chr19:55666950-55668450 | Known | TNNI3 |
| chr22:42320400-42323750 | Known | TNFRSF13C |
| chr8:119962100-119965650 | Known | TNFRSF11B |
| chr21:42873650-42881750 | Known | TMPRSS2 |
| chr20:1164650-1168700 | Known | TMEM74B |
| chr17:53797250-53803100 | Known | TMEM100 |
| chr11:119291200-119294700 | Known | THY1 |
| chr20:55203450-55206500 | Known | TFAP2C |
| chr6:10409250-10419650 | Known | TFAP2A; TFAP2A-AS1 |
| chr6:85471550-85475350 | Known | TBX18 |
| chr20:46411750-46414250 | Known | SULF2 |
| chr8:70403800-70408450 | Known | SULF1 |
| chr5:172753250-172757450 | Known | STC2 |
| chr14:38675750-38681750 | Known | SSTR1 |
| chr7:20824950-20827850 | Known | SP8 |
| chr13:95362100-95368650 | Known | SOX21; SOX21-AS1 |
| chr3:181428150-181434750 | Known | SOX2 |
| chr8:101660950-101662650 | Known | SNX31 |
| chr20:10197250-10201300 | Known | SNAP25; SNAP25-AS1 |
| chr20:48598400-48604100 | Known | SNAI1 |
| chr14:70346050-70347700 | Known | SMOC1 |
| chr12:85303950-85307700 | Known | SLC6A15 |
| chr19:17981100-17986400 | Known | SLC5A5 |
| chr2:228580350-228583450 | Known | SLC19A3 |
| chr3:121656650-121658300 | Known | SLC15A2 |
| chr6:100910100-100913300 | Known | SIM1 |
| chr21:44842150-44848700 | Known | SIK1 |
| chr7:37953600-37956950 | Known | SFRP4 |
| chr4:154708850-154714150 | Known | SFRP2 |
| chr16:23193600-23197800 | Known | SCNN1G |
| chr16:23312800-23315350 | Known | SCNN1B |
| chr2:200326950-200329550 | Known | SATB2 |

TABLE 13-continued

Somatic Promoters Overlapping EZH2/SUZ12 Binding Sites

| Loci | Annotation Status | Associated Gene |
|---|---|---|
| chr20:50415800-50419950 | Known | SALL4 |
| chr20:981750-984100 | Known | RSPO4 |
| chr1:148247000-148248800 | Known | RP11-89F3.2 |
| chr12:54472600-54477950 | Known | RP11-834C11.6; RP11-834C11.7 |
| chr5:72746300-72748200 | Known | RP11-79P5.7 |
| chr1:61103800-61106600 | Known | RP11-776H12.1 |
| chr11:134335600-134339750 | Known | RP11-627G23.1 |
| chr11:69830350-69834850 | Known | RP11-626H12.1 |
| chr16:89987550-89991500 | Known | RP11-566K11.4; TUBB3 |
| chr16:86319900-86321550 | Known | RP11-514D23.1 |
| chr3:50191700-50195800 | Known | RP11-493K19.3; SEMA3F |
| chr3:132756350-132758550 | Known | RP11-469L4.1; TMEM108 |
| chr6:26613750-26615600 | Known | RP11-457M11.6 |
| chr3:87841650-87842700 | Known | RP11-451B8.1 |
| chr1:113391350-113395900 | Known | RP11-426L16.8; RP3-522D1.1 |
| chr12:85711250-85713200 | Known | RP11-408B11.2 |
| chr6:106807450-106809950 | Known | RP11-404H14.1 |
| chr1:149230550-149232000 | Known | RP11-403I13.5 |
| chr1:222138950-222144050 | Known | RP11-400N13.2 |
| chr3:178577000-178578500 | Known | RP11-385J1.2 |
| chr17:46721450-46725800 | Known | RP11-357H14.17 |
| chr5:522450-524750 | Known | RP11-310P5.2; SLC9A3 |
| chr15:80542500-80545200 | Known | RP11-2E17.1 |
| chr5:74343750-74351250 | Known | RP11-229C3.2 |
| chr5:63460450-63463050 | Known | RNF180 |
| chr1:228742450-228743450 | Known | RNA5SP19 |
| chr1:228781900-228785450 | Known | RNA5S17; RNA5SP18 |
| chr21:38379100-38379750 | Known | RIPPLY3 |
| chr21:43180350-43189850 | Known | RIPK4 |
| chr8:104510350-104514700 | Known | RIMS2; RP11-1C8.4 |
| chr10:62758000-62762450 | Known | RHOBTB1 |
| chr15:90039550-90040150 | Known | RHCG |
| chr2:86564650-86566000 | Known | REEP1 |
| chr4:82964050-82966400 | Known | RASGEF1B; RP11-689K5.3 |
| chr3:75707050-75708850 | Known | RARRES2P1 |
| chr8:85093500-85097700 | Known | RALYL |
| chr8:128805200-128810000 | Known | PVT1 |

TABLE 13-continued

Somatic Promoters Overlapping EZH2/SUZ12 Binding Sites

| Loci | Annotation Status | Associated Gene |
|---|---|---|
| chr1:29562850-29565950 | Known | PTPRU |
| chr7:158378250-158380350 | Known | PTPRN2 |
| chr1:170630400-170636550 | Known | PRRX1; RP1-79C4.4 |
| chr6:150463250-150464400 | Known | PPP1R14C |
| chr12:133264050-133266950 | Known | POLE; PXMP2; RP13-672B3.2 |
| chr5:74990850-74992350 | Known | POC5 |
| chr20:56280450-56287350 | Known | PMEPA1 |
| chr16:57315850-57319550 | Known | PLLP |
| chr1:6544500-6545600 | Known | PLEKHG5 |
| chr14:69950300-69951550 | Known | PLEKHD1 |
| chr1:201251800-201254650 | Known | PKP1 |
| chr2:42275400-42282950 | Known | PKDCC |
| chr12:130823500-130825600 | Known | PIWIL1 |
| chr4:111557000-111559350 | Known | PITX2 |
| chr7:32107350-32111900 | Known | PDE1C |
| chr1:55504650-55507550 | Known | PCSK9 |
| chr15:102029650-102031300 | Known | PCSK6 |
| chr3:142606500-142609050 | Known | PCOLCE2 |
| chr14:37129750-37133800 | Known | PAX9 |
| chr1:17443850-17446850 | Known | PADI2 |
| chr8:99951150-99961750 | Known | OSR2; RP11-44N12.5; STK3 |
| chr1:161991300-161994850 | Known | OLFML2B |
| chr7:8473050-8474100 | Known | NXPH1 |
| chr9:87282200-87286150 | Known | NTRK2 |
| chr19:15309800-15311950 | Known | NOTCH3 |
| chr4:56500900-56504300 | Known | NMU |
| chr1:183385400-183388500 | Known | NMNAT2 |
| chr8:41502400-41510150 | Known | NKX6-3 |
| chr10:134596450-134599400 | Known | NKX6-2; RP11-288G11.3 |
| chr4:85417400-85421400 | Known | NKX6-1 |
| chr2:233791350-233792700 | Known | NGEF |
| chrX:107016000-107021000 | Known | NCBP2L; TSC22D3 |
| chr11:1150000-1157350 | Known | MUC5AC |
| chr7:100607850-100613600 | Known | MUC12; MUC3A; RP11-395B7.2 |
| chr16:56699800-56705700 | Known | MT1G; MT1H |
| chr12:132313150-132317650 | Known | MMP17 |
| chr7:73036850-73039200 | Known | MLXIPL |

TABLE 13-continued

Somatic Promoters Overlapping EZH2/SUZ12 Binding Sites

| Loci | Annotation Status | Associated Gene |
|---|---|---|
| chr19:54482850-54485950 | Known | MIR935 |
| chr9:21554500-21561150 | Known | MIR31HG |
| chr17:46800050-46802400 | Known | MIR3185; PRAC1; PRAC2 |
| chr1:1562700-1565700 | Known | MIB2 |
| chr1:205537050-205540700 | Known | MFSD4 |
| chr13:31480150-31483050 | Known | MEDAG |
| chr2:132152200-132153000 | Known | MED15P3 |
| chr3:150959500-150960300 | Known | MED12L |
| chr2:149894250-149897500 | Known | LYPD6B |
| chr11:1889150-1894600 | Known | LSP1 |
| chr1:156896950-156898350 | Known | LRRC71 |
| chr11:61275250-61276400 | Known | LRRC10B; MIR4488 |
| chr9:103789900-103792650 | Known | LPPR1 |
| chr16:1013250-1015550 | Known | LMF1 |
| chr1:2980250-2991900 | Known | LINC00982; PRDM16 |
| chr3:75719150-75723200 | Known | LINC00960 |
| chr20:21085550-21087550 | Known | LINC00237 |
| chr19:55127750-55130550 | Known | LILRB1 |
| chr7:103968400-103969950 | Known | LHFPL3 |
| chr1:202182400-202184350 | Known | LGR6 |
| chr1:202161700-202163400 | Known | LGR6 |
| chr1:65991250-65992850 | Known | LEPR |
| chr1:205424550-205426850 | Known | LEMD1; RP11-576D8.4 |
| chr20:9494050-9498000 | Known | LAMP5; RP5-1119D9.4 |
| chr6:129203450-129207800 | Known | LAMA2 |
| chr19:51485750-51487700 | Known | KLK7 |
| chr3:126073900-126077300 | Known | KLF15 |
| chr1:245315950-245321950 | Known | KIF26B |
| chr1:180880350-180883200 | Known | KIAA1614 |
| chr15:81070500-81075050 | Known | KIAA1199 |
| chr20:43728950-43730250 | Known | KCNS1 |
| chr14:88788450-88791000 | Known | KCNK10 |
| chr7:119911950-119914550 | Known | KCND2 |
| chr1:111210100-111218300 | Known | KCNA3 |
| chr16:31366400-31369100 | Known | ITGAX |
| chr20:13200350-13202100 | Known | ISM1 |
| chr16:54316250-54322800 | Known | IRX3 |

TABLE 13-continued

Somatic Promoters Overlapping EZH2/SUZ12 Binding Sites

| Loci | Annotation Status | Associated Gene |
|---|---|---|
| chr5:2748900-2751450 | Known | IRX2 |
| chr17:38016450-38022250 | Known | IKZF3 |
| chr22:23229500-23237350 | Known | IGLC1; IGLJ1; IGLL5 |
| chr19:46579500-46581300 | Known | IGFL4 |
| chr7:45927300-45929150 | Known | IGFBP1 |
| chr7:23506000-23515500 | Known | IGF2BP3 |
| chr6:87646350-87648250 | Known | HTR1E |
| chr5:175084150-175086850 | Known | HRH2 |
| chr3:11195250-11198600 | Known | HRH1 |
| chr4:175439400-175445700 | Known | HPGD |
| chr12:54386800-54395700 | Known | HOXC6; HOXC9; HOXC-AS1; HOXC-AS2 |
| chr12:54421700-54423400 | Known | HOXC6 |
| chr12:54410150-54413050 | Known | HOXC4; HOXC6; RP11-834C11.14 |
| chr12:54446200-54449350 | Known | HOXC4 |
| chr12:54331500-54334550 | Known | HOXC13; HOXC-AS5 |
| chr12:54375250-54381900 | Known | HOXC10; HOXC-AS3; RP11-834C11.12 |
| chr17:46701450-46705000 | Known | HOXB9 |
| chr17:46804450-46808100 | Known | HOXB13 |
| chr7:27159450-27164850 | Known | HOXA3; HOXA-AS2 |
| chr7:27208400-27220700 | Known | HOXA10; HOXA9; HOXA-AS4; MIR196B; RP1-170019.20 |
| chr7:27221300-27251300 | Known | HOTTIP; HOXA11; HOXA11-AS; HOXA13; RP1-170019.14 |
| chr12:54365950-54373250 | Known | HOTAIR; HOXC11 |
| chr1:6478800-6480950 | Known | HES2 |
| chr11:2016000-2021350 | Known | H19 |
| chr11:45942850-45946400 | Known | GYLTL1B |
| chr9:140056700-140058300 | Known | GRIN1 |
| chr15:72488700-72491050 | Known | GRAMD2 |
| chr17:72425800-72433550 | Known | GPRC5C |
| chr5:89854500-89855350 | Known | GPR98 |
| chrX:133117900-133120700 | Known | GPC3 |
| chr19:2700850-2702900 | Known | GNG7 |
| chr7:99526050-99527900 | Known | GJC3; RP4-604G5.1 |
| chr8:75230900-75235150 | Known | GDAP1; JPH1 |
| chr7:74379400-74380400 | Known | GATSL1 |
| chr20:61046800-61052500 | Known | GATA5; RP13-379024.3 |
| chr8:11533800-11540650 | Known | GATA4 |

TABLE 13-continued

Somatic Promoters Overlapping EZH2/SUZ12 Binding Sites

| Loci | Annotation Status | Associated Gene |
|---|---|---|
| chr8:11557150-11568950 | Known | GATA4 |
| chr11:11640700-11644650 | Known | GALNT18 |
| chr12:130645350-130646800 | Known | FZD10; FZD10-AS1 |
| chr6:96460900-96466650 | Known | FUT9 |
| chr13:39259850-39263000 | Known | FREM2 |
| chr16:86600550-86601800 | Known | FOXC2; RP11-46309.5 |
| chr6:1608550-1611700 | Known | FOXC1 |
| chr14:38051900-38070050 | Known | FOXA1; TTC6 |
| chr17:39965500-39970950 | Known | FKBP10; LEPREL4 |
| chr9:133813800-133816150 | Known | FIBCD1 |
| chr11:69630950-69635350 | Known | FGF3 |
| chr3:13973700-13975200 | Known | FGD5P1 |
| chr10:95325600-95329150 | Known | FFAR4 |
| chr7:121942750-121947900 | Known | FEZF1; FEZF1-AS1 |
| chr16:86529000-86534050 | Known | FENDRR |
| chr21:42687850-42691150 | Known | FAM3B |
| chr17:66593700-66598900 | Known | FAM20A |
| chr1:179711850-179712600 | Known | FAM163A |
| chr8:53476650-53479500 | Known | FAM150A |
| chr4:187025100-187028650 | Known | FAM149A |
| chr12:124778800-124786100 | Known | FAM101A |
| chr7:27281600-27284150 | Known | EVX1; EVX1-AS |
| chrX:103498450-103500200 | Known | ESX1 |
| chr1:216892850-216898200 | Known | ESRRG |
| chr19:55590850-55593800 | Known | EPS8L1 |
| chr8:144950100-144953650 | Known | EPPK1 |
| chr17:48608600-48615100 | Known | EPN3 |
| chr1:23037600-23041300 | Known | EPHB2 |
| chr9:112080500-112082950 | Known | EPB41L4B |
| chr7:155250600-155253200 | Known | EN2 |
| chr19:14885900-14888350 | Known | EMR2 |
| chr22:37821950-37823900 | Known | ELFN2; RP1-63G5.5 |
| chr19:1286150-1288700 | Known | EFNA2; MUM1 |
| chr20:57874800-57877300 | Known | EDN3 |
| chr15:45399500-45410700 | Known | DUOX2; DUOXA2 |
| chr16:30021900-30023950 | Known | DOC2A |
| chr7:96633500-96636700 | Known | DLX6; DLX6-AS1; DLX6-AS2 |

TABLE 13-continued

Somatic Promoters Overlapping EZH2/SUZ12 Binding Sites

| Loci | Annotation Status | Associated Gene |
|---|---|---|
| chr7:96652750-96654900 | Known | DLX5 |
| chr19:6474700-6477300 | Known | DENND1C |
| chr10:94831200-94834300 | Known | CYP26A1 |
| chr4:48987500-48989500 | Known | CWH43 |
| chr8:104382100-104385900 | Known | CTHRC1 |
| chr5:174177950-174179050 | Known | CTD-2532K18.1; MIR4634 |
| chr14:19924450-19925600 | Known | CTD-2314B22.3 |
| chr14:19640850-19641750 | Known | CTD-2314B22.1 |
| chr15:97838750-97841300 | Known | CTD-2147F2.1 |
| chr5:134912900-134915350 | Known | CTC-321K16.1; CXCL14 |
| chr5:134371700-134375750 | Known | CTC-276P9.1 |
| chr16:21288600-21290700 | Known | CRYM |
| chr2:102002650-102005250 | Known | CREG2 |
| chr15:78632500-78634200 | Known | CRABP1 |
| chr3:9745600-9747050 | Known | CPNE9 |
| chr16:89640950-89643950 | Known | CPNE7 |
| chr3:99355450-99359900 | Known | COL8A1 |
| chr6:33160200-33161450 | Known | COL11A2 |
| chr6:35754500-35755750 | Known | CLPSL1 |
| chr21:36041150-36045150 | Known | CLIC6 |
| chr17:7161850-7167950 | Known | CLDN7; RP1-4G17.5 |
| chr7:73181100-73185850 | Known | CLDN3 |
| chr3:190034900-190041800 | Known | CLDN1; CLDN16 |
| chr7:29184550-29187650 | Known | CHN2; CPVL |
| chr2:27340450-27342750 | Known | CGREF1 |
| chr13:28538700-28543950 | Known | CDX2 |
| chr5:149545100-149550500 | Known | CDX1 |
| chr16:68677900-68681200 | Known | CDH3; RP11-61512.2 |
| chr16:68770300-68774200 | Known | CDH1 |
| chr11:6279800-6283200 | Known | CCKBR |
| chr18:57363700-57365350 | Known | CCBE1; RP11-2N1.2 |
| chr8:76189900-76191050 | Known | CASC9 |
| chr6:17392850-17396100 | Known | CAP2 |
| chr1:20808950-20814450 | Known | CAMK2N1 |
| chr7:44265350-44266400 | Known | CAMK2B |
| chr8:86350000-86351450 | Known | CA3 |
| chr5:2751850-2754050 | Known | C5orf38; IRX2 |

TABLE 13-continued

Somatic Promoters Overlapping EZH2/SUZ12 Binding Sites

| Loci | Annotation Status | Associated Gene |
|---|---|---|
| chr3:138664900-138667100 | Known | C3orf72; FOXL2 |
| chr17:77019250-77024000 | Known | C1QTNF1; C1QTNF1-AS1 |
| chr1:223565950-223567600 | Known | C1orf65 |
| chr1:190440800-190450200 | Known | BRINP3; RP11-161I10.1; RP11-54717.2 |
| chr2:198650550-198651850 | Known | BOLL |
| chr15:83952250-83953300 | Known | BNC1 |
| chr4:42152300-42155900 | Known | BEND4 |
| chr17:47209750-47211400 | Known | B4GALNT2 |
| chr11:134279600-134282050 | Known | B3GAT1 |
| chr4:94748600-94754050 | Known | ATOH1 |
| chr9:120175650-120177900 | Known | ASTN2 |
| chr9:133319400-133324650 | Known | ASS1 |
| chr11:2285750-2292550 | Known | ASCL2 |
| chr16:329250-332250 | Known | ARHGDIG |
| chr8:145908800-145912600 | Known | ARHGAP39 |
| chr4:86395150-86399900 | Known | ARHGAP24 |
| chr18:24443050-24445900 | Known | AQP4; AQP4-AS1 |
| chr11:71318250-71320050 | Known | AP000867.1 |
| chr5:79864800-79866650 | Known | ANKRD34B |
| chr2:133014850-133015750 | Known | ANKRD30BL; MIR663B |
| chr12:85672750-85675650 | Known | ALX1 |
| chr6:168195400-168198750 | Known | AL009178.1; C6orf123 |
| chr10:4867450-4870200 | Known | AKR1E2 |
| chr16:3232300-3234150 | Known | AJ003147.8 |
| chr8:11203650-11206800 | Known | AF131216.5; TDH |
| chr17:15847250-15850800 | Known | ADORA2B |
| chr7:5601050-5603800 | Known | ACTB |
| chr7:100490350-100495550 | Known | ACHE |
| chr3:18734950-18736300 | Known | AC144521.1 |
| chr2:131593950-131595800 | Known | AC133785.1; ARHGEF4 |
| chr4:44447900-44452050 | Known | AC131951.1; KCTD8 |
| chr17:7982650-7984350 | Known | AC129492.6; ALOX12B |
| chr5:1003400-1005850 | Known | AC116351.2; RP11-43F13.4 |
| chr2:100721300-100722600 | Known | AC092667.2; AFF3 |
| chr2:286750-288600 | Known | AC079779.4; FAM150B |
| chr2:132121200-132122150 | Known | AC073869.1 |
| chr2:233282700-233286450 | Known | AC068134.5; AC068134.6 |

TABLE 13-continued

Somatic Promoters Overlapping EZH2/SUZ12 Binding Sites

| Loci | Annotation Status | Associated Gene |
|---|---|---|
| chr16:31495650-31500700 | Known | AC026471.6; SLC5A2 |
| chr12:54348250-54351050 | Known | AC012531.23; HOXC12 |
| chr2:118561200-118562150 | Known | AC009312.1 |
| chr16:51182700-51185700 | Known | AC009166.5; SALL1 |
| chr2:171671550-171676200 | Known | AC007405.8; GAD1 |
| chr2:66801200-66811950 | Known | AC007392.3 |
| chr2:71113350-71116800 | Known | AC007040.5 |
| chr7:15720950-15728900 | Known | AC005550.4; MEOX2 |
| chr6:1611750-1616000 | Unknown | — |
| chr15:96958950-96961350 | Unknown | — |
| chr2:66652100-66655200 | Unknown | — |
| chr2:8833050-8834200 | Unknown | — |
| chr9:17905350-17908250 | Unknown | — |
| chr5:2746900-2748550 | Unknown | — |
| chr7:45001800-45003250 | Unknown | — |
| chr12:52257150-52258000 | Unknown | — |
| chr2:218874000-218875450 | Unknown | — |
| chr19:30214300-30216100 | Unknown | — |
| chr8:140717350-140719650 | Unknown | — |
| chr7:27264550-27266100 | Unknown | — |
| chr19:48900250-48904400 | Unknown | — |
| chr16:51186150-51187850 | Unknown | — |
| chr9:132458700-132461300 | Unknown | — |
| chr11:44337850-44339250 | Unknown | — |
| chr17:46694850-46697150 | Unknown | — |
| chr10:124898400-124900700 | Unknown | — |
| chr6:10382900-10384750 | Unknown | — |
| chr8:144489000-144490750 | Unknown | — |
| chr20:49837550-49839250 | Unknown | — |
| chr3:193921100-193922050 | Unknown | — |
| chr13:100619800-100623100 | Unknown | — |
| chr1:165320950-165322700 | Unknown | — |
| chr1:180203650-180205650 | Unknown | — |
| chr1:23543800-23544900 | Unknown | — |
| chr8:144842350-144844000 | Unknown | — |
| chr5:174162150-174163450 | Unknown | — |
| chr1:184632450-184634700 | Unknown | — |

TABLE 13-continued

Somatic Promoters Overlapping EZH2/SUZ12 Binding Sites

| Loci | Annotation Status | Associated Gene |
|---|---|---|
| chr13:21295150-21296450 | Unknown | — |
| chr1:156893100-156894550 | Unknown | — |
| chr20:46434400-46435400 | Unknown | — |
| chr11:33398050-33400750 | Unknown | — |
| chr6:134216650-134218050 | Unknown | — |
| chr2:45176050-45177700 | Unknown | — |
| chr13:36044350-36045800 | Unknown | — |
| chr2:45227500-45229600 | Unknown | — |
| chr10:43427950-43429950 | Unknown | — |
| chr1:152079200-152081300 | Unknown | — |
| chr7:54731350-54733200 | Unknown | — |
| chr20:4201500-4202700 | Unknown | — |
| chr8:145555300-145556800 | Unknown | — |
| chr7:64733800-64735500 | Unknown | — |
| chrX:119124000-119127100 | Unknown | — |
| chr3:14642850-14644150 | Unknown | — |
| chr10:102488400-102492200 | Unknown | — |
| chr5:42999400-43001150 | Unknown | — |
| chr21:38063750-38066650 | Unknown | — |
| chr2:131010400-131011600 | Unknown | — |
| chr19:30018700-30020150 | Unknown | — |
| chr5:72731550-72734700 | Unknown | — |
| chr8:102092150-102094400 | Unknown | — |
| chr4:4867350-4869600 | Unknown | — |
| chr4:4854350-4855850 | Unknown | — |
| chr7:156735150-156736500 | Unknown | — |
| chr1:161442450-161443650 | Unknown | — |
| chr12:54356450-54358100 | Unknown | — |
| chr1:48174300-48176650 | Unknown | — |
| chr7:25900700-25903050 | Unknown | — |
| chr10:102830000-102833650 | Unknown | — |
| chr6:137310350-137312150 | Unknown | — |
| chr1:152081400-152084100 | Unknown | — |
| chr7:27274550-27276500 | Unknown | — |
| chr12:113904650-113906650 | Unknown | — |
| chr1:17024500-17028900 | Unknown | — |
| chr5:72528750-72529950 | Unknown | — |

TABLE 13-continued

Somatic Promoters Overlapping EZH2/SUZ12 Binding Sites

| Loci | Annotation Status | Associated Gene |
|---|---|---|
| chr9:99481850-99483650 | Unknown | — |
| chr1:46954600-46956800 | Unknown | — |
| chr17:26119900-26121850 | Unknown | — |
| chr1:2253650-2254650 | Unknown | — |
| chr7:73060250-73063150 | Unknown | — |
| chr19:1754200-1758750 | Unknown | — |
| chr9:29211200-29215700 | Unknown | — |
| chr7:31375200-31377000 | Unknown | — |
| chr1:165344500-165346650 | Unknown | — |
| chr10:57389650-57391700 | Unknown | — |
| chr1:163441550-163443100 | Unknown | — |
| chr1:200842700-200844850 | Unknown | — |
| chr20:44639000-44640950 | Unknown | — |
| chr2:176952400-176953750 | Unknown | — |
| chr20:6031700-6033850 | Unknown | — |
| chr5:2738550-2740800 | Unknown | — |
| chr3:74662150-74664400 | Unknown | — |
| chr10:134600350-134602350 | Unknown | — |
| chr1:152084900-152085650 | Unknown | — |
| chr8:52520450-52521550 | Unknown | — |
| chr1:121279850-121280850 | Unknown | — |
| chr13:37729350-37731000 | Unknown | — |
| chr7:8390700-8392150 | Unknown | — |
| chr12:32818500-32820350 | Unknown | — |
| chr16:15350450-15351950 | Unknown | — |
| chr2:58342200-58346950 | Unknown | — |
| chr3:112383300-112384750 | Unknown | — |
| chr19:1682300-1683350 | Unknown | — |
| chr4:27077050-27078000 | Unknown | — |
| chr8:23507850-23509050 | Unknown | — |
| chr4:10782250-10783600 | Unknown | — |
| chr17:12927950-12928650 | Unknown | — |
| chr2:11989300-11990550 | Unknown | — |
| chr7:23074700-23076100 | Unknown | — |
| chr22:28479200-28480250 | Unknown | — |
| chr9:36763800-36766950 | Unknown | — |
| chr6:28757250-28758600 | Unknown | — |

TABLE 13-continued

| Somatic Promoters Overlapping EZH2/SUZ12 Binding Sites | | |
|---|---|---|
| Loci | Annotation Status | Associated Gene |
| chr1:50032150-50033200 | Unknown | — |
| chr6:4334150-4335300 | Unknown | — |
| chr1:195732150-195733300 | Unknown | — |
| chr6:170483200-170484200 | Unknown | — |
| chr12:38447100-38448600 | Unknown | — |
| chr7:86667750-86669950 | Unknown | — |
| chr16:9683650-9684650 | Unknown | — |
| chr1:171342100-171343300 | Unknown | — |
| chr20:47203350-47204450 | Unknown | — |
| chr20:62030950-62034000 | Unknown | — |
| chr1:168323150-168325650 | Unknown | — |
| chr6:10133900-10134950 | Unknown | — |
| chr4:71924850-71926200 | Unknown | — |
| chrX:130711450-130713600 | Unknown | — |
| chr12:38549550-38551600 | Unknown | — |
| chr2:131094200-131095000 | Unknown | — |
| chr1:183626800-183628050 | Unknown | — |
| chr6:28918100-28918850 | Unknown | — |
| chr2:198504700-198507250 | Unknown | — |
| chr11:71350450-71351500 | Unknown | — |
| chr20:47001000-47003900 | Unknown | — |
| chr21:10600500-10603150 | Unknown | — |
| chr3:34131250-34132150 | Unknown | — |
| chr5:7170200-7171750 | Unknown | — |
| chr17:50486700-50487400 | Unknown | — |
| chr2:122809550-122810150 | Unknown | — |
| chr8:57178000-57179050 | Unknown | — |
| chr4:142803450-142805000 | Unknown | — |
| chr10:118367950-118370350 | Unknown | — |
| chrX:115004100-115005700 | Unknown | — |
| chr3:53961050-53963000 | Unknown | — |
| chr6:28920750-28922800 | Unknown | — |
| chr17:11769750-11770850 | Unknown | — |
| chr6:1594950-1595600 | Unknown | — |
| chr15:79783300-79784500 | Unknown | — |
| chr7:83684250-83685650 | Unknown | — |
| chr18:2246500-2247900 | Unknown | — |

TABLE 13-continued

| Somatic Promoters Overlapping EZH2/SUZ12 Binding Sites | | |
|---|---|---|
| Loci | Annotation Status | Associated Gene |
| chr10:36147250-36148500 | Unknown | — |
| chr7:91023500-91025650 | Unknown | — |
| chr2:79337900-79339650 | Unknown | — |
| chrX:115002950-115003900 | Unknown | — |
| chr1:34557900-34558600 | Unknown | — |
| chr19:523250-524300 | Unknown | — |
| chr13:91315500-91317200 | Unknown | — |
| chr6:26330700-26333000 | Unknown | — |
| chr9:115565950-115567400 | Unknown | — |
| chr14:42380150-42381450 | Unknown | — |
| chr7:76356350-76358750 | Unknown | — |
| chr13:108578200-108579350 | Unknown | — |
| chr8:90569800-90570900 | Unknown | — |
| chr3:185842600-185844550 | Unknown | — |
| chr1:207903150-207904800 | Unknown | — |
| chr2:14988000-14988950 | Unknown | — |
| chr12:47819700-47821500 | Unknown | — |
| chr1:83728350-83730000 | Unknown | — |
| chr11:105384700-105387850 | Unknown | — |
| chr3:88557900-88558600 | Unknown | — |
| chr6:142290050-142291600 | Unknown | — |
| chr3:83265600-83268250 | Unknown | — |

To experimentally test if inhibiting EZH2/PRC2 activity might modulate somatic promoter usage in GC, we treated IM95 GC cells with GSK126, a highly selective small-molecule inhibitor of EZH2 methyltransferase activity. This line was selected as it has previously shown to be sensitive to EZH2 depletion (FIG. 14). RNA-seq analysis of GSK126-treated IM95 cells at two treatment time points (Day 6 and 9) confirmed that genes upregulated upon EZH2 inhibition are enriched in previously identified PRC2 target gene sets (FIG. 18). GSK126 treatment caused deregulation of 2134 promoters in total. Of 1959 promoters exhibiting somatic alterations in primary GCs (FIG. 1D), GSK126 treatment caused deregulation of 251 somatic promoters in IM95 cells (12.8%). This proportion was significantly greater than the proportion of unaltered promoters exhibiting deregulation after GSK126 challenge (8.8%, OR 1.46 $P<0.001$, Fisher Test, FIG. 5B), suggesting heightened sensitivity of somatic promoters to EZH2 inhibition. The proportion of somatic promoters deregulated after EZH2 inhibition was also greater than the total proportion of genes (as defined by Gencode) regulated by GSK126 (1.5%, OR 9.21, $P<0.001$, FIG. 5B). Of those promoters exhibiting both GSK126 deregulation and also mapping to somatic promoters lost in primary GC, 89.6% were reactivated following GSK126 administration (78/87, FC>=2, qval<0.1, Methods and Materials), consistent with EZH2 functioning to repress these promoters. For example, FIGS. 5C and 5D highlights two lost somatic promoters (SLC9A9 and PSCA), exhibiting expression gain after GSK126 treatment (FIG. 5). These results thus suggest a general role for EZH2 in regulating epigenomic promoter alterations in GC.

Somatic Promoters Reveal Novel Cancer-Associated Transcripts

Finally, when analyzing the altered somatic promoters with respect to both proximity to known genes, we found that somatic promoters could be classified into annotated and unannotated categories. Annotated promoters were defined as promoters mapping close (<500 bp) to a known Gencode transcription start site (TSS), while unannotated promoters refer to those mapping to genomic regions devoid of known Gencode TSSs. The majority of promoters present in non-malignant tissues, and also promoters unchanged between tumors and normal tissues, mapped closely to previously annotated TSSs (72%-92%). In contrast, only 41% of promoters mapped to annotated promoter locations, while the remaining 59% mapped to "unannotated" locations, distant from Gencode TSSs and in many cases 2-10 kb away (FIG. 6*a*).

To test the functional relevance of these unannotated promoters, we used GenoCanyon, a nucleotide level quantification of genomic functional potential that integrates multiple levels of conservation and epigenomic information. We observed that 81% of the unannotated promoter regions exhibited a maximum genome wide functional score of greater than 0.9 (range 0-1), indicating high functional potential. To ascertain tissue type specificities, we then applied tissue specific annotations using GenoSkyline, an extension of the GenoCanyon framework integrating Roadmap Epigenomics data We observed that GI tissues had the $3^{rd}$ highest median score after ESC and fetal tissues, consistent with our tumors being gastric in lineage and also de-differentiated (FIG. 5*b*). In a separate analysis, recent studies have also suggested that endogenous repeat elements in the human genome may contribute significantly to regulatory element variation, and hypomethylation of repeat elements can induce cancer-associated transcription. We found that unannotated promoters, were also significantly enriched for the repeat elements ERV1 (P<0.0001 Unannotated vs. All) and L1 (P<0.0001 Unannotated vs. All, FIG. 13).

Compared to annotated promoters, unannotated promoters exhibited weaker H3K27ac signals suggesting that the former might have lower activity and decreased gene expression levels (FIG. 13). Supporting this, somatic promoters, even those supported by CAGE tags (indicating true promoters), exhibited significantly lower RNA-seq expression levels compared CAGE tag supported all promoters (FIG. 5*c*). We thus hypothesized that unannotated promoters might be associated with low transcript levels, thereby rendering them more challenging to detect by conventional depth transcriptome sequencing given the very wide dynamic range of cellular transcriptomes (10-10,000 transcripts per cell for different genes) (FIG. 5*d*). To test this possibility, we employed both down-sampling and up-sampling analysis. Not surprisingly, decreasing levels of RNA-seq depth caused a concomitant decrease in detected somatic promoter transcripts. For example, downsampling to ~40M reads caused ~250 transcripts (FPKM>0, FIG. 5*e*) to be rendered undetectable at somatic promoters. More convincingly, in the reciprocal experiment, we experimentally generated deep RNA-seq data for matched 5 GC/normal pairs (average read depth 140M compared to standard 100M), and confirmed the additional detection of 435 new somatic promoter-associated transcripts (FPKM>0) (FIG. 5*e*). We estimate that usage of deep RNA-sequencing data allowed us to discover additional transcripts for 22% of the unannotated promoters, not previously detectible at regular depth RNA-seq (FIG. 5*f*). These results demonstrate that despite being associated with bona-fide cancer associated transcripts, many somatic promoters defined by epigenomic profiling may have been missed by conventional-depth RNA-seq.

Discussion

Identifying somatically-altered cis-regulatory elements, and understanding how these elements direct cancer-associated gene expression represents a critical scientific goal. Here, we defined close to 2000 promoters exhibiting altered activity in GC, indicating that somatic promoters in GC are pervasive. Promoters are canonically defined as proximal cis-regulatory elements that recruit general transcription factors to initiate transcription. However, selection and activation of TSSs by RNA polymerase at core promoters is dependent on multiple factors. Core promoters are differentially distributed between genes of different functions, and chromatin distributions and epigenetic landscapes of core promoter regions can also differ in a tissue specific manner. Presence of multiple transcription initiation sites within the same gene can generate distinct transcript isoforms with different 5'UTRs that can act as switches to regulate gene expression, and usage of alternative 5'UTRs can also impact both translation and protein stability of cancer associated genes such as BRCA1, TGF-β and ERG Such findings demonstrate that specific promoter element activity is complex and cell context dependent, with impact on downstream transcriptional, translational, and functional processes.

A significant proportion (~18%) of somatic promoters corresponded to alternative promoters. In cancer, alternative promoter utilization is of major relevance, as increasing numbers of genes (e.g. LEF1, TP53, TGFB3) are now being shown to exhibit distinct alternative-promoter associated isoforms that differentially affect malignant growth. In the current study, we identified alternative promoters in genes both known and novel to GC biology with significant clinical and translational implications. For example, we discovered an alternative promoter at the EpCAM gene locus specifically activated in gastric tumors. In GC, EpCAM encodes a transmembrane glycoprotein which has been proposed as a marker for circulating tumor cells and EpCAM expression levels have been correlated with GC patient prognosis. However, little is known about the specific cellular mechanisms driving high EpCAM expression in GC. Our finding that EpCAM is regulated in GC not through its canonical promoter, but instead through a cancer-specific alternative promoter may lend credence to recent reports suggesting that in addition to acting as an experimentally convenient surface marker, EpCAM may actually play a more direct pro-oncogenic role in stimulating cellular proliferation.

Another novel example of an alternative promoter-associated gene, identified for the first time in our study, was RASA3. While a functional role for RASA3 in cancer remains to definitely established, studies from other biological fields have shown that RASA3 can inhibit RAP1, which in turn has been implicated in invasion and metastasis in various cancers. RASA3 depletion can enhance signaling by integrins and mitogen-activated protein kinases, and the possibility that RASA3 can act as tumor suppressor has also been recently suggested through independent cross-species cancer studies. A plausible role for RASA3 as a potential tumor suppressor is consistent with our own results where expression of wild-type RASA3 potently inhibited cell migration and invasion in GC cell lines, while N-terminal variant RASA3 enhanced migration and invasion in normal gastric epithelial cells. A third example of an alternative-promoter driven genes was MET, which has been extensively investigated as a target for cancer therapy. While we and others have previously reported expression of an N-terminal truncated MET variant in cancer, functional implications of this truncated MET variant have remained unclear. In the present study, experimental assessment of MET wild-type and variant signaling revealed that truncated MET variants may have different downstream signaling effects compared to full-length MET isoforms. Under the experimental conditions used, we observed significant differences in phosphorylation patterns of ERK, STAT3 and GAB1, in a manner consistent with MET-Var being more pro-oncogenic compared to MET-Var, as both ERK, STAT3, and GAB1 have been shown to facilitate MET-induced signaling. The MET signaling pathway is known to be particularly complex with multiple feedback loops, and understanding how expression of the N terminal short MET isoform might modulate downstream survival signaling will be an important subject of future research, particularly in light of recent clinical trials targeting MET in lung cancer using antibodies which have been unsuccessful.

Our study also revealed an unexpected relationship between somatic promoters and tumor immunity. Specifically, we discovered that alternative promoter isoforms overexpressed in GC were significantly depleted of N-terminal peptides predicted to be potentially immunogenic, based on computational predictions of high-affinity MHC Class I binding and other immunological assays. We believe that finding is relevant to cancer immunity, as it builds on previous findings from the literature establishing the existence of self-reactive T-cells, the potential immunogenicity of overexpressed tumor antigens, and the process of tumor immunoediting. First, while the majority of self-reactive T-cells are clonally deleted during early development, numerous groups have also demonstrated the frequent persistence of self-reactive T cells in the periphery. For example, analysis of transgenic mice has shown that 25-40% of autoreactive T cells are likely to escape clonal deletion even in the presence of the deleting ligand, and in humans, Yu et al has demonstrated that clonal deletion prunes the T-cell repertoire but does not fully eliminate self-reactive T-cell clones. Importantly, while such self-reactive T-cells are typically low-avidity and are not capable of recognizing self-antigens under normal physiological conditions, they still retain the ability to become activated and to produce effector and memory cells under conditions of appropriate stimulation, such as infection and the mounting of anti-tumor responses.

Second, in cancer, several studies have shown that self-reactive T-cells can exhibit immunologic activity towards overexpressed tumor antigens, even if these antigens are also expressed at lower levels in normal tissues. One well-known example is the melanocyte differentiation antigen Melan-A/MART-1, which is expressed by both normal melanocytes and overexpressed in malignant melanoma cells. T-cell recognition of Melan-A/MART-1 has been detected in 50% of melanoma patients, and even healthy individuals have been shown to exhibit a disproportionately high frequency of Melan-A/MART-1-specific T cells in the peripheral blood. Besides Melan-A/MART-1, other examples of tumor associated self-antigens inducing immunological recognition in both healthy individuals and cancer patients include tyrosinase-related proteins (TRP-1 and TRP-2) and glycoprotein (gp) 100 in melanoma, and PIA in mastocytoma cells. Such examples clearly demonstrate that in certain cases, normally expressed proteins can still become immunogenic when overexpressed in cancer. Third, tumor immunoediting—the acquired capacity of developing tumors to escape immune control, is a recognized hallmark of cancer. Tumor immune escape can occur via different mechanisms, such as through upregulation of immune checkpoint inhibitors (eg PD-L1), and altered transcription of antigen presenting genes or tumor-specific antigens. For example, decreased expression of melanoma antigens (eg gp100, MART-1, and PIA) has been associated with melanoma progression to later disease stages. Besides overt downregulation of the entire gene, it is thus highly plausible that transcriptional changes affecting splice forms and promoter variants may also contribute to tumor immunoediting. For example, very recent work in B-cell acute lymphoblastic leukemia (B-ALL) has described the production of N-terminally truncated CD19 transcript variants in response to CD19 CART (chimeric antigen receptor-armed T cells) therapy, clearly showing that promoter transcript variants can indeed arise as a consequence of immunologic pressure. Taken collectively, we believe that these previously established findings all point to a plausible role for alternative promoters in reducing the immunogenic potential of tumors. In this regard, our observation that regions exhibiting somatic promoter alterations showed a significant overlap with binding targets of the Polycomb repressive complex 2 (PRC2) epigenetic regulator complex, and are particularly sensitive to EZH2 inhibition, suggests that pharmacologic approaches for reawakening somatic promoter-associated epitopes might represent an attractive strategy for increasing anti-tumor T-cell immunoreactivity and anti-tumor activity.

In conclusion, our study indicates an important role for somatic promoters in GC. We also note that a significant portion (52%) of the somatic promoters localized to unannotated TSSs, consistent with recent studies indicating the existence of hundreds of transcript loci remaining to be annotated. Interestingly, a large portion of the human transcriptome has been shown to originate from repetitive elements that can exhibit promoter activity and/or express noncoding RNAs. Unannotated promoters activated in our GC study were found to be enriched in ERV-1 and L1 repeat elements which have been shown to be associated with stage specific transcription in early human embryonic cells, suggesting a yet unknown functional role for these promoters. Analysis of these unannotated promoters is likely to provide fertile ground for new and hitherto unanticipated insights into mechanisms of GC development and progression.

What is claimed is:

1. A method for detecting the presence of at least one promoter in a cancerous biological sample that is associated with tumor immunity, comprising:

i) contacting the cancerous biological sample with at least one antibody specific for histone modification H3K4me3 and at least one antibody specific for histone modification H3K4me1;

ii) isolating nucleic acid from the cancerous biological sample having a signal ratio of H3K4me3 relative to H3K4me1 greater than 1, wherein the isolated nucleic acid comprises at least one region specific to said histone modifications;

iii) detecting an increase in signal intensity of H3K4me3 in the isolated nucleic acid relative to the signal intensity of H3K4me3 in a non-cancerous biological sample of greater than 1.5 fold thereby identifying at least one cancer-associated alternative promoter that is associated with a canonical promoter; and iv) detecting the presence of a transcript variant in the cancerous biological sample driven by the at least one cancer-associated alternative promoter of step iii), wherein the at least one cancer-associated promoter is a promoter of a gene encoding a polypeptide associated with tumor immunity, wherein the transcript variant encodes an N-terminal truncated peptide and wherein said truncated peptide is a non-immunogenic peptide compared to an untruncated variant of the peptide encoded by a transcript expressed from the associated canonical promoter.

2. The method of claim 1, wherein the cancerous and noncancerous biological sample comprises a single cell, multiple cells, fragments of cells, body fluid or tissue; optionally wherein the cancerous and non-cancerous biological sample is obtained from the same subject; optionally wherein the cancerous and non-cancerous biological samples are each obtained from different subjects.

3. The method of claim 1, wherein the contacting step comprises immunoprecipitation of chromatin with the antibodies specific for the histone modifications.

4. The method of claim 1, further comprising mapping at least one cancer-associated alternative promoter from the cancerous biological sample against at least one reference nucleic acid sequence to identify a gene transcript associated with the at least one promoter; optionally wherein the at least one reference nucleic acid sequence comprises a nucleic acid sequence derived from:

i) an annotated genome sequence;

ii) a de novo transcriptome assembly; and/or iii) a non-cancerous nucleic acid sequence library or database.

5. The method of claim 1, wherein the activity of the at least one cancer-associated promoter correlates with an increase of SUZ12 or EZH2 binding sites relative to the total promoter population.

6. The method of claim 5, wherein the increase of SUZ12 or EZH2 binding sites correlates with an upregulation of the activity of the at least one cancer-associated promoter.

7. The method of claim 1, wherein the transcription start site of the transcript variant driven by the at least one cancer-associated alternative promoter is associated with a gene selected from the group consisting of DNAH3, DST, EPS8LI, FRMD4B, LAMA3, MET, MIB2, MRC2, NOS2, PLEC, PLEKHG5, PTGDS, RASA3, TRPM2, and IKZF3.

8. The method of claim 1, wherein the cancerous biological sample is a gastric cancer sample or a colon cancer sample.

9. The method of claim 1, wherein the canonical promoter is present in both the cancerous biological sample and the non-cancerous biological sample, and wherein the alternative promoter is only present in the cancerous biological sample; optionally wherein the at least one cancer-associated alternative promoter is an unannotated promoter that is positioned more than 500 bp away from a gene transcription start site.

10. The method of claim 9, further comprising:

measuring the expression level of the at least one cancer-associated alternative promoter in the cancerous biological sample and non-cancerous biological sample, wherein the measuring comprises digital profiling of reporter probes; and determining the differential expression level of the at least one cancer-associated alternative promoter in the cancerous biological sample relative to the non-cancerous biological sample, based on the digital profiling of the reporter probes, to validate the presence of at least one cancer-associated alternative promoter in the cancerous biological sample relative to a non-cancerous biological sample.

11. The method of claim 10, wherein said step of measuring is conducted using a digital fluorescent barcode technology with customized probes for direct multiplex analysis of the nucleic acid content.

12. The method of claim 1, comprising detecting the signal intensity of H3K4me3 in the isolated nucleic acid at a read depth of 20M.

13. The method of claim 5, wherein the increase of SUZ12 or EZH2 binding sites correlates with a downregulation of the activity of the at least one cancer-associated promoter.

14. The method of claim 6, wherein the at least one cancer-associated promoter is positioned within 500 bp from a known gene transcription start site.

15. The method of claim 13, wherein the at least one cancer-associated promoter is positioned within 500 bp from a known gene transcription start site.

16. The method of claim 1, wherein the non-immunogenic peptide has reduced binding affinity to MHC Class I compared to the untruncated variant of the peptide.

* * * * *